(12) United States Patent
Ibrahim et al.

(10) Patent No.: US 8,791,102 B2
(45) Date of Patent: *Jul. 29, 2014

(54) ACETANILIDE SPHINGOSINE-1-PHOSPHATE RECEPTOR ANTAGONISTS

(75) Inventors: Mohamed Abdulkader Ibrahim, Mountain View, CA (US); Joon Won Jeong, Belmont, CA (US); Henry William Beecroft Johnson, San Bruno, CA (US); Patrick Kearney, San Francisco, CA (US); James W. Leahy, San Leandro, CA (US); Gary L. Lewis, San Francisco, CA (US); Robin Tammie Noguchi, San Bruno, CA (US); John M. Nuss, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 13/124,604

(22) PCT Filed: Oct. 16, 2009

(86) PCT No.: PCT/US2009/061044
§ 371 (c)(1),
(2), (4) Date: Jul. 28, 2011

(87) PCT Pub. No.: WO2010/045580
PCT Pub. Date: Apr. 22, 2010

(65) Prior Publication Data
US 2011/0288076 A1    Nov. 24, 2011

Related U.S. Application Data

(60) Provisional application No. 61/196,495, filed on Oct. 17, 2008.

(51) Int. Cl.
| | |
|---|---|
| A61K 31/4196 | (2006.01) |
| A61K 31/417 | (2006.01) |
| A61K 31/4192 | (2006.01) |
| A61K 31/167 | (2006.01) |
| A61K 31/341 | (2006.01) |
| A61K 31/4015 | (2006.01) |
| A61K 31/455 | (2006.01) |
| A61K 31/506 | (2006.01) |
| A61K 31/541 | (2006.01) |
| A61K 31/55 | (2006.01) |
| A61P 35/00 | (2006.01) |
| A61P 35/02 | (2006.01) |
| C07D 207/452 | (2006.01) |
| C07D 213/56 | (2006.01) |
| C07D 223/04 | (2006.01) |
| C07D 307/54 | (2006.01) |
| C07D 403/04 | (2006.01) |
| C07D 403/06 | (2006.01) |
| C07D 417/06 | (2006.01) |

(52) U.S. Cl.
USPC ......... 514/217.12; 514/227.8; 514/252.14; 514/350; 514/355; 514/425; 514/471; 514/616; 514/383; 514/422; 514/400; 544/58.5; 544/295; 546/298; 546/316; 548/204; 548/255; 548/267.6; 548/265.6; 548/546

(58) Field of Classification Search
CPC ........... A61K 31/4196; A61K 31/4192; C07D 249/04; C07D 249/08
USPC ........... 514/283, 422, 217.12, 400, 383, 616, 514/471, 425, 355, 350, 252.14, 227.8; 548/204, 267.6, 255, 265.6, 546; 544/295, 58.5; 540/610; 546/316, 298; 549/488; 564/158
See application file for complete search history.

(56) References Cited

U.S. PATENT DOCUMENTS

| | | | | |
|---|---|---|---|---|
| 5,955,616 | A | * | 9/1999 | Ohtani et al. ............ 548/183 |
| 6,028,087 | A | * | 2/2000 | Bondinell et al. ........ 514/357 |
| 2006/0223866 | A1 | | 10/2006 | Evindar et al. |
| 2008/0171783 | A1 | | 7/2008 | Cameron et al. |
| 2011/0301188 | A1 | * | 12/2011 | Shankar et al. ........... 514/283 |

FOREIGN PATENT DOCUMENTS

| | | | | |
|---|---|---|---|---|
| EP | 183271 | A2 | * | 6/1986 |
| WO | 99/11657 | A1 | | 3/1999 |
| WO | 01/053274 | A1 | | 7/2001 |
| WO | 02/076968 | A1 | | 10/2002 |
| WO | WO 2002/076968 | A1 | * | 10/2002 ........... C07D 307/20 |
| WO | 2005/041899 | A2 | | 5/2005 |
| WO | 2007/003934 | a2 | | 1/2007 |
| WO | 2007/027742 | A2 | | 3/2007 |
| WO | WO 2008077555 | A2 | * | 7/2008 |

OTHER PUBLICATIONS

Patani et al., Chem Rev, 1996, vol. 96 (8), especially p. 3149.*
Chemical Abstract Service (CAS) STN Registry Database No. 334666-99-8 [entered STN: May 4, 2001].*
Chemical Abstract Service (CAS) STN Registry Database No. 334667-05-9 [entered STN: May 4, 2001].*
Ito et al. Cancer Sci. 2003, 94(1), 3-8.*
XP002569183, Database Caplus [Online], Chemical Abstracts Service, 2009, "Preparation of glycine aryl amides as beta-secretase inhibitors".

* cited by examiner

Primary Examiner — Samantha Shterengarts
Assistant Examiner — Amanda L Aguirre
(74) Attorney, Agent, or Firm — McDonnell Boehnen Hulbert & Berghoff LLP

(57) ABSTRACT

This disclosure relates to sphingosine-1-phosphate (S1P) receptor antagonists, compositions comprising the S1P receptor antagonists and methods for using and processes for making the S1P receptor antagonists. In particular, this disclosure relates to sphingosine-1-phosphate 1 (S1P1) receptor antagonists, compositions comprising the S1P1 receptor antagonist and methods for using the S1P1 receptor antagonist, such as in the treatment of cancer, and processes for making the S1P1 receptor antagonists.

15 Claims, No Drawings

ACETANILIDE SPHINGOSINE-1-PHOSPHATE RECEPTOR ANTAGONISTS

CROSS REFERENCE TO RELATED APPLICATIONS

This application is a US national phase of International Application No. PCT/US2009/061044 filed on Oct. 16, 2009, which claims the benefit of U.S. Provisional Application No. 61/196,495 filed on Oct. 17, 2008, the disclosures of which are incorporated herein by reference in their entirety.

FIELD OF THE INVENTION

This disclosure relates to sphingosine-1-phosphate (S1P) receptor antagonists, compositions comprising the S1P receptor antagonists and methods for using and processes for making the SIP receptor antagonists. In particularly, this disclosure relates to sphingosine-1-phosphate 1 (S1P1) receptor antagonists, compositions comprising the S1P1 receptor antagonist and methods for using the S1P1 receptor antagonist, such as in the treatment of cancer, and processes for making the S1P1 receptor antagonists.

BACKGROUND OF THE INVENTION

Sphingosine 1-phosphate (S1P) is derived from sphingosine, which provides the backbone to all sphingolipids. Phosphorylation of sphingosine, a metabolite of the pro-apoptotic lipid ceramide, to S1P, is mediated by lipid kinases called sphingosine kinases (SphK). There are two SphK isoenzymes: SphK1 or SphK2. SIP may be reversibly deactivated through dephosphorylation by several phosphatases or irreversibly deactivated by S1P lyase. S1P is produced intracellularly in organelles and the plasma membrane and then secreted. The newly generated S1P is then secreted and is bound extensively by albumin and other plasma proteins. This provides a stable reservoir in extracellular fluids, presumably at higher total concentrations than in tissues, and rapid delivery to cell surface receptors. SIP, via its five cognate G-protein coupled receptors (GPCRs), S1P1-5 Rs, regulates diverse biological functions, including inflammatory responses, cell proliferation, apoptosis, cell migration, lymphocyte trafficking and cell senescence. Thus, coordinated activities of biosynthetic and biodegradative enzymes help maintain and regulate concentrations of SIP in the range required for physiological activities.

SIP has been shown to be an important mediator of angiogenesis and tumorigenesis. One way to modulate SIP levels is to target SphK, and thereby affect biosynthesis of SIP. SphK1 has been shown to stimulate proliferation in vitro, and is tumorigenic in vivo. It also imparts resistance to radiotherapy and chemotherapy and is elevated in some solid tumors. SphK1 inhibitors have been shown to have anti-cancer effects in vivo. These effects have been attributed to the inhibition of formation of SIP. Further, a monoclonal antibody against SIP reduces progression of or eliminates tumors in murine xenograft and allograft models. Thus, lowering levels of SIP by inhibiting SphK or by an SIP-specific antibody has anti-tumorigenic effects.

Since many, if not all effects of SIP are mediated by five GPCRs, an alternative approach to cancer therapy may be inhibition of SIP receptors. Of the five known SP receptors, S1P1R has been shown to play an important role in vascular permeability and S1P1R knock-out mice have an embryonic lethal phenotype. Furthermore, there is increasing evidence for cross-talk between S1P1R and other growth factor receptors such as PDGFR. Thus, S1P1 receptor antagonists have the potential to offer clinical benefit as anti-cancer therapeutics.

SUMMARY OF THE INVENTION

An aspect of the invention is a compound of Formula I:

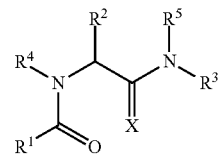

wherein:

X is O or $NR^6$;

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, —$X^1OR^7$, —$X^1C(O)OR^7$, —$X^1C(O)NR^7R^7$, —$X^1NR^7C(O)OR^7$, —$X^1OC(O)NR^7R^7$, —$X^1NR^7C(O)NR^7R^7$, —$X^1S(O)_{n1}OR^7$, —$X^1S(O)_{n1}NR^7R^7$, —$X^1NR^7S(O)_{n1}NR^7R^7$, —$X^1NR^7R^7$, —$X^1C(O)R^7$, —$X^1OC(O)R^8$, —$X^1NR^7C(O)R^8$, —$X^1S(O)_{n1}R^8$, —$X^1OS(O)_{n1}R^8$ or —$X^1NR^7S(O)_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is —$X^2CR^9R^9R^{11}$, —$X^2OR^{11}$, —$X^2C(O)OR^{11}$, —$X^2C(O)NR^{10}R^{11}$, —$X^2NR^{10}C(O)OR^{11}$, —$X^2OC(O)NR^{10}R^{11}$, —$X^2NR^{10}C(O)NR^{10}R^{11}$, —$X^2S(O)_{n2}OR^{11}$, —$X^2S(O)_{n2}NR^{10}R^{11}$, —$X^2NR^{10}S(O)_{n2}NR^{10}R^{11}$, —$X^2NR^{10}R^{11}$, —$X^2C(O)R^{11}$, —$X^2OC(O)R^{11}$, —$X^2NR^{10}C(O)R^{11}$, —$X^2S(O)_{n2}R^{11}$, —$X^2OS(O)_{n2}R^{11}$ or —$R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is —$X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with —$X^4CR^{13}R^{13}R^{15}$, —$X^4OR^{15}$, —$X^4C(O)OR^{15}$, —$X^4C(O)NR^{14}R^{15}$, —$X^4NR^{14}C(O)OR^{15}$, —$X^4OC(O)NR^{14}R^{15}$, —$X^4NR^{14}C(O)NR^{14}R^{15}$, —$X^4S(O)_{n3}OR^{15}$, —$X^4S(O)_{n3}NR^{14}R^{15}$, —$X^4NR^{14}S(O)_{n3}NR^{14}R^{15}$, —$X^4NR^{14}R^{15}$, —$X^4C(O)R^{15}$, —$X^4OC(O)R^{15}$, —$X^4NR^{14}C(O)R^{15}$, —$X^4S(O)_{n3}R^{15}$, —$X^4OS(O)_{n3}R^{15}$ or —$R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is —$X^5R^{16}$ wherein $X^5$ is a bond or $(C_{1-3})$alkylene and $R^{16}$ is cycloalkyl, aryl, heterocycloalkyl or heteroaryl, wherein: any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, —$X^6OR^{17}$, —$X^6C(O)OR^{17}$, —$X^6C(O)NR^{17}R^{17}$, —$X^6NR^{17}C(O)OR^{17}$, —$X^6OC(O)NR^{17}R^{17}$, —$X^6NR^{17}C(O)NR^{17}R^{17}$, —$X^6S(O)_{n7}OR^{17}$, —$X^6S(O)_{n4}NR^{17}R^{17}$, —$X^6NR^{17}S(O)_{n4}NR^{17}R^{17}$, —$X^6NR^{17}R^{17}$, —$X^6C(O)R^{17}$, —$X^6OC(O)R^{18}$, —$X^6NR^{17}C(O)R^{18}$, —$X^6S(O)_{n4}R^{18}$, —$X^6OS(O)_{n4}R^{18}$ and —$X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl;

$R^2$ is $-X^7NHC(O)R^{19}$, $-X^7NR^{20}C(O)OR^{22}$, $-X^7CR^{21}R^{21}R^{22}$, $-X^7OR^{22}$, $-X^7S(O)_{n5}OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl, $R^{21}$ is halo and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

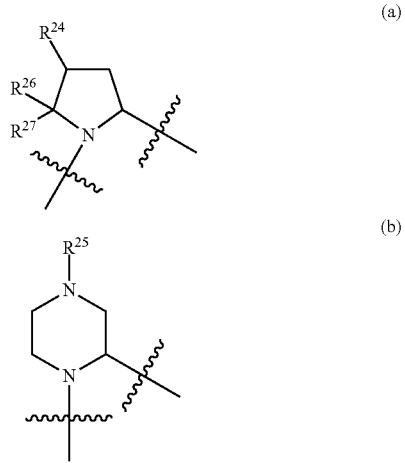

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}NR^{28}C(O)OR^{29}$, $-X^{10}NR^{28}R^{29}$, $-X^9C(O)OR^{29}$ or $-R^{29}$ wherein $X^9$ is a bond or $(C_{1-3})$alkylene, $X^{10}$ is $(C_{1-3})$alkylene and $R^{28}$ is hydrogen, $(C_{1-4})$alkyl or halo-substituted $(C_{1-4})$alkyl and $R^{29}$ is $-X^{11}R_{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo or thioxo;

$R^3$ is phenyl substituted with $-R^{31}$ or $R^3$ is a group of Formula (c):

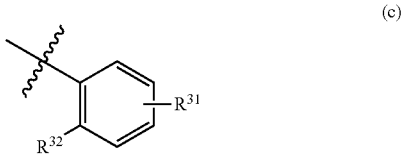

wherein $R^{31}$ is $-OR^{33}$, $-SR^{33}$ or $-CH_2R^{33}$, wherein $R^{33}$ is $-X^{12}R^{34}$, wherein $X^{12}$ is a bond or methylene and $R^{34}$ is five or six membered cycloalkyl or heterocycloalkyl, phenyl or five or six membered heteroaryl, and $R^{32}$ together with $R^6$ forms a bond, wherein any cyclic moiety within $R^3$ independently may be substituted with one or two $(C_{1-4})$alkyl, halo or $-OR^{35}$, wherein $R^{35}$ is $(C_{1-4})$alkyl;

$R^4$ is hydrogen, alkyl or as defined above; and $R^5$ is hydrogen or alkyl; and any individual stereoisomer or mixture of stereoisomers; and any pharmaceutically acceptable salts thereof An aspect of the invention is a compound of Formula I, as defined immediately above, provided that $R^3$ is not 4-phenoxyphenyl when X is O and $R^2$ is benzyloxymethyl; and any individual stereoisomer or mixture of stereoisomers; and any pharmaceutically acceptable salts thereof.

An aspect of the invention is a compound of Formula II:

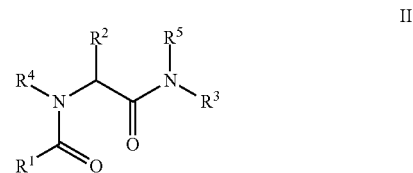

wherein:

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, $-X^1OR^7$, $-X^1C(O)OR^7$, $-X^1C(O)NR^7R^7$, $-X^1NR^7C(O)OR^7$, $-X^1OC(O)NR^7R^7$, $-X^1NR^7C(O)NR^7R^7$, $-X^1S(O)_{n1}OR^7$, $-X^1S(O)_{n1}NR^7R^7$, $-X^1NR^7S(O)_{n1}NR^7R^7$, $-X^1NR^7R^7$, $-X^1C(O)R^7$, $-X^1OC(O)R^8$, $-X^1NR^7C(O)R^8$, $-X^1S(O)_{n1}R^8$, $-X^1OS(O)_{n1}R^8$ or $-X^1NR^7S(O)_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $-X^2CR^9R^9R^{11}$, $-X^2OR^{11}$, $-X^2C(O)OR^{11}$, $-X^2C(O)NR^{10}R^{11}$, $-X^2NR^{10}C(O)OR^{11}$, $-X^2OC(O)NR^{10}R^{11}$, $-X^2NR^{10}C(O)NR^{10}R^{11}$, $-X^2S(O)_{n2}OR^{11}$, $-X^2S(O)_{n2}NR^{10}R^{11}$, $-X^2NR^{10}S(O)_{n2}NR^{10}R^{11}$, $-X^2NR^{10}R^{11}$, $-X^2C(O)R^{11}$, $-X^2OC(O)R^{11}$, $-X^2NR^{10}C(O)R^{11}$, $-X^2S(O)_{n2}R^{11}$, $-X^2OS(O)_{n2}R^{11}$ or $-R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is $-X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with $-X^4CR^{13}R^{13}R^{15}$, $-X^4OR^{15}$, $-X^4C(O)OR^{15}$, $-X^4C(O)NR^{14}R^{15}$, $-X^4NR^{14}C(O)OR^{15}$, $-X^4OC(O)NR^{14}R^{15}$, $-X^4NR^{14}C(O)NR^{14}R^{15}$, $-X^4S(O)_{n3}R^{15}$, $-X^4S(O)_{n3}NR^{14}R^{15}$, $-X^4NR^{14}S(O)_{n3}NR^{14}R^{15}$, $-X^4NR^{14}R^{15}$, $-X^4C(O)R^{15}$, $-X^4OC(O)R^{15}$, $X^4NR^{14}C(O)R^{15}$, $-X^4S(O)_{n3}R^{15}$, $-X^4OS(O)_{n3}R^{15}$ or $-R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is $-X^5R^{16}$ wherein $X^5$ is a bond or $(C_{1-3})$alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, $-X^6OR^{17}$, $-X^6C(O)OR^{17}$, $-X^6C(O)NR^{17}R^{17}$, $-X^6NR^{17}C(O)OR^{17}$, $-X^6OC(O)NR^{17}R^{17}$, $-X^6NR^{17}C(O)NR^{17}R^{17}$, $-X^6S(O)_{n4}OR^{17}$, $-X^6S(O)_{n4}NR^{17}R^{17}$, $-X^6NR^{17}S(O)_{n4}NR^{17}R^{17}$, $-X^6NR^{17}R^{17}$, $-X^6C(O)R^{17}$, $-X^6OC(O)R^{18}$, $-X^6NR^{17}C(O)R^{18}$, $-X^6S(O)_{n4}R^{18}$, —X⁶OS(O)_{n4}R¹⁸ and —X⁶NR¹⁷S(O)_{n4}R¹⁸, wherein n4 is 0, 1, or 2, X⁶ is a bond or (C_{1-3})alkylene, R¹⁷ at each occurrence independently is hydrogen, (C_{1-4})alkyl or halo-substituted (C_{1-4})alkyl and R¹⁸ is C_{1-4})alkyl or halo-substituted (C_{1-4}) alkyl;

R² is —X⁷NHC(O)R¹⁹, —X⁷NR²⁰C(O)OR²², —X⁷CR²¹R²¹R²², —X⁷OR²², —X⁷S(O)_{n5}OR²² or —R²², wherein n5 is 0, 1, or 2, X⁷ is (C_{1-3})alkylene, R¹⁹ is (C_{1-4})alkyl or halo-substituted (C_{1-4})alkyl, R²⁰ is hydrogen, (C_{1-4})alkyl or halo-substituted (C_{1-4})alkyl, R²¹ is halo and R²² is —X⁸R²³, wherein X⁸ is a bond or (C_{1-3})alkylene, and R²³ is phenyl, or R² together with R⁴ and the atoms to which R² and R⁴ are attached form a five or six membered ring of Formula (a) or (b):

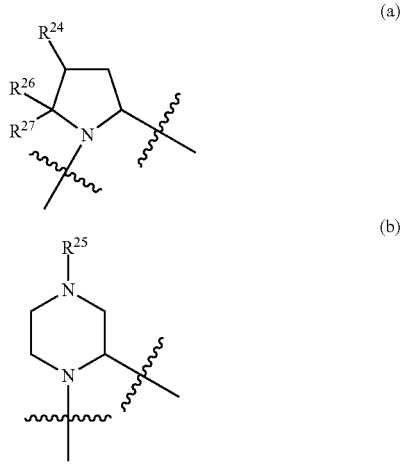

wherein R²⁴ is —X⁹OR²⁹, —X⁹NR²⁸C(O)OR²⁹, —X⁹NR²⁸R²⁹, —X⁹C(O)OR²⁹ or —R²⁹ and R²⁵ is —X¹⁰OR²⁹, —X¹⁰NR²⁸C(O)OR²⁹, —X¹⁰NR²⁸R²⁹, —X⁹C(O)OR²⁹ or —R²⁹ wherein X⁹ is a bond or (C_{1-3})alkylene, X¹⁰ is (C_{1-3})alkylene and R²⁸ is hydrogen, (C_{1-4})alkyl or halo-substituted (C_{1-4})alkyl and R²⁹ is —X¹¹R₃₀ wherein X¹¹ is a bond or (C_{1-3})alkylene and R³⁰ is phenyl or heteroaryl, wherein R³⁰ may be substituted with one to three substituents independently selected from (C_{1-4})alkyl, (C_{1-4})alkoxy, halo and trifluoromethyl, and R²⁶ and R²⁷ are both hydrogen or together form oxo or thioxo;

R³ is phenyl substituted with —R³¹, wherein R³¹ is —OR³³, —SR³³ or —CH₂R³³, wherein R³³ is —X¹²R³⁴, wherein X¹² is a bond or methylene and R³⁴ is five or six membered cycloalkyl or heterocycloalkyl, phenyl or five or six membered heteroaryl, wherein any cyclic moiety within R³ independently may be substituted with one or two (C_{1-4}) alkyl, halo or —OR³⁵, wherein R³⁵ is (C_{1-4})alkyl;

R⁴ is hydrogen, alkyl or as defined above; and

R⁵ is hydrogen or alkyl; and any individual stereoisomer or mixture of stereoisomers; and any pharmaceutically acceptable salts thereof An aspect of the invention is a compound of Formula II, as defined immediately above, provided that R³ is not 4-phenoxyphenyl when X is O and R² is benzyloxymethyl; and any individual stereoisomer or mixture of stereoisomers; and any pharmaceutically acceptable salts thereof.

An aspect of the invention is a compound of Formula III:

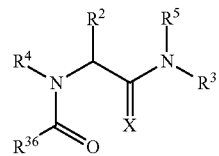

wherein:
X is O or NR⁶;
R³⁶ is 1-(4-chlorobenzyl)-5-oxopyrrolidin-3-yl, 2-fluorobenzyl, 1H-imidazol-4-ylmethyl, 1H-indol-4-yl, 2-methylthiopyrid-3-yl, 1R-hydroxy-2-phenylethyl, 2-hydroxyphenoxymethyl, 1S-acetyloxyethyl, (R)-2-chlorophenyl (hydroxy)methyl, tetrahydrofur-2R-yl, 3-methyloxazol-5-yl, 2,2,2-trifluoroethyl, 2-cyclopropylcarbonylethyl, 2-bromo-5-fluorophenyl, indol-4-yl, indol-5-yl, indol-6-yl, indan-2-yl, 3-methyl-2-nitrophenyl, methylsulphonylmethyl, 5-methylpyrid-3-yl, 4-acetyloxyphenyl, 3-hydroxyphenyl(hydroxyl)methyl, 5-(2,5-dioxo-2,5-dihydro-1H-pyrrol-1-yl) pentyl, fur-2-ylcarbonyl, 2R-methyl-2-phenylethyl, 3-chloro-2-fluorobenzyl, 5-chloro-2-fluorobenzyl, 3-chloro-2-fluorobenzyl, 1-acetylpyrrolidin-2-yl, N-benzoyl-N-methylaminomethyl, 1H-imdazol-4-ylmethyl, 1H-tetrazol-1-ylmethyl, 1-methylimidazol-4-yl, 2-fluorobenzyl, 1H-1,2,4-triazol-1-ylmethyl, thien-2-ylmethyl, 2,5-dichlorobenzyl, ((1-methyl-1H-benzo[d]imidazol-2-yl)methylamino)methyl or 2,5-dioxoimidazolidin-4-ylmethyl;

R² is —X⁷NHC(O)R¹⁹, —X⁷NR²⁰C(O)OR²², —X⁷CR²¹R²¹R²², —X⁷OR²², —X⁷S(O)_{n5}OR²² or —R²², wherein n5 is 0, 1, or 2, X⁷ is (C_{1-3})alkylene, R¹⁹ is (C_{1-4})alkyl or halo-substituted (C_{1-4})alkyl, R²⁰ is hydrogen, (C_{1-4})alkyl or halo-substituted (C_{1-4})alkyl, R²¹ is halo and R²² is —X⁸R²³, wherein X⁸ is a bond or (C_{1-3})alkylene, and R²³ is phenyl, wherein R²³ may be substituted with one or two substituents independently selected from halo, trifluoromethoxy or trifluoromethyl, or R² together with R⁴ and the atoms to which R² and R⁴ are attached form a five or six membered ring of Formula (a) or (b):

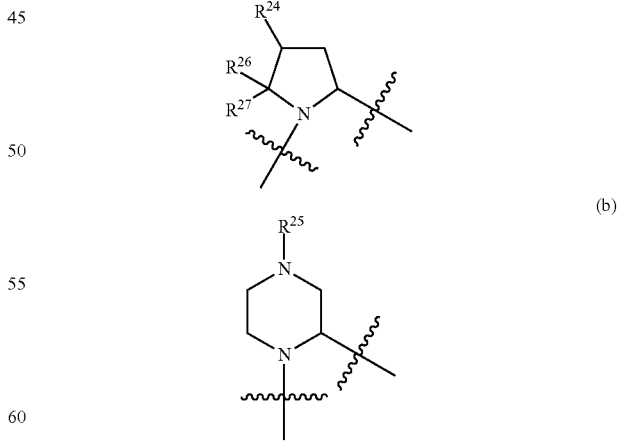

wherein R²⁴ is —X⁹OR²⁹, —X⁹NR²⁸C(O)OR²⁹, —X⁹NR²⁸R²⁹, —X⁹C(O)OR²⁹ or —R²⁹ and R²⁵ is —X¹⁰R²⁹, —X¹⁰NR²⁸C(O)OR²⁹, —X¹⁰NR²⁸R²⁹, —X⁹C(O)OR²⁹ or —R²⁹ wherein X⁹ is a bond or (C_{1-3})alkylene, X¹⁰ is (C_{1-3})alkylene and R²⁸ is hydrogen, (C_{1-4})alkyl or halo-substituted ($C_{1-4}$)alkyl and $R^{29}$ is —$X^{11}R^{30}$ wherein $X^{11}$ is a bond or ($C_{1-3}$)alkylene and $R^{30}$ is phenyl or heteroaryl, wherein $R^{30}$ may be substituted with one to three substituents independently selected from ($C_{1-4}$)alkyl, ($C_{1-4}$)alkoxy, halo and trifluoromethyl, and $R^{26}$ and $R^{27}$ are both hydrogen or together form oxo or thioxo;

$R^3$ is phenyl substituted with —$R^{31}$ or $R^3$ is a group of Formula (c):

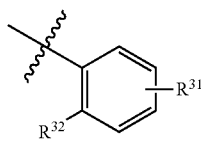

wherein $R^{31}$ is —$OR^{33}$, —$SR^{33}$ or —$CH_2R^{33}$, wherein $R^{33}$ is —$X^{12}R^{34}$, wherein rein $X^{12}$ is a bond or methylene and $R^{34}$ is five or six membered cycloalkyl or heterocycloalkyl, phenyl or five or six membered heteroaryl, and $R^{32}$ together with $R^6$ forms a bond, wherein any cyclic moiety within $R^3$ independently may be substituted with one or two ($C_{1-4}$)alkyl, halo or —$OR^{35}$, wherein $R^{35}$ is ($C_{1-4}$)alkyl;

$R^4$ is hydrogen, alkyl or as defined above; and $R^5$ is hydrogen or alkyl; and any individual stereoisomer or mixture of stereoisomers; and any pharmaceutically acceptable salts thereof.

An aspect of the invention is a compound of Formula IV:

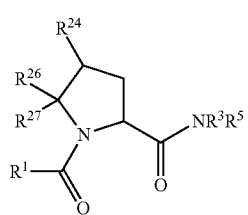

wherein:

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, —$X^1OR^7$, —$X^1C(O)OR^7$, —$X^1C(O)NR^7R^7$, —$X^1NR^7C(O)OR^7$, —$X^1OC(O)NR^7R^7$, —$X^1NR^7C(O)NR^7R^7$, —$X^1S(O)_{n1}OR^7$, —$X^1S(O)_{n1}NR^7R^7$, —$X^1NR^7S(O)_{n1}NR^7R^7$, —$X^1NR^7R^7$, —$X^1C(O)R^7$, —$X^1OC(O)R^8$, —$X^1NR^7C(O)R^8$, —$X^1S(O)_{n1}R^8$, —$X^1OS(O)_{n1}R^8$ or —$X^1NR^7S(O)_{n1}R^8$, wherein n1 is 0, 1, or 2, $X^1$ is a bond or alkylene, $R^7$ at each occurrence independently is hydrogen, ($C_{1-4}$)alkyl, alkoxy-substituted ($C_{1-4}$)alkyl or halo-substituted ($C_{1-4}$)alkyl and $R^8$ is ($C_{1-4}$)alkyl, alkoxy-substituted ($C_{1-4}$)alkyl or halo-substituted ($C_{1-4}$)alkyl, or $R^1$ is —$X^2CR^9R^9R^{11}$, —$X^2OR^{11}$, —$X^2C(O)OR^{11}$, —$X^2C(O)NR^{10}R^{11}$, —$X^2NR^{10}C(O)OR^{11}$, —$X^2OC(O)NR^{10}R^{11}$, —$X^2NR^{10}C(O)NR^{10}R^{11}$, —$X^2S(O)_{n2}OR^{11}$, —$X^2S(O)_{n2}NR^{10}R^{11}$, —$X^2NR^{10}S(O)_{n2}NR^{10}R^{11}$, —$X^2NR^{10}R^{11}$, —$X^2C(O)R^{11}$, —$X^2OC(O)R^{11}$, —$X^2NR^{10}C(O)R^{11}$, —$X^2S(O)_{n2}R^{11}$, —$X^2OS(O)_{n2}R^{11}$ or —$R^{11}$, wherein n2 is 0, 1, or 2, $X^2$ is a bond or alkylene, $R^9$ at each occurrence independently is halo, $R^{10}$ at each occurrence independently is hydrogen, ($C_{1-4}$)alkyl or halo-substituted ($C_{1-4}$)alkyl and $R^{11}$ is —$X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with —$X^4CR^{13}R^{13}R^{15}$, —$X^4OR^{15}$, —$X^4C(O)OR^{15}$, —$X^4C(O)NR^{14}R^{15}$, —$X^4NR^{14}C(O)OR^{15}$, —$X^4OC(O)NR^{14}R^{15}$, —$X^4C(O)NR^{14}R^{15}$, —$X^4S(O)_{n3}OR^{15}$, —$X^4S(O)_{n3}NR^{14}R^{15}$, —$X^4NR^{14}S(O)_{n3}NR^{14}R^{15}$, —$X^4NR^{14}R^{15}$, —$X^4C(O)R^{15}$, —$X^4OC(O)R^{15}$, —$X^4NR^{14}C(O)R^{15}$, —$X^4S(O)_{n3}R^{15}$, —$X^4OS(O)_{n3}R^{15}$ or —$R^{15}$, wherein n3 is 0, 1, or 2, $X^4$ is a bond or ($C_{1-3}$)alkylene, $R^{13}$ at each occurrence independently is halo, $R^{14}$ at each occurrence independently is hydrogen, ($C_{1-4}$)alkyl or halo-substituted ($C_{1-4}$)alkyl and $R^{15}$ is —$X^5R^{16}$ wherein $X^5$ is a bond or ($C_{1-3}$)alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from ($C_{1-4}$)alkyl, alkylidene, azido, cyano, halo, nitro, oxo, thioxo, halo-substituted ($C_{1-4}$)alkyl, nitro-substituted ($C_{1-4}$)alkyl, ($C_{2-4}$)alkenyl, —$X^6OR^{17}$, —$X^6C(O)OR^{17}$, —$X^6C(O)NR^{17}R^{17}$, —$X^6NR^{17}C(O)OR^{17}$, $X^6OC(O)NR^{17}R^{17}$, —$X^6NR^{17}C(O)NR^{17}R^{17}$, —$X^6S(O)_{n4}OR^{17}$, —$X^6S(O)_{n4}NR^{17}R^{17}$, —$X^6NR^{17}S(O)_{n4}NR^{17}R^{17}$, —$X^6NR^{17}R^{17}$, —$X^6C(O)R^{17}$, —$X^6OC(O)R^{18}$, —$X^6NR^{17}C(O)R^{18}$, —$X^6S(O)_{n4}R^{18}$, —$X^6OS(O)_{n4}R^{18}$ and —$X^6NR^{17}S(O)_{n4}R^{18}$, wherein n4 is 0, 1, or 2, $X^6$ is a bond or ($C_{1-3}$)alkylene, $R^{17}$ at each occurrence independently is hydrogen, ($C_{1-4}$)alkyl or halo-substituted ($C_{1-4}$)alkyl and $R^{18}$ is ($C_{1-4}$)alkyl or halo-substituted ($C_{1-4}$)alkyl;

$R^{24}$ is —$X^9OR^{29}$, —$X^9NR^{28}C(O)OR^{29}$, —$X^9NR^{28}R^{29}$, —$X^9C(O)OR^{29}$ or —$R^{29}$, wherein $X^9$ is a bond or ($C_{1-3}$)alkylene and $R^{28}$ is hydrogen, ($C_{1-4}$)alkyl or halo-substituted ($C_{1-4}$)alkyl and $R^{29}$ is —$X^{11}R^{30}$ wherein $X^{11}$ is a bond or ($C_{1-3}$)alkylene and $R^{30}$ is phenyl or heteroaryl, wherein $R^{30}$ may be substituted with one to three substituents independently selected from ($C_{1-4}$)alkyl, ($C_{1-4}$)alkoxy, halo and trifluoromethyl;

$R^{26}$ and $R^{27}$ are both hydrogen or together form oxo or thioxo;

$R^3$ is phenyl substituted with —$R^{31}$, wherein $R^{31}$ is —$OR^{33}$, —$SR^{33}$ or —$CH_2R^{33}$, wherein $R^{33}$ is —$^{12}R^{34}$, wherein $X^{12}$ is a bond or methylene and $R^{34}$ is five or six membered cycloalkyl or heterocycloalkyl, phenyl or five or six membered heteroaryl, wherein any cyclic moiety within $R^3$ independently may be substituted with one or two ($C_{1-4}$) alkyl, halo or —$OR^{35}$, wherein $R^{35}$ is ($C_{1-4}$)alkyl;

$R^4$ is hydrogen, alkyl or as defined above; and $R^5$ is hydrogen or alkyl; and any individual stereoisomer or mixture of stereoisomers; and any pharmaceutically acceptable salts thereof An aspect of the invention is a method for preparing a compound of Formula I, I(a), II, II(a), III, III(a), IV or IV(a), which method comprises reacting a compound of Formula V:

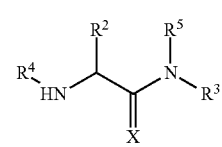

with a compound of the formula $R^1COOH$, wherein each X, $R^2$, $R^3$, $R^4$ and $R^5$ are as described for Formula I, II, III or IV, respectively, in the Summary of the Invention.

An aspect of the invention is a compound of Formula V(a)

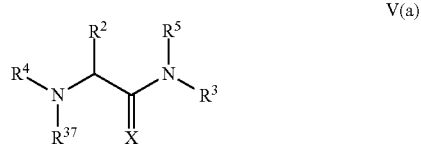

wherein R$^{37}$ is hydrogen or a nitrogen protecting group and each X, R$^1$, R$^2$, R$^3$, R$^4$ and R$^5$ are as described for Formula II in the Summary of the Invention.

An aspect of the invention is a compound of Formula V(b):

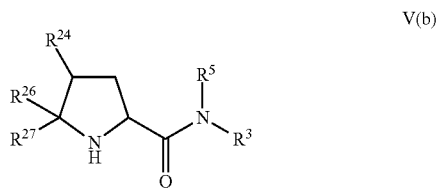

wherein each R$^3$, R$^5$, R$^{24}$, R$^{26}$ and R$^{27}$ are as described for Formula IV in the Summary of the Invention.

An aspect of the invention is a method for preparing a compound of Formula I, I(a), II, II(a), III, III(a), IV or IV(a), wherein R$^1$ is —CH$_2$R$^{12}$, were R$^{12}$ is an azolyl derivative, which method comprises reacting a compound of Formula V(c):

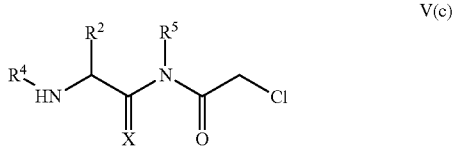

with an azole derivative, wherein L is a leaving group and each X, R$^2$, R$^3$, R$^4$ and R$^5$ are as described for Formula I, II, III or IV, respectively, in the Summary of the Invention.

An aspect of the invention is a pharmaceutical composition which contains a compound of Formula I, I(a), II, II(a), III, III(a), IV or IV(a) or an individual isomer or mixture of isomers or a pharmaceutically acceptable salt thereof in admixture with one or more suitable excipients.

An aspect of the invention is a method of treating cancer, which method comprises administering to a patient having the disease a therapeutically effective amount of a compound of Formula I, I(a), II, II(a), III, III(a), IV or IV(a) or a pharmaceutically acceptable salt thereof alone or in combination with one or more other anticancer agents.

DETAILED DESCRIPTION OF THE INVENTION

Definitions

"Acetamido" means acetylamino, i.e., the group —NHC(O)CH$_3$.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents and/or treatments (e.g., surgery, radiation, chemotherapy, and the like), "administration" and its variants are each understood to include concurrent and sequential introduction of the compound or prodrug thereof and other agents.

"Alkenyl" means a straight or branched hydrocarbon radical having from 2 to 10 carbon atoms and at least one double bond. Representative examples include vinyl, propenyl, 1-but-3-enyl, pent-3-enyl, hex-5-enyl, 4-methylhex-2-enyl, 4-methylhepta-2,5-dienyl, dimethylocta-2,5-dienyl, and the like.

"Alkoxy" means the group —OR wherein R is alkyl, as defined herein. Representative examples include methoxy, ethoxy, propoxy, butoxy, pentyloxy, hexyloxy, 4-methylhexyloxy, 4-methylheptyloxy, 4,7-dimethyloctyloxy, and the like.

"Alkoxy-substituted alkylene means alkylene substituted with 1 to 3 alkoxy groups independently selected from methoxy, ethoxy, propoxy, isopropoxy, butoxy, sec-butoxy, isobutoxy and tert-butoxy. Representative examples of alkoxy-substituted (C$_{1-4}$)alkyl include methoxymethylene, 2-methoxyethylene, ethoxyethylethylene, and the like.

"Alkyl" means a linear or branched hydrocarbon group having from 1 to 10 carbon atoms or the number of carbon atoms indicated. Representative examples for alkyl include methyl, ethyl, propyl, butyl, pentyl, hexyl, 4-methylhexyl, 4-methylheptyl, 4,7-dimethyloctyl, and the like. (C$_{1-4}$)alkyl means methyl, ethyl, propyl, isopropyl, butyl, sec-butyl, isobutyl and tert-butyl.

"Alkylene" refers to a straight or branched divalent hydrocarbon, containing no unsaturation and having from 1 to 8 carbon atoms or the number of carbon atoms indicated. Representative examples of alkylene include methylene (—CH$_2$—), methylmethylene (—CH(CH$_3$)—), ethylmethylene (—CH(CH$_2$CH$_3$)—), ethylene (—CH$_2$CH$_2$—), 2-methylethylene (—CH$_2$CH(CH$_3$)—), dimethylmethylene (—C(CH$_3$)$_2$—), 1-methylethylene (—CH(CH$_3$)CH$_2$—), trimethylene (—CH$_2$CH$_2$CH$_2$—), 2,2-dimethyltrimethylene (—CH$_2$C(CH$_3$)$_2$CH$_2$—), and the like. (C$_{1-3}$)alkylene means methylene, methylmethylene, ethylmethylene, ethylene, 2-methylethylene, 1-methylethylene and trimethylene.

"Alkynyl" means a straight or branched hydrocarbon radical having from 2 to 10 carbon atoms and at least one triple bond and includes ethynyl, propynyl, butynyl, pentyn-2-yl and the like.

"Amino" means a —NH$_2$ group.

"Aryl" means a monovalent, monocyclic or polycyclic radical having 6 to 14 ring carbon atoms. The monocyclic aryl radical is aromatic and whereas the polycyclic aryl radical may be partially saturated, at least one of the rings comprising a polycyclic radical is aromatic. The polycyclic aryl radical includes fused, bridged, and spiro ring systems. Any 1 or 2 ring carbon atoms of any nonaromatic rings comprising a polycyclic aryl radical may be replaced by a —C(O)—, —C(S)—, or —C(=NH)— group. Rx is hydrogen, alkyl, hydroxy, alkoxy, acyl, or alkylsulfonyl. Unless stated otherwise, the valency may be located on any atom of any ring of the aryl group, valency rules permitting. Representative examples include phenyl, naphthyl, indanyl, and the like.

"Azole derivative" means a class of five-membered nitrogen ring compounds which may contain other heteroatoms, e.g., nitrogen, sulfur or oxygen. Suitable azole compounds include pyrrole, pyrazole, imidazole, triazole, tetrazole, pentazole, oxazole, isooxazole, thiazole and isothiazole. An azole derivative may be substituted with one to three groups independently selected from (C$_{1-4}$)alkyl, alkylidene, azido, cyano, halo, nitro, oxo, thioxo, halo-substituted (C$_{1-4}$)alkyl, nitro-substituted $(C_{1-4})$alkyl, $(C_{2-4})$ alkenyl, —$X^6OR^{17}$, —$X^6C(O)OR^{17}$, —$X^6C(O)NR^{17}R^{17}$, —$X^6NR^{17}C(O)R^{17}$, —$X^6OC(O)NR^{17}R^{17}$, —$X^6NR^{17}C(O)NR^{17}R^{17}$, —$X^6S(O)_{n4}OR^{17}$, —$X^6S(O)_{n4}NR^{17}R^{17}$, —$X^6NR^{17}S(O)_{n4}NR^{17}R^{17}$, —$X^6NR^{17}R^{17}$, —$X^6C(O)R^{17}$, —$X^6OC(O)R^{18}$, —$X^6NR^{17}C(O)R^{18}$, —$X^6S(O)_{n4}R^{18}$, —$X^6OS(O)_{n4}R^{18}$ and —$X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl.

"Azolyl derivative" means a class of five-membered nitrogen ring moieties which contain other heteroatoms, e.g., nitrogen, sulfur or oxygen. Suitable azolyl compounds include pyrrolyl, pyrazolyl, imidazolyl, triazolyl, tetrazolyl, pentazolyl, oxazolyl, isooxazolyl, thiazolyl and isothiazolyl. An azolyl derivative may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, —$X^6OR^{17}$, —$X^6C(O)OR^{17}$, —$X^6C(O)NR^{17}R^{17}$, —$X^6NR^{17}C(O)OR^{17}$, —$X^6OC(O)NR^{17}R^{17}$, —$X^6NR^{17}C(O)NR^{17}R^{17}$, —$X^6S(O)_{n4}OR^{17}$, —$X^6S(O)_{n4}NR^{17}R^{17}$, —$X^6NR^{17}S(O)_{n4}NR^{17}R^{17}$, —$X^6NR^{17}R^{17}$, —$X^6C(O)R^{17}$, —$X^6OC(O)R^{18}$, —$X^6NR^{17}C(O)R^{18}$, —$X^6S(O)_{n4}R^{18}$, —$X^6OS(O)_{n4}R^{18}$ and —$X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is 1 $(C_{1-4})$alkyl or halo-substituted $(C_{1-4})$alkyl.

"Carbamoyl" means aminocarbonyl, i.e., —$C(O)NH_2$ group.

"Carboxy-substituted alkyl" means an alkyl group, as defined herein, substituted with one, two, or three —$C(O)OH$ groups.

"Cyano" means a —CN group.

"Cyano-substituted alkyl" or "cyano-substituted alkenyl" or means an alkyl or alkenyl radical, as defined herein, substituted with at least one, for example one, two or three, cyano groups.

"Cycloalkyl" means a monocyclic or polycyclic hydrocarbon radical having 3 to 13 carbon ring atoms. The cycloalkyl radical may be saturated or partially unsaturated, but cannot contain an aromatic ring. The cycloalkyl radical includes fused, bridged and spiro ring systems. Examples of such radicals include cyclopropyl, cyclobutyl, cyclopentyl and cyclohexyl.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e., saturated ring structures) can contain two substitution groups.

"Halo" means a fluoro, chloro, bromo or iodo group.

"Halo-substituted alkyl" or "halo-substituted alkenyl" means an alkyl or alkenyl radical, as defined herein, substituted with one or more halo atoms. For example, halo-substituted $(C_{1-4})$alkyl includes trifluoromethyl, 2,2-dichloroethyl, 2,2,2-trifluoroethyl, perchloroethyl, 2-bromopropyl, and the like.

"Heteroaryl" means a monovalent monocyclic or polycyclic radical having 5 to 14 ring atoms of which one or more of the ring atoms, for example one, two, three, or four ring atoms, are heteroatoms independently selected from —O—, —$S(O)_n$— (n is 0, 1, or 2), —N—, —$N(R^x)$—, and the remaining ring atoms are carbon atoms, The monocyclic heteroaryl radical is aromatic and whereas the polycyclic heteroaryl radical may be partially saturated, at least one of the rings comprising a polycyclic radical is aromatic. The polycyclic heteroaryl radical includes fused, bridged and spiro ring systems. Any 1 or 2 ring carbon atoms of any nonaromatic rings comprising a polycyclic heteroaryl radical may be replaced by a —C(O)—, —C(S)—, or —C(=NH)— group. Rx is hydrogen, alkyl, hydroxy, alkoxy, acyl, or alkylsulfonyl. Unless stated otherwise, the valency may be located on any atom of any ring of the heteroaryl group, valency rules permitting. In particular, when the point of valency is located on the nitrogen, Rx is absent. More specifically, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl, 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl, tetrahydroisoquinolin-6-yl, and the like), 2,3,3a,7a-tetrahydro-1H-isoindolyl, pyrrolo[3,2-c]pyridinyl (including, for example, pyrrolo[3,2-c]pyridin-2-yl, pyrrolo[3,2-c]pyridin-7-yl, and the like), benzopyranyl, thiazolyl, isothiazolyl, thiadiazolyl, benzothiazolyl, benzothienyl, and the N-oxide derivatives thereof.

"Heterocycloalkyl" means a monovalent, monocyclic or polycyclic hydrocarbon radical having 3 to 13 ring atoms of which one or more of the ring atoms, for example 1, 2, 3 or 4 ring atoms, are heteroatoms independently selected from —O—, —$S(O)_n$— (n is 0, 1, or 2), —N= and —$N(R^y)$— (where $R^y$ is hydrogen, alkyl, hydroxy, alkoxy, acyl or alkylsulfonyl, as defined herein), and the remaining ring atoms are carbon. The heterocycloalkyl radical may be saturated or partially unsaturated, but cannot contain an aromatic ring. The heterocycloalkyl radical includes fused, bridged and spiro ring systems. Any 1 or 2 ring carbon atoms independently may be replaced by a —C(O)—, —C(S)—, or —C(=NH)— group. Unless otherwise stated, the valency of the group may be located on any atom of any ring within the radical, valency rules permitting. In particular, when the point of valency is located on a nitrogen atom, $R^y$ is absent. More specifically the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 1,4-dioxa-8-azaspiro[4.5]decan-8-yl and tetrahydropyranyl, and the N-oxide derivatives thereof.

"Hydroxy-substituted alkylene" means an alkylene radical, as defined herein, substituted with at least one, for example one, two, or three, hydroxy group(s), provided that if two hydroxy groups are present they are not both on the same carbon atom. Representative examples include, but are not limited to, hydroxymethylene, 2-hydroxyethylene, 2-hydroxytrimethylene, 3-hydroxytrimethylene, 1-(hydroxymethyl)-2-methyltrimethylene, 2-hydroxytetramethylene, 3-hydroxytetramethyene, 4-hydroxytetramethylene, 2,3-dihydroxytrimethylene, 1-(hydroxymethyl)-2-hydroxyethylene, 2,3-dihydroxytetramethylene, 3,4-dihydroxytetramethylene, 2-(hydroxymethyl)-3-hydroxytrimethylene, 2-hydroxyethylene, 2,3-dihydroxytrimethylene, 1-(hydroxymethyl)-2-hydroxyethylene, and the like.

"Nitro" means a —NO$_2$ group.

"Nitro-substituted alkyl" or "nitro-substituted alkenyl" means an alkyl or alkenyl radical, as defined herein, means an alkylene radical, as defined herein, substituted with at least one, for example one, two, or three, nitro group(s), provided that if two nitro groups are present they are not both on the same carbon atom.

The term "may be substituted" means the substitution may or may not occur and includes instances where said substitution occurs and instances in which it does not. One of ordinary skill in the art would understand that with respect to any molecule described as containing one or more substituents, only sterically practical and/or synthetically feasible compounds are meant to be included.

"Propanamido" means propionylamino, i.e., —NHC(O)CH$_2$CH$_3$.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane and 1,2,3,4,4a,5,8,8a-octahydro-naphthalene are all included in the class "saturated bridged ring system."

"Spiro ring" refers to a ring originating from a particular annular carbon of another ring. For example, as depicted below:

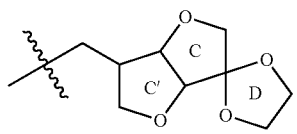

a ring atom of a saturated bridged ring system (rings C and C'), but not a bridgehead atom, can be a shared atom between the saturated bridged ring system and a spiro ring (ring D) attached thereto. A representative example of a spiro ring system is 2,3-dioxa-8-azaspiro[4.5]decan-8-yl.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry," 3rd edition, March, Jerry, John Wiley & Sons, New York, 1985). The names and illustration used in this application to describe compounds of the invention, unless indicated otherwise, are meant to be encompassed all possible stereoisomers and any mixture, racemic or otherwise, thereof.

The compounds described herein, as well as their corresponding metabolites, pharmaceutically acceptable salts, esters, prodrugs, solvates, hydrates or other derivatives thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine and chloride, such as $^2$H (deuterium), $^3$H (tritium), $^{13}$C, $^{14}$C, $^{15}$N, $^{18}$O, $^{17}$O, $^{31}$P, $^{32}$P, $^{35}$S, $^{18}$F and $^{36}$Cl, respectively. Isotopically labeled compounds of the present invention, as well as pharmaceutically acceptable salts, esters, prodrugs, solvates, hydrates or other derivatives thereof, generally can be prepared by carrying out the procedures disclosed in the Schemes and/or in the Examples and Preparations below, by substituting a readily available isotopically labeled reagent for a non-isotopically labeled reagent.

In the compounds of the invention, unless otherwise stated, any atom not specifically designated as a particular isotope is meant to represent any stable isotope of that atom at its natural abundance. When a position is designated as "H" or "hydrogen", the position is to be understood to have hydrogen at its natural abundance isotopic composition, with the understanding that some variation of natural isotopic abundance occurs in a synthesized compound depending upon the origin of chemical materials used in the synthesis. When a particular position is designated as "D" or "deuterium", it is to be understood that the abundance of deuterium at that position is substantially greater than the natural abundance of deuterium, which is 0.015%, and typically has at least 50% deuterium incorporation at that position.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements).

Moreover, certain isotopically-labeled compounds, for example those into which radioactive isotopes such as $^3$H and $^{14}$C are incorporated, are useful in drug and/or substrate tissue distribution assays such as positron emission tomography (PET). Tritiated, ($^3$H) and carbon-14 ($^{14}$C) isotopes are useful for these embodiments because of their detectability.

The present invention also includes N-oxide derivatives of the compounds of the invention. N-oxide derivatives mean derivatives of compounds of the invention in which nitrogens are in an oxidized state (i.e., N→O), e.g., pyridine N-oxide, and which possess the desired pharmacological activity.

"Cancer" refers to any cellular-proliferative disease state, including but not limited to lung cancer, Karposi's sarcoma, ovarian cancer and breast cancer. Thus, the term "cancerous cell" as provided herein, includes a cell afflicted by any one of the above-identified conditions.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see goodman and gilman, "The Pharmacological Basis of Therapeutics" 8.sup.th Ed., Pergamon Press, gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences,* 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference. It is also understood that the compound can have one or more pharmaceutically acceptable salts associated with it.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium and magnesium salts. Salts derived from pharmaceutically acceptable organic non-toxic bases include, but are not limited to, salts of primary, secondary and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Aommon examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" is an amount of a compound of the invention, that when administered to a patient, effectively treats the disease. The amount of a compound of the invention which constitutes a "therapeutically effective amount" will vary depending upon a sundry of factors including the activity, metabolic stability, rate of excretion and duration of action of the compound, the age, weight, general health, sex, diet and species of the patient, the mode and time of administration of the compound, the concurrent administration of adjuvants or additional therapies and the severity of the disease for which the therapeutic effect is sought. The therapeutically effective amount for a given circumstance can be determined without undue experimentation.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, the age, weight, general health, sex, diet and species of the patient, the mode and time of administration of the compound, the concurrent administration of adjuvants or additional therapeutically active ingredients and the severity of the disease for which the therapeutic effect is sought may be necessary, and will be ascertainable with routine experimentation.

Other Aspects of the Invention:

An aspect of the invention is a compound of Formula I wherein:

X is O or $NR^6$;

$R^1$ is alkyl, alkenyl, halo-substituted alkyl, nitro-substituted alkyl, cyano-substituted alkyl, $-X^1OR^7$, $-X^1C(O)OR^7$, $-X^1C(O)NR^7R^7$, $-X^1NR^7R^7$, $-X^1C(O)R^7$, $-X^1S(O)_{n1}R^8$ or $-X^1OC(O)R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $X^2NR^{10}R^{11}$, $-X^2OR^{11}$, $-X^2C(O)R^{11}$, $-X^2NR^{10}C(O)R^{11}$ — or $-R^{11}$, wherein $X^2$ is a bond or alkylene, $R^{10}$ is hydrogen, alkyl or halo-substituted alkyl and $R^{11}$ is $-X^3R^{12}$ wherein $X^3$ is a bond, alkylene or hydroxy-substituted alkylene and $R^{12}$ is cycloalkyl, aryl, heterocycloalkyl or heteroaryl, wherein $R^{12}$ may be substituted with $-X^4C(O)R^{15}$ or $-R^{15}$, wherein $X^4$ is a bond or $(C_{1-3})$alkylene and $R^{15}$ is $-X^5R^{16}$, wherein $X^5$ is a bond or $(C_{1-3})$alkylene and $R^{16}$ is cycloalkyl, aryl, heterocycloalkyl or heteroaryl, wherein any cycloalkyl, aryl, heterocycloalkyl or heteroaryl within $R^1$ independently may be substituted with one to three groups independently selected from $(C_{1-3})$alkyl, halo, nitro, halo-substituted $(C_{1-3})$alkyl, $-X^6OR^{17}$, $-X^6C(O)OR^{17}$, $-X^6NR^{17}R^{17}$, $-X^6C(O)R^{17}$, $-X^6C(O)NR^{17}R^{17}$, $-X^6OC(O)R^{18}$ and $-X^6S(O)_{n4}R^{18}$, wherein $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl;

$R^2$ is $-X^7NHC(O)R^{19}$, $-X^7NR^{20}C(O)OR^{22}$, $-X^7OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

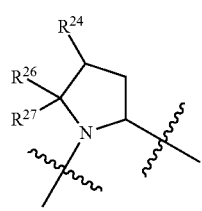

(a)

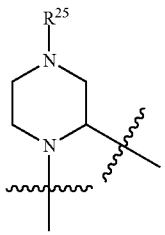

(b)

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}NR^{28}C(O)OR^{29}$, $-X^{10}NR^{28}R^{29}$, $-X^9C(O)OR^{29}$ or $-R^{29}$ wherein $X^9$ is a bond or $(C_{1-3})$alkylene, $X^{10}$ is $(C_{1-3})$alkylene and $R^{28}$ is hydrogen, $(C_{1-4})$alkyl or halo substituted $(C_{1-4})$alkyl and $R^{29}$ is $-X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo;

$R^3$ is phenyl substituted with $-R^{31}$ or $R^3$ is a group of Formula (c):

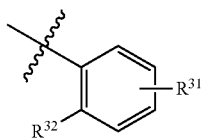

(c)

wherein $R^{31}$ is $-OR^{33}$, $-SR^{33}$ or $-CH_2R^{33}$, wherein $R^{33}$ — $X^{12}R^{34}$ wherein $X^{12}$ is a bond or methylene and $R^{34}$ is five or six membered cycloalkyl or heterocycloalkyl, phenyl or five or six membered heteroaryl, and $R^{32}$ together with $R^6$ forms a bond, wherein any cyclic moiety within $R^3$ independently may be substituted with one or two $(C_{1-4})$alkyl, halo or $-OR^{35}$, wherein $R^{35}$ is $(C_{1-4})$alkyl;

$R^4$ is hydrogen, alkyl or as defined above; and $R^5$ is hydrogen or alkyl; and any individual stereoisomer or mixture of stereoisomers; and any pharmaceutically acceptable salts thereof.

An aspect of the invention is a compound of Formula I, as defined immediately above, provided that $R^3$ is not 4-phenoxyphenyl when X is O and $R^2$ is benzyloxymethyl; and any pharmaceutically acceptable salts thereof. An aspect of the invention is a compound of Formula I(a):

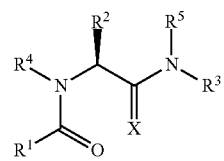

wherein X, $R^1$, $R^2$, $R^3$, $R^4$ and $R^5$ are as defined in the Summary of the Invention or in any other aspect of the invention for a compound of Formula I; and any individual stereoisomer or mixture of stereoisomers; and any pharmaceutically acceptable salts thereof.

An aspect of the invention is a compound of Formula II wherein:

$R^1$ is alkyl, alkenyl, halo-substituted alkyl, nitro-substituted alkyl, cyano-substituted alkyl, $-X^1OR^7$, $-X^1C(O)OR^7$, $-X^1C(O)NR^7R^7$, $-X^1NR^7R^7$, $-X^1C(O)R^7$, $-X^1S(O)_{n1}R^8$ or $-X^1OC(O)R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $-X^2NR^{10}R^{11}$, $-X^2OR^{11}$, $-X^2C(O)R^{11}$, $-X^2NR^{10}C(O)R^{11}$ or $-R^{11}$, wherein $X^2$ is a bond or alkylene, $R^{10}$ is hydrogen, alkyl or halo-substituted alkyl and $R^{11}$ is $-X^3R^{12}$ wherein $X^3$ is a bond, alkylene or hydroxy-substituted alkylene and $R^{12}$ is cycloalkyl, aryl, heterocycloalkyl or heteroaryl, wherein $R^{12}$ may be substituted with $-X^4C(O)R^{15}$ or $-R^{15}$, wherein $X^4$ is a bond or $(C_{1-3})$alkylene and $R^{15}$ is $-X^5R^{16}$, wherein $X^5$ is a bond or $(C_{1-3})$alkylene and $R^{16}$ is cycloalkyl, aryl, heterocycloalkyl or heteroaryl, wherein any cycloalkyl, aryl, heterocycloalkyl or heteroaryl within $R^1$ independently may be substituted with one to three groups independently selected from $(C_{1-3})$alkyl, halo, nitro, halo-substituted $(C_{1-3})$alkyl, $-X^6OR^{17}$, $-X^6C(O)OR^{17}$, $-X^6NR^{17}R^{17}$, $-X^6C(O)R^{17}$, $-X^6C(O)NR^{17}R^{17}$, $-X^6OC(O)R^{18}$ and $-X^6S(O)_{n4}R^{18}$, wherein $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl;

$R^2$ is $-X^7NHC(O)R^{19}$, $-X^7NR^{20}C(O)OR^{22}$, $-X^7OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

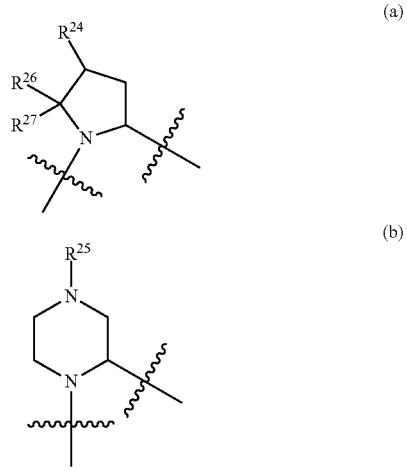

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}R^{28}C(O)OR^{29}$, $-X^{10}NR^{28}R^{29}$, $-X^9C(O)OR^{29}$ or $-R^{29}$ wherein $X^9$ is a bond or $(C_{1-3})$alkylene, $X^{10}$ is $(C_{1-3})$alkylene and $R^{28}$ is hydrogen, $(C_{1-4})$alkyl or halo-substituted $(C_{1-4})$alkyl and $R^{29}$ is $-X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo;

$R^3$ is phenyl substituted with $-R^{31}$ wherein $R^{31}$ is $-OR^{33}$, $-SR^{33}$ or $-CH_2R^{33}$, wherein $R^{33}$ is $-X^{12}R^{34}$, wherein $X^{12}$ is a bond or methylene and $R^{34}$ is five or six membered cycloalkyl or heterocycloalkyl, phenyl or five or six membered heteroaryl, wherein any cyclic moiety within $R^3$ independently may be substituted with one or two $(C_{1-4})$alkyl, halo or $-OR^{35}$, wherein $R^{35}$ is $(C_{1-4})$alkyl.

$R^4$ is hydrogen, alkyl or as defined above; and $R^5$ is hydrogen or alkyl; and any individual stereoisomer or mixture of stereoisomers; and any pharmaceutically acceptable salts thereof.

An aspect of the invention is a compound of Formula II, as defined immediately above, provided that $R^3$ is not 4-phenoxyphenyl when X is O and $R^2$ is benzyloxymethyl; and any pharmaceutically acceptable salts thereof.

An aspect of the invention is a compound of Formula II(a):

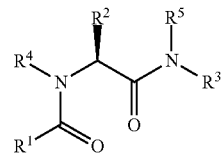

wherein $R^1$, $R^2$, $R^3$, $R^4$ and $R^5$ are as defined in the Summary of the Invention or in any other aspect of the invention for a compound of Formula II; and any individual stereoisomer or mixture of stereoisomers; and any pharmaceutically acceptable salts thereof.

An aspect of the invention is a compound of Formula III wherein:

X is O or $NR^6$;

$R^{36}$ is 1-(4-chlorobenzyl)-5-oxopyrrolidin-3-yl, 2-fluorobenzyl, 1H-imidazol-4-ylmethyl, 1H-indol-4-yl, 2-methylthiopyrid-3-yl, 1R-hydroxy-2-phenylethyl, 2-hydroxyphenoxymethyl, 1S-acetyloxyethyl, (R)-2-chlorophenyl(hydroxy)methyl, tetrahydrofur-2R-yl, 3-methyloxazol-5-yl, 2,2,2-trifluoroethyl, 2-cyclopropylcarbonylethyl, 2-bromo-5-fluorophenyl, indol-4-yl, indol-5-yl, indol-6-yl, indan-2-yl, 3-methyl-2-nitrophenyl, methylsulphonylmethyl, 5-methylpyrid-3-yl, 4-acetyloxyphenyl, 3-hydroxyphenyl(hydroxyl)methyl, 5-(2,5-dioxo-2,5-dihydro-1H-pyrrol-1-yl)pentyl, fur-2-ylcarbonyl, 2R-methyl-2-phenylethyl, 3-chloro-2-fluorobenzyl, 5-chloro-2-fluorobenzyl, 3-chloro-2-fluorobenzyl, 1-acetylpyrrolidin-2-yl, N-benzoyl-N-methylaminomethyl, 1H-imdazol-4-ylmethyl, 1H-tetrazol-1-ylmethyl, 1-methylimidazol-4-yl, 2-fluorobenzyl, 1H-1,2,4-triazol-1-ylmethyl, thien-2-ylmethyl, 2,5-dichlorobenzyl, ((1-methyl-1H-benzo[d]imidazol-2-yl)methylamino)methyl or 2,5-dioxoimidazolidin-4-ylmethyl;

$R^2$ is $-X^7NHC(O)R^{19}$, $-X^7NR^{20}C(O)OR^{22}$, $-X^7OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

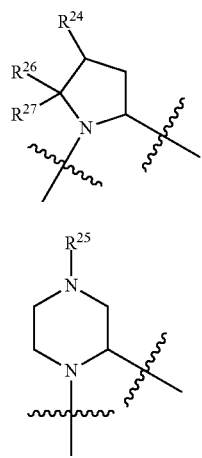

(a)

(b)

wherein R²⁴ is —X⁹OR²⁹, —X⁹NR²⁸C(O)OR²⁹, —X⁹NR²⁸R²⁹, —X⁹C(O)OR²⁹ or —R²⁹ and R²⁵ is —X¹⁰OR²⁹, —X¹⁰NR²⁸C(O)OR²⁹, —X¹⁰NR²⁸R²⁹, —X⁹C(O)OR²⁹ or —R²⁹ wherein X⁹ is a bond or ($C_{1-3}$)alkylene, X¹⁰ is ($C_{1-3}$)alkylene and R²⁸ is hydrogen, ($C_{1-4}$)alkyl or halo-substituted ($C_{1-4}$)alkyl and R²⁹ is —X¹¹R³⁰ wherein X¹¹ is a bond or ($C_{1-3}$)alkylene and R³⁰ is phenyl or heteroaryl, wherein R³⁰ may be substituted with one to three substituents independently selected from ($C_{1-4}$)alkyl, ($C_{1-4}$)alkoxy, halo and trifluoromethyl, and R²⁶ and R²⁷ are both hydrogen or together form oxo;

R³ is phenyl substituted with —R³¹ or R³ is a group of Formula (c):

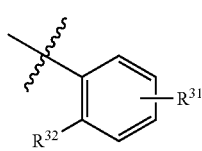

(c)

wherein R³¹ is —OR³³, —SR³³ or —CH₂R³³, wherein R³³ is —X¹²R³⁴, wherein X¹² is a bond or methylene and R³⁴ is five or six membered cycloalkyl or heterocycloalkyl, phenyl or five or six membered heteroaryl, and R³² together with R⁶ forms a bond, wherein any cyclic moiety within R³ independently may be substituted with one or two ($C_{1-4}$)alkyl, halo or —OR³⁵, wherein R³⁵ is ($C_{1-4}$)alkyl;

R⁴ is hydrogen, alkyl or as defined above; and

R⁵ is hydrogen or alkyl; and any individual stereoisomer or mixture of stereoisomers; and any pharmaceutically acceptable salts thereof.

An aspect of the invention is a compound of Formula III(a):

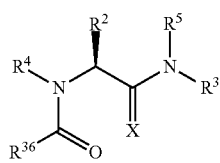

wherein X, R², R³, R⁴, R⁵ and R³⁶ are as defined in the Summary of the Invention or in any other aspect of the invention for a compound of Formula II; and any individual stereoisomer or mixture of stereoisomers; and any pharmaceutically acceptable salts thereof.

An aspect of the invention is a compound of Formula IV wherein:

R¹ is alkyl, alkenyl, halo-substituted alkyl, halo-substituted alkenyl, nitro-substituted alkyl, nitro-substituted alkenyl, cyano-substituted alkyl, cyano-substituted alkenyl, —X¹OR⁷, —X¹C(O)OR⁷, —X¹C(O)NR⁷R⁷, —X¹NR⁷C(O)OR⁷, —X¹OC(O)NR⁷R⁷, —X¹NR⁷C(O)NR⁷R⁷, —X¹S(O)$_{n1}$OR⁷, —X¹S(O)$_{n1}$NR⁷R⁷, —X¹NR⁷S(O)$_{n1}$NR⁷R⁷, —X¹NR⁷R⁷, —X¹C(O)R⁷, —X¹OC(O)R⁸, —X¹NR⁷C(O)R⁸, —X¹S(O)$_{n1}$R⁸, —X¹OS(O)$_{n1}$R⁸ or —X¹NR⁷S(O)$_{n1}$R⁸, wherein n1 is 0, 1, or 2, X¹ is a bond or alkylene, R⁷ at each occurrence independently is hydrogen, ($C_{1-4}$)alkyl, alkoxy-substituted ($C_{1-4}$)alkyl or halo-substituted ($C_{1-4}$)alkyl and R⁸ is ($C_{1-4}$)alkyl, alkoxy-substituted ($C_{1-4}$)alkyl or halo-substituted ($C_{1-4}$)alkyl, or R¹ is —X²CR⁹R⁹R¹¹, —X²OR¹¹, —X²C(O)OR¹¹, —X²C(O)NR¹⁰R¹¹, —X²NR¹⁰C(O)OR¹¹, —X²OC(O)NR¹⁰R¹¹, —X²NR¹⁰C(O)NR¹⁰R¹¹, —X²S(O)$_{n2}$OR¹¹, —X²S(O)$_{n2}$NR¹⁰R¹¹, —X²NR¹⁰S(O)$_{n2}$NR¹⁰R¹¹, —X²NR¹⁰R¹¹, —X²C(O)R¹¹, —X²OC(O)R¹¹, —X²NR⁹C(O)R¹¹, —X²S(O)$_{n2}$R¹¹, —X²OS(O)$_{n2}$R¹¹ or —R¹¹, wherein n2 is 0, 1, or 2, X² is a bond or alkylene, R⁹ at each occurrence independently is halo, R¹⁰ at each occurrence independently is hydrogen, ($C_{1-4}$)alkyl or halo-substituted ($C_{1-4}$)alkyl and R¹¹ is —X³R¹², wherein X³ is a bond, alkylene or hydroxy-substituted alkylene and R¹² is cycloalkyl, aryl, heterocycloalkyl or heteroaryl, wherein:

any cycloalkyl, aryl, heterocycloalkyl or heteroaryl group within R¹ independently may be substituted with one to three groups independently selected from ($C_{1-4}$)alkyl, alkylidene, azido, cyano, halo, nitro, oxo, thioxo, halo-substituted ($C_{1-4}$)alkyl, nitro-substituted ($C_{1-4}$)alkyl, ($C_{2-4}$) alkenyl, —X⁶OR¹⁷, —X⁶C(O)OR¹⁷, —X⁶C(O)NR¹⁷R¹⁷, —X⁶NR¹⁷C(O)OR¹⁷, —X⁶OC(O)NR¹⁷R¹⁷, —X⁶NR¹⁷C(O)NR¹⁷R¹⁷, —X⁶S(O)$_{n4}$OR¹⁷, —X⁶S(O)$_{n4}$NR¹⁷R¹⁷, —X⁶NR¹⁷S(O)$_{n4}$NR¹⁷R¹⁷, —X⁶NR¹⁷R¹⁷, —X⁶C(O)R¹⁷, —X⁶OC(O)R¹⁸, —X⁶NR¹⁷C(O)R¹⁸, —X⁶S(O)$_{n4}$R¹⁸, —X⁶OS(O)$_{n4}$R¹⁸ and —X⁶NR¹⁷S(O)$_{n4}$R¹⁸, wherein n4 is 0, 1, or 2, X⁶ is a bond or ($C_{1-3}$)alkylene, R¹⁷ at each occurrence independently is hydrogen, ($C_{1-4}$)alkyl or halo-substituted ($C_{1-4}$)alkyl and R¹⁸ is ($C_{1-4}$)alkyl or halo-substituted ($C_{1-4}$) alkyl;

R²⁴ is —X¹¹R³⁰, wherein X¹¹ is methylene, and R³⁰ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl;

R²⁶ and R²⁷ are both hydrogen;

R³ is 4-(4-fluorophenoxy)phenyl, wherein any cyclic moiety within R³ independently may be substituted with one or two ($C_{1-4}$)alkyl, halo or —OR³⁵, wherein R³⁵ is ($C_{1-4}$)alkyl; and R⁵ is hydrogen; and any individual stereoisomer or mixture of stereoisomers; and any pharmaceutically acceptable salts thereof.

An aspect of the invention is a compound of Formula IV wherein:

R¹ is alkyl, alkenyl, halo-substituted alkyl, nitro-substituted alkyl, cyano-substituted alkyl, —X¹OR⁷, —X¹C(O)OR⁷, —X¹C(O)NR⁷R⁷, —X¹NR⁷R⁷, —X¹C(O)R⁷, —X¹S(O)$_{n1}$R⁸ or —X¹OC(O)R⁸, wherein n1 is 0, 1, or 2, X¹ is a bond or alkylene, R⁷ at each occurrence independently is hydrogen, ($C_{1-4}$)alkyl, alkoxy-substituted ($C_{1-4}$)alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $-X^2NR^{10}R^{11}$, $-X^2OR^{11}$, $-X^2C(O)R^{11}$, $-X^2NR^{10}C(O)R^{11}$ or $-R^{11}$, wherein $X^2$ is a bond or alkylene, $R^{10}$ is hydrogen, alkyl or halo-substituted alkyl and $R^{11}$ is $-X^3R^{12}$ wherein $X^3$ is a bond, alkylene or hydroxy-substituted alkylene and $R^{12}$ is cycloalkyl, aryl, heterocycloalkyl or heteroaryl, wherein any cycloalkyl, aryl, heterocycloalkyl or heteroaryl within $R^1$ independently may be substituted with one to three groups independently selected from $(C_{1-3})$ alkyl, halo, nitro, halo-substituted $(C_{1-3})$alkyl, $-X^6OR^{17}$, $-X^6C(O)OR^{17}$, $-X^6NR^{17}R^{17}$, $-X^6C(O)R^{17}$, $-X^6C(O)$ $NR^{17}R^{17}$, $-X^6OC(O)R^{18}$ and $-X^6S(O)_{n4}R^{18}$, wherein $X^6$ is a bond or $(C_{1-3})$alkylene, $R^{17}$ at each occurrence independently is hydrogen, $(C_{1-4})$alkyl or halo-substituted $(C_{1-4})$ alkyl and $R^{18}$ is $(C_{1-4})$alkyl or halo-substituted $(C_{1-4})$alkyl;

$R^{24}$ is $-X^{11}R^{30}$, wherein $X^{11}$ is methylene, and $R^{30}$ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl;

$R^{26}$ and $R^{27}$ are both hydrogen;

$R^3$ is 4-(4-fluorophenoxy)phenyl, wherein any cyclic moiety within $R^3$ independently may be substituted with one or two $(C_{1-4})$alkyl, halo or $-OR^{35}$, wherein $R^{35}$ is $(C_{1-4})$alkyl; and $R^5$ is hydrogen; and any individual stereoisomer or mixture of stereoisomers; and any pharmaceutically acceptable salts thereof.

An aspect of the invention is a compound of Formula IV(a):

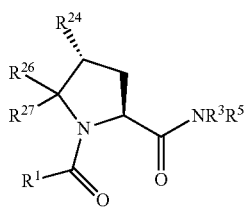

IV(a)

wherein $R^1$, $R^2$, $R^3$, $R^4$ and $R^5$ are as defined in the Summary of the Invention or in any other aspect of the invention for a compound of Formula IV; and any pharmaceutically acceptable salts thereof.

An aspect of the invention is a compound of Formula IV(a):

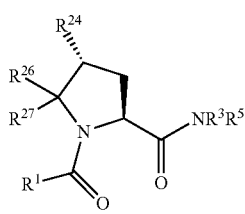

IV(a)

wherein $R^1$ is five-membered heteroaryl, $R^3$ is 4-(4-fluorophenoxy)phenyl, $R^5$ is hydrogen, $R^{24}$ is $-X^{11}R^{30}$, wherein $X^{11}$ is methylene, and $R^{30}$ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl; and $R^{26}$ and $R^{27}$ are both hydrogen; and any pharmaceutically acceptable salts thereof.

An aspect of the invention is a compound of Formula IV(a) wherein $R^1$ is 2H-1,2,3-triazol-2-ylmethyl, 1H-1,2,4-triazol-1-ylmethyl or 1H-1,2,3-triazol-1-yl; $R^3$ is 4-(4-fluorophenoxy)phenyl, $R^5$ is hydrogen, $R^{24}$ is $-X^{11}R^{30}$, wherein $X^{11}$ is methylene, and $R^{30}$ is phenyl or thienyl, wherein the phenyl may be substituted with one or two substituents independently selected from chloro, fluoro, methoxy, methyl and trifluoromethyl and the thienyl may be substituted with one substituent selected from bromo, chloro and fluoro and $R^{26}$ and $R^{27}$ are both hydrogen; and any pharmaceutically acceptable salts thereof.

An aspect of the invention is a compound selected from the group consisting of: (2S,4R)-1-(2-(1H-1,2,4-triazol-1-yl) acetyl)-4-benzyl-N-(4-(4-fluorophenoxy)phenyl)pyrrolidine-2-carboxamide; (2S,4R)-1-(2-(1H-1,2,4-triazol-1-yl) acetyl)-4-(4-fluorobenzyl)-N-(4-(4-fluorophenoxy)phenyl) pyrrolidine-2-carboxamide; (2S,4R)-1-(2-(1H-1,2,4-triazol-1-yl)acetyl)-4-(2-chlorobenzyl)-N-(4-(4-fluorophenoxy) phenyl)pyrrolidine-2-carboxamide; (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide; (2S,4R)-1-(2-(1H-1,2,3-triazol-1-yl)acetyl)-4-benzyl-N-(4-(4-fluorophenoxy)phenyl)pyrrolidine-2-carboxamide; (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide; (2S,4R)-1-(2-(1H-1,2,4-triazol-1-yl)acetyl)-N-(4-(4-fluorophenoxy)phenyl)-4-(2-methylbenzyl)pyrrolidine-2-carboxamide; (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide; (2S,4R)-1-(2-(1H-1,2,4-triazol-1-yl)acetyl)-N-(4-(4-fluorophenoxy)phenyl)-4-(2-(trifluoromethyl) benzyl)pyrrolidine-2-carboxamide; (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide; (2S,4R)-1-(2-(1H-1,2,4-triazol-1-yl)acetyl)-N-(4-(4-fluorophenoxy) phenyl)-4-(thiophen-3-ylmethyl)pyrrolidine-2-carboxamide; (2S,4R)-1-(2-(1H-1,2,4-triazol-1-yl)acetyl)-4-(2,4-difluorobenzyl)-N-(4-(4-fluorophenoxy)phenyl) pyrrolidine-2-carboxamide; (2S,4R)-1-(2-(1H-1,2,4-triazol-1-yl)acetyl)-4-(3-chlorobenzyl)-N-(4-(4-fluorophenoxy) phenyl)pyrrolidine-2-carboxamide; (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide; (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide; (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide; (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide; (2S,4R)-5-(2-(1H-1,2,4-triazol-1-yl)acetyl)-N-(4-(4-fluorophenoxy)phenyl)-4-(4-methylbenzyl) pyrrolidine-2-carboxamide; (2S,4R)-1-(2-(2H-1,2,3-triazol-2-yl)acetyl)-4-(3-fluorobenzyl)-N-(4-(4-fluorophenoxy) phenyl)pyrrolidine-2-carboxamide; (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide; (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide; (2S,4R)-1-(2-(1H-1,2,3-triazol-1-yl)acetyl)-4-(4-fluoro-2-methylbenzyl)-N-(4-(4-fluorophenoxy) phenyl)pyrrolidine-2-carboxamide; (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide; (2S,4R)-1-(2-(2H-1,2,3-triazol-2-yl)acetyl)-N-(4-(4-fluorophenoxy) phenyl)-4-(3-methoxybenzyl)pyrrolidine-2-carboxamide;

(2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide; (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide; (2S,4S)-1-(2-(2H-1,2,3-triazol-2-yl)acetyl)-N-(4-(4-fluorophenoxy)phenyl)-4-thien-2-ylmethylpyrrolidine-2-carboxamide; (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide; (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide; (2S,4R)-1-(2-(2H-1,2,3-triazol-2-yl)acetyl)-N-(4-(4-fluorophenoxy)phenyl)-4-(2-methylbenzyl)pyrrolidine-2-carboxamide; (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide; (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide; (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide; (2S,4R)-1-(2-(1H-1,2,4-triazol-1-yl)acetyl)-N-(4-(4-fluorophenoxy)phenyl)-4-(3-methylbenzyl)pyrrolidine-2-carboxamide; (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide; (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide; (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide; (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide; (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide; and (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide; and any pharmaceutically acceptable salts thereof.

An aspect of the invention is a compound of Formula I, I(a), II, II(a), IV or IV(a) wherein $R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, —$X^1OR^7$, —$X^1C(O)OR^7$, —$X^1C(O)NR^7R^7$, —$X^1NR^7C(O)R^7$, —$X^1OC(O)NR^7R^7$, —$X^1NR^7C(O)NR^7R^7$, —$X^1S(O)_{n1}OR^7$, —$X^1S(O)_{n1}NR^7R^7$, —$X^1NR^7S(O)_{n1}NR^7R^7$, —$X^1NR^7R^7$, —$X^1C(O)R^7$, —$X^1OC(O)R^8$, —$X^1NR^7C(O)R^8$, —$X^1S(O)_{n1}R^8$, —$X^1OS(O)_{n1}R^8$ or —$X^1NR^7S(O)_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is —$X^2CR^9R^9R^{11}$, —$X^2OR^{11}$, —$X^2C(O)OR^{11}$, —$X^2C(O)NR^{10}R^{11}$, —$X^2NR^{10}C(O)OR^{11}$, —$X^2OC(O)NR^{10}R^{11}$, —$X^2NR^{10}C(O)NR^{10}R^{11}$, —$X^2S(O)_{n2}OR^{11}$, —$X^2S(O)_{n2}NR^{10}R^{11}$, —$X^2NR^{10}S(O)_{n2}R^{11}$, —$X^2NR^{10}R^{11}$, —$X^2C(O)R^{11}$, —$X^2OC(O)R^{11}$, —$X^2NR^{10}C(O)R^{11}$, —$X^2S(O)_{n2}R^{11}$, —$X^2OS(O)_{n2}R^{11}$ or —$R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is —$X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with —$X^4CR^{13}R^{13}R^{15}$, —$X^4OR^{15}$, —$X^4C(O)OR^{15}$, —$X^4C(O)NR^{14}R^{15}$, —$X^4NR^{14}C(O)OR^{15}$, —$X^4OC(O)NR^{14}R^{15}$, —$X^4NR^{14}C(O)NR^{14}R^{15}$, —$X^4S(O)_{n3}OR^{15}$, —$X^4S(O)_{n3}NR^{14}R^{15}$, —$X^4NR^{14}S(O)_{n3}NR^{14}R^{15}$, —$X^4NR^{14}R^{15}$, —$X^4C(O)R^{15}$, —$X^4OC(O)R^{15}$, —$X^4NR^{14}C(O)R^{15}$, —$X^4S(O)_{n3}R^{15}$, —$X^4OS(O)_{n3}R^{15}$ or —$R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is —$X^5R^{16}$ wherein $X^5$ is a bond or $(C_{1-3})$alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, —$X^6OR^{17}$, —$X^6C(O)OR^{17}$, —$X^6C(O)NR^{17}R^{17}$, —$X^6NR^{17}C(O)OR^{17}$, —$X^6OC(O)NR^{17}R^{17}$, —$X^6NR^{17}C(O)NR^{17}R^{17}$, —$X^6S(O)_{n4}OR^{17}$, —$X^6S(O)_{n4}NR^{17}R^{17}$, —$X^6NR^{17}S(O)_{n4}NR^{17}R^{17}$, —$X^6NR^{17}R^{17}$, —$X^6C(O)R^{17}$, —$X^6OC(O)R^{18}$, —$X^6NR^{17}C(O)R^{18}$, —$X^6S(O)_{n4}R^{18}$, —$X^6OS(O)_{n4}R^{18}$ and —$X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$ alkyl.

An aspect of the invention is a compound of Formula I, I(a), II, II(a), IV or IV(a) wherein $R^1$ is alkyl, alkenyl, halo-substituted alkyl, nitro-substituted alkyl, cyano-substituted alkyl, —$X^1OR^7$, —$X^1C(O)OR^7$, —$X^1C(O)NR^7R^7$, —$X^1NR^7R^7$, —$X^1C(O)R^7$, —$X^1S(O)_{n1}R^8$ or —$X^1OC(O)R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$ alkyl, alkoxy-substituted $(C_{1-4})$alkyl or halo-substituted $(C_{1-4})$alkyl, or $R^1$ is —$X^2NR^{10}R^{11}$, —$X^2OR^{11}$, —$X^2C(O)R^{11}$, —$X^2NR^{10}C(O)R^{11}$— or —$R^{11}$, wherein $X^2$ is a bond or alkylene, $R^{10}$ is hydrogen, alkyl or halo-substituted alkyl and $R^{11}$ is —$X^3R^{12}$ wherein $X^3$ is a bond, alkylene or hydroxy-substituted alkylene and $R^{12}$ is cycloalkyl, aryl, heterocycloalkyl or heteroaryl, wherein $R^{12}$ may be substituted with —$X^4C(O)R^{15}$ or —$R^{15}$, wherein $X^4$ is a bond or $(C_{1-3})$alkylene and $R^{15}$ is —$X^5R^{16}$, wherein $X^5$ is a bond or $(C_{1-3})$alkylene and $R^{16}$ is cycloalkyl, aryl, heterocycloalkyl or heteroaryl, wherein any cycloalkyl, aryl, heterocycloalkyl or heteroaryl within $R^1$ independently may be substituted with one to three groups independently selected from $(C_{1-3})$alkyl, halo, nitro, halo-substituted $(C_{1-3})$alkyl, —$X^6OR^{17}$, —$X^6C(O)OR^{17}$, —$X^6NR^{17}R^{17}$, —$X^6C(O)R^{17}$, —$X^6C(O)NR^{17}R^{17}$, —$X^6OC(O)R^{18}$ and —$X^6S(O)_{n4}R^{18}$, wherein $X^6$ is a bond or $(C_{1-3})$alkylene, $R^{17}$ at each occurrence independently is hydrogen, $(C_{1-4})$alkyl or halo-substituted $(C_{1-4})$ alkyl and $R^{18}$ is $(C_{1-4})$alkyl or halo-substituted $(C_{1-4})$alkyl.

An aspect of the invention is a compound of Formula I, I(a), II, II(a), IV or IV(a) wherein $R^1$ is 4-morpholin-4-ylpiperidin-1-ylmethyl, 3-diethylaminopyrrolidin-1-ylmethyl, 2-methylpyrrolidin-1-ylmethyl, 4-ethylpiperazin-1-ylmethyl, 3-fluoro-4-trifluoromethylbenzyl, 3-piperidin-1-ylmethyl, 4-pyrrolidin-1-ylpiperidin-1-ylmethyl, azepan-1-ylmethyl, pent-3-enyl, 1H-imidazol-4-ylmethyl, 4-(3-methoxyphenyl)piperazin-1-ylmethyl, 4-methoxy-3-chlorophenethyl, 4-pyrimidin-2-ylpiperazin-1-ylmethyl, 4-(3-trifluoromethylpyrid-2-yl)piperazin-1-ylmethyl, 2-(1-methylpyrrolidin-2-ylmethyl)piperidin-1-ylmethyl, 4-tetrahydrofur-2-ylmethylpiperazin-1-ylmethyl, 4-methylpiperidin-1-ylmethyl, 4-isopropylpiperazin-1-ylmethyl, 4-tert-butoxycarbonylpyrrolidin-1-ylmethyl, 3-trifluoromethoxybenzyl, 4-(2-fluorophenyl)piperazin-1-ylmethyl, 4-pyrid-2-ylpiperazin-1-ylmethyl, decahydroquinolin-1-ylmethyl, 4-phenylbutryl, decahydroisoquinolin-2-ylmethyl, 3-methylbutryl, 1,4-dioxa-8-azaspiro[4.5]decan-8-ylmethyl, 3-bromobenzyl, 4-(tetrahydrofur-2-ylcarbonyl)piperazin-1-ylmethyl, 4-(4-acetylphenyl)piperazin-1-ylmethyl, 4-(2-methoxyethyl)piperazin-1-ylmethyl, 4-(4-methoxyphenyl)piperazin-1-ylmethyl, 4-(2-methoxyphenyl)piperazin-1-ylmethyl, 4-benzylpiperidin-1-ylmethyl, indol-4-yl, 2,4-chlorobenzyl, isoindolin-2-ylmethyl, pyrrolidin-1-ylmethyl, 4-acetylpiperazin-1-yl, thiazolidin-3-yl, 4-(4-fluorophenyl)piperazin-1-ylmethyl, benzyl, 4-(2-ethoxyethyl)piperazin-1-yl, 4-phenylpiperazin-1-ylmethyl, 3-diethylcarbamoylpiperidin-1-ylmethyl, 2R,6-dimethylhept-5-enyl, cis-2,6-dimethylmorpholin-4-ylmethyl, 2-dimethylaminoethyl, 2-(1H-imidazol-4-yl)ethylaminomethyl, thien-2-ylmethyl, 4-fur-2-ylcarbonylpiperazin-1-ylmethyl, 1,2,3,4-tetrahydroisoquinol-2-ylmethyl, thiomorpholin-4-ylmethyl, 1-(1H-1,2,4-triazol-1-yl)-1-methylethyl, 4-formylpiperazin-1-ylmethyl, 5-fluoroindol-3-ylmethyl, 2,5-dihydropyrrol-1-ylmethyl, 3,5-dimethyl-1H-1,2,4-triazol-1-ylmethyl, piperazin-1-ylmethyl, 2-nitroethyl, 4-(2-chloro-6-fluorophenyl)piperazin-1-yl, 1,6-dimethylmorpholin-4-ylmethyl, 1-(1H-imidazol-4-yl)-1-methylethyl, pyrid-3-ylmethyl, 2-(1H-imidazol-4-yl)ethyl, pyrimidin-5-ylmethyl, 1H-1,2,3-triazol-1-ylmethyl, pyrid-2-ylmethyl, 3,5-dimethyloxazol-4-ylmethyl, 1,2,3,4-tetrazol-1-ylmethyl, 1H-1,2,3-benzotriazol-1-ylmethyl, 1-(1H-imidazol-4-yl)ethyl, morpholin-4-ylmethyl, 4-methyl-1H-1,2,3-triazol-1-ylmethyl, 2-methyl-1H-imidazol-1-ylmethyl, 5-methyl-1H-pyrazol-3-ylmethyl, 3,5-dimethyl-1H-pyrazol-4-ylmethyl, pyrazin-2-ylmethyl, 2-methyl-1H-imidazol-4-yl, 2H-1,2,3-triazol-2-ylmethyl, 3,5-dimethyloxazol-4-ylamino, 1H-1,2,4-triazol-2-ylmethyl, chloromethyl or 1H-imidazol-1-ylmethyl.

An aspect of the invention is a compound of Formula I, I(a), II, II(a), IV or IV(a) wherein $R^1$ is five-membered heteroarylmethyl.

An aspect of the invention is a compound of Formula I, I(a), II, II(a). IV or IV(a) wherein $R^1$ is 2H-1,2,3-triazol-2-ylmethyl, 1H-1,2,4-triazol-1-ylmethyl or 1H-1,2,3-triazol-1-yl.

An aspect of the invention is a compound of Formula I, I(a), II, II(a), III or III(a) wherein $R^2$ is $-X^7NHC(O)R^{19}$, $-X^7NR^{20}C(O)OR^{22}$, $-X^7CR^{21}R^{21}R^{22}$, $-X^7OR^{22}$, $-X^7S(O)_{n5}OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl, $R^{21}$ is halo and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

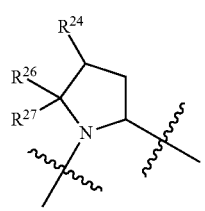

(a)

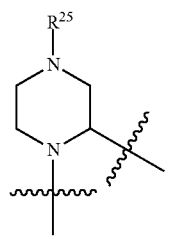

(b)

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}NR^{28}C(O)OR^{29}$, $-X^{10}NR^{28}R^{29}$, $-X^9C(O)OR^{29}$ or $-R^{29}$ wherein $X^9$ is a bond or $(C_{1-3})$alkylene, $X^{10}$ is $(C_{1-3})$alkylene and $R^{28}$ is hydrogen, $(C_{1-4})$alkyl or halo-substituted $(C_{1-4})$alkyl and $R^{29}$ is $-X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo or thioxo.

An aspect of this invention is a compound of Formula I, I(a), II, II(a), III or III(a) in which $R^2$ is $-X^7NHC(O)R^{19}$, $-X^7NR^{20}C(O)OR^{22}$ $-X^7OR^{22}$ or $-R^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

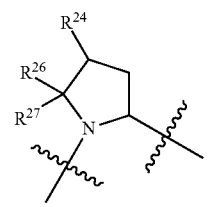

(a)

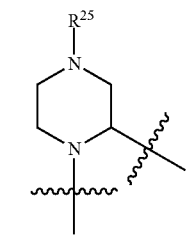

(b)

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}NR^{20}C(O)OR^{29}$, $-X^{10}NR^{28}R^{29}$, $-X^9C(O)OR^{29}$ or $-R^{29}$ wherein $X^9$ is a bond or $(C_{1-3})$alkylene, $X^{10}$ is $(C_{1-3})$alkylene and $R^{28}$ is hydrogen, $(C_{1-4})$alkyl or halo-substituted $(C_{1-4})$alkyl and $R^{29}$ is $-X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo.

An aspect of the invention is a compound of Formula I, I(a), II, II(a), III or III(a) wherein $R^2$ is $—X^7OR^{22}$ or $—X^7R^{22}$, wherein n5 is 0, 1, or 2, $X^7$ is alkylene and $R^{23}$ is phenyl, wherein $R^{23}$ may be substituted with one or two halo.

An aspect of the invention is a compound of Formula I, I(a), II, II(a), III or III(a) wherein $R^2$ is $—X^7OR^{22}$ or $—X^7R^{22}$, wherein $X^7$ is alkylene and $R^{23}$ is phenyl, wherein $R^{23}$ may be substituted with one halo.

An aspect of the invention is a compound of Formula I, I(a), II, II(a), III or III(a) wherein $R^2$ is 3-phenylpropyl or 4-fluorobenzyloxymethyl.

An aspect of the invention is a compound of Formula IV or IV(a) wherein $R^{24}$ is $—X^9OR^{29}$, $—X^9NR^{28}C(O)OR^{29}$, $—X^9NR^{28}R^{29}$, $—X^9C(O)OR^{29}$ or $—R^{29}$, wherein $X^9$ is a bond or $(C_{1-3})$alkylene and $R^{28}$ is hydrogen, $(C_{1-4})$alkyl or halo-substituted $(C_{1-4})$alkyl and $R^{29}$ is $—X^{11}R^{30}$ wherein $X''$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl.

An aspect of the invention is a compound of Formula IV or IV(a) wherein $R^{24}$ is $—X^{11}R^{30}$, wherein $X^{11}$ is methylene, and $R^{30}$ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl.

An aspect of the invention is a compound of Formula I, I(a), II, II(a), III, III(a), IV or IV(a) wherein $R^3$ is phenyl substituted with $—R^{31}$ or $R^3$ is a group of Formula (c):

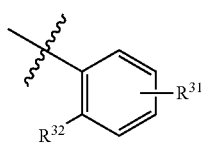

(c)

wherein $R^{31}$ is $—OR^{33}$, $—SR^{33}$ or $—CH_2R^{33}$, wherein $R^{33}$ is $—X^{12}R^{34}$, wherein $X^{12}$ is a bond or methylene and $R^{34}$ is five or six membered cycloalkyl or heterocycloalkyl, phenyl or five or six membered heteroaryl, and $R^{32}$ together with $R^6$ forms a bond, wherein any cyclic moiety within $R^3$ independently may be substituted with one or two $(C_{1-4})$alkyl, halo or $—OR^{35}$, wherein $R^{35}$ is $(C_{1-4})$alkyl.

An aspect of the invention is a compound of Formula I, I(a), II, II(a), III, III(a) or IV(a) wherein $R^3$ is 4-(4-fluorophenoxy) phenyl, wherein any cyclic moiety within $R^3$ independently may be substituted with one or two $(C_{1-4})$alkyl, halo or $—OR^{35}$, wherein $R^{35}$ is $(C_{1-4})$alkyl.

An aspect of the invention is a compound of Formula I, I(a), II, II(a), III, III(a), IV or IV(a) wherein $R^3$ is 4-(4-fluorophenoxy)phenyl.

An aspect of the invention is a compound of Formula I, I(a), II, II(a), III or III(a) wherein X is O or $NR^6$.

An aspect of the invention is a compound of Formula I, I(a), II, II(a), III or III(a) wherein X is O.

An aspect of the invention is a compound of Formula I, I(a), II, II(a), III or III(a) wherein $R^4$ is hydrogen or alkyl.

An aspect of the invention is a compound of Formula I, I(a), II, II(a), III or III(a) wherein $R^4$ is hydrogen.

An aspect of the invention is a compound of Formula I, I(a), II, II(a), III, III(a), IV or IV(a) wherein $R^5$ is hydrogen or alkyl.

An aspect of the invention is a compound of Formula I, I(a), II, II(a), III, III(a), IV or IV(a) wherein $R^5$ is hydrogen.

An aspect of the invention is a compound of Formula I wherein $R^3$ is phenyl substituted with $—OR^{20}$, wherein $R^{20}$ is $—X^9R^{21}$, wherein $X^9$ is a bond or alkylene and $R^{21}$ is cyclohexyl, phenyl or heteroaryl, wherein any cyclohexyl, phenyl or heteroaryl within $R^3$ independently may be substituted with alkyl, halo or $—OR^{22}$, wherein $R^{22}$ is alkyl.

An aspect of the invention is a compound of Formula I wherein $R^3$ is phenyl substituted with $—OR^{20}$, wherein $R^{20}$ is $—X^9R^{21}$, wherein $X^9$ is a bond and $R^{21}$ is phenyl or heteroaryl, wherein any phenyl or heteroaryl within $R^3$ independently may be substituted with alkyl or halo.

An aspect of the invention is a compound of Formula I wherein $R^3$ is phenyl substituted with $—OR^{20}$, wherein $R^{20}$ is $—X^9R^{21}$, wherein $X^9$ is a bond and $R^{21}$ is phenyl or heteroaryl, wherein $R^{21}$ may be substituted with alkyl or halo.

An aspect of the invention is a compound of Formula I wherein $R^3$ is 4-(4-fluorophenoxy)-2-methylphenyl, 4-cyclohexyloxyphenyl, 4-benzyloxyphenyl, 4-(4-methoxyphenoxy)phenyl, 3-chloro-4-phenoxyphenyl, 3-chloro-4-(4-chlorophenoxy)phenyl, 4-(5-bromothiazol-2-yloxy)phenyl, 4-(4-methylphenoxy)phenyl, 4-phenoxyphenyl, 4-(4-chlorophenoxy)phenyl or 4-(4-fluorophenoxy)phenyl.

An aspect of the invention is a compound of Formula I wherein $R^3$ is 3-chloro-4-phenoxyphenyl, 3-chloro-4-(4-chlorophenoxy)phenyl, 4-(5-bromothiazol-2-yloxy)phenyl, 4-(4-methylphenoxy)phenyl, 4-phenoxyphenyl, 4-(4-chlorophenoxy)phenyl or 4-(4-fluorophenoxy)phenyl.

An aspect of the invention is a compound of Formula I wherein $R^3$ is 4-(5-bromothiazol-2-yloxy)phenyl, 4-(4-methylphenoxy)phenyl, 4-phenoxyphenyl, 4-(4-chlorophenoxy) phenyl or 4-(4-fluorophenoxy)phenyl.

An aspect of the invention is a compound of Formula I wherein $R^3$ is 4-phenoxyphenyl, 4-(4-chlorophenoxy)phenyl or 4-(4-fluorophenoxy)phenyl.

An aspect of the invention is a compound of Formula I wherein $R^4$ is hydrogen or alkyl or $R^2$ together with $R^4$ and the atoms to which $R^2$ and $R^4$ are attached form a five to six membered ring, wherein the ring may be substituted with $—X^6C(O)OR^{20}$, $—X^8NR^{18}C(O)OR^{20}$, $—X^8NR^{18}R^{18}$ or $—X^8R^{19}$, wherein $X^8$ is a bond or alkylene and $R^{18}$ is halo and $R^{19}$ is phenyl, wherein $R^{19}$ may be substituted with one or two halo.

An aspect of the invention is a compound of Formula I wherein $R^4$ is hydrogen or $R^2$ together with $R^4$ and the atoms to which $R^2$ and $R^4$ are attached form a five membered ring, wherein the ring may be substituted with $—X^8R^{19}$, wherein $X^8$ is a bond or alkylene and $R^{19}$ is phenyl, wherein $R^{19}$ may be substituted with one or two halo.

An aspect of the invention is a compound of Formula I wherein $R^4$ is hydrogen or methyl or $R^2$ together with $R^4$ and the atoms to which $R^2$ and $R^4$ are attached form 4-benzyloxycarbonylpiperazin-1,2-ylene, 4-benzyloxycarbonylaminopyrrolidin-1,2-ylene, 4-phenylpyrrolidin-1,2-ylene, 4-benzylaminopyrrolidin-1,2-ylene or 4-benzylpyrrolidin-1,2-ylene.

An aspect of the invention is a compound of Formula I wherein $R^4$ is hydrogen or $R^2$ together with $R^4$ and the atoms to which $R^2$ and $R^4$ are attached form 4-benzylpyrrolidin-1, 2-ylene.

An aspect of the invention is a compound of Formula I wherein $R^5$ is hydrogen or alkyl.

An aspect of the invention is a compound of Formula I wherein $R^5$ is hydrogen or alkyl.

An aspect of the invention is a compound of Formula I wherein $R^5$ is hydrogen.

An aspect of the invention is a compound of Formula V(a)

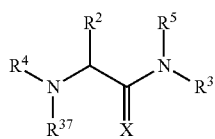

V(a)

wherein R³⁷ is hydrogen or a nitrogen protecting group and each X, R¹, R², R³, R⁴ and R⁵ are as described for Formula II in the Summary of the Invention.

An aspect of the invention is a compound of Formula V(b):

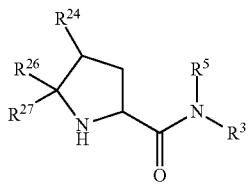

V(b)

wherein each R³, R⁵, R²⁴, R²⁶ and R²⁷ are as described for Formula IV in the Summary of the Invention.

An aspect of the invention is a compound of Formula I, I(a), II, II(a), IV or IV(a) wherein any of the above-disclosed alternative aspects for each of R¹, R², R³, R⁴ and R⁵ is present in combination with any other of the above-disclosed alternative aspects of R¹, R², R³, R⁴ and R⁵ and any individual stereoisomer or mixture of stereoisomers; and any pharmaceutically acceptable salts of any such combination. Furthermore, an aspect of the invention is a compound of Formula I, I(a), II, II(a), IV or IV(a) wherein any subgroups of R¹, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³, R²⁴, R²⁵, R²⁶, R²⁷, R²⁸, R²⁹, R³⁰, R³¹, R³², R³³, R³⁴, R³⁵, R³⁶ and R³⁷, and any subgroups of any substituents thereof are present in combination with any other subgroups of R¹, R², R³, R⁴, R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R²⁰, R²¹, R²², R²³, R²⁴, R²⁵, R²⁶, R²⁷, R²⁸, R²⁹, R³⁰, R³¹, R³², R³³, R³⁴, R³⁵, R³⁶ and R³⁷, and any subgroups of any substituents thereof.

Representative compounds of the inventions are set forth in the following Table 1.

TABLE 1

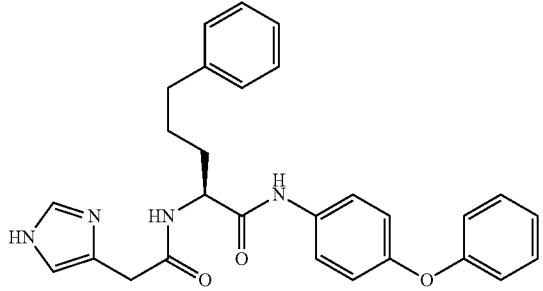 [SMILES: O=C(Cc1c[nH]cn1)N[C@@H](CCCc1ccccc1)C(=O)Nc1ccc(Oc2ccccc2)cc1]

1

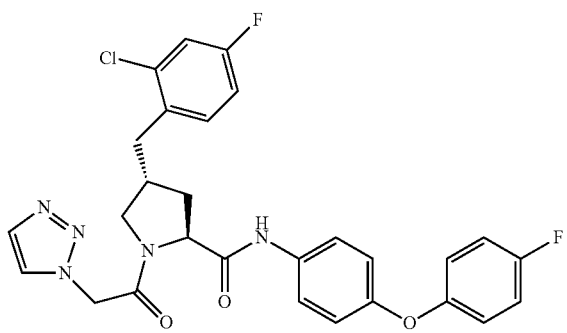 [SMILES: O=C(Nc1ccc(Oc2ccc(F)cc2)cc1)[C@@H]1C[C@@H](Cc2ccc(F)cc2Cl)CN1C(=O)Cn1ccnn1]

2

TABLE 1-continued
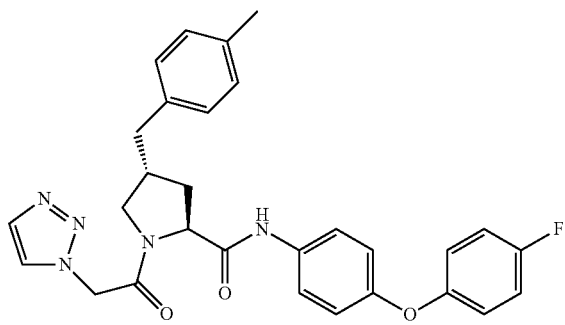 [SMILES: Cc1ccc(C[C@@H]2C[C@@H](C(=O)Nc3ccc(Oc4ccc(F)cc4)cc3)N(C(=O)Cn3ccnn3)C2)cc1]
3
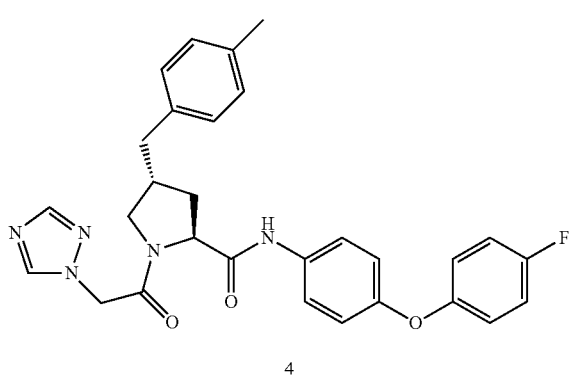
4
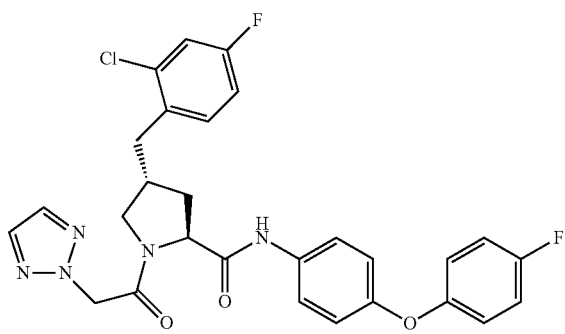 [SMILES: O=C(Nc1ccc(Oc2ccc(F)cc2)cc1)[C@@H]1C[C@@H](Cc2ccc(F)cc2Cl)CN1C(=O)Cn1nccn1]
5
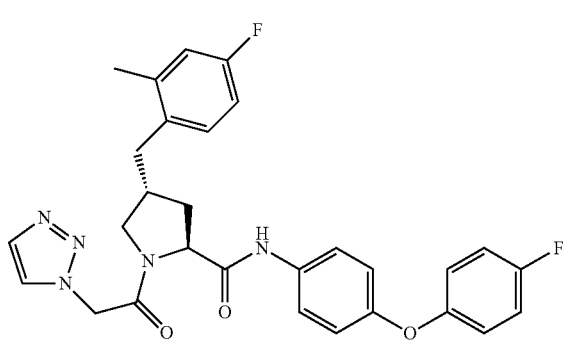 [SMILES: Cc1cc(F)ccc1C[C@@H]1C[C@@H](C(=O)Nc2ccc(Oc3ccc(F)cc3)cc2)N(C(=O)Cn2ccnn2)C1]
6

TABLE 1-continued
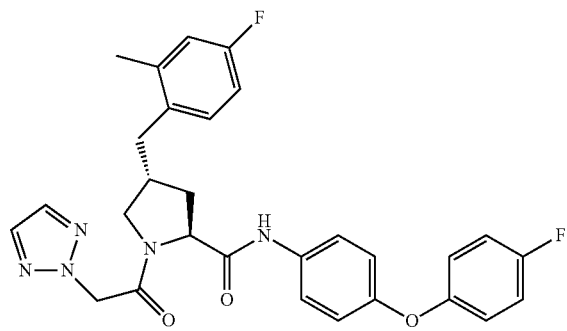
7
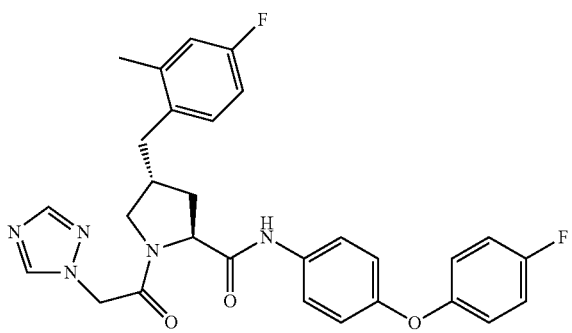
8
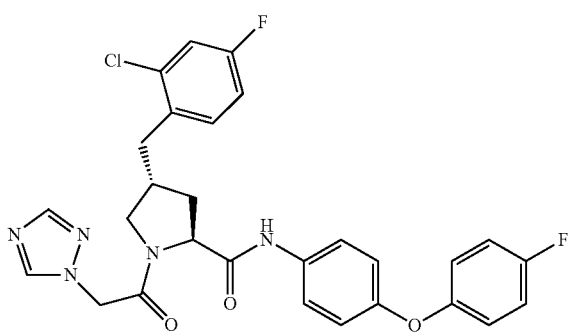 [SMILES: O=C(Nc1ccc(Oc2ccc(F)cc2)cc1)[C@@H]1C[C@@H](Cc2ccc(F)cc2Cl)CN1C(=O)Cn1cncn1]
9
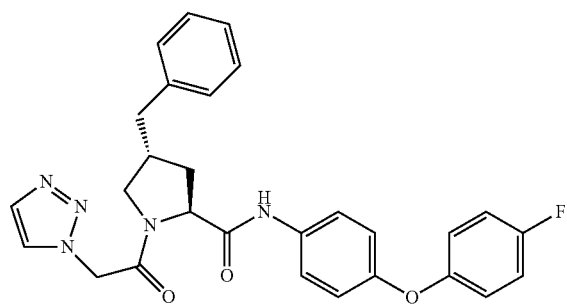 [SMILES: O=C(Nc1ccc(Oc2ccc(F)cc2)cc1)[C@@H]1C[C@@H](Cc2ccccc2)CN1C(=O)Cn1ccnn1]
10

TABLE 1-continued
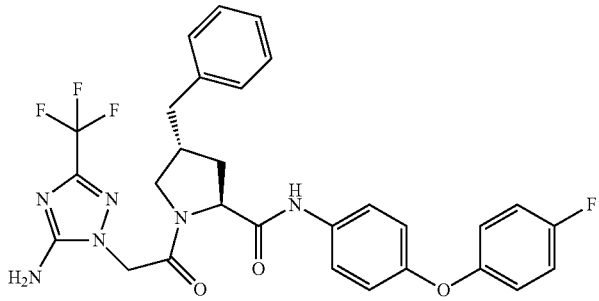 [SMILES: Nc1nc(C(F)(F)F)nn1CC(=O)N1C[C@H](Cc2ccccc2)C[C@H]1C(=O)Nc1ccc(Oc2ccc(F)cc2)cc1]
11
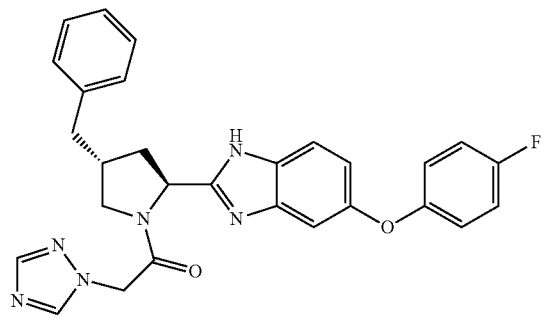 [SMILES: O=C(Cn1cncn1)N1C[C@H](Cc2ccccc2)C[C@H]1c1nc2cc(Oc3ccc(F)cc3)ccc2[nH]1]
12
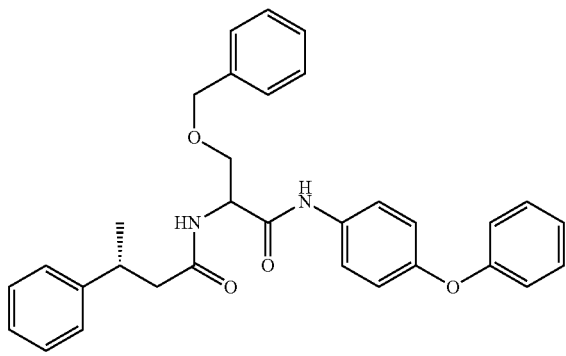 [SMILES: C[C@H](CC(=O)NC(COCc1ccccc1)C(=O)Nc1ccc(Oc2ccccc2)cc1)c1ccccc1]
13
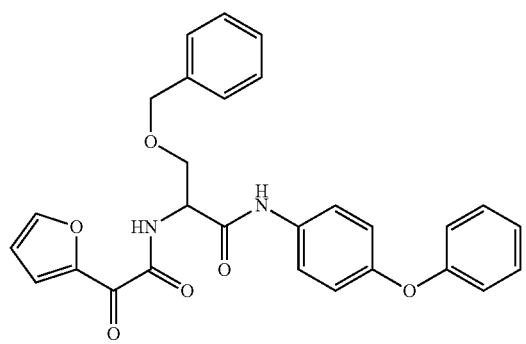 [SMILES: O=C(NC(COCc1ccccc1)C(=O)Nc1ccc(Oc2ccccc2)cc1)C(=O)c1ccco1]
14

TABLE 1-continued
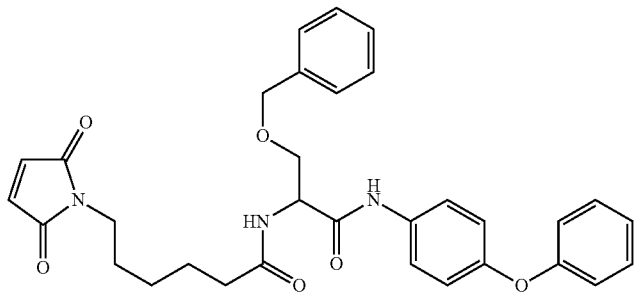 [SMILES: O=C(CCCCCN1C(=O)C=CC1=O)NC(COCc1ccccc1)C(=O)Nc1ccc(Oc2ccccc2)cc1]
15
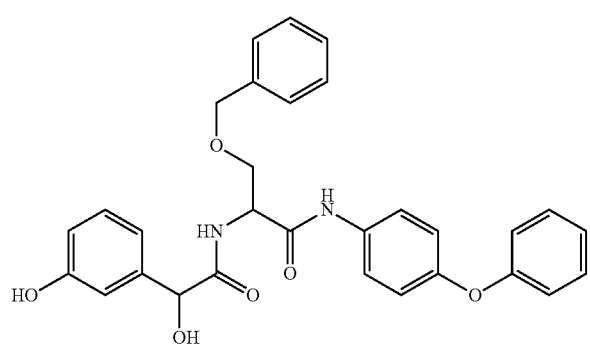 [SMILES: O=C(Nc1ccc(Oc2ccccc2)cc1)C(COCc1ccccc1)NC(=O)C(O)c1cccc(O)c1]
16
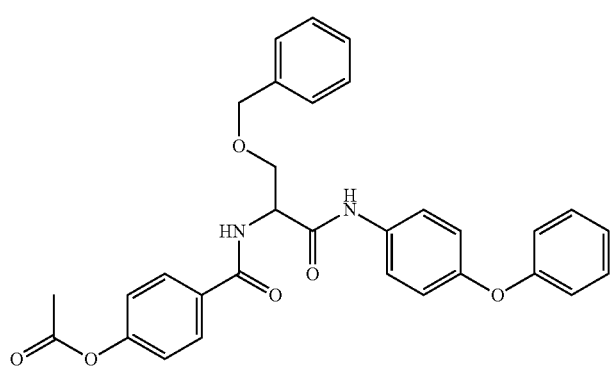 [SMILES: CC(=O)Oc1ccc(C(=O)NC(COCc2ccccc2)C(=O)Nc2ccc(Oc3ccccc3)cc2)cc1]
17
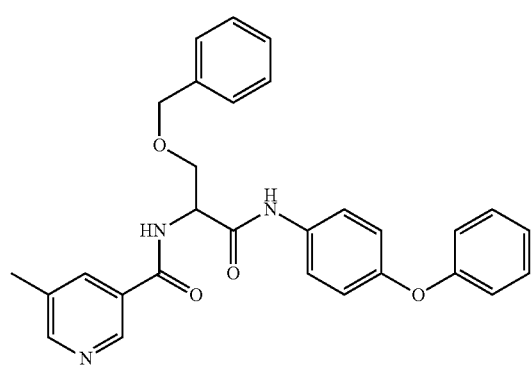 [SMILES: Cc1cncc(C(=O)NC(COCc2ccccc2)C(=O)Nc2ccc(Oc3ccccc3)cc2)c1]
18

TABLE 1-continued
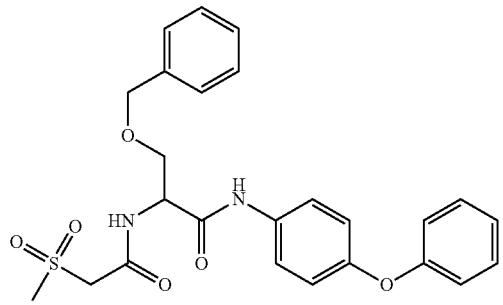 [SMILES: CS(=O)(=O)CC(=O)NC(COCc1ccccc1)C(=O)Nc1ccc(Oc2ccccc2)cc1]
19
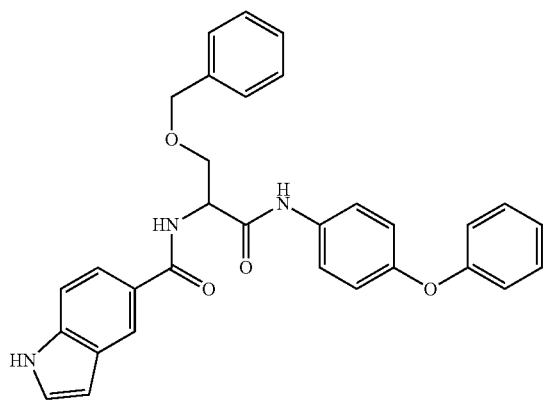 [SMILES: O=C(NC(COCc1ccccc1)C(=O)Nc1ccc(Oc2ccccc2)cc1)c1ccc2[nH]ccc2c1]
20
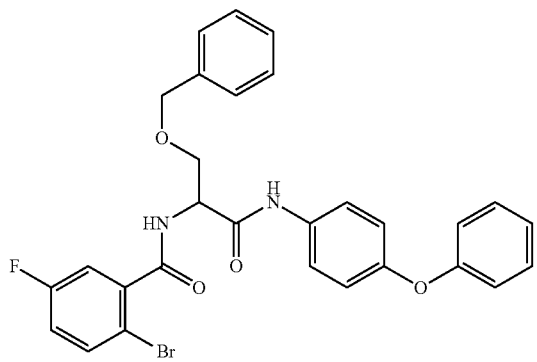 [SMILES: O=C(NC(COCc1ccccc1)C(=O)Nc1ccc(Oc2ccccc2)cc1)c1cc(F)ccc1Br]
21
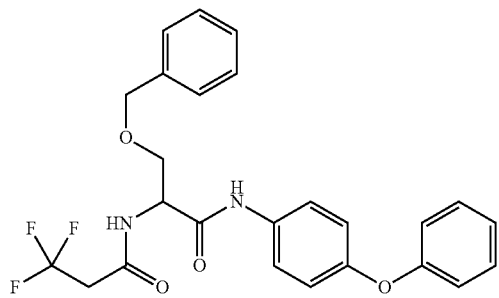 [SMILES: O=C(CC(F)(F)F)NC(COCc1ccccc1)C(=O)Nc1ccc(Oc2ccccc2)cc1]
22

TABLE 1-continued
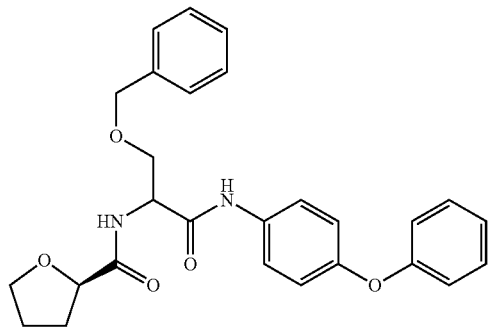 [SMILES: O=C(Nc1ccc(Oc2ccccc2)cc1)C(COCc1ccccc1)NC(=O)[C@H]1CCCO1]
23
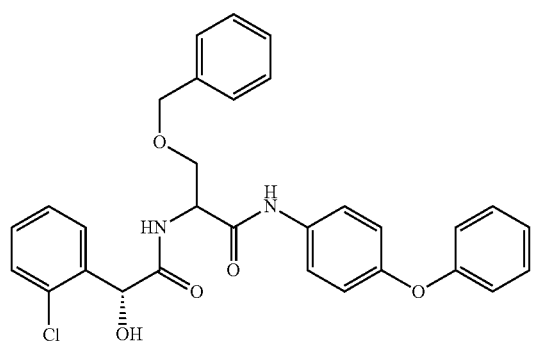 [SMILES: O=C(Nc1ccc(Oc2ccccc2)cc1)C(COCc1ccccc1)NC(=O)[C@H](O)c1ccccc1Cl]
24
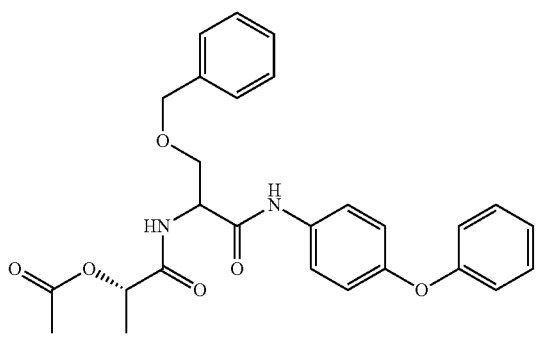 [SMILES: CC(=O)O[C@@H](C)C(=O)NC(COCc1ccccc1)C(=O)Nc1ccc(Oc2ccccc2)cc1]
25
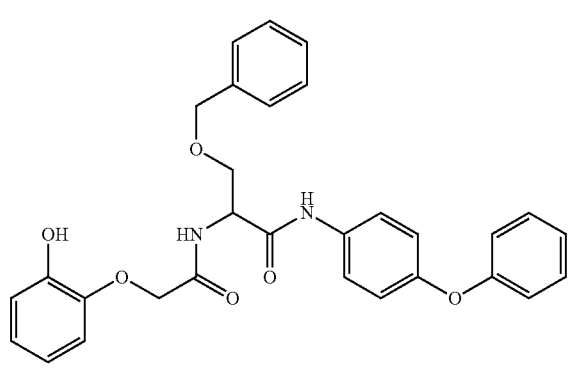 [SMILES: O=C(COc1ccccc1O)NC(COCc1ccccc1)C(=O)Nc1ccc(Oc2ccccc2)cc1]
26

TABLE 1-continued
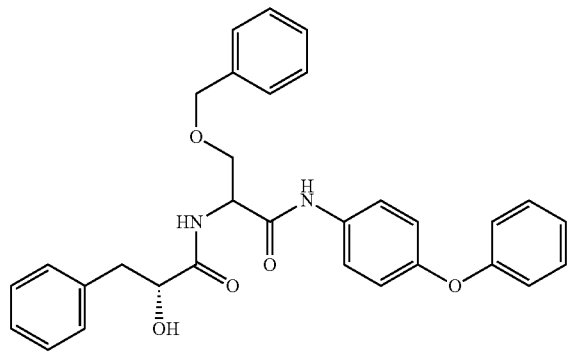 [SMILES: O=C(Nc1ccc(Oc2ccccc2)cc1)C(COCc1ccccc1)NC(=O)[C@H](O)Cc1ccccc1]
27
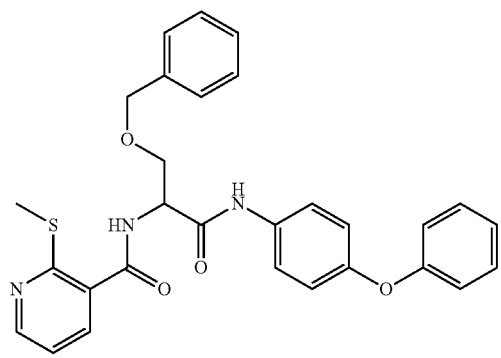 [SMILES: CSc1ncccc1C(=O)NC(COCc1ccccc1)C(=O)Nc1ccc(Oc2ccccc2)cc1]
28
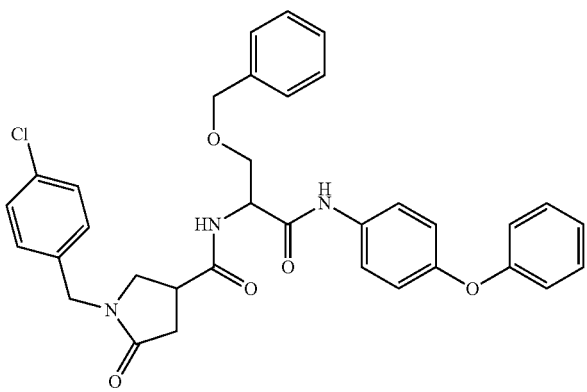 [SMILES: O=C(NC(COCc1ccccc1)C(=O)Nc1ccc(Oc2ccccc2)cc1)C1CC(=O)N(Cc2ccc(Cl)cc2)C1]
29
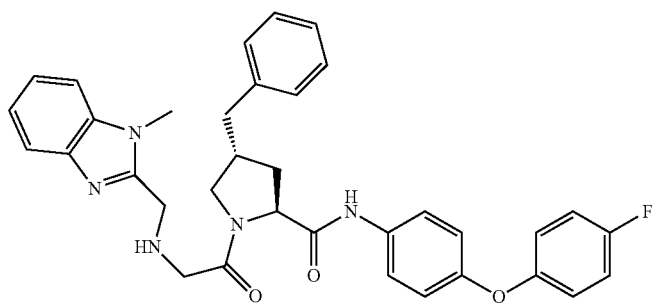 [SMILES: Cn1c(CNCC(=O)N2C[C@H](Cc3ccccc3)C[C@H]2C(=O)Nc2ccc(Oc3ccc(F)cc3)cc2)nc2ccccc21]
30

TABLE 1-continued
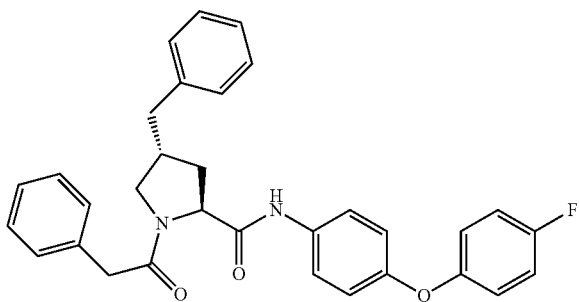 [SMILES: O=C(Nc1ccc(Oc2ccc(F)cc2)cc1)[C@@H]1C[C@@H](Cc2ccccc2)CN1C(=O)Cc1ccccc1]
31
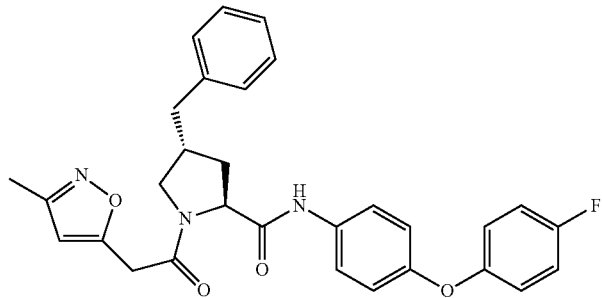 [SMILES: Cc1cc(CC(=O)N2C[C@H](Cc3ccccc3)C[C@H]2C(=O)Nc2ccc(Oc3ccc(F)cc3)cc2)on1]
32
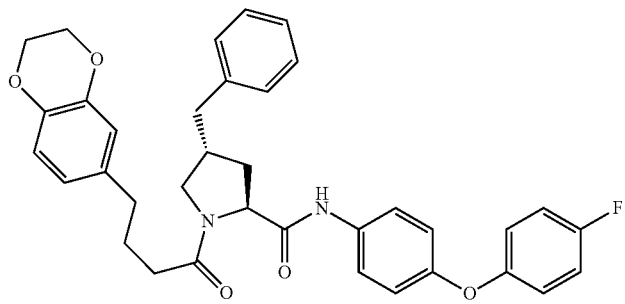 [SMILES: O=C(Nc1ccc(Oc2ccc(F)cc2)cc1)[C@@H]1C[C@@H](Cc2ccccc2)CN1C(=O)CCCc1ccc2c(c1)OCCO2]
33
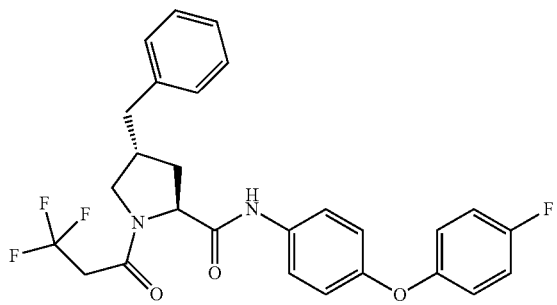 [SMILES: O=C(Nc1ccc(Oc2ccc(F)cc2)cc1)[C@@H]1C[C@@H](Cc2ccccc2)CN1C(=O)CC(F)(F)F]
34

TABLE 1-continued
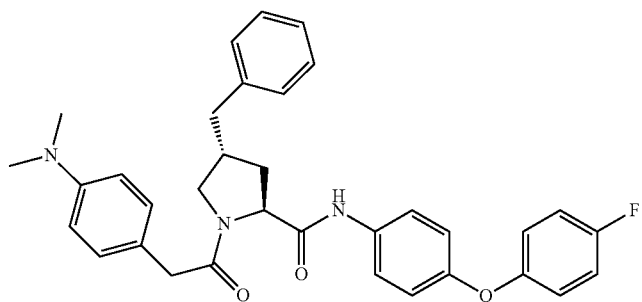 [SMILES: CN(C)c1ccc(CC(=O)N2C[C@H](Cc3ccccc3)C[C@H]2C(=O)Nc2ccc(Oc3ccc(F)cc3)cc2)cc1]
35
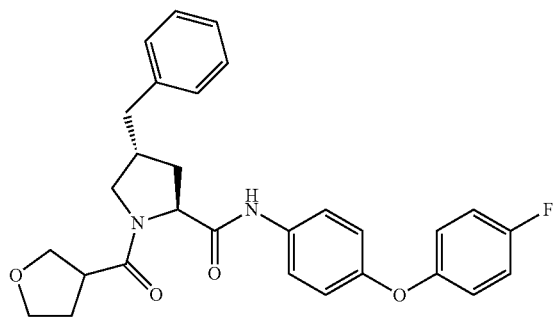 [SMILES: O=C(Nc1ccc(Oc2ccc(F)cc2)cc1)[C@@H]1C[C@@H](Cc2ccccc2)CN1C(=O)C1CCOC1]
36
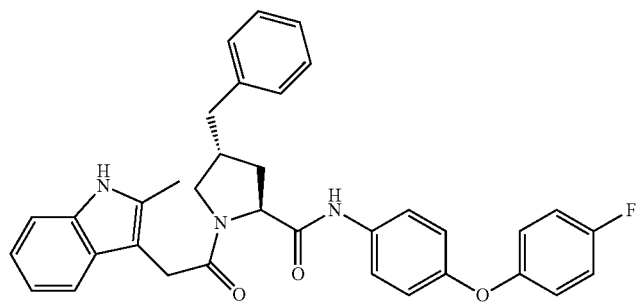
37
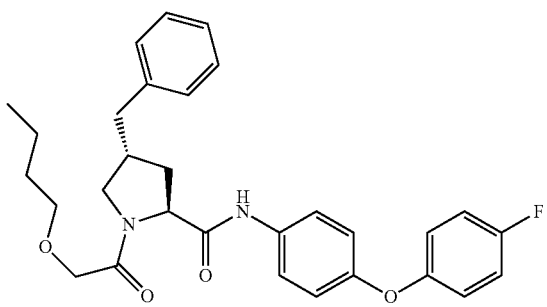 [SMILES: CCCCOCC(=O)N1C[C@H](Cc2ccccc2)C[C@H]1C(=O)Nc1ccc(Oc2ccc(F)cc2)cc1]
38

TABLE 1-continued
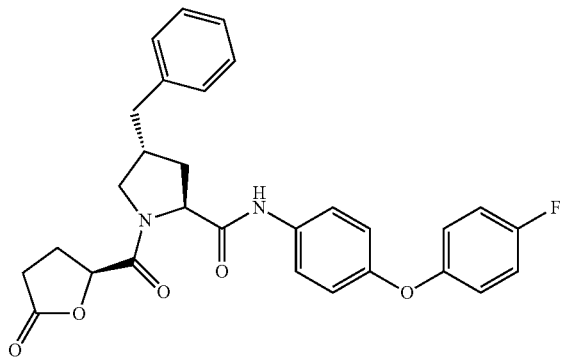 [SMILES: O=C1CC[C@@H](C(=O)N2C[C@H](Cc3ccccc3)C[C@H]2C(=O)Nc2ccc(Oc3ccc(F)cc3)cc2)O1]
39
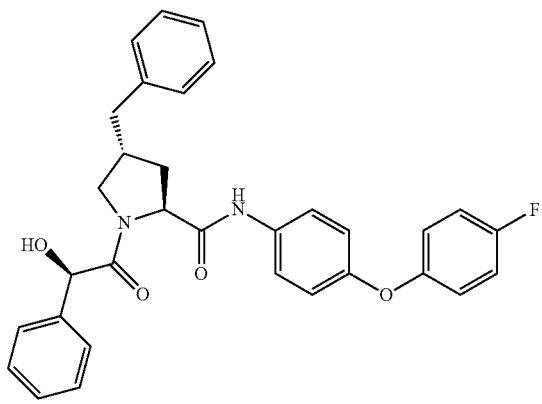 [SMILES: O=C(Nc1ccc(Oc2ccc(F)cc2)cc1)[C@@H]1C[C@@H](Cc2ccccc2)CN1C(=O)[C@H](O)c1ccccc1]
40
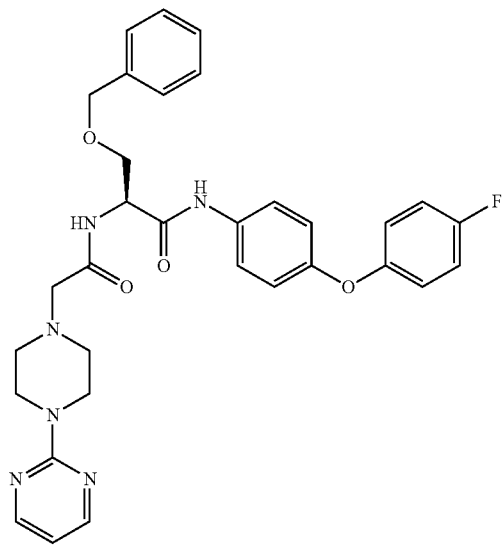 [SMILES: O=C(CN1CCN(c2ncccn2)CC1)N[C@@H](COCc1ccccc1)C(=O)Nc1ccc(Oc2ccc(F)cc2)cc1]
41

TABLE 1-continued
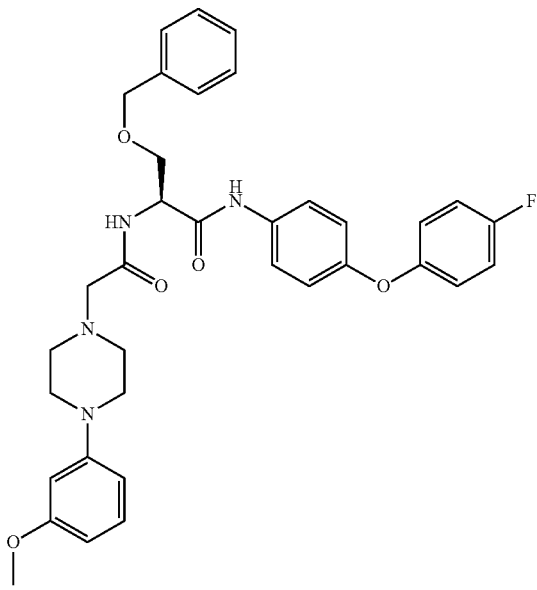 [SMILES: COc1cccc(N2CCN(CC(=O)N[C@@H](COCc3ccccc3)C(=O)Nc3ccc(Oc4ccc(F)cc4)cc3)CC2)c1]
42
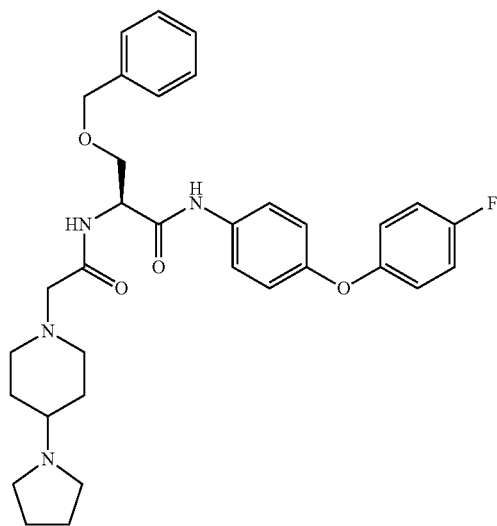 [SMILES: O=C(CN1CCC(N2CCCC2)CC1)N[C@@H](COCc1ccccc1)C(=O)Nc1ccc(Oc2ccc(F)cc2)cc1]
43

TABLE 1-continued
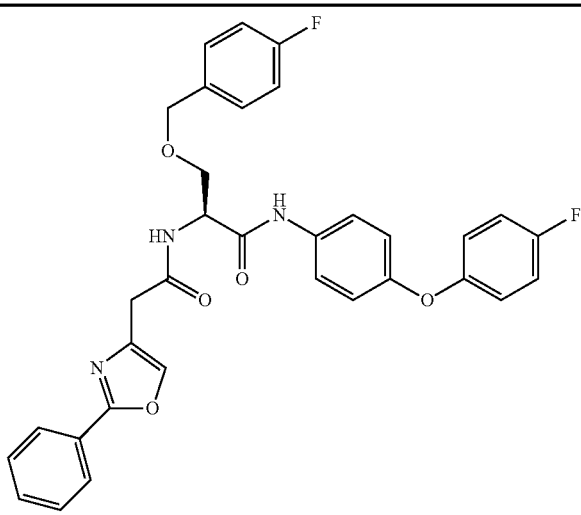
44
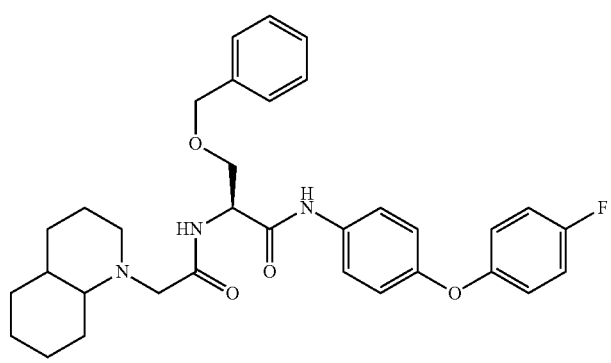 [SMILES: O=C(CN1CCCC2CCCCC21)N[C@@H](COCc1ccccc1)C(=O)Nc1ccc(Oc2ccc(F)cc2)cc1]
45
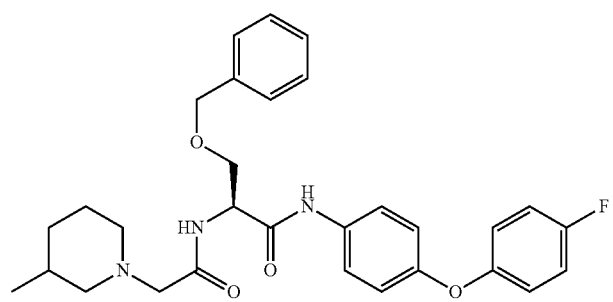 [SMILES: CC1CCCN(CC(=O)N[C@@H](COCc2ccccc2)C(=O)Nc2ccc(Oc3ccc(F)cc3)cc2)C1]
46
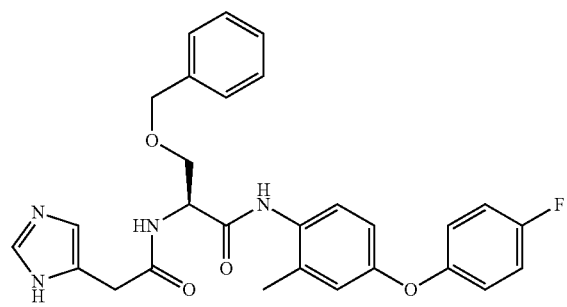 [SMILES: Cc1cc(Oc2ccc(F)cc2)ccc1NC(=O)[C@H](COCc1ccccc1)NC(=O)Cc1cnc[nH]1]
47

TABLE 1-continued
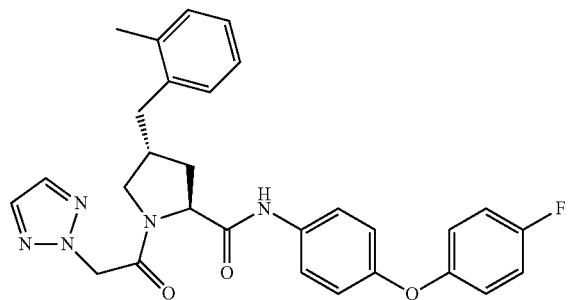 [SMILES: Cc1ccccc1C[C@@H]1C[C@@H](C(=O)Nc2ccc(Oc3ccc(F)cc3)cc2)N(C(=O)Cn2nccn2)C1]
48
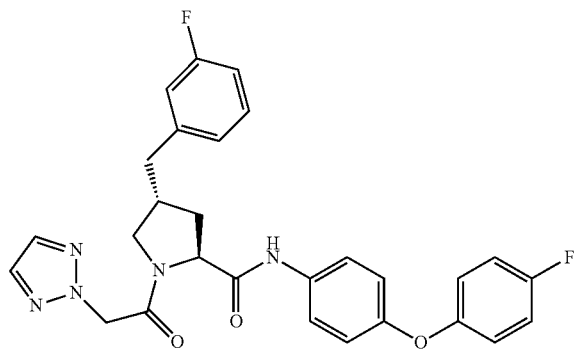 [SMILES: O=C(Nc1ccc(Oc2ccc(F)cc2)cc1)[C@@H]1C[C@@H](Cc2cccc(F)c2)CN1C(=O)Cn1nccn1]
49
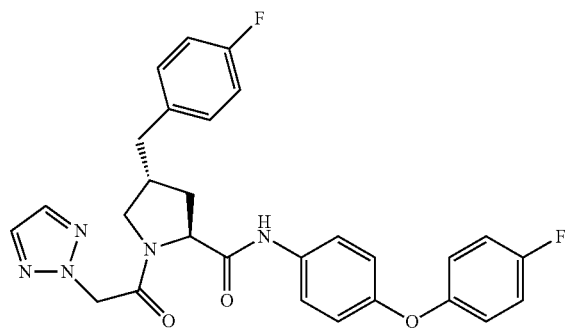 [SMILES: O=C(Nc1ccc(Oc2ccc(F)cc2)cc1)[C@@H]1C[C@@H](Cc2ccc(F)cc2)CN1C(=O)Cn1nccn1]
50
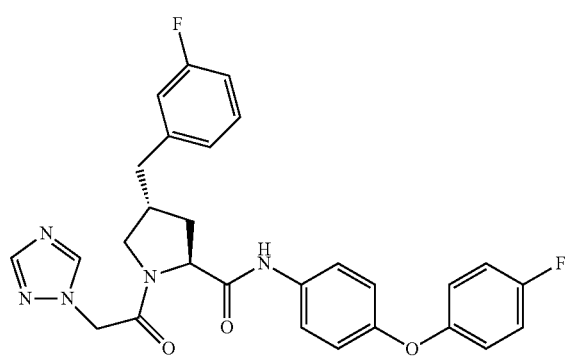 [SMILES: O=C(Nc1ccc(Oc2ccc(F)cc2)cc1)[C@@H]1C[C@@H](Cc2cccc(F)c2)CN1C(=O)Cn1cncn1]
51

TABLE 1-continued
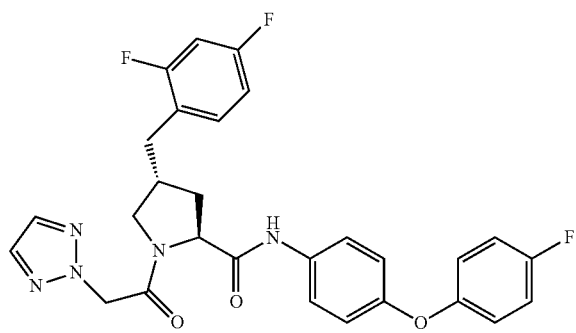 [SMILES: O=C(Nc1ccc(Oc2ccc(F)cc2)cc1)[C@@H]1C[C@@H](Cc2ccc(F)cc2F)CN1C(=O)Cn1nccn1]
52
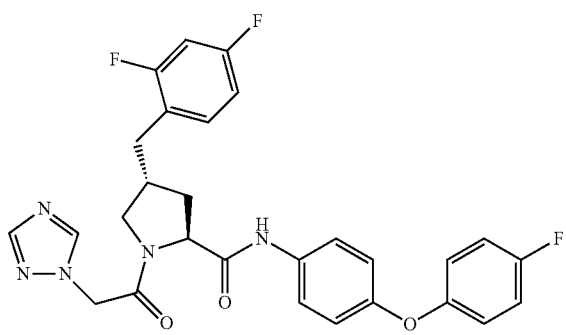 [SMILES: O=C(Nc1ccc(Oc2ccc(F)cc2)cc1)[C@@H]1C[C@@H](Cc2ccc(F)cc2F)CN1C(=O)Cn1cncn1]
53
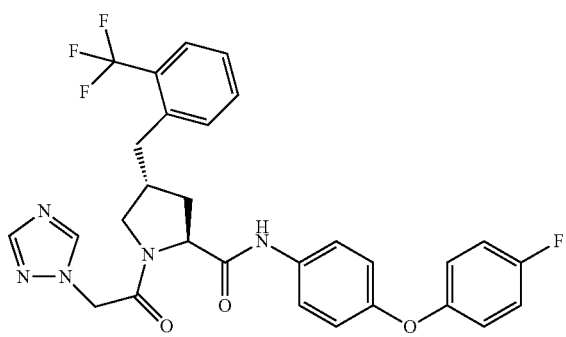 [SMILES: O=C(Nc1ccc(Oc2ccc(F)cc2)cc1)[C@@H]1C[C@@H](Cc2ccccc2C(F)(F)F)CN1C(=O)Cn1cncn1]
54
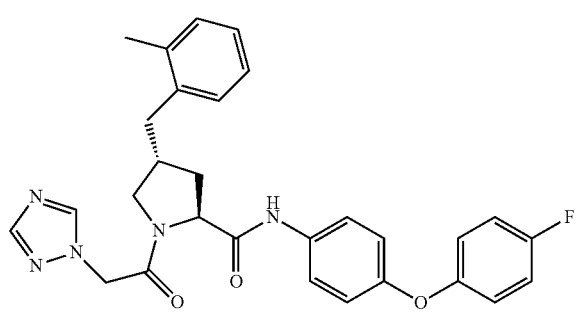 [SMILES: Cc1ccccc1C[C@@H]1C[C@@H](C(=O)Nc2ccc(Oc3ccc(F)cc3)cc2)N(C(=O)Cn2cncn2)C1]
55

TABLE 1-continued
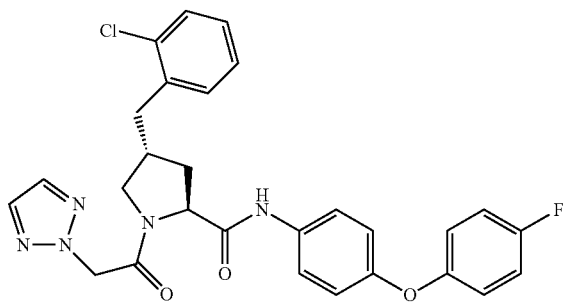 [SMILES: O=C(Nc1ccc(Oc2ccc(F)cc2)cc1)[C@@H]1C[C@@H](Cc2ccccc2Cl)CN1C(=O)Cn1nccn1]
56
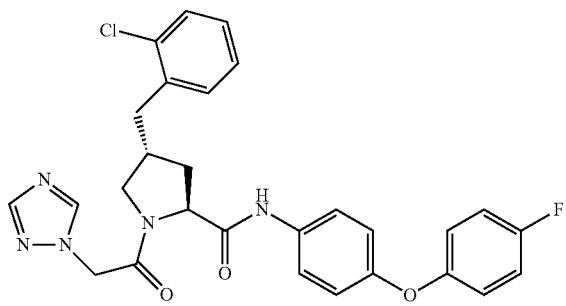 [SMILES: O=C(Nc1ccc(Oc2ccc(F)cc2)cc1)[C@@H]1C[C@@H](Cc2ccccc2Cl)CN1C(=O)Cn1cncn1]
57
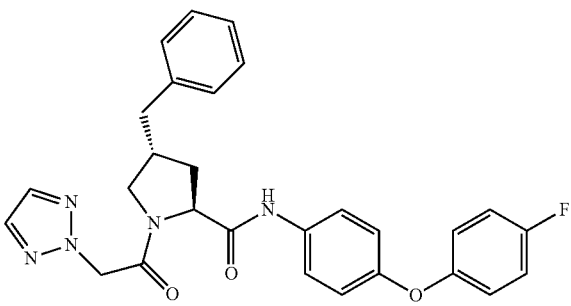 [SMILES: O=C(Nc1ccc(Oc2ccc(F)cc2)cc1)[C@@H]1C[C@@H](Cc2ccccc2)CN1C(=O)Cn1nccn1]
58
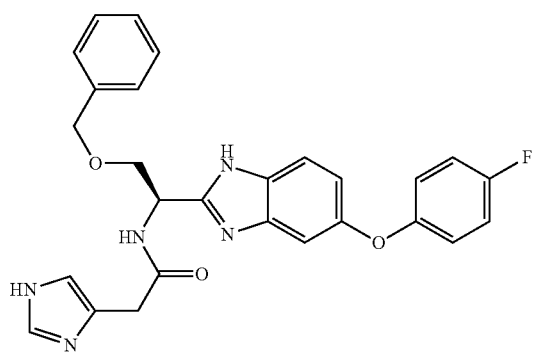 [SMILES: O=C(Cc1c[nH]cn1)N[C@@H](COCc1ccccc1)c1nc2cc(Oc3ccc(F)cc3)ccc2[nH]1]
59

TABLE 1-continued
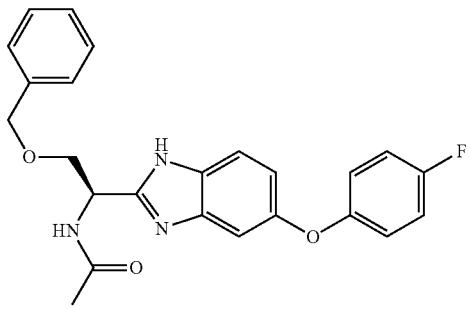 [SMILES: CC(=O)N[C@@H](COCc1ccccc1)c1nc2cc(Oc3ccc(F)cc3)ccc2[nH]1]
60
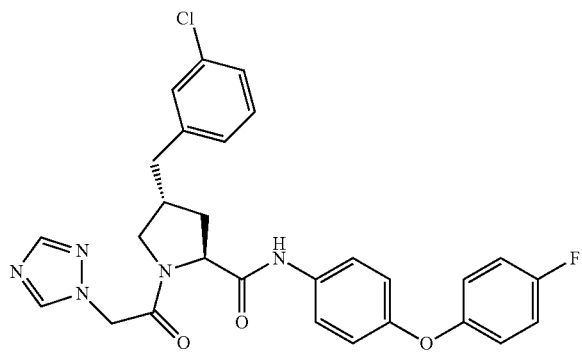 [SMILES: O=C(Nc1ccc(Oc2ccc(F)cc2)cc1)[C@@H]1C[C@@H](Cc2cccc(Cl)c2)CN1C(=O)Cn1cncn1]
61
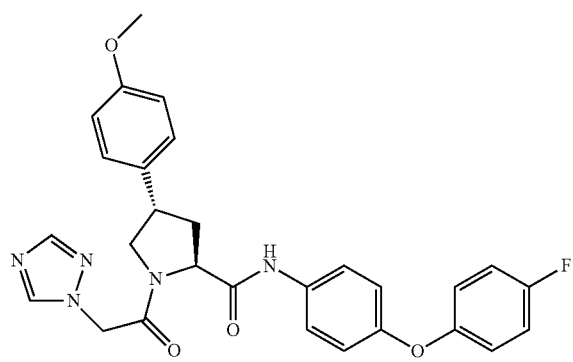 [SMILES: COc1ccc([C@@H]2C[C@@H](C(=O)Nc3ccc(Oc4ccc(F)cc4)cc3)N(C(=O)Cn3cncn3)C2)cc1]
62
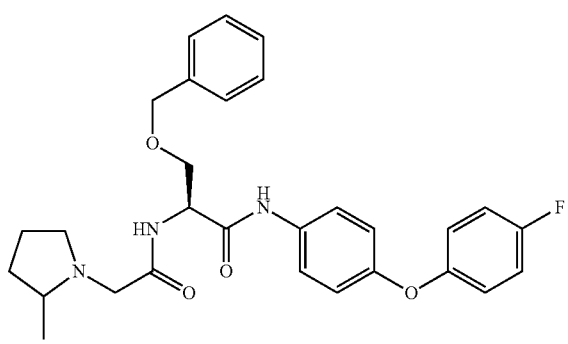 [SMILES: CC1CCCN1CC(=O)N[C@@H](COCc1ccccc1)C(=O)Nc1ccc(Oc2ccc(F)cc2)cc1]
63

TABLE 1-continued
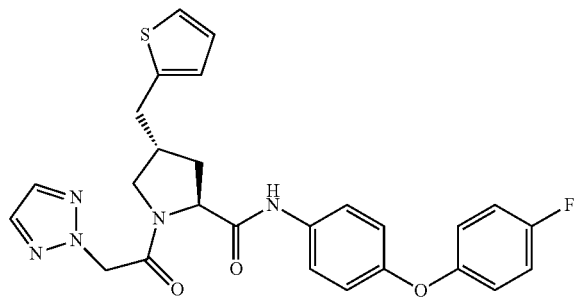 [SMILES: O=C(Nc1ccc(Oc2ccc(F)cc2)cc1)[C@@H]1C[C@@H](Cc2cccs2)CN1C(=O)Cn1nccn1]
64
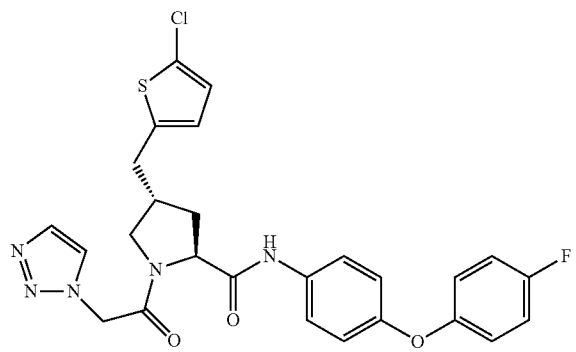 [SMILES: O=C(Nc1ccc(Oc2ccc(F)cc2)cc1)[C@@H]1C[C@@H](Cc2ccc(Cl)s2)CN1C(=O)Cn1ccnn1]
65
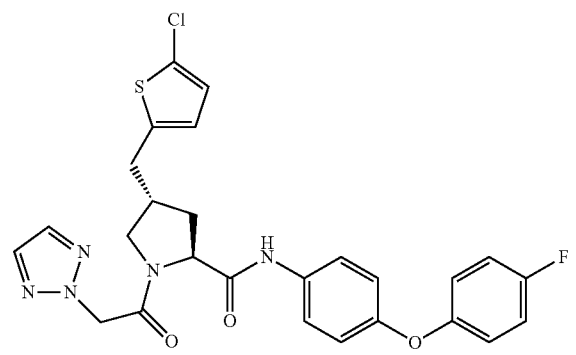 [SMILES: O=C(Nc1ccc(Oc2ccc(F)cc2)cc1)[C@@H]1C[C@@H](Cc2ccc(Cl)s2)CN1C(=O)Cn1nccn1]
66
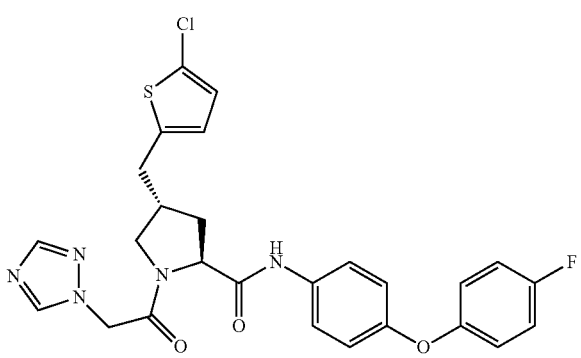 [SMILES: O=C(Nc1ccc(Oc2ccc(F)cc2)cc1)[C@@H]1C[C@@H](Cc2ccc(Cl)s2)CN1C(=O)Cn1cncn1]
67

TABLE 1-continued
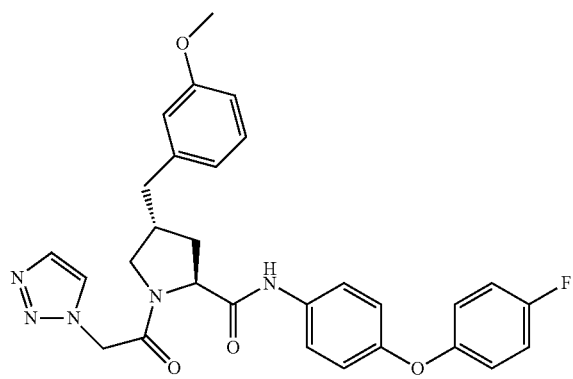 [SMILES: COc1cccc(C[C@@H]2C[C@@H](C(=O)Nc3ccc(Oc4ccc(F)cc4)cc3)N(C(=O)Cn3ccnn3)C2)c1]
68
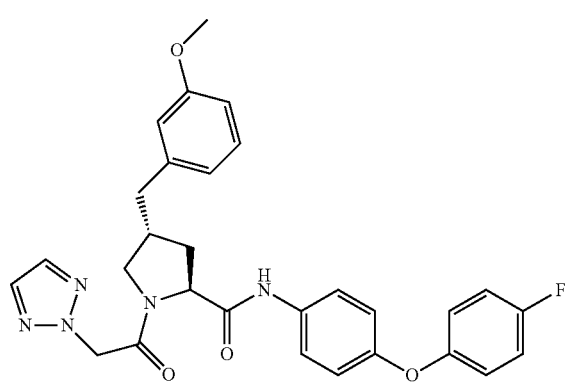 [SMILES: COc1cccc(C[C@@H]2C[C@@H](C(=O)Nc3ccc(Oc4ccc(F)cc4)cc3)N(C(=O)Cn3nccn3)C2)c1]
69
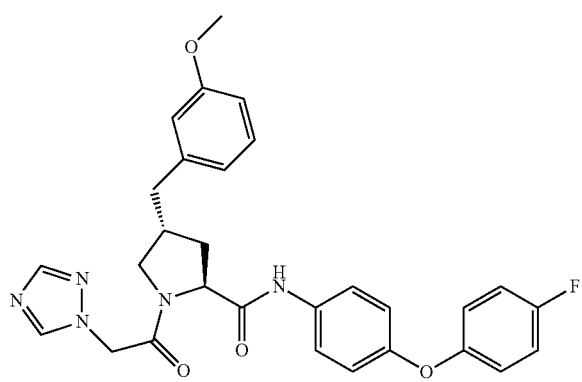 [SMILES: COc1cccc(C[C@@H]2C[C@@H](C(=O)Nc3ccc(Oc4ccc(F)cc4)cc3)N(C(=O)Cn3cncn3)C2)c1]
70

TABLE 1-continued
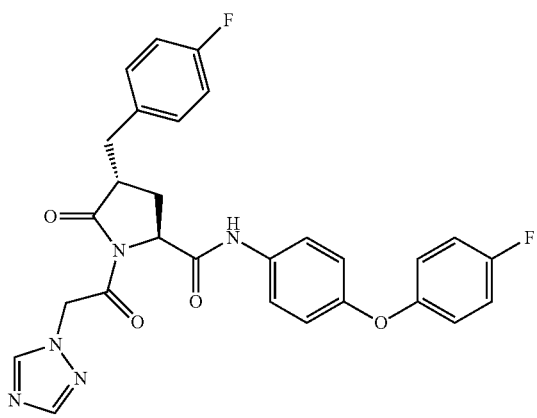 [SMILES: O=C(Nc1ccc(Oc2ccc(F)cc2)cc1)[C@@H]1C[C@@H](Cc2ccc(F)cc2)C(=O)N1C(=O)Cn1cncn1]
71
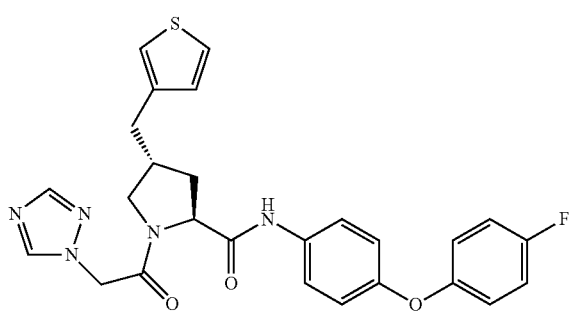 [SMILES: O=C(Nc1ccc(Oc2ccc(F)cc2)cc1)[C@@H]1C[C@@H](Cc2ccsc2)CN1C(=O)Cn1cncn1]
72
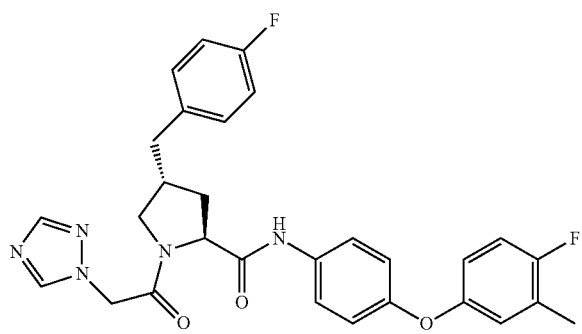 [SMILES: Cc1cc(Oc2ccc(NC(=O)[C@@H]3C[C@@H](Cc4ccc(F)cc4)CN3C(=O)Cn3cncn3)cc2)ccc1F]
73
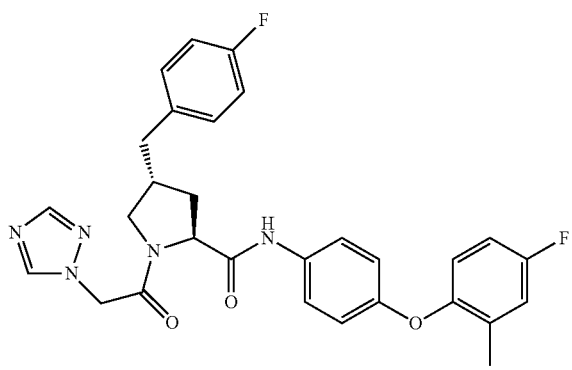 [SMILES: Cc1cc(F)ccc1Oc1ccc(NC(=O)[C@@H]2C[C@@H](Cc3ccc(F)cc3)CN2C(=O)Cn2cncn2)cc1]
74

TABLE 1-continued
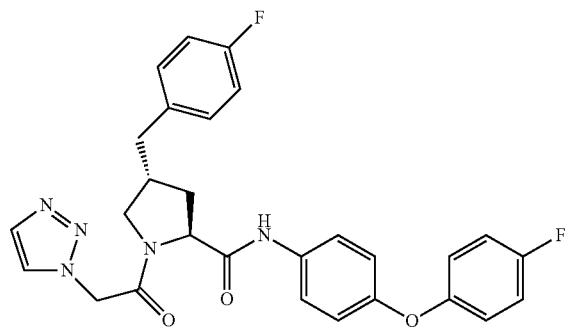 [SMILES: O=C(Nc1ccc(Oc2ccc(F)cc2)cc1)[C@@H]1C[C@@H](Cc2ccc(F)cc2)CN1C(=O)Cn1ccnn1]
75
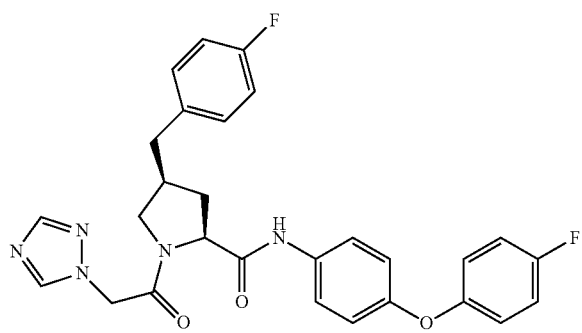 [SMILES: O=C(Nc1ccc(Oc2ccc(F)cc2)cc1)[C@@H]1C[C@H](Cc2ccc(F)cc2)CN1C(=O)Cn1cncn1]
76
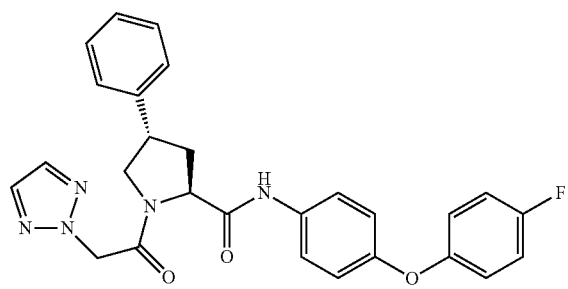 [SMILES: O=C(Nc1ccc(Oc2ccc(F)cc2)cc1)[C@@H]1C[C@@H](c2ccccc2)CN1C(=O)Cn1nccn1]
77
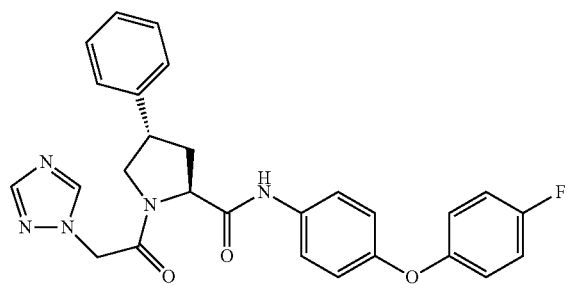 [SMILES: O=C(Nc1ccc(Oc2ccc(F)cc2)cc1)[C@@H]1C[C@@H](c2ccccc2)CN1C(=O)Cn1cncn1]
78

TABLE 1-continued
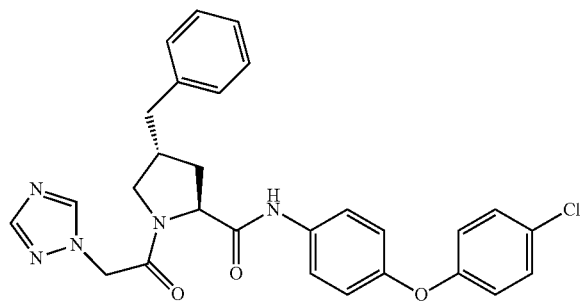 [SMILES: O=C(Nc1ccc(Oc2ccc(Cl)cc2)cc1)[C@@H]1C[C@@H](Cc2ccccc2)CN1C(=O)Cn1cncn1]
79
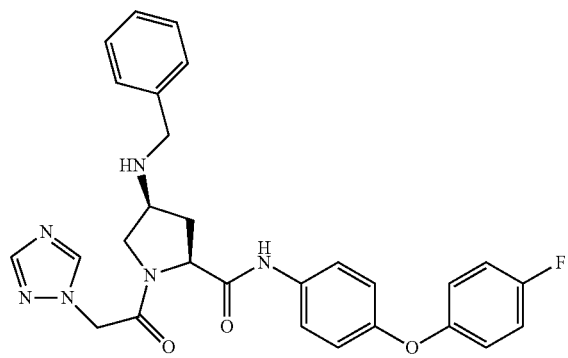 [SMILES: O=C(Nc1ccc(Oc2ccc(F)cc2)cc1)[C@@H]1C[C@H](NCc2ccccc2)CN1C(=O)Cn1cncn1]
80
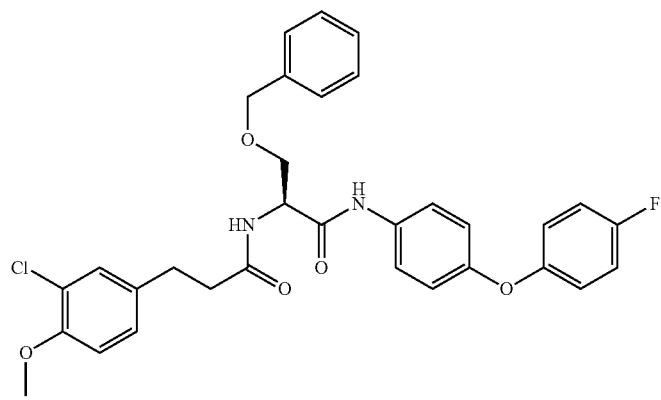 [SMILES: COc1ccc(CCC(=O)N[C@@H](COCc2ccccc2)C(=O)Nc2ccc(Oc3ccc(F)cc3)cc2)cc1Cl]
81
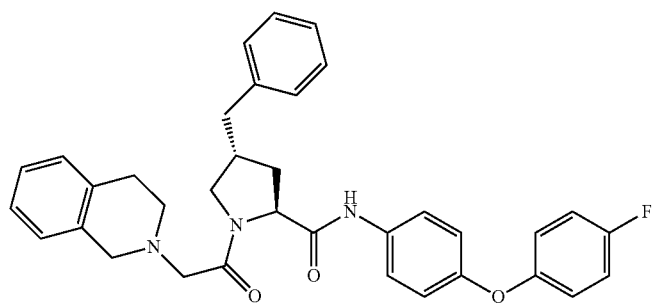 [SMILES: O=C(Nc1ccc(Oc2ccc(F)cc2)cc1)[C@@H]1C[C@@H](Cc2ccccc2)CN1C(=O)CN1CCc2ccccc2C1]
82

TABLE 1-continued
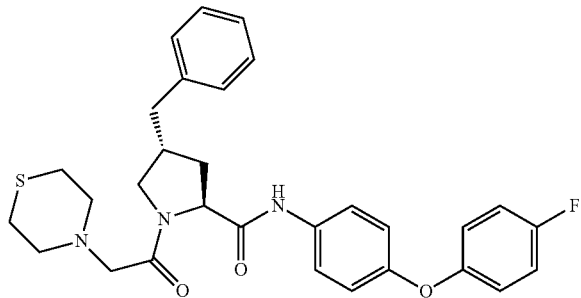
83
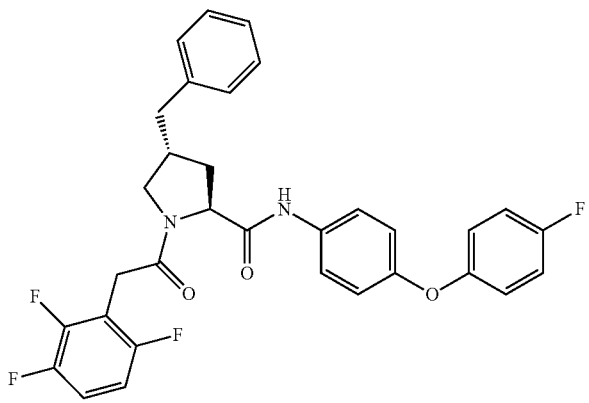 [SMILES: O=C(Nc1ccc(Oc2ccc(F)cc2)cc1)[C@@H]1C[C@@H](Cc2ccccc2)CN1C(=O)Cc1c(F)ccc(F)c1F]
84
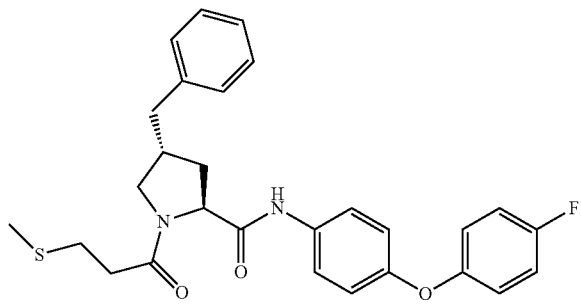
85
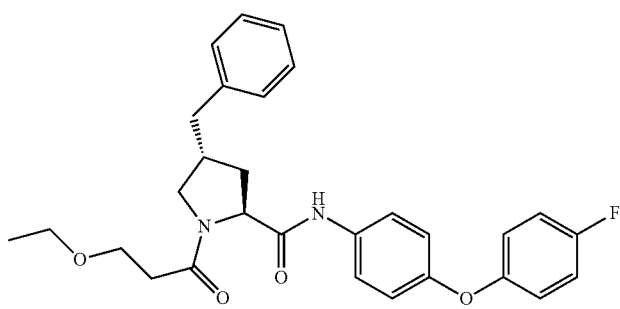 [SMILES: CCOCCC(=O)N1C[C@H](Cc2ccccc2)C[C@H]1C(=O)Nc1ccc(Oc2ccc(F)cc2)cc1]
86

TABLE 1-continued
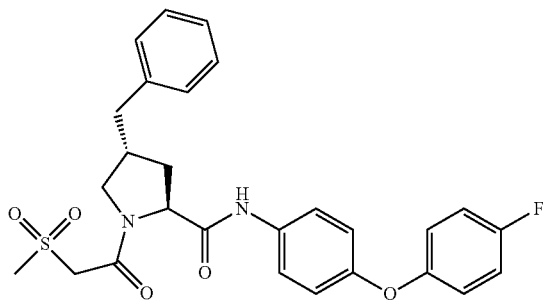 [SMILES: CS(=O)(=O)CC(=O)N1C[C@H](Cc2ccccc2)C[C@H]1C(=O)Nc1ccc(Oc2ccc(F)cc2)cc1]
87
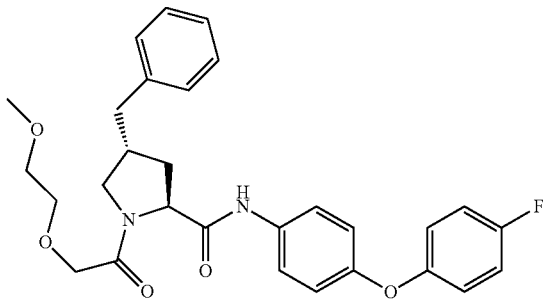 [SMILES: COCCOCC(=O)N1C[C@H](Cc2ccccc2)C[C@H]1C(=O)Nc1ccc(Oc2ccc(F)cc2)cc1]
88
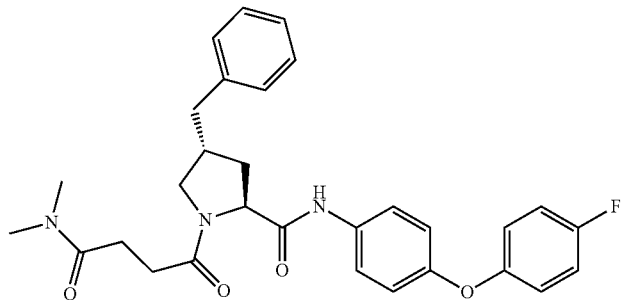 [SMILES: CN(C)C(=O)CCC(=O)N1C[C@H](Cc2ccccc2)C[C@H]1C(=O)Nc1ccc(Oc2ccc(F)cc2)cc1]
89
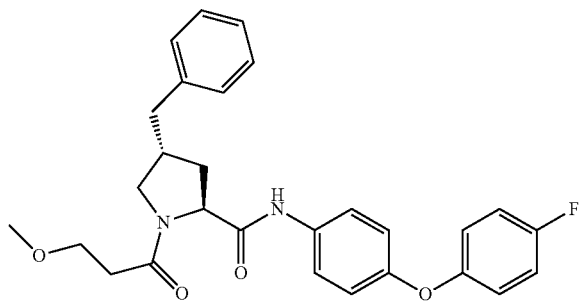
90

TABLE 1-continued
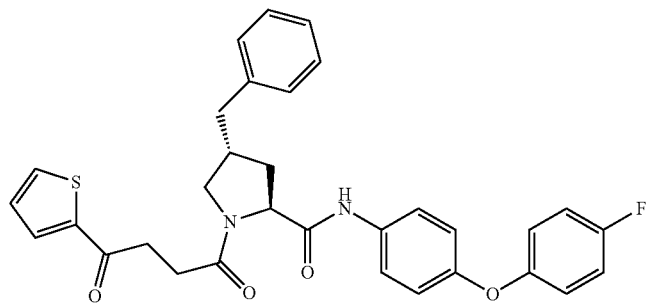 [SMILES: O=C(CCC(=O)N1C[C@H](Cc2ccccc2)C[C@H]1C(=O)Nc1ccc(Oc2ccc(F)cc2)cc1)c1cccs1]
91
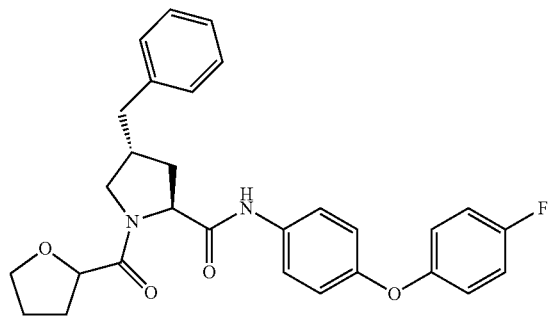 [SMILES: O=C(Nc1ccc(Oc2ccc(F)cc2)cc1)[C@@H]1C[C@@H](Cc2ccccc2)CN1C(=O)C1CCCO1]
92
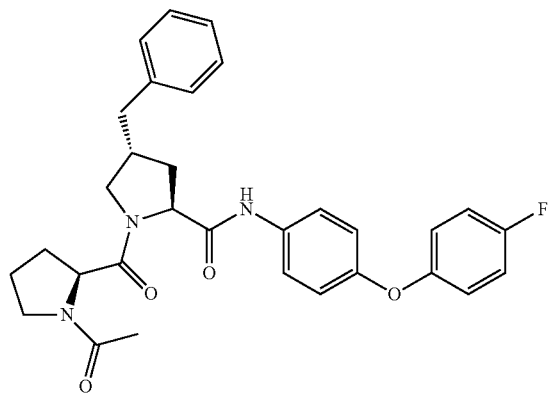 [SMILES: CC(=O)N1CCC[C@H]1C(=O)N1C[C@H](Cc2ccccc2)C[C@H]1C(=O)Nc1ccc(Oc2ccc(F)cc2)cc1]
93
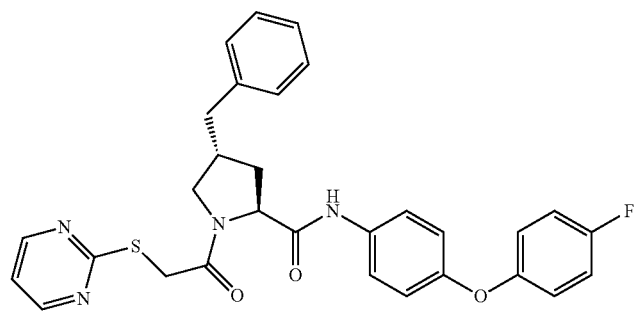 [SMILES: O=C(Nc1ccc(Oc2ccc(F)cc2)cc1)[C@@H]1C[C@@H](Cc2ccccc2)CN1C(=O)CSc1ncccn1]
94

TABLE 1-continued
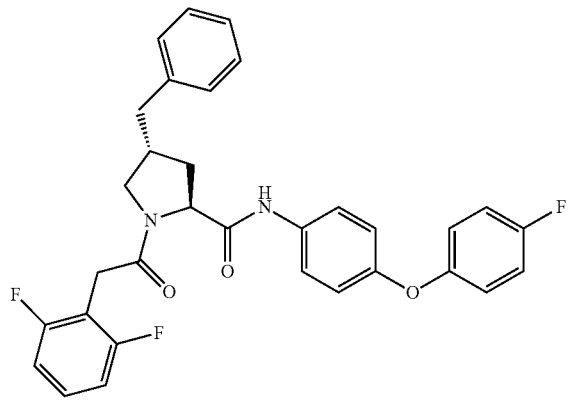 [SMILES: O=C(Nc1ccc(Oc2ccc(F)cc2)cc1)[C@@H]1C[C@@H](Cc2ccccc2)CN1C(=O)Cc1c(F)cccc1F]
95
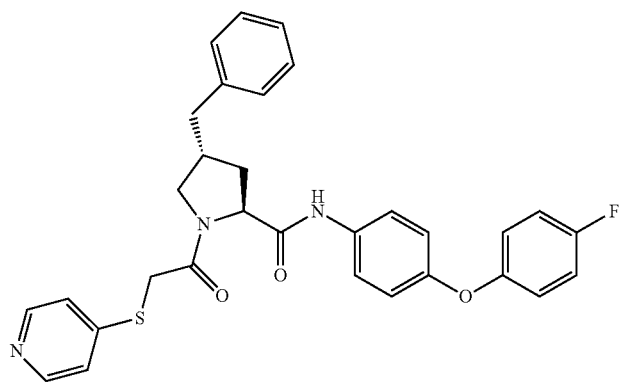 [SMILES: O=C(Nc1ccc(Oc2ccc(F)cc2)cc1)[C@@H]1C[C@@H](Cc2ccccc2)CN1C(=O)CSc1ccncc1]
96
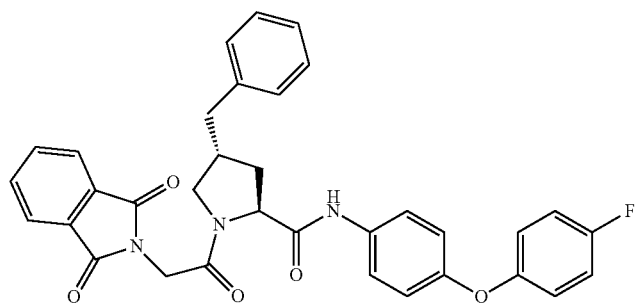 [SMILES: O=C(Nc1ccc(Oc2ccc(F)cc2)cc1)[C@@H]1C[C@@H](Cc2ccccc2)CN1C(=O)CN1C(=O)c2ccccc2C1=O]
97
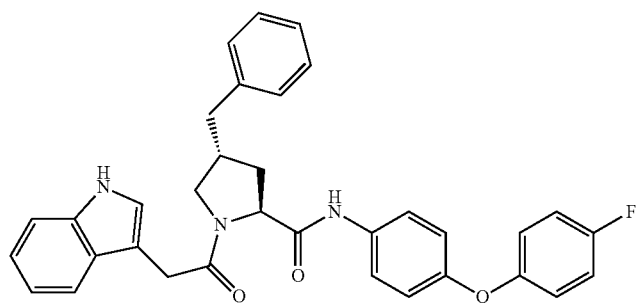 [SMILES: O=C(Nc1ccc(Oc2ccc(F)cc2)cc1)[C@@H]1C[C@@H](Cc2ccccc2)CN1C(=O)Cc1c[nH]c2ccccc12]
98

TABLE 1-continued
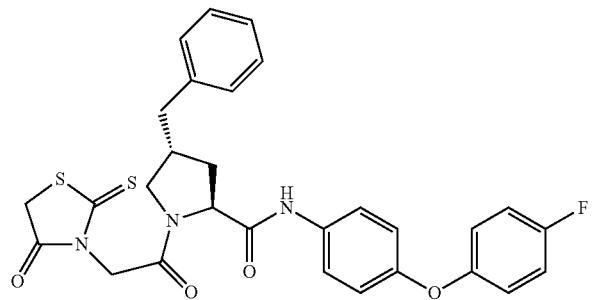 [SMILES: O=C(Nc1ccc(Oc2ccc(F)cc2)cc1)[C@@H]1C[C@@H](Cc2ccccc2)CN1C(=O)CN1C(=O)CSC1=S]
99
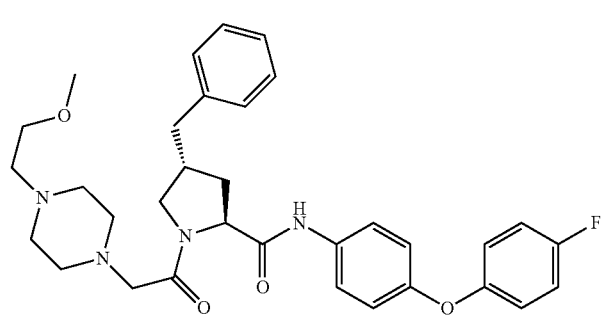 [SMILES: COCCN1CCN(CC(=O)N2C[C@H](Cc3ccccc3)C[C@H]2C(=O)Nc2ccc(Oc3ccc(F)cc3)cc2)CC1]
100
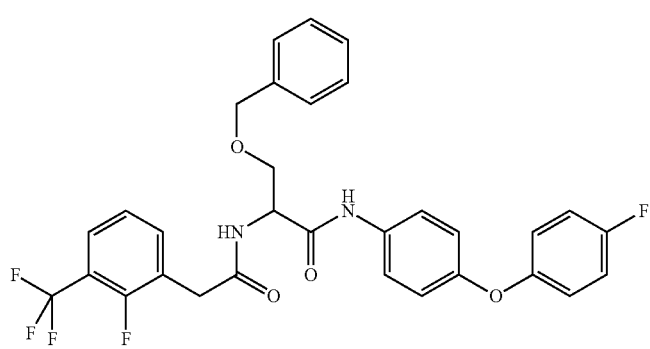 [SMILES: O=C(Cc1cccc(C(F)(F)F)c1F)NC(COCc1ccccc1)C(=O)Nc1ccc(Oc2ccc(F)cc2)cc1]
101
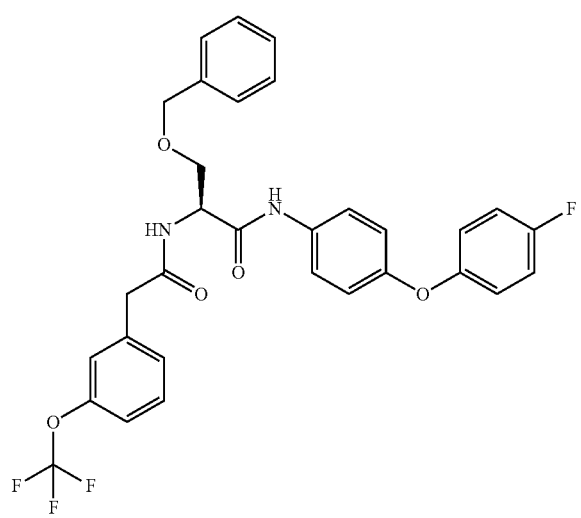 [SMILES: O=C(Cc1cccc(OC(F)(F)F)c1)N[C@@H](COCc1ccccc1)C(=O)Nc1ccc(Oc2ccc(F)cc2)cc1]
102

TABLE 1-continued
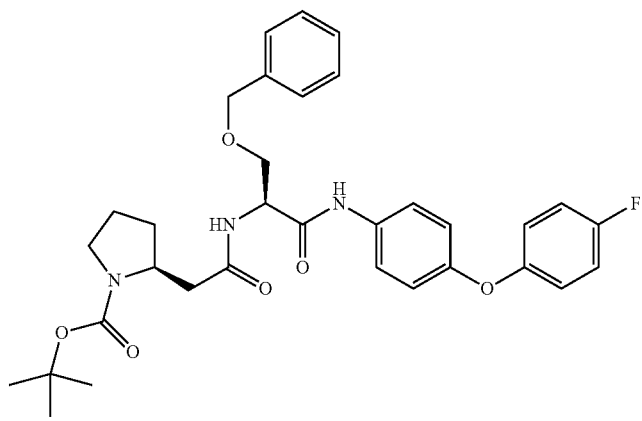 [SMILES: CC(C)(C)OC(=O)N1CCC[C@H]1CC(=O)N[C@@H](COCc1ccccc1)C(=O)Nc1ccc(Oc2ccc(F)cc2)cc1]
103
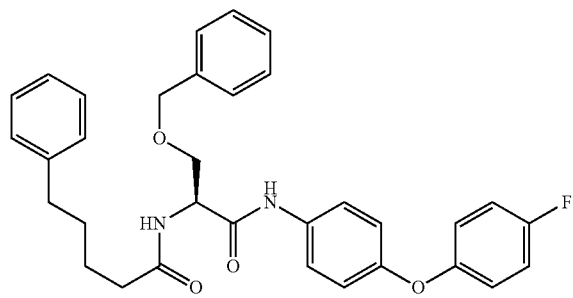 [SMILES: O=C(CCCCc1ccccc1)N[C@@H](COCc1ccccc1)C(=O)Nc1ccc(Oc2ccc(F)cc2)cc1]
104
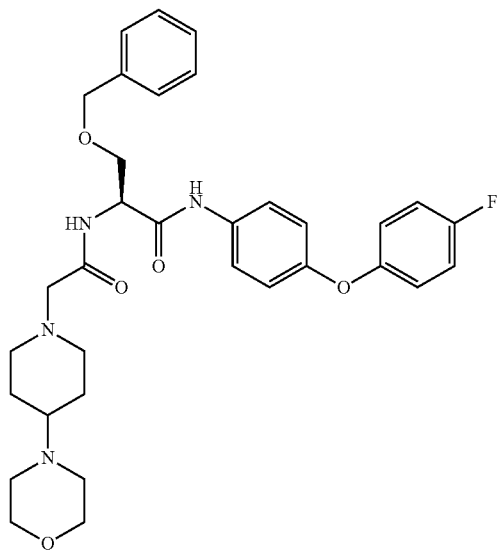 [SMILES: O=C(CN1CCC(N2CCOCC2)CC1)N[C@@H](COCc1ccccc1)C(=O)Nc1ccc(Oc2ccc(F)cc2)cc1]
105

TABLE 1-continued
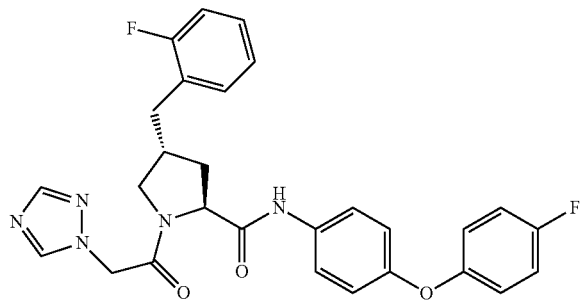 [SMILES: O=C(Nc1ccc(Oc2ccc(F)cc2)cc1)[C@@H]1C[C@@H](Cc2ccccc2F)CN1C(=O)Cn1cncn1]
106
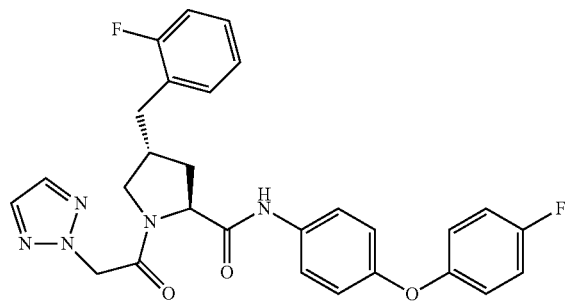 [SMILES: O=C(Nc1ccc(Oc2ccc(F)cc2)cc1)[C@@H]1C[C@@H](Cc2ccccc2F)CN1C(=O)Cn1nccn1]
107
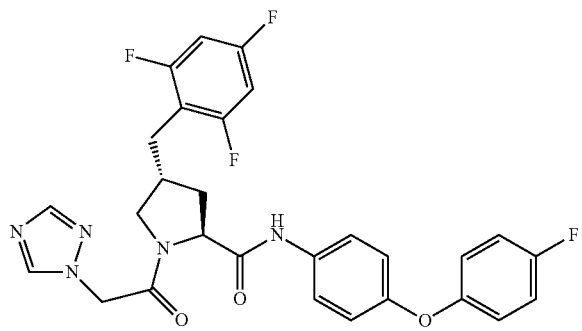 [SMILES: O=C(Nc1ccc(Oc2ccc(F)cc2)cc1)[C@@H]1C[C@@H](Cc2c(F)cc(F)cc2F)CN1C(=O)Cn1cncn1]
108
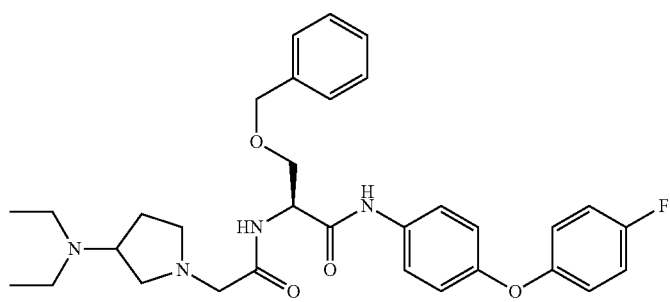 [SMILES: CCN(CC)C1CCN(CC(=O)N[C@@H](COCc2ccccc2)C(=O)Nc2ccc(Oc3ccc(F)cc3)cc2)C1]
109

TABLE 1-continued
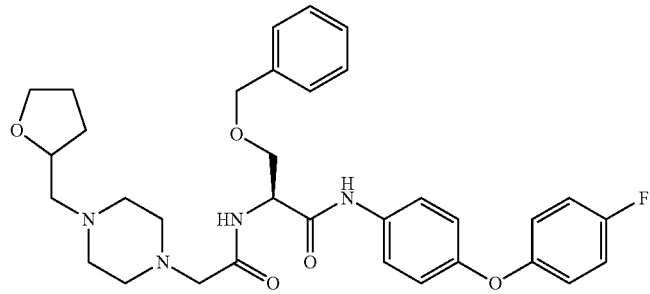 [SMILES: O=C(CN1CCN(CC2CCCO2)CC1)N[C@@H](COCc1ccccc1)C(=O)Nc1ccc(Oc2ccc(F)cc2)cc1]
110
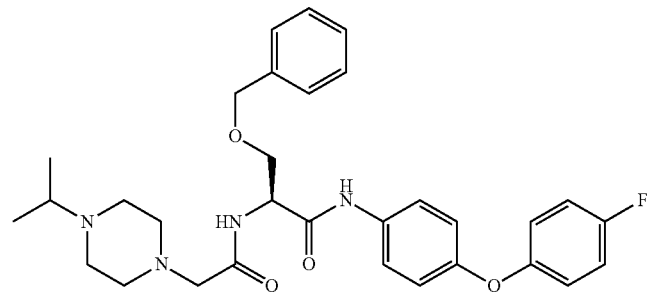 [SMILES: CC(C)N1CCN(CC(=O)N[C@@H](COCc2ccccc2)C(=O)Nc2ccc(Oc3ccc(F)cc3)cc2)CC1]
111
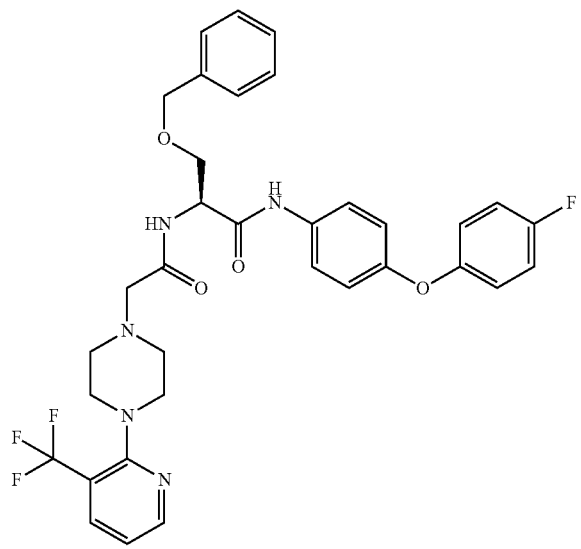 [SMILES: O=C(CN1CCN(c2ncccc2C(F)(F)F)CC1)N[C@@H](COCc1ccccc1)C(=O)Nc1ccc(Oc2ccc(F)cc2)cc1]
112

TABLE 1-continued
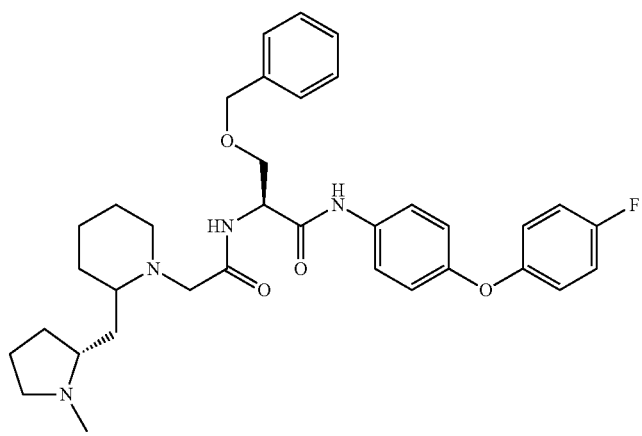 [SMILES: CN1CCC[C@@H]1CC1CCCCN1CC(=O)N[C@@H](COCc1ccccc1)C(=O)Nc1ccc(Oc2ccc(F)cc2)cc1]
113
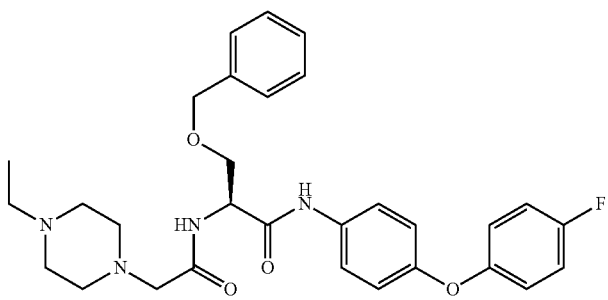 [SMILES: CCN1CCN(CC(=O)N[C@@H](COCc2ccccc2)C(=O)Nc2ccc(Oc3ccc(F)cc3)cc2)CC1]
114
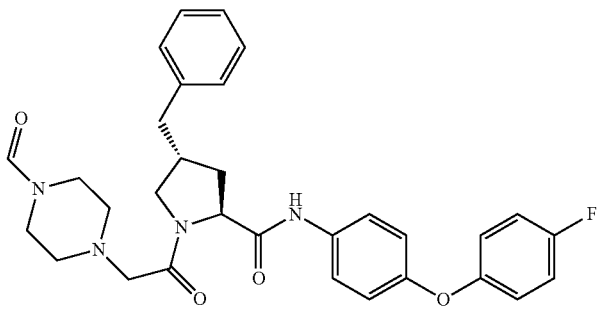 [SMILES: O=CN1CCN(CC(=O)N2C[C@H](Cc3ccccc3)C[C@H]2C(=O)Nc2ccc(Oc3ccc(F)cc3)cc2)CC1]
115
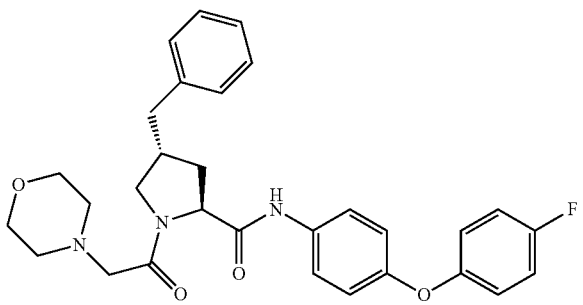 [SMILES: O=C(Nc1ccc(Oc2ccc(F)cc2)cc1)[C@@H]1C[C@@H](Cc2ccccc2)CN1C(=O)CN1CCOCC1]
116

TABLE 1-continued
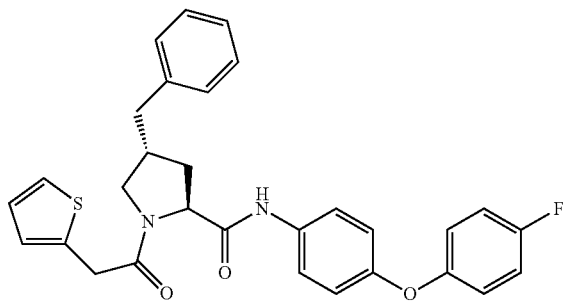 [SMILES: O=C(Nc1ccc(Oc2ccc(F)cc2)cc1)[C@@H]1C[C@@H](Cc2ccccc2)CN1C(=O)Cc1cccs1]
117
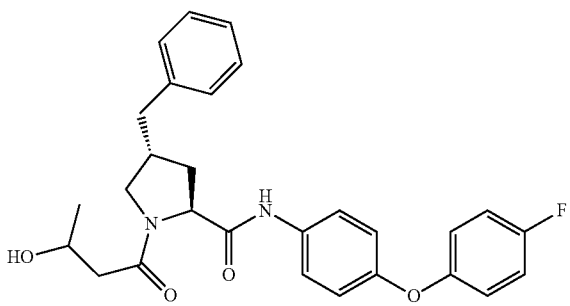 [SMILES: CC(O)CC(=O)N1C[C@H](Cc2ccccc2)C[C@H]1C(=O)Nc1ccc(Oc2ccc(F)cc2)cc1]
118
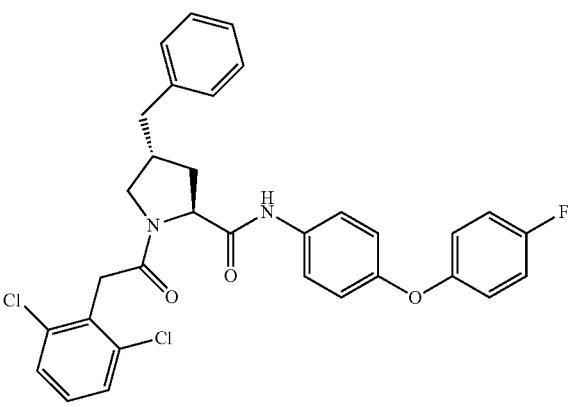 [SMILES: O=C(Nc1ccc(Oc2ccc(F)cc2)cc1)[C@@H]1C[C@@H](Cc2ccccc2)CN1C(=O)Cc1c(Cl)cccc1Cl]
119
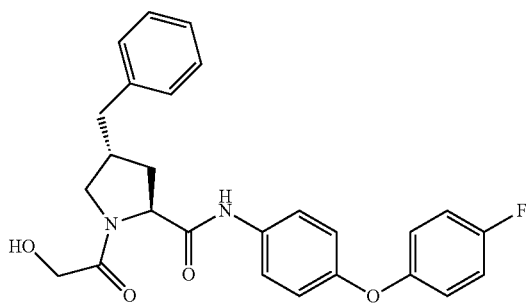 [SMILES: O=C(Nc1ccc(Oc2ccc(F)cc2)cc1)[C@@H]1C[C@@H](Cc2ccccc2)CN1C(=O)CO]
120

TABLE 1-continued
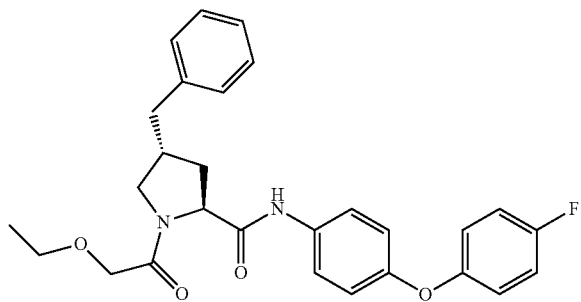
121
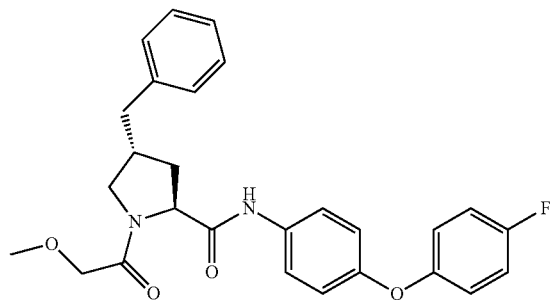 [SMILES: COCC(=O)N1C[C@H](Cc2ccccc2)C[C@H]1C(=O)Nc1ccc(Oc2ccc(F)cc2)cc1]
122
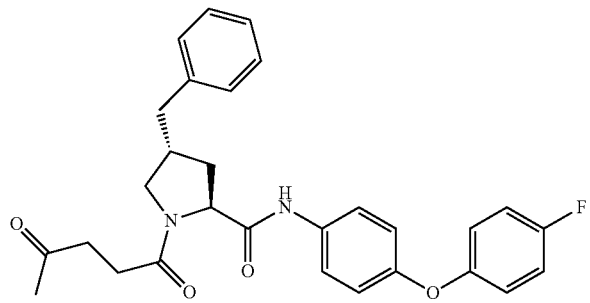 [SMILES: CC(=O)CCC(=O)N1C[C@H](Cc2ccccc2)C[C@H]1C(=O)Nc1ccc(Oc2ccc(F)cc2)cc1]
123
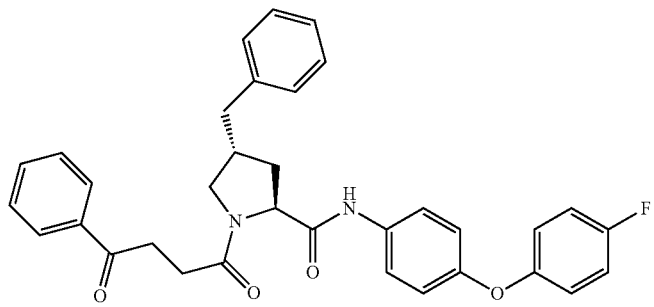 [SMILES: O=C(CCC(=O)N1C[C@H](Cc2ccccc2)C[C@H]1C(=O)Nc1ccc(Oc2ccc(F)cc2)cc1)c1ccccc1]
124

TABLE 1-continued
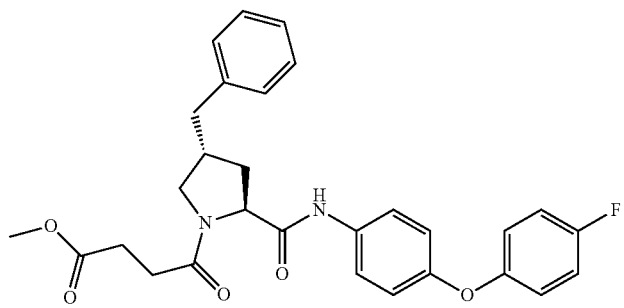 [SMILES: COC(=O)CCC(=O)N1C[C@H](Cc2ccccc2)C[C@H]1C(=O)Nc1ccc(Oc2ccc(F)cc2)cc1]
125
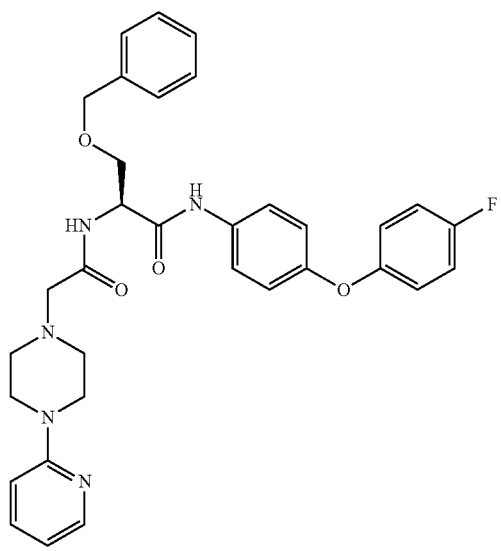 [SMILES: O=C(CN1CCN(c2ccccn2)CC1)N[C@@H](COCc1ccccc1)C(=O)Nc1ccc(Oc2ccc(F)cc2)cc1]
126
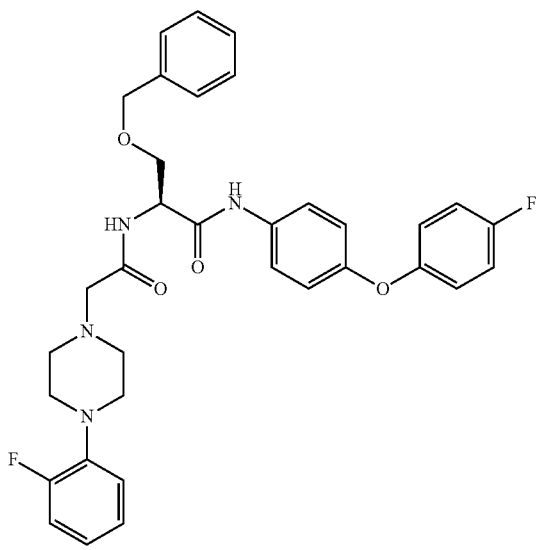 [SMILES: O=C(CN1CCN(c2ccccc2F)CC1)N[C@@H](COCc1ccccc1)C(=O)Nc1ccc(Oc2ccc(F)cc2)cc1]
127

TABLE 1-continued
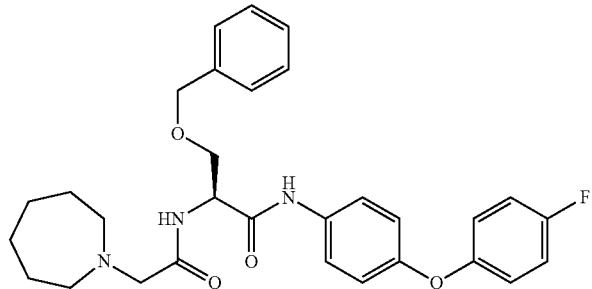 [SMILES: O=C(CN1CCCCCC1)N[C@@H](COCc1ccccc1)C(=O)Nc1ccc(Oc2ccc(F)cc2)cc1]
128
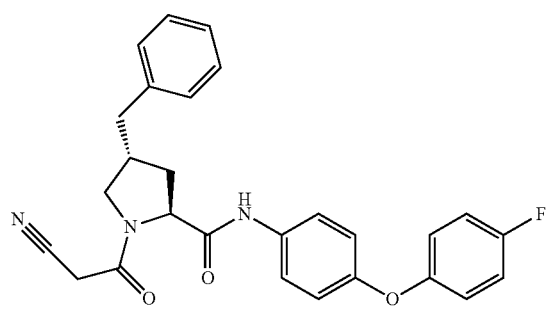 [SMILES: N#CCC(=O)N1C[C@H](Cc2ccccc2)C[C@H]1C(=O)Nc1ccc(Oc2ccc(F)cc2)cc1]
129
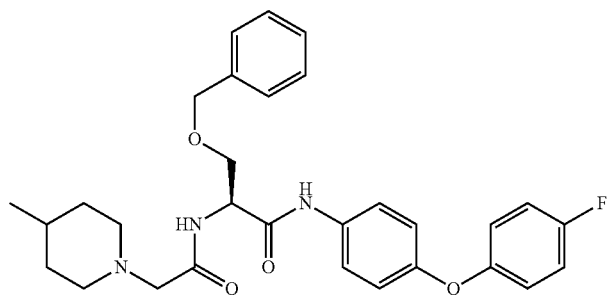
130
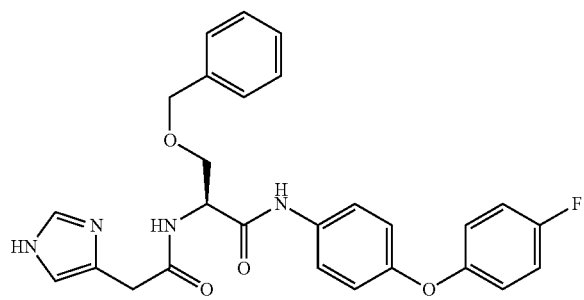 [SMILES: O=C(Cc1c[nH]cn1)N[C@@H](COCc1ccccc1)C(=O)Nc1ccc(Oc2ccc(F)cc2)cc1]
131

TABLE 1-continued
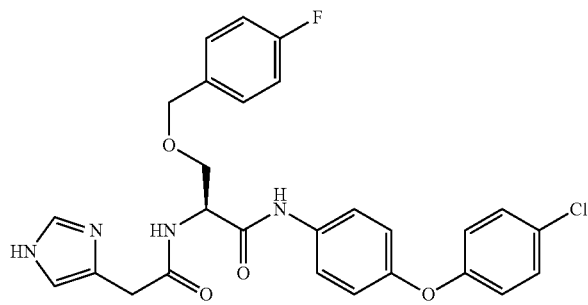 [SMILES: O=C(Cc1c[nH]cn1)N[C@@H](COCc1ccc(F)cc1)C(=O)Nc1ccc(Oc2ccc(Cl)cc2)cc1]
132
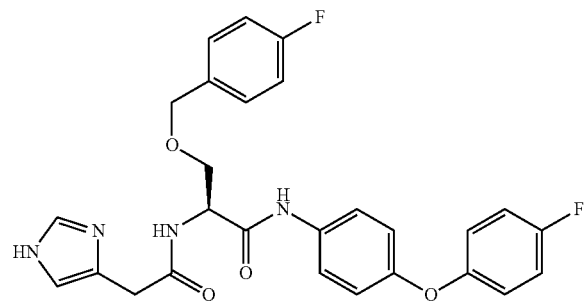 [SMILES: O=C(Cc1c[nH]cn1)N[C@@H](COCc1ccc(F)cc1)C(=O)Nc1ccc(Oc2ccc(F)cc2)cc1]
133
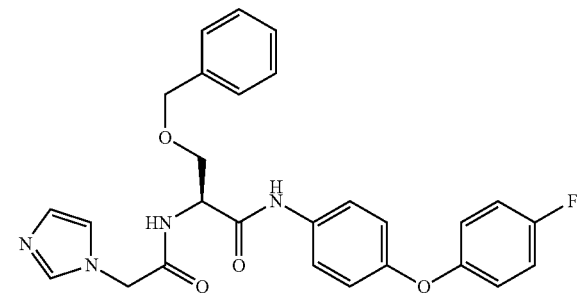 [SMILES: O=C(Cn1ccnc1)N[C@@H](COCc1ccccc1)C(=O)Nc1ccc(Oc2ccc(F)cc2)cc1]
134
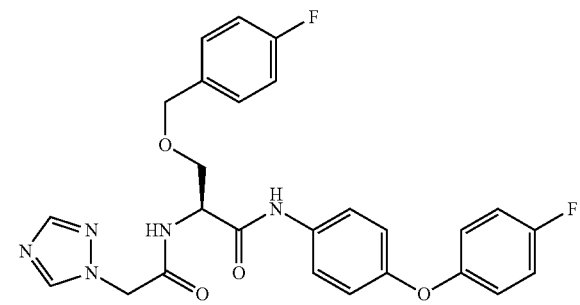 [SMILES: O=C(Cn1cncn1)N[C@@H](COCc1ccc(F)cc1)C(=O)Nc1ccc(Oc2ccc(F)cc2)cc1]
135

TABLE 1-continued
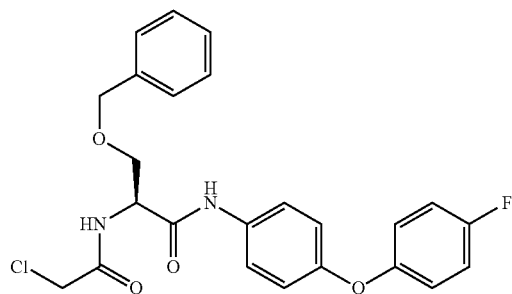 [SMILES: O=C(CCl)N[C@@H](COCc1ccccc1)C(=O)Nc1ccc(Oc2ccc(F)cc2)cc1]
136
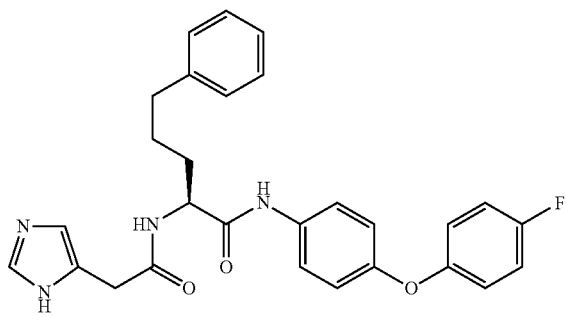 [SMILES: O=C(Cc1cnc[nH]1)N[C@@H](CCCc1ccccc1)C(=O)Nc1ccc(Oc2ccc(F)cc2)cc1]
137
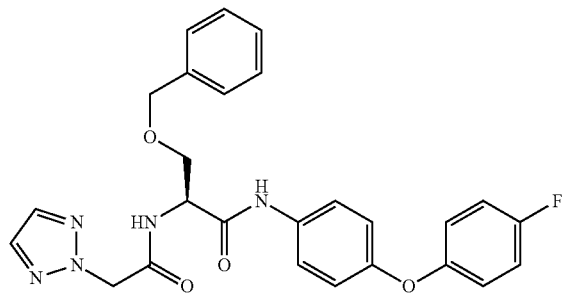 [SMILES: O=C(Cn1nccn1)N[C@@H](COCc1ccccc1)C(=O)Nc1ccc(Oc2ccc(F)cc2)cc1]
138
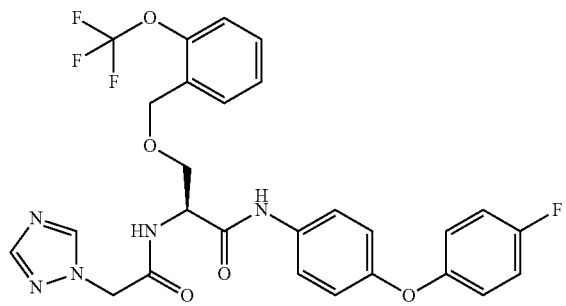 [SMILES: O=C(Cn1cncn1)N[C@@H](COCc1ccccc1OC(F)(F)F)C(=O)Nc1ccc(Oc2ccc(F)cc2)cc1]
139

TABLE 1-continued
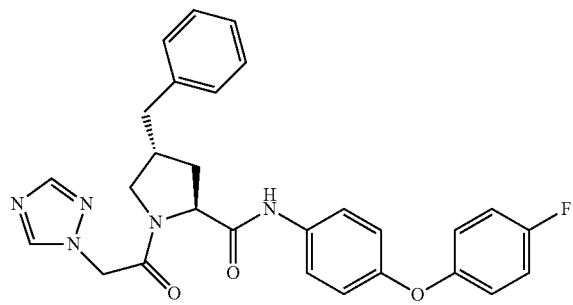 [SMILES: O=C(Nc1ccc(Oc2ccc(F)cc2)cc1)[C@@H]1C[C@@H](Cc2ccccc2)CN1C(=O)Cn1cncn1]
140
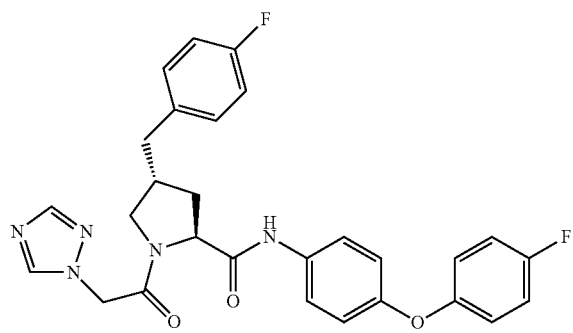 [SMILES: O=C(Nc1ccc(Oc2ccc(F)cc2)cc1)[C@@H]1C[C@@H](Cc2ccc(F)cc2)CN1C(=O)Cn1cncn1]
141
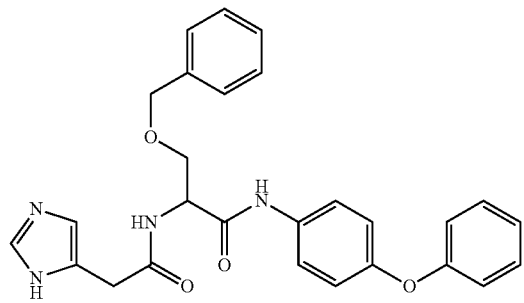 [SMILES: O=C(Cc1cnc[nH]1)NC(COCc1ccccc1)C(=O)Nc1ccc(Oc2ccccc2)cc1]
142
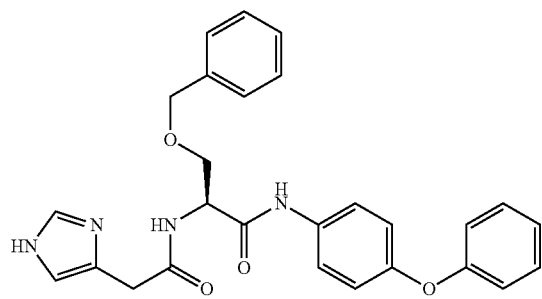
143

TABLE 1-continued
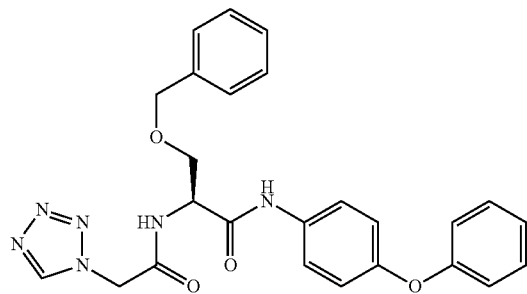 [SMILES: O=C(Cn1cnnn1)N[C@@H](COCc1ccccc1)C(=O)Nc1ccc(Oc2ccccc2)cc1]
144
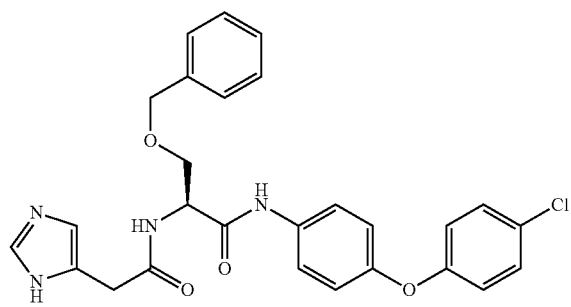 [SMILES: O=C(Cc1cnc[nH]1)N[C@@H](COCc1ccccc1)C(=O)Nc1ccc(Oc2ccc(Cl)cc2)cc1]
145
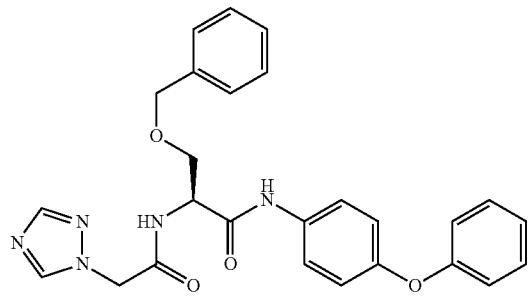 [SMILES: O=C(Cn1cncn1)N[C@@H](COCc1ccccc1)C(=O)Nc1ccc(Oc2ccccc2)cc1]
146
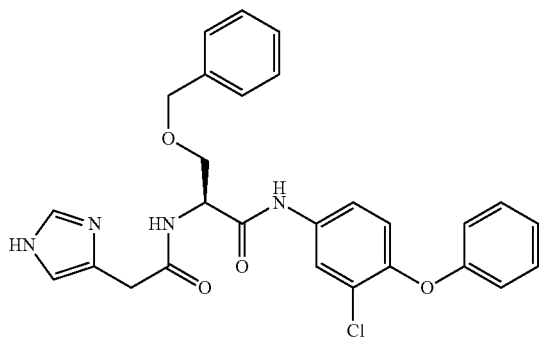 [SMILES: O=C(Cc1c[nH]cn1)N[C@@H](COCc1ccccc1)C(=O)Nc1ccc(Oc2ccccc2)c(Cl)c1]
147

TABLE 1-continued
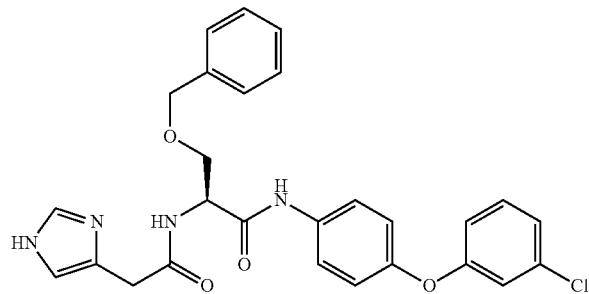 [SMILES: O=C(Cc1c[nH]cn1)N[C@@H](COCc1ccccc1)C(=O)Nc1ccc(Oc2cccc(Cl)c2)cc1]
148
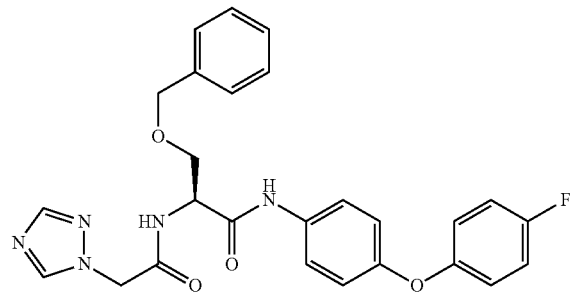 [SMILES: O=C(Cn1cncn1)N[C@@H](COCc1ccccc1)C(=O)Nc1ccc(Oc2ccc(F)cc2)cc1]
149
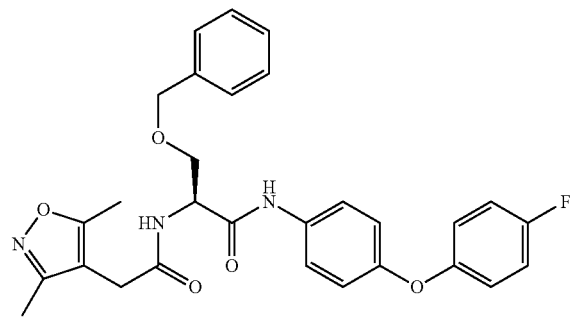 [SMILES: Cc1noc(C)c1CC(=O)N[C@@H](COCc1ccccc1)C(=O)Nc1ccc(Oc2ccc(F)cc2)cc1]
150
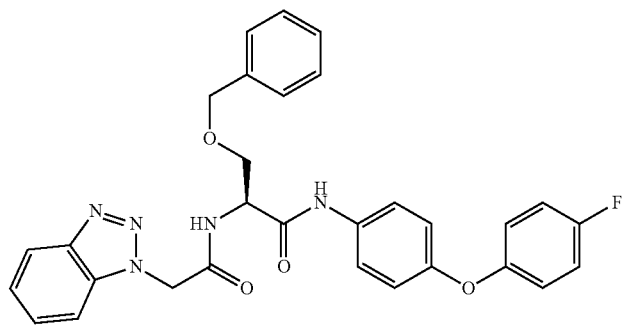 [SMILES: O=C(Cn1nnc2ccccc21)N[C@@H](COCc1ccccc1)C(=O)Nc1ccc(Oc2ccc(F)cc2)cc1]
151

TABLE 1-continued
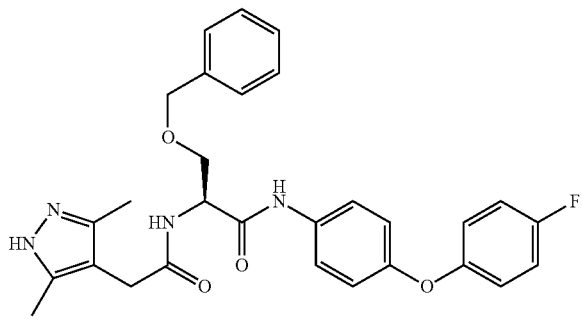 [SMILES: Cc1n[nH]c(C)c1CC(=O)N[C@@H](COCc1ccccc1)C(=O)Nc1ccc(Oc2ccc(F)cc2)cc1]
152
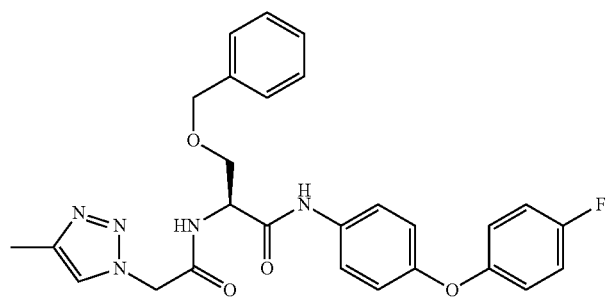 [SMILES: Cc1cn(CC(=O)N[C@@H](COCc2ccccc2)C(=O)Nc2ccc(Oc3ccc(F)cc3)cc2)nn1]
153
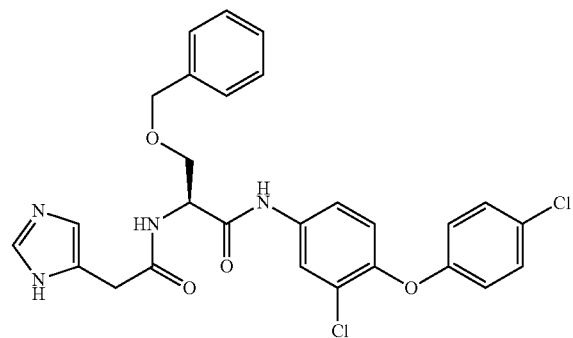 [SMILES: O=C(Cc1cnc[nH]1)N[C@@H](COCc1ccccc1)C(=O)Nc1ccc(Oc2ccc(Cl)cc2)c(Cl)c1]
154
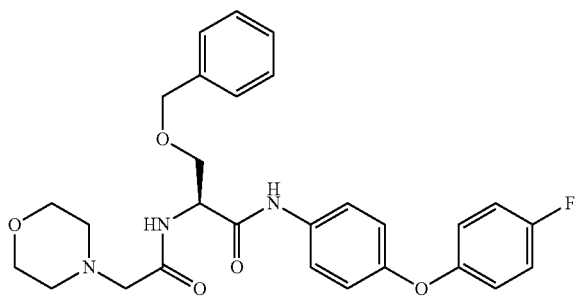 [SMILES: O=C(CN1CCOCC1)N[C@@H](COCc1ccccc1)C(=O)Nc1ccc(Oc2ccc(F)cc2)cc1]
155

TABLE 1-continued
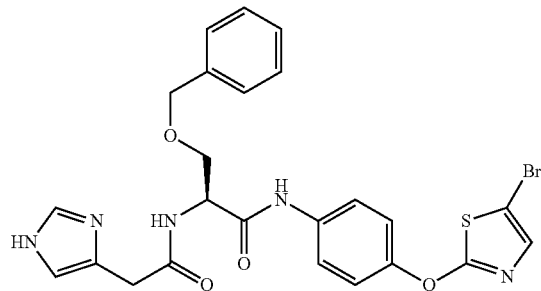 [SMILES: O=C(Cc1c[nH]cn1)N[C@@H](COCc1ccccc1)C(=O)Nc1ccc(Oc2ncc(Br)s2)cc1]
156
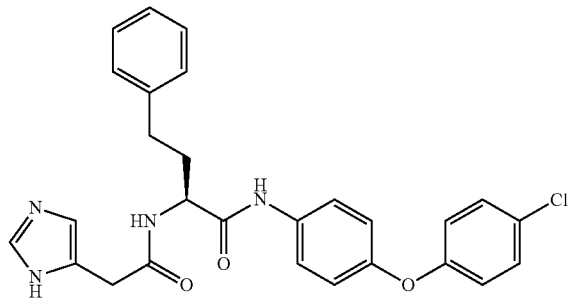 [SMILES: O=C(Cc1cnc[nH]1)N[C@@H](CCc1ccccc1)C(=O)Nc1ccc(Oc2ccc(Cl)cc2)cc1]
157
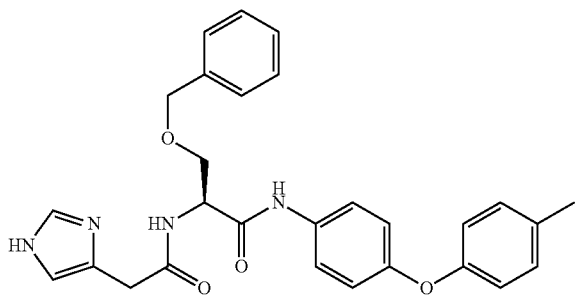
158
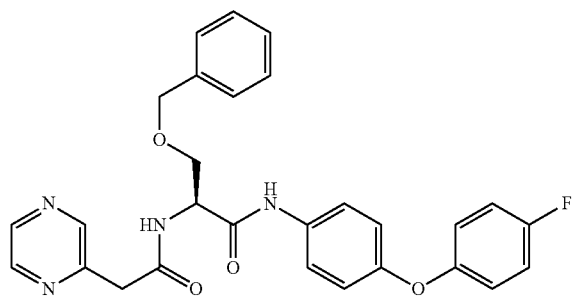 [SMILES: O=C(Cc1cnccn1)N[C@@H](COCc1ccccc1)C(=O)Nc1ccc(Oc2ccc(F)cc2)cc1]
159

TABLE 1-continued
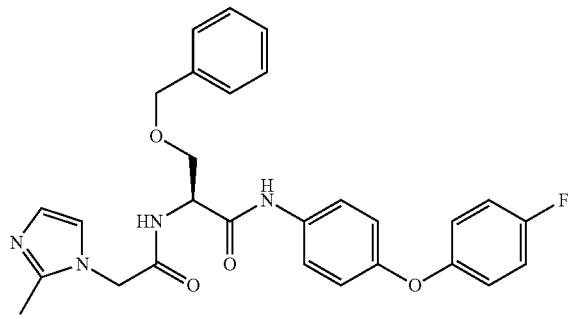 [SMILES: Cc1nccn1CC(=O)N[C@@H](COCc1ccccc1)C(=O)Nc1ccc(Oc2ccc(F)cc2)cc1]
160
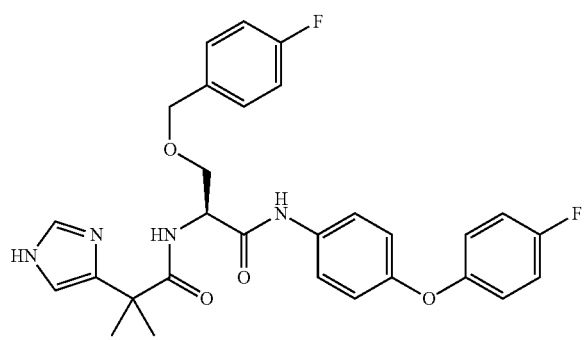 [SMILES: CC(C)(C(=O)N[C@@H](COCc1ccc(F)cc1)C(=O)Nc1ccc(Oc2ccc(F)cc2)cc1)c1c[nH]cn1]
161
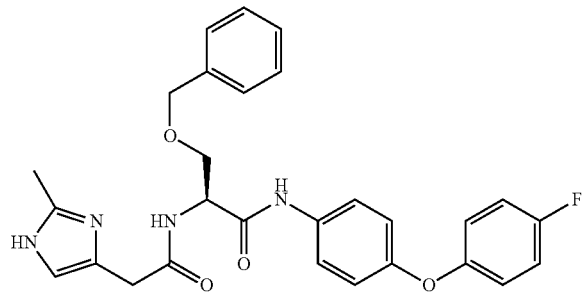 [SMILES: Cc1nc(CC(=O)N[C@@H](COCc2ccccc2)C(=O)Nc2ccc(Oc3ccc(F)cc3)cc2)c[nH]1]
162
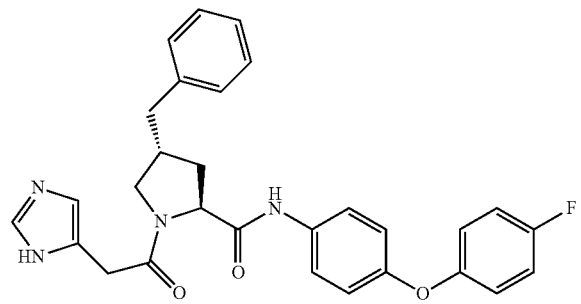 [SMILES: O=C(Nc1ccc(Oc2ccc(F)cc2)cc1)[C@@H]1C[C@@H](Cc2ccccc2)CN1C(=O)Cc1cnc[nH]1]
163

TABLE 1-continued
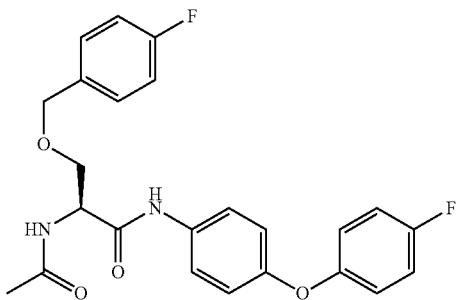 [SMILES: CC(=O)N[C@@H](COCc1ccc(F)cc1)C(=O)Nc1ccc(Oc2ccc(F)cc2)cc1]
164
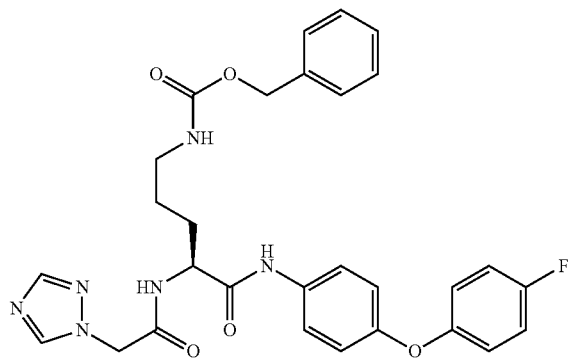 [SMILES: O=C(Cn1cncn1)N[C@@H](CCCNC(=O)OCc1ccccc1)C(=O)Nc1ccc(Oc2ccc(F)cc2)cc1]
165
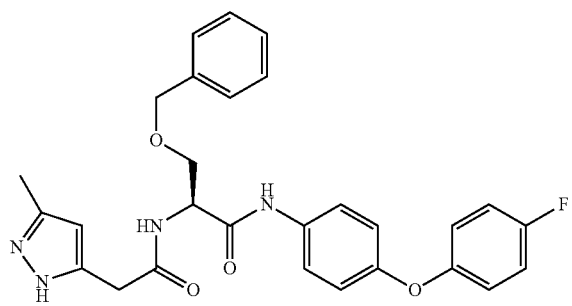 [SMILES: Cc1cc(CC(=O)N[C@@H](COCc2ccccc2)C(=O)Nc2ccc(Oc3ccc(F)cc3)cc2)[nH]n1]
166
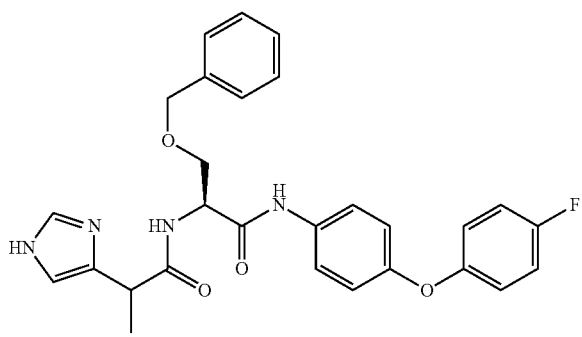 [SMILES: CC(C(=O)N[C@@H](COCc1ccccc1)C(=O)Nc1ccc(Oc2ccc(F)cc2)cc1)c1c[nH]cn1]
167

TABLE 1-continued
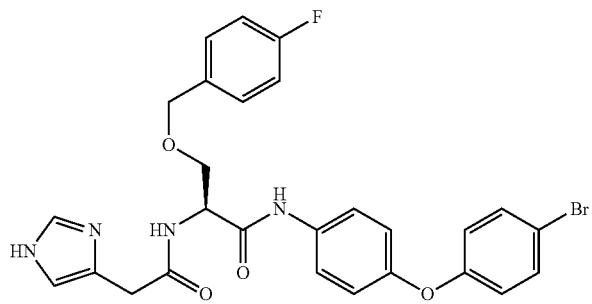 [SMILES: O=C(Cc1c[nH]cn1)N[C@@H](COCc1ccc(F)cc1)C(=O)Nc1ccc(Oc2ccc(Br)cc2)cc1]
168
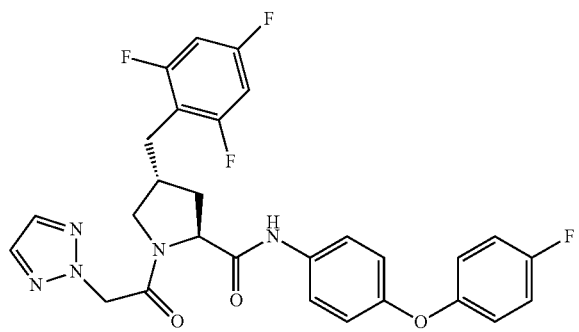 [SMILES: O=C(Nc1ccc(Oc2ccc(F)cc2)cc1)[C@@H]1C[C@@H](Cc2c(F)cc(F)cc2F)CN1C(=O)Cn1nccn1]
169
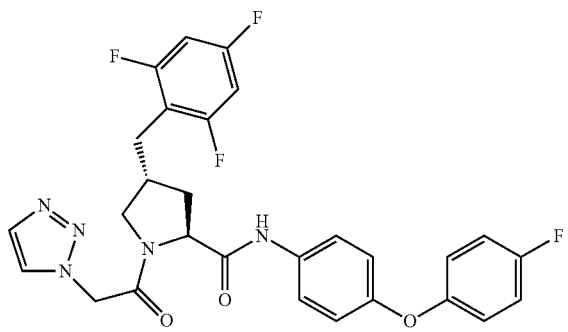
170
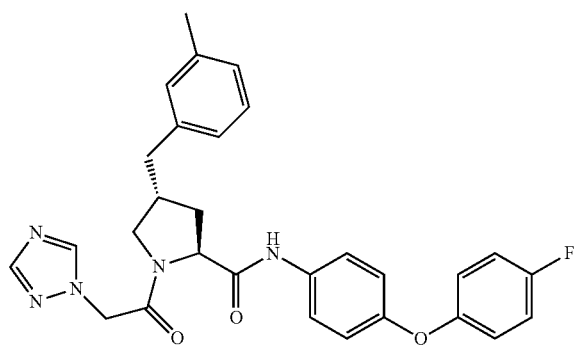 [SMILES: Cc1cccc(C[C@@H]2C[C@@H](C(=O)Nc3ccc(Oc4ccc(F)cc4)cc3)N(C(=O)Cn3cncn3)C2)c1]
171

TABLE 1-continued
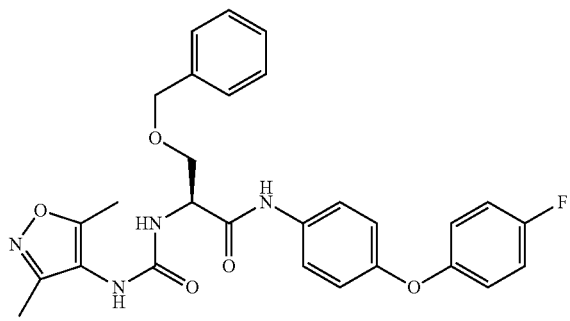 [SMILES: Cc1noc(C)c1NC(=O)N[C@@H](COCc1ccccc1)C(=O)Nc1ccc(Oc2ccc(F)cc2)cc1]
172
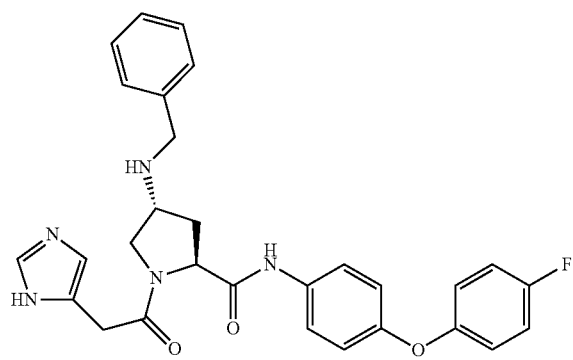 [SMILES: O=C(Nc1ccc(Oc2ccc(F)cc2)cc1)[C@@H]1C[C@@H](NCc2ccccc2)CN1C(=O)Cc1cnc[nH]1]
173
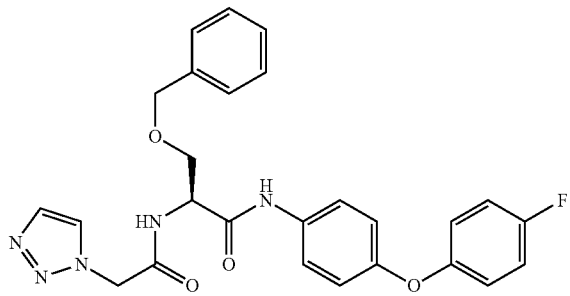 [SMILES: O=C(Cn1ccnn1)N[C@@H](COCc1ccccc1)C(=O)Nc1ccc(Oc2ccc(F)cc2)cc1]
174
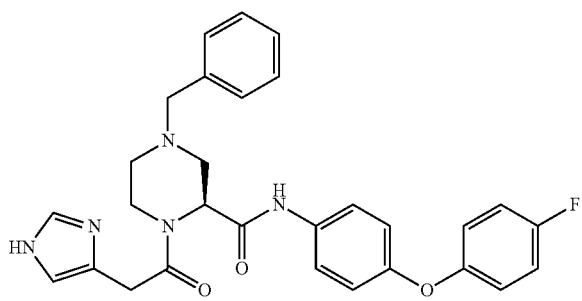 [SMILES: O=C(Nc1ccc(Oc2ccc(F)cc2)cc1)[C@@H]1CN(Cc2ccccc2)CCN1C(=O)Cc1c[nH]cn1]
175

TABLE 1-continued
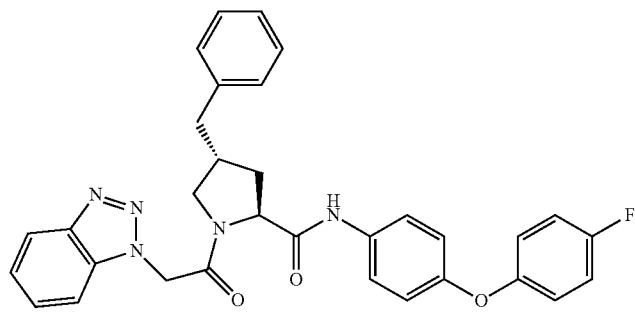 [SMILES: O=C(Nc1ccc(Oc2ccc(F)cc2)cc1)[C@@H]1C[C@@H](Cc2ccccc2)CN1C(=O)Cn1nnc2ccccc21]
176
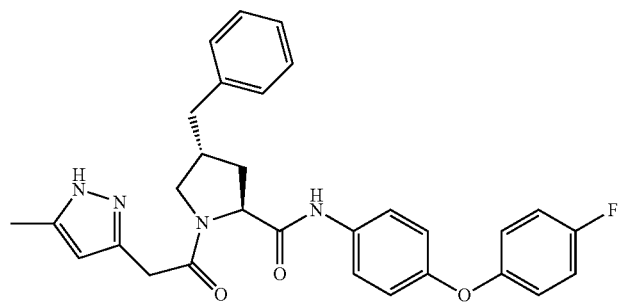 [SMILES: Cc1cc(CC(=O)N2C[C@H](Cc3ccccc3)C[C@H]2C(=O)Nc2ccc(Oc3ccc(F)cc3)cc2)n[nH]1]
177
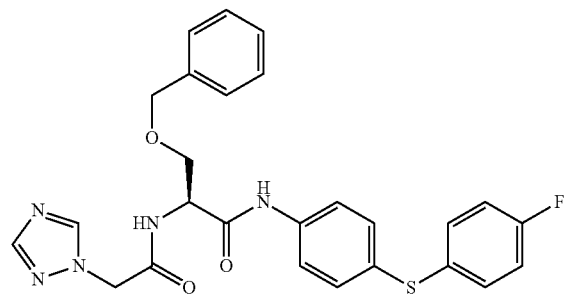
178
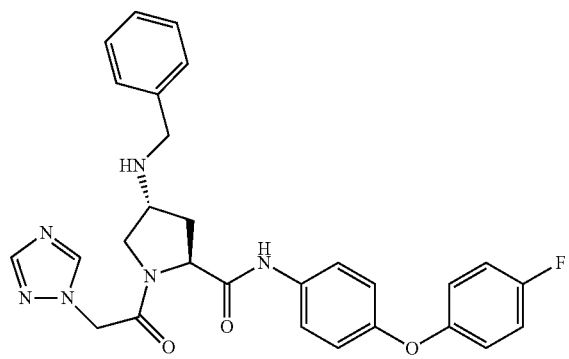 [SMILES: O=C(Nc1ccc(Oc2ccc(F)cc2)cc1)[C@@H]1C[C@@H](NCc2ccccc2)CN1C(=O)Cn1cncn1]
179

TABLE 1-continued
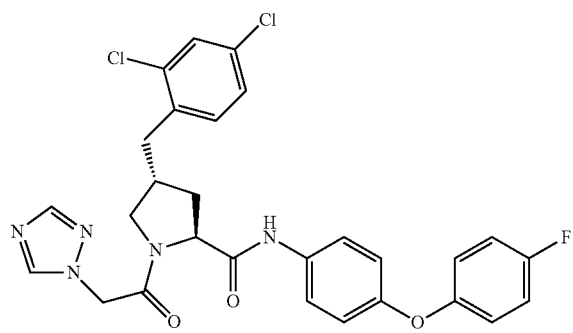 [SMILES: O=C(Nc1ccc(Oc2ccc(F)cc2)cc1)[C@@H]1C[C@@H](Cc2ccc(Cl)cc2Cl)CN1C(=O)Cn1cncn1]
180
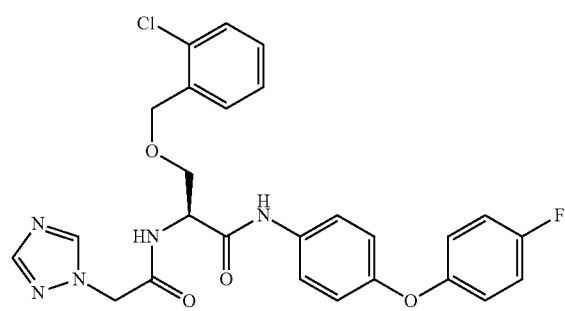 [SMILES: O=C(Cn1cncn1)N[C@@H](COCc1ccccc1Cl)C(=O)Nc1ccc(Oc2ccc(F)cc2)cc1]
181
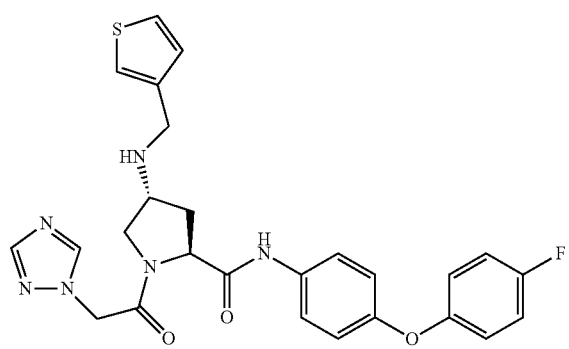 [SMILES: O=C(Nc1ccc(Oc2ccc(F)cc2)cc1)[C@@H]1C[C@@H](NCc2ccsc2)CN1C(=O)Cn1cncn1]
182
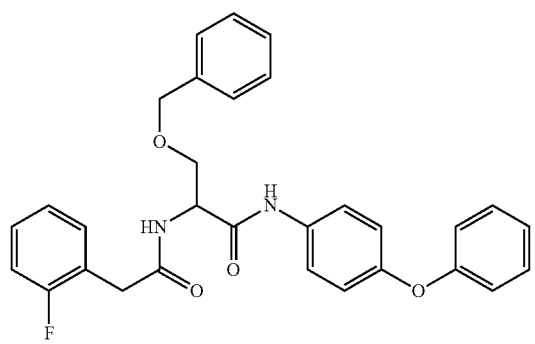 [SMILES: O=C(Cc1ccccc1F)NC(COCc1ccccc1)C(=O)Nc1ccc(Oc2ccccc2)cc1]
183

TABLE 1-continued
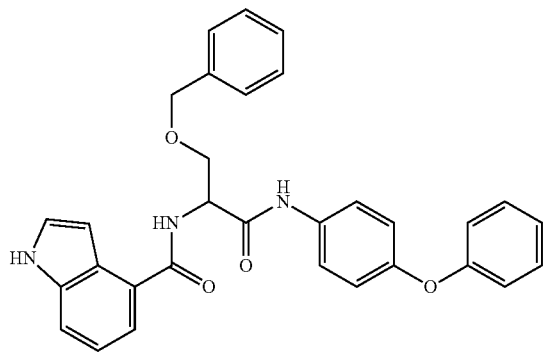 [SMILES: O=C(NC(COCc1ccccc1)C(=O)Nc1ccc(Oc2ccccc2)cc1)c1cccc2[nH]ccc12]
184
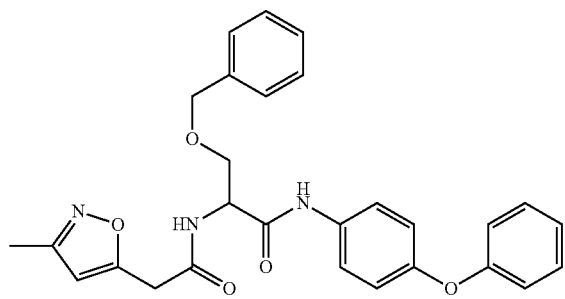 [SMILES: Cc1cc(CC(=O)NC(COCc2ccccc2)C(=O)Nc2ccc(Oc3ccccc3)cc2)on1]
185
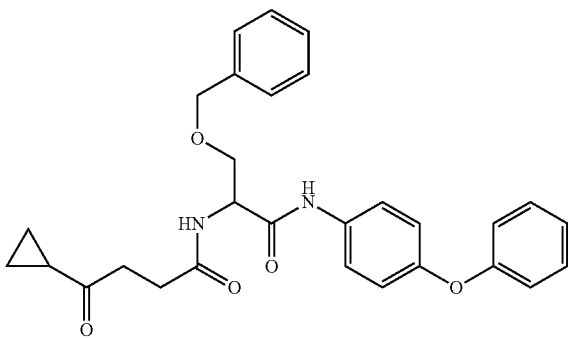 [SMILES: O=C(CCC(=O)C1CC1)NC(COCc1ccccc1)C(=O)Nc1ccc(Oc2ccccc2)cc1]
186
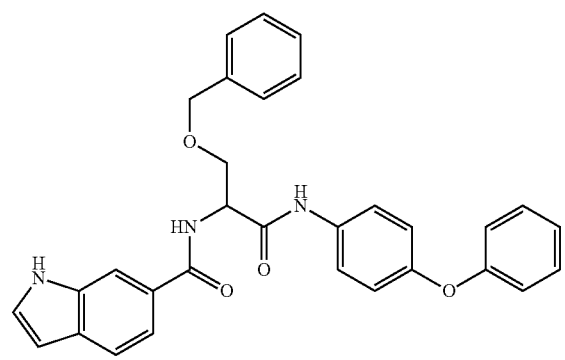 [SMILES: O=C(NC(COCc1ccccc1)C(=O)Nc1ccc(Oc2ccccc2)cc1)c1ccc2cc[nH]c2c1]
187

TABLE 1-continued
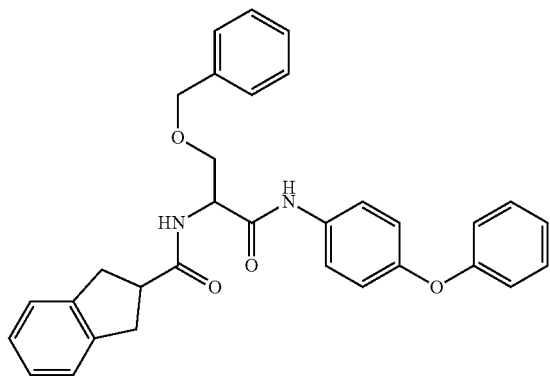 [SMILES: O=C(NC(COCc1ccccc1)C(=O)Nc1ccc(Oc2ccccc2)cc1)C1Cc2ccccc2C1]
188
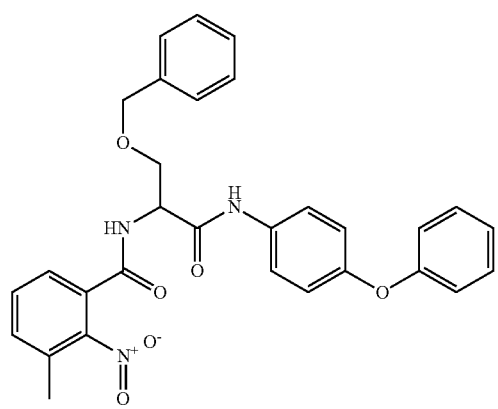
189
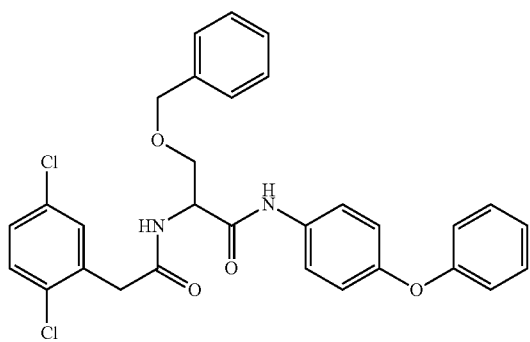 [SMILES: O=C(Cc1cc(Cl)ccc1Cl)NC(COCc1ccccc1)C(=O)Nc1ccc(Oc2ccccc2)cc1]
190
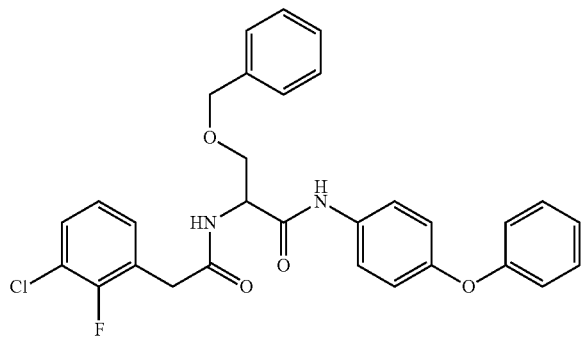 [SMILES: O=C(Cc1cccc(Cl)c1F)NC(COCc1ccccc1)C(=O)Nc1ccc(Oc2ccccc2)cc1]
191

TABLE 1-continued
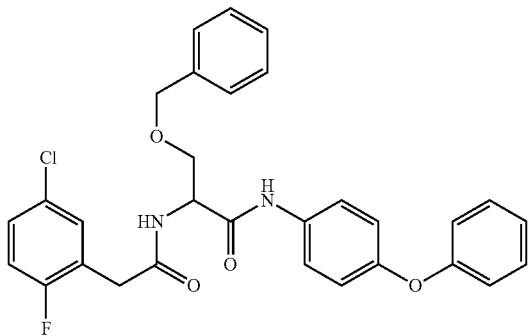 [SMILES: O=C(Cc1cc(Cl)ccc1F)NC(COCc1ccccc1)C(=O)Nc1ccc(Oc2ccccc2)cc1]
192
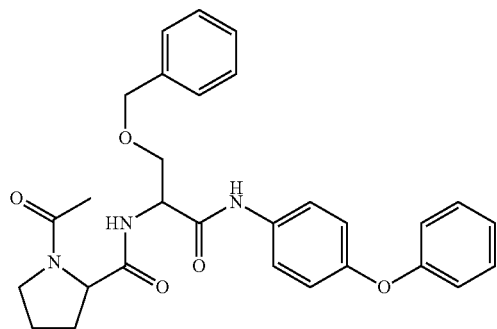 [SMILES: CC(=O)N1CCCC1C(=O)NC(COCc1ccccc1)C(=O)Nc1ccc(Oc2ccccc2)cc1]
193
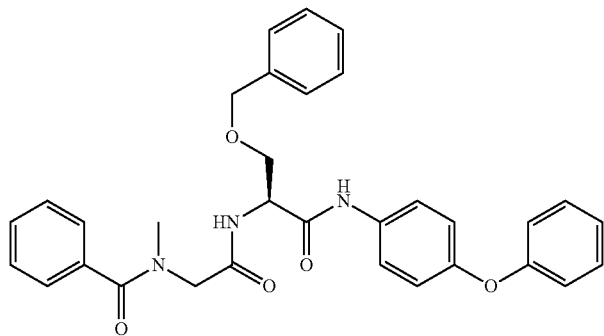 [SMILES: CN(CC(=O)N[C@@H](COCc1ccccc1)C(=O)Nc1ccc(Oc2ccccc2)cc1)C(=O)c1ccccc1]
194
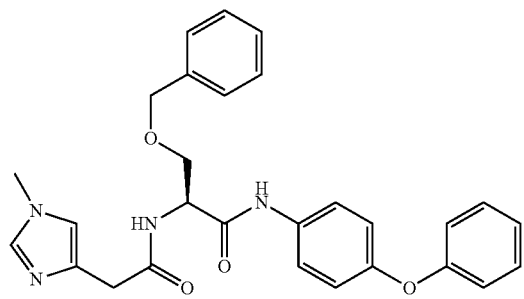 [SMILES: Cn1cnc(CC(=O)N[C@@H](COCc2ccccc2)C(=O)Nc2ccc(Oc3ccccc3)cc2)c1]
195

TABLE 1-continued
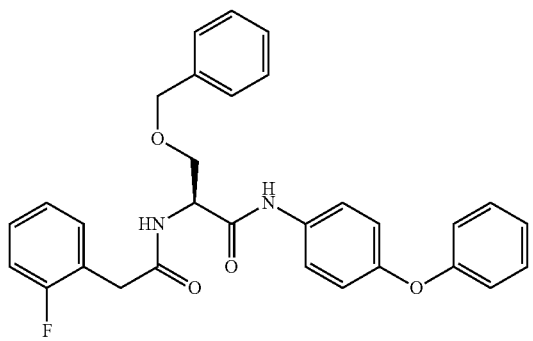 [SMILES: O=C(Cc1ccccc1F)N[C@@H](COCc1ccccc1)C(=O)Nc1ccc(Oc2ccccc2)cc1]
196
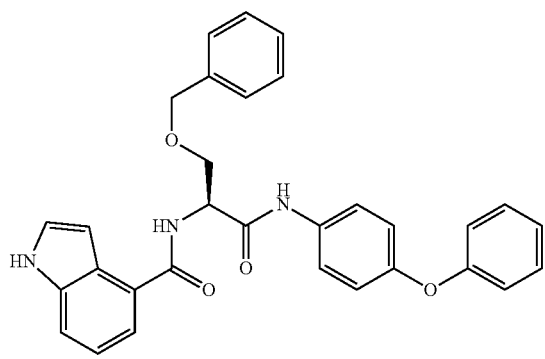 [SMILES: O=C(N[C@@H](COCc1ccccc1)C(=O)Nc1ccc(Oc2ccccc2)cc1)c1cccc2[nH]ccc12]
197
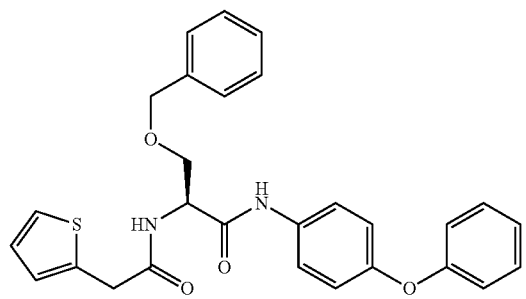 [SMILES: O=C(Cc1cccs1)N[C@@H](COCc1ccccc1)C(=O)Nc1ccc(Oc2ccccc2)cc1]
198
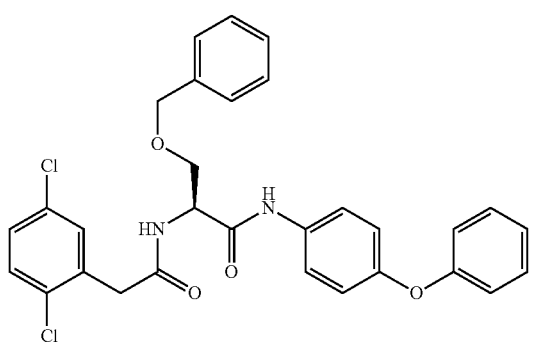 [SMILES: O=C(Cc1cc(Cl)ccc1Cl)N[C@@H](COCc1ccccc1)C(=O)Nc1ccc(Oc2ccccc2)cc1]
199

TABLE 1-continued
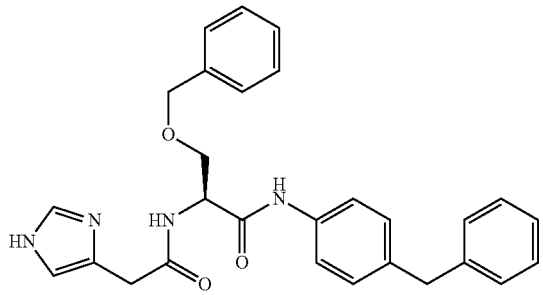 [SMILES: O=C(Cc1c[nH]cn1)N[C@@H](COCc1ccccc1)C(=O)Nc1ccc(Cc2ccccc2)cc1]
200
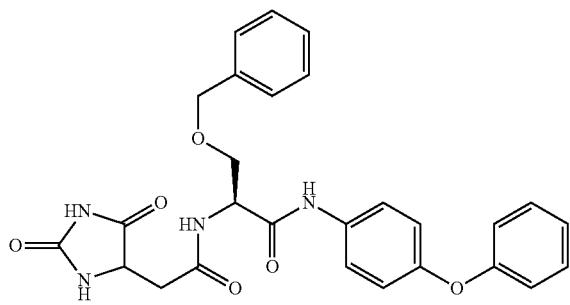 [SMILES: O=C(CC1NC(=O)NC1=O)N[C@@H](COCc1ccccc1)C(=O)Nc1ccc(Oc2ccccc2)cc1]
201
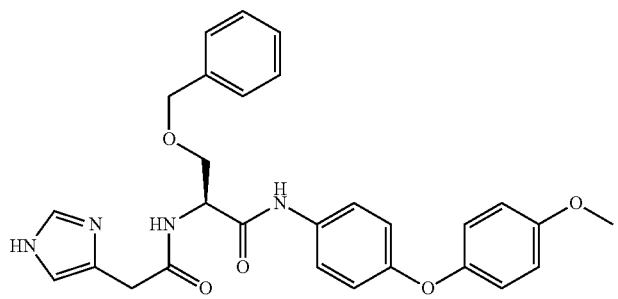 [SMILES: COc1ccc(Oc2ccc(NC(=O)[C@H](COCc3ccccc3)NC(=O)Cc3c[nH]cn3)cc2)cc1]
202
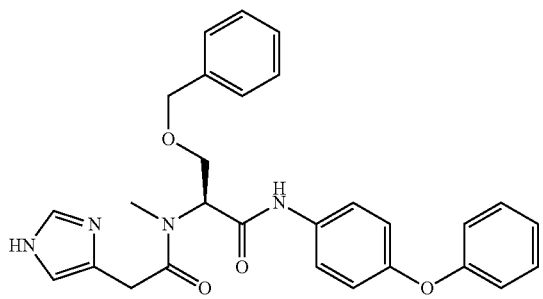 [SMILES: CN(C(=O)Cc1c[nH]cn1)[C@@H](COCc1ccccc1)C(=O)Nc1ccc(Oc2ccccc2)cc1]
203

TABLE 1-continued
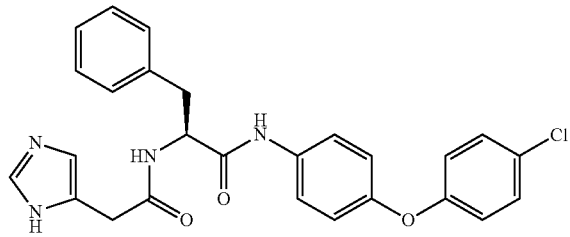 [SMILES: O=C(Cc1cnc[nH]1)N[C@@H](Cc1ccccc1)C(=O)Nc1ccc(Oc2ccc(Cl)cc2)cc1]
204
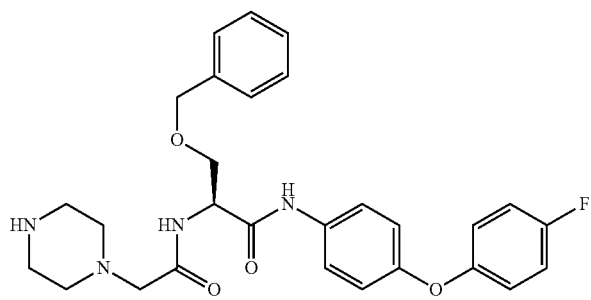 [SMILES: O=C(CN1CCNCC1)N[C@@H](COCc1ccccc1)C(=O)Nc1ccc(Oc2ccc(F)cc2)cc1]
205
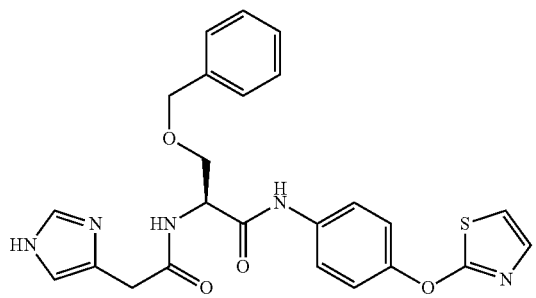 [SMILES: O=C(Cc1c[nH]cn1)N[C@@H](COCc1ccccc1)C(=O)Nc1ccc(Oc2nccs2)cc1]
206
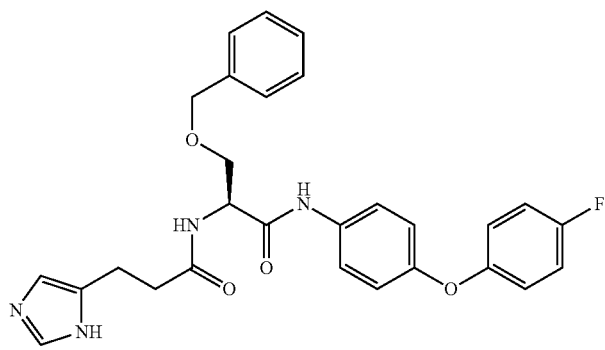 [SMILES: O=C(CCc1cnc[nH]1)N[C@@H](COCc1ccccc1)C(=O)Nc1ccc(Oc2ccc(F)cc2)cc1]
207

TABLE 1-continued
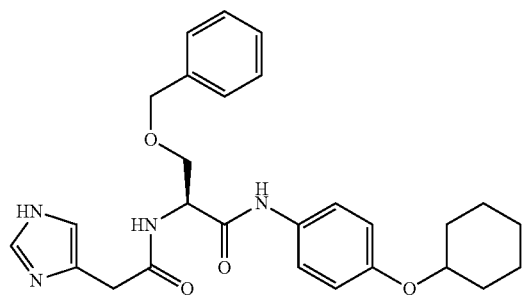 [SMILES: O=C(Cc1c[nH]cn1)N[C@@H](COCc1ccccc1)C(=O)Nc1ccc(OC2CCCCC2)cc1]
208
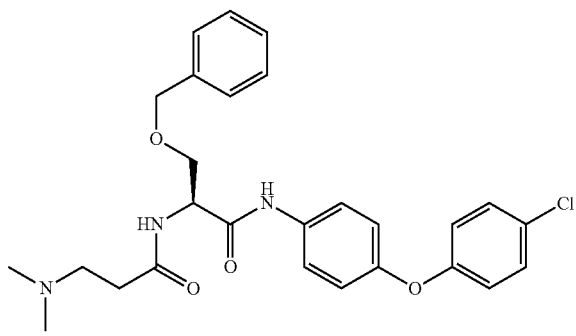 [SMILES: CN(C)CCC(=O)N[C@@H](COCc1ccccc1)C(=O)Nc1ccc(Oc2ccc(Cl)cc2)cc1]
209
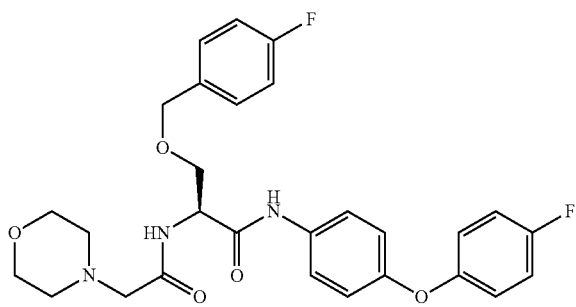 [SMILES: O=C(CN1CCOCC1)N[C@@H](COCc1ccc(F)cc1)C(=O)Nc1ccc(Oc2ccc(F)cc2)cc1]
210
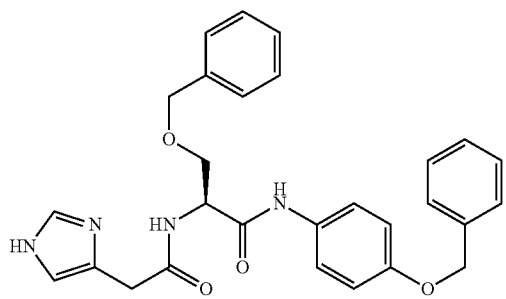 [SMILES: O=C(Cc1c[nH]cn1)N[C@@H](COCc1ccccc1)C(=O)Nc1ccc(OCc2ccccc2)cc1]
211

TABLE 1-continued
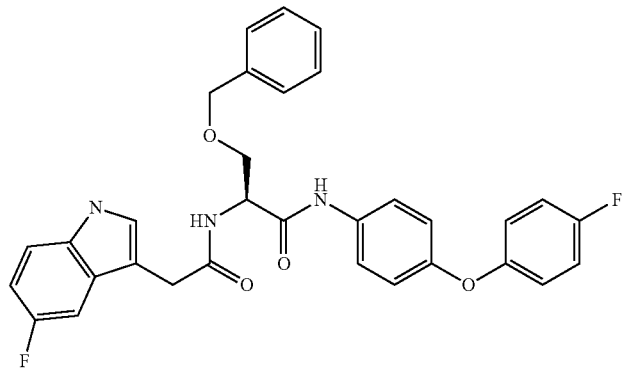 [SMILES: O=C(Cc1c[nH]c2ccc(F)cc12)N[C@@H](COCc1ccccc1)C(=O)Nc1ccc(Oc2ccc(F)cc2)cc1]
212
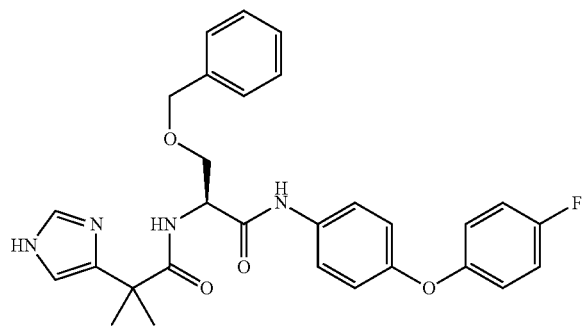 [SMILES: CC(C)(C(=O)N[C@@H](COCc1ccccc1)C(=O)Nc1ccc(Oc2ccc(F)cc2)cc1)c1c[nH]cn1]
213
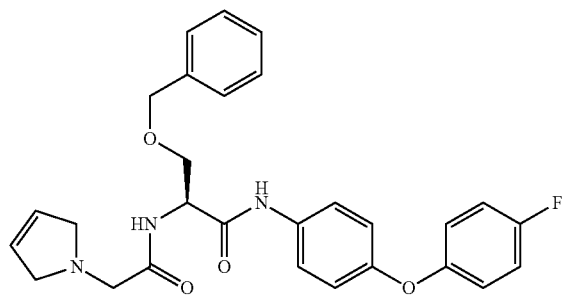 [SMILES: O=C(CN1CC=CC1)N[C@@H](COCc1ccccc1)C(=O)Nc1ccc(Oc2ccc(F)cc2)cc1]
214
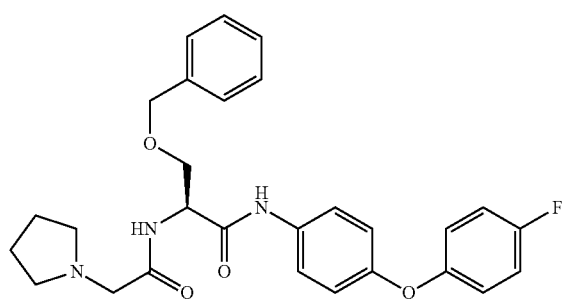 [SMILES: O=C(CN1CCCC1)N[C@@H](COCc1ccccc1)C(=O)Nc1ccc(Oc2ccc(F)cc2)cc1]
215

TABLE 1-continued
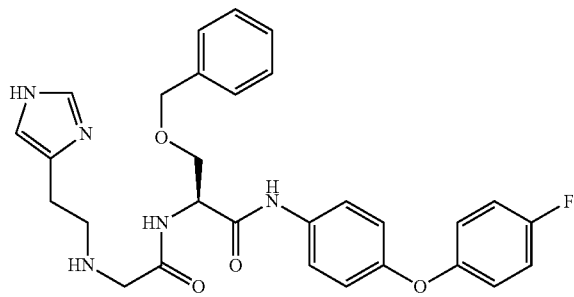 [SMILES: O=C(CNCCc1c[nH]cn1)N[C@@H](COCc1ccccc1)C(=O)Nc1ccc(Oc2ccc(F)cc2)cc1]
216
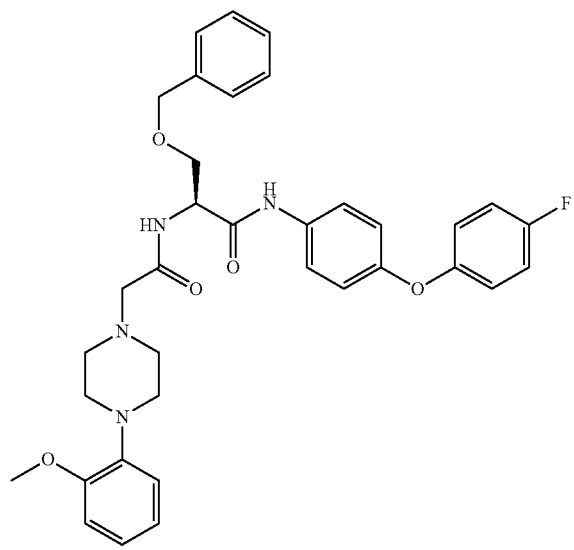 [SMILES: COc1ccccc1N1CCN(CC(=O)N[C@@H](COCc2ccccc2)C(=O)Nc2ccc(Oc3ccc(F)cc3)cc2)CC1]
217
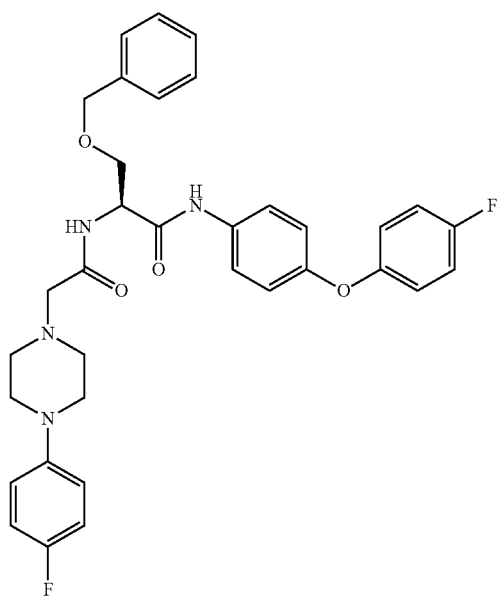 [SMILES: O=C(CN1CCN(c2ccc(F)cc2)CC1)N[C@@H](COCc1ccccc1)C(=O)Nc1ccc(Oc2ccc(F)cc2)cc1]
218

TABLE 1-continued
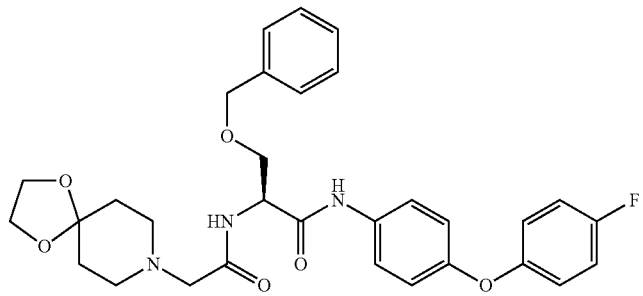 [SMILES: O=C(CN1CCC2(CC1)OCCO2)N[C@@H](COCc1ccccc1)C(=O)Nc1ccc(Oc2ccc(F)cc2)cc1]
219
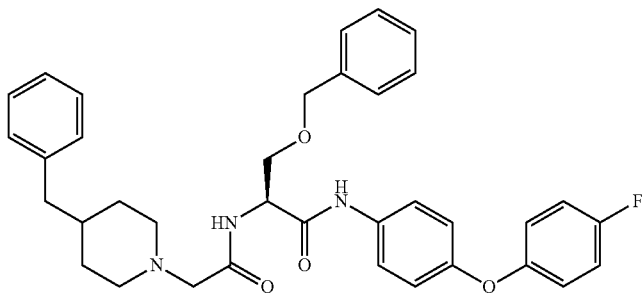 [SMILES: O=C(CN1CCC(Cc2ccccc2)CC1)N[C@@H](COCc1ccccc1)C(=O)Nc1ccc(Oc2ccc(F)cc2)cc1]
220
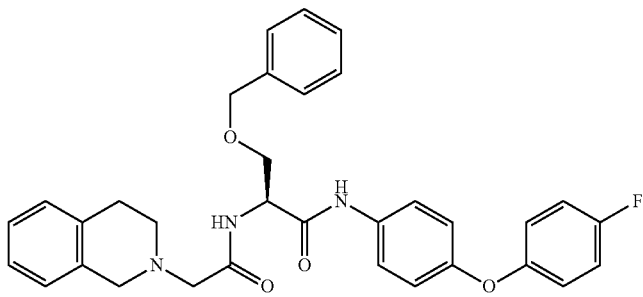 [SMILES: O=C(CN1CCc2ccccc2C1)N[C@@H](COCc1ccccc1)C(=O)Nc1ccc(Oc2ccc(F)cc2)cc1]
221
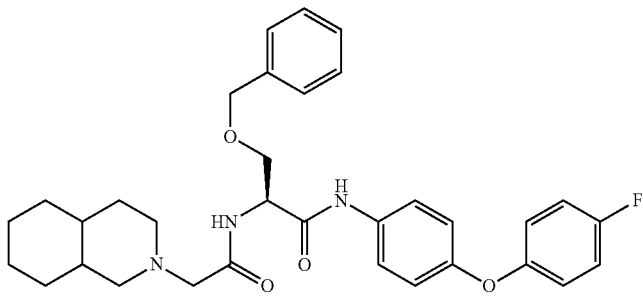 [SMILES: O=C(CN1CCC2CCCCC2C1)N[C@@H](COCc1ccccc1)C(=O)Nc1ccc(Oc2ccc(F)cc2)cc1]
222

TABLE 1-continued
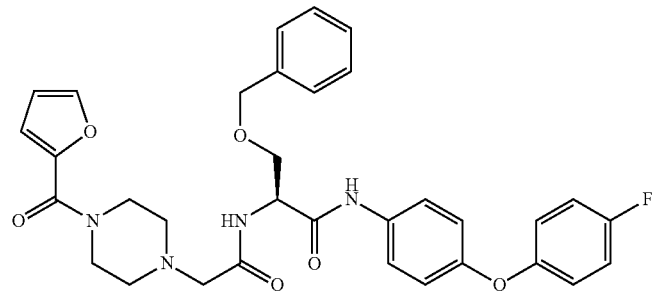 [SMILES: O=C(CN1CCN(C(=O)c2ccco2)CC1)N[C@@H](COCc1ccccc1)C(=O)Nc1ccc(Oc2ccc(F)cc2)cc1]
223
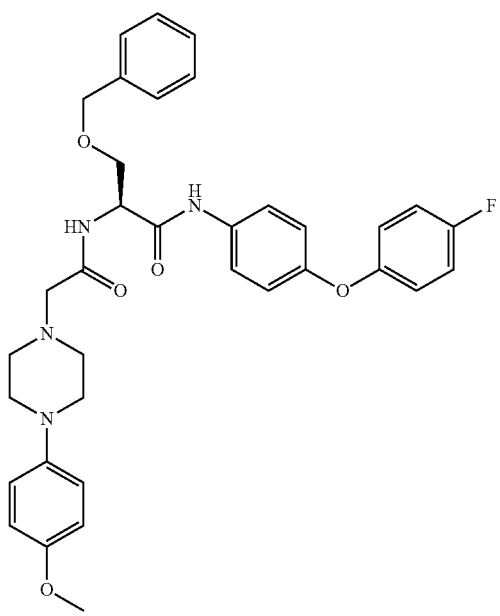 [SMILES: COc1ccc(N2CCN(CC(=O)N[C@@H](COCc3ccccc3)C(=O)Nc3ccc(Oc4ccc(F)cc4)cc3)CC2)cc1]
224
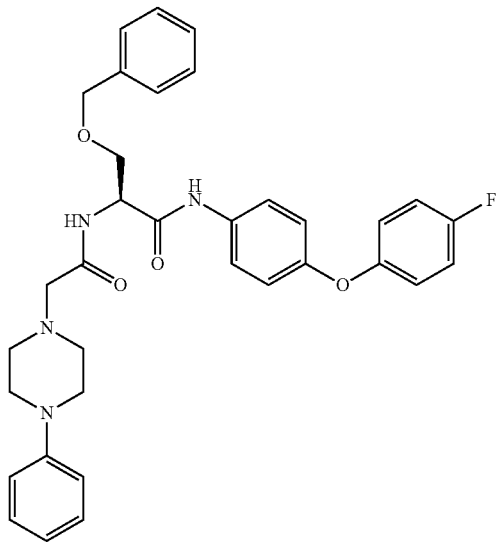 [SMILES: O=C(CN1CCN(c2ccccc2)CC1)N[C@@H](COCc1ccccc1)C(=O)Nc1ccc(Oc2ccc(F)cc2)cc1]
225

TABLE 1-continued
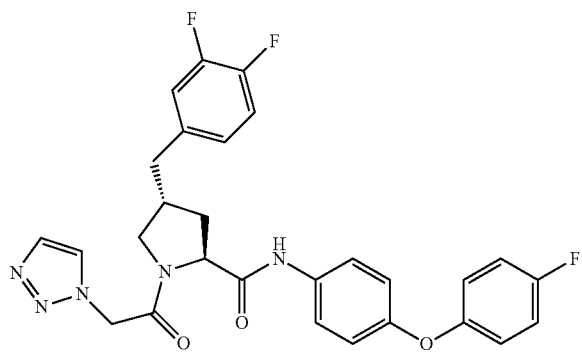 [SMILES: O=C(Nc1ccc(Oc2ccc(F)cc2)cc1)[C@@H]1C[C@@H](Cc2ccc(F)c(F)c2)CN1C(=O)Cn1ccnn1]
226
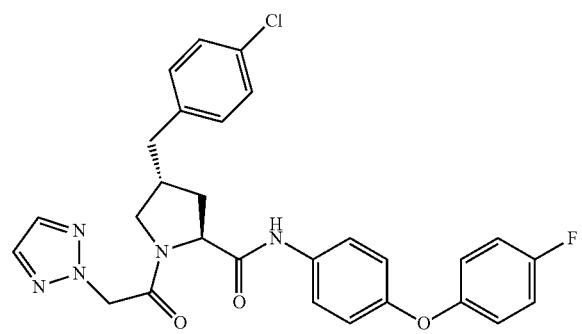 [SMILES: O=C(Nc1ccc(Oc2ccc(F)cc2)cc1)[C@@H]1C[C@@H](Cc2ccc(Cl)cc2)CN1C(=O)Cn1nccn1]
227
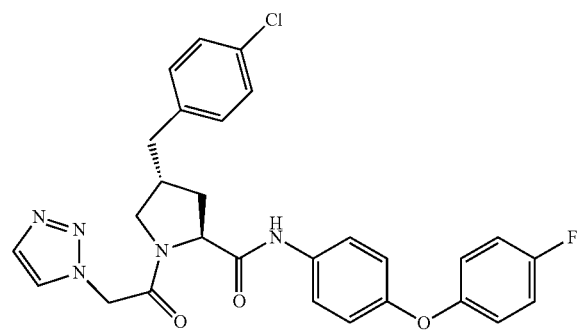 [SMILES: O=C(Nc1ccc(Oc2ccc(F)cc2)cc1)[C@@H]1C[C@@H](Cc2ccc(Cl)cc2)CN1C(=O)Cn1ccnn1]
228

TABLE 1-continued
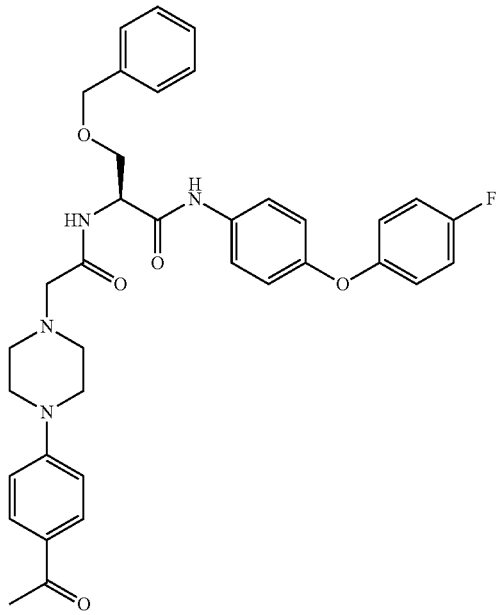 [SMILES: CC(=O)c1ccc(N2CCN(CC(=O)N[C@@H](COCc3ccccc3)C(=O)Nc3ccc(Oc4ccc(F)cc4)cc3)CC2)cc1]
229
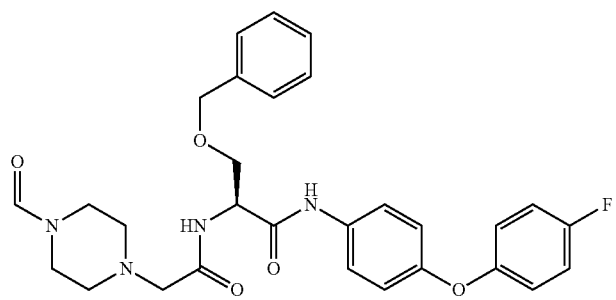 [SMILES: O=CN1CCN(CC(=O)N[C@@H](COCc2ccccc2)C(=O)Nc2ccc(Oc3ccc(F)cc3)cc2)CC1]
230
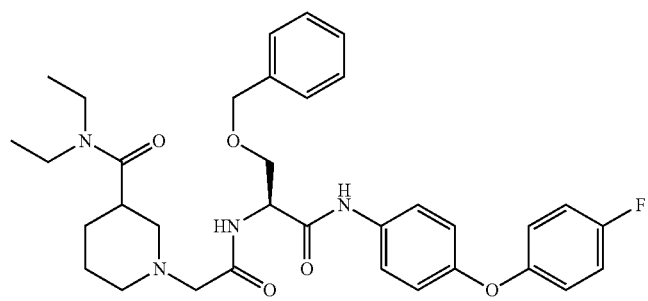 [SMILES: CCN(CC)C(=O)C1CCCN(CC(=O)N[C@@H](COCc2ccccc2)C(=O)Nc2ccc(Oc3ccc(F)cc3)cc2)C1]
231

TABLE 1-continued
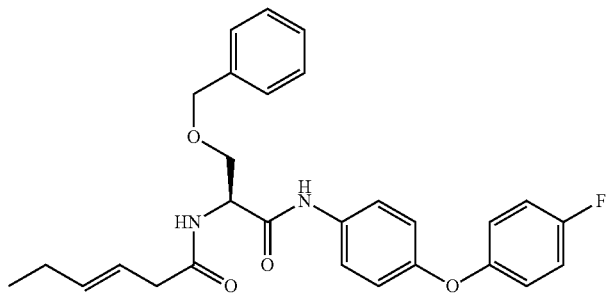 [SMILES: CC/C=C/CC(=O)N[C@@H](COCc1ccccc1)C(=O)Nc1ccc(Oc2ccc(F)cc2)cc1]
232
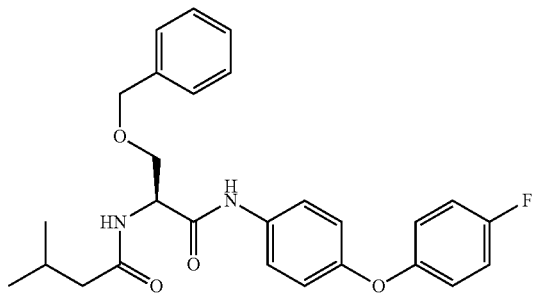 [SMILES: CC(C)CC(=O)N[C@@H](COCc1ccccc1)C(=O)Nc1ccc(Oc2ccc(F)cc2)cc1]
233
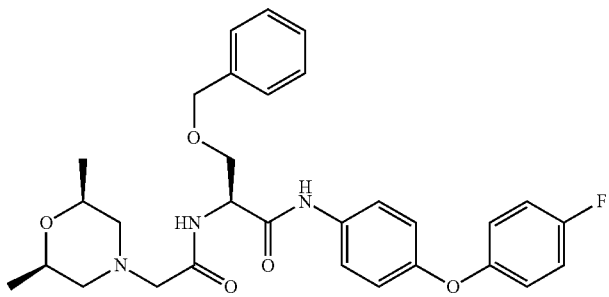 [SMILES: C[C@@H]1CN(CC(=O)N[C@@H](COCc2ccccc2)C(=O)Nc2ccc(Oc3ccc(F)cc3)cc2)C[C@H](C)O1]
234
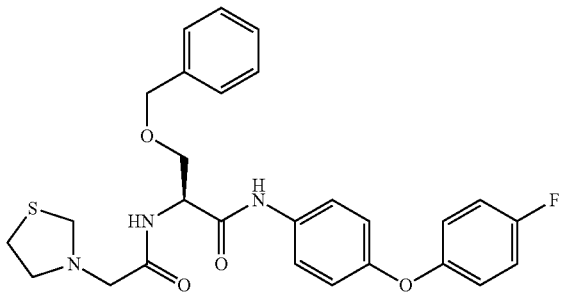 [SMILES: O=C(CN1CCSC1)N[C@@H](COCc1ccccc1)C(=O)Nc1ccc(Oc2ccc(F)cc2)cc1]
235

TABLE 1-continued
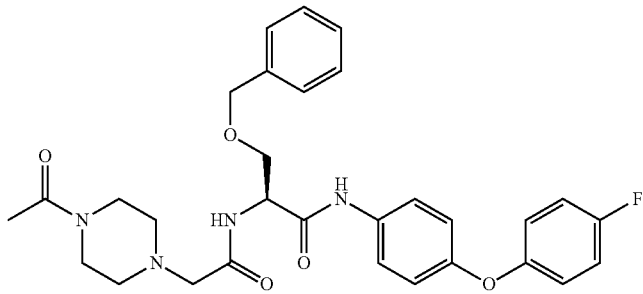
236
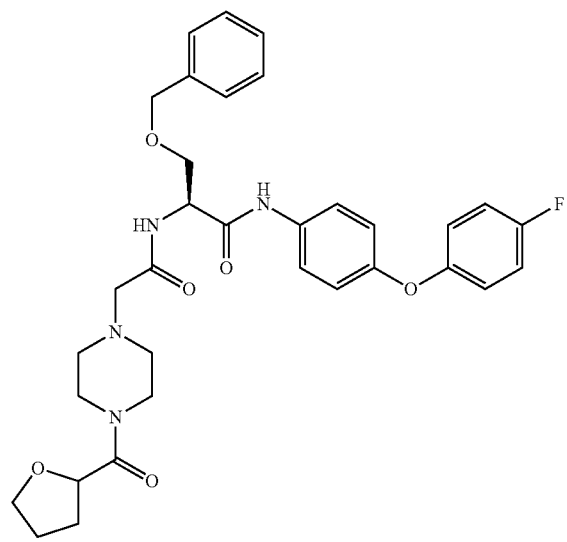 [SMILES: O=C(CN1CCN(C(=O)C2CCCO2)CC1)N[C@@H](COCc1ccccc1)C(=O)Nc1ccc(Oc2ccc(F)cc2)cc1]
237
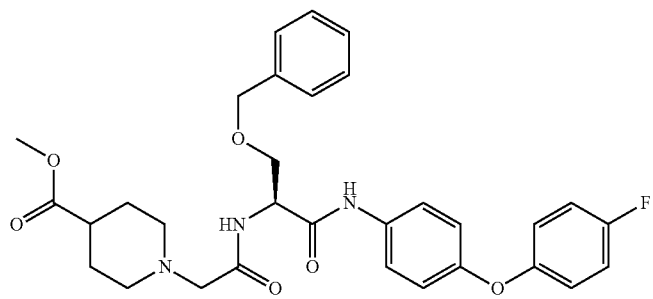 [SMILES: COC(=O)C1CCN(CC(=O)N[C@@H](COCc2ccccc2)C(=O)Nc2ccc(Oc3ccc(F)cc3)cc2)CC1]
238

TABLE 1-continued
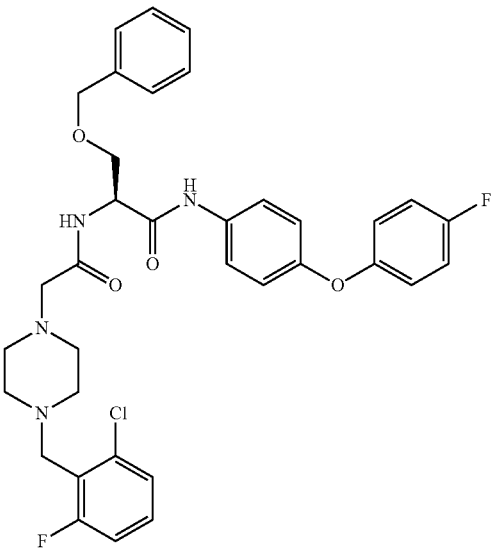 [SMILES: O=C(CN1CCN(Cc2c(F)cccc2Cl)CC1)N[C@@H](COCc1ccccc1)C(=O)Nc1ccc(Oc2ccc(F)cc2)cc1]
239
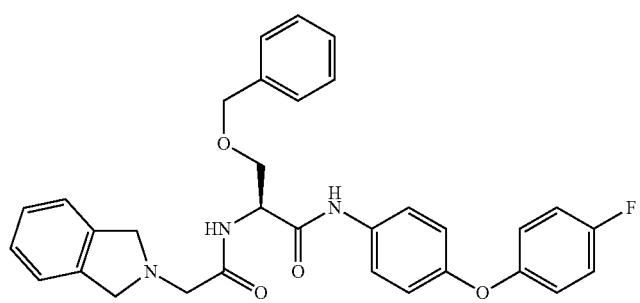 [SMILES: O=C(CN1Cc2ccccc2C1)N[C@@H](COCc1ccccc1)C(=O)Nc1ccc(Oc2ccc(F)cc2)cc1]
240
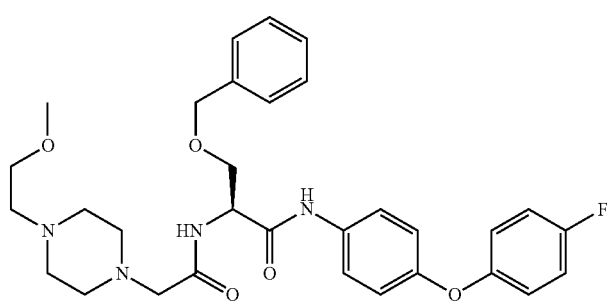 [SMILES: COCCN1CCN(CC(=O)N[C@@H](COCc2ccccc2)C(=O)Nc2ccc(Oc3ccc(F)cc3)cc2)CC1]
241
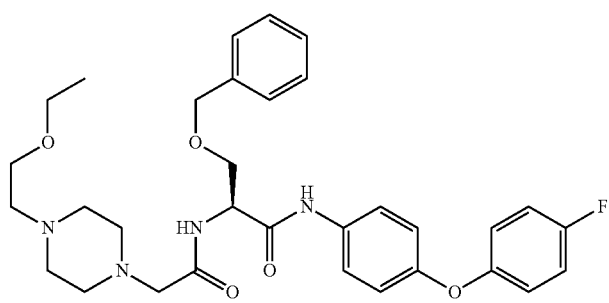 [SMILES: CCOCCN1CCN(CC(=O)N[C@@H](COCc2ccccc2)C(=O)Nc2ccc(Oc3ccc(F)cc3)cc2)CC1]
242

TABLE 1-continued
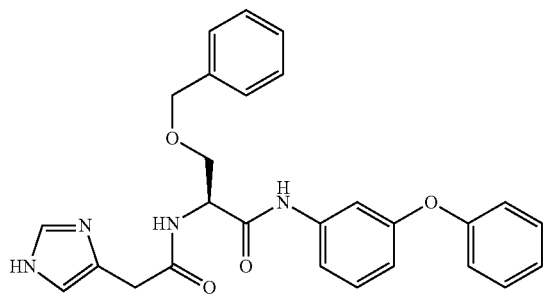 [SMILES: O=C(Cc1c[nH]cn1)N[C@@H](COCc1ccccc1)C(=O)Nc1cccc(Oc2ccccc2)c1]
243
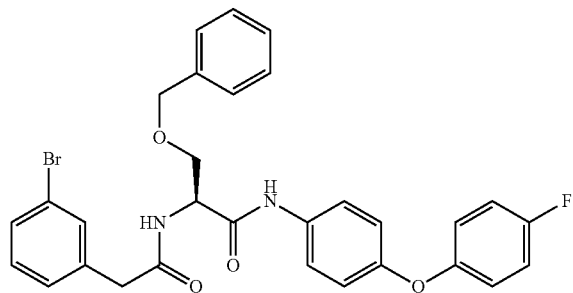 [SMILES: O=C(Cc1cccc(Br)c1)N[C@@H](COCc1ccccc1)C(=O)Nc1ccc(Oc2ccc(F)cc2)cc1]
244
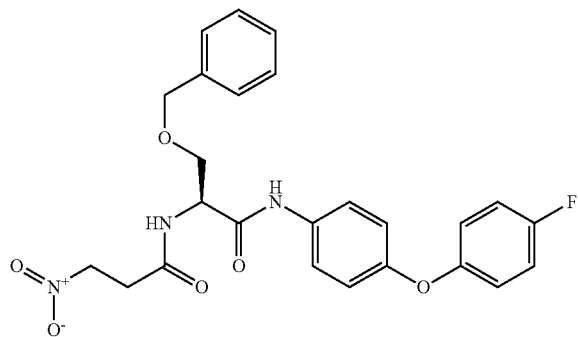 [SMILES: O=C(CC[N+](=O)[O-])N[C@@H](COCc1ccccc1)C(=O)Nc1ccc(Oc2ccc(F)cc2)cc1]
245
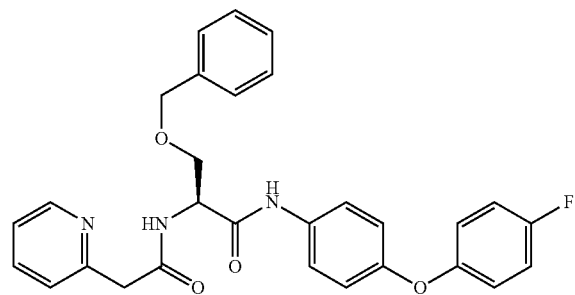 [SMILES: O=C(Cc1ccccn1)N[C@@H](COCc1ccccc1)C(=O)Nc1ccc(Oc2ccc(F)cc2)cc1]
246

TABLE 1-continued
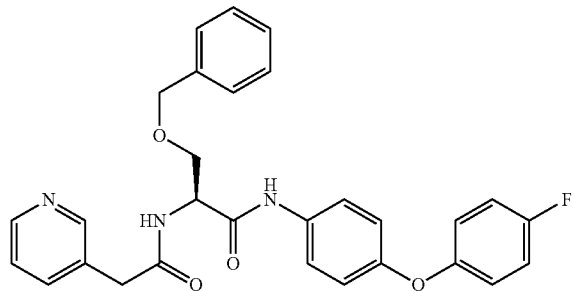 [SMILES: O=C(Cc1cccnc1)N[C@@H](COCc1ccccc1)C(=O)Nc1ccc(Oc2ccc(F)cc2)cc1]
247
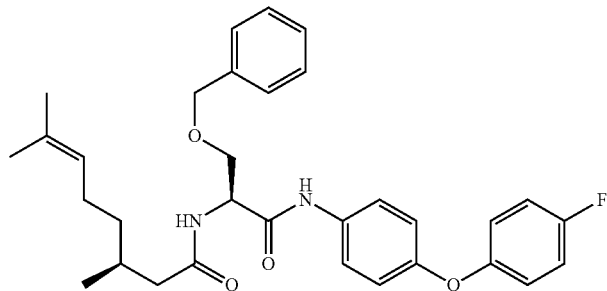 [SMILES: CC(C)=CCC[C@H](C)CC(=O)N[C@@H](COCc1ccccc1)C(=O)Nc1ccc(Oc2ccc(F)cc2)cc1]
248
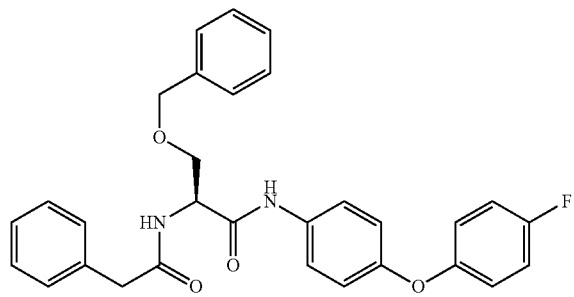 [SMILES: O=C(Cc1ccccc1)N[C@@H](COCc1ccccc1)C(=O)Nc1ccc(Oc2ccc(F)cc2)cc1]
249
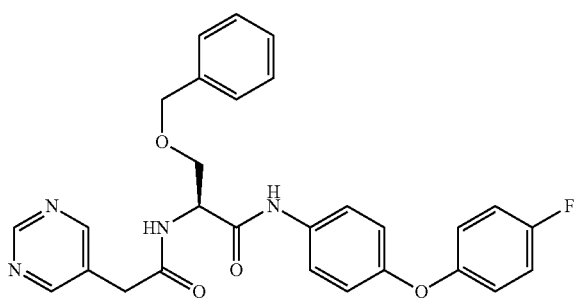 [SMILES: O=C(Cc1cncnc1)N[C@@H](COCc1ccccc1)C(=O)Nc1ccc(Oc2ccc(F)cc2)cc1]
250

TABLE 1-continued
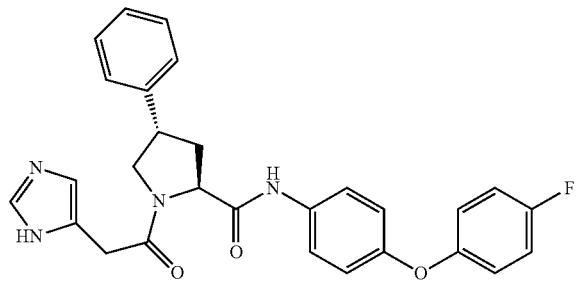 [SMILES: O=C(Nc1ccc(Oc2ccc(F)cc2)cc1)[C@@H]1C[C@@H](c2ccccc2)CN1C(=O)Cc1cnc[nH]1]
251
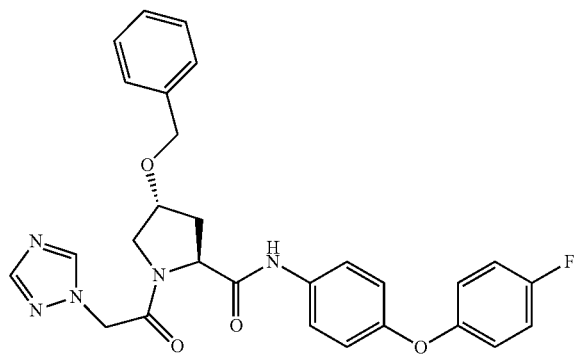 [SMILES: O=C(Nc1ccc(Oc2ccc(F)cc2)cc1)[C@@H]1C[C@@H](OCc2ccccc2)CN1C(=O)Cn1cncn1]
252
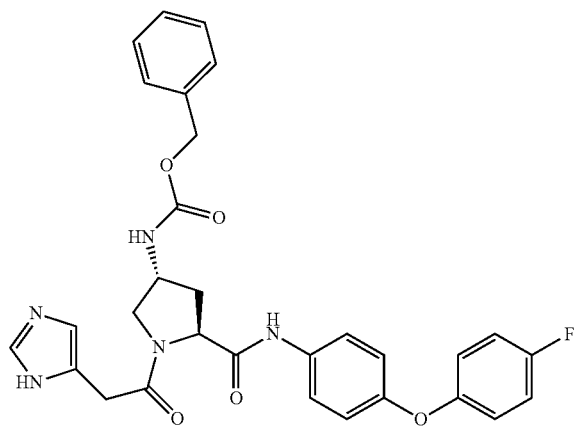 [SMILES: O=C(N[C@@H]1C[C@@H](C(=O)Nc2ccc(Oc3ccc(F)cc3)cc2)N(C(=O)Cc2cnc[nH]2)C1)OCc1ccccc1]
253
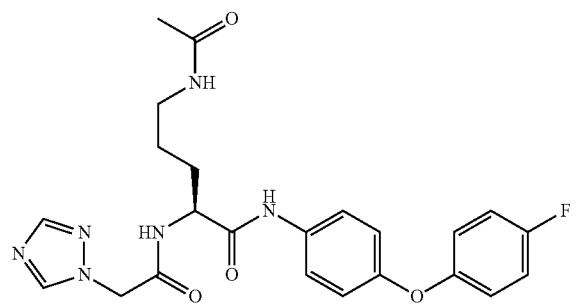 [SMILES: CC(=O)NCCC[C@H](NC(=O)Cn1cncn1)C(=O)Nc1ccc(Oc2ccc(F)cc2)cc1]
254

TABLE 1-continued
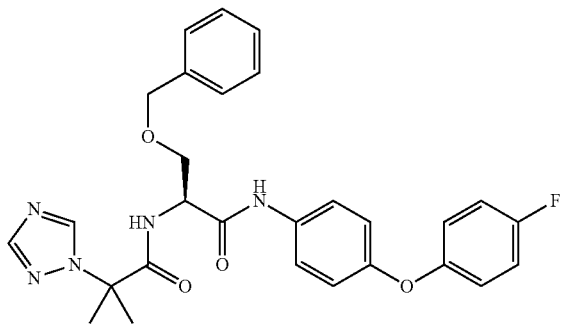 [SMILES: CC(C)(C(=O)N[C@@H](COCc1ccccc1)C(=O)Nc1ccc(Oc2ccc(F)cc2)cc1)n1cncn1]
255
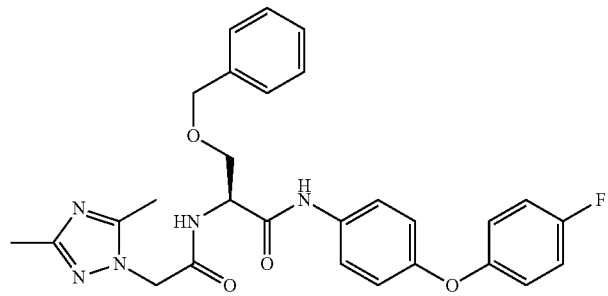 [SMILES: Cc1nc(C)n(CC(=O)N[C@@H](COCc2ccccc2)C(=O)Nc2ccc(Oc3ccc(F)cc3)cc2)n1]
256
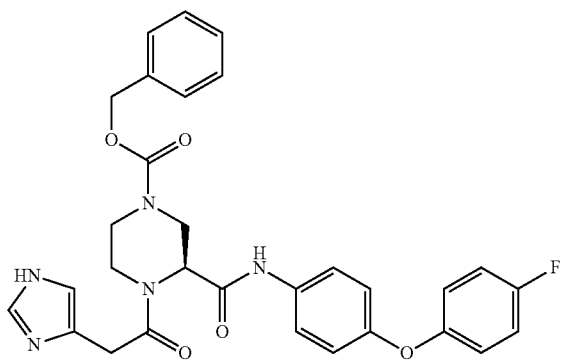 [SMILES: O=C(Nc1ccc(Oc2ccc(F)cc2)cc1)[C@@H]1CN(C(=O)OCc2ccccc2)CCN1C(=O)Cc1c[nH]cn1]
257
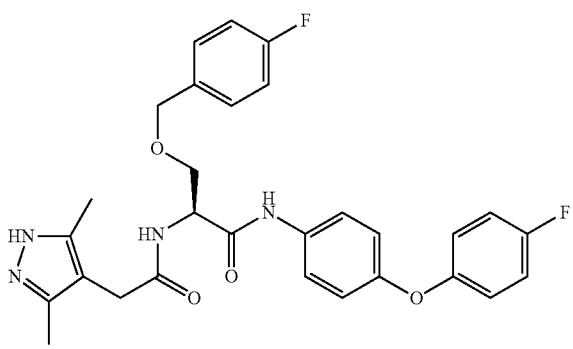 [SMILES: Cc1n[nH]c(C)c1CC(=O)N[C@@H](COCc1ccc(F)cc1)C(=O)Nc1ccc(Oc2ccc(F)cc2)cc1]
258

TABLE 1-continued
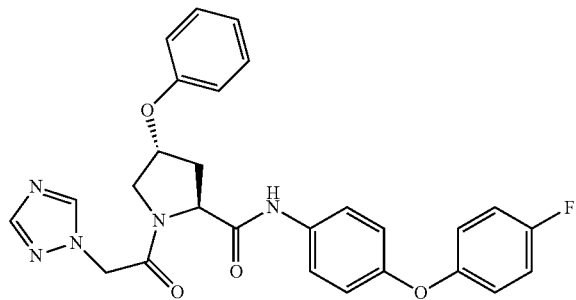 [SMILES: O=C(Nc1ccc(Oc2ccc(F)cc2)cc1)[C@@H]1C[C@@H](Oc2ccccc2)CN1C(=O)Cn1cncn1]
259
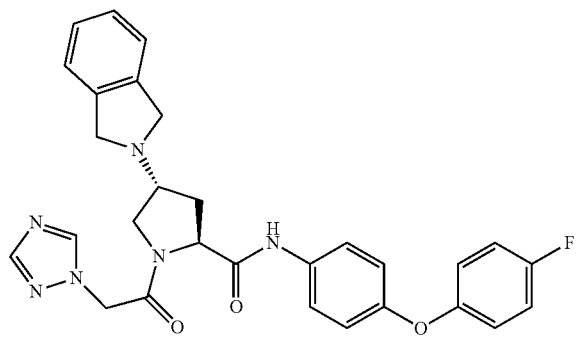 [SMILES: O=C(Nc1ccc(Oc2ccc(F)cc2)cc1)[C@@H]1C[C@@H](N2Cc3ccccc3C2)CN1C(=O)Cn1cncn1]
260
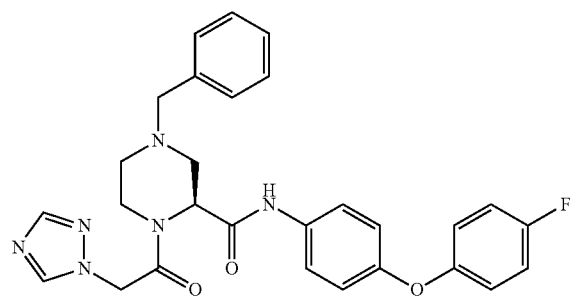 [SMILES: O=C(Nc1ccc(Oc2ccc(F)cc2)cc1)[C@@H]1CN(Cc2ccccc2)CCN1C(=O)Cn1cncn1]
261
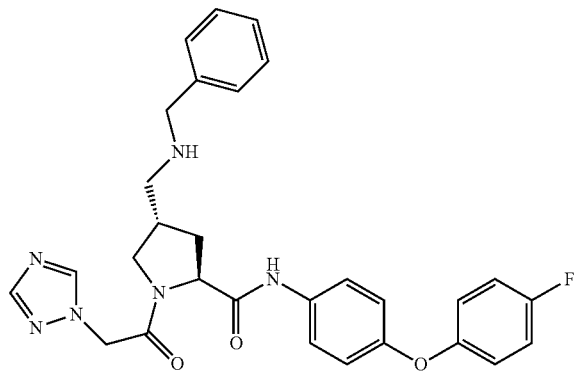 [SMILES: O=C(Nc1ccc(Oc2ccc(F)cc2)cc1)[C@@H]1C[C@@H](CNCc2ccccc2)CN1C(=O)Cn1cncn1]
262

TABLE 1-continued
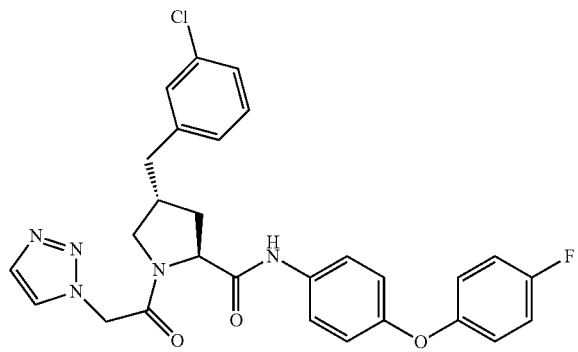 [SMILES: O=C(Nc1ccc(Oc2ccc(F)cc2)cc1)[C@@H]1C[C@@H](Cc2cccc(Cl)c2)CN1C(=O)Cn1ccnn1]
263
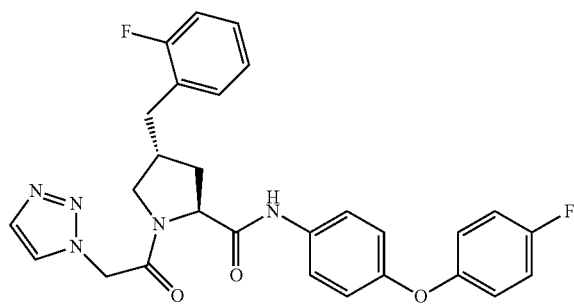 [SMILES: O=C(Nc1ccc(Oc2ccc(F)cc2)cc1)[C@@H]1C[C@@H](Cc2ccccc2F)CN1C(=O)Cn1ccnn1]
264
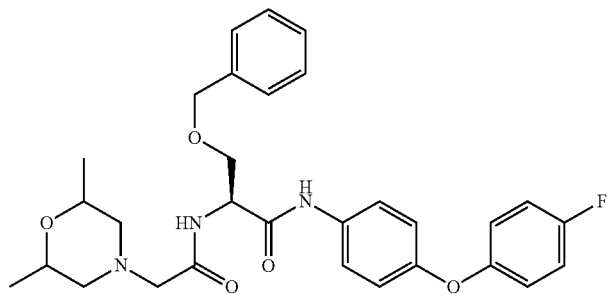
265
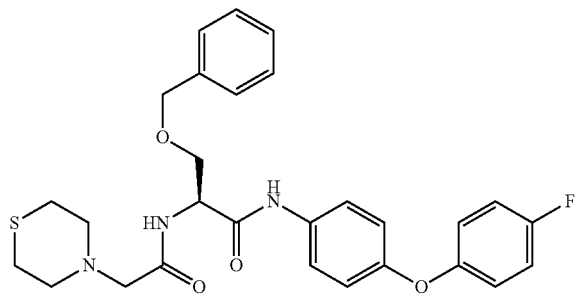 [SMILES: O=C(CN1CCSCC1)N[C@@H](COCc1ccccc1)C(=O)Nc1ccc(Oc2ccc(F)cc2)cc1]
266

TABLE 1-continued
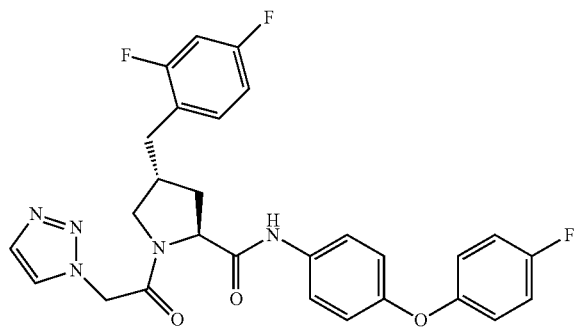 [SMILES: O=C(Nc1ccc(Oc2ccc(F)cc2)cc1)[C@@H]1C[C@@H](Cc2ccc(F)cc2F)CN1C(=O)Cn1ccnn1]
267
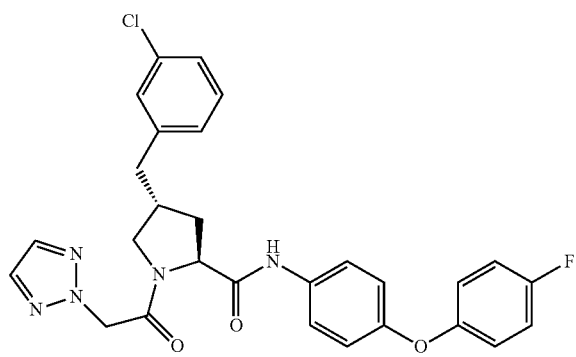 [SMILES: O=C(Nc1ccc(Oc2ccc(F)cc2)cc1)[C@@H]1C[C@@H](Cc2cccc(Cl)c2)CN1C(=O)Cn1nccn1]
268
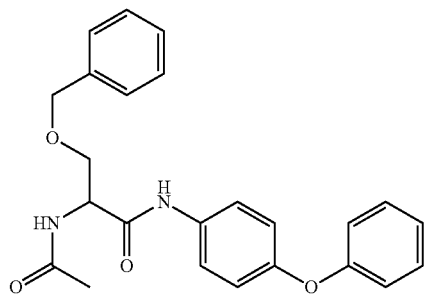 [SMILES: CC(=O)NC(COCc1ccccc1)C(=O)Nc1ccc(Oc2ccccc2)cc1]
269
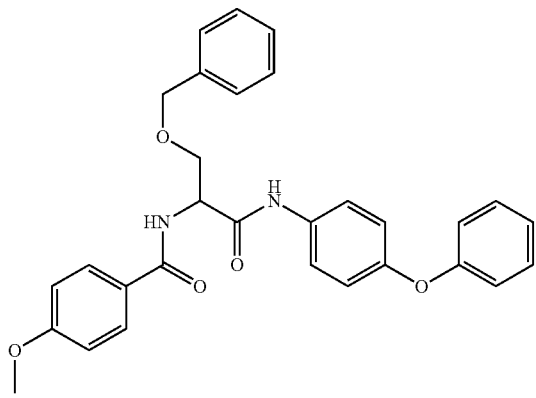 [SMILES: COc1ccc(C(=O)NC(COCc2ccccc2)C(=O)Nc2ccc(Oc3ccccc3)cc2)cc1]
270

TABLE 1-continued
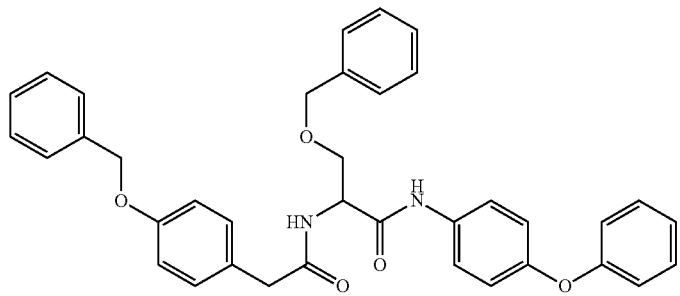 [SMILES: O=C(Cc1ccc(OCc2ccccc2)cc1)NC(COCc1ccccc1)C(=O)Nc1ccc(Oc2ccccc2)cc1]
271
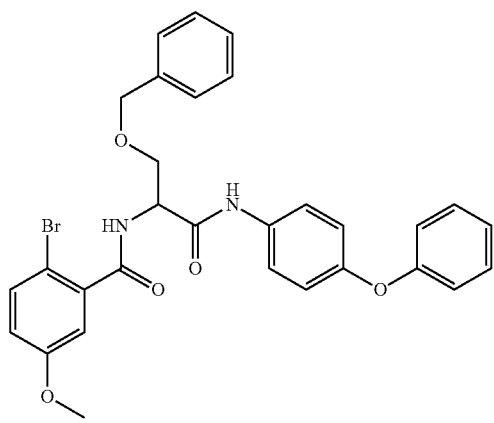 [SMILES: COc1ccc(Br)c(C(=O)NC(COCc2ccccc2)C(=O)Nc2ccc(Oc3ccccc3)cc2)c1]
272
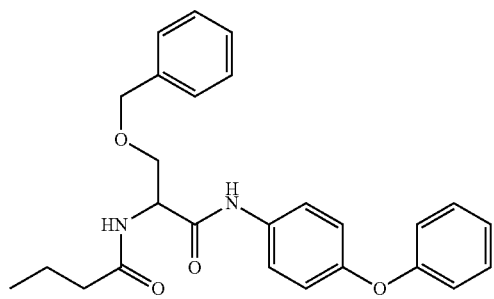
273
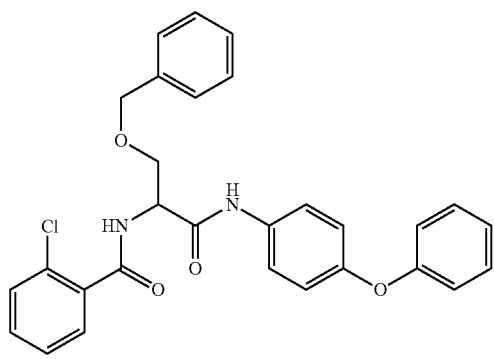 [SMILES: O=C(NC(COCc1ccccc1)C(=O)Nc1ccc(Oc2ccccc2)cc1)c1ccccc1Cl]
274

TABLE 1-continued
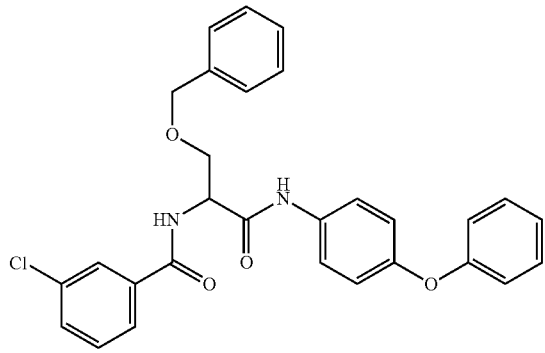 [SMILES: O=C(NC(COCc1ccccc1)C(=O)Nc1ccc(Oc2ccccc2)cc1)c1cccc(Cl)c1]
275
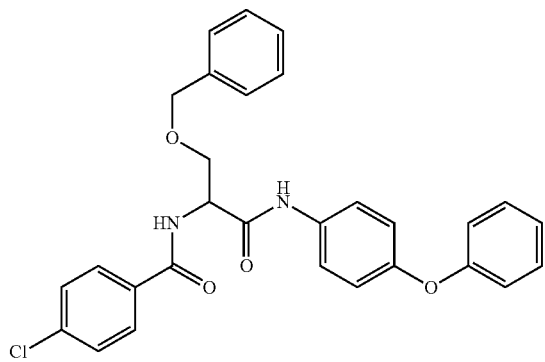 [SMILES: O=C(NC(COCc1ccccc1)C(=O)Nc1ccc(Oc2ccccc2)cc1)c1ccc(Cl)cc1]
276
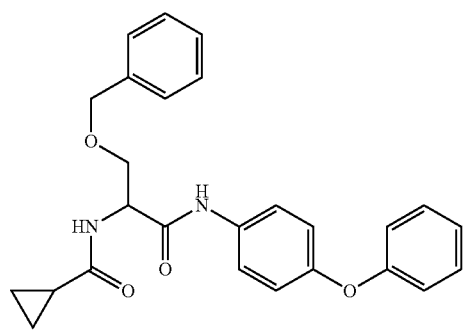 [SMILES: O=C(NC(COCc1ccccc1)C(=O)Nc1ccc(Oc2ccccc2)cc1)C1CC1]
277
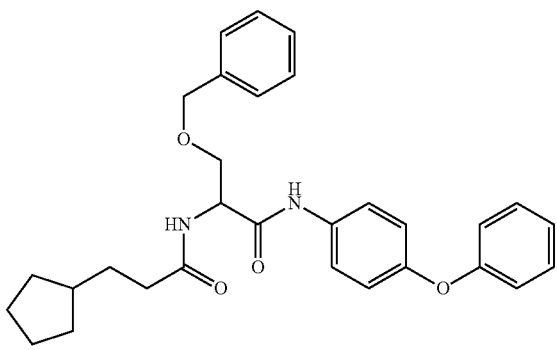 [SMILES: O=C(CCC1CCCC1)NC(COCc1ccccc1)C(=O)Nc1ccc(Oc2ccccc2)cc1]
278

TABLE 1-continued
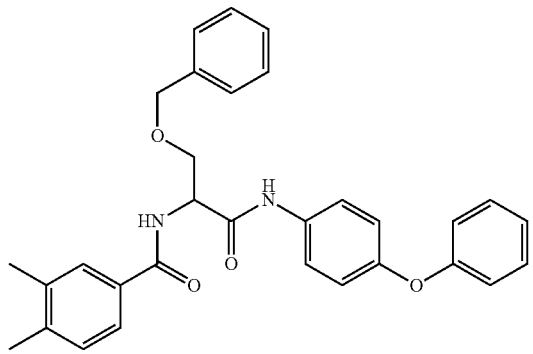 [SMILES: Cc1ccc(C(=O)NC(COCc2ccccc2)C(=O)Nc2ccc(Oc3ccccc3)cc2)cc1C]
279
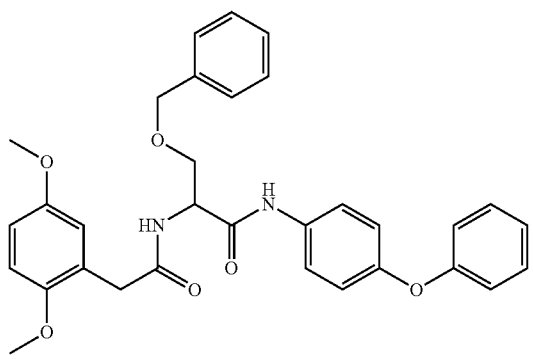 [SMILES: COc1ccc(OC)c(CC(=O)NC(COCc2ccccc2)C(=O)Nc2ccc(Oc3ccccc3)cc2)c1]
280
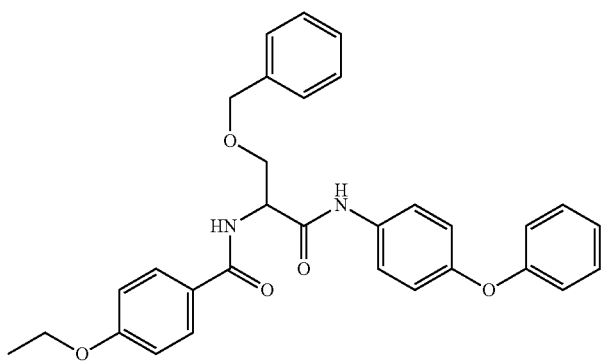 [SMILES: CCOc1ccc(C(=O)NC(COCc2ccccc2)C(=O)Nc2ccc(Oc3ccccc3)cc2)cc1]
281
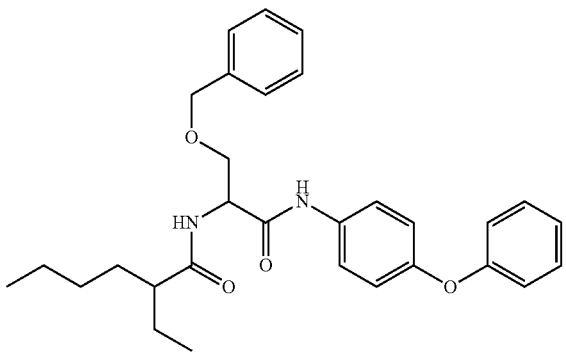 [SMILES: CCCCC(CC)C(=O)NC(COCc1ccccc1)C(=O)Nc1ccc(Oc2ccccc2)cc1]
282

TABLE 1-continued
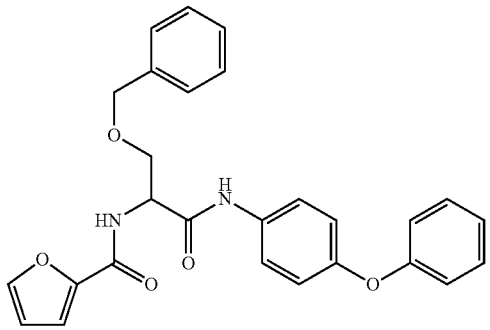 [SMILES: O=C(NC(COCc1ccccc1)C(=O)Nc1ccc(Oc2ccccc2)cc1)c1ccco1]
283
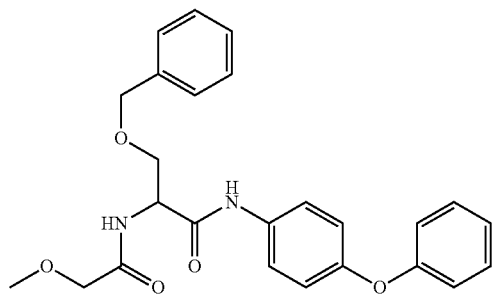 [SMILES: COCC(=O)NC(COCc1ccccc1)C(=O)Nc1ccc(Oc2ccccc2)cc1]
284
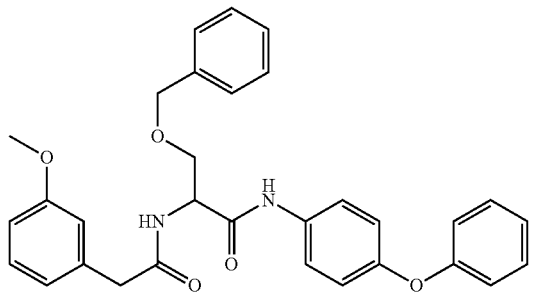 [SMILES: COc1cccc(CC(=O)NC(COCc2ccccc2)C(=O)Nc2ccc(Oc3ccccc3)cc2)c1]
285
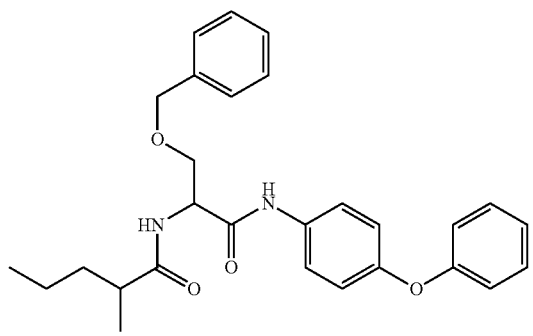 [SMILES: CCCC(C)C(=O)NC(COCc1ccccc1)C(=O)Nc1ccc(Oc2ccccc2)cc1]
286

TABLE 1-continued
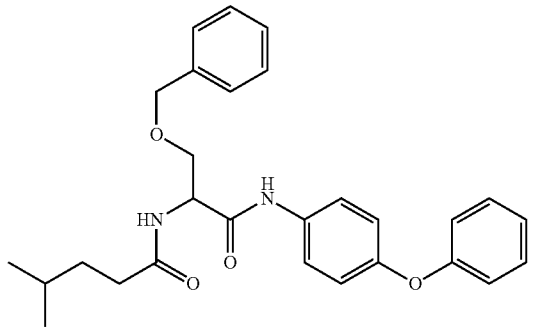 [SMILES: CC(C)CCC(=O)NC(COCc1ccccc1)C(=O)Nc1ccc(Oc2ccccc2)cc1]
287
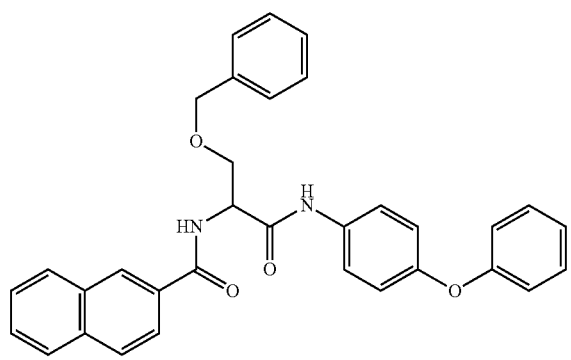 [SMILES: O=C(NC(COCc1ccccc1)C(=O)Nc1ccc(Oc2ccccc2)cc1)c1ccc2ccccc2c1]
288
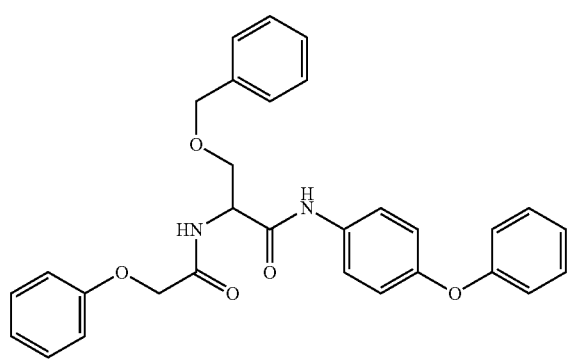 [SMILES: O=C(COc1ccccc1)NC(COCc1ccccc1)C(=O)Nc1ccc(Oc2ccccc2)cc1]
289
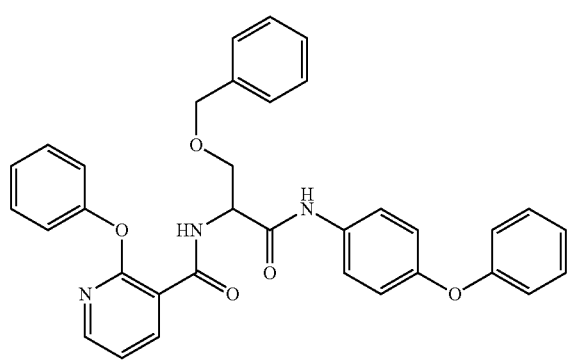 [SMILES: O=C(NC(COCc1ccccc1)C(=O)Nc1ccc(Oc2ccccc2)cc1)c1cccnc1Oc1ccccc1]
290

TABLE 1-continued
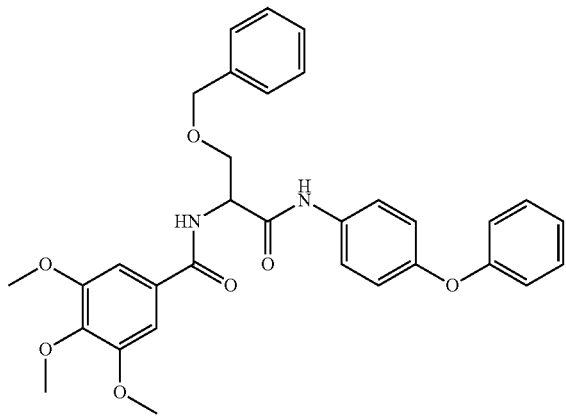 [SMILES: COc1cc(C(=O)NC(COCc2ccccc2)C(=O)Nc2ccc(Oc3ccccc3)cc2)cc(OC)c1OC]
291
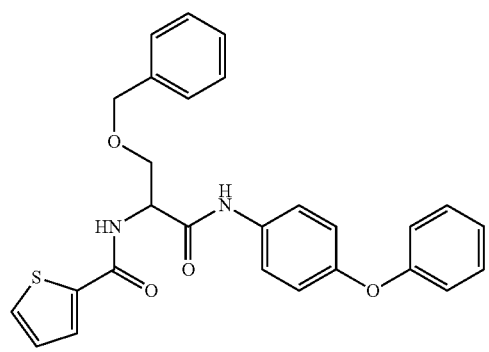 [SMILES: O=C(NC(COCc1ccccc1)C(=O)Nc1ccc(Oc2ccccc2)cc1)c1cccs1]
292
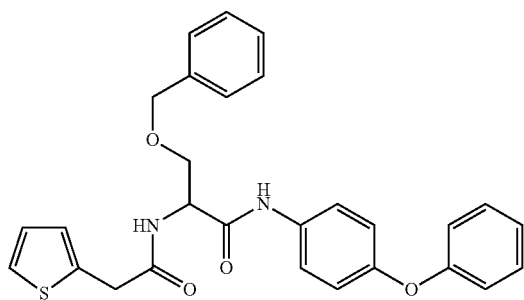 [SMILES: O=C(Cc1cccs1)NC(COCc1ccccc1)C(=O)Nc1ccc(Oc2ccccc2)cc1]
293
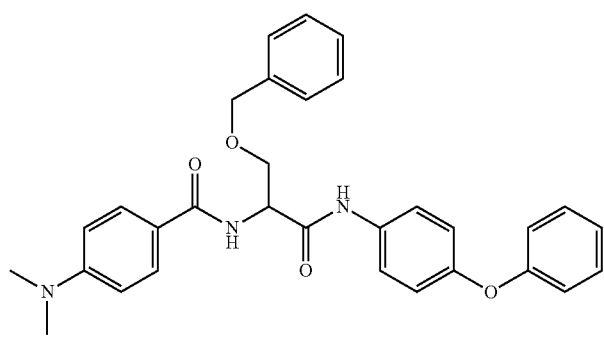 [SMILES: CN(C)c1ccc(C(=O)NC(COCc2ccccc2)C(=O)Nc2ccc(Oc3ccccc3)cc2)cc1]
294

TABLE 1-continued
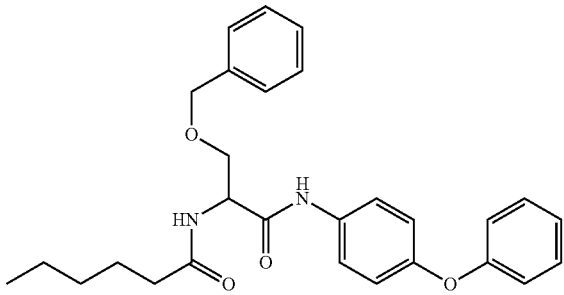
295
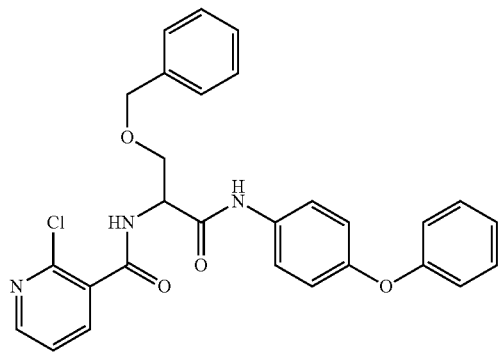 [SMILES: O=C(NC(COCc1ccccc1)C(=O)Nc1ccc(Oc2ccccc2)cc1)c1cccnc1Cl]
296
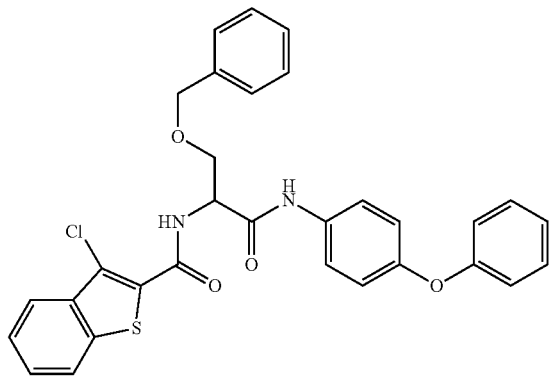 [SMILES: O=C(NC(COCc1ccccc1)C(=O)Nc1ccc(Oc2ccccc2)cc1)c1sc2ccccc2c1Cl]
297
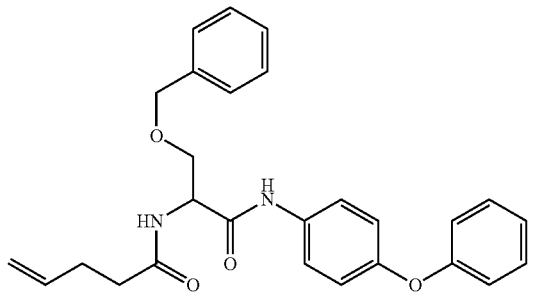 [SMILES: C=CCCC(=O)NC(COCc1ccccc1)C(=O)Nc1ccc(Oc2ccccc2)cc1]
298

TABLE 1-continued
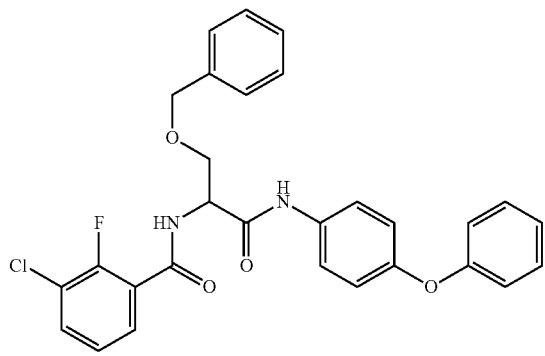 [SMILES: O=C(NC(COCc1ccccc1)C(=O)Nc1ccc(Oc2ccccc2)cc1)c1cccc(Cl)c1F]
299
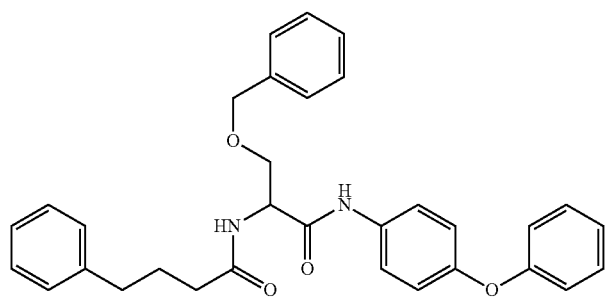 [SMILES: O=C(CCCc1ccccc1)NC(COCc1ccccc1)C(=O)Nc1ccc(Oc2ccccc2)cc1]
300
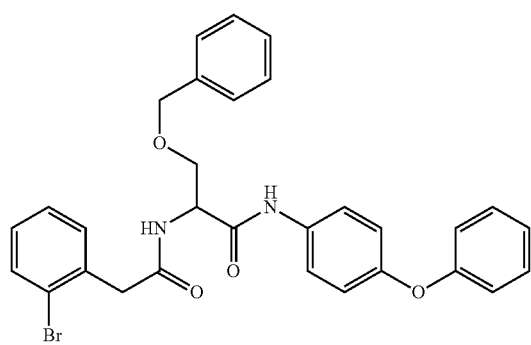
301
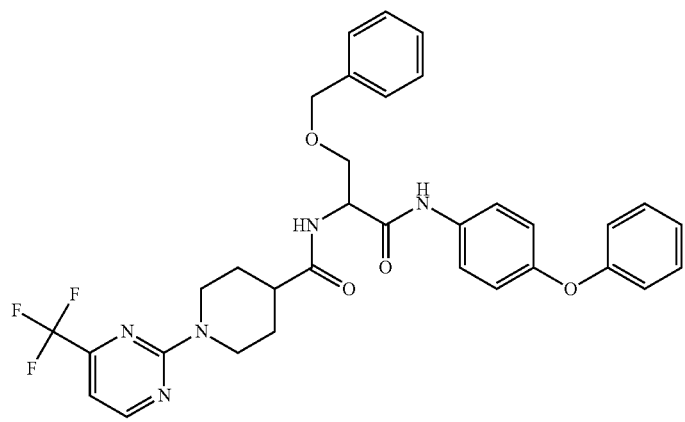 [SMILES: O=C(NC(COCc1ccccc1)C(=O)Nc1ccc(Oc2ccccc2)cc1)C1CCN(c2nccc(C(F)(F)F)n2)CC1]
302

TABLE 1-continued
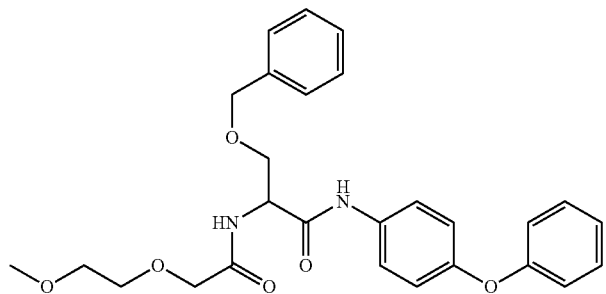 [SMILES: COCCOCC(=O)NC(COCc1ccccc1)C(=O)Nc1ccc(Oc2ccccc2)cc1]
303
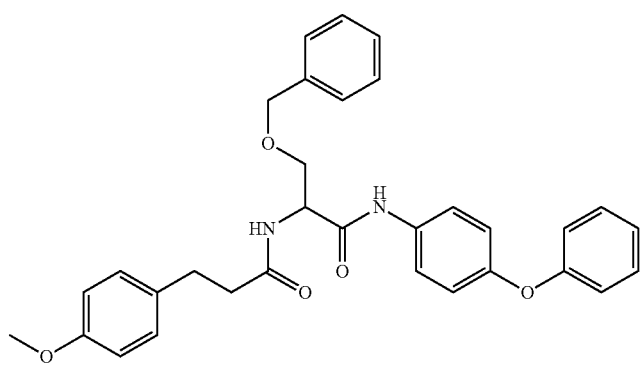 [SMILES: COc1ccc(CCC(=O)NC(COCc2ccccc2)C(=O)Nc2ccc(Oc3ccccc3)cc2)cc1]
304
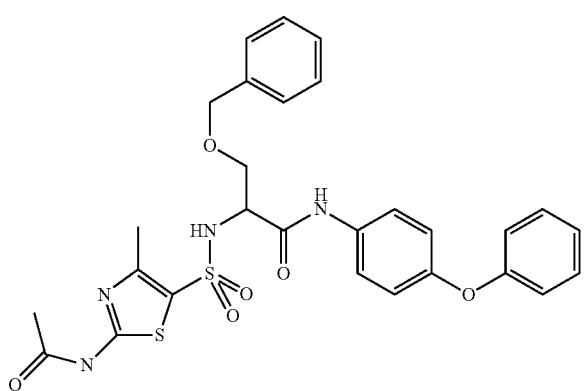 [SMILES: CC(=O)Nc1nc(C)c(S(=O)(=O)NC(COCc2ccccc2)C(=O)Nc2ccc(Oc3ccccc3)cc2)s1]
305
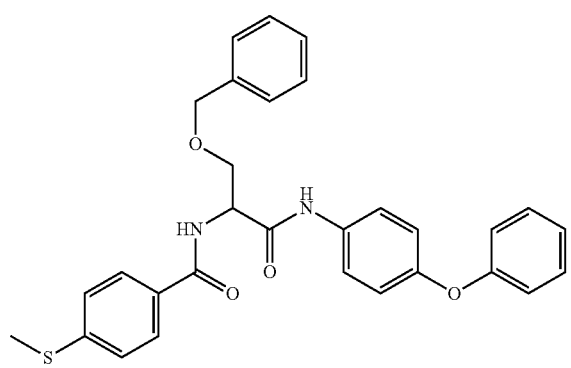 [SMILES: CSc1ccc(C(=O)NC(COCc2ccccc2)C(=O)Nc2ccc(Oc3ccccc3)cc2)cc1]
306

TABLE 1-continued
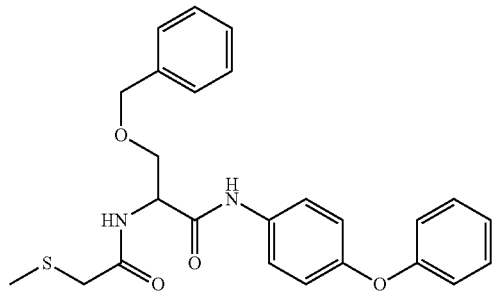
307
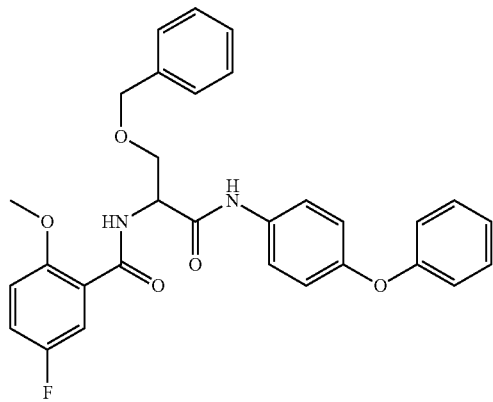 [SMILES: COc1ccc(F)cc1C(=O)NC(COCc1ccccc1)C(=O)Nc1ccc(Oc2ccccc2)cc1]
308
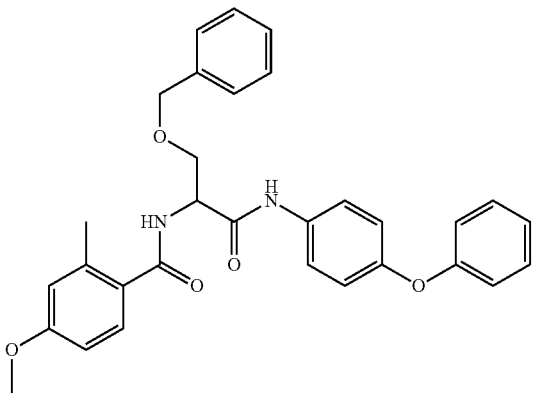 [SMILES: COc1ccc(C(=O)NC(COCc2ccccc2)C(=O)Nc2ccc(Oc3ccccc3)cc2)c(C)c1]
309
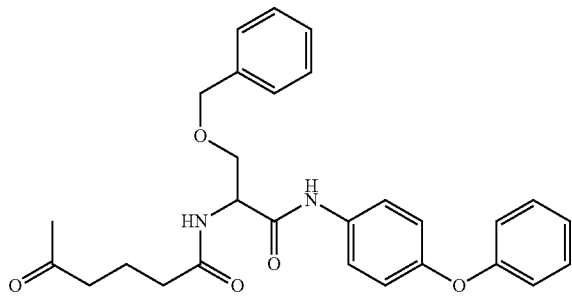 [SMILES: CC(=O)CCCC(=O)NC(COCc1ccccc1)C(=O)Nc1ccc(Oc2ccccc2)cc1]
310

TABLE 1-continued
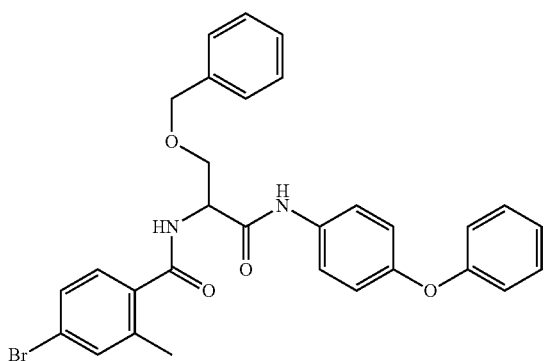 [SMILES: Cc1cc(Br)ccc1C(=O)NC(COCc1ccccc1)C(=O)Nc1ccc(Oc2ccccc2)cc1]
311
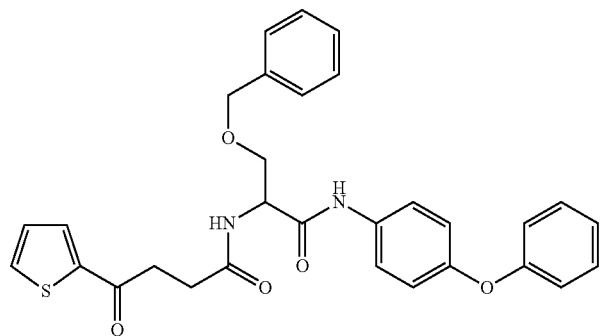 [SMILES: O=C(CCC(=O)c1cccs1)NC(COCc1ccccc1)C(=O)Nc1ccc(Oc2ccccc2)cc1]
312
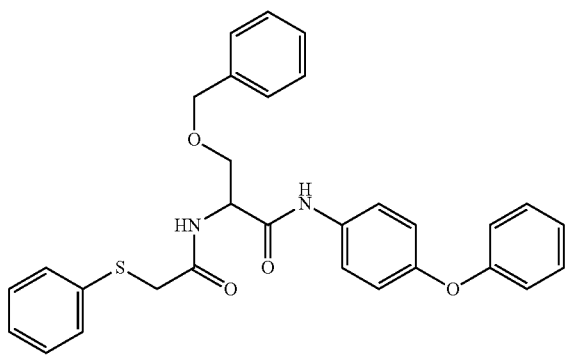
313
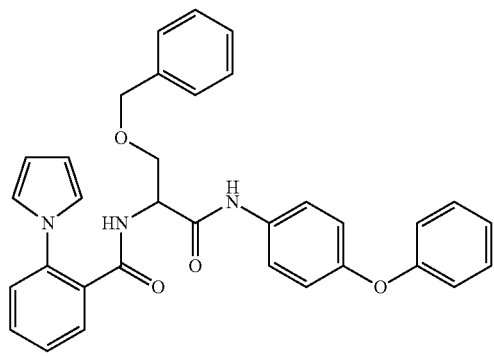 [SMILES: O=C(NC(COCc1ccccc1)C(=O)Nc1ccc(Oc2ccccc2)cc1)c1ccccc1-n1cccc1]
314

TABLE 1-continued
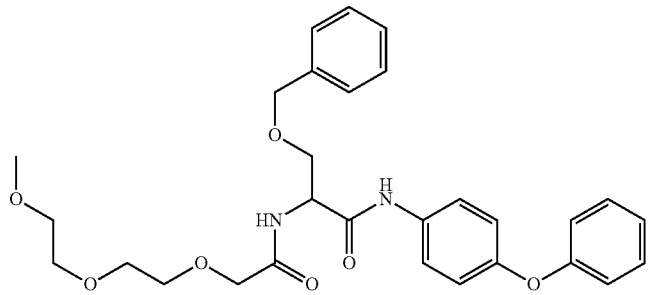 [SMILES: COCCOCCOCC(=O)NC(COCc1ccccc1)C(=O)Nc1ccc(Oc2ccccc2)cc1]
315
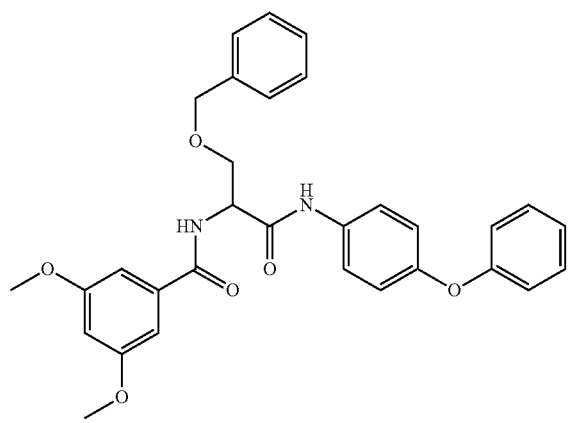 [SMILES: COc1cc(OC)cc(C(=O)NC(COCc2ccccc2)C(=O)Nc2ccc(Oc3ccccc3)cc2)c1]
316
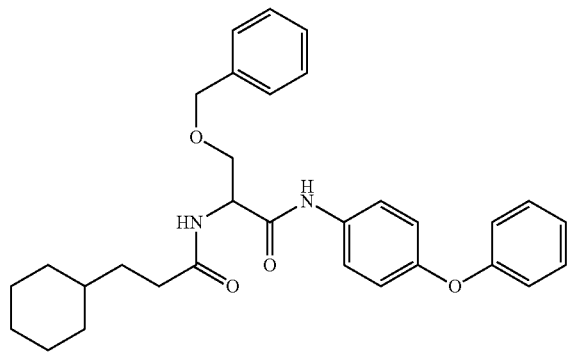 [SMILES: O=C(CCC1CCCCC1)NC(COCc1ccccc1)C(=O)Nc1ccc(Oc2ccccc2)cc1]
317
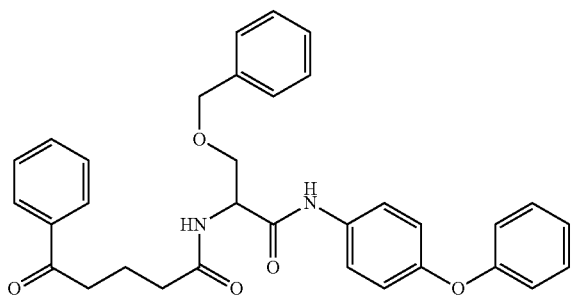 [SMILES: O=C(CCCC(=O)c1ccccc1)NC(COCc1ccccc1)C(=O)Nc1ccc(Oc2ccccc2)cc1]
318

TABLE 1-continued
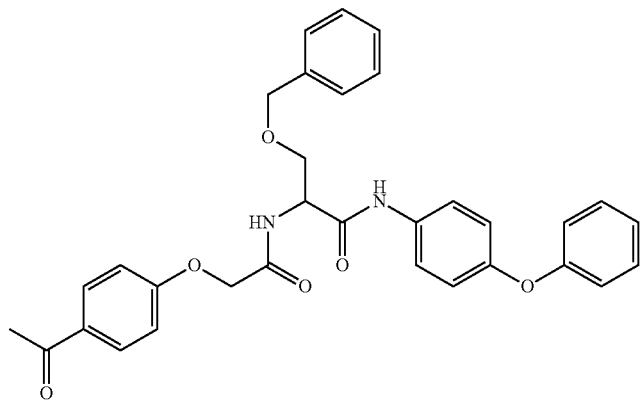 [SMILES: CC(=O)c1ccc(OCC(=O)NC(COCc2ccccc2)C(=O)Nc2ccc(Oc3ccccc3)cc2)cc1]
319
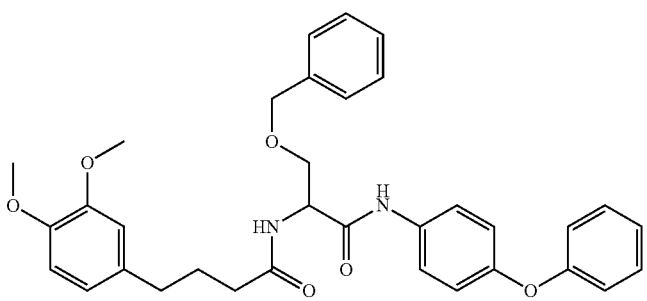 [SMILES: COc1ccc(CCCC(=O)NC(COCc2ccccc2)C(=O)Nc2ccc(Oc3ccccc3)cc2)cc1OC]
320
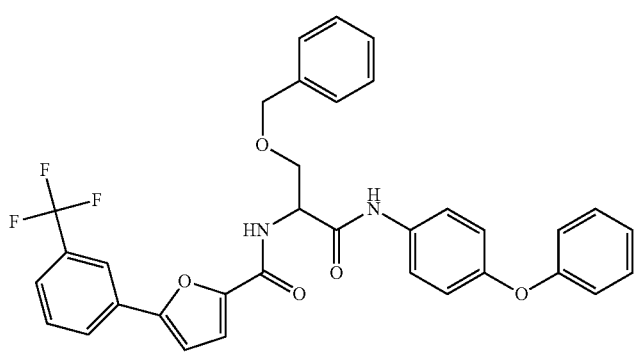 [SMILES: O=C(NC(COCc1ccccc1)C(=O)Nc1ccc(Oc2ccccc2)cc1)c1ccc(-c2cccc(C(F)(F)F)c2)o1]
321
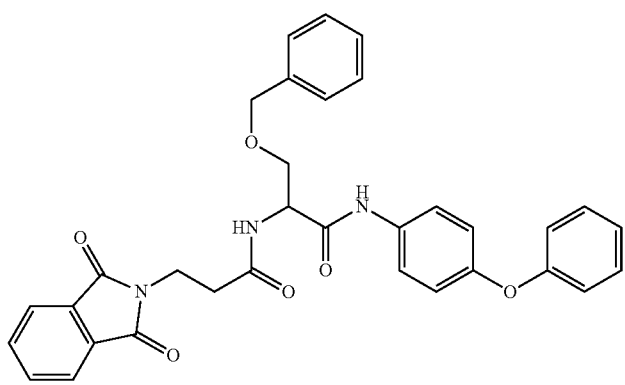 [SMILES: O=C(CCN1C(=O)c2ccccc2C1=O)NC(COCc1ccccc1)C(=O)Nc1ccc(Oc2ccccc2)cc1]
322

TABLE 1-continued
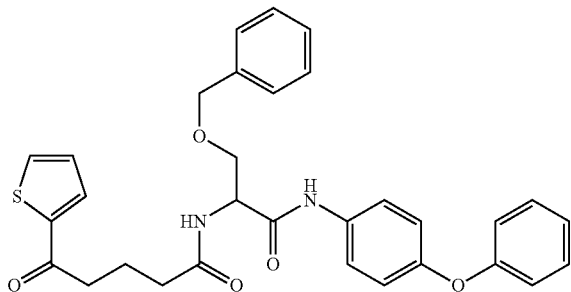 [SMILES: O=C(CCCC(=O)c1cccs1)NC(COCc1ccccc1)C(=O)Nc1ccc(Oc2ccccc2)cc1]
323
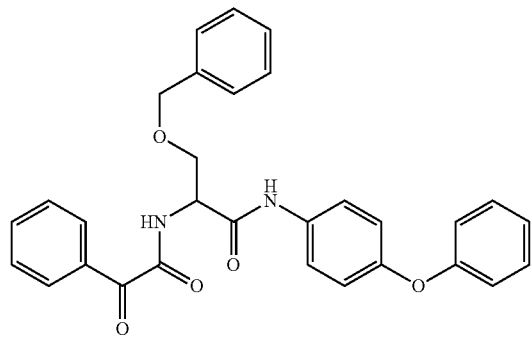 [SMILES: O=C(NC(COCc1ccccc1)C(=O)Nc1ccc(Oc2ccccc2)cc1)C(=O)c1ccccc1]
324
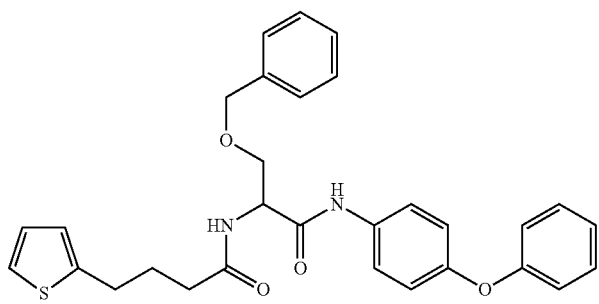 [SMILES: O=C(CCCc1cccs1)NC(COCc1ccccc1)C(=O)Nc1ccc(Oc2ccccc2)cc1]
325
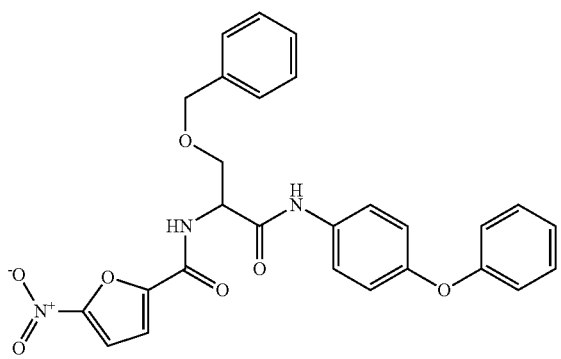
326

TABLE 1-continued
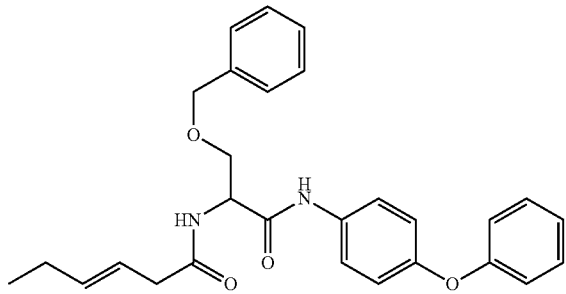 [SMILES: CC/C=C/CC(=O)NC(COCc1ccccc1)C(=O)Nc1ccc(Oc2ccccc2)cc1]
327
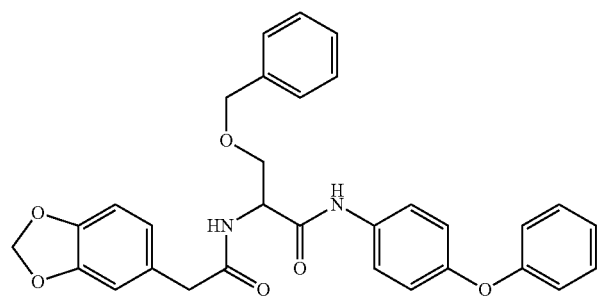 [SMILES: O=C(Cc1ccc2c(c1)OCO2)NC(COCc1ccccc1)C(=O)Nc1ccc(Oc2ccccc2)cc1]
328
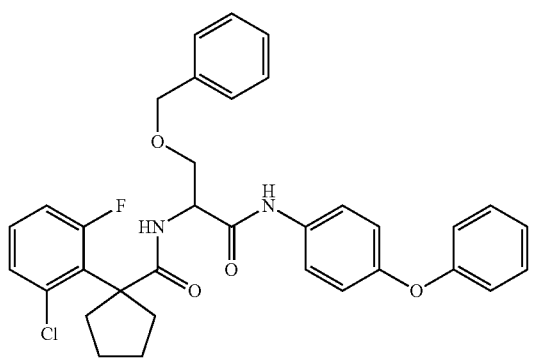 [SMILES: O=C(Nc1ccc(Oc2ccccc2)cc1)C(COCc1ccccc1)NC(=O)C1(c2c(F)cccc2Cl)CCCC1]
329
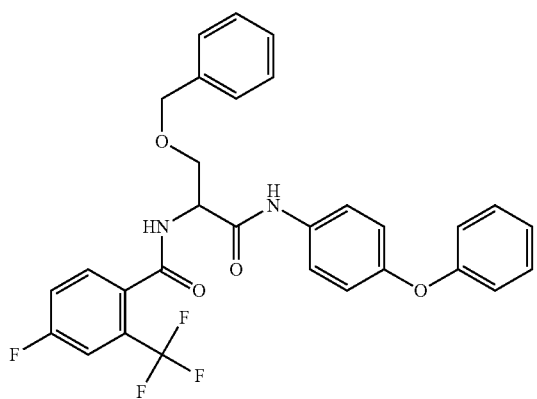 [SMILES: O=C(NC(COCc1ccccc1)C(=O)Nc1ccc(Oc2ccccc2)cc1)c1ccc(F)cc1C(F)(F)F]
330

TABLE 1-continued
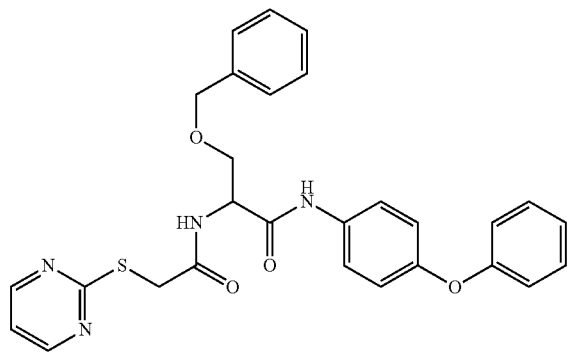 [SMILES: O=C(CSc1ncccn1)NC(COCc1ccccc1)C(=O)Nc1ccc(Oc2ccccc2)cc1]
331
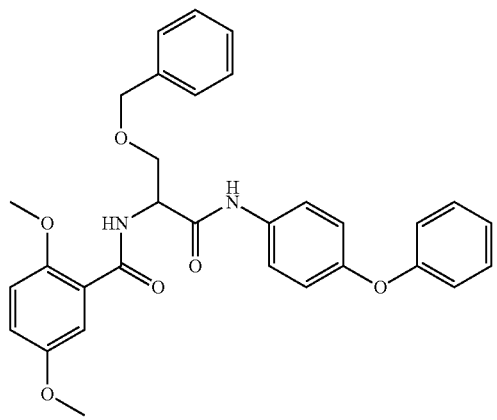 [SMILES: COc1ccc(OC)c(C(=O)NC(COCc2ccccc2)C(=O)Nc2ccc(Oc3ccccc3)cc2)c1]
332
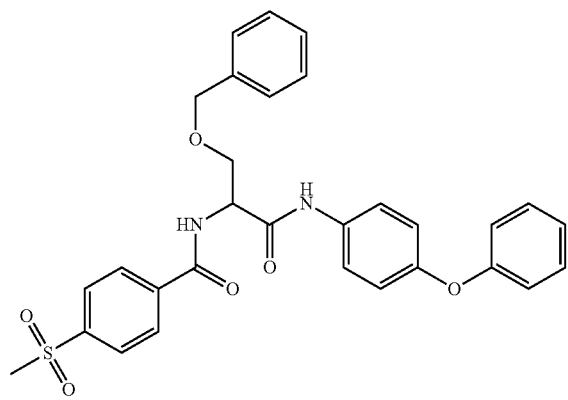 [SMILES: CS(=O)(=O)c1ccc(C(=O)NC(COCc2ccccc2)C(=O)Nc2ccc(Oc3ccccc3)cc2)cc1]
333

TABLE 1-continued
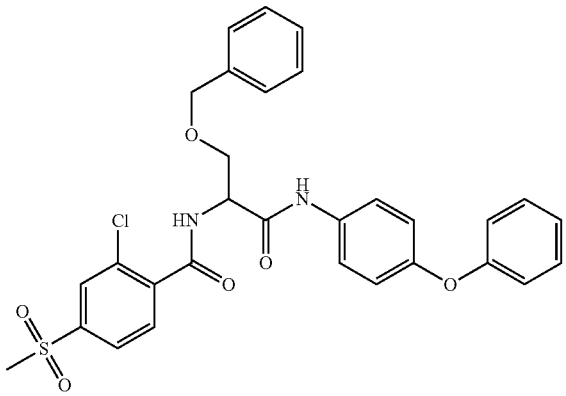 [SMILES: CS(=O)(=O)c1ccc(C(=O)NC(COCc2ccccc2)C(=O)Nc2ccc(Oc3ccccc3)cc2)c(Cl)c1]
334
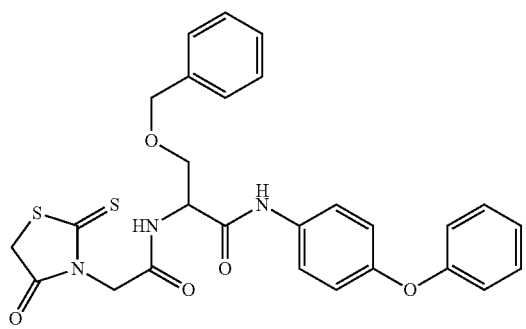 [SMILES: O=C(CN1C(=O)CSC1=S)NC(COCc1ccccc1)C(=O)Nc1ccc(Oc2ccccc2)cc1]
335
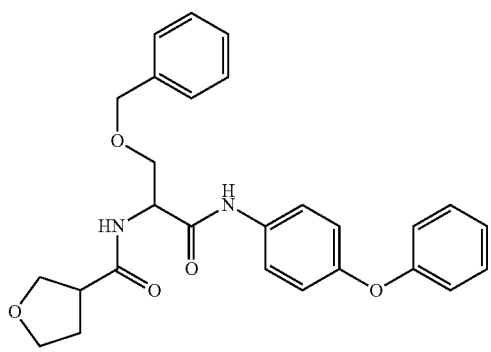 [SMILES: O=C(NC(COCc1ccccc1)C(=O)Nc1ccc(Oc2ccccc2)cc1)C1CCOC1]
336
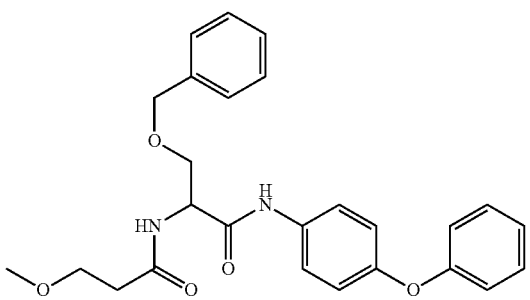 [SMILES: COCCC(=O)NC(COCc1ccccc1)C(=O)Nc1ccc(Oc2ccccc2)cc1]
337

TABLE 1-continued
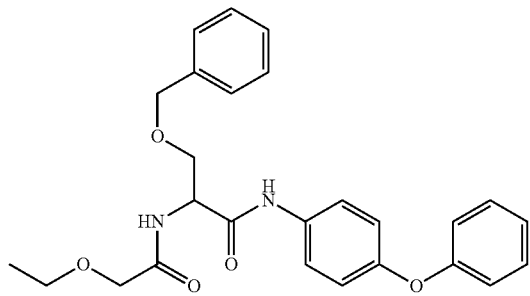 [SMILES: CCOCC(=O)NC(COCc1ccccc1)C(=O)Nc1ccc(Oc2ccccc2)cc1]
338
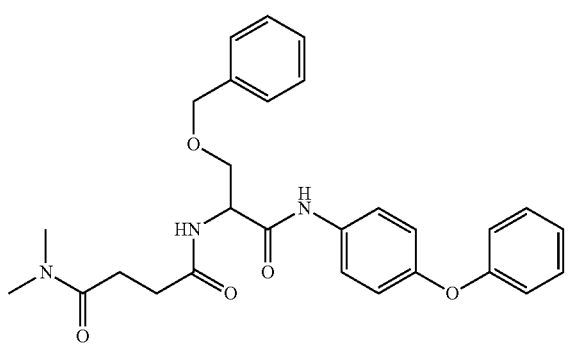 [SMILES: CN(C)C(=O)CCC(=O)NC(COCc1ccccc1)C(=O)Nc1ccc(Oc2ccccc2)cc1]
339
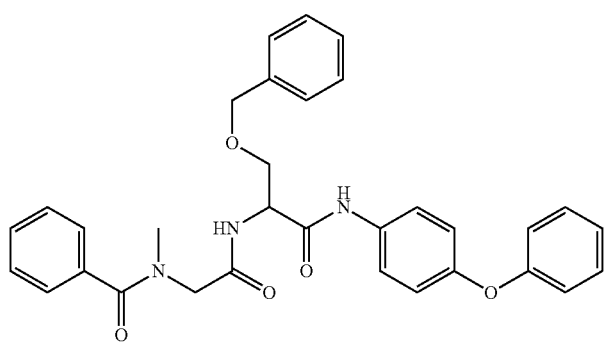 [SMILES: CN(CC(=O)NC(COCc1ccccc1)C(=O)Nc1ccc(Oc2ccccc2)cc1)C(=O)c1ccccc1]
340
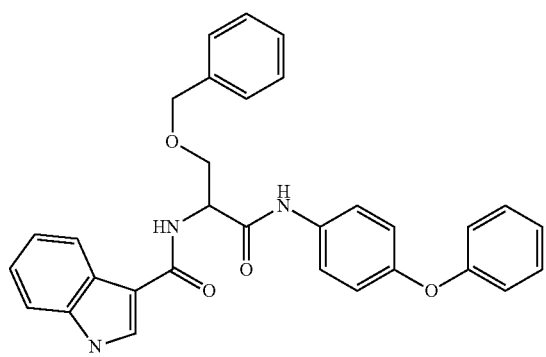 [SMILES: O=C(NC(COCc1ccccc1)C(=O)Nc1ccc(Oc2ccccc2)cc1)c1c[nH]c2ccccc12]
341

TABLE 1-continued
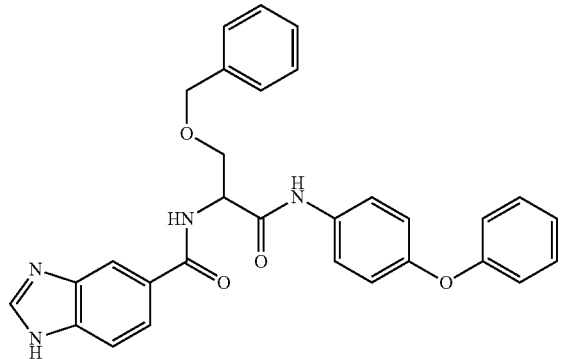 [SMILES: O=C(NC(COCc1ccccc1)C(=O)Nc1ccc(Oc2ccccc2)cc1)c1ccc2[nH]cnc2c1]
342
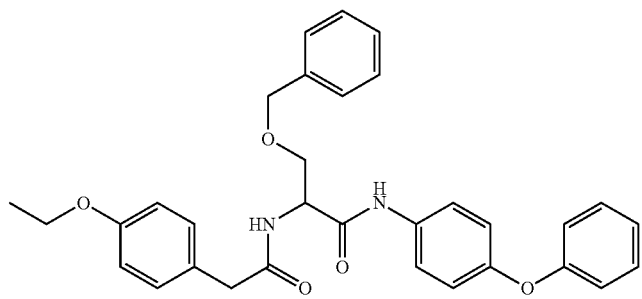 [SMILES: CCOc1ccc(CC(=O)NC(COCc2ccccc2)C(=O)Nc2ccc(Oc3ccccc3)cc2)cc1]
343
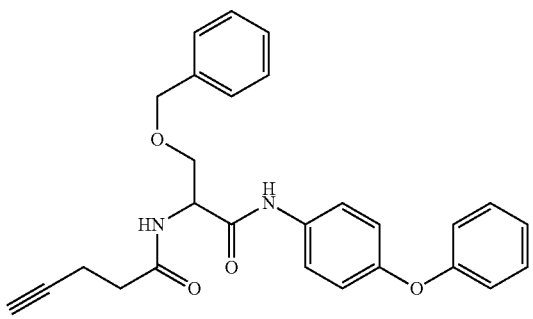 [SMILES: C#CCCC(=O)NC(COCc1ccccc1)C(=O)Nc1ccc(Oc2ccccc2)cc1]
344
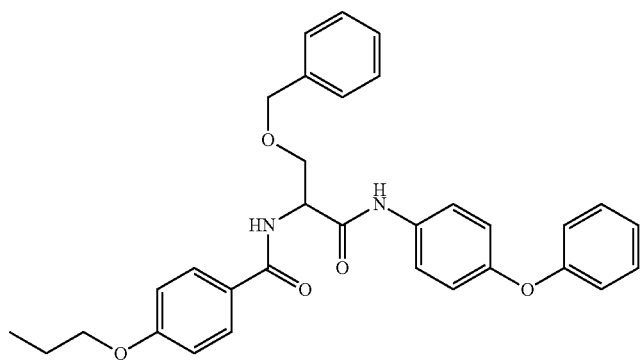 [SMILES: CCCOc1ccc(C(=O)NC(COCc2ccccc2)C(=O)Nc2ccc(Oc3ccccc3)cc2)cc1]
345

TABLE 1-continued
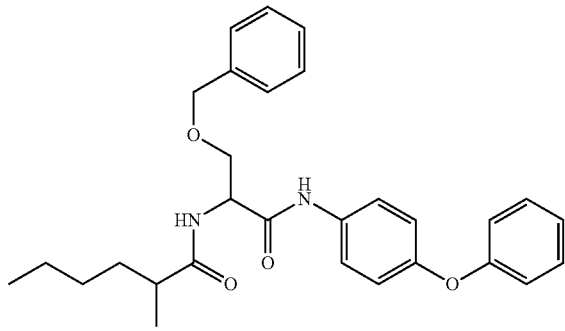 [SMILES: CCCCC(C)C(=O)NC(COCc1ccccc1)C(=O)Nc1ccc(Oc2ccccc2)cc1]
346
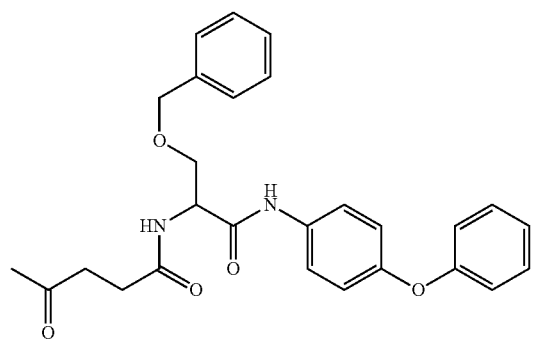 [SMILES: CC(=O)CCC(=O)NC(COCc1ccccc1)C(=O)Nc1ccc(Oc2ccccc2)cc1]
347
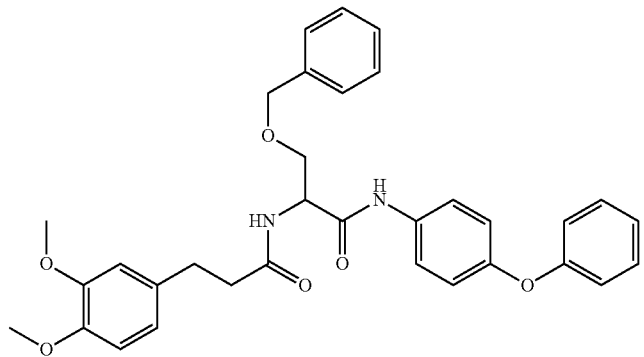 [SMILES: COc1ccc(CCC(=O)NC(COCc2ccccc2)C(=O)Nc2ccc(Oc3ccccc3)cc2)cc1OC]
348
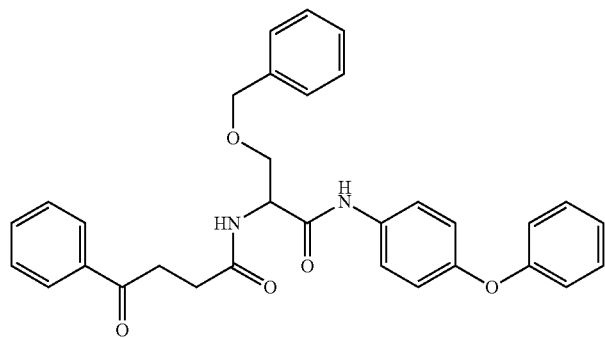 [SMILES: O=C(CCC(=O)c1ccccc1)NC(COCc1ccccc1)C(=O)Nc1ccc(Oc2ccccc2)cc1]
349

TABLE 1-continued
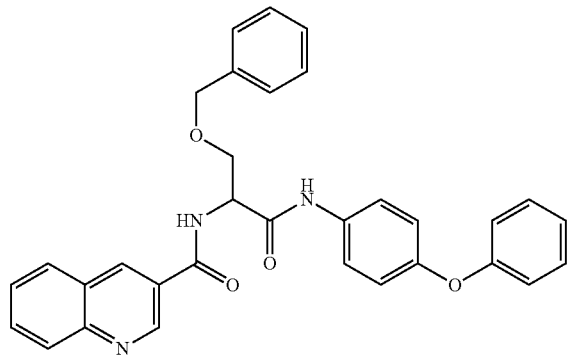 [SMILES: O=C(NC(COCc1ccccc1)C(=O)Nc1ccc(Oc2ccccc2)cc1)c1cnc2ccccc2c1]
350
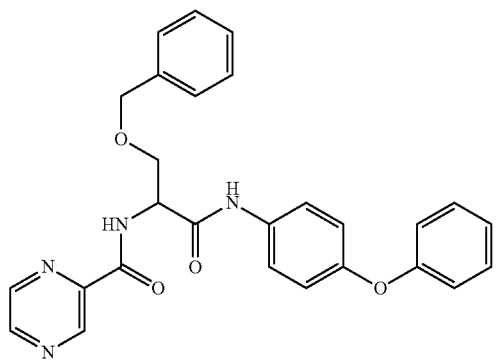 [SMILES: O=C(NC(COCc1ccccc1)C(=O)Nc1ccc(Oc2ccccc2)cc1)c1cnccn1]
351
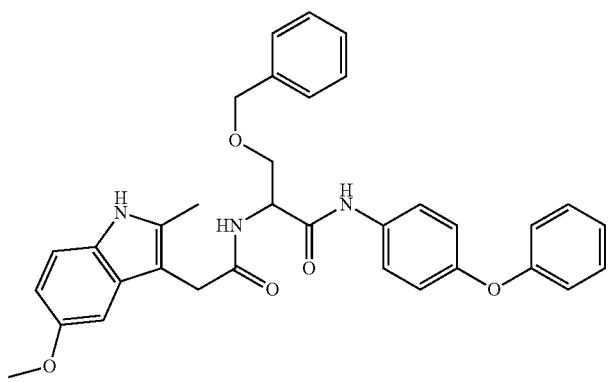 [SMILES: COc1ccc2[nH]c(C)c(CC(=O)NC(COCc3ccccc3)C(=O)Nc3ccc(Oc4ccccc4)cc3)c2c1]
352
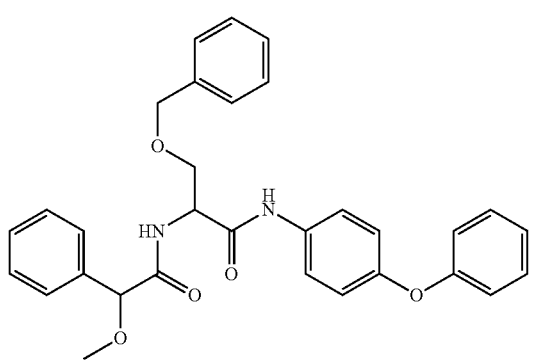 [SMILES: COC(C(=O)NC(COCc1ccccc1)C(=O)Nc1ccc(Oc2ccccc2)cc1)c1ccccc1]
353

TABLE 1-continued
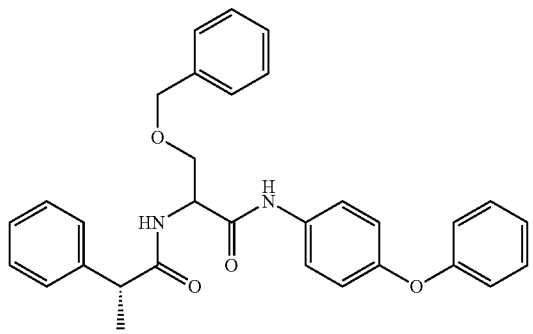
354
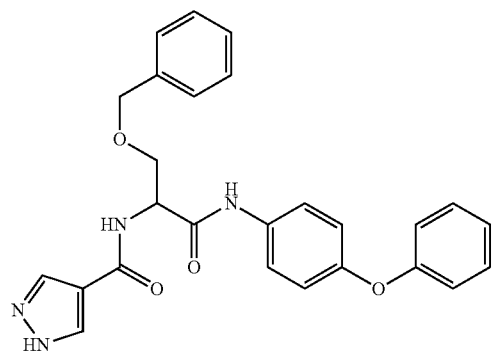 [SMILES: O=C(NC(COCc1ccccc1)C(=O)Nc1ccc(Oc2ccccc2)cc1)c1cn[nH]c1]
355
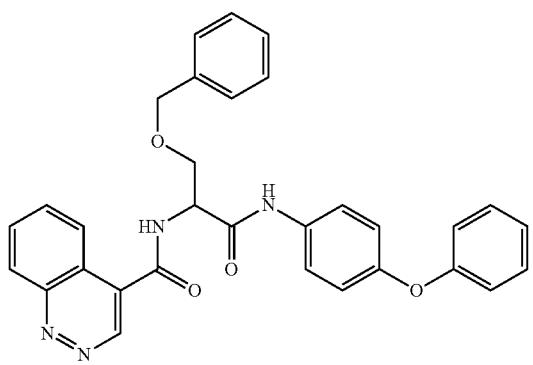 [SMILES: O=C(NC(COCc1ccccc1)C(=O)Nc1ccc(Oc2ccccc2)cc1)c1cnnc2ccccc12]
356
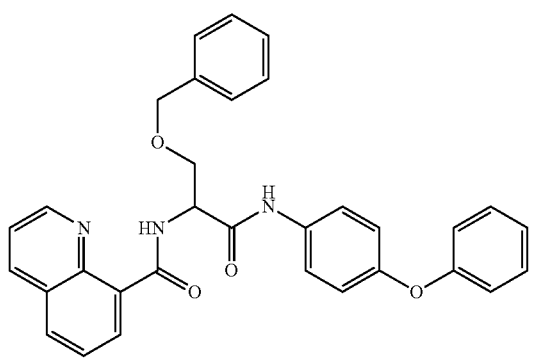 [SMILES: O=C(NC(COCc1ccccc1)C(=O)Nc1ccc(Oc2ccccc2)cc1)c1cccc2cccnc12]
357

TABLE 1-continued
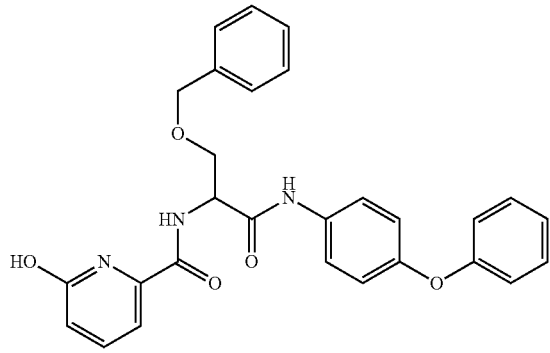 [SMILES: O=C(NC(COCc1ccccc1)C(=O)Nc1ccc(Oc2ccccc2)cc1)c1cccc(O)n1]
358
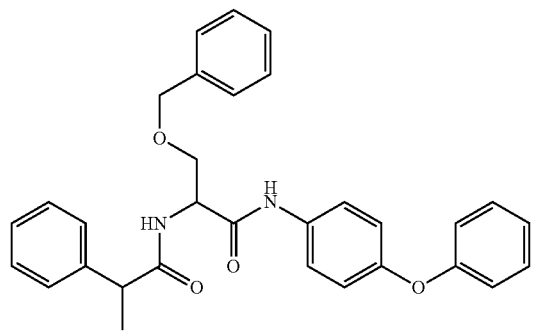 [SMILES: CC(C(=O)NC(COCc1ccccc1)C(=O)Nc1ccc(Oc2ccccc2)cc1)c1ccccc1]
359
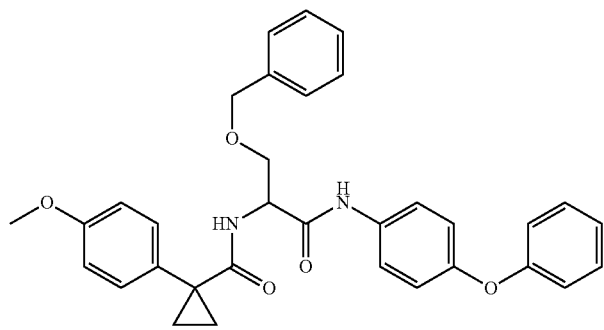 [SMILES: COc1ccc(C2(C(=O)NC(COCc3ccccc3)C(=O)Nc3ccc(Oc4ccccc4)cc3)CC2)cc1]
360
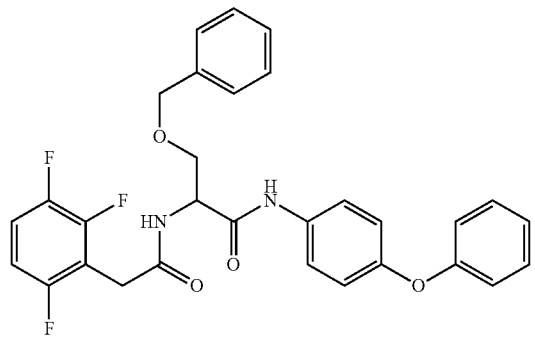 [SMILES: O=C(Cc1c(F)ccc(F)c1F)NC(COCc1ccccc1)C(=O)Nc1ccc(Oc2ccccc2)cc1]
361

TABLE 1-continued
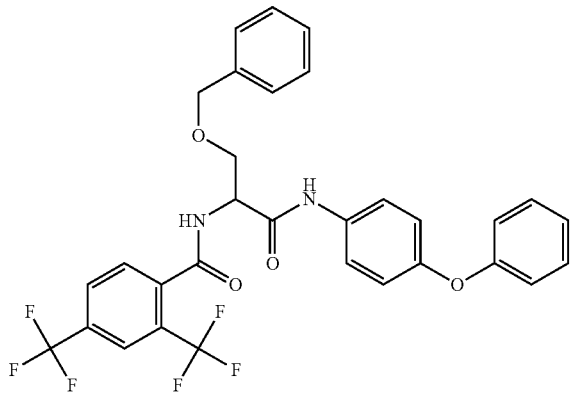 [SMILES: O=C(NC(COCc1ccccc1)C(=O)Nc1ccc(Oc2ccccc2)cc1)c1ccc(C(F)(F)F)cc1C(F)(F)F]
362
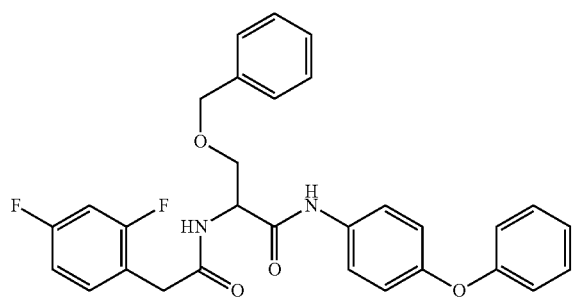 [SMILES: O=C(Cc1ccc(F)cc1F)NC(COCc1ccccc1)C(=O)Nc1ccc(Oc2ccccc2)cc1]
363
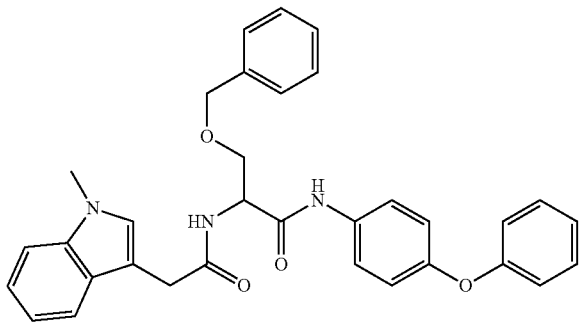 [SMILES: Cn1cc(CC(=O)NC(COCc2ccccc2)C(=O)Nc2ccc(Oc3ccccc3)cc2)c2ccccc21]
364
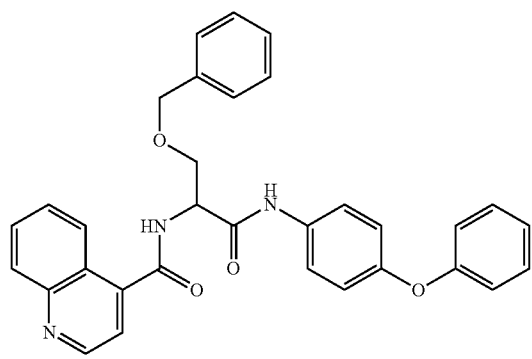 [SMILES: O=C(NC(COCc1ccccc1)C(=O)Nc1ccc(Oc2ccccc2)cc1)c1ccnc2ccccc12]
365

TABLE 1-continued
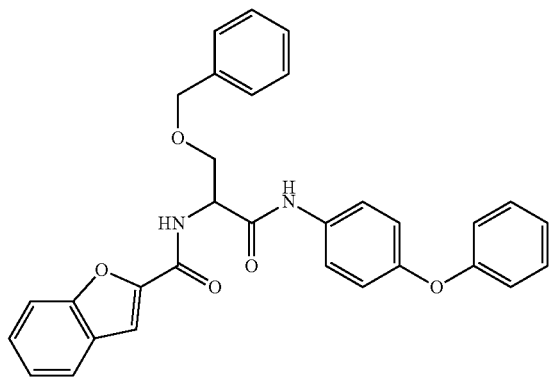 [SMILES: O=C(NC(COCc1ccccc1)C(=O)Nc1ccc(Oc2ccccc2)cc1)c1cc2ccccc2o1]
366
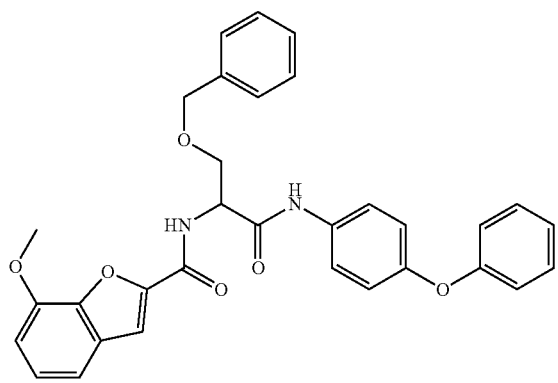 [SMILES: COc1cccc2cc(C(=O)NC(COCc3ccccc3)C(=O)Nc3ccc(Oc4ccccc4)cc3)oc12]
367
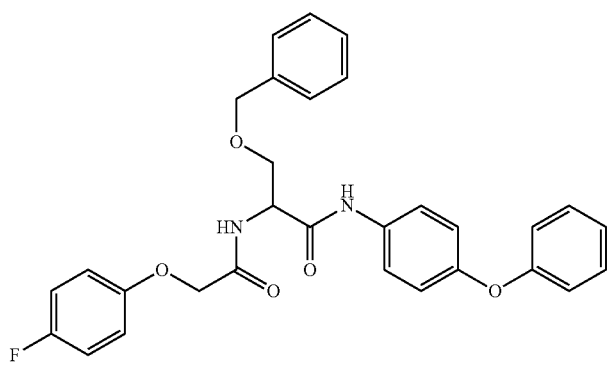 [SMILES: O=C(COc1ccc(F)cc1)NC(COCc1ccccc1)C(=O)Nc1ccc(Oc2ccccc2)cc1]
368
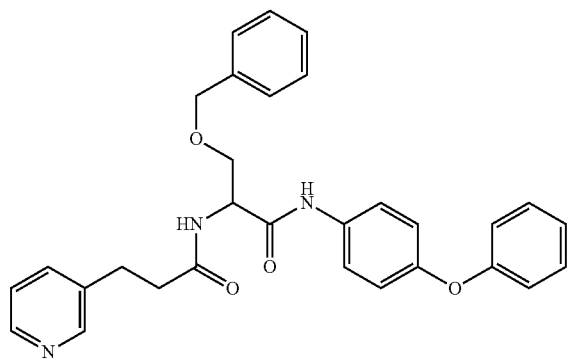 [SMILES: O=C(CCc1cccnc1)NC(COCc1ccccc1)C(=O)Nc1ccc(Oc2ccccc2)cc1]
369

TABLE 1-continued
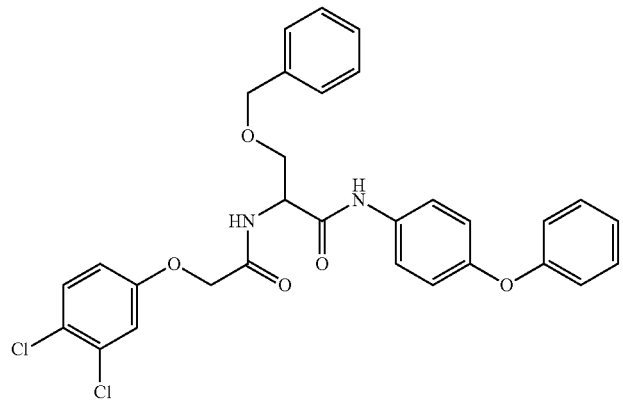 [SMILES: O=C(COc1ccc(Cl)c(Cl)c1)NC(COCc1ccccc1)C(=O)Nc1ccc(Oc2ccccc2)cc1]
370
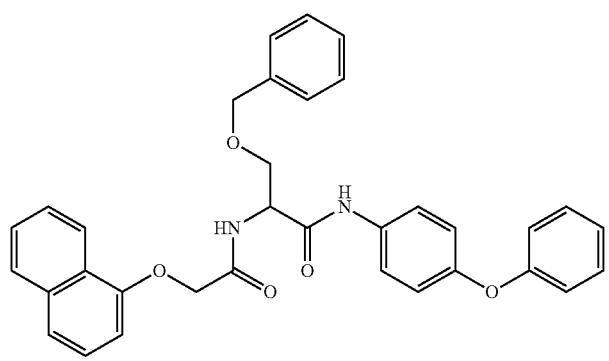 [SMILES: O=C(COc1cccc2ccccc12)NC(COCc1ccccc1)C(=O)Nc1ccc(Oc2ccccc2)cc1]
371
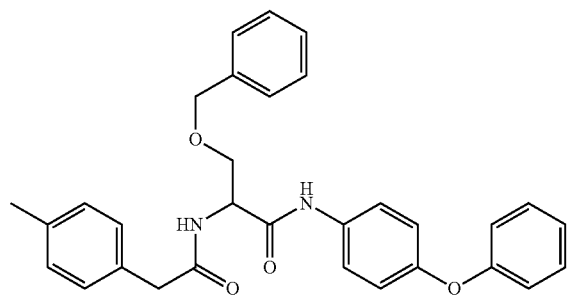 [SMILES: Cc1ccc(CC(=O)NC(COCc2ccccc2)C(=O)Nc2ccc(Oc3ccccc3)cc2)cc1]
372
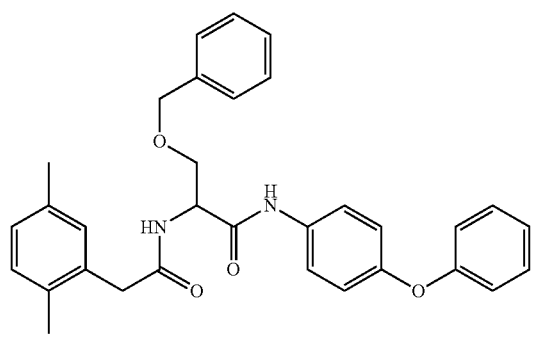 [SMILES: Cc1ccc(C)c(CC(=O)NC(COCc2ccccc2)C(=O)Nc2ccc(Oc3ccccc3)cc2)c1]
373

TABLE 1-continued
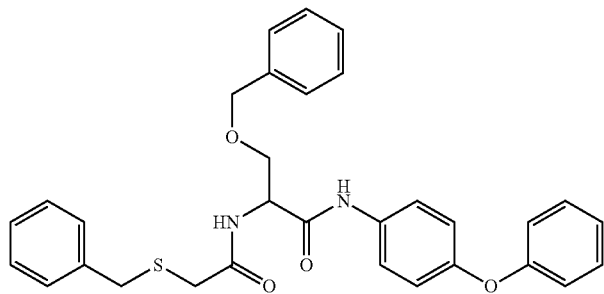 [SMILES: O=C(CSCc1ccccc1)NC(COCc1ccccc1)C(=O)Nc1ccc(Oc2ccccc2)cc1]
374
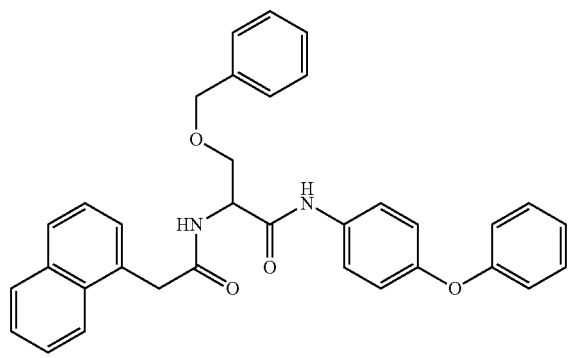 [SMILES: O=C(Cc1cccc2ccccc12)NC(COCc1ccccc1)C(=O)Nc1ccc(Oc2ccccc2)cc1]
375
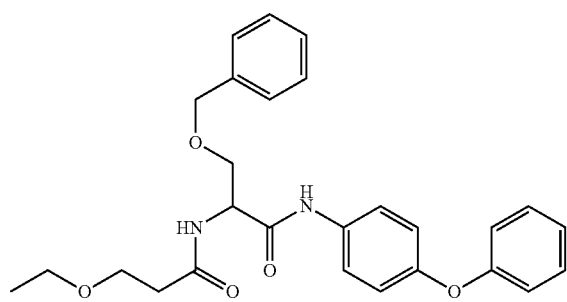
376
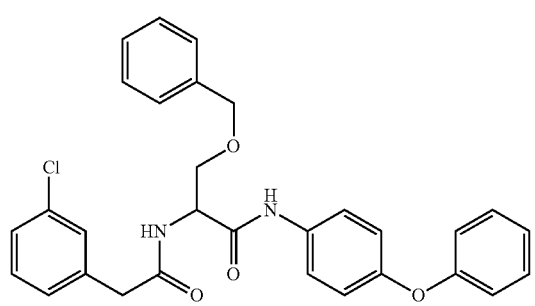 [SMILES: O=C(Cc1cccc(Cl)c1)NC(COCc1ccccc1)C(=O)Nc1ccc(Oc2ccccc2)cc1]
377

TABLE 1-continued
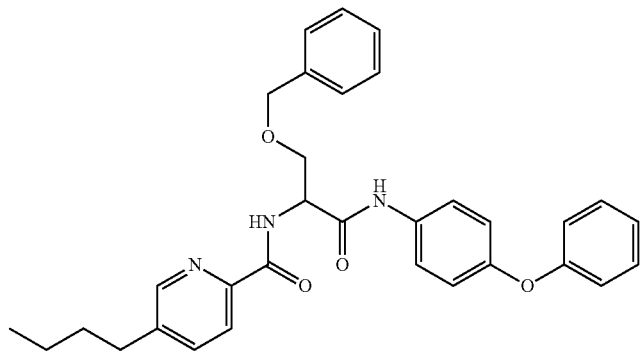 [SMILES: CCCCc1ccc(C(=O)NC(COCc2ccccc2)C(=O)Nc2ccc(Oc3ccccc3)cc2)nc1]
378
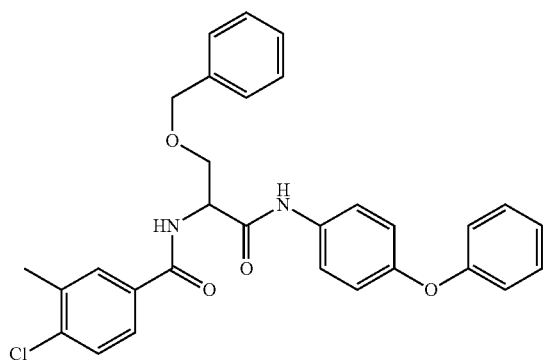 [SMILES: Cc1cc(C(=O)NC(COCc2ccccc2)C(=O)Nc2ccc(Oc3ccccc3)cc2)ccc1Cl]
379
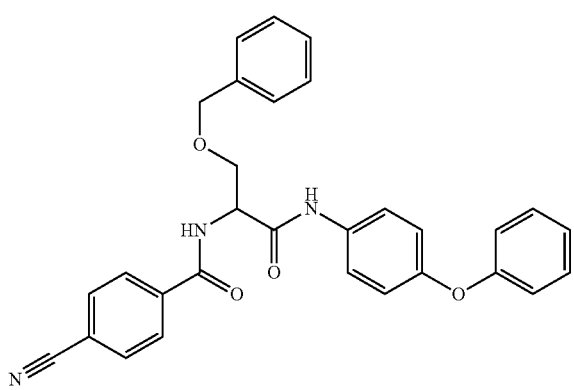 [SMILES: N#Cc1ccc(C(=O)NC(COCc2ccccc2)C(=O)Nc2ccc(Oc3ccccc3)cc2)cc1]
380
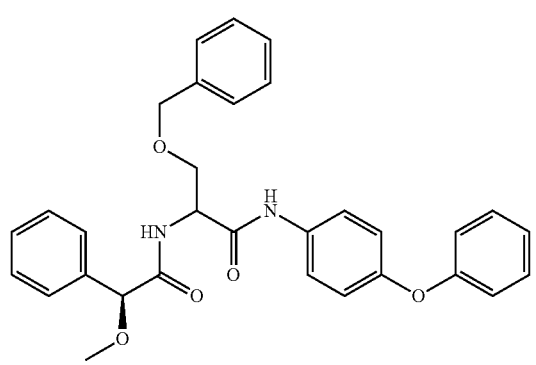
381

TABLE 1-continued
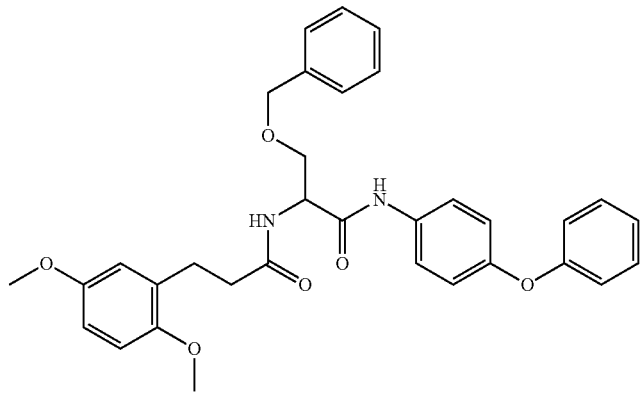 [SMILES: COc1ccc(OC)c(CCC(=O)NC(COCc2ccccc2)C(=O)Nc2ccc(Oc3ccccc3)cc2)c1]
382
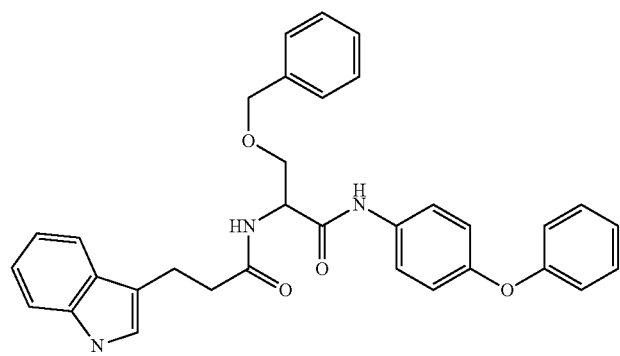 [SMILES: O=C(CCc1c[nH]c2ccccc12)NC(COCc1ccccc1)C(=O)Nc1ccc(Oc2ccccc2)cc1]
383
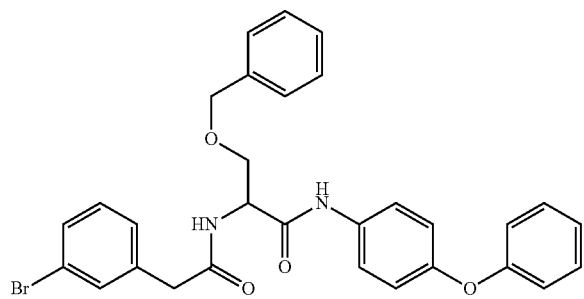 [SMILES: O=C(Cc1cccc(Br)c1)NC(COCc1ccccc1)C(=O)Nc1ccc(Oc2ccccc2)cc1]
384
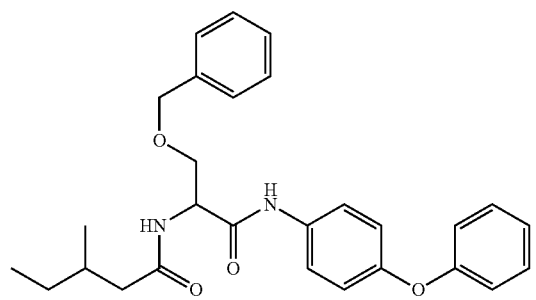 [SMILES: CCC(C)CC(=O)NC(COCc1ccccc1)C(=O)Nc1ccc(Oc2ccccc2)cc1]
385

TABLE 1-continued
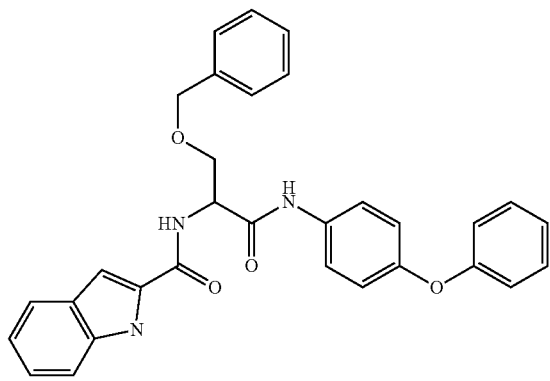 [SMILES: O=C(NC(COCc1ccccc1)C(=O)Nc1ccc(Oc2ccccc2)cc1)c1cc2ccccc2[nH]1]
386
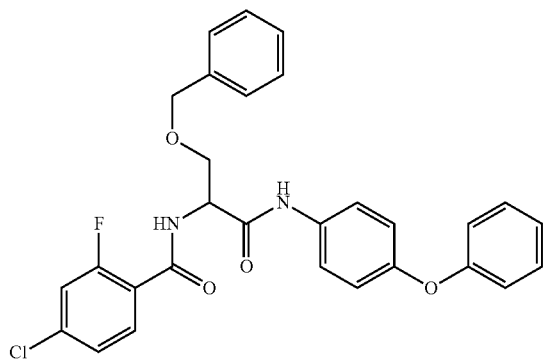 [SMILES: O=C(NC(COCc1ccccc1)C(=O)Nc1ccc(Oc2ccccc2)cc1)c1ccc(Cl)cc1F]
387
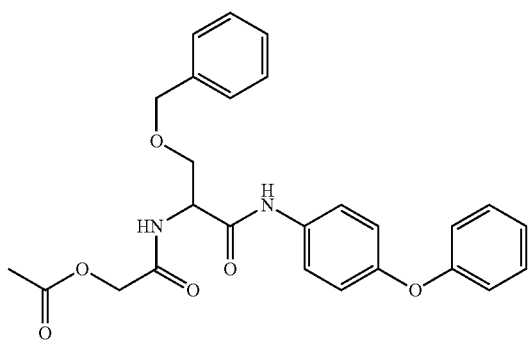
388
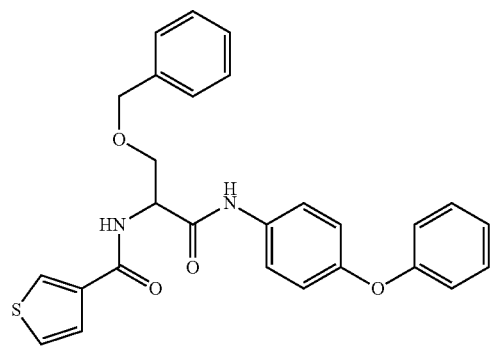 [SMILES: O=C(NC(COCc1ccccc1)C(=O)Nc1ccc(Oc2ccccc2)cc1)c1ccsc1]
389

TABLE 1-continued
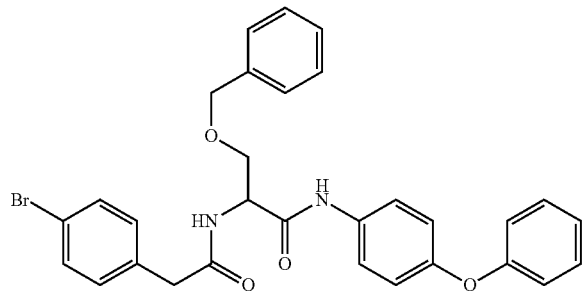 [SMILES: O=C(Cc1ccc(Br)cc1)NC(COCc1ccccc1)C(=O)Nc1ccc(Oc2ccccc2)cc1]
390
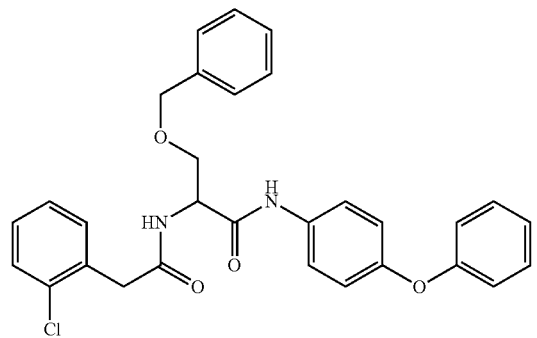 [SMILES: O=C(Cc1ccccc1Cl)NC(COCc1ccccc1)C(=O)Nc1ccc(Oc2ccccc2)cc1]
391
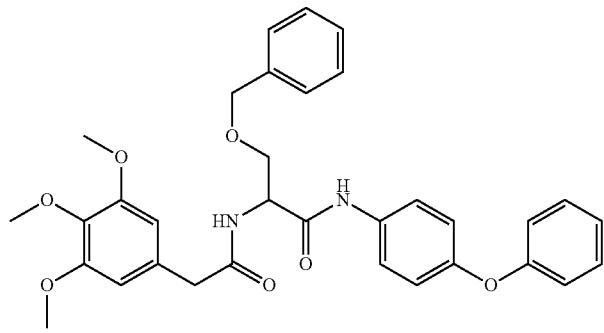 [SMILES: COc1cc(CC(=O)NC(COCc2ccccc2)C(=O)Nc2ccc(Oc3ccccc3)cc2)cc(OC)c1OC]
392
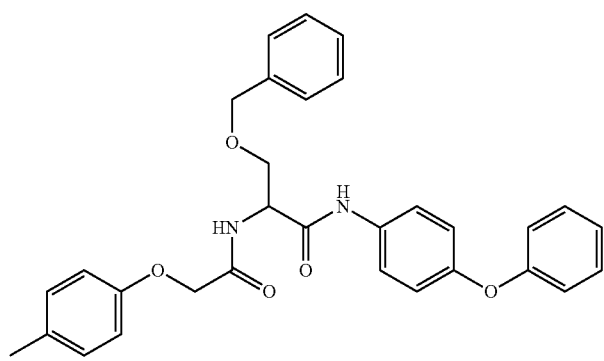 [SMILES: Cc1ccc(OCC(=O)NC(COCc2ccccc2)C(=O)Nc2ccc(Oc3ccccc3)cc2)cc1]
393

TABLE 1-continued
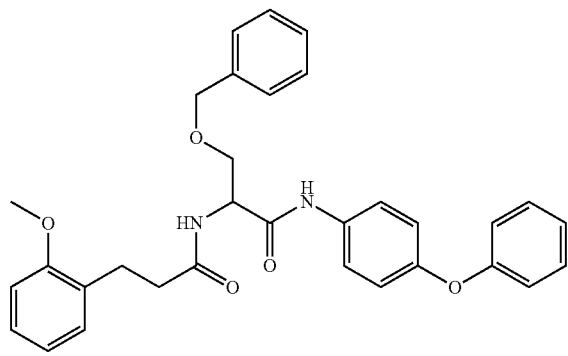 [SMILES: COc1ccccc1CCC(=O)NC(COCc1ccccc1)C(=O)Nc1ccc(Oc2ccccc2)cc1]
394
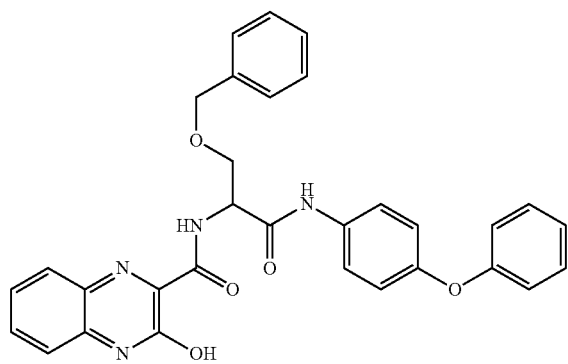 [SMILES: O=C(NC(COCc1ccccc1)C(=O)Nc1ccc(Oc2ccccc2)cc1)c1nc2ccccc2nc1O]
395
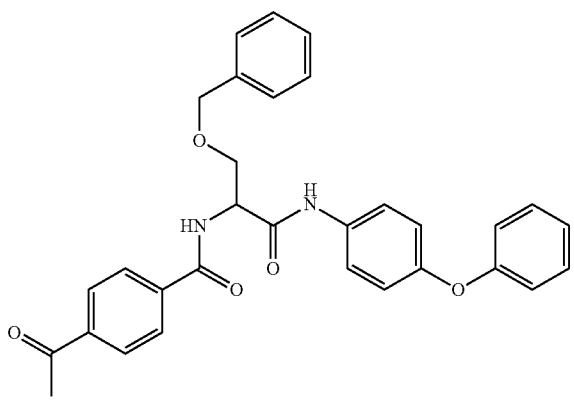 [SMILES: CC(=O)c1ccc(C(=O)NC(COCc2ccccc2)C(=O)Nc2ccc(Oc3ccccc3)cc2)cc1]
396

TABLE 1-continued
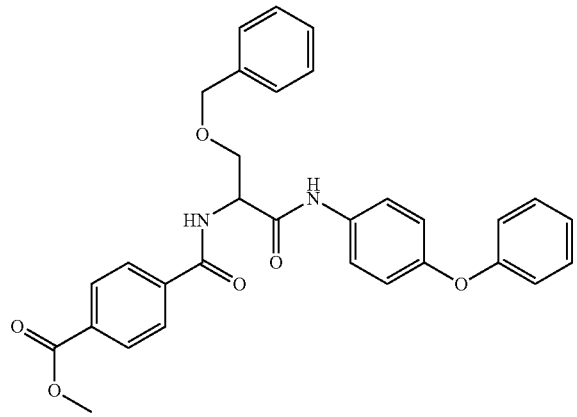 [SMILES: COC(=O)c1ccc(C(=O)NC(COCc2ccccc2)C(=O)Nc2ccc(Oc3ccccc3)cc2)cc1]
397
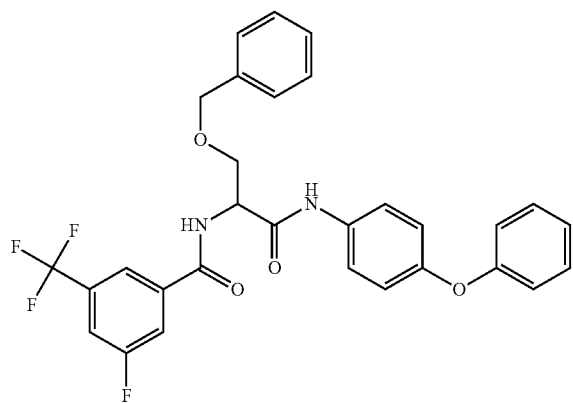 [SMILES: O=C(NC(COCc1ccccc1)C(=O)Nc1ccc(Oc2ccccc2)cc1)c1cc(F)cc(C(F)(F)F)c1]
398
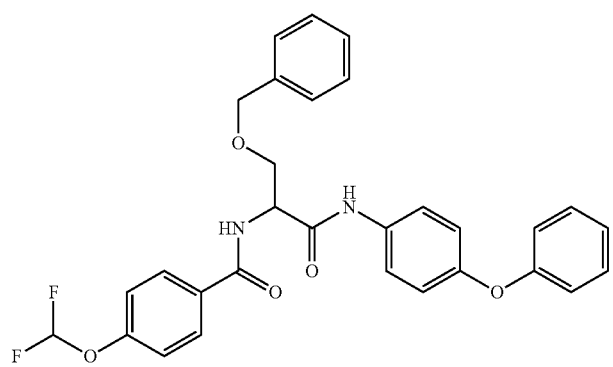 [SMILES: O=C(NC(COCc1ccccc1)C(=O)Nc1ccc(Oc2ccccc2)cc1)c1ccc(OC(F)F)cc1]
399

TABLE 1-continued
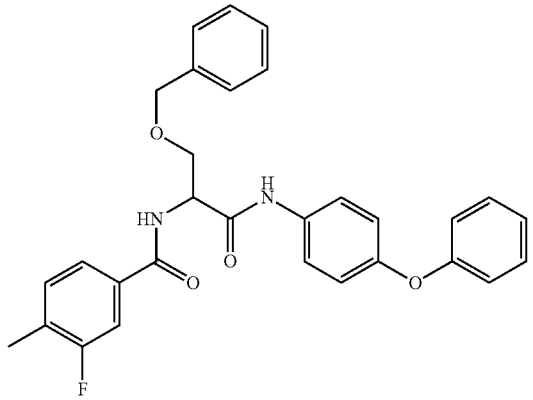 [SMILES: Cc1ccc(C(=O)NC(COCc2ccccc2)C(=O)Nc2ccc(Oc3ccccc3)cc2)cc1F]
400
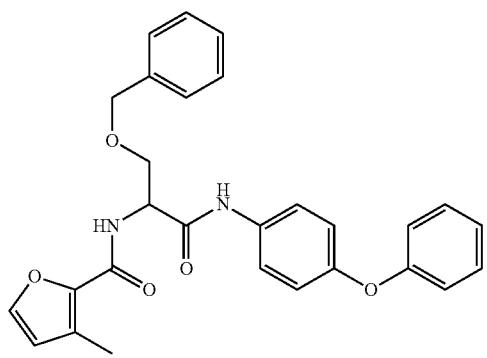 [SMILES: Cc1ccoc1C(=O)NC(COCc1ccccc1)C(=O)Nc1ccc(Oc2ccccc2)cc1]
401
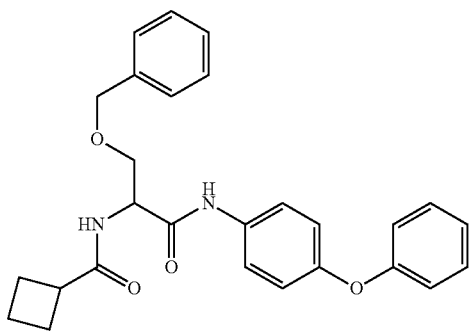 [SMILES: O=C(NC(COCc1ccccc1)C(=O)Nc1ccc(Oc2ccccc2)cc1)C1CCC1]
402
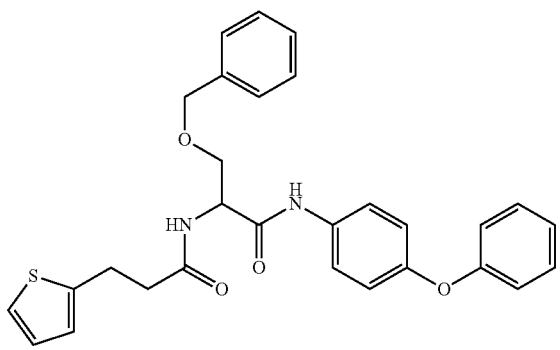 [SMILES: O=C(CCc1cccs1)NC(COCc1ccccc1)C(=O)Nc1ccc(Oc2ccccc2)cc1]
403

The compounds of the invention include the entire group of compounds or any consecutively or non-consecutively numbered subgroup of compounds or any individual compound.

Compositions and Administration:

A compound of the invention can be administered to a patient by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

A compound of the invention can be administered in any acceptable solid, semi-solid, liquid or gaseous dosage form. Acceptable dosage forms include, but are not limited to, aerosols, creams, emulsions, gases, gels, grains, liniments, lotions, ointments, pastes, powders, solutions, suspensions, syrups and tablets. Acceptable delivery systems include, but are not limited to, biodegradable implants (e.g., poly(DL-lactide), lactide/glycolide copolymers and lactide/caprolactone copolymers), capsules, douches, enemas, inhalers, intrauterine devices, nebulizers, patches, pumps and suppositories.

A dosage form of the invention may be comprised solely of a compound of the invention or the compound of the invention may be formulated along with conventional excipients, pharmaceutical carriers, adjuvants and/or other medicinal or pharmaceutical agents. Acceptable excipients include, but are not limited to, (a) antiadherents, such as croscarmellose sodium, crosprovidone, sodium starch glycolate, microcrystalline cellulose, starch and talc; (b) binders, such as cellulose, gelatin, hydroxypropyl cellulose, lactose, maltitol, polyethylene glycol, polyvinyl pyrrolidone, sorbitol, starch, sugar, sucrose and xylitol; (c) coatings, such as cellulose, shellac and zein; (d) disintegrants, such as cellulose, crosslinked polyvinyl pyrrolidone, sodium carboxymethyl cellulose, methylcellulose, microcrystalline cellulose, sodium starch glycolate and starch; (e) filling agents, such as calcium carbonate, cellulose, dibasic calcium phosphate, glucose, lactose, mannitol, sorbitol and sucrose; (f) flavoring agents; (g) coloring agents; (h) glidants, such as calcium stearate, colloidal silicon dioxide, glyceryl behenate, glyceryl monostearate, glyceryl palmitostearate, hydrogenated vegetable oil, magnesium stearate, magnesium trisilicate, mineral oil, polyethylene glycols, silicon dioxide, starch, stearate, stearic acid, talc, sodium stearyl fumarate, sodium benzoate and zinc; (i) lubricants, such as calcium stearate, hydrogenated vegetable oils, magnesium stearate, mineral oil, polyethylene glycol, sodium stearyl fumarate, stearin, stearic acid and talc; and (j) preservatives, such as chlorobutanol, citric acid, cysteine, methionine, methyl paraben, phenol, propyl paraben, retinyl palmitate, selenium, sodium citrate, sorbic acid, vitamin A, vitamin C and vitamin E. Pharmaceutical carriers include soluble polymers, microparticles made of insoluble or biodegradable natural and synthetic polymers, microcapsules, lipoproteins, liposomes and micelles.

A pharmaceutical composition of the invention will contain a therapeutically effective amount of a compound of the invention, or an individual stereoisomer or mixture of stereoisomers thereof, or a pharmaceutically acceptable salt thereof, with the remainder of the pharmaceutical composition comprised of one or more pharmaceutically acceptable excipients. Generally, a compound of the invention, or an individual stereoisomer or mixture of stereoisomers thereof, or a pharmaceutically acceptable salt thereof will comprise from 1% to 99% by weight of a pharmaceutically acceptable composition, with the remainder of the composition comprised of one or more pharmaceutically acceptable excipients. Typically, a compound of the invention, or an individual stereoisomer or mixture of stereoisomers thereof, or a pharmaceutically acceptable salt thereof will comprise from 5% to 75% by weight of a pharmaceutically acceptable composition, with the remainder of the composition comprised of one or more pharmaceutically acceptable excipients. Methods for preparing the dosage forms of the invention are known, or will be apparent, to those skilled in this art; for example, see Remington's Pharmaceutical Sciences, 18th Ed., (Mack Publishing Company, Easton, Pa., 1990).

A therapeutically effective amount of a compound of the invention will vary depending upon a sundry of factors including the activity, metabolic stability, rate of excretion and duration of action of the compound, the age, weight, general health, sex, diet and species of the patient, the mode and time of administration of the compound, the presence of adjuvants or additional therapeutically active ingredients in a composition and the severity of the disease for which the therapeutic effect is sought.

The compounds of the invention can be administered to human patients at dosage levels in the range of about 0.1 to about 10,000 mg per day. Thus, a normal human adult having a body weight of about 70 kilograms can be administered a dosage in the range of from about 0.15 µg to about 150 mg per kilogram of body weight per day. Typically, a normal adult human will be administered from about 3 mg to about 100 mg per kilogram of body weight per day. The optimum dose of a compound of the invention for a particular patient can be determined by one of ordinary skill in the art.

The compounds of the invention can be administered alone as the sole therapeutically active ingredient or in combination with one or more additional therapeutically active ingredients and/or treatments. Suitable therapeutically active ingredients (for and/or treatments that can be used in combination with a compound of the invention for treating cancer include, but are not limited to (a) topoisomerase I inhibitors, such as camptothecin, topotecan, 9-nitrocamptothecin, 9-aminocamptothecin, karenitecin, irinotecan, and the like; (b) topoisomerase II inhibitors, such as etoposide, etoposide phosphate, teniposide, amsacrine, epipodophyllotoxin derivatives, razoxane, dexrazoxane (Zinecard), and the like; (c) classical alkylating agents, such as (i) nitrogen mustards, such as mechlorethamine, cyclophosphamide, ifosfamide, chlorambucil, melphalan, and the like, (ii) aziridines, such as, thiotepa, trenimon, triethylenemelamine, and the like, (iii) epoxides, such as dianhydrogalactitol, dibromodulcitol, and the like, (iv) alkyl alkane sulfonates, such as busulfan, dimethylsulfate, and the like, (v) nitrosoureas, such as chloroethylnitrosourea, BCNU, CCNU (lomustine), methyl-CCNU (semustine), streptozotocin, chlorozotocin, and the like and (vi) alkylating agent-steroid conjugates, such as prednimustine (chlorambucil-prednisolone), estramustine (nornitrogen mustard-estradiol), and the like; (d) non-classical alkylating agents, such as procarbazine, dacarbazine, hexamethylmelamine, pentamethylmelamine, temozolomide, and the like; (e) other DNA damaging/binding agents, such as cisplatins, such as cisplatin, carboplatin, oxaliplatin, bleomycin, and the like; (f)

antibiotics, such as dactinomycin, mithramycin, mitomycin C, and the like; (g) anthracyclines/anthracenediones, such as daunorubicin, doxorubicin, epirubicin, idarubicin, and the like; (h) antimetabolites, such as (i) antifolates, such as methotrexate, edatrexate, trimethoprim, nolatrexed, raltitrexed (Tomudex), hydroxyurea, and the like; and (ii) nucleic acid analogs such as 5-fluorouracil, ftorafur, capecitabine, furtulon, eniluracil, ara-C (Cytosine arabinose), 5-azacytidine, gemcitabine, mercaptopurine, thioguanine, pentostatin, and the like; (i) ribonucleic acid related agents, such as antisense DNA, antisense RNA, antisense DNA/RNA hybrids, ribozymes, and the like; (j) radiation, such as ultraviolet, and the like; (k) vinca alkaloids, such as vincristine, vinblastine, and the like; (l) other anti-cancer agents having mechanisms of action that may or may not involve DNA damage; (m) taxanes, such as axel, docetaxel, tesetaxel, ortataxel, ARG100, and the like; (n) enzymes, such as L-asparaginase and the like; (o) natural products; (p) miscellaneous agents, such as kinase inhibitors, imatinib, and the like; (q) mitotane; (r) aminoglutethimide; (s) hormones and antagonists, such as diethylstilbestrol, ethinyl estradiol, tamoxifen, anastrozole, testosterone propionate, fluoxymesterone, flutamide, leuprolide, prednisone, hydroxyprogesterone caproate, medroxyprogesterone aacetate, megestrol acetate, and the like; (t) ixabepilone; (u) epothilonesan; (v) vascular disrupting agents which target tubulin (for example, OXi4503, CYT997, BNC-105, MPC-6827, indibulin, crinobulin, denibulin, tosbretabulin, plinabulin, E7974 and ABT751); (w) 5-fluoruracil; (x) biological response modifiers, such as interferon-alfa, interleukin, and the like; and (y) antibodies (such as VEGF-trap (aflibercept), and antibodies conjugated to tubulin active drugs such as trastuzumab-DM1, SAR-3419, brentuximab vedotin, MEDI-547, BIIB-015, and huN901-DM1).

In another embodiment, suitable therapeutically active ingredients (for and/or treatments that can be used in combination with a compound of the invention for treating cancer include, but are not limited to, The compounds of the invention can be administered alone as the sole therapeutically active ingredient or in combination with one or more additional therapeutically active ingredients and/or treatments. Suitable therapeutically active ingredients (for and/or treatments that can be used in combination with a compound of the invention for treating cancer include, but are not limited to (a) topoisomerase I inhibitors, such as camptothecin, topotecan, 9-nitrocamptothecin, 9-aminocamptothecin, karenitecin, irinotecan, and the like; (b) topoisomerase II inhibitors, such as etoposide, etoposide phosphate, teniposide, amsacrine, epipodophyllotoxin derivatives, razoxane, dexrazoxane (Zinecard), and the like; (c) classical alkylating agents, such as (i) nitrogen mustards, such as mechlorethamine, cyclophosphamide, ifosfamide, chlorambucil, melphalan, and the like, (ii) aziridines, such as, thiotepa, trenimon, triethylenemelamine, and the like, (iii) epoxides, such as dianhydrogalactitol, dibromodulcitol, and the like, (iv) alkyl alkane sulfonates, such as busulfan, dimethylsulfate, and the like, (v) nitrosoureas, such as chloroethylnitrosourea, BCNU, CCNU (lomustine), methyl-CCNU (semustine), streptozotocin, chlorozotocin, and the like and (vi) alkylating agent-steroid conjugates, such as prednimustine (chlorambucil-prednisolone), estramustine (nornitrogen mustard-estradiol), and the like; (d) non-classical alkylating agents, such as procarbazine, dacarbazine, hexamethylmelamine, pentamethylmelamine, temozolomide, and the like; (e) other DNA damaging/binding agents, such as cisplatins, such as cisplatin, carboplatin, oxaliplatin, bleomycin, and the like; (f) antibiotics, such as dactinomycin, mithramycin, mitomycin C, and the like; (g) anthracyclines/anthracenediones, such as daunorubicin, doxorubicin, epirubicin, idarubicin, and the like; (h) antimetabolites, such as (i) antifolates, such as methotrexate, edatrexate, trimethoprim, nolatrexed, raltitrexed (Tomudex), hydroxyurea, and the like; and (ii) nucleic acid analogs such as 5-fluorouracil, ftorafur, capecitabine, furtulon, eniluracil, ara-C (Cytosine arabinose), 5-azacytidine, gemcitabine, mercaptopurine, thioguanine, pentostatin, and the like; (i) ribonucleic acid related agents, such as antisense DNA, antisense RNA, antisense DNA/RNA hybrids, ribozymes, and the like; (j) radiation, such as ultraviolet, and the like; (k) vinca alkaloids, such as vincristine, vinblastine, and the like; (l) other anti-cancer agents having mechanisms of action that may or may not involve DNA damage; (m) taxanes, such as axel, docetaxel, tesetaxel, ortataxel, ARG100, and the like; (n) enzymes, such as L-asparaginase and the like; (o) natural products; (p) miscellaneous agents, such as kinase inhibitors, imatinib, and the like; (q) mitotane; (r) aminoglutethimide; (s) hormones and antagonists, such as diethylstilbestrol, ethinyl estradiol, tamoxifen, anastrozole, testosterone propionate, fluoxymesterone, flutamide, leuprolide, prednisone, hydroxyprogesterone caproate, medroxyprogesterone aacetate, megestrol acetate, and the like; (t) ixabepilone; (u) epothilonesan; (v) vascular disrupting agents which target tubulin (for example, OXi4503, CYT997, BNC-105, MPC-6827, indibulin, crinobulin, denibulin, tosbretabulin, plinabulin, E7974 and ABT751); (w) 5-fluoruracil; (x) biological response modifiers, such as interferon-alfa, interleukin, and the like; and (y) antibodies (such as VEGF-trap (aflibercept), and antibodies conjugated to tubulin active drugs such as trastuzumab-DM1, SAR-3419, brentuximab vedotin, MEDI-547, BIIB-015, and huN901-DM1).

In another embodiment, the suitable therapeutically active ingredients (for and/or treatments that can be used in combination with a compound of the invention for treating cancer include, but are not limited to (a) topoisomerase I inhibitors, such as camptothecin, topotecan, 9-nitrocamptothecin, 9-aminocamptothecin, karenitecin, irinotecan, and the like; (b) topoisomerase II inhibitors, such as etoposide, etoposide phosphate, teniposide, amsacrine, epipodophyllotoxin derivatives, razoxane, dexrazoxane (Zinecard), and the like; (c) classical alkylating agents, such as (i) nitrogen mustards, such as mechlorethamine, cyclophosphamide, ifosfamide, chlorambucil, melphalan, and the like, (ii) aziridines, such as, thiotepa, trenimon, triethylenemelamine, and the like, (iii) epoxides, such as dianhydrogalactitol, dibromodulcitol, and the like, (iv) alkyl alkane sulfonates, such as busulfan, dimethylsulfate, and the like, (v) nitrosoureas, such as chloroethylnitrosourea, BCNU, CCNU (lomustine), methyl-CCNU (semustine), streptozotocin, chlorozotocin, and the like and (vi) alkylating agent-steroid conjugates, such as prednimustine (chlorambucil-prednisolone), estramustine (nornitrogen mustard-estradiol), and the like; (d) non-classical alkylating agents, such as procarbazine, dacarbazine, hexamethylmelamine, pentamethylmelamine, temozolomide, and the like; (e) other DNA damaging/binding agents, such as cisplatins, such as cisplatin, carboplatin, oxaliplatin, bleomycin, and the like; (f) antibiotics, such as dactinomycin, mithramycin, mitomycin C, and the like; (g) anthracyclines/anthracenediones, such as daunorubicin, doxorubicin, epirubicin, idarubicin, and the like; (h) antimetabolites, such as (i) antifolates, such as methotrexate, edatrexate, trimethoprim, nolatrexed, raltitrexed (Tomudex), hydroxyurea, and the like; and (ii) nucleic acid analogs such as 5-fluorouracil, ftorafur, capecitabine, furtulon, eniluracil, ara-C (Cytosine arabinose), 5-azacytidine, gemcitabine, mercaptopurine, thioguanine, pentostatin, and the like; (i) ribonucleic acid related agents, such as antisense DNA, antisense RNA, antisense DNA/RNA hybrids, ribozymes, and the like; (j) radiation, such as ultraviolet, and the like; (k) enzymes, such as L-asparaginase and the like; (l) natural products; (m) miscellaneous agents, such as kinase inhibitors, imatinib, and the like; (n) mitotane; (o) aminoglutethimide; (p) hormones and antagonists, such as diethylstilbestrol, ethinyl estradiol, tamoxifen, anastrozole, testosterone propionate, fluoxymesterone, flutamide, leuprolide, prednisone, hydroxyprogesterone caproate, medroxyprogesterone aacetate, megestrol acetate, and the like; (q) ixabepilone; (r) epothilonesan; (s) vascular disrupting agents which target tubulin (for example, OXi4503, CYT997, BNC-105, MPC-6827, indibulin, crinobulin, denibulin, tosbretabulin, plinabulin, E7974 and ABT751); (t) 5-fluoruracil; (u) biological response modifiers, such as interferon-alfa, interleukin, and the like; and (v) antibodies (such as VEGF-trap (aflibercept), and antibodies conjugated to tubulin active drugs such as trastuzumab-DM1, SAR-3419, brentuximab vedotin, MEDI-547, BIIB-015, and huN901-DM1).

In another embodiment, the suitable therapeutically active ingredients (for and/or treatments that can be used in combination with a compound of the invention for treating cancer include, but are not limited to (a) topoisomerase I inhibitors; (b) topoisomerase II inhibitors (c) classical alkylating agents; (d) non-classical alkylating agents; (e) other DNA damaging/binding agents; (f) antibiotics; (g) biological response modifiers; (h) antibodies (i) ribonucleic acid related agents; (j) radiation; (k) enzymes; (l) natural products; (m) kinase inhibitors; (n) mitotane; (o) aminoglutethimide; (p) hormones and antagonists; (q) ixabepilone; (r) epothilonesan; and (s) 5-fluoruracil. In another embodiment, suitable therapeutically active ingredients (for and/or treatments that can be used in combination with a compound of the invention for treating cancer include, but are not limited to taxanes (such as paclitaxel, docetaxel, tesetaxel, ortataxel and ARG100), vascular disrupting agents which target tubulin (for example, OXi4503, CYT997, BNC-105, MPC-6827, indibulin, crinobulin, denibulin, tosbretabulin, plinabulin, E7974 and ABT751), vincristine, vinblastine, ixabepilone, 5-fluoruracil and epothilones.

In another embodiment, suitable therapeutically active ingredients (for and/or treatments that can be used in combination with a compound of the invention for treating cancer include, but are not limited to paclitaxel, docetaxel and vincristine.

Other agents suitable for use in combination with a compound of the invention are disclosed in "Cancer Chemotherapy and Biotherapy: Principles and Practice," Third edition, B. A. Chabner and D. L. Longo, eds., 2001, Lippincott Williams and Wilkins, Philadelphia, U.S.A.; P. Calabresi and B. A. Chabner, "Chemotherapy of Neoplastic Diseases" in "Goodman and gilman's The Pharmacological Basis of Therapeutics," Tenth edition, J. g. Hardman and L. E. Limbird, eds., 2001, McGraw-Hill, New York, USA, pp. 1381-1388; and B. A. Chabner, D. P. Ryan, L. Paz-Ares, R. garcia-Carbonero, and P. Calabresi, "Antineoplastic Agents" in "Goodman and gilman's The Pharmacological Basis of Therapeutics," Tenth edition, J. g. Hardman and L. E. Limbird, eds., 2001, McGraw-Hill, New York, USA, pp. 1389-1459.

The compounds of the invention can be administered to a patient by any means of administration, either alone or in combination, with other therapeutically active ingredients and/or treatments as described above for treating a disease, disorder or syndrome. In another embodiment, the disease being treated is cancer, and the compound being administered is a compound of Formula I, I(a), II, II(a), III, III(a), IV or IV(a), or a pharmaceutically acceptable salt thereof, either alone or in combination with other therapeutically active ingredients and/or treatments as described above. Non-limiting examples of cancers that can be treated in any of the above embodiments include, but are not limited to, NSCLC, breast cancer, prostate cancer, ovarian cancer, head and neck cancer, gastric adenomas, lymphomas, leukemias, multiple myelomas, testicular cancer, pediatric cancers (for example, rhabdomyosarcoma, Wilms tumor, ad neuroblastoma).

Representative pharmaceutical formulations containing a compound of Formula I, I(a), II, II(a), III, III(a), IV or IV(a), or a pharmaceutically acceptable salt thereof, are described below in the Pharmaceutical Composition Examples.

Chemistry:

Compounds of Formula I can be made by proceeding as in Scheme 1:

Scheme 1

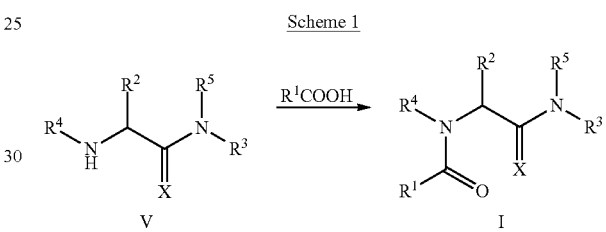

wherein each X, $R^1$, $R^2$, $R^3$, $R^4$ and $R^5$ are as defined for Formula I in the Summary of the Invention. Compounds of Formula II, III and IV can be prepared by proceeding in an analogous fashion.

Scheme 1 depicts a general procedure for preparing compounds of Formula I, in which a compound of Formula V is reacted with a carboxylic acid of formula $R^1COOH$. The reaction is carried out in the presence of a suitable coupling reagent, e.g., dicyclohexylcarbodiimide (DCC), diisopropylcarbodiimide (DIC), 1-benzotriazole (BTA), diethylphosphate-1-cyclohexyl-3-(2-morpholinylethyl) carbodiimide (BDP), 1-(3-dimethylaminopropyl-3-ethyl-carbodiimide hydrochloride (EDC), benzotriazol-1-yloxytris(dimethylamino)phosphonium hexafluorophosphate (BOP), O-benzotriazol-1-yl-N,N,N',N'-tetramethyluronium (HBTU), O-(7-azabenzotriazole-1-yl)-N,N,N',N'-tetramethyluronium hexafluorophosphate (HATU), and the like, preferably HATU, and a suitable base, e.g., diisopropylethylamine (DIEA), N-methylmorpholine (NMM), N-methylpiperidine, pyridine, tributylamine (TBA), triethylamine (TEA), trimethylamine (TMA), and the like, preferably DIEA, in a suitable aprotic solvent, e.g., acetone, acetonitrile (ACN), N,N-dimethylformamide (DMF), dimethyl sulfoxide (DMSO), ethyl acetate (EA), methyl ethyl ketone (MEK), tetrahydrofuran (THF), and the like, preferably DMF, at ambient to reflux temperatures and requires 0.25 to 20 hours for completion. A detailed description of procedures for making compounds of Formula I in accordance with Scheme 1 are set forth in Examples 1, 2 and 13, infra.

Compounds of Formula V, wherein X is O, can be made by proceeding as in Scheme 2:

Scheme 2

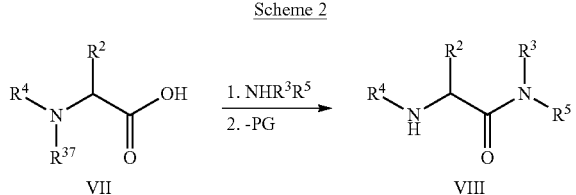

in which each $R^2$, $R^3$, $R^4$, $R^5$ and $R^{37}$ are as defined in the Summary of the Invention for a compound of Formula II.

Scheme 2 depicts a general procedure for making compounds of Formula V, wherein X is O (Formula VIII), in which a compound of Formula VII is reacted with an amine of the formula $NHR^3R^5$ and then a deprotection step is carried out when $R^{37}$ is a nitrogen protecting group. The reaction with the amine is carried out in the presence of a suitable coupling reagent, e.g., DCC, DIC, BTA, BDP, EDC, BOP, HBTU, HATU, and the like, preferably HATU, and a suitable base, e.g., DIEA, NMM, N-methylpiperidine, pyridine, TBA, TEA, TMA, and the like, preferably DIEA, in a suitable aprotic solvent, e.g., acetone, ACN, DMF, DMSO, EA, MEK, THF, and the like, preferably DMF, at ambient to reflux temperatures and requires from 0.25 to 20 hours for completion. The deprotection step is carried out with a suitable acid, e.g., trifluoroacetic acid, hydrochloric acid, and the like, in suitable solvent e.g., dioxane, hexane, methylene chloride, diethyl ether, and the like, at ambient to reflux temperatures and requires 1 to 20 hours for completion. A detailed description of the procedures for making compounds of Formula VIII in accordance with Scheme 2 are set forth in References 5, 6 and 10 and Example 13, infra Compounds of Claim VII are commercially available or can be made by methods ordinarily known in the art. For example, compounds of Formula VII wherein $R^2$ together with $R^4$ and the atoms to which $R^2$ and $R^4$ are attached form a five membered ring can be made by proceeding as in Scheme 3:

Scheme 3

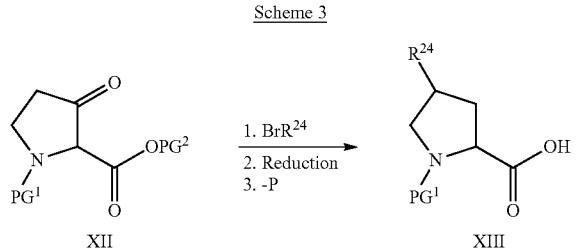

in which $PG^1$ is a nitrogen protecting group, $PG^2$ is an oxygen protecting group and $R^{24}$ is as defined in the Summary of the Invention for a compound of Formula IV.

Scheme 3 depicts a general procedure for making compounds of Formula VII wherein $R^2$ together with $R^4$ and the atoms to which $R^2$ and $R^4$ are attached form a five membered ring (Formula XIII) in which (1) a compound of Formula XII is reacted with a bromide of the formula $BrR^{24}$ to give a corresponding 4-substituted 3-oxopyrrolidine, (2) the 3-oxopyrrolidine is reduced to a corresponding 4-substituted pyrrolidine and (3) the oxygen protecting group ($PG^2$) is removed. The reaction with the bromide is carried out in the presence of a strong base e.g., sodium hexamethyldisilazide (NaHMDS), potassium hexamethyldisilazane (KHMDS), lithium hexamethyldisilazide (LiHMDS), and the like, preferably LiHMDS, in a suitable solvent, e.g., acetone, ACN, DMF, DMSO, EA, MEK, THF, and the like, preferably THF, at about −78° C. and requires from 1 to 3 hours for completion.

The reduction is carried out with suitable reducing conditions, e.g., a mixture of borane and boron trifluoride diethyl etherate in a suitable solvent, e.g., dioxane, hexane, methylene chloride, diethyl ether, and the like, at 0° C. to ambient temperatures and requires 1 to 2 hours to complete. Deprotection is carried out with a suitable base, e.g., lithium hydroxide, and in a suitable solvent, e.g., a mixture of water and methanol, at ambient temperatures and requires 1 to 2 hours for completion. Detailed descriptions for preparing compounds of Formula XIII in accordance with Scheme 3 are set forth in References 3 and 4, infra.

Compounds having the formula $NHR^3R^5$ are commercially available or can be made by methods ordinarily known in the art. For example, methods for making compounds having the formula $NHR^3R^5$ are set forth in References 1 and 2, infra.

Compounds of Formula VI wherein X is $NR^6$ can be made by proceeding as in Scheme 4:

Scheme 4

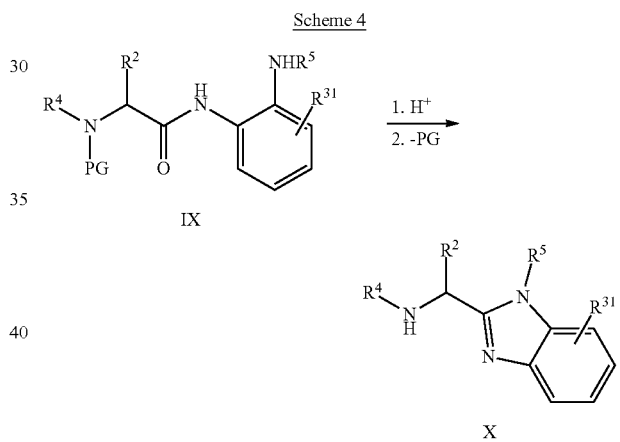

wherein PG is a nitrogen protecting group and each $R^2$, $R^4$, $R^5$ and $R^{31}$ are as defined in the Summary of the Invention for a compound of Formula I.

Scheme 4 depicts a general procedure for preparing compounds of Formula VI wherein X is $NR^6$ (Formula X) in which an aniline of Formula IX is treated with acid to effect ring closing and then the nitrogen protecting group (PG) is removed. The ring closing is carried out with a suitable acid, e.g., acetic acid, or the like, at 50° C. to reflux temperature and requires 0.5 to 2 hours for completion. Deprotection is carried out with a suitable acid, e.g., trifluoroacetic acid, hydrochloric acid, and the like, in suitable solvent e.g., dioxane, hexane, methylene chloride, diethyl ether, and the like, at ambient to reflux temperatures and requires 0.5 to 20 hours for completion. A detailed description for making a compound of Formula X in accordance with Scheme 4 is set forth in Reference 9, Step (d), infra Compounds of Formula IX can be made by reacting a compound of Formula VII, as described above, wherein $R^{37}$ is a nitrogen protecting group with a compound of Formula XI:

XI

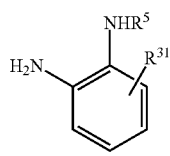

wherein each $R^5$ and $R^{31}$ are as defined in the Summary of the Invention for a compound of Formula I. The reaction is carried out in the presence of a suitable coupling reagent, e.g., DCC, DIC, BTA, BDP, EDC, BOP, HBTU, HATU, and the like, preferably HATU, and a suitable base, e.g., DIEA, NMM, N-methylpiperidine, pyridine, TBA, TEA, TMA, and the like, preferably DIEA, in a suitable aprotic solvent, e.g., acetone, ACN, DMF, DMSO, EA, MEK, THF, and the like, preferably DMF, at ambient to reflux temperatures and requires from 0.25 to 20 hours for completion.

Compounds of Formula XI are made by reducing a corresponding 2-nitroaniline. The reduction is carried out with suitable reducing conditions, e.g., under hydrogen gas in the presence of 10% palladium on carbon, in the presence of ammonium formate and 10% palladium on carbon, and the like, in a suitable solvent, e.g., methanol, ethanol, and the like, at ambient to reflux temperatures and requires 0.5 to 5 hours for completion. Suitable 2-nitroanilines are commercially available or can be prepared by methods ordinarily known in the art. A detailed description for making a compound of Formula IX is set forth in Reference 11, infra.

Compounds of Formula IV in which $R^{24}$ is —$X^9NHR^{29}$ can be made by proceeding as in Scheme 5:

Scheme 5

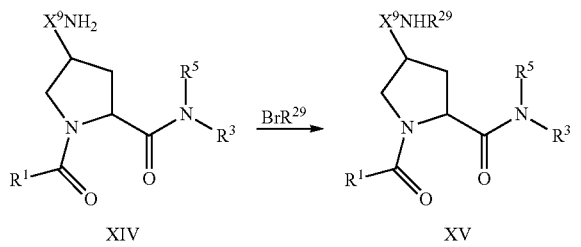

wherein each $X^9$, $R^1$, $R^3$, $R^5$ and $R^{29}$ are as defined in the Summary of the Invention for a compound of Formula IV.

Scheme 5 depicts a general procedure for preparing compounds of Formula IV wherein $R^{26}$ and $R^{27}$ are hydrogen and $R^{24}$ is —$X^9NHR^{29}$ in which a compound of Formula XIV is reacted with a compound of $BrR^{29}$. The reaction is carried out in the presence of a suitable base, e.g., potassium carbonate, or the like, in a suitable solvent, e.g., acetone, ACN, DMF, DMSO, EA, MEK, THF, and the like, preferably DMF, at ambient to reflux temperatures and requires 0.5 to 1 hour to complete. Detailed descriptions for making compounds of Formula IV in accordance with Scheme 5 are set for in Examples 5, 6 and 7, infra. Compounds of Formula IV in which $R^{24}$ is isoindolin-2-yl can be prepared by proceeding as in Scheme 5, but substituting 1,2-bis(bromomethyl)benzene.

Compounds of Formula IV in which $R^{24}$ is —$X^9NHX^{10}R^{30}$, wherein $X^9$, $X^{10}$ and $R^{30}$ are as defined in the Summary of the Invention for a compound of Formula IV, can be prepared by reacting a compound of Formula XIV with an aldehyde of the formula $C(O)X^{13}R^{30}$ wherein $X^{13}$ is a bond or $(C_{1-2})$alkylene. The reaction is carried out under suitable reducing conditions, e.g., in the presence of sodium triacetoxyborohydride, or the like, a catalytic amount of acid, e.g., acetic acid, or the like, in a suitable solvent, e.g., acetone, ACN, DMF, DMSO, EA, MEK, THF, and the like, preferably DMF, at ambient to reflux temperatures and requires 16 to 24 hours to complete, see Example 8, infra.

Compounds of Formula XIV can be prepared from a corresponding compound of Formula IV in which $R^{28}$ is benzyloxycarbonyl or 9H-fluoren-9-yl)methyloxycarbonyl. The 9H-fluoren-9-yl)methyloxycarbonyl group is removed under basic conditions. A secondary amine base such as piperidine, piperazine or morpholine in an inert solvent, for example, DMF, is particularly useful for this purpose. The reaction is carried out at ambient to reflux temperatures and requires 0.5 to 1 hour for completion, see Example 6, infra The benzylozycarbonyl group is removed with suitable reducing conditions, e.g., under hydrogen gas in the presence of 10% palladium on carbon, in a suitable solvent, e.g., methanol, ethanol, and the like, preferably methanol, at ambient to reflux temperatures and requires 1 to 2 hours for completion, see Example 5, infra. Alternatively, a compound of Formula XIV wherein $X^9$ is methylene can be prepared by reducing the corresponding pyrrolidine-3-carbonitrile. The reaction is carried out in the presence of acid, e.g., hydrochloric acid, and suitable reducing conditions, e.g., under hydrogen gas in the presence of 10% palladium on carbon, in a suitable solvent, e.g., methanol, ethanol, and the like, preferably methanol, at ambient to reflux temperatures and requires 18 to 24 hours for completion, e.g., see Example 7, infra. The carbonitrile is prepared by methods analogous to that for preparing compounds of Formula I, see Reference 11, infra.

Compounds of Formula IV in which $R^{24}$ is —$X^9OR^{29}$ can be made by proceeding as in Scheme 6:

Scheme 6

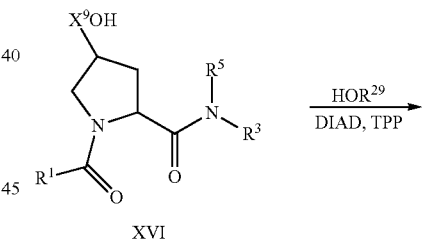

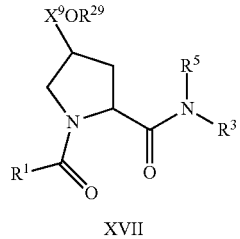

wherein each $X^9$, $R^1$, $R^3$, $R^5$ and $R^{29}$ are as defined in the Summary of the Invention for a compound of Formula IV.

Scheme 6 depicts a general procedure for preparing compounds of Formula IV wherein $R^{26}$ and $R^{27}$ are hydrogen and is $R^{24}$ is —$X^9OR^{29}$ in which a compound of Formula XVI is reacted with an alcohol of the formula $HOR^{29}$. The reaction is conveniently carried out in the presence triphenylphosphine together with diisopropylazodicarboxylate or diethyl azodicarboxylate in a suitable solvent, e.g., acetone, ACN, DMF, DMSO, EA, MEK, THF, and the like, preferably THF, at ambient to reflux temperatures and requires 0.5 to 1 hour to complete, see Example 3, infra.

Compounds of Formula IV in which $R^{24}$ is $-X^{10}R^{30}$ can be prepared by proceeding as in Scheme 7:

Scheme 7

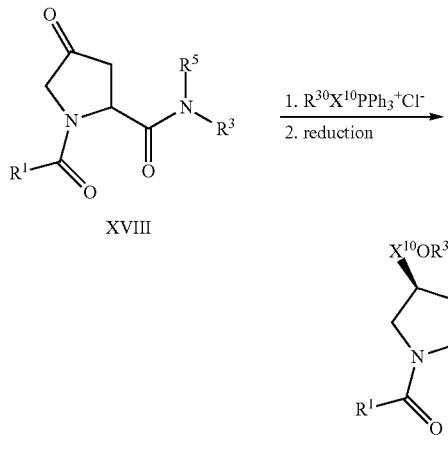

wherein each $X^{10}$, $R^1$, $R^3$, $R^5$ and $R^{30}$ are as defined in the Summary of the Invention for a compound of Formula IV.

Scheme 7 depicts a general procedure for preparing compounds of Formula IV wherein $R^{26}$ and $R^{27}$ are hydrogen and is $R^{24}$ is $-X^{10}R^{30}$ in which a 4-oxopyrrolidine-2-carboxamide of Formula XVIII is reacted with a triphenylphosphine chloride of the formula $R^{30}X^{10}PPh_3^+$ $Cl^-$ to obtain a corresponding 4-ylidenepyrrolidine-2-carboxamide, which then is reduced to give the compound of Formula XIX. The reaction with the triphenylphosphine is carried out in the presence of an excess of strong base, e.g., sodium hydride, lithium diisopropyl amine, and the like, in a suitable solvent, e.g., acetone, ACN, DMF, DMSO, EA, MEK, THF, and the like, preferably DMSO, at ambient to reflux temperatures and requires 12 to 24 hours to complete.

The reduction is carried out with suitable reducing conditions, e.g., under hydrogen gas in the presence of 10% palladium on carbon, or the like, in a suitable solvent, e.g., methanol, ethanol, and the like, at ambient to reflux temperatures and requires 1 to 3 hours to complete. Compounds of Formula XVIII can be made from a corresponding 4-hydroxypyrrolidine-2-carboxamide by methods ordinarily known in the art. A detailed description for making compounds of Formula IV in accordance with Scheme 7 is set for in Example 12, infra. Suitable triphenylphosphine chlorides are commercially available or can be prepared by reacting a compound of the formula $R^{30}X^{10}Cl$ with triphenylphosphine.

Compounds of Formula I wherein $R^2$ together with $R^4$ and the atoms to which $R^2$ and $R^4$ are attached form a piperizine ring of Formula (b) can be made by proceeding as in Scheme 8:

Scheme 8

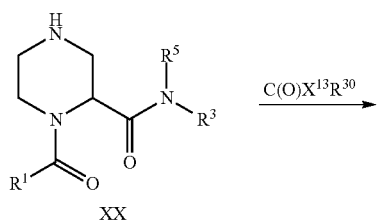

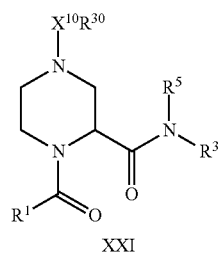

wherein $X^{13}$ is $(C_{1-2})$alkylene and each $X^{10}$, $R^1$, $R^3$, $R^5$ and $R^{30}$ are as defined in the Summary of the Invention for a compound of Formula I.

Scheme 8 depicts a general procedure for preparing compounds of Formula I wherein $R^2$ together with $R^4$ and the atoms to which $R^2$ and $R^4$ are attached form a piperizine ring of Formula (b) in which a compound of Formula XX is reacted with an aldehyde of the formula $C(O)X^{13}R^{30}$ wherein $X^{13}$ is a bond or $(C_{1-2})$alkylene. The reaction is carried out under reducing conditions, e.g., in the presence sodium triacetoxyborohydride, or the like, in a suitable solvent, e.g., methanol, ethanol, and the like, at ambient to reflux temperatures and requires 0.5 to 1 hour to complete, see Example 14, Step (b), infra Compounds of Formula XX can be prepared by reducing a corresponding compound of Formula I in which $R^{25}$ is benzyloxycarbonyl. The reduction is carried with suitable reducing conditions, e.g., under hydrogen gas in the presence of 10% palladium on carbon, or the like, in a suitable solvent, e.g., methanol, ethanol, or the like, at ambient to reflux temperatures and requires 12 to 24 hours to complete, see Example 14, Step (a).

Compound of Formula I, I(a), II, II(a), III, III(a), IV or IV(a), wherein $R^1$ is $-CH_2R^{12}$, were $R^{12}$ is an azolyl derivative, can be made by proceeding as in Scheme 9:

Scheme 9

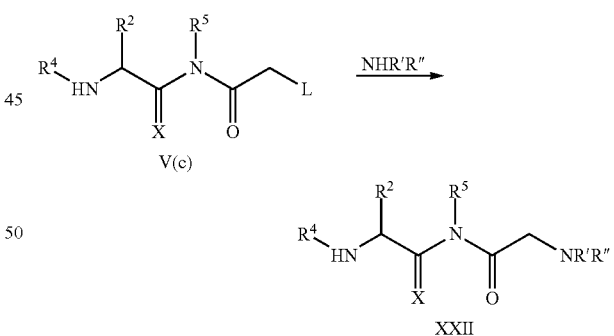

wherein L is a leaving group, R' and R" together with nitrogen atom to which each is attached form an azole or azolyl derivative and each $R^2$, $R^4$ and $R^5$ are as defined in the Summary of the Invention for a compound of Formula I.

Scheme 9 depicts a general procedure for preparing compounds of Formula I, I(a), II, II(a), III, III(a), IV or IV(a), wherein $R^1$ is $-CH_2R^{12}$, were $R^{12}$ is an azolyl derivative, in which a compound of Formula V(c) is reacted with an azole derivative of the formula NHR'R". The reaction is carried out in a suitable solvent, e.g., acetone, ACN, DMF, DMSO, EA, MEK, THF, and the like, preferably DMF, at ambient to reflux temperatures and requires 0.5 to 1 hour to complete. Suitable leaving groups include chloro, bromo, iodo, and the like. A detailed description for making compounds of Formula XXII in accordance with Scheme 9 is set for in Example 16, infra.

Compounds of Formula V(c) can be prepared by methods analogous to those set forth in Scheme 1. A detailed description for making compounds of Formula V(c) is set forth in Example 15, infra.

Reference 1

4-(5-Bromothiazol-2-yloxy)aniline

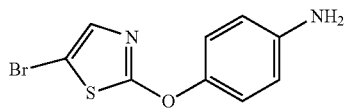 [SMILES: Nc1ccc(Oc2ncc(Br)s2)cc1]

Sodium hydride (60% dispersion in mineral oil, 342 mg, 8.55 mmol) was added to a flask charged with 4-nitrophenol (1 g, 7.19 mmol) and DMF (10 mL). The mixture was stirred at 100° C. for 16 hours and then diluted with ethyl acetate (20 mL). The dilution was washed with hydrochloric acid (1N, 20 mL), dried over anhydrous sodium sulfate, filtered and concentrated. The residue was combined with methanol (20 mL), palladium on carbon (100 mg) and ammonium formate (1 g, 16.1 mmol). The reaction mixture was heated at 70° C. for 1 hour then cooled to ambient temperature, filtered and concentrated. Product was purified from the residue by reverse phase HPLC to provide 4-(5-bromothiazol-2-yloxy)aniline (600 mg, 2.20 mmol, 31%) as an off-white solid. MS (EI) for $C_9H_7BrN_2OS$. found 273.2 (MH+).

Reference 2

4-(4-Fluoro-2-methylphenoxy)aniline

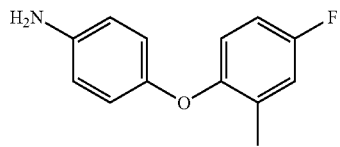 [SMILES: Cc1cc(F)ccc1Oc1ccc(N)cc1]

A microwave vessel was charged with 4'-bromoacetanilide (1.19 g, 5.56 mmol), 2,2,6,6-tetramethyl-3,5-heptanedione (0.23 mL, 1.1 mmol), copper(I) chloride (0.22 g, 2.2 mmol), cesium carbonate (5.42 g, 16.7 mmol), 4-fluoro-2-methylphenol (0.70 g, 5.6 mmol), and N-methyl-2-pyrrolidone (5 mL). The reaction mixture was heated at 200° C. in a microwave oven for 20 minutes. The reaction mixture then was cooled to ambient temperature and diluted with deionized water (20 mL). The dilution was extracted with ethyl acetate (20 mL) and the extract combined with saturated sodium bicarbonate (aq., 100 mL). The mixture was washed with brine (30 mL), dried over anhydrous sodium sulfate, filtered and concentrated. The residue was diluted with concentrated hydrochloric acid (15 mL) and the dilution was heated at 100° C. for 2 hours. The reaction mixture was cooled to ambient temperature and diluted with 4N sodium hydroxide until basic. The dilution was extracted with methylene chloride (30 mL) and the extract was washed with brine (30 mL), dried over anhydrous sodium sulfate, filtered and concentrated. Product was purified from the residue by reverse phase HPLC to give 4-(4-fluoro-2-methylphenoxy)aniline (0.33 g, 1.5 mmol, 27% yield) as off-white solid. MS (EI) for $C_{13}H_{12}FNO$. found 218.1 (MH+).

Proceeding as in Reference 2, but substituting 4-fluoro-3-methylphenol, gave 4-(4-fluoro-3-methylphenoxy)aniline (0.35 g, 1.6 mmol, 28% yield). MS (EI) for $C_{13}H_{12}FNO$. found 218.1 (MH+).

Reference 3

(2S,4R)-1-(tert-Butoxycarbonyl)-4-(4-fluorobenzyl)pyrrolidine-2-carboxylic acid

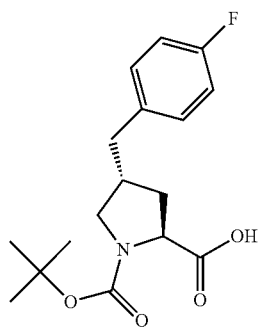 [SMILES: CC(C)(C)OC(=O)N1C[C@H](Cc2ccc(F)cc2)C[C@H]1C(=O)O]

Step (a) Triethyl orthoformate (16.6 mL, 100 mmol) and p-toluenesulfonic acid monohydrate (0.95 g, 5 mmol) were added to a solution of (S)-5-oxopyrrolidine-2-carboxylic acid (12.9 g, 100 mmol) in dry ethanol (100 mL). The solution was heated to reflux for 1.5 hours, distilling off ethyl formate (~18 mL). The reflux was continued for 2.5 hours and then the mixture was concentrated by evaporation under reduced pressure. The residue was placed under vacuum at 50° C. for 30 minutes to remove residual solvent. The residue was dissolved in acetonitrile (80 mL) and the solution was cooled to 0° C. Di-tert-butyl dicarbonate (24 g, 110 mmol) and 4-(dimethylamino)pyridine (1.22 g, 10 mmol) were added to the solution and the mixture was stirred for 16 hours at ambient temperature. The mixture was concentrated and the residue was partitioned between methylene chloride (100 mL) and 0.1N hydrochloric acid (100 mL). The organic phase was separated, washed with water, saturated sodium bicarbonate and then brine, dried over magnesium sulfate, filtered and concentrated. The residue was dissolved in hexane (100 mL) and methyl tert-butyl ether (50 mL) and the solution was seeded while stirring at ambient temperature to induce crystallization. The mixture was cooled to 0° C. and the solids were collected by cold filtration, washed with a single portion of hexane and dried to give (S)-1-tert-butyl 2-ethyl 5-oxopyrrolidine-1,2-dicarboxylate (14.9 g, 58%) as off-white fine needles. $^1$H NMR (400 MHz, CDCl3) δ 4.6 (dd, J=3.2, 9.6, 1H), 4.24 (q, J=7.2, 2H), 2.69-2.59 (m, 1H), 2.53-2.46 (m, 1H), 2.38-2.27 (m, 1H), 2.07-1.99 (m, 1H), 1.50 (s, 9H), 1.30 (t, J=7.2, 3H).

Step (b) 1M LiHMDS (27.5 mL, 27.5 mmol) was added to a solution of (S)-1-tert-butyl 2-ethyl 5-oxopyrrolidine-1,2-dicarboxylate (6.4 g, 25 mmol) in THF (20 mL) at −78° C. The mixture was stirred for 50 minutes and then 4-fluorobenzyl bromide (3.25 mL, 26.5 mmol) in THF (2 mL) was added dropwise. The mixture was stirred for 1 hour and 40 minutes and quenched with excess saturated ammonium chloride. The mixture was warmed to ambient temperature and extracted with ethyl acetate. The extract was washed with water and then brine, dried over magnesium sulfate, filtered and concentrated. The solid residue was dissolved in a 3:1 hexane/methyl tert-butyl ether solvent mixture (100 mL) and slow crystallization was allowed at ambient temperature. The mixture was cooled to 0° C. and the solid was collected by filtration, washed with a 3:1 hexane/methyl tert-butyl ether solvent mixture (50 mL) and dried to give (2S,4R)-1-tert-butyl 2-ethyl 4-(4-fluorobenzyl)-5-oxopyrrolidine-1,2-dicarboxylate (3.59 g, 39%) as a white solid. $^1$H NMR (400 MHz, CDCl$_3$) δ 7.15-7.12 (m, 2H), 7.01-6.96 (m, 2H), 4.47 (dd, J=2.0, 9.2, 1H), 4.22-4.17 (m, 2H), 3.22 (dd, J=4.4, 14.4, 1H), 2.94-2.85 (m, 1H), 2.71-2.65 (m, 1H), 2.08-1.94 (m, 2H), 1.50 (s, 9H), 1.26 (t, 3H).

Step (c) 1M borane in THF (10 mL, 10 mmol) followed by boron trifluoride diethyl etherate (1.25 mL, 10 mmol) were added to a solution of (2S,4R)-1-tert-butyl 2-ethyl 4-(4-fluorobenzyl)-5-oxopyrrolidine-1,2-dicarboxylate (1.8 g, 5 mmol) in methylene chloride (20 mL) at 0° C. The reaction was allowed to warm to ambient temperature while stirring for 1 hour. The mixture was cooled to 0° C. and then saturated ammonium chloride (25 mL) was slowly added. Water was added to dissolve precipitated solids and then the mixture was extracted with methylene chloride. The extract was washed with brine, dried over anhydrous sodium sulfate, filtered and concentrated. The residue was dissolved in methanol (15 mL) and then water (5 mL) followed by lithium hydroxide (1.05 g, 25 mmol) were added to the solution. The mixture was stirred at ambient temperature for 1 hour, concentrated under reduced pressure and diluted with water (20 mL). The aqueous solution was partitioned with methyl tert-butyl ether and the aqueous phase was separated, filtered, cooled to 0° C., acidified (pH≤3) with 6N hydrochloric acid and extracted twice with methylene chloride. The combined extract was washed with brine, dried over anhydrous sodium sulfate, filtered and concentrated to give (2S,4R)-1-(tert-butoxycarbonyl)-4-(4-fluorobenzyl)pyrrolidine-2-carboxylic acid (1.31 g, 81%) as a white solid. $^1$H NMR (400 MHz, CD$_3$OD) δ 7.22-7.18 (m, 2H), 7.03-6.99 (m, 2H), 4.29-4.22 (m, 1H), 3.57-3.50 (m, 1H), 3.07 (dd, J=8.0, 10.4, 1H), 2.68-2.65 (m, 2H), 2.58-2.50 (m, 1H), 2.04-1.97 (m, 2H), 1.44, 1.41 (2 s, 9H); MS (EI) for C$_{17}$H$_{22}$FNO$_4$. found 322.1 (M-H)$^-$.

Reference 4

(2S,4R)-1-(tert-butoxycarbonyl)-4-(4-fluoro-2-methylbenzyl)pyrrolidine-2-carboxylic acid

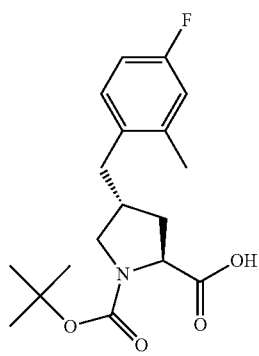 [SMILES: Cc1cc(F)ccc1C[C@@H]1C[C@@H](C(=O)O)N(C(=O)OC(C)(C)C)C1]

Step (a) Aqueous perchloric acid (70%, 5 mL) was added to a solution of (S)-5-oxopyrrolidine-2-carboxylic acid (20 g, 154.9 mmol) in tert-butyl acetate (260 mL) at ambient temperature. The mixture was stirred at ambient temperature for 18 hrs in a 500 mL round bottom flask sealed with a rubber septum and then poured carefully into sat. sodium bicarbonate (200 mL). The mixture was extracted with ethyl acetate (2×200 mL) and the combined extract was dried over anhydrous sodium sulfate and concentrated in vacuo. The crude product solidified under high vacuum. The solid was treated with a 10:1 hexanes/diethyl ether mixture. The solids were collect by filtration and dried to give (S)-tert-butyl 5-oxopyrrolidine-2-carboxylate (21.65 g, 116.9 mmol, 75.5%), clean as a white solid.

Step (b) The (S)-tert-butyl 5-oxopyrrolidine-2-carboxylate (21.65 g, 116.9 mmol) was dissolved in acetonitrile (300 mL) with 4-dimethylaminopyridine (1.29 g, 10.6 mmol) and the mixture was cooled to 0° C. in a cooling bath. A solution of di-tert-butyl dicarbonate (33.20 g, 152.0 mmol) in acetonitrile (30 mL) was added slowly to the mixture over 5 minutes. The cooling bath was removed after 30 minutes and the mixture was stirred at ambient temperature for 48 hours. The mixture was concentrated in vacuo and the residue was dissolved in a 1:1 hexanes/diethyl ether mixture (400 mL). The solution was washed with saturated sodium bicarbonate (2×20 mL) and then brine (40 mL) and dried over anhydrous sodium sulfate. The solvent was removed in vacuo and the residue was passed through a short column of silica gel (eluted with a 4:1 hexanes/ethyl acetate mixture) to give a light yellow oil, which solidified upon standing. The solid was treated with hexanes and the solids were collected by filtration and dried to give a white solid (24.22 g). The mother liquor was concentrated to give a white solid (4.05 g). The solids were combined to give (S)-di-tert-butyl 5-oxopyrrolidine-1,2-dicarboxylate (28.27 g, 99.2 mmol, 84.8%).

Step (c) (S)-Di-tert-butyl 5-oxopyrrolidine-1,2-dicarboxylate (1.15 g, 4.0 mmol) was dissolved in dry THF (20 mL) and the solution was cooled to −78° C. A solution of LiHMDS (1M in hexanes, 4.4 mL, 4.4 mmol) then was added dropwise under nitrogen. The mixture was cooled at −78° C. for 40 minutes and then a solution of 2-methyl-4-fluorobenzyl bromide (975 mg, 4.8 mmol) in THF (5 mL) was added slowly. The mixture was stirred at −78° C. for 2 hours and then quenched with saturated ammonium chloride (20 mL). The mixture was extracted with diethyl ether (3×70 mL) and the combined extract was washed with brine (30 mL), dried over anhydrous sodium sulfate and concentrated in vacuo. Product was purified from the residue by flash column (eluted with a 4:1 hexanes/diethyl ether mixture) to give (2S,4R)-di-tert-butyl 4-(4-fluoro-2-methylbenzyl)-5-oxopyrrolidine-1,2-dicarboxylate (810 mg, 2.0 nmol, 49.7%), clean as a white solid.

Step (d) The (2S,4R)-di-tert-butyl 4-(4-fluoro-2-methylbenzyl)-5-oxopyrrolidine-1,2-dicarboxylate (810 mg, 2.0 mmol) was dissolved in dry THF (5 mL). The solution was cooled to −78° C. with a cooling bath and then a solution of lithium triethylborohydride (1M in THF, 2.4 mL, 2.4 mmol) was added dropwise. The cooling bath was removed after 30 minutes and saturated sodium bicarbonate (5 mL) was added. The reaction mixture vessel was immersed in an ice water bath and 30% aqueous hydrogen peroxide (10 drops) was added. The mixture was stirred for 20 minutes at 0° C. and then concentrated in vacuo. The residue was diluted with water (10 mL) and the dilution was extracted with methylene chloride (3×40 mL). The combined extract was dried over anhydrous sodium sulfate and concentrated in vacuo. The residue was dissolved in methylene chloride (20 mL) and triethylsilane (0.31 mL, 2.0 mmol). The solution was cooled to −78° C. and then boron trifluoride etherate (0.27 mL, 2.13 mmol) was added dropwise. The mixture was stirred at −78°

C. for 30 minutes and then additional triethylsilane (0.31 mL, 2.0 mmol) and boron trifluoride etherate (0.27 mL, 2.13 mmol) were added. The mixture was stirred at −78° C. for 2 hours and then the cooling bath was removed and saturated sodium bicarbonate (4 mL) was added. The mixture was let stand for 5 minutes and then extracted with methylene chloride (3×40 mL). The combined extract was dried over anhydrous sodium sulfate and concentrated in vacuo. The residue was dissolved in methylene chloride (5 mL) and trifluoroacetic acid (5 mL) added to the solution. The mixture was stirred at ambient temperature for 5 hours and then concentrated in vacuo. The residue was dried under high vacuum to give (2S,4R)-4-(4-fluoro-2-methylbenzyl)pyrrolidine-2-carboxylic acid trifluoroacetic acid salt (651 mg, 100%) as a light yellow oil.

Step (e) (2S,4R)-4-(4-Fluoro-2-methylbenzyl)pyrrolidine-2-carboxylic acid trifluoroacetic acid salt (703 mg, 2.0 mmol) was dissolved in dioxane (10 mL), acetonitrile (16 mL), and N,N-diisopropylethylamine (0.94 mL) at ambient temperature and then a solution of di-tert-butyl dicarbonate (640 mg, 2.94 mmol) in acetonitrile (6 mL) was added to the mixture. The mixture was stirred at ambient temperature for 24 hours and concentrated in vacuo. The residue was dissolved in saturated sodium bicarbonate (60 mL) and the solution was washed with diethyl ether (3×40 mL). The aqueous layer was acidified with citric acid to pH 4 and then extracted with methylene chloride (3×40 mL). The combined extract was dried over anhydrous sodium sulfate and concentrated in vacuo to give (2S,4R)-1-(tert-butoxycarbonyl)-4-(4-fluoro-2-methylbenzyl)pyrrolidine-2-carboxylic acid (540 mg, 1.6 mmol, 76.8%) as a colorless oil.

Proceeding as in Reference 4, but substituting 2-chloro-4-fluorobenzyl bromide, gave (2S,4R)-1-(tert-butoxycarbonyl)-4-(2-chloro-4-fluorobenzyl)pyrrolidine-2-carboxylic acid.

Proceeding as in Reference 4, but substituting 4-methylbenzyl bromide, gave (2S,4R)-1-(tert-butoxycarbonyl)-4-(4-methylbenzyl)pyrrolidine-2-carboxylic acid (100 mg, 50%).

Proceeding as in Reference 4, but substituting benzyl bromide gave (2S,4R)-1-(tert-butoxycarbonyl)-4-(benzyl)pyrrolidine-2-carboxylic acid (200 mg, 60%).

Proceeding as in Reference 4, but substituting 3-fluorobenzyl bromide, gave (2S,4R)-1-(tert-butoxycarbonyl)-4-(3-fluorobenzyl)pyrrolidine-2-carboxylic acid (200 mg, 50%).

Proceeding as in Reference 4, but substituting 2-trifluoromethylbenzyl bromide, gave (2S,4R)-1-(tert-butoxycarbonyl)-4-(2-trifluoromethylbenzyl)pyrrolidine-2-carboxylic acid (180 mg, 55%).

Proceeding as in Reference 4, but substituting 2-chlorobenzyl bromide, gave (2S,4R)-1-(tert-butoxycarbonyl)-4-(2-chlorobenzyl)pyrrolidine-2-carboxylic acid (185 mg, 50%).

Proceeding as in Reference 4, but substituting 3-chlorobenzyl bromide, gave (2S,4R)-1-(tert-butoxycarbonyl)-4-(3-chlorobenzyl)pyrrolidine-2-carboxylic acid (200 mg, 60%).

Proceeding as in Reference 4, but substituting 2-methylbenzyl bromide, gave (2S,4R)-1-(tert-butoxycarbonyl)-4-(2-methylbenzyl)pyrrolidine-2-carboxylic acid (210 mg, 50%).

Proceeding as in Reference 4, but substituting 4-methoxybenzyl bromide, gave (2S,4R)-1-(tert-butoxycarbonyl)-4-(4-methoxybenzyl)pyrrolidine-2-carboxylic acid (200 mg, 50%).

Proceeding as in Reference 4, but substituting 5-chlorothien-2-ylmethyl bromide, gave (2S,4R)-1-(tert-butoxycarbonyl)-4-(5-chlorothien-2-yl)pyrrolidine-2-carboxylic acid (180 mg, 50%).

Proceeding as in Reference 4, but substituting 3-methoxybenzyl bromide, gave (2S,4R)-1-(tert-butoxycarbonyl)-4-(3-methoxybenzyl)pyrrolidine-2-carboxylic acid (180 mg, 50%).

Proceeding as in Reference 4, but substituting 2,4-dichlorobenzyl bromide, gave (2S,4R)-1-(tert-butoxycarbonyl)-4-(2,4-dichlorobenzyl)pyrrolidine-2-carboxylic acid (180 mg, 50%).

Proceeding as in Reference 4, but substituting 2-fluorobenzyl bromide, gave (2S,4R)-1-(tert-butoxycarbonyl)-4-(2-fluorobenzyl)pyrrolidine-2-carboxylic acid (180 mg, 55%).

Proceeding as in Reference 4, but substituting phenyl bromide, gave (2S,4R)-1-(tert-butoxycarbonyl)-4-(phenyl)pyrrolidine-2-carboxylic acid (180 mg, 55%).

Proceeding as in Reference 4, but substituting 3-methylbenzyl bromide, gave (2S,4R)-1-(tert-butoxycarbonyl)-4-(3-methylbenzyl)pyrrolidine-2-carboxylic acid.

Proceeding as in Reference 4, but substituting (2S,4R)-1-(tert-butoxycarbonyl)-4-(3,4-difluorobenzyl)pyrrolidine-2-carboxylic acid.

Proceeding as in Reference 4, but substituting 4-chlorobenzyl bromide, gave (2S,4R)-1-(tert-butoxycarbonyl)-4-(4-chlorobenzyl)pyrrolidine-2-carboxylic acid.

Proceeding as in Reference 4, but substituting 2,4,6-trifluorobenzyl bromide, gave (2S,4R)-1-(tert-butoxycarbonyl)-4-(2,4,6-trifluorobenzyl)pyrrolidine-2-carboxylic acid.

Reference 5

2-Amino-3-benzyloxy-N-(4-phenoxyphenyl)propanamide

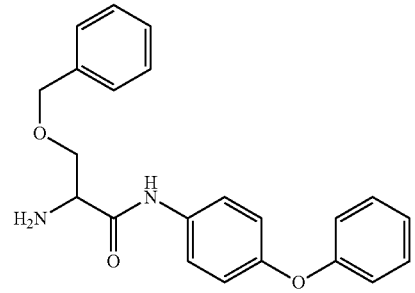 [SMILES: NC(COCc1ccccc1)C(=O)Nc1ccc(Oc2ccccc2)cc1]

A flask was charged with 3-benzyloxy-2-tert-butoxycarbonylaminopropionic acid (5.0 g, 16.9 mmoles), HATU (7.0 g, 18.6 mmoles) and DMF (5 mL). DIEA (8.8 mL, 50.7 mmoles) was added and the mixture was stirred for 15 minutes. 4-Phenoxyaniline (3.4 g, 18.6 mmoles) was added and the mixture was stirred at ambient temperature for 18 hours. The reaction mixture was partitioned between ethyl acetate and deionized water. The aqueous layer was separated and extracted twice with ethyl acetate. The combined extract was washed sequentially with 5% lithium chloride (3×10 mL), 1N sodium bicarbonate (2×10 mL), 5% citric acid (2×10 mL), deionized water (2×10 mL) and then brine (1×10 mL), dried over anhydrous sodium sulfate, filtered and concentrated in vacuo. The crude material was recrystallized from methanol to afford a white solid. The solid was combined with 4N hydrogen chloride in dioxane (25 mL). The mixture was stirred at ambient temperature for 18 hours. Volatiles then were removed under rotary evaporation. The resultant oil was partitioned between 1N sodium bicarbonate and ethyl acetate. The aqueous layer was extracted with ethyl acetate. The combined extract was washed with brine (2×10 mL), dried over anhydrous sodium sulfate, filtered and concentrated in vacuo. The crude was recrystallized from methanol to give 2-amino-3-benzyloxy-N-(4-phenoxyphenyl)propanamide (2 g, 5.47 mmoles, 33% yield), as an off-white solid. $^1$H-NMR (400 MHz, CDCl$_3$): δ 9.55 (s, 1H), 7.60-7.50 (m, 2H), 7.40-7.27 (m, 5H), 7.08 (t, 1H), 7.01-6.95 (m, 3H), 4.57 (t, 2H), 3.85-3.70 (m, 3H), 1.97 (2, 2H). MS (D) for C$_{22}$H$_{22}$N$_2$O$_3$. found 363.0 (MH+).

Proceeding as in Reference 5, but substituting (S)-2-(tert-butoxycarbonylamino)-5-phenylpentanoic acid, gave (S)-2-amino-N-(4-phenoxyphenyl)-5-phenylpentanamide (200 mg, 90%).

Proceeding as in Reference 5, but substituting 3-phenoxyaniline and (S)-23-(benzyloxy)-2-(tert-butoxycarbonylamino) propanoic acid, gave (S)-2-amino-3-(benzyloxy)-N-(3-phenoxyphenyl)propanamide (250 mg, 90%).

Proceeding as in Reference 5, but substituting (S)-3-(benzyloxy)-2-(tert-butoxycarbonylamino)propanoic acid, gave (S)-2-amino-3-(benzyloxy)-N-(4-phenoxyphenyl)propanamide (2700 mg, 44%).

Proceeding as in Reference 5, but substituting 4-(p-tolyloxy)aniline and (S)-3-(benzyloxy)-2-(tert-butoxycarbonylamino)propanoic acid, gave (S)-2-amino-3-(benzyloxy)-N-(4-(p-tolyloxy)phenyl)propanamide (350 mg, 92%).

Proceeding as in Reference 5, but substituting 4-(benzyloxy)aniline and (S)-3-(benzyloxy)-2-(tert-butoxycarbonylamino)propanoic acid, gave (S)-2-amino-3-(benzyloxy)-N-(4-(benzyloxy)phenyl)propanamide (160 mg, 84%).

Proceeding as in Reference 5, but substituting 4-(4-chlorophenoxy)aniline and (S)-2-(tert-butoxycarbonylamino)-4-phenylbutanoic acid, gave (S)-2-amino-N-(4-(4-chlorophenoxy)phenyl)-4-phenylbutanamide (320 mg, 94%).

Proceeding as in Reference 5, but substituting 4-(4-fluorophenoxy)aniline and (S)-2-(tert-butoxycarbonylamino)-5-phenylpentanoic acid, gave (S)-2-amino-N-(4-(4-fluorophenoxy)phenyl)-5-phenylpentanamide (165 mg, 21%).

Proceeding as in Reference 5, but substituting 4-(4-chlorophenoxy)aniline and (S)-2-(tert-butoxycarbonylamino)-3-phenylpropanoic acid, gave (S)-2-amino-N-(4-(4-chlorophenoxy)phenyl)-3-phenylpropanamide (45 mg, 13%).

Proceeding as in Reference 5, but substituting 4-(thiazol-2-yloxy)aniline and (S)-3-(benzyloxy)-2-(tert-butoxycarbonylamino)propanoic acid, gave (S)-2-amino-3-(benzyloxy)-N-(4-thiazol-2-yloxyphenyl)propanamide (200 mg, 60%).

Proceeding as in Reference 5, but substituting 4-(4-fluorophenoxy)aniline and (S)-5-acetamido-2-(tert-butoxycarbonylamino)pentanoic acid, gave (S)-5-acetamido-2-amino-N-(4-(4-fluorophenoxy)phenyl)pentanamide (200 mg, 56%).

Proceeding as in Reference 5, but substituting 4-(cyclohexyloxy)aniline and (S)-3-(benzyloxy)-2-(tert-butoxycarbonylamino)propanoic acid, gave (S)-2-amino-3-(benzyloxy)-N-(4-(cyclohexyloxy)phenyl)propanamide (200 mg, 50%).

Proceeding as in Reference 5, but substituting (S)-3-(benzyloxy)-2-(tert-butoxycarbonyl(methyl)amino)propanoic acid, gave (S)-3-(benzyloxy)-2-(methylamino)-N-(4-phenoxyphenyl)propanamide (192 mg, 90%).

Proceeding as in Reference 5, but substituting 3-chloro-4-phenoxyaniline and (S)-3-(benzyloxy)-2-(tert-butoxycarbonylamino)propanoic acid, gave (S)-2-amino-3-(benzyloxy)-N-(3-chloro-4-phenoxyphenyl)propanamide (470 mg, 70%).

Proceeding as in Reference 5, but substituting 4-(4-fluorophenoxy)aniline and (S)-3-(benzyloxy)-2-(tert-butoxycarbonylamino)propanoic acid, gave (S)-2-amino-3-(benzyloxy)-N-(4-(4-fluorophenoxy)phenyl)propanamide (443 mg, 69%).

Proceeding as in Reference 5, but substituting 4-(4-chlorophenoxy)aniline (329 mg, 1.5 mmoles) and (S)-3-(benzyloxy)-2-(tert-butoxycarbonylamino)propanoic acid (487 mg, 1.65 mmoles), gave (S)-2-amino-3-(benzyloxy)-N-(4-(4-chlorophenoxy)phenyl)propanamide (290 mg, 48%).

Proceeding as in Reference 5, but substituting 4-(3-chlorophenoxy)aniline and (S)-3-(benzyloxy)-2-(tert-butoxycarbonylamino)propanoic acid, gave (S)-2-amino-3-(benzyloxy)-N-(4-(3-chlorophenoxy)phenyl)propanamide (349 mg, 90%).

Proceeding as in Reference 5, but substituting 4-(4-chlorophenylthio)aniline and (S)-3-(benzyloxy)-2-(tert-butoxycarbonylamino)propanoic acid, gave (S)-2-amino-3-(benzyloxy)-N-(4-(4-fluorophenylthio)phenyl)propanamide (200 mg, 90%).

Proceeding as in Reference 5, but substituting 4-(4-methoxyphenoxy)aniline and (S)-3-(benzyloxy)-2-(tert-butoxycarbonylamino)propanoic acid, gave (S)-2-amino-3-(benzyloxy)-N-(4-(4-methoxyphenoxy)phenyl)propanamide (710 mg, 90%).

Proceeding as in Reference 5, but substituting 4-(5-bromothiazol-2-yloxy)aniline and (S)-3-(benzyloxy)-2-(tert-butoxycarbonylamino)propanoic acid, gave (S)-2-amino-3-(benzyloxy)-N-(4-(5-bromothiazol-2-yloxy)phenyl) propanamide (200 mg, 20%).

Proceeding as in Reference 5, but substituting 4-(4-fluorophenoxy)aniline and (S)-5-(benzyloxycarbonylamino)-2-(tert-butoxycarbonylamino)pentanoic acid, gave (S)-benzyl 4-amino-5-(4-(4-fluorophenoxy)phenylamino)-5-oxopentylcarbamate (1901 mg, 80%).

Proceeding as in Reference 5, but substituting 4-(4-fluorophenoxy)aniline and (S)-2-(tert-butoxycarbonylamino)-3-(4-fluorobenzyloxy)propanoic acid, gave (S)-2-amino-3-(4-fluorobenzyloxy)-N-(4-(4-fluorophenoxy)phenyl) propanamide (200 mg, 84%).

Proceeding as in Reference 5, but substituting 4-(4-bromophenoxy)aniline and (S)-2-(tert-butoxycarbonylamino)-3-(4-fluorobenzyloxy)propanoic acid, gave (S)-2-amino-N-(4-(4-bromophenoxy)phenyl)-3-(4-fluorobenzyloxy) propanamide (200 mg, 50%).

Proceeding as in Reference 5, but substituting 4-(4-chlorophenoxy)aniline and (S)-2-(tert-butoxycarbonylamino)-3-(4-fluorobenzyloxy)propanoic acid, gave (S)-2-amino-N-(4-(4-chlorophenoxy)phenyl)-3-(4-fluorobenzyloxy) propanamide (200 mg, 50%).

Proceeding as in Reference 5, but substituting 3-chloro-4-(4-chlorophenoxy)aniline and (S)-3-(benzyloxy)-2-(tert-butoxycarbonylamino)propanoic acid, gave (S)-2-amino-3-(benzyloxy)-N-(3-chloro-4-(4-chlorophenoxy)phenyl) propanamide (80 mg, 89%).

Proceeding as in Reference 5, but substituting 4-(4-fluorophenoxy)-2-methylaniline and (S)-3-(benzyloxy)-2-(tert-butoxycarbonylamino)propanoic acid, gave (S)-2-amino-3-(benzyloxy)-N-(4-(4-fluorophenoxy)-2-methylphenyl) propanamide (613 mg, 58%).

Proceeding as in Reference 5, but substituting 4-(4-fluorophenoxy)aniline and (S)-2-(tert-butoxycarbonylamino)-3-(2-(trifluoromethoxy)benzyloxy)propanoic acid, gave (S)-2-amino-N-(4-(4-fluorophenoxy)phenyl)-3-(2-(trifluoromethoxy)benzyloxy)propanamide (150 mg, 80%).

Proceeding as in Reference 5, but substituting (2S,4R)-1-(tert-butoxycarbonyl)-4-hydroxypyrrolidine-2-carboxylic acid and 4-(4-fluorophenoxy)aniline, gave (2S,4R)-tert-butyl 2-(4-(4-fluorophenoxy)phenylcarbamoyl)-4-hydroxypyrrolidine-1-carboxylate.

Proceeding as in Reference 5, but substituting (2S,4S)-4-(((9H-fluoren-9-yl)methoxy)carbonylamino)pyrrolidine-2- carboxylic acid and 4-(4-fluorophenoxy)aniline, gave (2S,4S)-4-(((9H-fluoren-9-yl)methoxy)carbonylamino)pyrrolidine-2-carboxylic acid.

Reference 6

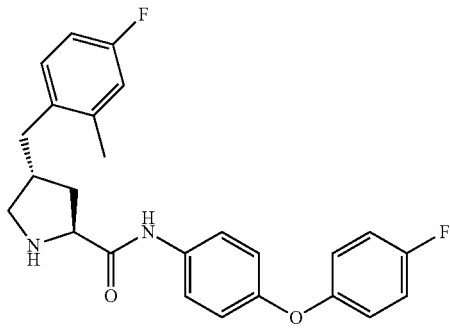 [SMILES: Cc1cc(F)ccc1C[C@H]1CN[C@H](C(=O)Nc2ccc(Oc3ccc(F)cc3)cc2)C1]

(2S,4R)-(4-fluoro-2-methylbenzyl)-N-4-(4-fluorophenoxy)phenyl)pyrrolidine-2-carboxamide trifluoroacetic acid Step (a) A mixture of (2S,4R)-1-(tert-butoxycarbonyl)-4-(4-fluoro-2-methylbenzyl)pyrrolidine-2-carboxylic acid (540 mg, 1.54 mmol), prepared as in Reference 4, 4-(4-fluorophenoxy)aniline (313 mg, 1.54 mmol), DIEA (0.4 mL) and HATU (586 mg, 1.54 mmol) in DMF (3 mL) was stirred at ambient temperature for 1 hour. The mixture was diluted with ethyl acetate (100 mL), washed with saturated sodium bicarbonate (20 mL) and then brine (20 mL), dried over anhydrous sodium sulfate and concentrated in vacuo. Product was purified from the residue by flash column (eluted with a 3:1 hexanes/ethyl acetate mixture) to give (2S,4R)-tert-butyl 4-(4-fluoro-2-methylbenzyl)-2-(4-(4-fluorophenoxy)phenylcarbamoyl)pyrrolidine-1-carboxylate (826 mg, 1.59 mmol, 103%) as a reddish oil.

Step (b) The (2S,4R)-tert-butyl 4-(4-fluoro-2-methylbenzyl)-2-(4-(4-fluorophenoxy)phenylcarbamoyl)pyrrolidine-1-carboxylate (826 mg, 1.59 mmol) was dissolved in methylene chloride (5 mL) and then trifluoroacetic acid (5 mL) was added to the solution. The mixture was stirred at ambient temperature for 1 hour, concentrated in vacuo and dried under high vacuum to give (2S,4R)-4-(4-fluoro-2-methylbenzyl)-N-(4-(4-fluorophenoxy)phenyl)pyrrolidine-2-carboxamide trifluoroacetic acid (826 mg, 1.54 mmol, 100%) as a yellow oil.

Proceeding as in Reference 6, but substituting (2S,4R)-1-(tert-butoxycarbonyl)-4-(benzyl)pyrrolidine-2-carboxylic acid, gave (2S,4R)-4-benzyl-N-(4-(4-fluorophenoxy)phenyl)pyrrolidine-2-carboxamide (200 mg, 50%).

Proceeding as in Reference 6, but substituting 4-(4-chlorophenoxy)aniline and (2S,4R)-1-(tert-butoxycarbonyl)-4-(benzyl)pyrrolidine-2-carboxylic acid, gave (2S,4R)-4-benzyl-N-(4-(4-chlorophenoxy)phenyl)pyrrolidine-2-carboxamide (190 mg, 47%).

Proceeding as in Reference 6, but substituting (2S,4R)-1-(tert-butoxycarbonyl)-4-(4-fluorobenzyl)pyrrolidine-2-carboxylic acid, gave (2S,4R)-4-(4-fluorobenzyl)-N-(4-(4-fluorophenoxy)phenyl)pyrrolidine-2-carboxamide (340 mg, 45%).

Proceeding as in Reference 6, but substituting (2S,4R)-1-(tert-butoxycarbonyl)-4-(2,4-dichlorobenzyl)pyrrolidine-2-carboxylic acid, gave (2S,4R)-4-(2,4-dichlorobenzyl)-N-(4-(4-fluorophenoxy)phenyl)pyrrolidine-2-carboxamide (54 mg, 77%).

Proceeding as in Reference 6, but substituting 4-(4-fluoro-3-methylphenoxy)aniline and (2S,4R)-1-(tert-butoxycarbonyl)-4-(4-fluorobenzyl)pyrrolidine-2-carboxylic acid, gave (2S,4R)—N-(4-(4-fluoro-3-methylphenoxy)phenyl)-4-(4-fluorobenzyl)pyrrolidine-2-carboxamide (282 mg, 73%).

Proceeding as in Reference 6, but substituting 4-(4-fluoro-2-methylphenoxy)aniline and (2S,4R)-1-(tert-butoxycarbonyl)-4-(4-fluorobenzyl)pyrrolidine-2-carboxylic acid, gave (2S,4R)—N-(4-(4-fluoro-2-methylphenoxy)phenyl)-4-(4-fluorobenzyl)pyrrolidine-2-carboxamide (359 mg, 93%).

Proceeding as in Reference 6, but substituting (2S,4R)-1-(tert-butoxy carbonyl)-4-(2-methylbenzyl)pyrrolidine-2-carboxylic acid, gave (2S,4R)—N-(4-(4-fluorophenoxy)phenyl)-4-(2-methylbenzyl)pyrrolidine-2-carboxamide (262 mg, 38%).

Proceeding as in Reference 6, but substituting (2S,4R)-1-(tert-butoxycarbonyl)-4-(2-chlorobenzyl)pyrrolidine-2-carboxylic acid, gave (2S,4R)-4-(2-chlorobenzyl)-N-(4-(4-fluorophenoxy)phenyl)pyrrolidine-2-carboxamide (460 mg, 73%).

Proceeding as in Reference 6, but substituting (2S,4R)-1-(tert-butoxycarbonyl)-4-(3-fluorobenzyl)pyrrolidine-2-carboxylic acid, gave (2S,4R)-4-(3-fluorobenzyl)-N-(4-(4-fluorophenoxy)phenyl)pyrrolidine-2-carboxamide (360 mg, 92%).

Proceeding as in Reference 6, but substituting (2S,4R)-1-(tert-butoxy carbonyl)-4-(3-chlorobenzyl)pyrrolidine-2-carboxylic acid, gave (2S,4R)-4-(3-chlorobenzyl)-N-(4-(4-fluorophenoxy)phenyl)pyrrolidine-2-carboxamide (200 mg, 75%).

Proceeding as in Reference 6, but substituting (2S,4R)-1-(tert-butoxy carbonyl)-4-(2-trifluoromethylbenzyl)pyrrolidine-2-carboxylic acid, gave (2S,4R)—N-(4-(4-fluorophenoxy)phenyl)-4-(2-(trifluoromethyl)benzyl)pyrrolidine-2-carboxamide (90 mg, 74%).

Proceeding as in Reference 6, but substituting (2S,4R)-1-(tert-butoxy carbonyl)-4-(2-chloro-4-fluoromethylbenzyl)pyrrolidine-2-carboxylic acid, gave (2S,4R)-4-(2-chloro-4-fluorobenzyl)-N-(4-(4-fluorophenoxy)phenyl)pyrrolidine-2-carboxamide (90 mg, 95%).

Proceeding as in Reference 6, but substituting (2S,4R)-1-(tert-butoxy carbonyl)-4-(2,4-difluoromethylbenzyl)pyrrolidine-2-carboxylic acid, gave (2S,4R)-4-(2,4-difluorobenzyl)-N-(4-(4-fluorophenoxy)phenyl)pyrrolidine-2-carboxamide (475 mg, 79%).

Proceeding as in Reference 6, but substituting (2S,4R)-1-(tert-butoxy carbonyl)-4-(phenyl)pyrrolidine-2-carboxylic acid, gave (2S,4S)—N-(4-(4-fluorophenoxy)phenyl)-4-(phenyl)pyrrolidine-2-carboxamide (375 mg, 68%).

Proceeding as in Reference 6, but substituting (2S,4R)-1-(tert-butoxy carbonyl)-4-(4-methoxyphenyl)pyrrolidine-2-carboxylic acid, gave (2S,4S)—N-(4-(4-fluorophenoxy)phenyl)-4-(4-methoxyphenyl)pyrrolidine-2-carboxamide (200 mg, 70%).

Proceeding as in Reference 6, but substituting (2S,4R)-1-(tert-butoxy carbonyl)-4-(benzyloxy)pyrrolidine-2-carboxylic acid, obtained commercially, gave (2S,4R)-4-(benzyloxy)-N-(4-(4-fluorophenoxy)phenyl)pyrrolidine-2-carboxamide (190 mg, 29%).

Proceeding as in Reference 6, but substituting (2S,4R)-1-(tert-butoxy carbonyl)-4-(3-methoxybenzyl)pyrrolidine-2-carboxylic acid, gave (2S,4R)—N-(4-(4-fluorophenoxy)phenyl)-4-(3-methoxybenzyl)pyrrolidine-2-carboxamide (525 mg, 47%).

Proceeding as in Reference 6, but substituting (2S,4R)-1-(tert-butoxy carbonyl)-4-(5-chlorothien-2-ylmethyl)pyrrolidine-2-carboxylic acid, gave (2S,4S)-4-((5-chlorothien-2-yl)methyl)-N-(4-(4-fluorophenoxy)phenyl)pyrrolidine-2-carboxamide (600 mg, 46%).

Proceeding as in Reference 6, but substituting (2S,4R)-1-(tert-butoxy carbonyl)-4-(thien-3-ylmethyl)pyrrolidine-2-carboxylic acid, gave (2S,4R)—N-(4-(4-fluorophenoxy)phenyl)-4-(thien-3-ylmethyl)pyrrolidine-2-carboxamide (348 mg, 90%).

Proceeding as in Reference 6, but substituting (2S,4R)-1-(tert-butoxy carbonyl)-4-(3-methylbenzyl)pyrrolidine-2-carboxylic acid, gave (2S,4R)—N-(4-(4-fluorophenoxy)phenyl)-4-(3-methylbenzyl)pyrrolidine-2-carboxamide.

Proceeding as in Reference 6, but substituting (2S,4R)-1-(tert-butoxy carbonyl)-4-(3,4-difluorobenzyl)pyrrolidine-2-carboxylic acid, gave (2S,4R)-4-(3,4-difluorobenzyl)-N-(4-(4-fluorophenoxy)phenyl)pyrrolidine-2-carboxamide.

Proceeding as in Reference 6, but substituting (2S,4R)-1-(tert-butoxy carbonyl)-4-(4-chlorobenzyl)pyrrolidine-2-carboxylic acid, gave (2S,4R)-4-(4-chlorobenzyl)-N-(4-(4-fluorophenoxy)phenyl)pyrrolidine-2-carboxamide.

Proceeding as in Reference 6, but substituting (2S,4R)-1-(tert-butoxycarbonyl)-4-(2-fluorobenzyl)pyrrolidine-2-carboxylic acid, gave (2S,4R)-4-(2-fluorobenzyl)-N-(4-(4-fluorophenoxy)phenyl)pyrrolidine-2-carboxamide.

Proceeding as in Reference 6, but substituting (2S,4R)-1-(tert-butoxycarbonyl)-4-(2,4,6-trifluorobenzyl)pyrrolidine-2-carboxylic acid, gave (2S,4R)—N-(4-(4-fluorophenoxy)phenyl)-4-(2,4,6-trifluorobenzyl)pyrrolidine-2-carboxamide.

Reference 7

(2S,4S)—N-(4-(4-Fluorophenoxy)phenyl)-4-hydroxypyrrolidine-2-carboxamide

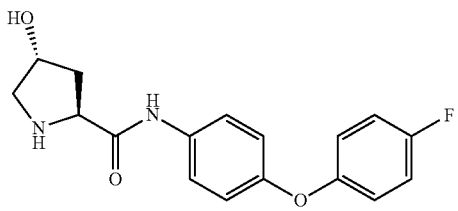 [SMILES: O=C(Nc1ccc(Oc2ccc(F)cc2)cc1)[C@@H]1C[C@@H](O)CN1]

Step (a) A flask was charged with (2S,4R)-1-(tert-butoxycarbonyl)-4-hydroxypyrrolidine-2-carboxylic acid (2.1 g, 9.1 mmol), HATU (3.80 g, 10.0 mmol), 4-(4-fluorophenoxy) aniline (1.85 g, 9.09 mmol), DIEA (4.8 mL, 27 mmol) and DMF (20 mL). The reaction mixture was stirred at ambient temperature for 30 minutes and then quenched with saturated sodium bicarbonate (aq., 20 mL). The mixture was extracted with ethyl acetate (60 mL) and the extract was washed with deionized water (30 mL) and then brine (30 mL), dried over anhydrous sodium sulfate, filtered and concentrated to give crude (2S,4R)-tert-butyl 2-(4-(4-fluorophenoxy)phenylcarbamoyl)-4-hydroxypyrrolidine-1-carboxylate, which was carried forward without further purification.

Step (b) (2S,4R)-tert-butyl 2-(4-(4-fluorophenoxy)phenylcarbamoyl)-4-hydroxypyrrolidine-1-carboxylate was combined with hydrogen chloride (4N in dioxane, 20 mL) and the mixture was stirred at ambient temperature for 1 hour and then quenched with saturated sodium bicarbonate (aq., 100 mL). This mixture was extracted with ethyl acetate (30 mL) and the extract was washed with deionized water (30 mL) and then brine (30 mL), dried over anhydrous sodium sulfate, filtered and concentrated. The residue was triturated with ethyl acetate to give (2S,4R)—N-(4-(4-fluorophenoxy)phenyl)-4-hydroxypyrrolidine-2-carboxamide (1.47 g, 4.65 mmol, 51% yield) as an off-white solid.

Reference 8

(2S,4R)-4-cyano-N-(4-(4-fluorophenoxy)phenyl)pyrrolidine-2-carboxamide

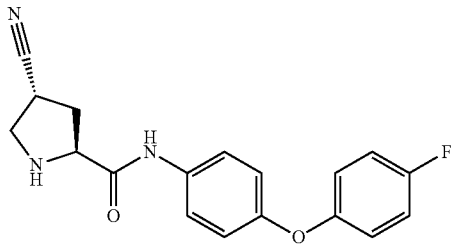 [SMILES: N#C[C@H]1CN[C@H](C(=O)Nc2ccc(Oc3ccc(F)cc3)cc2)C1]

Step (a) A flask was charged with (2S,4R)-1-(tert-butoxycarbonyl)-4-cyanopyrrolidine-2-carboxylic acid (1.0 g, 4.16 mmol), HATU (1.74 g, 4.58 mmol), 4-(4-fluorophenoxy) aniline (0.844 g, 4.16 mmol), DIEA (4.8 mL, 27 mmol) and DMF (10 mL). The reaction mixture was stirred at ambient temperature for 30 minutes and then quenched with saturated sodium bicarbonate (aq., 20 mL). The mixture was extracted with ethyl acetate (60 mL) and the extract was washed with deionized water (30 mL), and then brine (30 mL), dried over anhydrous sodium sulfate, filtered, and concentrated to give (2S,4R)-tert-butyl 4-cyano-2-(4-(4-fluorophenoxy)phenylcarbamoyl)pyrrolidine-1-carboxylate. The crude mixture was used without further purification.

Step (b) The crude (2S,4R)-tert-butyl 4-cyano-2-(4-(4-fluorophenoxy)phenylcarbamoyl)pyrrolidine-1-carboxylate was combined with hydrogen chloride (4N in dioxane, 20 mL). The mixture was stirred at ambient temperature for 1 hour and then quenched with saturated sodium bicarbonate (aq., 100 mL). The mixture was extracted with ethyl acetate (30 mL) and the extract was washed with deionized water (30 mL) and then brine (30 mL), dried over anhydrous sodium sulfate, filtered and concentrated. The residue was triturated with ethyl acetate to give (2S,4R)-4-cyano-N-(4-(4-fluorophenoxy)phenyl)pyrrolidine-2-carboxamide (0.88 g, 2.69 mmol, 65% yield over 2 steps) as an off-white solid.

Reference 9

(R)-2-(Benzyloxy)-1-(5-(4-fluorophenoxy)-1H-benzo[d]imidazol-2-yl)ethanamine

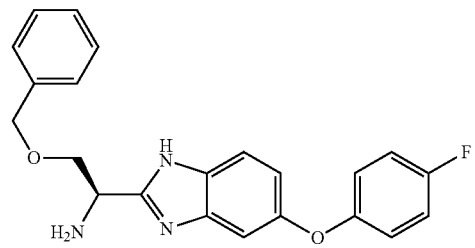 [SMILES: N[C@@H](COCc1ccccc1)c1nc2cc(Oc3ccc(F)cc3)ccc2[nH]1]

Step (a) A mixture of 5-chloro-2-nitroaniline (345 mg, 2.00 mmol), 4-fluorophenol (224 mg, 2 mmol), potassium carbonate (549 mg, 4 mmol) and DMF (8 mL) was stirred at 120° C. for 1 day. The mixture was cooled and then water (10 mL) was added. The mixture was extracted with ethyl acetate (4×2 mL). The combined extract was dried over magnesium sulfate and concentrated. Product was purified from the residue by silica gel column chromatography (eluted with a 6:1 mixture of hexane/EtOAc) to give 5-(4-fluorophenoxy)-2-nitroaniline (510 mg, quant) as a yellow powder.

Step (b) A mixture of 5-(4-fluorophenoxy)-2-nitroaniline (410 mg, 1.65 mmol), ammonium formate (520 mg, 8.26 mmol), 10% palladium on carbon (123 mg, 0.116 mmol) and methanol (10 mL) was stirred at ambient temperature for 30 minutes. The mixture was filtered and filtrate was concentrated. Product was purified from the residue by silica gel column chromatography (eluted with a 2:3→1:2 of hexane/EtOAc) to give 4-(4-fluorophenoxy)benzene-1,2-diamine (370 mg, quant) as a brown oil.

Step (c) DIEA (0.88 mL, 5.10 mmol) and HATU (750 mg, 2 mmol) were added to a stirred solution of 4-(4-fluorophenoxy)benzene-1,2-diamine (370 mg, 1.7 mmol), (S)-3-(benzyloxy)-2-(tert-butoxycarbonylamino)propanoic acid (550 mg, 1.86 mmol) and DMF (4 mL) at ambient temperature. The mixture was stirred for 1 hour and then aqueous saturated sodium bicarbonate solution (8 mL) was added. The resulting solution was extracted with ethyl acetate (4×2 mL) and the combined extract was dried over magnesium sulfate and concentrated. Product was purified from the residue by silica gel column chromatography (eluting with a 3:1→2:1 mixture of hexane/EtOAc) to give (S)-tert-butyl 1-(2-amino-4-(4-fluorophenoxy)phenylamino)-3-(benzyloxy)-1-oxo-propan-2-ylcarbamate (610 mg, 72%) as a brown foam.

Step (d) A mixture of (S)-tert-butyl 1-(2-amino-4-(4-fluorophenoxy)phenylamino)-3-(benzyloxy)-1-oxopropan-2-ylcarbamate (610 mg, 1.23 mmol) and acetic acid (6 mL) was stirred at 60° C. for 1 hour. The acetic acid was remove under vacuum and the residue was dissolve in hydrogen chloride (4 mL, 4N in dioxane). The resulting solution was stirred at ambient temperature for 30 minutes and then concentration. Product was purified from the residue by PrepLC to give (R)-2-(benzyloxy)-1-(5-(4-fluorophenoxy)-1H-benzo[d]imidazol-2-yl)ethanamine (250 mg, 54%) as a pale yellow foam.

Reference 10

Benzyl (3R,5S)-5-(4-(4-fluorophenoxy)phenylcarbamoyl)pyrrolidin-3-ylcarbamate

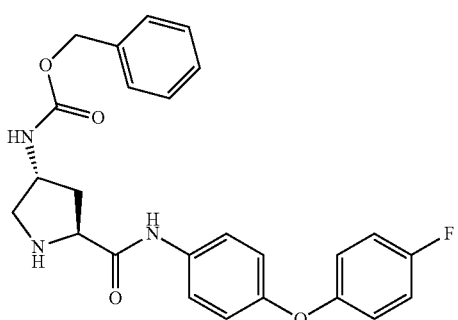

Step (a) Benzyl chloroformate (1.40 mL, 9.79 mmol) was added to a flask charged with (2S,4R)-1-tert-butyl 2-methyl 4-aminopyrrolidine-1,2-dicarboxylate hydrochloride salt (2.5 g, 8.9 mmol), DIEA (5.0 mL, 29 mmol), and THF (20 mL). The mixture was stirred for 5 minutes at ambient temperature and then quenched with saturated sodium bicarbonate (aq., 20 mL). The mixture was extracted with methylene chloride (40 mL) and the extract was dried over anhydrous sodium sulfate, filtered and concentrated. The residue was diluted with methanol (30 mL) and 2N potassium hydroxide (10 mL, 20 mmol) and the mixture was stirred at ambient temperature for 3 hours. The reaction mixture then was concentrated to approximately one-half the volume and quenched with cold 1N hydrochloric acid (30 mL, 30 mmol). The mixture was extracted with methylene chloride (30 mL) and the extract dried over anhydrous sodium sulfate, filtered and concentrated to give (2S,4R)-4-(benzyloxycarbonylamino)-1-(tert-butoxycarbonyl)pyrrolidine-2-carboxylic acid (2.51 g, 6.86 mmol) as a white solid.

Step (b) A flask was charged with (2S,4R)-4-(benzyloxycarbonylamino)-1-(tert-butoxycarbonyl)pyrrolidine-2-carboxylic acid (2.51 g, 6.86 mmol), HATU (2.87 g, 7.55 mmol), 4-fluorophenoxyaniline (1.41 g, 6.86 mmol), DIEA (5.0 mL, 29 mmol) and DMF (20 mL). The reaction mixture was stirred at ambient temperature for 30 minutes and then quenched with saturated sodium bicarbonate (aq., 20 mL). The mixture was extracted with ethyl acetate (60 mL) and the extract was washed with deionized water (30 mL) and then brine (30 mL), dried over anhydrous sodium sulfate, filtered and concentrated to give (2S,4R)-tert-butyl 4-(benzyloxycarbonylamino)-2-(4-(4-fluorophenoxy)phenylcarbamoyl)pyrrolidine-1-carboxylate as a crude mixture which was carried forward without further purification.

Step (c) A flask was charged with (2S,4R)-tert-butyl 4-(benzyloxycarbonylamino)-2-(4-(4-fluorophenoxy)phenylcarbamoyl)pyrrolidine-1-carboxylate and hydrogen chloride (4N in dioxane, 20 mL). The reaction mixture was stirred at ambient temperature for 1 hour and then quenched with saturated sodium bicarbonate (aq., 100 mL). The mixture was extracted with ethyl acetate (30 mL) and the extract was washed with deionized water (30 mL) and then brine (30 mL), dried over anhydrous sodium sulfate, filtered, and concentrated. The residue was triturated with ethyl acetate to provide benzyl (3R,5S)-5-(4-(4-fluorophenoxy)phenylcarbamoyl)pyrrolidin-3-ylcarbamate (1.20 g, 2.67 mmol, 30% yield over 4 steps) as an off-white solid.

Reference 11

(2S,4R)-1-(2-(1H-1,2,4-Triazol-1-yl)acetyl)-4-cyano-N-(4-(4-fluorophenoxy)phenyl)pyrrolidine-2-carboxamide

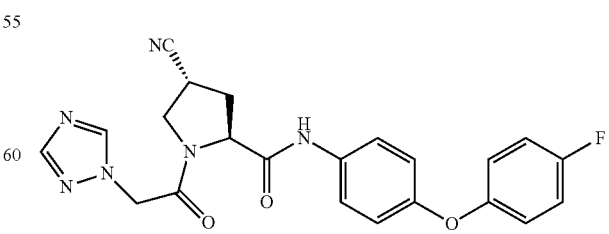

A flask was charged with (2S,4R)-4-cyano-N-(4-(4-fluorophenoxy)phenyl)pyrrolidine-2-carboxamide (0.88 g, 2.69 mmol), prepared as in Reference 8, 2-(1H-1,2,4-triazol-1-yl)

acetic acid (340 mg, 2.69 mmol), DIEA (3.0 mL, 17 mmol), HATU (1.12 g, 2.96 mmol) and DMF (10 mL). The reaction mixture was stirred at ambient temperature for 20 minutes and then quenched with saturated sodium bicarbonate (aq., 10 mL). The mixture was ethyl acetate (20 mL) and the extract was washed with deionized water (10 mL) and then brine (10 mL), dried over anhydrous sodium sulfate, filtered and concentrated. Product was purified from the residue by chromatography (EtOAc to EtOAc/MeOH (9:1)+1% NEt$_3$) to give (2S,4R)-1-(2-(1H-1,2,4-triazol-1-yl)acetyl)-4-cyano-N-(4-(4-fluorophenoxy)phenyl)pyrrolidine-2-carboxamide (0.72 g, 1.66 mmol, 62% yield) as an off-white solid. $^1$H-NMR (400 MHz, DMSO-d6): 10.20 (s, 1H), 8.46 (s, 1H), 7.97 (s, 1H), 7.57 (d, J=8.8 Hz, 2H), 7.22-7.17 (m, 2H), 7.03-6.95 (m, 4H), 5.38-5.26 (m, 2H), 4.59-4.55 (m, 1H), 4.08-3.94 (m, 2H), 3.84-3.50 (m, 2H), 2.39-2.32 (m, 1H). MS (EI) for $C_{22}H_{19}FN_6O_3$. found 517.3 (MH+).

Proceeding as in Reference 11, but substituting 2-(1H-1,2,4-triazol-1-yl)acetic acid and (2S,4R)-tert-butyl 2-(4-(4-fluorophenoxy)phenylcarbamoyl)-4-hydroxypyrrolidine-1-carboxylate, gave (2S,4R)-1-(2-(1H-1,2,4-triazol-1-yl)acetyl)-N-(4-(4-fluorophenoxy)phenyl)-4-hydroxypyrrolidine-2-carboxamide.

Proceeding as in Reference 11, but substituting (2R,4R)—N-(4-(4-fluorophenoxy)phenyl)-4-hydroxypyrrolidine-2-carboxamide and 2-(1H-1,2,4-triazol-1-yl)acetic acid gave (2R,4R)-1-(2-(1H-1,2,4-triazol-1-yl)acetyl)-N-(4-(4-fluorophenoxy)phenyl)-4-hydroxypyrrolidine-2-carboxamide (1.37 g, 3.25 mmol, 70% yield) as an off-white solid.

Reference 12

(2S,4S)-1-(2-(1H-1,2,4-triazol-1-yl)acetyl)-4-aminomethyl-N-(4-(4-fluorophenoxy)phenyl)pyrrolidine-2-carboxamide hydrochloride salt

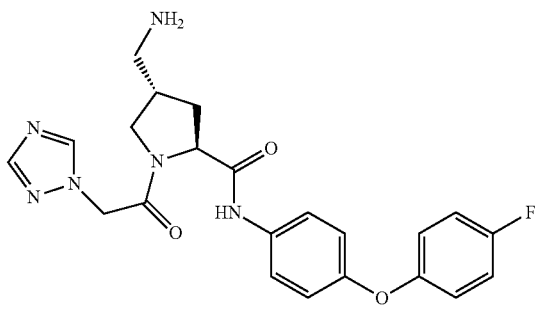 [SMILES: NC[C@@H]1C[C@@H](C(=O)Nc2ccc(Oc3ccc(F)cc3)cc2)N(C(=O)Cn2cncn2)C1]

A flask was charged with (2S,4R)-1-(2-(1H-1,2,4-triazol-1-yl)acetyl)-4-cyano-N-(4-(4-fluorophenoxy)phenyl)pyrrolidine-2-carboxamide (260 mg, 0.599 mmol), prepared as in Reference 11, methanol (4 mL), hydrogen chloride (4N in dioxane, 16 mmol) and palladium on carbon (10%, 100 mg) and the mixture was placed under a hydrogen atmosphere (balloon). The mixture was stirred for 18 hours at ambient temperature, filtered and concentrated to give crude (2S,4S)-1-(2-(1H-1,2,4-triazol-1-yl)acetyl)-4-aminomethyl-N-(4-(4-fluorophenoxy)phenyl)pyrrolidine-2-carboxamide hydrochloride salt (0.247 g, 0.564 mmol).

Example 1

2-(2-(1H-Imidazol-5-yl)acetamido)-3-benzyloxy-N-(4-phenoxyphenyl)propanamide

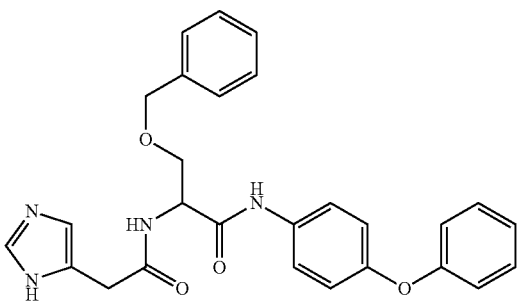 [SMILES: O=C(Cc1cnc[nH]1)NC(COCc1ccccc1)C(=O)Nc1ccc(Oc2ccccc2)cc1]

A flask was charged with 2-amino-3-benzyloxy-N-(4-phenoxyphenyl)propanamide (150 mg, 0.42 mmoles), prepared as in Reference 5, 1H-imidazol-4-ylacetic acid hydrochloride (81 mg, 0.50 mmoles), HATU (188 mg, 0.50 moles) and DMF (1 mL). DIEA (370 μL, 2.1 mmoles) was added and the mixture was stirred at ambient temperature for 18 hours. The reaction mixture was partitioned between ethyl acetate and deionized H$_2$O. The aqueous layer was separated and extracted with ethyl acetate. The combined organic layer was washed with 5% lithium chloride (3×5 mL), 1N sodium bicarbonate (2×5 mL) and then deionized water (2×5 mL) and concentrated in vacuo. Product was purified from the residue by preparative HPLC (ammonium acetate/acetonitrile). The purified product was taken up into methanol and the solution was neutralized with basic resin, filtered and concentrated in vacuo to give Compound 142, 2-(2-(1H-imidazol-5-yl)acetamido)-3-benzyloxy-N-(4-phenoxyphenyl)propanamide (118 mg, 60% yield), as a white solid. $^1$H-NMR (400 MHz, CDCl$_3$): 9.23 (s, 1H), 7.53-7.40 (m, 4H), 7.35-7.27 (m, 6H), 7.08 (t, 1H), 7.00-6.92 (m, 3H), 6.87 (s, 1H), 4.77 (m, 1H), 4.55 (dd, 2H), 4.18 (dd, 1H), 3.70-3.58 (m, 3H). MS (EI) for $C_{27}H_{26}N_4O_4$. found 471.0 (MH+).

Proceeding as in Example 1, but substituting (S)-2-amino-3-(benzyloxy)-N-(4-(4-chlorophenoxy)phenyl)propanamide, gave Compound 145, (S)-2-(2-(1H-imidazol-5-yl)acetamido)-3-benzyloxy-N-(4-(4-chlorophenoxy)phenyl)propanamide (250 mg, 71%). Major isomer: $^1$H-NMR (400 MHz, DMSO-D$_6$): σ 11.95 (br s, 1H), 10.28 (s, 1H), 8.45 (d, 1H), 7.66-7.63 (m, 3H), 7.43-7.39 (m, 2H), 7.33-7.25 (m, 5H), 7.05-6.98 (m, 5H), 4.72-4.65 (m, 1H), 4.51 (s, 1H), 3.73-3.63 (m, 2H), 3.54-3.40 (m, 2H). MS (EI) for $C_{27}H_{25}ClN_4O_4$. found 505.0 (MH+).

Proceeding as in Example 1, but substituting (S)-2-amino-3-(benzyloxy)-N-(4-phenoxyphenyl)propanamide, gave Compound 143, (S)-2-(2-(1H-imidazol-5-yl)acetamido)-3-benzyloxy-N-(4-phenoxyphenyl)propanamide (45 mg, 20%). $^1$H-NMR (400 MHz, CDCl$_3$): 9.23 (s, 1H), 7.53-7.40 (m, 4H), 7.35-7.27 (m, 6H), 7.08 (t, 1H), 7.00-6.92 (m, 3H), 6.87 (s, 1H), 4.77 (m, 1H), 4.55 (dd, 2H), 4.18 (dd, 1H), 3.70-3.58 (m, 3H). MS (EI) for $C_{27}H_{26}N_4O_4$. found 471.0 (MH+).

Proceeding as in Example 1, but substituting (S)-2-(1H-tetrazol-1-yl)acetic acid hydrochloride, gave Compound 144, (S)-2-(2-(1H-tetrazol-1-yl)acetamido)-3-benzyloxy-N-(4- phenoxyphenyl)propanamide (25 mg, 66%). $^1$H-NMR (400 MHz, CDCl3): δ 8.85 (s, 1H), 8.34 (s, 1H), 7.38 (m, 9H), 7.13 (t, 1H), 6.99 (m, 5H), 5.19 (s, 2H), 4.69 (m, 2H), 4.59 (d, 1H), 3.99 (m, 1H), 3.62 (t, 1H). MS (EI) for $C_{25}H_{24}N_6O_4$ found 473.1 (MH+).

Proceeding as in Example 1, but substituting 2-(3-methylisoxazol-5-yl)acetic acid hydrochloride, gave Compound 185, 2-(2-(3-methylisoxazol-5-yl)acetamido)-3-benzyloxy-N-(4-phenoxyphenyl)propanamide (125 mg, 63%). $^1$H-NMR (400 MHz, CDCl$_3$): 8.40 (s, 1H), 7.40-7.30 (m, 8H), 7.12-7.06 (m, 1H), 7.00-6.94 (m, 3H), 6.78 (d, 1H), 6.10 (s, 1H), 4.70 (m, 1H), 4.73-4.53 (dd, 2H), 3.98 (m, 1H), 3.75 (s, 2H), 3.60 (t, 1H), 2.28 (s, 3H). MS (EI) for $C_{28}H_{27}N_3O_5$. found 486.0 (MH+).

Proceeding as in Example 1, but substituting (S)-2-((benzoyl)(methyl)amino)acetic acid hydrochloride, gave Compound 194, (S)-2-{2-((benzoyl)(methyl)amino)acetamido}-3-benzyloxy-N-(4-phenoxyphenyl)propanamide (63 mg, 84%). $^1$H-NMR (400 MHz, CDCl$_3$): 8.80 (s, 1H), 7.63 (d, 2H), 7.53-7.30 (m, 11H), 7.10-6.92 (m, 5H), 4.72 (m, 1H), 4.60 (dd, 2H), 4.28-4.15 (m, 2H) 4.10-4.00 (m, 2H), 3.70 (m, 2H), 3.17 (s, 3H). MS (EI) for $C_{32}H_{31}N_3O_5$. found 538.0 (MH+).

Proceeding as in Example 1, but substituting (S)-2-(1-methyl-1H-imidazol-4-yl)acetic acid hydrochloride, gave Compound 195, (S)-2-(2-(1-methyl-1H-imidazol-4-yl)acetamido)-3-benzyloxy-N-(4-phenoxyphenyl)propanamide (10.1 mg, 8%). $^1$H-NMR (400 MHz, CDCl$_3$): δ 9.25 (s, 1H), 7.51-7.34 (m, 3H), 7.35-7.30 (m, 7H), 7.10-7.59 (m, 1H), 6.99-6.96 (m, 4H), 6.79 (s, 1H), 4.79-4.75 (m, 1H), 4.62 (d, 1H), 4.53 (d, 1H), 4.14 (dd, 1H), 3.68-3.65 (m, 1H), 3.64 (s, 3H), 3.59 (d, 2H). MS (EI) for $C_{28}H_{28}N_4O_4$. found 485.3 (MH+).

Proceeding as in Example 1, but substituting 2-(1-acetylpyrrolidin-2-yl)acetic acid hydrochloride, gave Compound 193, 2-(2-(1-acetylpyrrolidin-2-yl)acetamido)-3-benzyloxy-N-(4-phenoxyphenyl)propanamide (11 mg, 5%). $^1$H-NMR (400 MHz, CDCl$_3$): δ 8.78 (s, 1H), 7.70 (m, 2H), 7.39-7.25 (m, 8H), 7.10-6.94 (m, 5H), 4.68-4.58 (m, 2H), 4.54-4.45 (m, 2H), 4.21-4.15 (m, 1H), 3.72-3.66 (m, 1H), 3.63-3.48 (m, 2H), 2.23-2.16 (m, 2H), 2.09 (s, 3H), 2.05-1.91 (m, 2H). MS (EI) for $C_{29}H_{31}N_3O_5$. found 502.0 (MH+).

Proceeding as in Example 1, but substituting (S)-2-(thien-2-yl)acetic acid hydrochloride, gave Compound 198, (S)-2-(2-(thien-2-yl)acetamido)-3-benzyloxy-N-(4-phenoxyphenyl)propanamide (80 mg, 59%); Major isomer: $^1$H-NMR (400 MHz, DMSO-D$_6$): σ 10.28 (br s, 1H), 8.57-8.59 (d, 1H), 7.64-7.62 (d, 2H), 7.38-7.24 (m, 8H), 7.14-7.07 (t, 1H), 7.03-6.90 (m, 6H), 4.74-4.69 (m, 1H), 4.52 (s, 2H), 3.76 (s, 2H), 3.67-3.65 (m, 2H). MS (EI) for $C_{28}H_{26}N_2O_4S$. found 487.0 (MH+).

Proceeding as in Example 1, but substituting (S)-2-(2-fluorophenyl)acetic acid hydrochloride, gave Compound 196, (S)-2-(2-(2-fluorophenyl)acetamido)-3-benzyloxy-N-(4-phenoxyphenyl)propanamide (165 mg, 48%). $^1$H-NMR (400 MHz, CDCl$_3$): σ 8.43 (s, 1H), 7.40-7.22 (m, 10H), 7.18-7.04 (m, 2H), 7.01-6.89 (m, 3H), 6.60 (d, 1H), 4.76-4.68 (m, 1H), 4.64-4.47 (m, 2H), 4.03-3.95 (m, 1H), 3.66 (s, 2H), 3.61-3.54 (m, 1H). MS (EI) for $C_{30}H_{27}FN_2O_4$. found 498.9 (MH+).

Proceeding as in Example 1, but substituting (S)-2-(2,5-dichlorophenyl)acetic acid hydrochloride, gave Compound 199, (S)-2-(2-(2,5-dichlorophenyl)acetamido)-3-benzyloxy-N-(4-phenoxyphenyl)propanamide (60 mg, 79%); Major isomer: $^1$H-NMR (400 MHz, DMSO-D$_6$): σ 10.23 (br s, 1H), 8.62 (d, 1H), 7.66-7.62 (d, 2H), 7.50-7.44 (m, 2H), 7.39-7.34 (m, 3H), 7.32-7.25 (m, 5H), 7.13-7.08 (t, 1H), 7.03-6.96 (m, 4H), 4.78-4.70 (m, 1H), 4.55 (s, 2H), 3.76-3.65 (m, 4H). MS (EI) for $C_{30}H_{26}Cl_2N_2O_4$. found 549.0 (MH+).

Proceeding as in Example 1, but substituting (S)-2-(1H-indol-4-yl)acetic acid hydrochloride, gave Compound 197, (S)-2-(2-(1H-indol-4-yl)acetamido)-3-benzyloxy-N-(4-phenoxyphenyl)propanamide (111 mg, 80%). $^1$H-NMR (400 MHz, CDCl$_3$): σ 8.36 (s, 1H), 8.21 (s, 1H), 8.07 (s, 1H), 7.38-7.24 (m, 14H), 7.12-7.07 (m, 1H), 7.09-6.95 (m, 4H), 4.93 (s, 2H), 4.67-4.64 (m, 2H), 4.55 (d, 1H), 4.00 (dd, 1H), 3.57 (t, 1H). MS (EI) for $C_{31}H_{27}N_3O_4$. found 506.2 (MH+).

Proceeding as in Example 1, but substituting (S)-2-amino-3-(benzyloxy)-N-(4-(4-fluorophenoxy)phenyl)propanamide, gave Compound 131, (S)-2-(2-(1H-imidazol-5-yl)acetamido)-3-benzyloxy-N-(4-(4-fluorophenoxy)phenyl)propanamide (184 mg, 22%). $^1$H-NMR (400 MHz, DMSO-D$_6$): σ 11.94 (s, 1H), 10.23 (s, 1H), 8.43 (d, 1H), 7.61 (d, 2H), 7.31-7.14 (m, 8H), 7.04-6.94 (m, 4H), 4.70-4.64 (m, 1H), 4.51 (s, 2H), 3.73-3.63 (m, 2H), 3.54-3.25 (m, 2H). MS (EI) for $C_{27}H_{25}FN_4O_4$. found 489.3 (MH+).

Proceeding as in Example 1, but substituting (S)-2-amino-3-(4-fluoro)benzyloxy-N-(4-(4-fluorophenoxy)phenyl)propanamide, gave Compound 133, (S)-2-(2-(1H-imidazol-5-yl) acetamido)-3-(4-fluorobenzyloxy)-N-(4-(4-fluorophenoxy) phenyl)propanamide (24 mg, 8%). $^1$H-NMR (400 MHz, CDCl$_3$): σ 9.27 (s, 1H), 7.63 (s, 1H), 7.54 (d, 1H), 7.49-7.44 (m, 2H), 7.29-7.23 (m, 3H), 7.04-6.87 (m, 8H), 4.82-4.76 (m, 1H), 4.51 (q, 2H), 4.06 (dd, 1H), 3.70-3.56 (m, 3H). MS (EI) for $C_{27}H_{24}F_2N_4O_4$. found 506.9 (MH+).

Proceeding as in Example 1, but substituting (S)-2-amino-N-(4-phenoxyphenyl)-5-phenylpentanamide, gave Compound 1, (S)-2-(2-(1H-imidazol-5-yl)acetamido)-5-phenyl-N-(4-phenoxyphenyl)pentanamide (40 mg, 6%). $^1$H-NMR (400 MHz, CDCl$_3$): σ 9.17 (s, 1H), 7.60-7.40 (m, 4H), 7.33-7.19 (m, 4H), 7.18-7.02 (m, 4H), 6.98-6.86 (m, 3H), 6.81 (s, 1H), 4.66-4.55 (m, 1H), 3.62-3.49 (m, 2H), 2.68-2.51 (m, 2H), 2.07-1.91 (m, 1H), 1.81-1.59 (m, 3H). MS (EI) for $C_{28}H_{28}N_4O_3$. found 469.0 (MH+).

Proceeding as in Example 1, but substituting (S)-2-amino-N-(4-(4-fluorophenoxy)phenyl)-5-phenylpentanamide, gave Compound 137, (S)-2-(2-(1H-imidazol-5-yl)acetamido)-5-phenyl-N-(4-(4-fluorophenoxy)phenyl)pentanamide (69 mg, 84%). $^1$H-NMR (400 MHz, DMSO-D$_6$): σ 12.03 (s, 1H), 10.18 (s, 1H), 8.32 (d, 1H), 7.64-7.57 (m, 3H), 7.30-7.13 (m, 7H), 7.06-6.94 (m, 4H), 6.90 (s, 1H), 4.49-4.40 (m, 1H), 3.48-3.37 (m, 2H), 2.64-2.54 (m, 2H), 1.82-1.49 (m, 4H). MS (EI) for $C_{28}H_{27}FN_4O_3$. found 487.1 (MH+).

Proceeding as in Example 1, but substituting (S)-2-amino-3-(4-fluorobenzyloxy)-N-(4-(4-chlorophenoxy)phenyl)propanamide, gave Compound 132, (S)-2-(2-(1H-imidazol-5-yl) acetamido)-3-(4-fluorobenzyloxy)-N-(4-(4-chlorophenoxy) phenyl)propanamide (250 mg, 60%). $^1$H-NMR (400 MHz, DMSO-D$_6$): δ 10.10 (s, 1H), 8.40 (s, 1H), 7.50-7.25 (m, 7H), 7.15-6.90 (m, 8H), 4.60.00 (m, 1H), 4.40 (s, 2H), 3.60-3.80 (m, 4H). MS (EI) for $C_{27}H_{24}ClFN_4O_4$ found 523 (MH+).

Proceeding as in Example 1, but substituting (S)-2-amino-3-(4-fluorobenzyloxy)-N-(4-(4-fluorophenoxy)phenyl)propanamide and 2-(1H-1,2,4-triazol-1-yl)acetic acid hydrochloride, gave Compound 135, (S)-2-(2-(1H-1,2,4-triazol-1-yl)acetamido)-3-(4-fluorobenzyloxy)-N-(4-(4-fluorophenoxy)phenyl)propanamide (75 mg, 55%). $^1$H-NMR (400 MHz, CDCl$_3$): δ 8.40 (s, 1H), 8.20 (s, 1H), 8.00 (s, 1H), 7.40-7.25 (m, 7H), 7.15-6.90 (m, 6H), 5.00 (s, 2H), 4.79-4.60 (m, 3H), 4.00 (m, 1H), 3.70-3.60 (m, 1H). MS (EI) for $C_{26}H_{23}F_2N_5O_4$ found 508 (MH+).

Proceeding as in Example 1, but substituting (S)-2-amino-3-(benzyloxy)-N-(4-(4-fluorophenoxy)phenyl)propanamide and 2-(1H-1,2,4-triazol-1-yl)acetic acid hydrochloride, gave Compound 149, (S)-2-(2-(1H-1,2,4-triazol-1-yl)acetamido)-3-benzyloxy-N-(4-(4-fluorophenoxy)phenyl)propanamide (45 mg, 66%). Major isomer: $^1$H-NMR (400 MHz, DMSO-D$_6$): σ 10.26 (br s, 1H), 8.84-8.78 (s, 1H), 8.48 (s, 1H) 7.96 (s, 2H), 7.63-7.59 (d, 2H), 7.32-7.28 (m, 5H), 7.23-7.19 (t, 2H), 7.04-6.98 (m, 4H), 5.03 (s, 2H), 4.76-4.69 (m, 1H), 4.54 (s, 2H), 3.69-3.67 (d, 2H). MS (EI) for C$_{26}$H$_{24}$FN$_5$O$_4$. found 490.0 (MH+).

Proceeding as in Example 1, but substituting (S)-2-amino-3-(benzyloxy)-N-(4-(4-fluorophenoxy)phenyl)propanamide and 3,5-dimethylisoxazol-4-ylcarbamic acid hydrochloride, gave Compound 172, (S)-2-(3-(3,5-dimethylisoxazol-4-yl)ureido)-3-benzyloxy-N-(4-(4-fluorophenoxy)phenyl)propanamide. Major isomer: $^1$H-NMR (400 MHz, DMSO-D$_6$): σ 11.99 (br s, 1H), 9.62 (br s, 1H), 8.40-8.38 (d, 1H), 7.55 (s, 1H), 7.36-7.19 (m, 8H), 7.07-7.02 (m, 2H), 6.94-6.76 (m, 3H), 4.74-4.69 (m, 1H), 4.53 (s, 2H), 3.77-3.64 (m, 2H), 3.53-3.42 (m, 2H), 2.06 (s, 3H). MS (EI) for C$_{28}$H$_{27}$FN$_4$O$_4$. found 503.0 (MH+).

Proceeding as in Example 1, but substituting (S)-2-amino-3-(benzyloxy)-N-(4-(4-fluorophenoxy)phenyl)propanamide and 2-(2H-1,2,3-triazol-2-yl)acetic acid hydrochloride, gave Compound 138, (S)-2-(2-(2H-1,2,3-triazol-2-yl)acetamido)-3-(benzyloxy)-N-(4-(4-fluorophenoxy)phenyl)propanamide. $^1$H-NMR (400 MHz, CDCl$_3$): σ 8.33 (s, 1H), 7.75 (s, 1H), 7.52 (s, 1H), 7.38-7.21 (m, 7H), 7.04-7.00 (m, 2H), 6.96-6.89 (m, 4H), 5.29-5.20 (m, 2H), 4.71-4.61 (m, 3H), 4.53 (d, 1H), 4.03 (dd, 1H), 3.53 (t, 1H). MS (EI) for C$_{26}$H$_{24}$FN$_5$O$_4$. found 489.9 (MH+).

Proceeding as in Example 1, but substituting (S)-2-amino-N-(4-(4-chlorophenoxy)phenyl)-4-phenylbutanamide, gave Compound 157, (S)-2-(2-(1H-imidazol-5-yl)acetamido)-N-(4-(4-chlorophenoxy)phenyl)-4-phenylbutanamide (89 mg, 23%). $^1$H-NMR (400 MHz, DMSO-D$_6$): σ 10.23 (s, 1H), 8.52 (d, 1H), 7.84 (s, 1H), 7.65 (d, 2H), 7.40 (d, 2H), 7.32-7.24 (m, 2H), 7.23-7.15 (m, 2H), 7.08-6.94 (m, 4H), 4.46-4.37 (m, 1H), 3.58-3.47 (m, 2H), 2.74-2.53 (m, 2H), 2.11-1.84 (m, 2H). MS (EI) for C$_{27}$H$_{25}$ClN$_4$O$_3$. found 489.2 (MH+).

Proceeding as in Example 1, but substituting (S)-benzyl 4-amino-5-(4-(4-fluorophenoxy)phenylamino)-5-oxopentylcarbamate and 2-(1H-1,2,4-triazol-1-yl)acetic acid hydrochloride, gave Compound 165, (S)-benzyl 4-(2-(1H-1,2,4-triazol-1-yl)acetamido)-5-(4-(4-fluorophenoxy)phenylamino)-5-oxopentylcarbamate (90.1 mg, 20%). $^1$H-NMR (400 MHz, DMSO-D$_6$): σ 10.19 (s, 1H), 8.69 (d, 1H), 8.48 (s, 1H), 7.96 (s, 1H), 7.60 (d, 2H), 7.39-7.29 (m, 5H), 7.21 (m, 2H), 7.04-6.96 (m, 4H), 5.00-4.97 (m, 4H), 4.46-4.39 (m, 1H), 3.04-2.99 (m, 2H), 1.75-1.39 (m, 4H). MS (EI) for C$_{29}$H$_{29}$FN$_6$O$_5$. found 560.9 (MH+).

Proceeding as in Example 1, but substituting 1-(4-chlorobenzyl)-5-oxopyrrolidine-3-carboxylic acid hydrochloride, gave Compound 29, N-(3-(benzyloxy)-1-oxo-1-(4-phenoxyphenylamino)propan-2-yl)-1-(4-chlorobenzyl)-5-oxopyrrolidine-3-carboxamide MS (EI) for C$_{34}$H$_{32}$ClN$_3$O$_5$ found 598.4 (MH+).

Proceeding as in Example 1, but substituting 2-(2-fluorophenyl)acetic acid hydrochloride, gave Compound 183, 3-(benzyloxy)-2-(2-(2-fluorophenyl)acetamido)-N-(4-phenoxyphenyl)propanamide. MS (EI) for C$_{30}$H$_{27}$F N$_2$O$_4$ found 499.4 (MH+).

Proceeding as in Example 1, but substituting 1H-indole-4-carboxylic acid hydrochloride, gave Compound 184, N-(3-(benzyloxy)-1-oxo-1-(4-phenoxyphenylamino)propan-2-yl)-1H-indole-4-carboxamide. MS (EI) for C$_{31}$H$_{27}$N$_3$O$_4$ found 506.4 (MH+).

Proceeding as in Example 1, but substituting 2-methylthiopyridine-3-carboxylic acid hydrochloride, gave Compound 28, N-(3-(benzyloxy)-1-oxo-1-(4-phenoxyphenylamino)propan-2-yl)-2-(methylthio)nicotinamide. MS (EI) for C$_{29}$H$_{27}$N$_3$O$_4$S found 514.4 (MH+).

Proceeding as in Example 1, but substituting 3-phenyl-2R-hydroxypropionic acid hydrochloride, gave Compound 27, 3-(benzyloxy)-2-((R)-2-hydroxy-3-phenylpropanamido)-N-(4-phenoxyphenyl)propanamide. MS (EI) for C$_{31}$H$_{30}$N$_2$O$_5$ found 511.4 (MH+).

Proceeding as in Example 1, but substituting 2-(2-hydroxyphenoxy)acetic acid hydrochloride, gave Compound 26, 3-(benzyloxy)-2-(2-(2-hydroxyphenoxy)acetamido)-N-(4-phenoxyphenyl)propanamide. MS (EI) for C$_{30}$H$_{28}$N$_2$O$_6$ found 513.4 (MH+).

Proceeding as in Example 1, but substituting 2S-acetyloxypropionic acid hydrochloride, gave Compound 25, (2S)-1-(3-(benzyloxy)-1-oxo-1-(4-phenoxyphenylamino)propan-2-ylamino)-1-oxopropan-2-yl acetate. MS (EI) for C$_{27}$H$_{28}$N$_2$O$_6$ found 477.3 (MH+).

Proceeding as in Example 1, but substituting 2-(2-chlorophenyl)-2R-hydroxyacetic acid hydrochloride, gave Compound 24, 3-(benzyloxy)-2-((R)-2-(2-chlorophenyl)-2-hydroxyacetamido)-N-(4-phenoxyphenyl)propanamide. MS (EI) for C$_{30}$H$_{27}$ClN$_2$O$_5$ found 531.3 (MH+).

Proceeding as in Example 1, but substituting tetrahydrofuran-2R-carboxylic acid hydrochloride, gave Compound 23, (2R)—N-(3-(benzyloxy)-1-oxo-1-(4-phenoxyphenylamino)propan-2-yl)tetrahydrofuran-2-carboxamide. MS (EI) for C$_{27}$H$_{28}$N$_2$O$_5$ found 461.2 (MH+).

Proceeding as in Example 1, but substituting 3,3,3-trifluoropropionic acid hydrochloride, gave Compound 22, N-(3-(benzyloxy)-1-oxo-1-(4-phenoxyphenylamino)propan-2-yl)-3,3,3-trifluoropropanamide. MS (EI) for C$_{25}$H$_{23}$F$_3$N$_2$O$_4$ found 473.3 (MH+).

Proceeding as in Example 1, but substituting 3-cyclopropylcarbonylpropionic acid hydrochloride, gave Compound 186, N-(3-(benzyloxy)-1-oxo-1-(4-phenoxyphenylamino)propan-2-yl)-4-cyclopropyl-4-oxobutanamide. MS (EI) for C$_{29}$H$_{30}$N$_2$O$_5$ found 487.3 (MH+).

Proceeding as in Example 1, but substituting 2-bromo-5-fluorobenzoic acid hydrochloride, gave Compound 21, N-(3-(benzyloxy)-1-oxo-1-(4-phenoxyphenylamino)propan-2-yl)-2-bromo-5-fluorobenzamide. MS (EI) for C$_{29}$H$_{24}$BrFN$_2$O$_4$ found 563.2 (MH+).

Proceeding as in Example 1, but substituting indole-6-carboxylic acid hydrochloride, gave Compound 187, N-(3-(benzyloxy)-1-oxo-1-(4-phenoxyphenylamino)propan-2-yl)-1H-indole-6-carboxamide. MS (EI) for C$_{31}$H$_{27}$N$_3$O$_4$ found 506.3 (MH+).

Proceeding as in Example 1, but substituting indane-2-carboxylic acid hydrochloride, gave Compound 188, N-(3-(benzyloxy)-1-oxo-1-(4-phenoxyphenylamino)propan-2-yl)-2,3-dihydro-1H-indene-2-carboxamide. MS (EI) for C$_{32}$H$_{30}$N$_2$O$_4$ found 507.4 (MH+).

Proceeding as in Example 1, but substituting indole-5-carboxylic acid hydrochloride, gave Compound 20, N-(3-(benzyloxy)-1-oxo-1-(4-phenoxyphenylamino)propan-2-yl)-1H-indole-5-carboxamide. MS (EI) for C$_{31}$H$_{27}$N$_3$O$_4$ found 506.3 (MH+).

Proceeding as in Example 1, but substituting 3-methyl-2-nitro-benzoic acid hydrochloride, gave Compound 189, N-(3-(benzyloxy)-1-oxo-1-(4-phenoxyphenylamino)propan-2-yl)-3-methyl-2-nitrobenzamide. MS (EI) for C$_{30}$H$_{27}$N$_3$O$_6$ found 526.3 (MH+).

Proceeding as in Example 1, but substituting 2-methylsulfonylacetic acid hydrochloride, gave Compound 19, 3-(benzyloxy)-2-(2-(methylsulfonyl)acetamido)-N-(4-phenoxyphenyl)propanamide. MS (EI) for $C_{25}H_{26}N_2O_6S$ found 483.2 (MH+).

Proceeding as in Example 1, but substituting 5-methylnicotinic acid hydrochloride, gave Compound 18, N-(3-(benzyloxy)-1-oxo-1-(4-phenoxyphenylamino)propan-2-yl)-5-methylnicotinamide. MS (EI) for $C_{29}H_{27}N_3O_4$ found 482.3 (MH+).

Proceeding as in Example 1, but substituting 2,5-dichlorophenylacetic acid hydrochloride, gave Compound 190, 3-(benzyloxy)-2-(2-(2,5-dichlorophenyl)acetamido)-N-(4-phenoxyphenyl)propanamide. MS (EI) for $C_{30}H_{26}C_{12}N_2O_4$ found 549.3 (MH+).

Proceeding as in Example 1, but substituting 4-acetyloxybenzoic acid hydrochloride, gave Compound 17, 4-(3-(benzyloxy)-1-oxo-1-(4-phenoxyphenylamino)propan-2-ylcarbamoyl)phenyl acetate. MS (EI) for $C_{31}H_{28}N_2O_6$ found 525.3 (MH+).

Proceeding as in Example 1, but substituting 2-(2-hydroxyphenyl)-2-hydroxyacetic acid hydrochloride, gave Compound 16, 3-(benzyloxy)-2-(2-hydroxy-2-(2-hydroxyphenyl)acetamido)-N-(4-phenoxyphenyl)propanamide. MS (EI) for $C_{30}H_{28}N_2O_6$ found 513.3 (MH+).

Proceeding as in Example 1, but substituting 6-(2,5-dioxo-2,5-dihydro-1H-pyrrol-1-yl)hexanoic acid hydrochloride, gave Compound 15, N-(3-(benzyloxy)-1-oxo-1-(4-phenoxyphenylamino)propan-2-yl)-6-(2,5-dioxo-2,5-dihydro-1H-pyrrol-1-yl)hexanamide. MS (EI) for $C_{32}H_{33}N_3O_6$ found 556.4 (MH+).

Proceeding as in Example 1, but substituting 2-(furan-2-yl)-2-oxoacetic acid hydrochloride, gave Compound 14, 3-(benzyloxy)-2-(2-(furan-2-yl)-2-oxoacetamido)-N-(4-phenoxyphenyl)propanamide. MS (EI) for $C_{28}H_{24}N_2O_6$ found 485.3 (MH+).

Proceeding as in Example 1, but substituting 3S-phenyl-3-hydroxypropionic acid hydrochloride, gave Compound 13, 3-(benzyloxy)-2-((S)-3-hydroxy-3-phenylpropanamido)-N-(4-phenoxyphenyl)propanamide. MS (EI) for $C_{32}H_{32}N_2O_4$ found 509.4 (MH+).

Proceeding as in Example 1, but substituting 2-(3-chloro-2-fluorophenyl)acetic acid hydrochloride, gave Compound 191, 3-(benzyloxy)-2-(2-(3-chloro-2-fluorophenyl)acetamido)-N-(4-phenoxyphenyl)propanamide. MS (EI) for $C_{30}H_{26}ClFN_2O_4$ found 533.3 (MH+).

Proceeding as in Example 1, but substituting 2-(5-chloro-2-fluorophenyl)acetic acid hydrochloride, gave Compound 192, 3-(benzyloxy)-2-(2-(5-chloro-2-fluorophenyl)acetamido)-N-(4-phenoxyphenyl)propanamide. MS (EI) for $C_{30}H_{26}ClFN_2O_4$ found 533.3 (MH+).

Proceeding as in Example 1, but substituting 2-(1,2,4)-triazol-1-ylacetic acid hydrochloride and (S)-2-amino-3-(benzyloxy)-N-(4-phenoxyphenyl)propanamide, gave Compound 146, (S)-2-(2-(1H-1,2,4-triazol-1-yl)acetamido)-3-(benzyloxy)-N-(4-phenoxyphenyl)propanamide (106 mg, 82%). $^1$H-NMR (400 MHz, CDCl$_3$): σ 8.69 (s, 1H), 8.41 (br s, 1H), 7.64 (d, 1H), 7.58 (d, 1H), 7.44 (d, 2H), 7.39-7.25 (m, 6H), 7.10-7.06 (m, 2H), 6.99-6.97 (m, 4), 5.03-4.99 (m, 1H), 4.76 (d, 1H), 4.65 (d, 1H), 4.25 (dd, 1H), 3.78 (dd, 1H). MS (EI) for $C_{26}H_{25}N_5O_4$. found 472.1 (MH+).

Proceeding as in Example 1, but substituting (S)-2-amino-3-(benzyloxy)-N-(3-chloro-4-phenoxyphenyl)propanamide, gave Compound 147, (S)-2-(2-(1H-imidazol-4-yl)acetamido)-3-(benzyloxy)-N-(3-chloro-4-phenoxyphenyl)propanamide (394 mg, 46%). $^1$H-NMR (400 MHz, DMSO-D$_6$): σ 10.41 (s, 1H), 8.45 (d, 1H), 7.95 (s, 1H), 7.59 (s, 1H), 7.49 (d, 1H), 7.36-7.25 (m, 7H), 7.13 (d, 1H), 7.09-7.06 (m, 1H), 6.89 (d, 2H), 4.68-4.61 (m, 1H), 4.50 (s, 2H), 3.73-3.32 (m, 4H). MS (EI) for $C_{27}H_{25}ClN_4O_4$. found 504.9 (MH+).

Proceeding as in Example 1, but substituting (S)-2-amino-3-(benzyloxy)-N-(4-benzylphenyl)propanamide, gave Compound 200, (S)-2-(2-(1H-imidazol-4-yl)acetamido)-3-(benzyloxy)-N-(4-benzylphenyl)propanamide (225 mg, 47%). $^1$H-NMR (400 MHz, CDCl$_3$): σ 11.95 (s, 1H), 10.14 (s, 1H), 8.39 (d, 1H), 7.61 (s, 1H), 7.52 (d, 1H), 7.30-7.15 (m, 9H), 6.96 (s, 1H), 4.71-4.64 (m, 1H), 4.49 (s, 2H), 3.89 (s, 2H), 3.71-3.61 (m, 2H), 3.51-3.32 (m, 2H). MS (EI) for $C_{28}H_{28}N_4O_3$. found 469.3 (MH+).

Proceeding as in Example 1, but substituting 2-(2,4-dioxoimidazolidin-1-yl)acetic acid hydrochloride and (S)-2-amino-3-(benzyloxy)-N-(4-phenoxyphenyl)propanamide, gave Compound 201, (S)-3-(benzyloxy)-2-(2-(2,4-dioxoimidazolidin-1-yl)acetamido)-N-(4-phenoxyphenyl)propanamide (54.1 mg, 45%). $^1$H-NMR (400 MHz, DMSO-D$_6$): σ 10.62 (d, 1H), 10.15 (d, 1H), 8.47-8.41 (m, 1H), 7.83 (d, 1H), 7.65-7.61 (m, 2H), 7.39-7.26 (m, 6H), 7.10 (t, 1H), 7.02-6.96 (m, 4H), 4.73-4.66 (m, 1H), 4.53 (s, 2H), 4.25-4.20 (m, 1H), 3.71-3.63 (m, 2H), 2.73-2.63 (m, 1H). MS (EI) for $C_{27}H_{26}N_4O_6$. found 503.1 (MH+).

Proceeding as in Example 1, but substituting (S)-2-amino-3-(benzyloxy)-N-(4-(3-chlorophenoxy)phenyl)propanamide, gave Compound 148, (S)-2-(2-(1H-imidazol-4-yl)acetamido)-3-(benzyloxy)-N-(4-(3-chlorophenoxy)phenyl)propanamide (235 mg, 51%); Major isomer: $^1$H-NMR (400 MHz, DMSO-D$_6$): σ 10.32 (br s, 1H), 8.48 (d, 1H), 7.69-7.66 (d, 2H), 7.60 (s, 1H), 7.41-7.36 (t, 1H), 7.34-7.25 (m, 5H), 7.17-7.15 (d, 1H), 7.09-7.07 (d, 2H), 7.00-6.99 (m, 1H), 6.94-6.91 (m, 2H), 4.71-4.66 (m, 1H), 4.52 (s, 2H), 3.73-3.64 (m, 2H), 3.52-3.39 (m, 2H). MS (EI) for $C_{27}H_{25}ClN_4O_4$. found 505.0 (MH+).

Proceeding as in Example 1, but substituting (S)-2-amino-3-(benzyloxy)-N-(4-(4-methoxyphenoxy)phenyl)propanamide, gave Compound 202, (S)-2-(2-(1H-imidazol-4-yl)acetamido)-3-(benzyloxy)-N-(4-(4-methoxyphenoxy)phenyl)propanamide (251 mg, 63%). $^1$H-NMR (400 MHz, DMSO-D$_6$): σ 10.2 (s, 1H), 8.39 (d, 1H), 7.59-7.54 (m, 3H), 7.31-7.21 (m, 5H), 6.94-6.82 (m, 7H), 4.69-4.64 (m, 1H), 4.50 (s, 2H), 3.70 (s, 3H), 3.68-3.61 (m, 2H), 3.49-3.38 (m, 2H). MS (EI) for $C_{28}H_{28}N_4O_5$. found 501.2 (MH+).

Proceeding as in Example 1, but substituting 2-(3,5-dimethylisoxazol-4-yl)acetic acid hydrochloride and (S)-2-amino-3-(benzyloxy)-N-(4-(4-fluorophenoxy)phenyl)propanamide, gave Compound 150, (S)-3-(benzyloxy)-2-(2-(3,5-dimethylisoxazol-4-yl)acetamido)-N-(4-(4-fluorophenoxy)phenyl)propanamide (48 mg, 72%); Major isomer: $^1$H-NMR (400 MHz, DMSO-D$_6$): σ 10.22 (br s, 1H), 8.52-8.50 (d, 1H), 7.63-7.60 (d, 2H), 7.33-7.27 (m, 5H), 7.23-7.19 (t, 2H), 7.03-6.98 (m, 4H), 4.73-4.68 (m, 1H), 4.53 (s, 2H), 3.70-3.63 (m, 1H), 3.31 (s, 2H), 2.28 (s, 3H), 2.11 (s, 3H). MS (EI) for $C_{29}H_{28}FN_3O_5$. found 518.0 (MH+).

Proceeding as in Example 1, but substituting 2-(1H-benzo[d][1,2,3]triazol-1-yl)acetic acid hydrochloride and (S)-2-amino-3-(benzyloxy)-N-(4-(4-fluorophenoxy)phenyl)propanamide, gave Compound 151, (S)-2-(2-(1H-benzo[d][1,2,3]triazol-1-yl)acetamido)-3-(benzyloxy)-N-(4-(4-fluorophenoxy)phenyl)propanamide (41 mg, 59%); Major isomer: $^1$H-NMR (400 MHz, DMSO-D$_6$): σ 10.25 (br s, 1H), 9.04-9.02 (d, 1H), 8.05-8.03 (d, 1H), 7.78-7.76 (d, 1H), 7.64-7.60 (d, 2H), 7.53-7.49 (t, 1H), 7.41-7.38 (t, 1H), 7.33-7.28 (m, 5H), 7.23-7.19 (t, 2H), 7.05-6.98 (m, 4H), 5.59 (s, 1H), 4.77-4.72 (m, 1H), 4.56 (s, 1H), 3.73-3.72 (d, 2H). MS (EI) for $C_{30}H_{26}FN_5O_4$. found 540.0 (MH+).

Proceeding as in Example 1, but substituting (S)-3-(benzyloxy)-2-(methylamino)-N-(4-phenoxyphenyl)propanamide, gave Compound 203, (S)-2-(2-(1H-imidazol-4-yl)-N-methylacetamido)-3-(benzyloxy)-N-(4-phenoxyphenyl)propanamide (55 mg, 22%). 1:1 mixture of rotamers. $^1$H-NMR (400 MHz, DMSO-D$_6$): σ 12.3 (s, 1H), 12.0 (s, 1H), 11.9 (s, 1H), 10.2 (s, 1H), 7.94 (s, 1H), 7.65 (d, 2H), 7.61 (s, 1H), 7.60 (d, 2H), 7.40-7.27 (m, 14H), 7.14-7.09 (m, 3H), 7.04-6.96 (m, 9H), 5.35-5.30 (m, 2H), 4.62-4.48 (m, 4H), 4.04 (d, 1H), 3.95-3.76 (m, 4H), 3.75 (d, 1H), 3.59 (d, 1H), 3.41 (d, 1H), 3.08 (s, 3H), 2.70 (s, 3H). MS (EI) for C$_{28}$H$_{28}$N$_4$O$_4$. found 485.2 (MH+).

Proceeding as in Example 1, but substituting 2-(3,5-dimethyl-1H-pyrazol-4-yl)acetic acid hydrochloride and (S)-2-amino-3-(benzyloxy)-N-(4-(4-fluorophenoxy)phenyl)propanamide, gave Compound 152, (S)-3-(benzyloxy)-2-(2-(3,5-dimethyl-1H-pyrazol-4-yl)acetamido)-N-(4-(4-fluorophenoxy)phenyl)propanamide (28 mg, 42%); Major isomer: $^1$H-NMR (400 MHz, DMSO-D$_6$): σ 11.96 (br s, 1H) 10.20 (br s, 1H), 8.12-8.10 (d, 1H), 7.63-7.59 (d, 2H), 7.33-7.27 (m, 5H), 7.23-7.19 (t, 2H), 7.04-6.96 (m, 4H), 4.71-4.66 (m, 1H), 4.51 (s, 2H), 3.68-3.61 (d, 2H), 3.22 (s, 2H), 2.07 (s, 6H). MS (EI) for C$_{29}$H$_{29}$FN$_4$O$_4$. found 517.0 (MH+).

Proceeding as in Example 1, but substituting 2-(4-methyl-1,2,3-triazol-1-yl)acetic acid hydrochloride and (S)-2-amino-3-(benzyloxy)-N-(4-(4-fluorophenoxy)phenyl)propanamide, gave Compound 153, (S)-3-(benzyloxy)-N-(4-(4-fluorophenoxy)phenyl)-2-(2-(4-methyl-1H-1,2,3-triazol-1-yl)acetamido)propanamide (13 mg, 18%); Major isomer: $^1$H-NMR (400 MHz, DMSO-D$_6$): σ 10.24 (br s, 1H), 8.84-8.82 (d, 1H), 7.76 (s, 2H), 7.63-7.59 (d, 2H), 7.32-7.27 (m, 5H), 7.23-7.19 (t, 2H), 7.04-6.98 (m, 4H), 5.15 (s, 1H), 4.75-4.70 (m, 1H), 4.54 (s, 2H), 3.70-3.68 (d, 2H), 2.23 (s, 3H). MS (EI) for C$_{27}$H$_{26}$FN$_5$O$_4$. found 504.0 (MH+).

Proceeding as in Example 1, but substituting (S)-2-amino-N-(4-(4-chlorophenoxy)phenyl)-3-phenylpropanamide, gave Compound 204, (S)-2-(2-(1H-imidazol-5-yl)acetamido)-N-(4-(4-chlorophenoxy)phenyl)-3-phenylpropanamide (21 mg, 4%). $^1$H-NMR (400 MHz, DMSO-D$_6$): σ 11.98 (s, 1H), 10.25 (s, 1H), 8.43 (d, 1H), 7.65-7.57 (m, 3H), 7.44-7.38 (m, 2H), 7.30-7.16 (m, 4H), 7.07-6.95 (m, 4H), 6.80 (s, 1H), 4.70-4.61 (m, 1H), 3.44-3.27 (m, 2H), 3.11-3.03 (m, 1H), 2.93-2.82 (m, 1H). MS (EI) for C$_{26}$H$_{23}$ClN$_4$O$_3$. found 474.9 (MH+).

Proceeding as in Example 1, but substituting (S)-2-amino-3-(benzyloxy)-N-(3-chloro-4-(4-chlorophenoxy)phenyl)propanamide, gave Compound 154, (S)-2-(2-(1H-imidazol-4-yl)acetamido)-3-(benzyloxy)-N-(3-chloro-4-(4-chlorophenoxy)phenyl)propanamide (105 mg, 40%); Major isomer: $^1$H-NMR (400 MHz, DMSO-D$_6$): σ 11.96 (br s, 1H), 10.46 (br s, 1H), 8.49-8.47 (d, 1H), 7.99 (s, 1H), 7.63 (s, 1H), 7.56-7.50 (d, 1H), 7.43-7.38 (m, 2H), 7.26-7.23 (m, 5H), 7.23-7.20 (d, 1H), 6.98-6.90 (m, 3H), 4.69-4.64 (m, 1H), 4.52 (s, 2H), 3.74-3.65 (m, 2H), 3.53-3.35 (m, 2H). MS (EI) for C$_{27}$H$_{24}$Cl$_2$N$_4$O$_4$. found 539.0 (MH+).

Proceeding as in Example 1, but substituting 2-morpholin-4-ylacetic acid hydrochloride and (S)-2-amino-3-(benzyloxy)-N-(4-(4-fluorophenoxy)phenyl)propanamide, gave Compound 155, (S)-3-(benzyloxy)-N-(4-(4-fluorophenoxy)phenyl)-2-(2-morpholinoacetamido)propanamide (23 mg, 17%); Major isomer: $^1$H-NMR (400 MHz, DMSO-D$_6$): σ 10.20 (br s, 1H), 7.98-7.96 (d, 1H), 7.61-7.57 (d, 2H), 7.33-7.26 (m, 5H), 7.23-7.19 (t, 2H), 7.04-6.97 (m, 4H), 4.72-4.67 (m, 1H), 4.52 (s, 2H), 3.78-3.68 (m, 2H), 3.59-3.57 (t, 4H), 2.99 (s, 2H), 2.47-2.42 (m, 4H). MS (EI) for C$_{28}$H$_{30}$FN$_3$O$_5$. found 508.0 (MH+).

Proceeding as in Example 1, but substituting 2-piperazin-1-ylacetic acid hydrochloride and (S)-2-amino-3-(benzyloxy)-N-(4-(4-fluorophenoxy)phenyl)propanamide, gave Compound 205, (S)-3-(benzyloxy)-N-(4-(4-fluorophenoxy)phenyl)-2-(2-(piperazin-1-yl)acetamido)propanamide (15 mg, 11%); Major isomer: $^1$H-NMR (400 MHz, DMSO-D$_6$): σ 10.18 (br s, 1H), 7.97-7.95 (d, 1H), 7.61-7.57 (d, 2H), 7.33-7.27 (m, 5H), 7.23-7.19 (t, 2H), 7.04-6.97 (m, 4H), 4.71-4.69 (m, 1H), 4.52 (s, 2H), 3.78-3.67 (m, 2H), 2.96 (s, 2H), 2.77-2.75 (t, 4H), 2.42 (s, 4H), 1.91 (s, 1H). MS (EI) for C$_{28}$H$_{31}$FN$_4$O$_4$. found 507.0 (MH+).

Proceeding as in Example 1, but substituting (S)-2-amino-3-(benzyloxy)-N-(4-(5-bromothiazol-2-yloxy)phenyl)propanamide, gave Compound 156, (S)-2-(2-(1H-imidazol-4-yl)acetamido)-3-(benzyloxy)-N-(4-(5-bromothiazol-2-yloxy)phenyl)propanamide (170 mg, 69%). $^1$H-NMR (400 MHz, DMSO-D$_6$): σ 11.92 (br s, 1H), 10.39 (s, 1H), 8.46 (dd, 2H), 7.70 (d, 1H), 7.61-7.53 (m, 1H), 7.35-7.24 (m, 7H), 6.91 (br s, 1H), 4.70-4.64 (m, 1H), 4.57-4.52 (m, 1H), 4.49-4.45 (m, 2H), 3.74-3.56 (m, 3H). MS (EI) for C$_{24}$H$_{22}$BrN$_5$O$_4$S. found 556.2 (MH+).

Proceeding as in Example 1, but substituting 3-(1H-imidazol-5-yl)propanoic acid hydrochloride and (S)-2-amino-3-(benzyloxy)-N-(4-(4-fluorophenoxy)phenyl)propanamide, gave Compound 207, (S)-2-(3-(1H-imidazol-5-yl)propanamido)-3-(benzyloxy)-N-(4-(4-fluorophenoxy)phenyl)propanamide (18.4 mg, 5%). $^1$H-NMR (400 MHz, DMSO-D$_6$): σ 10.19 (s, 1H), 8.29 (d, 1H), 7.60 (d, 2H), 7.46 (s, 1H), 7.29-7.16 (m, 6H), 7.01-6.94 (m, 4H), 6.73 (s, 1H), 4.70-4.64 (m, 1H), 4.50 (s, 2H), 2.73-2.67 (m, 2H), 2.48-2.43 (m, 4H). MS (EI) for C$_{28}$H$_{27}$FN$_4$O$_4$. found 503.2 (MH+).

Proceeding as in Example 1, but substituting (S)-2-amino-3-(benzyloxy)-N-(4-(cyclohexyloxy)phenyl)propanamide, gave Compound 208, (S)-2-(2-(1H-imidazol-5-yl)acetamido)-3-(benzyloxy)-N-(4-(cyclohexyloxy)phenyl)propanamide (70 mg, 60%). $^1$H-NMR (400 MHz, CDCl$_3$): δ 8.95 (s, 1H), 7.70-7.50 (m, 2H), 7.37-7.25 (m, 7H), 6.96-6.87 (m, 3H), 4.79-4.73 (m, 1H), 4.63 (m, 2H), 4.17-4.10 (m, 2H), 3.68-3.59 (m, 4H), 1.20-1.80 (m, 10H). MS (EI) for C$_{27}$H$_{32}$N$_4$O$_4$ found 477 (MH+).

Proceeding as in Example 1, but substituting 3-dimethylaminopropionic acid hydrochloride and (S)-2-amino-3-(benzyloxy)-N-(4-(4-chlorophenoxy)phenyl)propanamide, gave Compound 209, (S)-3-(benzyloxy)-N-(4-(4-chlorophenoxy)phenyl)-2-(3-(dimethylamino)propanamido)propanamide (6 mg, 10%); Major isomer: $^1$H-NMR (400 MHz, DMSO-D$_6$): σ 10.15 (br s, 1H), 8.48-8.47 (d, 1H), 7.65-7.61 (d, 2H), 7.42-7.39 (d, 2H), 7.43-7.39 (m, 2H), 7.32-7.26 (m, 5H), 7.06-6.96 (m, 4H), 4.72-4.67 (m, 1H), 4.52 (s, 2H), 3.65-3.64 (d, 2H), 2.47-2.43 (m, 2H), 2.33-2.30 (m, 2H), 2.12 (s, 6H). MS (EI) for C$_{27}$H$_{30}$ClN$_3$O$_4$. found 496.0 (MH+).

Proceeding as in Example 1, but substituting (S)-2-amino-3-(benzyloxy)-N-(4-(p-tolyloxy)phenyl)propanamide, gave Compound 158, (S)-2-(2-(1H-imidazol-5-yl)acetamido)-3-(benzyloxy)-N-(4-(p-tolyloxy)phenyl)propanamide (136 mg, 28%). $^1$H-NMR (400 MHz, CDCl$_3$): σ 9.18-9.05 (m, 2H), 7.59 (s, 1H), 7.49-7.41 (m, 3H), 7.37-7.25 (m, 6H), 7.12 (d, 2H), 6.96-6.87 (m, 4H), 4.79-4.73 (m, 1H), 4.63 (d, 1H), 4.53 (d, 1H), 4.17-4.10 (m, 1H), 3.68-3.59 (m, 3H), 2.32 (s, 3H). MS (EI) for C$_{28}$H$_{28}$N$_4$O$_4$. found 485.3 (MH+).

Proceeding as in Example 1, but substituting 2-(pyrazin-2-yl)acetic acid hydrochloride and (S)-2-amino-3-(benzyloxy)-N-(4-(4-fluorophenoxy)phenyl)propanamide, gave Compound 159, (S)-3-(benzyloxy)-N-(4-(4-fluorophenoxy)phenyl)-2-(2-(pyrazin-2-yl)acetamido)propanamide (66 mg, 46%). $^1$H-NMR (400 MHz, CDCl$_3$): σ 8.63-8.44 (m, 4H), 7.40-7.19 (m, 9H), 7.05-6.92 (m, 3H), 4.74-4.70 (m, 1H), 4.66 (d, 1H), 4.55 (d, 1H), 4.10 (dd, 1H), 3.85 (s, 2H), 3.64 (dd, 1H). MS (EI) for C$_{28}$H$_{25}$FN$_4$O$_4$. found 501.2 (MH+).

Proceeding as in Example 1, but substituting 2-morpholin-4-ylacetic acid hydrochloride and (S)-2-amino-3-(4-fluorobenzyloxy)-N-(4-(4-fluorophenoxy)phenyl)propanamide, gave Compound 210, (S)-3-(4-fluorobenzyloxy)-N-(4-(4-fluorophenoxy)phenyl)-2-(2-morpholinoacetamido)propanamide (60 mg, 55%). $^1$H-NMR (400 MHz, CDCl$_3$): δ 8.45 (s, 1H), 8.00 (s, 1H), 7.37-7.25 (m, 5H), 7.10-6.90 (m, 7H), 4.79-4.73 (m, 1H), 4.63 (m, 2H), 4.00-3.80 (m, 6H), 3.20-3.10 (s, 2H), 2.60-2.45 (m, 4H). MS (EI) for $C_{28}H_{29}F_2N_3O_5$ found 526 (MH+).

Proceeding as in Example 1, but substituting 2-(1H-imidazol-4-yl)-2-methylpropanoic acid hydrochloride and (S)-2-amino-3-(4-fluorobenzyloxy)-N-(4-(4-fluorophenoxy)phenyl)propanamide, gave Compound 161, (S)-2-(2-(1H-imidazol-4-yl)-2-methylpropanamido)-3-(4-fluorobenzyloxy)-N-(4-(4-fluorophenoxy)phenyl)propanamide (92.2 mg, 60%). $^1$H-NMR (400 MHz, CDCl$_3$): δ 9.31 (s, 1H), 8.32 (br s, 1H), 7.49-7.45 (m, 3H), 7.38 (d, 1H), 7.22-7.18 (m, 2H), 7.02-6.88 (m, 7H), 6.83 (s, 1H), 4.72-4.68 (m, 1H), 4.51 (d, 1H), 4.44 (d, 1H), 4.04 (dd, 1H), 3.63 (dd, 1H), 1.56 (s, 3H), 1.55 (s, 3H). MS (EI) for $C_{29}H_{29}F_2N_4O_4$ found 535 (MH+).

Proceeding as in Example 1, but substituting (S)-2-amino-3-(benzyloxy)-N-(4-(benzyloxy)phenyl)propanamide, gave Compound 211, (S)-2-(2-(1H-imidazol-4-yl)acetamido)-3-(benzyloxy)-N-(4-(benzyloxy)phenyl)propanamide (40 mg, 41%). $^1$H-NMR (400 MHz, CDCl$_3$): σ 7.55 (s, 1H), 7.44-7.37 (m, 6H), 7.35-7.26 (m, 6H), 6.94-6.90 (m, 3H), 5.05 (s, 2H), 4.71 (dd, 1H), 4.59-4.50 (m, 2H), 3.98 (dd, 1H), 3.66 (dd, 1H), 3.60 (s, 2H). MS (EI) for $C_{28}H_{28}N_4O_4$ found 485.2 (MH+).

Proceeding as in Example 1, but substituting 2-(5-fluoro-1H-indol-3-yl)acetic acid hydrochloride and (S)-2-amino-3-(benzyloxy)-N-(4-(4-fluorophenoxy)phenyl)propanamide, gave Compound 212, (S)-3-(benzyloxy)-2-(2-(5-fluoro-1H-indol-3-yl)acetamido)-N-(4-(4-fluorophenoxy)phenyl)propanamide (78 mg, 70%). $^1$H-NMR (400 MHz, DMSO-D$_6$): σ 10.98 (s, 1H), 10.17 (s, 1H), 8.37 (d, 1H), 7.63-7.57 (m, 2H), 7.39-7.16 (m, 9H), 7.05-6.95 (m, 4H), 6.93-6.86 (m, 1H), 4.75-4.67 (m, 1H), 4.50 (s, 2H), 3.70-3.53 (m, 4H). MS (EI) for $C_{32}H_{27}F_2N_3O_4$ found 555.9 (MH+).

Proceeding as in Example 1, but substituting 2-(1H-imidazol-4-yl)-2-methylpropanoic acid hydrochloride and (S)-2-amino-3-(benzyloxy)-N-(4-(4-fluorophenoxy)phenyl)propanamide, gave Compound 213, (S)-2-(2-(1H-imidazol-4-yl)-2-methylpropanamido)-3-(benzyloxy)-N-(4-(4-fluorophenoxy)phenyl)propanamide (93.4 mg, 58%). $^1$H-NMR (400 MHz, CDCl$_3$): δ 9.30 (s, 1H), 7.52-7.46 (m, 3H), 7.37 (d, 1H), 7.33-7.22 (m, 5H), 7.03-6.98 (m, 2H), 6.95-6.88 (m, 4H), 6.82 (s, 1H), 4.73-4.68 (m, 1H), 4.58 (d, 1H), 4.47 (d, 1H), 4.08 (dd, 1H), 3.64 (dd, 1H), 1.56 (s, 3H), 1.55 (s, 3H). MS (EI) for $C_{29}H_{30}FN_4O_4$ found 517 (MH+).

Proceeding as in Example 1, but substituting 2-(2-methyl-1H-imidazol-4-yl)acetic acid hydrochloride and (S)-2-amino-3-(benzyloxy)-N-(4-(4-fluorophenoxy)phenyl)propanamide, gave Compound 162, (S)-3-(benzyloxy)-N-(4-(4-fluorophenoxy)phenyl)-2-(2-(2-methyl-1H-imidazol-4-yl)acetamido)propanamide (52 mg, 7%). $^1$H-NMR (400 MHz, DMSO-D$_6$): σ 10.19 (s, 1H), 8.40-8.36 (m, 2H), 7.61 (d, 2H), 7.32-7.18 (m, 6H), 7.04-6.97 (m, 3H), 6.74 (br s, 1H), 4.69-4.64 (m, 1H), 4.52 (s, 2H), 3.67-3.54 (m, 4H), 2.20 (s, 3H). MS (EI) for $C_{28}H_{27}FN_4O_4$ found 503.2 (MH+).

Proceeding as in Example 1, but substituting 2-(2,5-dihydro-1H-pyrrol-1-yl)acetic acid hydrochloride and (S)-2-amino-3-(benzyloxy)-N-(4-(4-fluorophenoxy)phenyl)propanamide, gave Compound 214, (S)-3-(benzyloxy)-2-(2-(2,5-dihydro-1H-pyrrol-1-yl)acetamido)-N-(4-(4-fluorophenoxy)phenyl)propanamide (25.7 mg, 65.6%); Major isomer: $^1$H-NMR (400 MHz, DMSO-D$_6$): σ 10.21 (s, 1H), 7.96 (d, 1H), 7.60 (d, 2H), 7.27-7.32 (m, 5H), 7.21 (m, 2H), 6.98-7.04 (m, 4H), 4.72 (m, 1H), 4.52 (s, 2H), 3.69-3.74 (m, 2H), 3.30 (s, 2H), 3.13 (d, 1H), 2.56 (d, 2H), 1.72 (s, 1H). MS (EI) for $C_{28}H_{28}FN_3O_4$. found 490.5 (MH+).

Proceeding as in Example 1, but substituting 2-(pyrrolidin-1-yl)acetic acid hydrochloride and (S)-2-amino-3-(benzyloxy)-N-(4-(4-fluorophenoxy)phenyl)propanamide, gave Compound 215, (S)-3-(benzyloxy)-N-(4-(4-fluorophenoxy)phenyl)-2-(2-(pyrrolidin-1-yl)acetamido)propanamide (29.4 mg, 74.8%); Major isomer: $^1$H-NMR (400 MHz, DMSO-D$_6$): σ 10.21 (s, 1H), 7.92 (d, 1H), 7.60 (d, 2H), 7.27-7.31 (m, 5H), 7.21 (d, 2H), 6.99-4.03 (m, 4H), 4.72 (m, 1H), 4.52 (s, 2H), 3.70-3.75 (m, 2H), 3.12 (d, 2H), 2.55 (d, 4H), 1.72 (m, 4H). MS (EI) for $C_{28}H_{30}FN_3O_4$. found 492.5 (MH+).

Proceeding as in Example 1, but substituting 2-(4-phenylpiperazin-1-yl)acetic acid hydrochloride and (S)-2-amino-3-(benzyloxy)-N-(4-(4-fluorophenoxy)phenyl)propanamide, gave Compound 225, (S)-3-(benzyloxy)-N-(4-(4-fluorophenoxy)phenyl)-2-(2-(4-phenylpiperazin-1-yl)acetamido)propanamide (13.4 mg, 28.7%); Major isomer: $^1$H-NMR (400 MHz, DMSO-D$_6$): σ 10.23 (s, 1H), 8.02 (s, 1H), 7.60 (d, 2H), 7.28-7.29 (m, 4H), 7.19-7.26 (m, 5H), 6.99-7.04 (m, 4H), 6.92 (d, 2H), 6.78 (t, 1H), 4.71 (m, 1H), 4.52 (s, 2H), 3.76 (m, 2H), 3.13 (m, 4H), 3.07 (s, 2H), 2.63 (m, 4H). MS (EI) for $C_{34}H_{35}FN_4O_4$. found 583.6 (MH+).

Proceeding as in Example 1, but substituting 2-(4-(2-methoxyphenyl)piperazin-1-yl)acetic acid hydrochloride and (S)-2-amino-3-(benzyloxy)-N-(4-(4-fluorophenoxy)phenyl)propanamide, gave Compound 217, (S)-3-(benzyloxy)-N-(4-(4-fluorophenoxy)phenyl)-2-(2-(4-(2-methoxyphenyl)piperazin-1-yl)acetamido)propanamide (19 mg, 38.8%); Major isomer: $^1$H-NMR (400 MHz, DMSO-D$_6$): σ 10.23 (1H), 5.02 (d, 1H), 7.61 (d, 2H), 7.25-4.30 (m, 4H), 7.20-7.23 (m, 3H), 4.00-7.04 (m, 3H), 6.85-6.98 (m, 5H), 4.71 (m, 1H), 4.53 (s. 2H), 3.80 (m, 1H), 3.77 (s, 3H), 3.72 (m, 1H), 3.05 (d, 2H), 2.99 (m, 4H), 2.62 (m, 4H). MS (EI) for $C_{35}H_{37}FN_4O_5$. found 613.6 (MH+).

Proceeding as in Example 1, but substituting 2-(4-(4-fluorophenyl)piperazin-1-yl)acetic acid hydrochloride and (S)-2-amino-3-(benzyloxy)-N-(4-(4-fluorophenoxy)phenyl)propanamide, gave Compound 218, (S)-3-(benzyloxy)-N-(4-(4-fluorophenoxy)phenyl)-2-(2-(4-(4-fluorophenyl)piperazin-1-yl)acetamido)propanamide (13.3 mg, 27.7%); Major isomer: $^1$H-NMR (400 MHz, DMSO-D$_6$): σ 10.21 (s, 1H), 8.01 (d, 1H), 7.60 (d, 2H), 7.26-7.30 (m, 5H), 7.19-7.25 (m, 2H), 6.98-7.01 (m, 6H), 6.92-6.95 (m, 2H), 4.70 (m, 1H), 4.52 (s, 2H), 3.72-3.80 (m, 2H), 3.07 (m, 6H), 2.59-2.65 (m, 4H). MS (EI) for $C_{34}H_{34}F_2N_4O_4$. found 601.6 (MH+).

Proceeding as in Example 1, but substituting 2-(2,6-dimethylmorpholino)acetic acid hydrochloride and (S)-2-amino-3-(benzyloxy)-N-(4-(4-fluorophenoxy)phenyl)propanamide, gave Compound 265, (2S)-3-(benzyloxy)-2-(2-(2,6-dimethylmorpholino)acetamido)-N-(4-(4-fluorophenoxy)phenyl)propanamide (11.1 mg, 25.9%); Major isomer: $^1$H-NMR (400 MHz, DMSO-D$_6$): σ 10.20 (s, 1H), 7.98 (d, 1H), 7.60 (d, 2H), 7.27-7.32 (m, 5H), 7.19-7.23 (m, 2H), 6.98-7.04 (m, 4H), 4.69-4.71 (m, 1H), 4.52 (s, 2H), 3.71-3.77 (m, 2H), 3.54-3.5 (m, 2H), 2.93-3.03 (m, 2H), 2.74 (dd, 2H), 1.73-1.80 (m, 2H), 1.00 (dd, 6H). MS (EI) for $C_{30}H_{34}FN_3O_5$. found 536.6 (MH+).

Proceeding as in Example 1, but substituting 2-thiomorpholinoacetic acid hydrochloride and (S)-2-amino-3-(benzyloxy)-N-(4-(4-fluorophenoxy)phenyl)propanamide, gave Compound 266, (S)-3-(benzyloxy)-N-(4-(4-fluorophenoxy)phenyl)-2-(2-thiomorpholinoacetamido)propanamide (14.2 g, 33.9%); Major isomer: $^1$H-NMR (400 MHz, DMSO-D$_6$): σ 10.21 (s, 1H), 7.96 (d, 1H), 7.60 (d, 2H), 7.28-7.34 (m, 5H), 7.19-7.23 (m, 2H), 6.98-7.04 (m, 4H), 4.68-4.69 (m, 1H), 4.52 (s, 2H), 3.70-3.77 (m, 2H), 3.01 (s, 2H), 2.67-2.73 (m, 4H), 2.60-2.63 (m, 4H). MS (EI) for C$_{28}$H$_{30}$FN$_3$O$_4$S. found 524.6 (MH+).

Proceeding as in Example 1, but substituting 2-(2,3-dioxa-8-azaspiro[4.5]decan-8-yl)acetic acid hydrochloride and (S)-2-amino-3-(benzyloxy)-N-(4-(4-fluorophenoxy)phenyl)propanamide, gave Compound 219, (2S)-2-(2-(2,3-dioxa-8-azaspiro[4.5]decan-8-yl)acetamido)-3-(benzyloxy)-N-(4-(4-fluorophenoxy)phenyl)propanamide (21.7 mg, 48.1%); Major isomer: $^1$H-NMR (400 MHz, DMSO-D$_6$): σ 10.21 (s, 1H), 8.00 (d, 1H), 7.60 (d, 2H), 7.27-7.33 (m, 5H), 7.20-7.23 (m, 2H), 6.98-7.04 (m, 4H), 4.68-4.70 (m, 1H), 4.52 (s, 2H), 3.88 (s, 4H), 3.69-3.79 (m, 2H), 3.00 (s, 2H), 2.51-2.54 (m, 4H), 2.63-2.65 (m, 4H). MS (EI) for C$_{31}$H$_{34}$FN$_3$O$_6$. found 564.6 (MH+).

Proceeding as in Example 1, but substituting 2-(4-methylpiperidin-1-yl)acetic acid hydrochloride and (S)-2-amino-3-(benzyloxy)-N-(4-(4-fluorophenoxy)phenyl)propanamide, gave Compound 130, (S)-3-(benzyloxy)-N-(4-(4-fluorophenoxy)phenyl)-2-(2-(4-methylpiperidin-1-yl)acetamido)propanamide (19.2 mg, 46.2%); Major isomer: $^1$H-NMR (400 MHz, DMSO-D$_6$): σ 10.21 (s, 1H), 7.94 (d, 1H), 7.60 (d, 2H), 7.29-7.33 (m, 5H), 7.19-7.27 (m, 2H), 6.98-7.04 (m, 4H), 4.67-4.71 (m, 1H), 4.52 (s, 2H), 3.68-0.80 (m, 2H), 2.94 (d, 2H), 2.77-2.90 (m, 2H), 2.00-2.06 (m, 2H), 1.54-1.60 (m, 2H), 1.30-1.33 (m, 1H), 1.13-1.19 (m, 2H), 0.89 (d, 3H). MS (EI) for C$_{30}$H$_{34}$FN$_3$O$_4$. found 520.6 (MH+).

Proceeding as in Example 1, but substituting 2-(4-benzylpiperidin-1-yl)acetic acid hydrochloride and (S)-2-amino-3-(benzyloxy)-N-(4-(4-fluorophenoxy)phenyl)propanamide, gave Compound 220, (S)-3-(benzyloxy)-2-(2-(4-benzylpiperidin-1-yl)acetamido)-N-(4-(4-fluorophenoxy)phenyl)propanamide (21.4 mg, 44.9%); Major isomer: $^1$H-NMR (400 MHz, DMSO-D$_6$): σ 10.21 (s, 1H), 7.93 (d, 1H), 7.60 (d, 2H), 7.26-7.34 (m, 7H), 7.14-7.24 (m, 5H), 6.98-7.04 (m, 4H), 4.67-4.71 (m, 1H), 4.52 (s, 2H), 3.68-3.80 (m, 2H), 2.92 (d, 2H), 2.78-2.87 (m, 2H), 2.47-2.50 (m, 2H), 1.94-2.02 (m, 2H), 1.43-1.55 (m, 3H), 1.17-1.24 (m, 2H). MS (EI) for C$_{36}$H$_{38}$FN$_3$O$_4$. found 596.7 (MH+).

Proceeding as in Example 1, but substituting 2-(4-(pyridin-2-yl)piperazin-1-yl)acetic acid hydrochloride and (S)-2-amino-3-(benzyloxy)-N-(4-(4-fluorophenoxy)phenyl)propanamide, gave Compound 126, (S)-3-(benzyloxy)-N-(4-(4-fluorophenoxy)phenyl)-2-(2-(4-(pyridin-2-yl)piperazin-1-yl)acetamido)propanamide (15.7 g, 33.6%); Major isomer: $^1$H-NMR (400 MHz, DMSO-D$_6$): σ 10.23 (s, 1H), 8.11-8.12 (m, 1H), 8.05 (d, 1H), 7.60 (d, 2H), 7.51-7.55 (m, 1H), 7.28-7.33 (m, 5H), 7.19-7.25 (m, 2H), 6.98-7.04 (m, 4H), 6.81 (d, 1H), 6.63-6.66 (m, 1H), 4.71 (m, 1H), 4.52 (s, 2H), 3.72-3.78 (m, 2H), 3.47-3.49 (m, 4H), 3.06 (s, 2H), 2.55-2.59 (m, 4H). MS (EI) for C$_{33}$H$_{34}$FN$_5$O$_4$. found 584.6 (MH+).

Proceeding as in Example 1, but substituting 2-(3,4-dihydroisoquinolin-2(1H)-yl)acetic acid hydrochloride and (S)-2-amino-3-(benzyloxy)-N-(4-(4-fluorophenoxy)phenyl)propanamide, gave Compound 221, (S)-3-(benzyloxy)-2-(2-(3,4-dihydroisoquinolin-2(1H)-yl)acetamido)-N-(4-(4-fluorophenoxy)phenyl)propanamide (15.6 mg, 35.2%); Major isomer: $^1$H-NMR (400 MHz, DMSO-D$_6$): σ 10.20 (s, 1H), 8.03 (d, 1H), 7.60 (d, 2H), 7.22-7.26 (m, 5H), 7.19-7.21 (m, 2H), 7.12-7.15 (m, 3H), 6.98-7.04 (m, 5H), 4.73 (m, 1H), 4.50 (s, 2H), 3.71-3.79 (m, 2H), 3.70 (s, 2H), 3.18 (s, 2H), 2.83-2.86 (m, 2H), 2.71-2.81 (m, 2H). MS (EI) for C$_{33}$H$_{32}$FN$_3$O$_4$: 554.6 (MH+).

Proceeding as in Example 1, but substituting 2-(azepan-1-yl)acetic acid hydrochloride and (S)-2-amino-3-(benzyloxy)-N-(4-(4-fluorophenoxy)phenyl)propanamide, gave Compound 128, (S)-2-(2-(azepan-1-yl)acetamido)-3-(benzyloxy)-N-(4-(4-fluorophenoxy)phenyl)propanamide (21.7 mg, 52.2%); Major isomer: $^1$H-NMR (400 MHz, DMSO-D$_6$): 10.22 (s, 1H), 7.99 (d, 1H), 7.60 (d, 2H), 7.27-7.33 (m, 5H), 7.19-7.23 (m, 2H), 6.99-7.04 (m, 4H), 4.70 (m, 1H), 4.52 (s, 2H), 3.67-3.79 (m, 2H), 3.10 (m, 2H), 2.51-2.63 (m, 4H), 1.55-1.60 (m, 8 h). MS (EI) for C$_{30}$H$_{34}$FN$_3$O$_4$. found 520.6 (MH+).

Proceeding as in Example 1, but substituting 2-(octahydroisoquinolin-2(1H)-yl)acetic acid hydrochloride and (S)-2-amino-3-(benzyloxy)-N-(4-(4-fluorophenoxy)phenyl)propanamide, gave Compound 222, (2S)-3-(benzyloxy)-N-(4-(4-fluorophenoxy)phenyl)-2-(2-(octahydroisoquinolin-2(1H)-yl)acetamido)propanamide (20.6 mg, 46%); Major isomer: $^1$H-NMR (400 MHz, DMSO-D$_6$): 10.21 (s, 1H), 7.96 (d, 1H), 7.60 (d, 2H), 7.29-7.31 (m, 5H), 7.19-7.23 (m, 2H), 6.98-7.04 (m, 4H), 4.68 (m, 1H), 4.49 (s, 2H), 3.29-3.79 (m, 2H), 2.77-3.01 (m, 2H), 2.63-2.73 (m, 2H), 2.01-2.99 (m, 2H), 0.81-1.86 (m, 12H). MS (EI) for C$_{33}$H$_{38}$FN$_3$O$_4$. found 560.6 (MH+).

Proceeding as in Example 1, but substituting 2-(4-(furan-2-carbonyl)piperazin-1-yl)acetic acid hydrochloride and (S)-2-amino-3-(benzyloxy)-N-(4-(4-fluorophenoxy)phenyl)propanamide, gave Compound 223, (S)-3-(benzyloxy)-N-(4-(4-fluorophenoxy)phenyl)-2-(2-(4-(furan-2-carbonyl)piperazin-1-yl)acetamido)propanamide (17 mg, 35.4%); Major isomer: $^1$H-NMR (400 MHz, DMSO-D$_6$): 10.22 (s, 1H), 8.04 (d, 1H), 7.84 (s, 1H), 7.61 (d, 2H), 7.26-7.31 (m, 5H), 7.19-7.23 (m, 2H), 6.98-7.04 (m, 5H), 6.63 (dd, 1H), 4.71 (m, 1H), 4.53 (s, 2H), 3.73-3.77 (m, 2H), 3.65 (s, 2H), 3.06 (m, 2H), 2.51-2.54 (m, 4H). MS (EI) for C$_{33}$H$_{33}$FN$_4$O$_6$. found 601.6 (MH+).

Proceeding as in Example 1, but substituting 2-(4-(2-fluorophenyl)piperazin-1-yl)acetic acid hydrochloride and (S)-2-amino-3-(benzyloxy)-N-(4-(4-fluorophenoxy)phenyl)propanamide, gave Compound 127, (S)-3-(benzyloxy)-N-(4-(4-fluorophenoxy)phenyl)-2-(2-(4-(2-fluorophenyl)piperazin-1-yl)acetamido)propanamide (13.1 mg, 27.3%); Major isomer: $^1$H-NMR (400 MHz, DMSO-D$_6$): 10.23 (s, 1H), 8.02 (d, 1H), 7.60 (d, 2H), 7.25-7.30 (m, 5H), 7.19-7.23 (m, 2H), 7.10-7.19 (m, 2H), 6.98-7.04 (m, 6H), 4.71 (m, 1H), 4.53 (s, 2H), 3.72-3.80 (m, 2H), 3.07 (d, 2H), 3.00 (m, 4H), 2.63 (m, 4H). MS (EI) for C$_{34}$H$_{34}$F$_2$N$_4$O$_4$. found 601.6 (MH+).

Proceeding as in Example 1, but substituting 2-(4-(4-methoxyphenyl)piperazin-1-yl)acetic acid hydrochloride and (S)-2-amino-3-(benzyloxy)-N-(4-(4-fluorophenoxy)phenyl)propanamide, gave Compound 224, (S)-3-(benzyloxy)-N-(4-(4-fluorophenoxy)phenyl)-2-(2-(4-(4-methoxyphenyl)piperazin-1-yl)acetamido)propanamide (17.2 g, 35.1%); Major isomer: $^1$H-NMR (400 MHz, DMSO-D$_6$): σ 10.21 (s, 1H), 8.00 (d, 1H), 7.60 (d, 2H), 7.30-7.65 (m, 5H), 7.19-7.25 (m, 2H), 6.98-7.04 (m, 4H), 6.87-6.90 (d, 2H), 6.81-6.84 (d, 2H), 4.71 (m, 1H), 4.52 (s, 2H), 3.70-3.80 (m, 2H), 3.69 (s, 3H), 3.06 (s, 2H), 3.02 (m, 4H), 2.59-2.67 (m, 4H). MS (EI) for C$_{35}$H$_{37}$FN$_4$O$_5$. found 613.6 (MH+).

Proceeding as in Example 1, but substituting (2S,3S)-3-benzyl-N-(4-(4-fluorophenoxy)phenyl)pyrrolidine-2-carboxamide, gave Compound 163, (2S,3S)-1-(2-(1H-imidazol-4-yl)acetyl)-3-benzyl-N-(4-(4-fluorophenoxy)phenyl) pyrrolidine-2-carboxamide (95 mg, 60%). Major isomer: $^1$H-NMR (400 MHz, DMSO-D$_6$): σ 12.28 (br s, 1H), 10.06 (s, 1H), 7.73-7.75 (m, 3H), 7.33-7.15 (m, 7H), 7.05-6.92 (m, 5H), 4.54-4.48 (m, 1H), 3.76-3.45 (m, 5H), 2.74-2.54 (m, 4H), 1.98-1.87 (m, 2H). MS (EI) for $C_{29}H_{27}FN_4O_3$. found 499.0 (MH+).

Proceeding as in Example 1, but substituting 2-(2-(1H-imidazol-4-yl)ethylamino)acetic acid hydrochloride and (S)-2-amino-3-(benzyloxy)-N-(4-(4-fluorophenoxy)phenyl)propanamide, gave Compound 216, (S)-2-(2-(2-(1H-imidazol-4-yl)ethylamino)acetamido)-3-(benzyloxy)-N-(4-(4-fluorophenoxy)phenyl)propanamide (11.2 mg, 26.3%). $^1$H-NMR (400 MHz, DMSO-D$_6$): σ 10.24 (s, 1H), 8.25 (d, 1H), 7.61 (d, 2H), 7.51 (s, 1H), 7.28 (m, 6H), 7.19 (t, 2H), 7.02 (m, 4H), 6.78 (s, 1H), 4.70 (m, 1H), 4.52 (s, 2H), 3.68 (m, 3H), 3.20 (s, 2H), 2.75 (m, 2H), 2.64 (m, 2H). MS (EI) for $C_{29}H_{30}FN_5O_4$: 532.6 (MH+).

Proceeding as in Example 1, but substituting 2-(4-(4-acetylphenyl)piperazin-1-yl)acetic acid hydrochloride and (S)-2-amino-3-(benzyloxy)-N-(4-(4-fluorophenoxy)phenyl) propanamide, gave Compound 229, (S)-2-(2-(4-(4-acetylphenyl)piperazin-1-yl)acetamido)-3-(benzyloxy)-N-(4-(4-fluorophenoxy)phenyl)propanamide (10.2 mg, 20.4%). $^1$H-NMR (400 MHz, DMSO-D$_6$): σ 10.23 (s, 1H), 8.04 (d, 1H), 7.81 (d, 2H), 7.60 (d, 2H), 7.23 (m, 7H), 7.01 (m, 6H), 4.71 (m, 1H), 4.52 (s, 2H), 3.74 (m, 1H), 3.33 (m, 5H), 3.07 (s, 2H), 2.61 (m, 4H), 2.46 (s, 3H). MS (EI) for $C_{36}H_{37}FN_4O_5$: 625.6 (MH+).

Proceeding as in Example 1, but substituting 2-(4-acetylpiperazin-1-yl)acetic acid hydrochloride and (S)-2-amino-3-(benzyloxy)-N-(4-(4-fluorophenoxy)phenyl)propanamide, gave Compound 230, (S)-2-(2-(4-acetylpiperazin-1-yl)acetamido)-3-(benzyloxy)-N-(4-(4-fluorophenoxy)phenyl)propanamide (13.4 mg, 31.3%). $^1$H-NMR (400 MHz, DMSO-D$_6$): σ 10.22 (s, 1H), 8.03 (d, 1H), 7.99 (s, 1H), 7.61 (d, 2H), 7.30 (m, 5H), 7.21 (t, 2H), 7.00 (m, 4H), 4.70 (m, 1H), 4.52 (s, 2H), 3.73 (m, 2H), 3.34 (m, 4H), 3.06 (s, 2H), 2.41 (m, 4H). MS (EI) for $C_{29}H_{31}FN_4O_5$: 535.4 (MH+).

Proceeding as in Example 1, but substituting 2-(3-(diethylcarbamoyl)piperidin-1-yl)acetic acid hydrochloride and (S)-2-amino-3-(benzyloxy)-N-(4-(4-fluorophenoxy)phenyl) propanamide, gave Compound 231, 1-(2-((S)-3-(benzyloxy)-1-(4-(4-fluorophenoxy)phenylamino)-1-oxopropan-2-ylamino)-2-oxoethyl)-N,N-diethylpiperidine-3-carboxamide (20.2 mg, 41.8%). $^1$H-NMR (400 MHz, DMSO-D$_6$): σ 10.22 (s, 1H), 8.01 (t, 1H), 7.61 (d, 2H), 7.27 (m, 6H), 7.00 (m, 4H), 4.70 (m, 1H), 4.52 (s, 2H), 3.71 (m, 2H), 3.27 (m, 4H), 3.02 (m, 6H), 2.15 (m, 2H), 1.63 (m, 3H), 1.35 (m, 1H), 1.06 (m, 3H), 0.93 (m, 3H). MS (EI) for $C_{34}H_{41}FN_4O_5$: 605.8 (MH+).

Proceeding as in Example 1, but substituting 2-(3-methylpiperidin-1-yl)acetic acid hydrochloride and (S)-2-amino-3-(benzyloxy)-N-(4-(4-fluorophenoxy)phenyl)propanamide, gave Compound 46, (2S)-3-(benzyloxy)-N-(4-(4-fluorophenoxy)phenyl)-2-(2-(3-methylpiperidin-1-yl) acetamido)propanamide (17.8 mg, 42.8%). $^1$H-NMR (400 MHz, DMSO-D$_6$): σ 10.20 (s, 1H), 7.94 (d, 1H), 7.56 (d, 2H), 7.29 (m, 5H), 7.21 (m, 2H), 7.01 (m, 4H), 4.69 (m, 1H), 4.52 (s, 2H), 3.73 (m, 2H), 2.93 (m, 2H), 2.73 (m, 2H), 1.98 (s, 1H), 1.58 (m 5H), 0.81 (m, 4H). MS (EI) for $C_{30}H_{34}FN_3O_4$: 520.7 (MH+).

Proceeding as in Example 1, but substituting 2-(octahydroquinolin-1(2H)-yl)acetic acid hydrochloride and (S)-2-amino-3-(benzyloxy)-N-(4-(4-fluorophenoxy)phenyl)propanamide, gave Compound 45, (2S)-3-(benzyloxy)-N-(4-(4-fluorophenoxy)phenyl)-2-(2-(octahydroquinolin-1(2H)-yl) acetamido)propanamide (20.1 mg, 44.9%). $^1$H-NMR (400 MHz, DMSO-D$_6$): σ 10.22 (s, 1H), 7.84 (m, 1H), 7.59 (d, 2H), 7.28 (m, 7H), 7.02 (m, 4H), 4.69 (m, 1H), 4.51 (m, 2H), 3.73 (m, 2H), 3.34 (m, 2H), 3.33 (m, 2H), 2.97 (m, 1H), 2.75 (m, 1H), 2.17 (m, 1H), 1.42 (m, 11H). MS (EI) for $C_{33}H_{38}FN_3O_4$: 560.5 (MH+).

Proceeding as in Example 1, but substituting 2-(2-methylpyrrolidin-1-yl)acetic acid hydrochloride and (S)-2-amino-3-(benzyloxy)-N-(4-(4-fluorophenoxy)phenyl)propanamide, gave Compound 63, (2S)-3-(benzyloxy)-N-(4-(4-fluorophenoxy)phenyl)-2-(2-(2-methylpyrrolidin-1-yl) acetamido)propanamide (19 mg, 47%). $^1$H-NMR (400 MHz, DMSO-D$_6$): σ 10.22 (s, 1H), 7.93 (t, 1H), 7.60 (d, 2H), 7.29 (m, 5H), 7.19 (m, 2H), 7.00 (m, 4H), 4.73 (s, 1H), 4.52 (s, 2H), 3.69 (m, 2H), 3.05 (m, 1H), 2.82 (m, 1H), 2.46 (m, 1H), 2.23 (m, 1H), 1.91 (m, 1H), 1.67 (m, 2H), 1.33 (m, 1H), 1.03 (d, 3H). MS (EI) for $C_{29}H_{32}FN_3O_4$: 506.5 (MH+).

Proceeding as in Example 1, but substituting 2-(4-(pyrrolidin-1-yl)piperidin-1-yl)acetic acid hydrochloride and (S)-2-amino-3-(benzyloxy)-N-(4-(4-fluorophenoxy)phenyl)propanamide, gave Compound 43, (S)-3-(benzyloxy)-N-(4-(4-fluorophenoxy)phenyl)-2-(2-(4-(pyrrolidin-1-yl)piperidin-1-yl)acetamido)propanamide (22.1 mg, 48.1%). $^1$H-NMR (400 MHz, DMSO-D$_6$): σ 10.22 (s, 1H), 7.96 (d, 1H), 7.59 (d, 2H), 7.30 (m, 5H), 7.21 (m, 2H), 7.01 (m, 4H), 4.68 (m, 1H), 4.52 (s, 2H), 3.75 (m, 2H), 3.25 (m, 2H), 2.95 (s, 2H), 2.83 (m, 2H), 2.09 (t, 2H), 2.00 (m, 1H), 1.79 (m, 2H), 1.68 (m, 5H), 1.44 (m, 4H). MS (EI) for $C_{33}H_{39}FN_4O_4$: 575.8 (MH+).

Proceeding as in Example 1, but substituting 2-(4-(3-methoxyphenyl)piperazin-1-yl)acetic acid hydrochloride and (S)-2-amino-3-(benzyloxy)-N-(4-(4-fluorophenoxy)phenyl)propanamide, gave Compound 42, (S)-3-(benzyloxy)-N-(4-(4-fluorophenoxy)phenyl)-2-(2-(4-(3-methoxyphenyl) piperazin-1-yl)acetamido)propanamide (15.7 mg, 32%). $^1$H-NMR (400 MHz, DMSO-D$_6$): σ 10.22 (s, 1H), 8.01 (d, 1H), 7.60 (d, 2H), 7.26 (m, 7H), 7.11 (t, 1H), 7.01 (m, 4H), 6.50 (d, 1H), 6.43 (s, 1H), 6.37 (d, 1H), 4.70 (m, 1H), 4.52 (s, 2H), 3.77 (m, 1H), 3.73 (m, 4H), 3.13 (m, 4H), 3.06 (s, 2H), 2.61 (m, 4H). MS (EI) for $C_{35}H_{37}FN_4O_5$: 613.7 (MH+).

Proceeding as in Example 1, but substituting 2-(4-(pyrimidin-2-yl)piperazin-1-yl)acetic acid hydrochloride and (S)-2-amino-3-(benzyloxy)-N-(4-(4-fluorophenoxy)phenyl)propanamide, gave Compound 41, (S)-3-(benzyloxy)-N-(4-(4-fluorophenoxy)phenyl)-2-(2-(4-(pyrimidin-2-yl)piperazin-1-yl)acetamido)propanamide (17.1 mg, 36.6%). $^1$H-NMR (400 MHz, DMSO-D$_6$): σ 10.22 (s, 1H), 8.36 (d, 2H), 8.06 (d, 1H), 7.60 (d, 2H), 7.23 (m, 7H), 7.02 (m, 4H), 6.63 (t, 1H), 4.71 (m, 1H), 4.53 (s, 2H), 3.73 (m, 7H), 3.06 (s, 2H), 2.54 (m, 5H). MS (EI) for $C_{32}H_{33}FN_6O_4$: 585.6 (MH+).

Proceeding as in Example 1, but substituting 2-(4-acetylpiperazin-1-yl)acetic acid hydrochloride and (S)-2-amino-3-(benzyloxy)-N-(4-(4-fluorophenoxy)phenyl)propanamide, gave Compound 236, (S)-2-(2-(4-acetylpiperazin-1-yl)acetamido)-3-(benzyloxy)-N-(4-(4-fluorophenoxy) phenyl)propanamide (14.4 mg, 32.8%). $^1$H-NMR (400 MHz, DMSO-D$_6$): σ 10.21 (s, 1H), 8.01 (d, 1H), 7.60 (d, 2H), 7.30 (s, 5H), 7.20 (t, 2H), 7.02 (m, 4H), 4.70 (m, 1H), 4.52 (s, 2H), 3.74 (m, 2H), 3.41 (m, 5H), 3.03 (s, 2H), 2.40 (m, 3H), 1.98 (s, 3H). MS (EI) for $C_{30}H_{33}FN_4O_5$: 549.7 (MH+).

Proceeding as in Example 1, but substituting 2-(thiazolidin-3-yl)acetic acid hydrochloride and (S)-2-amino-3-(benzyloxy)-N-(4-(4-fluorophenoxy)phenyl)propanamide, gave Compound 235, (S)-3-(benzyloxy)-N-(4-(4-fluorophenoxy) phenyl)-2-(2-(thiazolidin-3-yl)acetamido)propanamide (9.3 mg, 22.8%). MS (EI) for $C_{27}H_{28}FN_3O_4S$. found 510.5 (MH+).

Proceeding as in Example 1, but substituting 2-(4-ethylpiperazin-1-yl)acetic acid hydrochloride and (S)-2-amino-3-(benzyloxy)-N-(4-(4-fluorophenoxy)phenyl)propanamide, gave Compound 114, (S)-3-(benzyloxy)-2-(2-(4-ethylpiperazin-1-yl)acetamido)-N-(4-(4-fluorophenoxy)phenyl)propanamide (20.6 mg, 48.2%). Major isomer: $^1$H-NMR (400 MHz, DMSO-D$_6$): σ 10.21 (s, 1H), 7.93 (d, 1H), 7.60 (d, 2H), 7.31-7.25 (m, 5H), 7.21 (t, 2H), 7.04-6.99 (m, 4H), 4.69 (m, 1H), 4.51 (s, 2H), 3.76 (m, 1H), 3.71 (m, 1H), 2.97 (s, 2H), 2.46 (m, 3H), 2.38 (m, 3H), 2.33-2.28 (m, 4H), 0.98 (t, 3H). MS (EI) for $C_{30}H_{35}FN_4O_4$. found 535.6 (MH+).

Proceeding as in Example 1, but substituting 2-(2-(((S)-1-methylpyrrolidin-2-yl)methyl)piperidin-1-yl)acetic acid hydrochloride and (S)-2-amino-3-(benzyloxy)-N-(4-(4-fluorophenoxy)phenyl)propanamide, gave Compound 113, (2S)-3-(benzyloxy)-N-(4-(4-fluorophenoxy)phenyl)-2-(2-(2-(((S)-1-methylpyrrolidin-2-yl)methyl)piperidin-1-yl)acetamido)propanamide (20.9 mg, 43.3%). Major isomer: $^1$H-NMR (400 MHz, DMSO-D$_6$): σ 10.27 (d, 1H), 8.51 (s, 1H), 7.67-7.64 (m, 2H), 7.31 (m, 5H), 7.21 (t, 2H), 7.03-6.98 (m, 4H), 4.72 (m, 1H), 4.52 (d, 2H), 4.16 (m, 1H), 4.04 (m, 1H), 3.77-3.73 (m, 4H), 3.38 (s, 2H), 2.99 (s, 2H), 2.79 (m, 1H), 2.43 (m, 2H), 2.32 (m, 2H), 2.18 (m, 1H), 1.99 (m, 2H), 1.75 (m, 1H), 1.51 (m, 4H), 1.37 (m, 2H). MS (EI) for $C_{35}H_{43}FN_4O_4$. found 603.7 (MH+).

Proceeding as in Example 1, but substituting 2-((2R,6S)-2,6-dimethylmorpholino)acetic acid hydrochloride and (S)-2-amino-3-(benzyloxy)-N-(4-(4-fluorophenoxy)phenyl)propanamide, gave Compound 234, (S)-3-(benzyloxy)-2-(2-((2R,6S)-2,6-dimethylmorpholino)acetamido)-N-(4-(4-fluorophenoxy)phenyl)propanamide (14.8 mg, 34.5%). Major isomer: $^1$H-NMR (400 MHz, DMSO-D$_6$): σ 10.21 (s, 1H), 7.99 (d, 1H), 7.60 (d, 2H), 7.30 (m, 5H), 7.21 (t, 2H), 7.04-6.98 (m, 4H), 4.70 (m, 1H), 4.52 (s, 2H), 3.73 (m, 2H), 3.55 (m, 2H), 2.98 (d, 2H), 2.77 (d, 1H), 2.71 (d, 1H), 1.76 (dd, 2H), 1.02 (d, 3H), 0.98 (d, 3H). MS (EI) for $C_{30}H_{34}FN_3O_5$. found 536.6 (MH+).

Proceeding as in Example 1, but substituting 2-(4-(3-(trifluoromethyl)pyridin-2-yl)piperazin-1-yl)acetic acid hydrochloride and (S)-2-amino-3-(benzyloxy)-N-(4-(4-fluorophenoxy)phenyl)propanamide, gave Compound 112, (S)-3-(benzyloxy)-N-(4-(4-fluorophenoxy)phenyl)-2-(2-(4-(3-(trifluoromethyl)pyridin-2-yl)piperazin-1-yl)acetamido)propanamide (16.9 mg, 32.4%). Major isomer: $^1$H-NMR (400 MHz, DMSO-D$_6$): σ 10.23 (s, 1H), 8.54 (d, 1H), 8.06 (t, 2H), 7.61 (d, 2H), 7.30 (m, 4H), 7.27-7.19 (m, 4H), 7.04-6.98 (m, 4H), 4.72 (m, 1H), 4.53 (s, 2H), 3.76 (m, 2H), 3.20 (t, 4H), 3.08 (s, 2H), 2.63 (m, 4H). MS (EI) for $C_{34}H_{33}F_4N_5O_4$. found 652.6 (MH+).

Proceeding as in Example 1, but substituting 2-(4-isopropylpiperazin-1-yl)acetic acid hydrochloride and (S)-2-amino-3-(benzyloxy)-N-(4-(4-fluorophenoxy)phenyl)propanamide, gave Compound III, (S)-3-(benzyloxy)-N-(4-(4-fluorophenoxy)phenyl)-2-(2-(4-isopropylpiperazin-1-yl)acetamido)propanamide (19.8 mg, 45.1%). Major isomer: $^1$H-NMR (400 MHz, DMSO-D$_6$): σ 10.22 (s, 1H), 7.92 (d, 1H), 7.59 (d, 2H), 7.30 (m, 5H), 7.21 (t, 2H), 7.04-6.98 (m, 4H), 4.70 (m, 1H), 4.52 (s, 2H), 3.77 (m, 1H), 3.71 (m, 1H), 2.96 (d, 2H), 2.61 (m, 1H), 2.50 (t, 8H), 0.95 (d, 6H). MS (EI) for $C_{31}H_{37}FN_4O_4$. found 549.7 (MH+).

Proceeding as in Example 1, but substituting 2-(4-(tetrahydrofuran-2-carbonyl)piperazin-1-yl)acetic acid hydrochloride and (S)-2-amino-3-(benzyloxy)-N-(4-(4-fluorophenoxy)phenyl)propanamide, gave Compound 237, (2S)-3-(benzyloxy)-N-(4-(4-fluorophenoxy)phenyl)-2-(2-(4-(tetrahydrofuran-2-carbonyl)piperazin-1-yl)acetamido)propanamide (19.3 mg, 39.9%). Major isomer: $^1$H-NMR (400 MHz, DMSO-D$_6$): σ 10.24 (s, 1H), 8.03 (d, 1H), 7.61 (d, 2H), 7.30 (m, 5H), 7.21 (t, 2H), 7.04-6.99 (m, 4H), 4.70 (m, 1H), 4.65 (t, 1H), 4.53 (s, 2H), 3.78-3.72 (m, 4H), 3.35 (m, 6H), 3.04 (s, 2H), 2.44 (m, 2H), 1.97 (dd, 2H), 1.80 (m, 2H). MS (EI) for $C_{33}H_{37}FN_4O_6$. found 605.7 (MH+).

Proceeding as in Example 1, but substituting 2-(4-(methoxycarbonyl)piperidin-1-yl)acetic acid hydrochloride and (S)-2-amino-3-(benzyloxy)-N-(4-(4-fluorophenoxy)phenyl)propanamide, gave Compound 238, (S)-methyl 1-(2-(3-(benzyloxy)-1-(4-(4-fluorophenoxy)phenylamino)-1-oxopropan-2-ylamino)-2-oxoethyl)piperidine-4-carboxylate (22.7 mg, 50.3%). Major isomer: $^1$H-NMR (400 MHz, DMSO-D$_6$): σ 10.21 (s, 1H), 7.95 (d, 1H), 7.60 (d, 2H), 7.29 (m, 5H), 7.21 (t, 2H), 7.04-6.98 (m, 4H), 4.69 (m, 1H), 4.52 (s, 2H), 3.77 (m, 1H), 3.70 (m, 1H), 3.61 (s, 3H), 2.96 (s, 2H), 2.80 (m, 2H), 2.32 (m, 1H), 2.12 (t, 2H), 1.79 (m, 2H), 1.60 (m, 2H). MS (EI) for $C_{31}H_{34}FN_3O_6$. found 564.6 (MH+).

Proceeding as in Example 1, but substituting 2-(4-(2-methoxyethyl)piperazin-1-yl)acetic acid hydrochloride and (S)-2-amino-3-(benzyloxy)-N-(4-(4-fluorophenoxy)phenyl)propanamide, gave Compound 241, (S)-3-(benzyloxy)-N-(4-(4-fluorophenoxy)phenyl)-2-(2-(4-(2-methoxyethyl)piperazin-1-yl)acetamido)propanamide (18.8 mg, 41.6%). Major isomer: $^1$H-NMR (400 MHz, DMSO-D$_6$): σ 10.21 (s, 1H), 7.93 (d, 1H), 7.59 (d, 2H), 7.30 (m, 5H), 7.21 (t, 2H), 7.03-6.97 (m, 4H), 4.68 (m, 1H), 4.52 (s, 2H), 3.77 (m, 1H), 3.70 (m, 1H), 3.41 (t, 4H), 3.22 (s, 3H), 2.96 (s, 2H), 2.44 (t, 8H). MS (EI) for $C_{31}H_{37}FN_4O_5$. found 565.7 (MH+).

Proceeding as in Example 1, but substituting 2-(isoindolin-2-yl)acetic acid hydrochloride and (S)-2-amino-3-(benzyloxy)-N-(4-(4-fluorophenoxy)phenyl)propanamide, gave Compound 240, (S)-3-(benzyloxy)-N-(4-(4-fluorophenoxy)phenyl)-2-(2-(isoindolin-2-yl)acetamido)propanamide (11.7 g, 27.1%). Major isomer: $^1$H-NMR (400 MHz, DMSO-D$_6$): σ 10.23 (s, 1H), 8.08 (d, 1H), 7.60 (d, 2H), 7.26 (m, 5H), 7.22 (m, 6H), 7.04-6.98 (m, 4H), 4.75 (m, 1H), 4.52 (s, 2H), 4.00 (s, 4H), 3.73 (m, 2H), 3.42 (s, 2H). MS (EI) for $C_{32}H_{30}FN_3O_4$. found 540.6 (MH+).

Proceeding as in Example 1, but substituting 2-(4-(2-chloro-6-fluorobenzyl)piperazin-1-yl)acetic acid hydrochloride and (S)-2-amino-3-(benzyloxy)-N-(4-(4-fluorophenoxy)phenyl)propanamide, gave Compound 239, (S)-3-(benzyloxy)-2-(2-(4-(2-chloro-6-fluorobenzyl)piperazin-1-yl)acetamido)-N-(4-(4-fluorophenoxy)phenyl)propanamide (20.8 mg, 40.1%). Major isomer: $^1$H-NMR (400 MHz, DMSO-D$_6$): σ 10.21 (s, 1H), 7.93 (d, 1H), 7.60 (d, 2H), 7.37 (m, 2H), 7.29 (m, 5H), 7.21 (t, 3H), 7.04-6.98 (m, 4H), 4.68 (m, 1H), 4.51 (s, 2H), 3.77 (m, 1H), 3.70 (m, 1H), 3.60 (s, 2H), 2.96 (m, 2H), 2.51 (m, 8H). MS (EI) for $C_{35}H_{35}ClF_2N_4O_4$. found 650.1 (MH+).

Proceeding as in Example 1, but substituting 2-(4-(2-ethoxyethyl)piperazin-1-yl)acetic acid hydrochloride and (S)-2-amino-3-(benzyloxy)-N-(4-(4-fluorophenoxy)phenyl)propanamide, gave Compound 242, (S)-3-(benzyloxy)-N-(4-(4-fluorophenoxy)phenyl)-2-(2-(4-(2-ethoxyethyl)piperazin-1-yl)acetamido)propanamide (22.8 mg, 49.2%). Major isomer: $^1$H-NMR (400 MHz, DMSO-D$_6$): σ 10.21 (s, 1H), 7.93 (d, 1H), 7.59 (d, 2H), 7.30 (m, 5H), 7.21 (t, 2H), 7.04-6.98 (m, 4H), 4.69 (m, 1H), 4.51 (s, 2H), 3.77 (m, 1H), 3.70 (m, 1H), 3.46-3.38 (m, 6H), 2.97 (s, 2H), 2.45 (t, 8H), 1.09 (t, 3H). MS (EI) for $C_{32}H_{39}FN_4O_5$. found 579.7 (MH+).

Proceeding as in Example 1, but substituting 2-(4-((tetrahydrofuran-2-yl)methyl)piperazin-1-yl)acetic acid hydrochloride and (S)-2-amino-3-(benzyloxy)-N-(4-(4-fluorophenoxy)phenyl)propanamide, gave Compound 110, (2S)-3-(benzyloxy)-N-(4-(4-fluorophenoxy)phenyl)-2-(2-(4-((tetrahydrofuran-2-yl)methyl)piperazin-1-yl)acetamido) propanamide (23.1 mg, 48.9%). Major isomer: $^1$H-NMR (400 MHz, DMSO-D$_6$): σ 10.21 (s, 1H), 7.92 (d, 1H), 7.60 (d, 2H), 7.29 (m, 5H), 7.21 (t, 2H), 7.03-6.97 (m, 4H), 4.69 (m, 1H), 4.52 (s, 2H), 3.89 (m, 1H), 3.79-3.68 (m, 3H), 3.59 (m, 1H), 2.96 (s, 2H), 2.45 (m, 5H), 2.34 (m, 5H), 1.89 (m, 1H), 1.76 (m, 2H), 1.44 (m, 1H). MS (EI) for $C_{33}H_{39}FN_4O_5$. found 591.7 (MH+).

Proceeding as in Example 1, but substituting 2-(3-(diethylamino)pyrrolidin-1-yl)acetic acid hydrochloride and (S)-2-amino-3-(benzyloxy)-N-(4-(4-fluorophenoxy)phenyl)propanamide, gave Compound 109, (2S)-3-(benzyloxy)-2-(2-(3-(diethylamino)pyrrolidin-1-yl)acetamido)-N-(4-(4-fluorophenoxy)phenyl)propanamide (21.7 mg, 48.2%). Major isomer: $^1$H-NMR (400 MHz, DMSO-D$_6$): σ 10.22 (s, 1H), 7.87 (d, 1H), 7.61 (d, 2H), 7.29 (m, 5H), 7.21 (t, 2H), 7.03-6.98 (m, 4H), 4.71 (m, 1H), 4.52 (s, 2H), 3.76-3.67 (m, 2H), 3.31 (m, 1H), 3.15 (m, 1H), 3.03 (m, 1H), 2.69-2.58 (m, 3H), 2.48 (m, 5H), 1.88 (m, 1H), 1.55 (m, 1H), 0.92 (t, 6H). MS (EI) for $C_{32}H_{39}FN_4O_4$. found 563.7 (MH+).

Proceeding as in Example 1, but substituting 2-(4-morpholinopiperidin-1-yl)acetic acid hydrochloride and (S)-2-amino-3-(benzyloxy)-N-(4-(4-fluorophenoxy)phenyl)propanamide, gave Compound 105, (S)-3-(benzyloxy)-N-(4-(4-fluorophenoxy)phenyl)-2-(2-(4-morpholinopiperidin-1-yl)acetamido)propanamide (22.4 mg, 47.4%). Major isomer: $^1$H-NMR (400 MHz, DMSO-D$_6$): σ 10.21 (s, 1H), 7.94 (d, 1H), 7.60 (d, 2H), 7.30 (m, 5H), 7.22 (t, 2H), 7.03-6.98 (m, 4H), 4.69 (m, 1H), 4.52 (s, 2H), 3.78 (m, 1H), 3.70 (m, 1H), 3.56 (t, 4H), 2.96-2.83 (m, 4H), 2.41 (m, 4H), 2.05 (m, 3H), 1.73 (m, 2H), 1.39 (m, 2H). MS (EI) for $C_{33}H_{39}FN_4O_5$. found 591.7 (MH+).

Proceeding as in Example 1, but substituting 2-(2-phenyloxazol-4-yl)acetic acid hydrochloride and (S)-2-amino-3-(4-fluorobenzyloxy)-N-(4-(4-fluorophenoxy)phenyl)propanamide, gave Compound 44, (S)-3-(4-fluorobenzyloxy)-N-(4-(4-fluorophenoxy)phenyl)-2-(2-(2-phenyloxazol-4-yl)acetamido)propanamide (160 g, 70%). $^1$H-NMR (400 MHz, CDCl$_3$): σ 8.45 (s, 1H), 8.00 (m, 2H), 7.50-7.45 (m, 2H), 7.40-7.30 (m, 7H), 7.05-6.80 (m, 8H), 4.79-4.73 (m, 1H), 4.63 (m, 2H), 4.00-3.70 (m, 4H). MS (EI) for $C_{33}H_{27}F_2N_3O_5$ found 584 (MH+).

Proceeding as in Example 1, but substituting acetic acid hydrochloride and (S)-2-amino-3-(4-fluorobenzyloxy)-N-(4-(4-fluorophenoxy)phenyl)propanamide, gave Compound 164, (S)-2-acetamido-3-(4-fluorobenzyloxy)-N-(4-(4-fluorophenoxy)phenyl)propanamide (35 mg, 60%). $^1$H-NMR (400 MHz, CDCl$_3$): δ 8.40 (s, 1H), 7.40-7.25 (m, 5H), 7.10-6.90 (m, 7H), 6.45-6.40 (m, 1H), 4.80-4.45 (m, 3H), 4.00-3.90 (m, 1H), 3.60 (m, 1H), 1.60 (s, 3H). MS (EI) for $C_{24}H_{22}F_2N_2O_4$ found 441 (MH+).

Proceeding as in Example 1, but substituting 1H-imidazol-4-ylacetic acid hydrochloride and (S)-2-amino-3-(benzyloxy)-N-(3-phenoxyphenyl)propanamide, gave Compound 243, (S)-2-(2-(1H-imidazol-4-yl)acetamido)-3-(benzyloxy)-N-(3-phenoxyphenyl)propanamide (100 mg, 21%); Major isomer: $^1$H-NMR (400 MHz, DMSO-D$_6$): σ 11.87 (br s, 1H), 10.28 (s, 1H), 8.42-8.41 (d, 1H), 7.54-7.43 (m, 10H), 7.18-7.14 (t, 1H), 7.05-7.03 (d, 2H), 6.95 (s, 1H), 6.75-6.67 (d, 1H), 4.69-4.62 (m, 1H), 4.49 (s, 1H), 3.69-3.60 (m, 2H), 3.51-3.40 (m, 2H). MS (EI) for $C_{27}H_{26}N_4O_4$. found 471.0 (MH+).

Proceeding as in Example 1, but substituting 3-methylbutanoic acid hydrochloride and (S)-2-amino-3-(benzyloxy)-N-(4-(4-fluorophenoxy)phenyl)propanamide, gave Compound 233, (S)—N-(3-(benzyloxy)-1-(4-(4-fluorophenoxy)phenylamino)-1-oxopropan-2-yl)-3-methylbutanamide (3 mg, 53.8%). MS (EI) for $C_{27}H_{29}FN_2O_4$. found 465.5 (MH+).

Proceeding as in Example 1, but substituting (E)-hex-3-enoic acid hydrochloride and (S)-2-amino-3-(benzyloxy)-N-(4-(4-fluorophenoxy)phenyl)propanamide, gave Compound 232, (S,E)-N-(3-(benzyloxy)-1-(4-(4-fluorophenoxy)phenylamino)-1-oxopropan-2-yl)hex-3-enamide (3 mg, 52.5%). MS (EI) for $C_{28}H_{29}FN_2O_4$. found 477.5 (MH+).

Proceeding as in Example 1, but substituting 2-(3-bromophenyl)acetic acid hydrochloride and (S)-2-amino-3-(benzyloxy)-N-(4-(4-fluorophenoxy)phenyl)propanamide, gave Compound 244, (S)-3-(benzyloxy)-2-(2-(3-bromophenyl)acetamido)-N-(4-(4-fluorophenoxy)phenyl)propanamide (3 mg, 43.3%). MS (EI) for $C_{30}H_{26}BrFN_2O_4$. found 578.4 (MH+).

Proceeding as in Example 1, but substituting 5-phenylpentanoic acid hydrochloride and (S)-2-amino-3-(benzyloxy)-N-(4-(4-fluorophenoxy)phenyl)propanamide, gave Compound 104, (S)—N-(3-(benzyloxy)-1-(4-(4-fluorophenoxy)phenylamino)-1-oxopropan-2-yl)-5-phenylpentanamide (3 mg, 46.2%).

Proceeding as in Example 1, but substituting 3-nitropropanoic acid hydrochloride and (S)-2-amino-3-(benzyloxy)-N-(4-(4-fluorophenoxy)phenyl)propanamide, gave Compound 245, (S)-3-(benzyloxy)-N-(4-(4-fluorophenoxy)phenyl)-2-(3-nitropropanamido)propanamide (3 mg, 46.2%). MS (EI) for $C_{25}H_{24}FN_3O_6$. found 482.5 (MH+).

Proceeding as in Example 1, but substituting 2-(pyridin-2-yl)acetic acid hydrochloride and (S)-2-amino-3-(benzyloxy)-N-(4-(4-fluorophenoxy)phenyl)propanamide, gave Compound 246, (S)-3-(benzyloxy)-N-(4-(4-fluorophenoxy)phenyl)-2-(2-(pyridin-2-yl)acetamido)propanamide (3 mg, 50%). MS (EI) for $C_{29}H_{26}FN_3O_4$. found 500.5 (MH+).

Proceeding as in Example 1, but substituting 2-(pyridin-3-yl)acetic acid hydrochloride and (S)-2-amino-3-(benzyloxy)-N-(4-(4-fluorophenoxy)phenyl)propanamide, gave Compound 247, (S)-3-(benzyloxy)-N-(4-(4-fluorophenoxy)phenyl)-2-(2-(pyridin-3-yl)acetamido)propanamide (3 mg, 50%). MS (EI) for $C_{29}H_{26}FN_3O_4$. found 500.5 (MH+).

Proceeding as in Example 1, but substituting 2-(3-fluoro-4-(trifluoromethyl)phenyl)acetic acid hydrochloride and (S)-2-amino-3-(benzyloxy)-N-(4-(4-fluorophenoxy)phenyl)propanamide, gave Compound 101, (S)-3-(benzyloxy)-2-(2-(3-fluoro-4-(trifluoromethyl)phenyl)acetamido)-N-(4-(4-fluorophenoxy)phenyl)propanamide (3 mg, 42.8%). MS (EI) for $C_{31}H_{25}F_5N_2O_4$. found 585.5 (MH+).

Proceeding as in Example 1, but substituting 2-(4-(trifluoromethoxy)phenyl)acetic acid hydrochloride and (S)-2-amino-3-(benzyloxy)-N-(4-(4-fluorophenoxy)phenyl)propanamide, gave Compound 102, (S)-3-(benzyloxy)-N-(4-(4-fluorophenoxy)phenyl)-2-(2-(3-(trifluoromethoxy)phenyl)acetamido)propanamide (3 mg, 42.9%). MS (EI) for $C_{31}H_{26}F_4N_2O_5$. found 583.5 (MH+).

Proceeding as in Example 1, but substituting (S)-3,7-dimethyloct-6-enoic acid hydrochloride and (S)-2-amino-3-(benzyloxy)-N-(4-(4-fluorophenoxy)phenyl)propanamide, gave Compound 248, (S)—N—((S)-3-(benzyloxy)-1-(4-(4-fluorophenoxy)phenylamino)-1-oxopropan-2-yl)-3,7-dimethyloct-6-enamide (3 mg, 46.9%). MS (EI) for $C_{32}H_{37}FN_2O_4$. found 533.7 (MH+).

Proceeding as in Example 1, but substituting (S)-2-(2-(tert-butoxycarbonyl)pyrrolidin-1-yl)acetic acid hydrochloride and (S)-2-amino-3-(benzyloxy)-N-(4-(4-fluorophenoxy)phenyl)propanamide, gave Compound 103, (S)-tert-butyl 1-(2-((S)-3-(benzyloxy)-1-(4-(4-fluorophenoxy)phenylamino)-1-oxopropan-2-ylamino)-2-oxoethyl)pyrrolidine-2-carboxylate (3 mg, 42.3%). MS (EI) for $C_{33}H_{38}FN_3O_6$. found 592.7 (MH+).

Proceeding as in Example 1, but substituting 3-(3-chloro-4-methoxyphenyl)propanoic acid hydrochloride and (S)-2-amino-3-(benzyloxy)-N-(4-(4-fluorophenoxy)phenyl)propanamide, gave Compound 81, (S)-3-(benzyloxy)-2-(3-(3- chloro-4-methoxyphenyl)propanamido)-N-(4-(4-fluorophenoxy)phenyl)propanamide (3 mg, 43.3%). MS (EI) for $C_{32}H_{30}ClFN_2O_5$. found 578.1 (MH+).

Proceeding as in Example 1, but substituting 2-phenylacetic acid hydrochloride and (S)-2-amino-3-(benzyloxy)-N-(4-(4-fluorophenoxy)phenyl)propanamide, gave Compound 249, (S)-3-(benzyloxy)-N-(4-(4-fluorophenoxy)phenyl)-2-(2-phenylacetamido)propanamide (3 mg, 50.1%). MS (EI) for $C_{30}H_{27}FN_2O_4$. found 499.6 (MH+).

Proceeding as in Example 1, but substituting 2-(3-methyl-1H-pyrazol-5-yl)acetic acid hydrochloride and (S)-2-amino-3-(benzyloxy)-N-(4-(4-fluorophenoxy)phenyl)propanamide, gave Compound 166, (S)-3-(benzyloxy)-N-(4-(4-fluorophenoxy)phenyl)-2-(2-(3-methyl-1H-pyrazol-5-yl)acetamido)propanamide (48 mg, 49%). $^1$H-NMR (400 MHz, DMSO-D$_6$): σ 12.07 (s, 1H), 10.18 (s, 1H), 8.38 (s, 1H), 7.65-7.58 (m, 2H), 7.35-7.17 (m, 6H), 7.06-6.95 (m, 4H), 5.86 (s, 1H), 4.73-4.64 (m, 1H), 4.52 (s, 2H), 3.66 (d, 2H), 3.46 (s, 2H), 2.15 (s, 3H). MS (EI) for $C_{28}H_{27}FN_4O_4$. found 503.0 (MH+).

Proceeding as in Example 1, but substituting 2-(1H-imidazol-4-yl)propanoic acid hydrochloride and (S)-2-amino-3-(benzyloxy)-N-(4-(4-fluorophenoxy)phenyl)propanamide, gave Compound 167, (2S)-2-(2-(1H-imidazol-4-yl)propanamido)-3-(benzyloxy)-N-(4-(4-fluorophenoxy)phenyl)propanamide (49 mg, 21%). $^1$H-NMR (400 MHz, CDCl$_3$): δ 9.80 (s, 1H), 9.46 (s, 1H), 9.38 (br s, 1H), 7.80-7.15 (m, 9H), 7.00-6.79 (m, 6H), 4.82-4.71 (m, 1H), 4.54-4.38 (m, 2H), 4.01-3.59 (m, 3H), 1.45-1.34 (m, 3H). MS (EI) for $C_{28}H_{27}FN_4O_4$ found 503 (MH+).

Proceeding as in Example 1, but substituting (S)-2-amino-3-(benzyloxy)-N-(4-(4-fluorophenoxy)-2-methylphenyl)propanamide, gave Compound 47, (S)-2-(2-(1H-imidazol-5-yl)acetamido)-3-(benzyloxy)-N-(4-(4-fluorophenoxy)-2-methylphenyl)propanamide (18 mg, 14%); Major isomer: $^1$H-NMR (400 MHz, DMSO-D$_6$): σ 10.19 (br s, 1H), 7.82 (br s, 1H), 7.63-7.60 (d, 2H), 7.32-7.25 (m, 5H), 7.23-7.17 (m, 2H), 7.04-6.97 (m, 4H), 6.68-6.63 (d, 1H), 4.61-4.55 (m, 1H), 4.54 (s, 2H), 3.76-3.63 (m, 4H), 2.21 (s, 3H), 2.06 (s, 3H). MS (EI) for $C_{28}H_{27}FN_4O_5$. found 519.0 (MH+).

Proceeding as in Example 1, but substituting (2S,4S)—N-(4-(4-fluorophenoxy)phenyl)-4-phenylpyrrolidine-2-carboxamide, gave Compound 251, (2S,4S)-1-(2-(1H-imidazol-5-yl)acetyl)-N-(4-(4-fluorophenoxy)phenyl)-4-phenylpyrrolidine-2-carboxamide (97 mg, 33%). Major isomer: $^1$H-NMR (400 MHz, DMSO-D$_6$): σ 11.90 (s, 1H), 10.19 (s, 1H), 7.70-7.58 (m, 3H), 7.39-7.16 (m, 8H), 7.07-6.93 (m, 5H), 4.65-4.58 (m, 1H), 4.09 (t, 1H), 3.75-3.44 (m, 4H), 2.41-2.22 (m, 2H). MS (EI) for $C_{28}H_{25}FN_4O_3$. found 484.9 (MH+).

Proceeding as in Example 1, but substituting (S)-2-amino-N-(4-(4-bromophenoxy)phenyl)-3-(4-fluorobenzyloxy)propanamide, gave Compound 168, (S)-2-(2-(1H-imidazol-5-yl)acetamido)-N-(4-(4-bromophenoxy)phenyl)-3-(4-fluorobenzyloxy)propanamide (150 mg, 70%). $^1$H-NMR (400 MHz, CDCl$_3$): δ 9.20 (s, 1H), 7.60-7.20 (m, 9H), 7.10-6.80 (m, 7H), 4.79-4.70 (m, 1H), 4.63 (m, 2H), 4.17-4.10 (m, 1H), 3.68-3.59 (m, 3H). MS (EI) for $C_{27}H_{24}BrFN_4O_4$ found 567 (MH+).

Proceeding as in Example 1, but substituting 2-(1H-1,2,4-triazol-1-yl)acetic acid hydrochloride and (2S,4R)-4-(benzyloxy)-N-(4-(4-fluorophenoxy)phenyl)pyrrolidine-2-carboxamide, gave Compound 252, (2S,4R)-1-(2-(1H-1,2,4-triazol-1-yl)acetyl)-4-(benzyloxy)-N-(4-(4-fluorophenoxy)phenyl)pyrrolidine-2-carboxamide (36 mg, 30%). Major isomer: $^1$H-NMR (400 MHz, DMSO-D$_6$): σ 10.14 (s, 1H), 8.44 (s, 1H), 7.95 (s, 1H), 7.58 (d, 2H), 7.41-7.28 (m, 5H), 7.19 (t, 2H), 7.06-6.92 (m, 4H), 5.27 (q, 2H), 4.58 (d, 2H), 4.49 (t, 1H), 4.40-4.34 (m, 1H), 3.90-3.75 (m, 2H) 2.42-2.22 (m, 1H), 2.11-2.01 (ml H). MS (EI) for $C_{28}H_{26}FN_5O_4$. found 516.0 (MH+).

Proceeding as in Example 1, but substituting 2-methyl-2-(1H-1,2,4-triazol-1-yl)propanoic acid hydrochloride and (S)-2-amino-3-(benzyloxy)-N-(4-(4-fluorophenoxy)phenyl)propanamide, gave Compound 255, (S)-3-(benzyloxy)-N-(4-(4-fluorophenoxy)phenyl)-2-(2-methyl-2-(1H-1,2,4-triazol-1-yl)propanamido)propanamide (93.3 mg, 36%). $^1$H-NMR (400 MHz, CDCl$_3$): δ 8.45 (s, 1H), 8.30 (s, 1H), 8.07 (s, 1H), 7.42 (d, 2H), 7.39-7.24 (m, 7H), 7.11 (d, 1H), 7.05-6.91 (m, 5H), 4.65-4.59 (m, 2H), 4.50 (d, 1H), 4.00 (dd, 1H), 3.58-3.52 (m, 1H), 1.92 (s, 3H), 1.90 (s, 3H). MS (EI) for $C_{28}H_{28}FN_5O_4$ found 518 (MH+).

Proceeding as in Example 1, but substituting 2-(3,5-dimethyl-1H-1,2,4-triazol-1-yl)acetic acid hydrochloride and (S)-2-amino-3-(benzyloxy)-N-(4-(4-fluorophenoxy)phenyl)propanamide, gave Compound 256, (S)-3-(benzyloxy)-2-(2-(3,5-dimethyl-1H-1,2,4-triazol-1-yl)acetamido)-N-(4-(4-fluorophenoxy)phenyl)propanamide (219 mg, 27%). $^1$H-NMR (400 MHz, CDCl$_3$): σ 8.38 (s, 1H), 7.40-7.16 (m, 7H), 7.05-6.92 (m, 5H), 4.74 (s, 2H), 4.70-4.64 (m, 3H), 4.55 (d, 1H), 4.02-3.97 (m, 1H), 3.62-3.56 (m, 1H), 2.44 (s, 3H), 2.33 (s, 3H). MS (EI) for $C_{28}H_{28}FN_5O_4$. found 518.0 (MH+).

Proceeding as in Example 1, but substituting 2-(1H-1,2,3-triazol-1-yl)acetic acid hydrochloride and (S)-2-amino-3-(benzyloxy)-N-(4-(4-fluorophenoxy)phenyl)propanamide, gave Compound 174, (S)-2-(2-(1H-1,2,3-triazol-1-yl)acetamido)-3-(benzyloxy)-N-(4-(4-fluorophenoxy)phenyl)propanamide (17.6 mg, 7%). $^1$H-NMR (400 MHz, CDCl$_3$): σ 8.37 (s, 1H), 7.80 (s, 1H), 7.74 (s, 1H), 7.38-7.29 (m, 6H), 7.02 (t, 2H), 6.96-6.91 (m, 4H), 6.85 (d, 1H), 5.19-5.11 (m, 2H), 4.70-4.65 (m, 1H), 4.64 (d, 1H), 4.55 (d, 1H), 3.98 (dd, 1H), 3.58 (t, 1H). MS (EI) for $C_{26}H_{24}FN_5O_4$. found 490.2 (MH+).

Proceeding as in Example 1, but substituting 2-(3,5-dimethyl-1H-pyrazol-4-yl)acetic acid hydrochloride and (S)-2-amino-3-(4-fluorobenzyloxy)-N-(4-(4-fluorophenoxy)phenyl)propanamide, gave Compound 258, (S)-2-(2-(3,5-dimethyl-1H-pyrazol-4-yl)acetamido)-3-(4-fluorobenzyloxy)-N-(4-(4-fluorophenoxy)phenyl)propanamide (70 mg, 50%). $^1$H-NMR (400 MHz, CDCl$_3$): δ 8.55 (s, 1H), 7.40-7.25 (m, 6H), 7.15-6.90 (m, 7H), 6.50 (m, 1H), 4.79-4.73 (m, 1H), 4.63 (m, 2H), 3.80-3.50 (m, 4H), 2.20 (s, 6H). MS (EI) for $C_{29}H_{28}F_2N_4O_4$ found 535 (MH+).

Proceeding as in Example 1, but substituting 2-(1H-1,2,4-triazol-1-yl)acetic acid hydrochloride and (S)-2-amino-N-(4-(4-fluorophenoxy)phenyl)-3-(2-(trifluoromethoxy)benzyloxy)propanamide, gave Compound 139, (S)-2-(2-(1H-1,2,4-triazol-1-yl)acetamido)-N-(4-(4-fluorophenoxy)phenyl)-3-(2-(trifluoromethoxy)benzyloxy)propanamide (170 mg, 65%). $^1$H-NMR (400 MHz, CDCl$_3$): δ 8.40 (s, 1H), 8.20 (s, 1H), 8.00 (s, 1H), 7.50-7.25 (m, 7H), 7.15-6.90 (m, 6H), 5.00 (s, 2H), 4.79-4.60 (m, 3H), 4.00 (m, 1H), 3.70-3.60 (m, 1H). MS (EI) for $C_{27}H_{23}F_4N_5O_5$ found 574 (MH+).

Proceeding as in Example 1, but substituting 2-(1H-benzo[d][1,2,3]triazol-1-yl)acetic acid hydrochloride and (2S,4R)-4-benzyl-N-(4-(4-fluorophenoxy)phenyl)pyrrolidine-2-carboxamide, gave Compound 176, (2S,4R)-1-(2-(1H-benzo[d][1,2,3]triazol-1-yl)acetyl)-4-benzyl-N-(4-(4-fluorophenoxy)phenyl)pyrrolidine-2-carboxamide (17 mg, 12%). Major isomer: $^1$H-NMR (400 MHz, DMSO-D$_6$): σ 9.95 (s, 1H), 8.04 (d, 1H), 7.77-7.64 (m, 1H), 7.59-7.49 (m, 3H), 7.44-7.12 (m, 8H), 7.07-6.90 (m, 4H), 5.80 (q, 2H), 4.56-4.48 (m, 1H), 4.02-3.93 (m, 1H), 3.55-3.46 (m, 1H), 2.85-2.69 (m, 3H), 2.08-1.94 (m, 2H). MS (EI) for $C_{32}H_{28}FN_5O_3$. found 549.9 (MH+).

Proceeding as in Example 1, but substituting 2-(5-methyl-1H-pyrazol-3-yl)acetic acid hydrochloride and (2S,4R)-4-benzyl-N-(4-(4-fluorophenoxy)phenyl)pyrrolidine-2-carboxamide, gave Compound 177, (2S,4R)-4-benzyl-N-(4-(4-fluorophenoxy)phenyl)-1-(2-(5-methyl-1H-pyrazol-3-yl)acetyl)pyrrolidine-2-carboxamide (42 mg, 45%). Major isomer: $^1$H-NMR (400 MHz, DMSO-D$_6$): σ 12.25 (s, 1H), 9.92 (s, 1H), 7.63-7.54 (m, 2H), 7.33-7.26 (m, 2H), 7.25-7.15 (m, 6H), 7.05-6.93 (m, 4H), 5.87 (s, 1H), 4.52-4.45 (m, 1H), 3.77-3.45 (m, 2H), 3.34-3.27 (m, 2H), 2.24-1.85 (m, 6H). MS (EI) for $C_{30}H_{29}FN_4O_3$. found 513.0 (MH+).

Proceeding as in Example 1, but substituting 2-(1H-1,2,4-triazol-1-yl)acetic acid hydrochloride and (2S,4R)-4-benzyl-N-(4-(4-fluorophenoxy)phenyl)pyrrolidine-2-carboxamide, gave Compound 140, (2S,4R)-1-(2-(1H-1,2,4-triazol-1-yl)acetyl)-4-benzyl-N-(4-(4-fluorophenoxy)phenyl)pyrrolidine-2-carboxamide (63 mg, 70%). Major isomer: $^1$H-NMR (400 MHz, DMSO-D$_6$): σ 9.99 (s, 1H), 8.43 (s, 1H), 7.95 (s, 1H), 7.55 (d, 2H), 7.36-7.15 (m, 8H), 7.05-6.91 (m, 4H), 5.23 (q, 2H), 4.54-4.47 (m, 1H), 3.84-3.79 (m, 1H), 2.78-2.63 (m, 3H), 2.02-1.87 (m, 2H). MS (EI) for $C_{28}H_{26}FN_5O_3$. found 500.0 (MH+).

Proceeding as in Example 1, but substituting 2-(1H-1,2,4-triazol-1-yl)acetic acid hydrochloride and (2S,4R)-4-(4-fluorobenzyl)-N-(4-(4-fluorophenoxy)phenyl)pyrrolidine-2-carboxamide, gave Compound 141, (2S,4R)-1-(2-(1H-1,2,4-triazol-1-yl)acetyl)-4-(4-fluorobenzyl)-N-(4-(4-fluorophenoxy)phenyl)pyrrolidine-2-carboxamide (39 mg, 33%). Major isomer: $^1$H-NMR (400 MHz, DMSO-D$_6$): σ 10.00 (s, 1H), 8.43 (s, 1H), 7.95 (s, 1H), 7.57 (d, 2H), 7.35-7.08 (m, 7H), 7.05-6.90 (m, 4H), 5.23 (q, 2H), 4.56-4.47 (m, 1H), 3.87-3.74 (m, 1H), 3.39-3.29 (m, 1H), 2.79-2.62 (m, 3H), 2.04-1.89 (m, 2H). MS (EI) for $C_{28}H_{25}F_2N_5O_3$. found 517.9 (MH+).

Proceeding as in Example 1, but substituting 2-(1H-1,2,4-triazol-1-yl)acetic acid hydrochloride and (S)-2-amino-3-(benzyloxy)-N-(4-(4-fluorophenylthio)phenyl)propanamide, gave Compound 178, (S)-2-(2-(1H-1,2,4-triazol-1-yl)acetamido)-3-(benzyloxy)-N-(4-(4-fluorophenylthio)phenyl)propanamide (100.1 mg, 18%). $^1$H-NMR (400 MHz, CDCl$_3$): δ 8.57 (s, 1H), 8.19 (s, 1H), 8.03 (s, 1H), 7.38-7.21 (m, 13H), 7.03-6.96 (m, 2H), 4.92 (s, 2H), 4.73-4.67 (m, 1H), 4.61 (d, 1H), 4.52 (d, 1H), 3.97-3.91 (dd, 1H), 3.57 (t, 1H). MS (EI) for $C_{26}H_{25}FN_5O_3S$ found 506 (MH+).

Proceeding as in Example 1, but substituting 2-(1H-1,2,4-triazol-1-yl)acetic acid hydrochloride and (2S,4R)-4-(2,4-dichlorobenzyl)-N-(4-(4-fluorophenoxy)phenyl)pyrrolidine-2-carboxamide, gave Compound 180, (2S,4R)-1-(2-(1H-1,2,4-triazol-1-yl)acetyl)-4-(2,4-dichlorobenzyl)-N-(4-(4-fluorophenoxy)phenyl)pyrrolidine-2-carboxamide (48 mg, 35%). Major isomer: $^1$H-NMR (400 MHz, DMSO-D$_6$): σ 10.03 (s, 1H), 8.43 (s, 1H), 7.96 (s, 1H), 7.68-7.35 (m, 5H), 7.19 (t, 2H), 7.07-6.88 (m, 4H), 5.24 (q, 2H), 4.57-4.48 (m, 1H), 3.91-3.78 (m, 1H), 2.97-2.70 (m, 3H), 2.11-1.88 (m, 3H). MS (EI) for $C_{28}H_{24}FN_5O_3$. found 569.8 (MH+).

Proceeding as in Example 1, but substituting 2-(1H-1,2,4-triazol-1-yl)acetic acid hydrochloride and (S)-2-amino-3-(2-chlorobenzyloxy)-N-(4-(4-fluorophenoxy)phenyl)propanamide, gave Compound 181, (S)-2-(2-(1H-1,2,4-triazol-1-yl)acetamido)-3-(2-chlorobenzyloxy)-N-(4-(4-fluorophenoxy)phenyl)propanamide (100 mg, 50%). $^1$H-NMR (400 MHz, CDCl$_3$): δ 8.40 (s, 1H), 8.20 (s, 1H), 8.00 (s, 1H), 7.50-7.25 (m, 7H), 7.15-6.90 (m, 6H), 5.00 (s, 2H), 4.79-4.60 (m, 3H), 4.00 (m, 1H), 3.70-3.60 (m, 1H). MS (EI) for $C_{26}H_{23}ClFN_5O_4$ found 524 (MH+).

Proceeding as in Example 1, but substituting 2-(1H-1,2,4-triazol-1-yl)acetic acid hydrochloride and (2S,4R)-4-benzylpyrrolidin-2-yl)-5-(4-fluorophenoxy)-1H-benzo[d]imidazole, gave Compound 12, 1-((2S,4R)-4-benzyl-2-(5-(4-fluorophenoxy)-1H-benzo[d]imidazol-2-yl)pyrrolidin-1-yl)-2-(1H-1,2,4-triazol-1-yl)ethanone (133.3 mg, 56%). Major isomer: $^1$H-NMR (400 MHz, CDCl$_3$): δ 10.28 (br s, 1H), 8.21 (s, 1H), 7.99 (s, 1H), 7.35-7.20 (m, 7H), 7.03-6.91 (m, 5H), 5.45 (d, 1H), 5.00 (d, 1H), 4.89 (d, 1H), 3.57 (t, 1H), 3.32-3.11 (m, 4H), 2.65 (dd, 1H), 2.06-1.96 (m, 1H). MS (EI) for $C_{28}H_{25}FN_6O_2$ found 497 (MH+).

Proceeding as in Example 1, but substituting 2-(1H-1,2,4-triazol-1-yl)acetic acid hydrochloride and (2S,4R)-4-benzyl-N-(4-(4-chlorophenoxy)phenyl)pyrrolidine-2-carboxamide, gave Compound 79, (2S,4R)-1-(2-(1H-1,2,4-triazol-1-yl)acetyl)-4-benzyl-N-(4-(4-chlorophenoxy)phenyl)pyrrolidine-2-carboxamide (187 mg, 37%). $^1$H-NMR (400 MHz, CDCl$_3$): σ 9.04 (s, 1H), 8.24 (s, 1H), 7.99 (s, 1H), 7.43 (d, 2H), 7.31 (d, 2H), 7.27-7.18 (m, 4H), 6.93 (d, 2H), 6.88 (d, 2H), 5.03 (d, 1H), 4.95 (d, 1H), 4.81 (d, 1H), 3.63 (dd, 1H), 3.25 (dd, 1H), 3.05-2.90 (m, 3H), 2.70-2.63 (m, 2H). MS (EI) for $C_{28}H_{26}ClN_5O_3$. found 515.9 (MH+).

Proceeding as in Example 1, but substituting 2-(1H-1,2,4-triazol-1-yl)acetic acid hydrochloride and (2S,4S)—N-(4-(4-fluorophenoxy)phenyl)-4-phenylpyrrolidine-2-carboxamide, gave Compound 78, (2S,4S)-1-(2-(1H-1,2,4-triazol-1-yl)acetyl)-N-(4-(4-fluorophenoxy)phenyl)-4-phenylpyrrolidine-2-carboxamide (187 mg, 68%). $^1$H-NMR (400 MHz, CDCl$_3$): σ 9.08 (s, 1H), 8.27 (s, 1H), 8.01 (s, 1H), 7.46 (d, 2H), 7.40-7.37 (m, 2H), 7.33-7.29 (m, 2H), 7.04-6.99 (m, 2H), 6.96-6.92 (m, 4H), 5.04 (d, 2H), 4.96 (d, 1H), 4.06 (t, 1H), 3.96-3.86 (m, 1H), 3.61 (t, 1H), 2.90 (dd, 1H), 2.20-2.11 (m, 1H). MS (EI) for $C_{27}H_{24}FN_5O_3$. found 486.2 (MH+).

Proceeding as in Example 1, but substituting 2-(2H-1,2,3-triazol-2-yl)acetic acid hydrochloride and (2S,4S)—N-(4-(4-fluorophenoxy)phenyl)-4-phenylpyrrolidine-2-carboxamide, gave Compound 77, (2S,4S)-1-(2-(2H-1,2,3-triazol-2-yl)acetyl)-N-(4-(4-fluorophenoxy)phenyl)-4-phenylpyrrolidine-2-carboxamide (170 mg, 62%). $^1$H-NMR (400 MHz, CDCl$_3$): σ 9.21 (s, 1H), 7.74 (s, 2H), 7.48 (d, 2H), 7.40-7.36 (m, 2H), 7.32-7.29 (m, 3H), 7.04-6.99 (m, 2H), 6.96-6.92 (m, 4H), 5.35 (s, 2H), 5.00 (d, 1H), 3.93 (t, 1H), 3.89-3.80 (m, 1H), 3.54 (t, 1H), 2.91 (dd, 1H), 2.18-2.09 (m, 1H). MS (EI) for $C_{27}H_{24}FN_5O_3$. found 486.1 (MH+).

Proceeding as in Example 1, but substituting 2-(2H-1,2,3-triazol-2-yl)acetic acid hydrochloride and (2S,4R)-4-benzyl-N-(4-(4-fluorophenoxy)phenyl)pyrrolidine-2-carboxamide, gave Compound 58, (2S,4R)-1-(2-(2H-1,2,3-triazol-2-yl)acetyl)-4-benzyl-N-(4-(4-fluorophenoxy)phenyl)pyrrolidine-2-carboxamide (120 mg, 43%). Major isomer: $^1$H-NMR (400 MHz, DMSO-D$_6$): σ 9.95 (s, 1H), 7.73 (s, 2H), 7.57-7.49 (m, 2H), 7.34-7.12 (m, 4H), 7.03-6.89 (m, 4H), 5.46 (q, 2H), 4.51-4.44 (m, 1H), 3.85-3.76 (m, 1H), 2.77-2.60 (m, 3H), 2.17-1.85 (m, 3H). MS (EI) for $C_{28}H_{26}FN_5O_3$. found 500.0 (MH+).

Proceeding as in Example 1, but substituting 2-(5-amino-3-(trifluoromethyl)-1H-1,2,4-triazol-1-yl)acetic acid hydrochloride and (2S,4R)-4-benzyl-N-(4-(4-fluorophenoxy)phenyl)pyrrolidine-2-carboxamide, gave Compound 11, (2S,4R)-1-(2-(5-amino-3-(trifluoromethyl)-1H-1,2,4-triazol-1-yl)acetyl)-4-benzyl-N-(4-(4-fluorophenoxy)phenyl)pyrrolidine-2-carboxamide (100.1 mg, 51%). Major isomer: $^1$H-NMR (400 MHz, CDCl$_3$): δ 8.90 (s, 1H), 7.37-7.14 (m, 7H), 7.02-6.81 (m, 6H), 5.43 (s, 2H), 4.82 (d, 1H), 4.73 (d, 1H), 4.65 (d, 1H), 3.71 (t, 1H), 3.24 (t, 1H), 3.02-2.90 (m, 1H), 2.80 (dd, 1H), 2.65 (dd, 1H), 2.38 (dd, 1H), 1.99 (br s, 2H), 1.81-1.71 (m, 1H). MS (EI) for $C_{29}H_{27}F_4N_6O_3$ found 583 (MH+).

Proceeding as in Example 1, but substituting 2-(1H-1,2,4-triazol-1-yl)acetic acid hydrochloride and (2S,4R)-4-(2-chlorobenzyl)-N-(4-(4-fluorophenoxy)phenyl)pyrrolidine-2-carboxamide, gave Compound 57, (2S,4R)-1-(2-(1H-1,2,4-triazol-1-yl)acetyl)-4-(2-chlorobenzyl)-N-(4-(4-fluorophenoxy)phenyl)pyrrolidine-2-carboxamide (71 mg, 55%). Major isomer: $^1$H-NMR (400 MHz, DMSO-D$_6$): σ 10.03 (s, 1H), 8.44 (s, 1H), 7.96 (s, 1H), 7.59-7.52 (m, 2H), 7.49-7.15 (m, 6H), 7.05-6.90 (m, 4H), 5.25 (q, 2H), 4.60-4.49 (m, 1H), 3.92-3.79 (m, 1H), 2.97-2.73 (m, 3H), 2.30-1.88 (m, 2H). MS (EI) for $C_{28}H_{25}FN_5O_3$. found 533.9 (MH+).

Proceeding as in Example 1, but substituting 2-(1H-1,2,3-triazol-1-yl)acetic acid hydrochloride and (2S,4R)-4-(4-fluorobenzyl)-N-(4-(4-fluorophenoxy)phenyl)pyrrolidine-2-carboxamide, gave Compound 10, (2S,4R)-1-(2-(1H-1,2,3-triazol-1-yl)acetyl)-4-benzyl-N-(4-(4-fluorophenoxy)phenyl)pyrrolidine-2-carboxamide (75.2 mg, 44%). Major isomer: $^1$H-NMR (400 MHz, CDCl$_3$): δ 9.00 (s, 1H), 7.74 (d, 2H), 7.42-7.17 (m, 7H), 7.03-6.83 (m, 6H), 5.28 (d, 1H), 5.12 (d, 1H), 4.73 (d, 1H), 3.71-64 (m, 1H), 3.31-3.22 (m, 1H), 3.006-2.93 (m, 1H), 2.89 (dd, 1H), 2.71-2.64 (m, 1H), 2.52 (dd, 1H), 1.79-1.70 (m, 1H). MS (EI) for $C_{28}H_{27}FN_5O_3$ found 500 (MH+).

Proceeding as in Example 1, but substituting 2-(2H-1,2,3-triazol-2-yl)acetic acid hydrochloride and (2S,4R)-4-(2-chlorobenzyl)-N-(4-(4-fluorophenoxy)phenyl)pyrrolidine-2-carboxamide, gave Compound 56, (2S,4R)-1-(2-(2H-1,2,3-triazol-2-yl)acetyl)-4-(2-chlorobenzyl)-N-(4-(4-fluorophenoxy)phenyl)pyrrolidine-2-carboxamide (70 mg, 55%). Major isomer: $^1$H-NMR (400 MHz, DMSO-D$_6$): σ 10.00 (s, 1H), 7.80 (s, 2H), 7.58-7.51 (m, 2H), 7.48-7.39 (m, 2H), 7.35-7.25 (m, 2H), 7.23-7.15 (m, 2H), 7.06-6.91, (m, 4H), 5.50 (q, 2H), 4.56-4.48 (m, 1H), 3.92-3.81 (m, 1H), 3.44-3.36 (m, 1H), 2.94-2.73 (m, 3H), 2.28-1.86 (m, 2H). MS (EI) for $C_{28}H_{25}ClFN_5O_3$. found 533.9 (MH+).

Proceeding as in Example 1, but substituting 2-(1H-1,2,4-triazol-1-yl)acetic acid hydrochloride and (2S,4R)—N-(4-(4-fluorophenoxy)phenyl)-4-(2-methylbenzyl)pyrrolidine-2-carboxamide, gave Compound 55, (2S,4R)-1-(2-(1H-1,2,4-triazol-1-yl)acetyl)-N-(4-(4-fluorophenoxy)phenyl)-4-(2-methylbenzyl)pyrrolidine-2-carboxamide (36 mg, 28%). Major isomer: $^1$H-NMR (400 MHz, DMSO-D$_6$): σ 10.00 (s, 1H), 8.43 (s, 1H), 7.96 (s, 1H), 7.55 (d, 2H), 7.26-7.08 (m, 6H), 7.05-6.91 (m, 4H), 5.24 (q, 2H), 4.56-4.49 (m, 1H), 3.88-3.80 (m, 1H), 2.82-2.64 (m, 3H), 2.30 (s, 3H), 2.28-1.89 (m, 2H). MS (EI) for $C_{29}H_{28}FN_5O_3$. found 514.0 (MH+).

Proceeding as in Example 1, but substituting 2-(1H-1,2,4-triazol-1-yl)acetic acid hydrochloride and (2S,4R)—N-(4-(4-fluoro-2-methylphenoxy)phenyl)-4-(4-fluorobenzyl)pyrrolidine-2-carboxamide, gave Compound 74, (2S,4R)-1-(2-(1H-1,2,4-triazol-1-yl)acetyl)-N-(4-(4-fluoro-2-methylphenoxy)phenyl)-4-(4-fluorobenzyl)pyrrolidine-2-carboxamide (189 mg, 42%). $^1$H-NMR (400 MHz, CDCl$_3$): σ 8.96 (s,1H), 8.23 (s, 1H), 7.99 (s, 1H), 7.37 (d, 2H), 7.17-7.14 (m, 2H), 7.01 (t, 2H), 6.96-6.93 (m, 1H), 6.83-6.76 (m, 4H), 5.02 (d, 1H), 4.95 (d, 1H), 4.80 (d, 1H), 3.63 (t, 1H), 3.23 (t, 1H), 3.03-2.86 (m, 2H), 2.69-2.60 (m, 2H), 2.18 (s, 3H), 1.72-1.57 (m, 1H). MS (EI) for $C_{29}H_{27}F_2N_5O_3$. found 532.2 (MH+).

Proceeding as in Example 1, but substituting 2-(1H-1,2,4-triazol-1-yl)acetic acid hydrochloride and (2S,4R)—N-(4-(4-fluoro-3-methylphenoxy)phenyl)-4-(4-fluorobenzyl)pyrrolidine-2-carboxamide, gave Compound 73, (2S,4R)-1-(2-(1H-1,2,4-triazol-1-yl)acetyl)-N-(4-(4-fluoro-3-methylphenoxy)phenyl)-4-(4-fluorobenzyl)pyrrolidine-2-carboxamide (149 mg, 84%). $^1$H-NMR (400 MHz, CDCl$_3$): σ 8.90 (s, 1H), 8.24 (s, 1H), 7.99 (s, 1H), 7.40 (d, 2H), 7.17-7.14 (m, 2H), 7.00 (t, 2H), 6.95-6.88 (m, 3H), 6.79-6.72 (m, 2H), 5.03 (d, 1H), 4.95 (d, 1H), 4.80 (d, 1H), 3.64 (t, 1H), 3.23 (t, 1H), 3.05-2.85 (2H), 2.69-2.61 (m, 2H), 2.22 (s, 3H), 1.72-1.67 (m, 1H). MS (EI) for $C_{29}H_{27}F_2N_5O_3$. found 530.2 (MH−).

Proceeding as in Example 1, but substituting 2-(1H-1,2,4-triazol-1-yl)acetic acid hydrochloride and (2S,4S)—N-(4-(4-fluorophenoxy)phenyl)-4-(4-methoxyphenyl)pyrrolidine-2-carboxamide, gave Compound 62, (2S,4S)-1-(2-(1H-1,2,4-triazol-1-yl)acetyl)-N-(4-(4-fluorophenoxy)phenyl)-4-(4-methoxyphenyl)pyrrolidine-2-carboxamide (7 mg, 30%). $^1$H-NMR (400 MHz, CDCl$_3$): δ 8.35 (s, 1H), 8.00 (s, 1H), 7.40-7.20 (m, 6H), 6.90-6.80 (m, 7H), 5.00 (dd, 2H), 4.20 (m, 2H), 3.80 (m, 1H), 3.7 (s, 3H), 3.20 (m, 1H), 3.20-3.00 (m, 2H). MS (EI) for $C_{28}H_{26}FN_5O_4$ found 516 (MH+).

Proceeding as in Example 1, but substituting 2-(1H-1,2,4-triazol-1-yl)acetic acid hydrochloride and (2S,4R)—N-(4-(4-fluorophenoxy)phenyl)-4-(2-(trifluoromethyl)benzyl)pyrrolidine-2-carboxamide, gave Compound 54, (2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide. Major isomer: $^1$H-NMR (400 MHz, DMSO-D$_6$): σ 10.02 (s, 1H), 8.43 (s, 1H), 7.96 (s, 1H), 7.75-7.42 (m, 6H), 7.24-7.15 (m, 2H), 7.03-6.91 (m, 4H), 5.25 (q, 2H), 4.56-4.50 (m, 1H), 3.91-3.84 (m, 1H), 3.39 (t, 1H), 2.99-2.71 (m, 3H), 2.29-1.88 (m, 2H). MS (EI) for $C_{29}H_{25}F_4N_5O_3$. found 567.9 (MH+).

Proceeding as in Example 1, but substituting 2-cyanoacetic acid hydrochloride and (2S,4R)-4-benzyl-N-(4-(4-fluorophenoxy)phenyl)pyrrolidine-2-carboxamide, gave Compound 129, (2S,4R)-4-benzyl-1-(2-cyanoacetyl)-N-(4-(4-fluorophenoxy)phenyl)pyrrolidine-2-carboxamide (6.4 mg, 23.3%); Major isomer: $^1$H-NMR (400 MHz, DMSO-D$_6$): σ 9.99 (s, 1H), 7.55-7.60 (m, 2H), 7.29-7.32 (m, 2H), 7.17-7.23 (m, 5H), 6.95-7.02 (m, 4H), 4.49 (m, 1H), 4.00 (m, 2H), 3.64 (m, 1H), 3.22 (m, 2H), 3.67 (m, 3H), 1.93 (m, 2H). MS (EI) for $C_{27}H_{24}FN_3O_3$. found 458.5 (MH+).

Proceeding as in Example 1, but substituting 4-methoxy-4-oxobutanoic acid hydrochloride and (2S,4R)-4-benzyl-N-(4-(4-fluorophenoxy)phenyl)pyrrolidine-2-carboxamide, gave Compound 125, methyl 4-((2S,4R)-4-benzyl-2-(4-(4-fluorophenoxy)phenylcarbamoyl)pyrrolidin-1-yl)-4-oxobutanoate (8.3 mg, 27.4%); Major isomer: $^1$H-NMR (400 MHz, DMSO-D$_6$): σ 9.90 (s, 1H), 7.54-7.60 (m, 2H), 7.28-7.32 (m, 2H), 7.16-7.24 (m, 5H), 6.93-7.02 (m, 4H), 4.45 (m, 1H), 3.64-3.68 (m, 1H), 3.57 (s, 3H), 3.10-3.11 (m, 1H), 2.66 (m, 2H), 2.54 (m, 2H), 2.47 (m, 2H), 19.2 (m, 2H). MS (EI) for $C_{29}H_{29}FN_2O_5$. found 505.5 (MH+).

Proceeding as in Example 1, but substituting 4-oxo-4-phenylbutanoic acid hydrochloride and (2S,4R)-4-benzyl-N-(4-(4-fluorophenoxy)phenyl)pyrrolidine-2-carboxamide, gave Compound 124, (2S,4R)-4-benzyl-N-(4-(4-fluorophenoxy)phenyl)-1-(4-oxo-4-phenylbutanoyl)pyrrolidine-2-carboxamide (13.1 mg, 39.7%); Major isomer: $^1$H-NMR (400 MHz, DMSO-D$_6$): σ 9.87 (s, 1H), 7.94-7.99 (m, 2H), 7.60-7.605 (m, 2H), 7.50-7.56 (m, 3H), 7.30-7.34 (m, 2H), 7.17-7.23 (m, 5H), 6.95-7.02 (m, 4H), 4.46 (m, 1H), 3.73 (m, 1H), 3.28 (m, 4H), 3.13 (m, 1H), 2.66 (m, 3H), 1.93 (m, 2H). MS (EI) for $C_{34}H_{31}FN_2O_4$. found 551.6 (MH+).

Proceeding as in Example 1, but substituting 4-oxopentanoic acid hydrochloride and (2S,4R)-4-benzyl-N-(4-(4-fluorophenoxy)phenyl)pyrrolidine-2-carboxamide, gave Compound 123, (2S,4R)-4-benzyl-N-(4-(4-fluorophenoxy)phenyl)-1-(4-oxopentanoyl)pyrrolidine-2-carboxamide (2.2 mg, 7.5%); Major isomer: $^1$H-NMR (400 MHz, DMSO-D$_6$): σ 9.88 (s, 1H), 7.55-7.60 (m, 2H), 7.29-7.32 (m, 2H), 7.17-7.23 (m, 5H), 6.95-7.02 (m, 4H), 4.45 (m, 1H), 3.65 (m, 1H), 3.25 (m, 1H), 2.60-2.69 (m, 3H), 2.57-2.59 (m, 2H), 2.44-2.53 (m, 2H), 2.45 (s, 3H), 1.92 (m, 2H). MS (EI) for C$_{29}$H$_{29}$FN$_2$O$_4$. found 489.5 (MH+).

Proceeding as in Example 1, but substituting 2-methoxyacetic acid hydrochloride and (2S,4R)-4-benzyl-N-(4-(4-fluorophenoxy)phenyl)pyrrolidine-2-carboxamide, gave Compound 122, (2S,4R)-4-benzyl-N-(4-(4-fluorophenoxy) phenyl)-1-(2-methoxyacetyl)pyrrolidine-2-carboxamide (12 mg, 43.2%); Major isomer: $^1$H-NMR (400 MHz, DMSO-D$_6$): σ 9.97 (s, 1H), 7.56-7.59 (m, 2H), 7.28-7.32 (m, 2H), 7.17-7.23 (m, 5H), 6.94-7.02 (m, 4H), 4.50 (m, 1H), 4.04 (m, 1H), 3.60 (m, 1H), 3.28 (s. 3H), 3.18 (m, 2H), 2.65 (m, 3H), 1.90 (m, 2H). MS (EI) for C$_{27}$H$_{27}$FN$_2$O$_4$. found 463.5 (MH+).

Proceeding as in Example 1, but substituting 2-ethoxyacetic acid hydrochloride and (2S,4R)-4-benzyl-N-(4-(4-fluorophenoxy)phenyl)pyrrolidine-2-carboxamide, gave Compound 121, (2S,4R)-4-benzyl-1-(2-ethoxyacetyl)-N-(4-(4-fluorophenoxy)phenyl)pyrrolidine-2-carboxamide (9.4 mg, 32.9%); Major isomer: $^1$H-NMR (400 MHz, DMSO-D$_6$): σ 9.99 (s, 1H), 7.55-7.60 (m, 2H), 7.29-7.32 (m, 2H), 7.17-7.23 (m, 5H), 6.95-7.02 (m, 4H), 4.47 (m, 1H), 4.06 (d, 2H), 3.60-3.64 (m, 1H), 3.47-3.53 (m, 2H), 3.18-3.22 (m, 1H), 2.50-2.89 (m, 3H), 1.90 (m, 2H), 1.08 (m, 3H). MS (EI) for C$_{28}$H$_{29}$FN$_2$O$_4$. found 477.5 (MH+).

Proceeding as in Example 1, but substituting 2-hydroxyacetic acid hydrochloride and (2S,4R)-4-benzyl-N-(4-(4-fluorophenoxy)phenyl)pyrrolidine-2-carboxamide, gave Compound 120, (2S,4R)-4-benzyl-N-(4-(4-fluorophenoxy) phenyl)-1-(2-hydroxyacetyl)pyrrolidine-2-carboxamide (9.1 mg, 33.8%); Major isomer: $^1$H-NMR (400 MHz, DMSO-D$_6$): σ 9.97 (s, 1H), 7.55-7.59 (m, 2H), 7.28-7.32 (m, 2H), 7.17-7.23 (m, 5H), 6.94-7.02 (m, 4H), 4.50-4.52 (m, 1H), 4.02 (s, 2H), 3.50-3.59 (m, 1H), 3.15 (m, 1H), 2.63-2.73 (m, 3H), 1.89-1.93 (m, 2H). MS (EI) for C$_{26}$H$_{25}$FN$_2$O$_4$. found 449.4 (MH+).

Proceeding as in Example 1, but substituting 2-(2,6-dichlorophenyl)acetic acid hydrochloride and (2S,4R)-4-benzyl-N-(4-(4-fluorophenoxy)phenyl)pyrrolidine-2-carboxamide, gave Compound 119, (2S,4R)-4-benzyl-1-(2-(2,6-dichlorophenyl)acetyl)-N-(4-(4-fluorophenoxy)phenyl)pyrrolidine-2-carboxamide (12.1 mg, 34.9%); Major isomer: $^1$H-NMR (400 MHz, DMSO-D$_6$): a 9.92 (s, 1H), 7.54-7.60 (m, 2H), 7.44 (d, 2H), 7.25-7.34 (m, 5H), 7.15-7.24 (m, 3H), 6.93-7.03 (m, 4H), 4.48-4.51 (m, 1H), 3.95 (m, 2H), 3.50-3.59 (m, 1H), 3.15 (m, 1H), 2.63-2.73 (m, 3H), 1.89-1.93 (m, 2H). MS (EI) for C$_{32}$H$_{27}$C$_{12}$FN$_2$O$_3$. found 578.4 (MH+).

Proceeding as in Example 1, but substituting 3-hydroxybutanoic acid hydrochloride and (2S,4R)-4-benzyl-N-(4-(4-fluorophenoxy)phenyl)pyrrolidine-2-carboxamide, gave Compound 118, (2S,4R)-4-benzyl-N-(4-(4-fluorophenoxy) phenyl)-1-(3-hydroxybutanoyl)pyrrolidine-2-carboxamide (8.5 mg, 29.7%); Major isomer: $^1$H-NMR (400 MHz, DMSO-D$_6$): σ 9.93 (s, 1H), 7.55-7.60 (m, 2H), 7.28-7.35 (m, 2H), 7.17-7.24 (m, 5H), 6.94-7.02 (m, 4H), 4.67 (m, 1H), 4.47-4.50 (m, 1H), 3.90 (m, 1H), 3.68-3.70 (m, 1H), 3.25-3.30 (m, 1H), 2.63-2.73 (m, 3H), 2.35-2.47 (m, 1H), 2.70-2.30 (m, 1H), 1.86-1.96 (m, 2H), 1.01-1.13 (m, 3H). MS (EI) for C$_{28}$H$_{29}$FN$_2$O$_4$. found 477.5 (MH+).

Proceeding as in Example 1, but substituting 2-(thien-2-yl) acetic acid hydrochloride and (2S,4R)-4-benzyl-N-(4-(4-fluorophenoxy)phenyl)pyrrolidine-2-carboxamide, gave Compound 117, (2S,4R)-4-benzyl-N-(4-(4-fluorophenoxy) phenyl)-1-(2-(thien-2-yl)acetyl)pyrrolidine-2-carboxamide (12.3 mg, 39.8%); Major isomer: $^1$H-NMR (400 MHz, DMSO-D$_6$): σ 10.34 (s, 1H), 7.55-7.60 (m, 2H), 7.37-7.39 (m, 2H), 7.28-7.32 (m, 2H), 7.17-7.23 (m, 5H), 6.94-7.03 (m, 6H), 4.48-4.51 (m, 1H), 3.90 (d, 2H), 3.75-3.80 (m 1H), 3.56 (m, 1H), 2.63-2.73 (m, 3H), 1.88-1.97 (m, 2H). MS (EI) for C$_{30}$H$_{27}$FN$_2$O$_3$S. found 515.6 (MH+).

Proceeding as in Example 1, but substituting 2-(4-oxo-2-thioxothiazolidin-3-yl)acetic acid hydrochloride and (2S, 4R)-4-benzyl-N-(4-(4-fluorophenoxy)phenyl)pyrrolidine-2-carboxamide, gave Compound 99, (2S,4R)-4-benzyl-N-(4-(4-fluorophenoxy)phenyl)-1-(2-(4-oxo-2-thioxothiazolidin-3-yl)acetyl)pyrrolidine-2-carboxamide (13.5 mg, 39.9%). Major isomer: $^1$H-NMR (400 MHz, DMSO-D$_6$): σ 9.92 (s, 1H), 7.51 (d, 2H), 7.30-7.16 (m, 9H), 6.93 (m, 2H), 4.76 (m, 1H), 4.60 (m, 1H), 4.43 (m, 1H), 4.35 (m, 2H), 2.87 (s, 2H), 2.68 (m, 3H), 1.95 (m, 2H). MS (EI) for C$_{29}$H$_{26}$FN$_3$O$_4$S$_2$. found 564.7 (MH+).

Proceeding as in Example 1, but substituting 2-(1H-indol-3-yl)acetic acid hydrochloride and (2S,4R)-4-benzyl-N-(4-(4-fluorophenoxy)phenyl)pyrrolidine-2-carboxamide, gave Compound 98, (2S,4R)-1-(2-(1H-indol-3-yl)acetyl)-4-benzyl-N-(4-(4-fluorophenoxy)phenyl)pyrrolidine-2-carboxamide (12.9 mg, 39.3%). Major isomer: $^1$H-NMR (400 MHz, DMSO-D$_6$): σ 10.91 (s, 1H), 9.99 (s, 1H), 7.56 (m, 3H), 7.35-7.07 (m, 10H), 7.01-6.94 (m, 5H), 4.50 (m, 1H), 3.75 (m, 2H), 3.69 (s, 2H), 2.61 (m, 3H), 1.90 (m, 2H). MS (EI) for C$_{34}$H$_{30}$FN$_3$O$_3$. found 548.6 (MH+).

Proceeding as in Example 1, but substituting 2-(1,3-dioxo-2,3-dihydro-1H-inden-2-yl)acetic acid hydrochloride and (2S,4R)-4-benzyl-N-(4-(4-fluorophenoxy)phenyl)pyrrolidine-2-carboxamide, gave Compound 97, (2S,4R)-4-benzyl-1-(2-(1,3-dioxo-2,3-dihydro-1H-inden-2-yl)acetyl)-N-(4-(4-fluorophenoxy)phenyl)pyrrolidine-2-carboxamide (13.9 mg, 40.1%). Major isomer: $^1$H-NMR (400 MHz, DMSO-D$_6$): σ 9.94 (s, 1H), 7.86 (m, 4H), 7.51 (d, 2H), 7.31-7.13 (m, 9H), 6.91 (m, 2H), 4.52 (d, 1H), 4.47-4.40 (m, 2H), 3.84 (m, 1H), 3.39 (m, 1H), 2.67 (m, 3H), 1.94 (m, 2H). MS (EI) for C$_{34}$H$_{28}$FN$_3$O$_5$. found 578.6 (MH+).

Proceeding as in Example 1, but substituting 2-(pyridin-4-ylthio)acetic acid hydrochloride and (2S,4R)-4-benzyl-N-(4-(4-fluorophenoxy)phenyl)pyrrolidine-2-carboxamide, gave Compound 96, (2S,4R)-4-benzyl-N-(4-(4-fluorophenoxy) phenyl)-1-(2-(pyridin-4-ylthio)acetyl)pyrrolidine-2-carboxamide (4 mg, 12.3%). Major isomer: $^1$H-NMR (400 MHz, DMSO-D$_6$): σ 9.97 (s, 1H), 8.34 (d, 2H), 7.55 (m, 2H), 7.33-7.28 (m, 5H), 7.25-7.18 (m, 6H), 6.95 (m, 2H), 4.49 (m, 1H), 4.14 (m, 2H), 3.86 (m, 1H), 3.56 (m, 1H), 2.69 (m, 3H), 1.95 (m, 2H). MS (EI) for C$_{31}$H$_{28}$FN$_3$O$_3$S. found 542.6 (MH+).

Proceeding as in Example 1, but substituting 2-(2,6-difluorophenyl)acetic acid hydrochloride and (2S,4R)-4-benzyl-N-(4-(4-fluorophenoxy)phenyl)pyrrolidine-2-carboxamide, gave Compound 95, (2S,4R)-4-benzyl-1-(2-(2,6-difluorophenyl)acetyl)-N-(4-(4-fluorophenoxy)phenyl)pyrrolidine-2-carboxamide (12.3 mg, 37.6%). Major isomer: $^1$H-NMR (400 MHz, DMSO-D$_6$): a 9.92 (s, 1H), 7.53 (m, 3H), 7.28 (m, 3H), 7.24-7.14 (m, 6H), 6.97-6.91 (m, 4H), 4.46 (m, 1H), 3.82 (m, 1H), 3.70 (m, 2H), 3.37 (m, 1H), 2.70 (m, 3H), 1.19 (m, 2H). MS (EI) for C$_{32}$H$_{27}$F$_3$N$_2$O$_3$. found 545.6 (MH+).

Proceeding as in Example 1, but substituting 2-(pyrimidin-2-ylthio)acetic acid hydrochloride and (2S,4R)-4-benzyl-N-(4-(4-fluorophenoxy)phenyl)pyrrolidine-2-carboxamide, gave Compound 94, (2S,4R)-4-benzyl-N-(4-(4-fluorophenoxy)phenyl)-1-(2-(pyrimidin-2-ylthio)acetyl)pyrrolidine-2-carboxamide (10.9 mg, 33.5%). Major isomer: $^1$H-NMR (400 MHz, DMSO-D$_6$): a 9.92 (s, 1H), 8.59 (d, 2H), 7.53 (m, 2H), 7.27 (m, 2H), 7.23-7.15 (m, 8H), 6.93 (m, 2H), 4.47 (m, 1H), 4.09 (m, 2H), 3.78 (m, 1H), 3.39 (m, 1H), 2.68 (m, 3H), 1.93 (m, 2H). MS (EI) for $C_{30}H_{27}FN_4O_3S$. found 543.6 (MH+).

Proceeding as in Example 1, but substituting (S)-1-acetylpyrrolidine-2-carboxylic acid hydrochloride and (2S,4R)-4-benzyl-N-(4-(4-fluorophenoxy)phenyl)pyrrolidine-2-carboxamide, gave Compound 93, (2S,4R)-1-((S)-1-acetylpyrrolidine-2-carbonyl)-4-benzyl-N-(4-(4-fluorophenoxy)phenyl)pyrrolidine-2-carboxamide (11.5 mg, 36.2%). Major isomer: $^1$H-NMR (400 MHz, DMSO-$D_6$): σ 9.96 (s, 1H), 7.54 (m, 2H), 7.29-7.24 (m, 4H), 7.20-7.14 (m, 5H), 6.93 (m, 2H), 4.46 (m, 2H), 3.47-3.37 (m, 4H), 2.66 (m, 2H), 1.95-1.83 (m, 8H), 1.76-1.69 (m, 2H). MS (EI) for $C_{31}H_{32}FN_3O_4$. found 530.6 (MH+).

Proceeding as in Example 1, but substituting tetrahydrofuran-2-carboxylic acid hydrochloride and (2S,4R)-4-benzyl-N-(4-(4-fluorophenoxy)phenyl)pyrrolidine-2-carboxamide, gave Compound 92, (2S,4R)-4-benzyl-N-(4-(4-fluorophenoxy)phenyl)-1-(tetrahydrofuran-2-carbonyl)pyrrolidine-2-carboxamide (9.8 mg, 33.4%). Major isomer: $^1$H-NMR (400 MHz, DMSO-$D_6$): a 9.97 (s, 1H), 7.54 (m, 2H), 7.27 (m, 2H), 7.21-7.15 (m, 7H), 6.93 (m, 2H), 4.55-4.43 (m, 2H), 3.73 (m, 2H), 2.64 (m, 3H), 2.03-1.90 (m, 4H), 1.86-1.76 (m, 4H). MS (EI) for $C_{29}H_{29}FN_2O_4$. found 489.5 (MH+).

Proceeding as in Example 1, but substituting 4-oxo-4-(thien-2-yl)butanoic acid hydrochloride and (2S,4R)-4-benzyl-N-(4-(4-fluorophenoxy)phenyl)pyrrolidine-2-carboxamide, gave Compound 91, (2S,4R)-4-benzyl-N-(4-(4-fluorophenoxy)phenyl)-1-(4-oxo-4-(thien-2-yl)butanoyl)pyrrolidine-2-carboxamide (10.8 mg, 32.3%). Major isomer: $^1$H-NMR (400 MHz, DMSO-$D_6$): a 9.84 (s, 1H), 7.95 (m, 2H), 7.53 (m, 2H), 7.29 (m, 2H), 7.24-7.14 (m, 8H), 6.91 (m, 2H), 4.43 (t, 1H), 3.69 (m, 1H), 3.24 (m, 1H), 3.05 (m, 2H), 2.67-2.59 (m, 5H), 1.91 (m, 2H). MS (EI) for $C_{32}H_{29}FN_2O_4S$. found 557.7 (MH+).

Proceeding as in Example 1, but substituting 3-methoxypropanoic acid hydrochloride and (2S,4R)-4-benzyl-N-(4-(4-fluorophenoxy)phenyl)pyrrolidine-2-carboxamide, gave Compound 90, (2S,4R)-4-benzyl-N-(4-(4-fluorophenoxy)phenyl)-1-(3-methoxypropanoyl)pyrrolidine-2-carboxamide (6.9 mg, 24.1%). Major isomer: $^1$H-NMR (400 MHz, DMSO-$D_6$): 9.90 (s, 1H), 7.54 (m, 2H), 7.30-7.25 (m, 3H), 7.21-7.16 (m, 6H), 6.92 (m, 2H), 4.44 (m, 1H), 3.66 (m, 1H), 3.51 (m, 3H), 3.19 (s, 3H), 2.63 (m, 4H), 2.09 (m, 1H), 1.88 (m, 2H). MS (EI) for $C_{28}H_{29}FN_2O_4$. found 477.5 (MH+).

Proceeding as in Example 1, but substituting 4-(dimethylamino)-4-oxobutanoic acid hydrochloride and (2S,4R)-4-benzyl-N-(4-(4-fluorophenoxy)phenyl)pyrrolidine-2-carboxamide, gave Compound 89, (2S,4R)-4-benzyl-1-(4-(dimethylamino)-4-oxobutanoyl)-N-(4-(4-fluorophenoxy)phenyl)pyrrolidine-2-carboxamide (6.2 mg, 20%). Major isomer: $^1$H-NMR (400 MHz, DMSO-$D_6$): σ 9.68 (s, 1H), 7.57 (m, 2H), 7.27 (m, 2H), 7.23-7.15 (m, 7H), 6.93 (m, 2H), 4.43 (m, 1H), 3.68 (m, 1H), 3.27 (m, 1H), 2.94 (s, 3H), 2.78 (s, 3H), 2.67-2.58 (m, 4H), 2.44 (m, 3H), 1.91 (m, 2H). MS (EI) for $C_{30}H_{32}FN_3O_4$. found 518.6 (MH+).

Proceeding as in Example 1, but substituting 2-(2-methoxyethoxy)acetic acid hydrochloride and (2S,4R)-4-benzyl-N-(4-(4-fluorophenoxy)phenyl)pyrrolidine-2-carboxamide, gave Compound 88, (2S,4R)-4-benzyl-N-(4-(4-fluorophenoxy)phenyl)-1-(2-(2-methoxyethoxy)acetyl)pyrrolidine-2-carboxamide (8.1 mg, 26.6%). Major isomer: $^1$H-NMR (400 MHz, DMSO-$D_6$): σ 9.95 (s, 1H), 7.54 (m, 2H), 7.27 (m, 2H), 7.21-7.15 (m, 7H), 6.93 (m, 2H), 4.47 (m, 1H), 4.08 (m, 2H), 3.62-3.42 (m, 6H), 3.21 (s, 3H), 2.63 (m, 2H), 1.88 (m, 2H). MS (EI) for $C_{29}H_{31}FN_2O_5$. found 507.6 (MH+).

Proceeding as in Example 1, but substituting 2-(methylsulfonyl)acetic acid hydrochloride and (2S,4R)-4-benzyl-N-(4-(4-fluorophenoxy)phenyl)pyrrolidine-2-carboxamide, gave Compound 87, (2S,4R)-4-benzyl-N-(4-(4-fluorophenoxy)phenyl)-1-(2-(methylsulfonyl)acetyl)pyrrolidine-2-carboxamide (7.6 mg, 24.8%). Major isomer: $^1$H-NMR (400 MHz, DMSO-$D_6$): σ 9.96 (s, 1H), 7.55 (m, 2H), 7.27 (m, 2H), 7.23-7.16 (m, 7H), 6.94 (m, 2H), 4.50 (m, 1H), 4.38 (d, 2H), 3.82 (m, 1H), 3.35 (m, 1H), 3.08 (s, 3H), 2.63 (m, 3H), 1.92 (m, 2H). MS (EI) for $C_{27}H_{27}FN_2O_5S$. found 511.6 (MH+).

Proceeding as in Example 1, but substituting 3-ethoxypropanoic acid hydrochloride and (2S,4R)-4-benzyl-N-(4-(4-fluorophenoxy)phenyl)pyrrolidine-2-carboxamide, gave Compound 86, (2S,4R)-4-benzyl-1-(3-ethoxypropanoyl)-N-(4-(4-fluorophenoxy)phenyl)pyrrolidine-2-carboxamide (8.4 mg, 28.5%). Major isomer: $^1$H-NMR (400 MHz, DMSO-$D_6$): σ 9.91 (s, 1H), 7.55 (m, 2H), 7.28 (m, 2H), 7.21-7.16 (m, 7H), 6.93 (m, 2H), 4.45 (m, 1H), 3.64 (m, 1H), 3.54 (m, 2H), 3.38 (m, 2H), 3.24 (m, 1H), 2.63 (m, 5H), 1.88 (m, 2H), 1.04 (m, 3H). MS (EI) for $C_{29}H_{31}FN_2O_4$. found 491.6 (MH+).

Proceeding as in Example 1, but substituting 3-(methylthio)propanoic acid hydrochloride and (2S,4R)-4-benzyl-N-(4-(4-fluorophenoxy)phenyl)pyrrolidine-2-carboxamide, gave Compound 85, (2S,4R)-4-benzyl-N-(4-(4-fluorophenoxy)phenyl)-1-(3-(methylthio)propanoyl)pyrrolidine-2-carboxamide (8.3 mg, 28.1%). Major isomer: $^1$H-NMR (400 MHz, DMSO-$D_6$): σ 9.91 (s, 1H), 7.54 (d, 2H), 7.27 (m, 2H), 7.22-7.15 (m, 7H), 6.93 (m, 2H), 4.46 (t, 1H), 3.66 (m, 1H), 3.23 (m, 1H), 2.65-2.59 (m, 6H), 2.56 (m, 1H), 2.04 (s, 3H), 1.90 (m, 2H). MS (EI) for $C_{28}H_{29}FN_2O_3S$: 493.6 (MH+).

Proceeding as in Example 1, but substituting 2-(2,3,6-trifluorophenyl)acetic acid hydrochloride and (2S,4R)-4-benzyl-N-(4-(4-fluorophenoxy)phenyl)pyrrolidine-2-carboxamide, gave Compound 84, (2S,4R)-4-benzyl-N-(4-(4-fluorophenoxy)phenyl)-1-(2-(2,3,6-trifluorophenyl)acetyl)pyrrolidine-2-carboxamide (16.8 mg, 49.8%). Major isomer: $^1$H-NMR (400 MHz, DMSO-$D_6$): a 9.93 (s, 1H), 7.52 (d, 2H), 7.39 (m, 1H), 7.32-7.15 (m, 9H), 7.09 (m, 1H), 6.93 (m, 2H), 4.46 (m, 1H), 3.79 (m, 3H), 3.38 (m, 1H), 2.70 (m, 3H), 1.93 (m, 2H). MS (EI) for $C_{32}H_{26}F_4N_2O_3$. found 563.6 (MH+).

Proceeding as in Example 1, but substituting (R)-2-hydroxy-2-phenylacetic acid hydrochloride and (2S,4R)-4-benzyl-N-(4-(4-fluorophenoxy)phenyl)pyrrolidine-2-carboxamide, gave Compound 40, (2S,4R)-4-benzyl-N-(4-(4-fluorophenoxy)phenyl)-1-((R)-2-hydroxy-2-phenylacetyl)pyrrolidine-2-carboxamide (8.4 mg, 26.7%). $^1$H-NMR (400 MHz, DMSO-$D_6$): σ 10.03 (s, 1H), 7.56 (d, 2H), 7.27 (m, 11H), 6.97 (m, 5H), 5.20 (s, 1H), 4.44 (t, 1H), 2.86 (t, 2H), 2.71 (s, 1H), 2.45 (d, 2H), 1.80 (m, 2H). MS (EI) for $C_{32}H_{29}FN_2O_4$: 525.4 (MH+).

Proceeding as in Example 1, but substituting (S)-5-oxotetrahydrofuran-2-carboxylic acid hydrochloride and (2S,4R)-4-benzyl-N-(4-(4-fluorophenoxy)phenyl)pyrrolidine-2-carboxamide, gave Compound 39, (2S,4R)-4-benzyl-N-(4-(4-fluorophenoxy)phenyl)-1-((S)-5-oxotetrahydrofuran-2-carbonyl)pyrrolidine-2-carboxamide (8.8 mg, 29.2%). $^1$H-NMR (400 MHz, DMSO-$D_6$): σ 10.04 (s, 1H), 7.53 (m, 2H), 7.27 (m, 2H), 7.18 (m, 5H), 6.94 (m, 4H), 5.28 (m, 1H), 4.52 (dd, 1H), 3.65 (m, 1H), 2.39 (m, 3H), 2.46 (m, 3H), 2.15 (m, 2H), 2.89 (m, 2H). MS (EI) for $C_{29}H_{27}FN_2O_5$: 503.5 (MH+).

Proceeding as in Example 1, but substituting 2-butoxyacetic acid hydrochloride and (2S,4R)-4-benzyl-N-(4-(4-fluorophenoxy)phenyl)pyrrolidine-2-carboxamide, gave Compound 38, (2S,4R)-4-benzyl-1-(2-butoxyacetyl)-N-(4-(4-fluorophenoxy)phenyl)pyrrolidine-2-carboxamide (9.1 mg, 30.1%). $^1$H-NMR (400 MHz, DMSO-$D_6$): σ 9.95 (s, 1H), 7.56 (m, 2H), 7.27 (m, 2H), 7.19 (m, 5H), 6.96 (m, 4H), 4.47 (t, 1H), 4.03 (t, 1H), 3.60 (m, 1H), 3.42 (m, 2H), 3.29 (m, 2H), 2.65 (m, 3H), 1.89 (m, 2H), 1.35 (m, 4H), 0.85 (t, 3H). MS (EI) for $C_{30}H_{33}FN_2O_4$: 505.4 (MH+).

Proceeding as in Example 1, but substituting 2-(2-methyl-1H-indol-3-yl)acetic acid hydrochloride and (2S,4R)-4-benzyl-N-(4-(4-fluorophenoxy)phenyl)pyrrolidine-2-carboxamide, gave Compound 37, (2S,4R)-4-benzyl-N-(4-(4-fluorophenoxy)phenyl)-1-(2-(2-methyl-1H-indol-3-yl)acetyl)pyrrolidine-2-carboxamide (12.2 mg, 36.2%). $^1$H-NMR (400 MHz, DMSO-D$_6$): σ 10.78 (s, 1H), 9.91 (s, 1H), 7.53 (m, 2H), 7.41 (d, 1H), 7.15 (m, 8H), 6.94 (m, 6H), 4.59 (m, 1H), 3.67 (m, 2H), 3.54 (m, 1H), 3.33 (m, 1H), 3.19 (t, 1H), 2.87 (s, 2H), 2.60 (m, 2H), 2.24 (s, 3H). MS (EI) for $C_{35}H_{32}FN_3O_3$: 562.8 (MH+).

Proceeding as in Example 1, but substituting tetrahydrofuran-3-carboxylic acid and (2S,4R)-4-benzyl-N-(4-(4-fluorophenoxy)phenyl)pyrrolidine-2-carboxamide, gave Compound 36, (2S,4R)-4-benzyl-N-(4-(4-fluorophenoxy)phenyl)-1-(tetrahydrofuran-3-carbonyl)pyrrolidine-2-carboxamide (8.3 mg, 28.3%). $^1$H-NMR (400 MHz, DMSO-D$_6$): σ 9.95 (s, 1H), 7.56 (m, 2H), 7.27 (m, 2H), 7.19 (m, 5H), 6.92 (m, 4H), 4.46 (m, 1H), 3.86 (m, 1H), 3.66 (m, 4H), 3.31 (m, 2H), 2.63 (m, 3H), 1.94 (m, 4H). MS (EI) for $C_{29}H_{29}FN_2O_4$: 489.5 (MH+).

Proceeding as in Example 1, but substituting 2-(4-(dimethylamino)phenyl)acetic acid and (2S,4R)-4-benzyl-N-(4-(4-fluorophenoxy)phenyl)pyrrolidine-2-carboxamide, gave Compound 35, (2S,4R)-4-benzyl-1-(2-(4-(dimethylamino)phenyl)acetyl)-N-(4-(4-fluorophenoxy)phenyl)pyrrolidine-2-carboxamide (2.5 mg, 7.6%). $^1$H-NMR (400 MHz, DMSO-D$_6$): σ 9.95 (s, 1H), 7.56 (m, 2H), 7.23 (t, 2H), 7.12 (m, 5H), 6.98 (m, 6H), 6.64 (m, 2H), 4.46 (m, 1H), 3.49 (s, 2H), 3.24 (m, 1H), 2.84 (s, 6H), 2.60 (m, 3H), 1.87 (m, 2H). MS (EI) for $C_{34}H_{34}FN_3O_3$: 552.6 (MH+).

Proceeding as in Example 1, but substituting 3,3,3-trifluoropropanoic acid and (2S,4R)-4-benzyl-N-(4-(4-fluorophenoxy)phenyl)pyrrolidine-2-carboxamide, gave Compound 34, (2S,4R)-4-benzyl-N-(4-(4-fluorophenoxy)phenyl)-1-(3,3,3-trifluoropropanoyl)pyrrolidine-2-carboxamide (9.2 mg, 30.6%). $^1$H-NMR (400 MHz, DMSO-D$_6$): σ 9.98 (s, 1H), 7.54 (m, 2H), 7.22 (m, 2H), 7.17 (m, 5H), 6.93 (m, 4H), 4.49 (m, 1H), 3.60 (m, 2H), 3.26 (m, 1H), 2.65 (m, 3H), 1.91 (m, 2H). MS (EI) for $C_{27}H_{24}F_4N_2O_3$: 501.5 (MH+).

Proceeding as in Example 1, but substituting 4-(2,3-dihydrobenzo[b][1,4]dioxin-6-yl)butanoic acid hydrochloride and (2S,4R)-4-benzyl-N-(4-(4-fluorophenoxy)phenyl)pyrrolidine-2-carboxamide, gave Compound 33, (2S,4R)-4-benzyl-1-(4-(2,3-dihydrobenzo[b][1,4]dioxin-6-yl)butanoyl)-N-(4-(4-fluorophenoxy)phenyl)pyrrolidine-2-carboxamide (8.4 mg, 23.5%). $^1$H-NMR (400 MHz, DMSO-D$_6$): σ 9.93 (s, 1H), 7.54 (d, 2H), 7.26 (t, 2H), 7.18 (m, 5H), 6.98 (m, 4H), 6.71 (d, 1H), 6.45 (m, 2H), 4.45 (m, 1H), 4.17 (m, 4H), 3.57 (m, 1H), 3.14 (m, 1H), 2.64 (m, 3H), 2.64 (t, 2H), 2.19 (m, 2H), 1.87 (m, 2H), 1.70 (m, 2H). MS (EI) for $C_{36}H_{35}FN_2O_5$: 595.7 (MH+).

Proceeding as in Example 1, but substituting 2-(3-methylisoxazol-5-yl)acetic acid hydrochloride and (2S,4R)-4-benzyl-N-(4-(4-fluorophenoxy)phenyl)pyrrolidine-2-carboxamide, gave Compound 32, (2S,4R)-4-benzyl-N-(4-(4-fluorophenoxy)phenyl)-1-(2-(3-methylisoxazol-5-yl)acetyl)pyrrolidine-2-carboxamide (9 mg, 29.2%). $^1$H-NMR (400 MHz, DMSO-D$_6$): σ 9.97 (s, 1H), 7.54 (d, 2H), 7.27 (t, 2H), 7.19 (m, 4H), 6.67 (m, 4H), 6.20 (d, 1H), 4.48 (1H), 3.88 (m, 3H), 2.66 (m, 4H), 2.15 (s, 3H), 1.91 (m, 2H). MS (EI) for $C_{30}H_{28}FN_3O_4$: 514.6 (MH+).

Proceeding as in Example 1, but substituting 2-phenylacetic acid hydrochloride and (2S,4R)-4-benzyl-N-(4-(4-fluorophenoxy)phenyl)pyrrolidine-2-carboxamide, gave Compound 31, (2S,4R)-4-benzyl-N-(4-(4-fluorophenoxy)phenyl)-1-(2-phenylacetyl)pyrrolidine-2-carboxamide (13.4 mg, 43.9%). $^1$H-NMR (400 MHz, DMSO-D$_6$): σ 9.97 (s, 1H), 7.54 (t, 2H), 7.19 (m, 12H), 6.97 (m, 4H), 3.74 (m, 1H), 3.65 (s, 2H), 3.27 (m, 2H), 2.62 (m, 4H). MS (EI) for $C_{32}H_{29}FN_2O_3$: 509.6 (MH+).

Proceeding as in Example 1, but substituting 2-morpholinoacetic acid hydrochloride and (2S,4R)-4-benzyl-N-(4-(4-fluorophenoxy)phenyl)pyrrolidine-2-carboxamide, gave Compound 116, (2S,4R)-4-benzyl-N-(4-(4-fluorophenoxy)phenyl)-1-(2-morpholinoacetyl)pyrrolidine-2-carboxamide (9.2 mg, 25.4%); Major isomer: $^1$H-NMR (400 MHz, DMSO-D$_6$): σ 9.99 (s, 1H), 7.52-7.60 (m, 2H), 7.29-7.32 (m, 2H), 7.17-7.23 (m, 5H), 6.95-7.02 (m, 4H), 4.67-4.71 (m, 1H), 3.74 (m, 1H), 3.42-3.50 (m, 1H), 3.28-3.35 (m, 2H), 3.11-3.28 (m, 4H), 2.56-2.73 (m, 3H), 2.33-2.40 (m, 2H), 2.11-2.28 (m, 2H), 1.88-1.97 (m, 2H). MS (EI) for $C_{30}H_{32}FN_3O_4$. found 518.5 (MH+).

Proceeding as in Example 1, but substituting 2-(4-acetylpiperazin-1-yl)acetic acid hydrochloride and (2S,4R)-4-benzyl-N-(4-(4-fluorophenoxy)phenyl)pyrrolidine-2-carboxamide, gave Compound 115, (2S,4R)-1-(2-(4-acetylpiperazin-1-yl)acetyl)-4-benzyl-N-(4-(4-fluorophenoxy)phenyl)pyrrolidine-2-carboxamide (9.5 mg, 24.9%); Major isomer: $^1$H-NMR (400 MHz, DMSO-D$_6$): σ 9.96 (s, 1H), 7.96 (s, 1H), 7.53-7.60 (m, 2H), 7.25-7.30 (m, 2H), 7.14-7.22 (m, 5H), 6.92-6.99 (m, 4H), 4.67-4.71 (m, 1H), 3.70-3.75 (m, 1H), 3.45-3.50 (m, 1H), 3.23-3.30 (m, 2H), 3.10-3.27 (m, 4H), 2.53-2.62 (m, 3H), 2.37-2.45 (m, 2H), 2.14-2.30 (m, 2H), 1.85-1.99 (m, 2H). MS (EI) for $C_{31}H_{33}FN_4O_4$. found 545.6 (MH+).

Proceeding as in Example 1, but substituting 2-thiomorpholinoacetic acid hydrochloride and (2S,4R)-4-benzyl-N-(4-(4-fluorophenoxy)phenyl)pyrrolidine-2-carboxamide, gave Compound 83, (2S,4R)-4-benzyl-N-(4-(4-fluorophenoxy)phenyl)-1-(2-thiomorpholinoacetyl)pyrrolidine-2-carboxamide (13.9 mg, 37.2%). Major isomer: $^1$H-NMR (400 MHz, DMSO-D$_6$): σ 9.95 (s, 1H), 7.54 (d, 2H), 7.27 (m, 2H), 7.21-7.16 (m, 7H), 6.93 (m, 2H), 4.44 (m, 1H), 3.71 (m, 1H), 3.28 (m, 1H), 3.13 (m, 2H), 2.87 (m, 4H), 2.63 (m, 3H), 2.55 (m, 4H), 1.85 (m, 2H). MS (EI) for $C_{30}H_{32}FN_3O_3S$. found 534.7 (MH+).

Proceeding as in Example 1, but substituting 2-(3,4-dihydroisoquinolin-2(1H)-yl)acetic acid hydrochloride and (2S,4R)-4-benzyl-N-(4-(4-fluorophenoxy)phenyl)pyrrolidine-2-carboxamide, gave Compound 82, (2S,4R)-4-benzyl-1-(2-(3,4-dihydroisoquinolin-2(1H)-yl)acetyl)-N-(4-(4-fluorophenoxy)phenyl)pyrrolidine-2-carboxamide (13.7 mg, 34.7%). Major isomer: $^1$H-NMR (400 MHz, DMSO-D$_6$): σ 9.98 (s, 1H), 7.56 (d, 2H), 7.23-7.15 (m, 10H), 7.09 (m, 3H), 6.94 (m, 2H), 4.49 (m, 1H), 3.74 (m, 1H), 3.63 (d, 2H), 3.36 (m, 1H), 3.29 (s, 2H), 2.78-2.73 (m, 4H), 2.61 (m, 3H), 1.91 (m, 2H). MS (EI) for $C_{35}H_{34}FN_3O_3$. found 564.7 (MH+).

Proceeding as in Example 1, but substituting 2-(4-(2-methoxyethyl)piperazin-1-yl)acetic acid hydrochloride and (2S,4R)-4-benzyl-N-(4-(4-fluorophenoxy)phenyl)pyrrolidine-2-carboxamide, gave Compound 100, (2S,4R)-4-benzyl-N-(4-(4-fluorophenoxy)phenyl)-1-(2-(4-(2-methoxyethyl)piperazin-1-yl)acetyl)pyrrolidine-2-carboxamide (10.6 mg, 26.3%). Major isomer: $^1$H-NMR (400 MHz, DMSO-D$_6$): σ 9.96 (s, 1H), 7.61 (d, 1H), 7.54 (d, 1H), 7.28 (m, 2H), 7.22-7.13 (m, 5H), 6.99-6.92 (m, 4H), 4.45 (m, 1H), 3.73 (m, 1H), 3.39 (m, 2H), 3.23 (t, 1H), 3.20 (s, 2H), 3.13 (s, 2H), 3.07 (m, 1H), 2.63 (m, 2H), 2.48 (m, 8H), 2.43 (t, 2H), 2.09 (t, 1H), 1.91 (m, 2H). MS (EI) for $C_{33}H_{39}FN_4O_4$. found 575.7 (MH+).

Proceeding as in Example 1, but substituting 2-((1-methyl-1H-indol-2-yl)methylamino)acetic acid hydrochloride and (2S,4R)-4-benzyl-N-(4-(4-fluorophenoxy)phenyl)pyrrolidine-2-carboxamide, gave Compound 30, (2S,4R)-4-benzyl-N-(4-(4-fluorophenoxy)phenyl)-1-(2-((1-methyl-1H-indol-2-yl)methylamino)acetyl)pyrrolidine-2-carboxamide (12.6 mg, 30.4%). $^1$H-NMR (400 MHz, DMSO-D$_6$): σ 9.95 (s, 1H), 7.93 (m, 2H), 7.26 (m, 4H), 7.17 (m, 8H), 6.96 (m, 3H), 4.15 (m, 1H), 3.64 (m, 1H), 3.49 (m, 2H), 3.14 (m, 2H), 2.87 (s, 3H), 2.64 (m, 2H), 2.20 (m, 1H), 1.89 (m, 2H). MS (EI) for $C_{35}H_{34}FN_5O_3$: 592.7 (MH+).

Proceeding as in Example 1, but substituting 2-(1H-1,2,4-triazol-1-yl)acetic acid hydrochloride and (2S,4R)-4-(2-chloro-4-fluorobenzyl)-N-(4-(4-fluorophenoxy)phenyl)pyrrolidine-2-carboxamide, gave Compound 9, (2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide (35.4 mg, 36%). Major isomer $^1$H-NMR (400 MHz, CDCl$_3$): δ 9.08 (s, 1H), 8.27 (s, 1H), 7.98 (s, 1H), 7.37-7.33 (m, 2H), 7.23-7.19 (m, 1H), 7.16-7.12 (m, 1H), 7.02-6.82 (m, 7H), 5.07 (d, 1H), 5.00 (d, 1H), 4.73 (d, 1H), 3.75-3.69 (m, 1H), 3.31 (t, 1H), 3.08-2.98 (m, 1H), 2.88 (d, 2H), 2.46 (dd, 1H), 1.82-1.73 (m, 1H). MS (EI) for $C_{28}H_{24}ClF_2N_5O_3$ found 552 (MH+).

Proceeding as in Example 1, but substituting 2-(1H-1,2,4-triazol-1-yl)acetic acid hydrochloride and (2S,4R)—N-(4-(4-fluorophenoxy)phenyl)-4-(thien-3-ylmethyl)pyrrolidine-2-carboxamide, gave Compound 72, (2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide (172 mg, 35%). $^1$H-NMR (400 MHz, CDCl$_3$): δ 9.03 (s, 1H), 8.24 (s, 1H), 7.99 (s, 1H), 7.42 (d, 2H), 7.32-7.30 (m, 1H), 7.03-6.90 (m, 8H), 5.05 (d, 1H), 4.97 (d, 1H), 4.81 (d, 1H), 3.87 (t, 1H), 3.24 (t, 1H), 3.05-2.97 (m, 1H), 2.96-2.89 (m, 1H), 2.77-2.64 (m, 2H), 1.73-1.65 (m, 1H). MS (EI) for $C_{26}H_{24}FN_5O_3S$ found 505.9 (MH+).

Proceeding as in Example 1, but substituting 2-(1H-1,2,4-triazol-1-yl)acetic acid hydrochloride and (2S,4R)-4-(2,4-difluorobenzyl)-N-(4-(4-fluorophenoxy)phenyl)pyrrolidine-2-carboxamide, gave Compound 53, (2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide. Major isomer: $^1$H-NMR (400 MHz, DMSO-D$_6$): σ 10.02 (s, 1H), 8.43 (s, 1H), 7.96 (s, 1H), 7.56 (d, 2H), 7.47-7.37 (m, 1H), 7.27-7.15 (m, 4H), 7.10-6.92 (m, 7H), 5.24 (q, 2H), 4.55-4.49 (m, 1H), 3.88-3.80 (m, 1H), 3.39-3.30 (m, 1H), 2.84-2.65 (m, 3H), 2.02-1.92 (m, 1H). MS (EI) for $C_{28}H_{24}F_3N_5O_3$. found 535.9 (MH+).

Proceeding as in Example 1, but substituting 2-(1H-1,2,4-triazol-1-yl)acetic acid hydrochloride and (2S,4R)-4-(4-fluorobenzyl)-N-(4-(4-fluorophenoxy)phenyl)-5-oxopyrrolidine-2-carboxamide, gave Compound 71, (2S,4R)-1-(2-(1H-1,2,4-triazol-1-yl)acetyl)-4-(4-fluorobenzyl)-N-(4-(4-fluorophenoxy)phenyl)-5-oxopyrrolidine-2-carboxamide (18.2 mg, 4%). $^1$H-NMR (400 MHz, CDCl$_3$): σ 8.17 (s, 1H), 8.01 (s, 1H), 7.79 (s, 1H), 7.39 (d, 2H), 7.19-7.15 (m, 1H), 7.04-6.99 (m, 4H), 9.95-6.91 (m, 4H), 5.67 (d, 1H), 5.59 (d, 1H), 4.67 (d, 1H), 3.48-3.40 (m, 1H), 3.25 (dd, 1H), 2.78 (dd, 1H), 2.46 (dd, 1H), 2.06-1.97 (m, 1H). MS (EI) for $C_{28}H_{23}F_2N_5O_4$. found 532.2 (MH+).

Proceeding as in Example 1, but substituting 2-(1H-1,2,4-triazol-1-yl)acetic acid hydrochloride and (2S,4R)-4-(3-chlorobenzyl)-N-(4-(4-fluorophenoxy)phenyl)pyrrolidine-2-carboxamide, gave Compound 61, (2S,4R)-1-(2-(1H-1,2,4-triazol-1-yl)acetyl)-4-(3-chlorobenzyl)-N-(4-(4-fluorophenoxy)phenyl)pyrrolidine-2-carboxamide (65 mg, 60%). $^1$H-NMR (400 MHz, CDCl$_3$): δ 9.00 (s, 1H), 8.20 (s, 1H), 8.00 (s, 1H), 7.40-7.20 (m, 6H), 6.90-6.80 (m, 6H), 5.00 (dd, 2H), 4.90 (d, 1H), 3.80 (m, 1H), 3.20 (m, 1H), 3.00-2.80 (m, 5H). MS (EI) for $C_{28}H_{25}ClFN_5O_3$ found 534 (MH+).

Proceeding as in Example 1, but substituting 2-(2H-1,2,3-triazol-2-yl)acetic acid hydrochloride and (2S,4R)-4-(2,4-difluorobenzyl)-N-(4-(4-fluorophenoxy)phenyl)pyrrolidine-2-carboxamide, gave Compound 52, (2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide (77 mg, 63%). Major isomer: $^1$H-NMR (400 MHz, DMSO-D$_6$): σ 10.00 (s, 1H), 7.80 (s, 2H), 7.60-7.52 (m, 2H), 7.47-7.36 (m, 1H), 7.29-7.14 (m, 4H), 7.11-6.92 (m, 6H), 5.49 (q, 2H), 4.54-4.46 (m, 1H), 3.92-3.80 (m, 1H), 2.86-2.63 (m, 3H), 2.20-1.88 (m, 2H). MS (EI) for $C_{28}H_{24}F_3N_5O_3$. found 535.9 (MH+).

Proceeding as in Example 1, but substituting 2-(1H-1,2,4-triazol-1-yl)acetic acid hydrochloride and (2S,4R)-4-(3-fluorobenzyl)-N-(4-(4-fluorophenoxy)phenyl)pyrrolidine-2-carboxamide, gave Compound 51, (2S,4R)-1-(2-(1H-1,2,4-triazol-1-yl)acetyl)-4-(3-fluorobenzyl)-N-(4-(4-fluorophenoxy)phenyl)pyrrolidine-2-carboxamide (59 mg, 31%). Major isomer: $^1$H-NMR (400 MHz, DMSO-D$_6$): σ 10.00 (s, 1H), 8.42 (s, 1H), 7.95 (s, 1H), 7.58-7.52 (m, 2H), 7.40-7.31 (m, 1H), 7.25-6.92 (m, 10H), 5.24 (q, 2H), 4.55-4.48 (m, 1H), 3.89-3.76 (m, 1H), 2.84-2.66 (m, 3H), 2.03-1.90 (m, 2H). MS (EI) for $C_{28}H_{25}F_2N_5O_3$. found 517.9 (MH+).

Proceeding as in Example 1, but substituting 2-(1H-1,2,4-triazol-1-yl)acetic acid hydrochloride and (2S,4R)—N-(4-(4-fluorophenoxy)phenyl)-4-(4-methylbenzyl)pyrrolidine-2-carboxamide, gave Compound 4, (2S,4R)-5-(2-(1H-1,2,4-triazol-1-yl)acetyl)-N-(4-(4-fluorophenoxy)phenyl)-4-(4-methylbenzyl)pyrrolidine-2-carboxamide. $^1$H-NMR (400 MHz, CDCl$_3$): σ 9.02 (br s, 1H), 8.23 (s, 1H), 7.98 (s, 1H), 7.40 (m, 2H), 7.12 (d, 2H), 7.08 (d, 2H), 7.03-6.98 (m, 2H), 6.94-6.87 (m, 4H), 4.98 (dd, 2H), 4.78 (d, 1H), 3.62 (m, 1H), 3.23 (t, 1H), 3.02-2.87 (m, 2H), 2.65-2.60 (m, 2H), 2.34 (s, 3H), 1.74-1.66 (m, 1H); MS (EI) for $C_{29}H_{28}FN_5O_3$. found 514.1 (MH+).

Proceeding as in Example 1, but substituting 2-(1H-1,2,3-triazol-1-yl)acetic acid hydrochloride and (2S,4R)—N-(4-(4-fluorophenoxy)phenyl)-4-(4-methylbenzyl)pyrrolidine-2-carboxamide, gave Compound 3, (2S,4R)-5-(2-(1H-1,2,3-triazol-1-yl)acetyl)-N-(4-(4-fluorophenoxy)phenyl)-4-(4-methylbenzyl)pyrrolidine-2-carboxamide. $^1$H-NMR (400 MHz, CDCl$_3$): σ 8.96 (br s, 1H), 7.77 (s, 1H), 7.74 (s, 1H), 7.42 (m, 2H), 7.13 (d, 2H), 7.08 (d, 2H), 7.03-6.98 (m, 2H), 6.94-6.87 (m, 4H), 5.27 (d, 1H), 5.13 (d, 1H), 4.76 (d, 1H), 3.66 (m, 1H), 3.26 (t, 1H), 3.02-2.85 (m, 2H), 2.66-2.57 (m, 2H), 2.33 (s, 3H), 1.76-1.68 (m, 1H); MS (EI) for $C_{29}H_{28}FN_5O_3$. found 514.1 (MH+).

Proceeding as in Example 1, but substituting 2-(2H-1,2,3-triazol-2-yl)acetic acid hydrochloride and (2S,4R)-4-(3-fluorobenzyl)-N-(4-(4-fluorophenoxy)phenyl)pyrrolidine-2-carboxamide, gave Compound 49, (2S,4R)-1-(2-(2H-1,2,3-triazol-2-yl)acetyl)-4-(3-fluorobenzyl)-N-(4-(4-fluorophenoxy)phenyl)pyrrolidine-2-carboxamide (74 mg, 39%). Major isomer: $^1$H-NMR (400 MHz, DMSO-D$_6$): σ 9.96 (s, 1H), 7.79 (s, 2H), 7.57-7.51 (m, 2H), 7.38-7.29 (m, 1H), 7.22-6.90 (m, 10H), 5.56-5.41 (m, 2H), 4.52-4.54 (m, 1H), 3.84-3.77 (m, 1H), 2.79-2.63 (m, 3H), 2.01-1.87 (m, 2H). MS (EI) for $C_{28}H_{25}F_2N_5O_3$. found 517.9 (MH+).

Proceeding as in Example 1, but substituting 2-(1H-1,2,4-triazol-1-yl)acetic acid hydrochloride and (2S,4R)-4-(4- fluoro-2-methylbenzyl)-N-(4-(4-fluorophenoxy)phenyl)pyrrolidine-2-carboxamide, gave Compound 8, (2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide (127.6 mg, 41%). Major isomer $^1$H-NMR (400 MHz, CDCl$_3$): δ 9.02 (s, 1H), 8.25 (s, 1H), 7.99 (s, 1H), 7.42-7.37 (m, 2H), 7.31-6.82 (m, 9H), 5.06 (d, 1H), 4.98 (d, 1H), 4.79 (d, 1H), 3.69 (t, 1H), 3.27 (t, 1H), 3.04-2.91 (m, 1H), 2.84 (dd, 1H), 2.70 (dd, 1H), 2.59 (dd, 1H), 2.33 (s, 3H), 1.76-1.67 (m, 1H). MS (EI) for $C_{29}H_{28}F_2N_5O_3$ found 532 (MH+).

Proceeding as in Example 1, but substituting 2-(2H-1,2,3-triazol-2-yl)acetic acid hydrochloride and (2S,4R)-4-(4-fluoro-2-methylbenzyl)-N-(4-(4-fluorophenoxy)phenyl)pyrrolidine-2-carboxamide, gave Compound 7, (2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide (106.7 mg, 34%). Major isomer: $^1$H-NMR (400 MHz, CDCl$_3$): δ 9.15 (s, 1H), 7.72 (s, 2H), 7.43-7.38 (m, 2H), 7.09-6.81 (m, 9H), 5.29 (d, 2H), 4.84 (d, 1H), 3.59-3.53 (m, 1H), 3.19 (t, 1H), 2.96-2.87 (m, 1H), 2.82 (dd, 1H), 2.72-2.59 (m, 2H), 2.32 (s, 3H). MS (EI) for $C_{29}H_{28}F_2N_5O_3$ found 532 (MH+).

Proceeding as in Example 1, but substituting 2-(1H-1,2,3-triazol-1-yl)acetic acid hydrochloride and (2S,4R)-4-(4-fluoro-2-methylbenzyl)-N-(4-(4-fluorophenoxy)phenyl)pyrrolidine-2-carboxamide, gave Compound 6, (2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide (142 mg, 46%). Major isomer: $^1$H-NMR (400 MHz, CDCl$_3$): δ 8.96 (s, 1H), 7.76 (d, 2H), 7.40 (d, 2H), 7.11-6.83 (m, 9H), 5.31 (d, 1H), 5.15 (d, 1H), 4.77 (d, 1H), 3.71 (t, 1H), 3.30 (t, 1H), 3.02-2.91 (m, 1H), 2.82 (dd, 1H), 2.71 (dd, 1H), 2.57 (dd, 1H), 2.33 (s, 3H), 1.78-1.68 (m, 1H). MS (EI) for $C_{29}H_{28}F_2N_5O_3$ found 532 (MH+).

Proceeding as in Example 1, but substituting 2-(1H-1,2,4-triazol-1-yl)acetic acid hydrochloride and (2S,4R)—N-(4-(4-fluorophenoxy)phenyl)-4-(3-methoxybenzyl)pyrrolidine-2-carboxamide, gave Compound 70, (2S,4R)-1-(2-(1H-1,2,4-triazol-1-yl)acetyl)-N-(4-(4-fluorophenoxy)phenyl)-4-(3-methoxybenzyl)pyrrolidine-2-carboxamide (160 mg, 82%). $^1$H-NMR (400 MHz, CDCl$_3$): σ 9.00 (s, 1H), 8.23 (s, 1H), 7.99 (s, 1H), 7.41 (d, 2H), 7.00 (t, 2H), 6.93-6.89 (m, 4H), 6.80-6.73 (m, 4H), 5.03 (d, 1H), 4.95 (d, 1H), 4.80 (d, 1H), 3.81 (s, 3H), 3.63 (dd, 1H), 3.27-3.16 (m, 1H), 3.02-2.88 (m, 2H), 2.68-2.59 (m, 2H), 1.76-1.68 (m, 1H). MS (EI) for $C_{29}H_{28}FN_5O_4$. found 530.2 (MH+).

Proceeding as in Example 1, but substituting 2-(2H-1,2,3-triazol-2-yl)acetic acid hydrochloride and (2S,4R)—N-(4-(4-fluorophenoxy)phenyl)-4-(3-methoxybenzyl)pyrrolidine-2-carboxamide, gave Compound 69, (2S,4R)-1-(2-(2H-1,2,3-triazol-2-yl)acetyl)-N-(4-(4-fluorophenoxy)phenyl)-4-(3-methoxybenzyl)pyrrolidine-2-carboxamide (180 mg, 93%). $^1$H-NMR (400 MHz, CDCl$_3$): σ 9.15 (s, 1H), 7.71 (s, 2H), 7.42 (d, 2H), 7.00 (t, 2H), 6.93-6.89 (m, 4H), 6.80-6.72 (m, 4H), 5.32-5.23 (m, 1H), 4.84 (d, 1H), 4.80 (d, 1H), 3.81 (s, 3H), 3.51 (dd, 1H), 3.17 (t, 1H), 2.99-2.88 (m, 2H), 2.69-2.59 (m, 2H), 1.73-1.65 (m, 1H). MS (EI) for $C_{29}H_{28}FN_5O_4$. found 530.2 (MH+).

Proceeding as in Example 1, but substituting 2-(1H-1,2,3-triazol-1-yl)acetic acid hydrochloride and (2S,4R)—N-(4-(4-fluorophenoxy)phenyl)-4-(3-methoxybenzyl)pyrrolidine-2-carboxamide, gave Compound 68, (2S,4R)-1-(2-(1H-1,2,3-triazol-1-yl)acetyl)-N-(4-(4-fluorophenoxy)phenyl)-4-(3-methoxybenzyl)pyrrolidine-2-carboxamide (176 mg, 91%). $^1$H-NMR (400 MHz, CDCl$_3$): σ 8.95 (s, 1H), 7.78 (s, 1H), 7.75 (s, 1H), 7.43 (d, 2H), 7.00 (t, 2H), 6.93-6.89 (m, 4H), 6.79-6.88 (m, 4H), 5.27 (d, 1H), 5.15 (d, 1H), 4.78 (d, 1H), 4.80 (d, 1H), 3.81 (s, 3H), 3.67 (dd, 1H), 3.27 (t, 1H), 3.07-2.88 (m, 2H), 2.66-2.61 (m, 2H), 1.77-1.69 (m, 1H). MS (EI) for $C_{29}H_{28}FN_5O_4$. found 530.2 (MH+).

Proceeding as in Example 1, but substituting 2-(1H-1,2,4-triazol-1-yl)acetic acid hydrochloride and (2S,4S)-4-((5-chlorothien-2-yl)methyl)-N-(4-(4-fluorophenoxy)phenyl)pyrrolidine-2-carboxamide, gave Compound 67, (2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide (23.1 mg, 28%). $^1$H-NMR (400 MHz, CDCl$_3$): σ 9.01 (s, 1H), 8.24 (s, 1H), 7.99 (s, 1H), 7.42 (d, 2H), 7.00 (t, 2H), 6.95-6.90 (m, 4H), 6.75 (d, 1H), 6.63 (d, 1H), 5.03 (dd, 2H), 4.83 (d, 1H), 3.76 (dd, 1H), 3.27 (t, 1H), 3.06-2.93 (m, 2H), 2.85-2.79 (m, 1H), 2.71 (dd, 1H), 1.73-1.66 (m, 1H). MS (EI) for $C_{26}H_{23}ClFN_5O_3S$. found 540.1 (MH+).

Proceeding as in Example 1, but substituting 2-(2H-1,2,3-triazol-2-yl)acetic acid hydrochloride and (2S,4S)-4-((5-chlorothien-2-yl)methyl)-N-(4-(4-fluorophenoxy)phenyl)pyrrolidine-2-carboxamide, gave Compound 66, (2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide (58.3 mg, 58%). $^1$H-NMR (400 MHz, CDCl$_3$): σ 9.14 (s, 1H), 7.72 (s, 2H), 7.42 (d, 2H), 7.00 (t, 2H), 6.95-6.90 (m, 4H), 6.75 (d, 1H), 6.61 (d, 1H), 5.39 (s, 2H), 4.86 (d, 1H), 3.62 (dd, 1H), 3.19 (t, 1H), 3.03-2.85 (m, 2H), 2.83-2.77 (m, 1H), 2.72 (dd, 1H), 1.72-1.64 (m, 1H). MS (EI) for $C_{26}H_{23}ClFN_5O_3S$. found 540.1 (MH+).

Proceeding as in Example 1, but substituting 2-(1H-1,2,3-triazol-1-yl)acetic acid hydrochloride and (2S,4S)-4-((5-chlorothien-2-yl)methyl)-N-(4-(4-fluorophenoxy)phenyl)pyrrolidine-2-carboxamide, gave Compound 65, (2S,4S)-1-(2-(1H-1,2,3-triazol-1-yl)acetyl)-4-((5-chlorothien-2-yl)methyl)-N-(4-(4-fluorophenoxy)phenyl)pyrrolidine-2-carboxamide (60.2 mg, 65%). $^1$H-NMR (400 MHz, CDCl$_3$): σ 8.95 (s, 1H), 7.77 (d, 2H), 7.43 (d, 2H), 7.00 (t, 2H), 6.94-6.89 (m, 4H), 6.76 (d, 1H), 6.63 (d, 1H), 5.30 (d, 1H), 5.17 (d, 1H), 4.80 (d, 1H), 3.79 (dd, 1H), 3.30 (t, 1H), 3.04-2.93 (m, 2H), 2.87-2.78 (m, 1H), 2.68 (dd, 1H), 1.75-1.68 (m, 1H). MS (EI) for $C_{26}H_{23}ClFN_5O_3S$. found 540.1 (MH+).

Proceeding as in Example 1, but substituting 2-(2H-1,2,3-triazol-2-yl)acetic acid hydrochloride and (2S,4R)-4-(2-chloro-4-fluorobenzyl)-N-(4-(4-fluorophenoxy)phenyl)pyrrolidine-2-carboxamide, gave Compound 5, (2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide. $^1$H-NMR (400 MHz, CDCl$_3$): δ 9.15 (s, 1H), 7.70 (s, 2H), 7.40-7.36 (m, 2H), 7.23-7.12 (m, 2H), 7.02-6.84 (m, 7H), 5.31 (s, 2H), 4.80 (d, 1H), 3.62-3.57 (m, 1H), 3.24 (t, 1H), 3.04-2.95 (m, 1H), 2.90-2.85 (m, 1H), 2.53 (dd, 1H), 1.79-1.70 (m, 1H). MS (EI) for $C_{28}H_{25}ClF_2N_5O_3$ found 552 (MH+).

Proceeding as in Example 1, but substituting 2-(1H-1,2,3-triazol-1-yl)acetic acid hydrochloride and (2S,4R)-4-(2-chloro-4-fluorobenzyl)-N-(4-(4-fluorophenoxy)phenyl)pyrrolidine-2-carboxamide, gave Compound 2, (2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide. $^1$H-NMR (400 MHz, CDCl$_3$): δ 8.96 (s, 1H), 7.79-7.75 (m, 2H), 7.43-7.39 (m, 2H), 7.25-7.13 (m, 2H), 7.03-6.86 (m, 7H), 5.32 (d, 1H), 5.18 (d, 1H), 4.77 (d, 1H), 3.76-3.70 (m, 1H), 3.36 (t, 1H), 3.08-2.96 (m, 1H), 2.94-2.88 (m, 2H), 2.60-2.53 (m, 1H), 1.82-1.73 (m, 1H). MS (EI) for $C_{28}H_{25}ClF_2N_5O_3$ found 552 (MH+).

Proceeding as in Example 1, but substituting 2-(2H-1,2,3-triazol-2-yl)acetic acid hydrochloride and (2S,4R)—N-(4-(4-fluorophenoxy)phenyl)-4-(2-methylbenzyl)pyrrolidine-2-carboxamide, gave Compound 48, (2S,4R)-1-(2-(2H-1,2,3- triazol-2-yl)acetyl)-N-(4-(4-fluorophenoxy)phenyl)-4-(2-methylbenzyl)pyrrolidine-2-carboxamide. Major isomer: $^1$H-NMR (400 MHz, DMSO-D$_6$): δ 9.98 (s, 1H), 7.80 (s, 1H), 7.54 (d, 2H), 7.24-7.08 (m, 6H), 7.04-6.92 (m, 4H), 5.49 (q, 2H), 4.53-4.48 (m, 1H), 3.90-3.83 (m, 1H), 2.80-2.62 (m, 3H), 2.29 (s, 3H), 2.05-1.88 (m, 2H). MS (EI) for C$_{29}$H$_{28}$FN$_5$O$_3$. found 514.2 (MH+).

Proceeding as in Example 1, but substituting 2-(1H-1,2,4-triazol-1-yl)acetic acid and (2S,4S)-4-(((9H-fluoren-9-yl)methoxy)carbonylamino)pyrrolidine-2-carboxylic acid, gave (9H-fluoren-9-yl)methyl (3S,5S)-1-(2-(1H-1,2,4-triazol-1-yl)acetyl)-5-(4-(4-fluorophenoxy)phenylcarbamoyl)pyrrolidin-3-ylcarbamate.

Proceeding as in Example 1, but substituting 4-imidazoleacetic acid hydrochloride and benzyl (3R,5S)-5-(4-(4-fluorophenoxy)phenylcarbamoyl)pyrrolidin-3-ylcarbamate gave Compound 253, benzyl (3R,5S)-1-(2-(1H-imidazol-5-yl)acetyl)-5-(4-(4-fluorophenoxy)phenylcarbamoyl)pyrrolidin-3-ylcarbamate (1.01 g, 1.80 mmol, 67% yield). $^1$H-NMR (400 MHz, DMSO-d6): 11.92 (s, 1H), 10.06 (s, 1H), 7.92-7.42 (m, 4H), 7.40-7.28 (m, 5H), 7.23-7.17 (m, 2H), 7.06-6.94 (m, 5H), 5.02 (s, 2H), 4.50 (m, 1H), 4.28-4.13 (m, 1H), 3.85-3.41 (m, 4H), 2.38-2.02 (m, 2H). MS (EI) for C$_{30}$H$_{28}$FN$_5$O$_5$. found 557.9 (MH+).

Proceeding as in Example 1, but substituting benzyl (3R,5S)-5-(4-(4-fluorophenoxy)phenylcarbamoyl)pyrrolidin-3-ylcarbamate and 2-(1H-1,2,4-triazol-1-yl)acetic acid, gave benzyl (3R,5S)-1-(2-(1H-1,2,4-triazol-1-yl)acetyl)-5-(4-(4-fluorophenoxy)phenylcarbamoyl)pyrrolidin-3-ylcarbamate (1.57 g, 2.81 mmol, 72% yield).

Proceeding as in Example 1, but substituting (R)-2-(benzyloxy)-1-(5-(4-fluorophenoxy)-1H-benzo[d]imidazol-2-yl)ethanamine and 4-imidazoleacetic acid hydrochloride gave Compound 59, (R)—N-(2-(benzyloxy)-1-(5-(4-fluorophenoxy)-1H-benzo[d]imidazol-2-yl)ethyl)-2-(1H-imidazol-4-yl)acetamide (75 mg, 39%). $^1$H NMR (400 MHz, DMSO-d$_6$) δ 8.75 (d, J=8.0 Hz, 1H), 7.77 (s, 1H), 7.56 (d, J=9.2 Hz, 1H), 7.33-7.25 (m, 5H), 7.20-7.16 (m, 3H), 7.00-6.96 (m, 3H), 6.89 (dd, J=8.8, 2.0 Hz, 1H), 5.35-5.30 (m, 1H), 4.52 (s, 2H), 3.95-3.84 (m, 2H), 3.56-3.46 (m, 2H); ESI MS: m/z 486.2 (M+1).

Proceeding as in Example 1, but substituting acetic acid hydrochloride and (R)-2-(benzyloxy)-1-(5-(4-fluorophenoxy)-1H-benzo[d]imidazol-2-yl)ethanamine, gave Compound 60, (R)—N-(2-(benzyloxy)-1-(5-(4-fluorophenoxy)-1H-benzo[d]imidazol-2-yl)ethyl)acetamide (22 mg, 32%). $^1$H-NMR (400 MHz, CDCl$_3$): σ 7.50 (d, 1H), 7.38-7.30 (m, 5H), 7.13 (br s, 1H), 7.03-6.93 (m, 5H), 6.71 (d, 1H), 5.33 (q, 1H), 4.68-4.58 (m, 2H), 4.19 (dd, 1H), 3.86 (dd, 1H), 2.06 (s, 3H). MS (EI) for C$_{24}$H$_{22}$FN$_3$O$_3$. found 420.2 (MH+).

Proceeding as in Example 1, but substituting 2-(pyrimidin-5-yl)acetic acid hydrochloride and (S)-2-amino-3-(benzyloxy)-N-(4-(4-fluorophenoxy)phenyl)propanamide, gave Compound 250, (S)-3-(benzyloxy)-N-(4-(4-fluorophenoxy)phenyl)-2-(2-(pyrimidin-5-yl)acetamido)propanamide. $^1$H-NMR (400 MHz, CDCl$_3$): σ 9.17 (s, 1H), 8.72 (s, 1H), 8.36 (s, 1H), 7.42-7.21 (m, 7H), 7.06-6.91 (m, 5H), 6.68 (d, 1H), 4.70-4.63 (m, 3H), 4.57 (d, 1H), 3.98 (dd, 1H), 3.60-3.54 (m, 3H). MS (EI) for C$_{28}$H$_{25}$FN$_4$O$_4$. found 501.2 (MH+).

Proceeding as in Example 1, but substituting 2-(1H-1,2,3-triazol-1-yl)acetic acid hydrochloride and (2S,4R)-4-(3-chlorobenzyl)-N-(4-(4-fluorophenoxy)phenyl)pyrrolidine-2-carboxamide, gave Compound 263, (2S,4R)-1-(2-(1H-1,2,3-triazol-1-yl)acetyl)-4-(3-chlorobenzyl)-N-(4-(4-fluorophenoxy)phenyl)pyrrolidine-2-carboxamide.

$^1$H-NMR (400 MHz, CDCl$_3$): δ 9.00 (s, 1H), 7.80 (d, 2H), 7.40-7.20 (m, 6H), 6.90-6.80 (m, 6H), 5.30 (dd, 2H), 4.90 (d, 1H), 3.75 (m, 1H), 3.20 (m, 1H), 3.00-2.80 (m, 5H). MS (EI) for C$_{28}$H$_{25}$ClFN$_5$O$_3$ found 534 (MH+).

Proceeding as in Example 1, but substituting 2-(1H-1,2,3-triazol-1-yl)acetic acid hydrochloride and (2S,4R)-4-(2-fluorobenzyl)-N-(4-(4-fluorophenoxy)phenyl)pyrrolidine-2-carboxamide, gave Compound 264, (2S,4R)-1-(2-(1H-1,2,3-triazol-1-yl)acetyl)-4-(2-fluorobenzyl)-N-(4-(4-fluorophenoxy)phenyl)pyrrolidine-2-carboxamide.

$^1$H-NMR (400 MHz, CDCl$_3$): δ 8.96 (s, 1H), 7.76 (d, 2H), 7.43-7.39 (m, 2H), 7.26-7.19 (m, 2H), 7.14-6.85 (m, 8H), 5.29 (d, 1H), 5.18 (d, 1H), 4.76 (d, 1H), 3.74-3.68 (m, 1H), 3.33 (t, 1H), 3.03-2.77 (m, 3H), 2.58 (dd, 1H), 1.83-1.74 (m, 1H). MS (EI) for C$_{28}$H$_{25}$F$_2$N$_5$O$_3$ found 518 (MH+).

Proceeding as in Example 1, but substituting 2-(1H-1,2,4-triazol-1-yl)acetic acid and (2S,4R)—N-(4-(4-fluorophenoxy)phenyl)-4-(3-methylbenzyl)pyrrolidine-2-carboxamide, gave Compound 171, (2S,4R)-1-(2-(1H-1,2,4-triazol-1-yl)acetyl)-N-(4-(4-fluorophenoxy)phenyl)-4-(3-methylbenzyl)pyrrolidine-2-carboxamide. Major isomer: $^1$H-NMR (400 MHz, DMSO-D$_6$): σ 10.00 (s, 1H), 8.43 (s, 1H), 7.95 (s, 1H), 7.55 (d, 2H), 7.23-7.15 (m, 3H), 7.08-6.91 (m, 8H), 5.23 (q, 2H), 4.53-4.48 (m, 1H), 3.83-3.76 (m, 1H), 2.73-2.61 (m, 4H), 2.29 (s, 3H), 2.00-1.89 (m, 2H). MS (EI) for C$_{29}$H$_{28}$FN$_5$O$_3$. found 514.2 (MH+).

Proceeding as in Example 1, but substituting 2-(1H-1,2,3-triazol-1-yl)acetic acid and (2S,4R)-4-(3,4-difluorobenzyl)-N-(4-(4-fluorophenoxy)phenyl)pyrrolidine-2-carboxamide, gave Compound 226, (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide. Major isomer: $^1$H-NMR (400 MHz, DMSO-D$_6$): σ 9.97 (s, 1H), 8.00 (s, 1H), 7.72 (s, 1H), 7.56 (d, 2H), 7.42-7.31 (m, 2H), 7.24-7.06 (m, 3H), 7.04-6.91 (m, 4H), 5.44 (q, 2H), 4.55-4.49 (m, 1H), 3.88-3.78 (m, 1H), 3.42-3.33 (m, 2H), 2.80-2.68 (m, 3H), 2.02-1.94 (m, 2H). MS (EI) for C$_{28}$H$_{24}$F$_3$N$_5$O$_3$. found 536.2 (MH+).

Proceeding as in Example 1, but substituting 2-(2H-1,2,3-triazol-2-yl)acetic acid and (2S,4R)-4-(4-chlorobenzyl)-N-(4-(4-fluorophenoxy)phenyl)pyrrolidine-2-carboxamide, gave Compound 227, (2S,4R)-1-(2-(2H-1,2,3-triazol-2-yl)acetyl)-4-(4-chlorobenzyl)-N-(4-(4-fluorophenoxy)phenyl)pyrrolidine-2-carboxamide. $^1$H-NMR (400 MHz, CDCl$_3$): δ 9.14 (s, 1H), 7.72 (s, 1H), 7.42 (d, 2H), 7.29-7.26 (m, 2H), 7.12 (d, 2H), 7.00 (t, 2H), 6.94-6.89 (m, 4H), 5.28 (d, 2H), 4.85 (d, 1H), 3.51 (t, 1H), 3.15 (t, 1H), 2.96-2.85 (m, 2H), 2.68-2.62 (m, 2H), 1.70-1.61 (m, 1H). MS (EI) for C$_{28}$H$_{25}$ClFN$_5$O$_3$ found 534.2 (MH+).

Proceeding as in Example 1, but substituting 2-(1H-1,2,3-triazol-1-yl)acetic acid and (2S,4R)-4-(4-chlorobenzyl)-N-(4-(4-fluorophenoxy)phenyl)pyrrolidine-2-carboxamide, gave Compound 228, (2S,4R)-1-(2-(1H-1,2,3-triazol-1-yl)acetyl)-4-(4-chlorobenzyl)-N-(4-(4-fluorophenoxy)phenyl)pyrrolidine-2-carboxamide. $^1$H-NMR (400 MHz, CDCl$_3$): δ 8.94 (s, 1H), 7.79 (s, 1H), 7.56 (s, 1H), 7.43 (d, 2H), 7.30 (d, 2H), 7.14 (d, 2H), 7.00 (t, 2H), 6.94-6.89 (m, 4H), 5.28 (d, 1H), 5.14 (d, 1H), 4.78 (d, 1H), 3.68 (dd, 1H), 3.26 (t, 1H), 3.04-2.91 (m, 1H), 2.88 (dd, 1H), 2.71-2.59 (m, 2H), 1.73-1.65 (m, 1H). MS (EI) for C$_{28}$H$_{25}$ClFN$_5$O$_3$ found 534.2 (MH+).

Proceeding as in Example 1, but substituting 2-(1H-1,2,4-triazol-1-yl)acetic acid and (2S,4R)-4-(2-fluorobenzyl)-N-(4-(4-fluorophenoxy)phenyl)pyrrolidine-2-carboxamide, gave Compound 106, (2S,4R)-1-(2-(1H-1,2,4-triazol-1-yl)acetyl)-4-(2-fluorobenzyl)-N-(4-(4-fluorophenoxy)phenyl)pyrrolidine-2-carboxamide. Major isomer: $^1$H-NMR (400 MHz, CDCl$_3$): δ 9.00 (s, 1H), 8.24 (s, 1H), 7.98 (s, 1H), 7.42-7.38 (m, 2H), 7.27-7.18 (m, 3H), 7.13-6.86 (m, 7H), 5.06 (d, 1H), 4.98 (d, 1H), 4.78 (d, 1H), 3.72-3.66 (m, 1H), 3.31 (t, 1H), 3.004-2.92 (m, 1H), 2.90-2.77 (m, 2H), 2.60 (dd, 1H), 1.81-1.72 (m, 1H), 1.45-1.38 (m, 1H). MS (EI) for $C_{28}H_{25}F_2N_5O_3$ found 518 (MH+).

Proceeding as in Example 1, but substituting 2-(2H-1,2,3-triazol-2-yl)acetic acid and (2S,4R)-4-(2-fluorobenzyl)-N-(4-(4-fluorophenoxy)phenyl)pyrrolidine-2-carboxamide, gave Compound 107, (2S,4R)-1-(2-(2H-1,2,3-triazol-2-yl)acetyl)-4-(2-fluorobenzyl)-N-(4-(4-fluorophenoxy)phenyl)pyrrolidine-2-carboxamide. Major isomer: $^1$H-NMR (400 MHz, CDCl$_3$): δ 9.14 (s, 1H), 7.71 (s, 2H), 7.44-7.40 (m, 2H), 7.27-7.17 (m, 3H), 7.12-6.86 (m, 7H), 5.30 (d, 2H), 4.83 (d, 1H), 3.59-3.53 (m, 1H), 3.23 (t, 1H), 2.98-2.76 (m, 3H), 2.62 (dd, 1H), 1.78-1.69 (m, 1H). MS (EI) for $C_{28}H_{25}F_2N_5O_3$ found 518 (MH+).

Proceeding as in Example 1, but substituting 2-(1H-1,2,4-triazol-1-yl)acetic acid and (2S,4R)—N-(4-(4-fluorophenoxy)phenyl)-4-(2,4,6-trifluorobenzyl)pyrrolidine-2-carboxamide, gave Compound 108, (2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide. Major isomer: $^1$H-NMR (400 MHz, CDCl$_3$): δ 8.96 (s, 1H), 8.32 (s, 1H), 8.12 (s, 1H), 7.38 (d, 2H), 7.03-6.85 (m, 6H), 6.73-6.64 (m, 2H), 5.08 (d, 1H), 5.02 (d, 1H), 4.76 (d, 1H), 3.78-3.72 (m, 1H), 3.31 (t, 1H), 3.00-2.68 (m, 3H), 2.56 (dd, 1H), 1.82-1.72 (m, 1H). MS (EI) for $C_{28}H_{23}F_4N_5O_3$ found 554 (MH+).

Proceeding as in Example 1, but substituting 2-(2H-1,2,3-triazol-2-yl)acetic acid and (2S,4R)—N-(4-(4-fluorophenoxy)phenyl)-4-(2,4,6-trifluorobenzyl)pyrrolidine-2-carboxamide, gave Compound 169, (2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide. Major isomer: $^1$H-NMR (400 MHz, CDCl$_3$): δ 9.12 (s, 1H), 7.72 (s, 2H), 7.43-7.38 (m, 2H), 7.03-6.86 (m, 6H), 6.72-6.64 (m, 2H), 5.12 (s, 2H), 4.82 (d, 1H), 3.63-3.57 (m, 1H), 3.22 (t, 1H), 2.92-2.74 (m, 3H), 2.59 (dd, 1H), 1.78-1.69 (m, 1H). MS (EI) for $C_{28}H_{23}F_4N_5O_3$ found 554 (MH+).

Proceeding as in Example 1, but substituting 2-(1H-1,2,3-triazol-1-yl)acetic acid and (2S,4R)—N-(4-(4-fluorophenoxy)phenyl)-4-(2,4,6-trifluorobenzyl)pyrrolidine-2-carboxamide, gave Compound 170, (2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide. Major isomer: $^1$H-NMR (400 MHz, CDCl$_3$): δ 8.93 (s, 1H), 7.80-7.74 (m, 2H), 7.44-7.38 (m, 2H), 7.03-6.85 (m, 6H), 6.74-6.62 (m, 2H), 5.31 (d, 1H), 5.20 (d, 1H), 4.76 (d, 1H), 3.79-3.73 (m, 1H), 3.34 (t, 1H), 2.98-2.76 (m, 3H), 2.55 (dd, 1H), 1.83-1.74 (m, 1H). MS (EI) for $C_{28}H_{23}F_4N_5O_3$ found 554 (MH+).

Proceeding as in Example 1, but substituting 2-(1H-1,2,3-triazol-1-yl)acetic acid and (2S,4R)-4-(2,4-difluorobenzyl)-N-(4-(4-fluorophenoxy)phenyl)pyrrolidine-2-carboxamide, gave Compound 267, (2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide.

Proceeding as in Example 1, but substituting 2-(2H-1,2,3-triazol-2-yl)acetic acid and (2S,4R)-4-(3-chlorobenzyl)-N-(4-(4-fluorophenoxy)phenyl)pyrrolidine-2-carboxamide, gave Compound 268, (2S,4R)-1-(2-(2H-1,2,3-triazol-2-yl)acetyl)-4-(3-chlorobenzyl)-N-(4-(4-fluorophenoxy)phenyl)pyrrolidine-2-carboxamide.

Example 2

(2S,4S)-1-(2-(2H-1,2,3-triazol-2-yl)acetyl)-N-(4-(4-fluorophenoxy)phenyl)-4-thien-2-ylmethylpyrrolidine-2-carboxamide

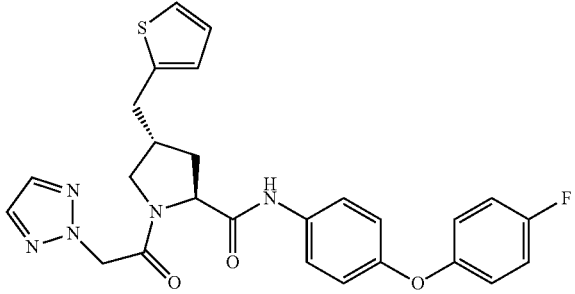 [SMILES: O=C(Nc1ccc(Oc2ccc(F)cc2)cc1)[C@@H]1C[C@@H](Cc2cccs2)CN1C(=O)Cn1nccn1]

Step (a): A flask was charged with (2S,4S)-4-((5-chlorothien-2-yl)methyl)-N-(4-(4-fluorophenoxy)phenyl)pyrrolidine-2-carboxamide (340 mg, 0.861 mmol), prepared as in Reference 6, palladium on carbon (10%, 50 mg), ammonium formate (200 mg, 3.33 mmol) and methanol (10 mL) and the mixture was heated to 80° C. The mixture was stirred at 80° C. for 30 minutes, filtered and then concentrated to give crude (2S,4S)—N-(4-(4-fluorophenoxy)phenyl)-4-(thien-2-ylmethyl)pyrrolidine-2-carboxamide (0.252 mg, 0.636 mmol), which was carried forward without further purification.

Step (b): A flask was charged with (2S,4S)—N-(4-(4-fluorophenoxy)phenyl)-4-(thien-2-ylmethyl)pyrrolidine-2-carboxamide (84 mg, 0.21 mmol), 2-(2H-1,2,3-triazol-2-yl)acetic acid (29 mg, 0.23 mmol), DIEA (0.5 mL, 2.9 mmol), HATU (81 mg, 0.21 mmol) and DMF (3 mL). The reaction mixture was stirred at ambient temperature for 20 minutes and quenched with saturated sodium bicarbonate (aq., 10 mL). The mixture was extracted with ethyl acetate (20 mL) and the extract was washed with deionized water (10 mL) and then brine (10 mL), dried over anhydrous sodium sulfate, filtered and concentrated. Product was purified from the residue by reverse phase HPLC to give Compound 64, (2S,4S)-1-(2-(2H-1,2,3-triazol-2-yl)acetyl)-N-(4-(4-fluorophenoxy)phenyl)-4-(thien-2-ylmethyl)pyrrolidine-2-carboxamide (6.1 mg, 0.012 mmol, 6% yield), as an off-white solid. $^1$H-NMR (400 MHz, CDCl$_3$): 9.15 (s, 1H), 7.72 (s, 2H), 7.44 (d, J=8.8 Hz, 2H), 7.18-7.16 (m, 1H), 7.03-6.82 (m, 8H), 5.29 (s, 2H), 4.86 (d, J=8.0 Hz), 3.63-3.58 (m, 1H), 3.25-3.20 (m, 1H), 3.12 (dd, J=13.6, 4.8 Hz, 1H), 3.01-2.87 (m, 2H), 2.73 (dd, J=12.4, 5.2 Hz, 1H), 1.75-1.68 (m, 1H). MS (EI) for $C_{26}H_{24}FN_5O_3S$. found 506.2 (MH+).

Example 3

(2S,4R)-1-(2-(1H-1,2,4-triazol-1-yl)acetyl)-N-(4-(4-fluorophenoxy)phenyl)-4-phenoxypyrrolidine-2-carboxamide

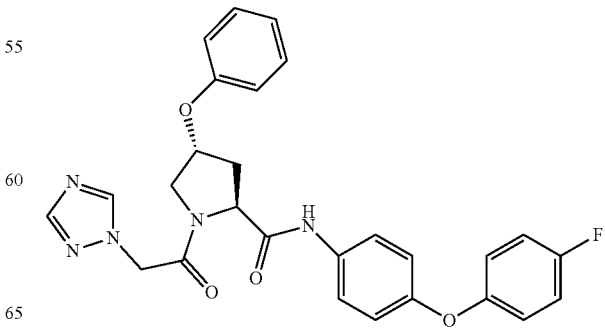

Diisopropylazodicarboxylate (0.111 mL, 0.551 mmol) was added to a flask charged with (2S,4R)-1-(2-(1H-1,2,4-triazol-1-yl)acetyl)-N-(4-(4-fluorophenoxy)phenyl)-4-hydroxypyrrolidine-2-carboxamide (233 mg, 0.551 mmol), prepared as in Reference 11, phenol (52 mg, 0.55 mmol), triphenylphosphine (145 mg, 0.551 mmol) and THF (3 mL). The reaction mixture was heated at 60° C. for 30 minutes and then concentrated. Product was purified from the residue by reverse phase HPLC to give Compound 259, (2S,4R)-1-(2-(1H-1,2,4-triazol-1-yl)acetyl)-N-(4-(4-fluorophenoxy)phenyl)-4-phenoxypyrrolidine-2-carboxamide (15 mg, 0.012 mmol, 5% yield), as an off-white solid. $^1$H-NMR (400 MHz, DMSO-d6): 10.17 (s, 1H), 8.45 (s, 1H), 7.94 (s, 1H), 7.58 (d, J=8.8 Hz, 2H), 7.37-7.32 (m, 2H), 7.21-7.17 (m, 2H), 7.04-6.95 (m, 7H). MS (EI) for $C_{27}H_{24}FN_5O_4$. found 502.3 (MH+).

Example 4

(S)-2-(2-(1H-imidazol-4-yl)acetamido)-3-(benzyloxy)-N-(4-(thiazol-2-yloxy)phenyl)propanamide

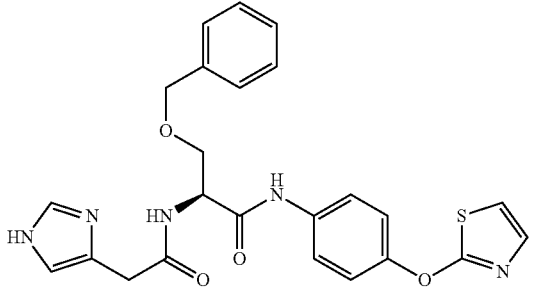 [SMILES: O=C(Cc1c[nH]cn1)N[C@@H](COCc1ccccc1)C(=O)Nc1ccc(Oc2nccs2)cc1]

A flask was charged with (S)-2-(2-(1H-imidazol-4-yl)acetamido)-3-(benzyloxy)-N-(4-(5-bromothiazol-2-yloxy)phenyl)propanamide (25 mg, 0.045 mmol), prepared as in Example 1, methanol (20 mL), ammonium formate (300 mg, 4.84 mmol), and palladium on carbon (10%, 100 mg) and the mixture was heated at 70° C. for 30 minutes. The mixture then was cooled to ambient temperature and filtered. Product was purified from the residue by chromatography (EtOAc to EtOAc/MeOH (9:1)) and then further purified by reverse phase HPLC to provide Compound 206, (S)-2-(2-(1H-imidazol-4-yl)acetamido)-3-(benzyloxy)-N-(4-(thiazol-2-yloxy)phenyl)propanamide (10.6 mg, 51%), as an off-white solid. $^1$H-NMR (400 MHz, DMSO-d6): 10.35 (s, 1H), 8.43 (d, J=6.4 Hz, 1H), 7.68 (d, J=11.2 Hz, 2H), 7.60 (s, 1H), 7.31-7.23 (m, 8H), 6.95 (s, 1H), 4.70-4.64 (m, 1H), 4.49 (s, 2H), 4.14-4.09 (m, 2H), 3.69-3.63 (m, 2H). MS (EI) for $C_{24}H_{23}N_5O_4S$. found 478.2 (MH+).

Example 5

(2S,4R)-1-(2-(1H-1,2,4-triazol-1-yl)acetyl)-4-(benzylamino)-N-(4-(4-fluorophenoxy)phenyl)pyrrolidine-2-carboxamide

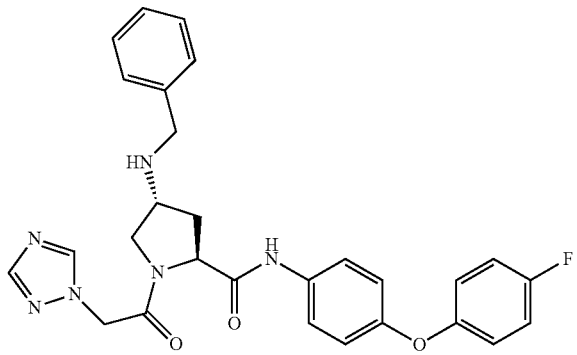 [SMILES: O=C(Nc1ccc(Oc2ccc(F)cc2)cc1)[C@@H]1C[C@@H](NCc2ccccc2)CN1C(=O)Cn1cncn1]

Step (a): A flask charged with benzyl (3R,5S)-1-(2-(1H-1,2,4-triazol-1-yl)acetyl)-5-(4-(4-fluorophenoxy)phenylcarbamoyl)pyrrolidin-3-ylcarbamate (1.20 g, 2.15 mmol), prepared as in Example 1, palladium on carbon (10%, 120 mg) and methanol (20 mL) and the mixture was placed under a hydrogen atmosphere (balloon). The mixture was stirred for 2 hours at ambient temperature, filtered and concentrated to give (2S,4R)-1-(2-(1H-1,2,4-triazol-1-yl)acetyl)-4-amino-N-(4-(4-fluorophenoxy)phenyl)pyrrolidine-2-carboxamide (1.44 g, 3.39 mmol), which was carried forward without further purification.

Step (b): Benzyl bromide (0.111 mL, 0.934 mmol) was added to a flask charged with (2S,4R)-1-(2-(1H-1,2,4-triazol-1-yl)acetyl)-4-amino-N-(4-(4-fluorophenoxy)phenyl)pyrrolidine-2-carboxamide (0.330 g, 0.778 mmol), DMF (3 mL) and potassium carbonate (0.429 g, 3.11 mmol). The reaction mixture was stirred at ambient temperature for 1 hour and then diluted with methanol (2 mL). Product was purified by reverse phase HPLC to give Compound 179, (2S,4R)-1-(2-(1H-1,2,4-triazol-1-yl)acetyl)-4-(benzylamino)-N-(4-(4-fluorophenoxy)phenyl)pyrrolidine-2-carboxamide (97 mg, 0.19 mmol, 24%) as an off-white solid. $^1$H-NMR (400 MHz, DMSO-d6): 10.08 (s, 1H), 8.44 (s, 1H), 7.95 (s, 1H), 7.57 (d, J=9.6 Hz, 2H), 7.38-7.30 (m, 4H), 7.26-7.16 (m, 3H), 7.03-6.93 (m, 4H), 5.24-5.21 (m, 2H), 4.53-4.48 (m, 1H), 3.85-3.79 (m, 1H), 3.75 (s, 2H), 3.51-3.45 (m, 2H), 3.17 (d, J=6.0 Hz, 1H), 2.15-2.00 (m, 2H). MS (EI) for $C_{28}H_{27}FN_6O_3$. found 515.2 (MH+).

Example 6

(2S,4S)-1-(2-(1H-1,2,4-Triazol-1-yl)acetyl)-4-(benzylamino)-N-(4-(4-fluorophenoxy)phenyl)pyrrolidine-2-carboxamide

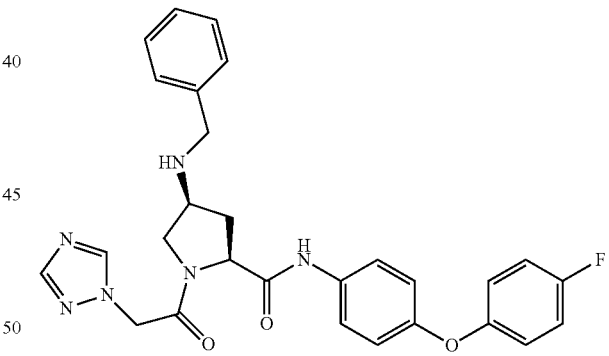

Step (a) Morpholine (10 mL) was added to a flask charged with the (9H-fluoren-9-yl)methyl (3S,5S)-1-(2-(1H-1,2,4-triazol-1-yl)acetyl)-5-(4-(4-fluorophenoxy)phenylcarbamoyl)pyrrolidin-3-ylcarbamate (0.859 g, 1.33 mmol), prepared as in prepared as in Example 1, and DMF (10 mL). The reaction mixture was stirred at ambient temperature for 30 minutes and then diluted with deionized water (20 mL). The dilution was extracted with ethyl acetate (60 mL) and the extract was washed with brine (30 mL), dried over anhydrous sodium sulfate, filtered and concentrated to give (2S,4S)-1(2-(1H-1,2,4-triazol-1-yl)acetyl)-4-amino-N-(4-(4-fluorophenoxy)phenyl)pyrrolidine-2-carboxamide (0.465 g, 1.10 mmol), which was carried forward without further purification. -

Step (b) Benzyl bromide (0.131 mL, 1.10 mmol) was added to a flask charged with (2S,4S)-1-(2-(1H-1,2,4-triazol-1-yl)acetyl)-4-amino-N-(4-(4-fluorophenoxy)phenyl)pyrrolidine-2-carboxamide (0.465 g, 1.10 mmol), DMF (10 mL), and $K_2CO_3$ (0.607 g, 4.40 mmol). The reaction mixture was stirred at ambient temperature for 30 minutes and then diluted with 1N hydrochloric acid (30 mL). The dilution was washed with ethyl acetate (30 mL). The aqueous layer was basified with 2N sodium hydroxide (40 mL) and then extracted with methylene chloride (40 mL). The extract was washed with brine (20 mL), dried over anhydrous sodium sulfate, filtered and concentrated. Product was purified from the residue by reverse phase HPLC to give Compound 80, (2S,4S)-1-(2-(1H-1,2,4-triazol-1-yl)acetyl)-4-(benzylamino)-N-(4-(4-fluorophenoxy)phenyl)pyrrolidine-2-carboxamide (126 mg, 0.245 mmol, 22%), as an off-white solid. $^1$H-NMR (400 MHz, $CDCl_3$): 12.08 (br. s, 1H), 11.13 (s, 1H), 9.05 (s, 1H), 8.24-8.16 (m, 1H), 7.99-7.94 (m, 1H), 7.41-7.20 (m, 4H), 7.04-6.82 (m, 7H), 5.21 (d, J=16.0 Hz, 1H), 5.00 (s, 1H), 4.93 (d, J=16.0 Hz, 1H), 4.74-4.57 (m, 1H), 3.96-5.59 (m, 3H), 3.14-3.07 (m, 2H), 2.62-2.00 (m, 2H). MS (EI) for $C_{28}H_{27}FN_6O_3$. found 515.2 (MH+).

Example 7

(2S,4S)-1-(2-(1H-1,2,4-Triazol-1-yl)acetyl)-4-((benzylamino)methyl)-N-(4-(4-fluorophenoxy)phenyl)pyrrolidine-2-carboxamide

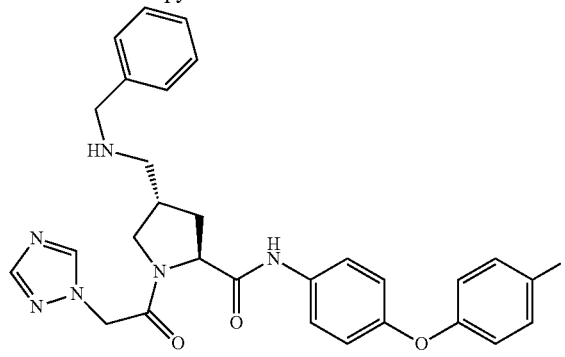

Benzyl bromide (0.067 mL, 0.56 mmol) was added to a mixture of (2S,4S)-1-(2-(1H-1,2,4-triazol-1-yl)acetyl)-4-aminomethyl-N-(4-(4-fluorophenoxy)phenyl)pyrrolidine-2-carboxamide hydrochloride salt (0.247 g, 0.564 mmol), DMF (10 mL) and $K_2CO_3$ (0.312 g, 2.26 mmol), prepared as in Reference 12. The reaction mixture was stirred at ambient temperature for 30 minutes and then diluted with 1N hydrochloric acid (30 mL). The dilution was washed with ethyl acetate (30 mL). The aqueous layer was basified with 2N sodium hydroxide (40 mL) and extracted with methylene chloride (40 mL). The extract was washed with brine (20 mL), dried over anhydrous sodium sulfate, filtered and concentrated. Product was purified from the residue by reverse phase HPLC to give Compound 262, (2S,4S)-1-(2-(1H-1,2,4-triazol-1-yl)acetyl)-4-((benzylamino)methyl)-N-(4-(4-fluorophenoxy)phenyl)pyrrolidine-2-carboxamide (23 mg, 0.044 mmol, 8%), as an off-white solid. $^1$H-NMR (400 MHz, DMSO-d6): 10.03 (s, 1H), 8.44 (s, 1H), 7.96 (s, 1H), 7.58 (d, J=7.6 Hz, 2H), 7.37-7.30 (m, 3H), 7.25-7.17 (m, 3H), 7.03-6.94 (m, 5H), 5.30, 5.19 (m, 2H), 4.49-4.46 (m, 2H), 3.89-3.84 (m, 1H), 3.74 (m, 2H), 2.69-2.52 (m, 2H), 2.16-1.87 (m, 2H). MS (EI) for $C_{29}H_{29}FN_6O_3$. found 529.3 (MH+).

Proceeding as in Example 7, but substituting 1,2-bis(bromomethyl)benzene and (2S,4R)-1-(2-(1H-1,2,4-triazol-1-yl)acetyl)-4-amino-N-(4-(4-fluorophenoxy)phenyl)pyrrolidine-2-carboxamide gave Compound 260, (2S,4R)-1-(2-(1H-1,2,4-triazol-1-yl)acetyl)-N-(4-(4-fluorophenoxy)phenyl)-4-(isoindolin-2-yl)pyrrolidine-2-carboxamide (47 mg, 0.088 mmol, 11%). $^1$H-NMR (400 MHz, DMSO-d6): 10.10 (s, 1H), 8.45 (s, 1H), 7.96 (s, 1H), 7.60 (d, J=10.0 Hz, 2H), 7.29-7.17 (m, 6H), 7.03-6.95 (m, 4H), 5.34-5.30 (m, 2H), 4.56-4.52 (m, 1H), 3.95 (s, 4H), 3.71-3.60 (m, 1H), 3.52-3.46 (m, 2H), 2.31-2.24 (m, 1H), 2.17-2.09 (m, 1H). MS (EI) for $C_{29}H_{27}FN_6O_3$. found 527.2 (MH+).

Proceeding as in Example 7, but substituting 2-(chloromethyl)thiophene and (2S,4R)-1-(2-(1H-1,2,4-triazol-1-yl)acetyl)-4-amino-N-(4-(4-fluorophenoxy)phenyl)pyrrolidine-2-carboxamide gave Compound 182, (2S,4R)-1-(2-(1H-1,2,4-triazol-1-yl)acetyl)-N-(4-(4-fluorophenoxy)phenyl)-4-(thien-3-ylmethylamino)pyrrolidine-2-carboxamide (30 mg, 0.058 mmol, 12%). $^1$H-NMR (400 MHz, DMSO-d6): 10.05 (s, 1H), 8.44 (s, 1H), 7.95 (s, 1H), 7.57 (d, J=9.6 Hz, 2H), 7.50-7.46 (m, 1H), 7.32-7.30 (m, 1H), 7.21-7.17 (m, 2H), 7.12-7.08 (m, 1H), 7.01-6.94 (m, 4H), 5.23 (s, 2H), 4.51-4.47 (m, 1H), 3.84-3.79 (m, 1H), 3.75 (s, 2H), 3.50-3.45 (m, 2H), 2.13-1.99 (m, 2H). MS (EI) for $C_{26}H_{25}FN_6O_3S$. found 521.2 (MH+).

Example 8

(2S,4R)-1-(2-(1H-Imidazol-5-yl)acetyl)-4-(benzylamino)-N-(4-(4-fluorophenoxy)phenyl)pyrrolidine-2-carboxamide

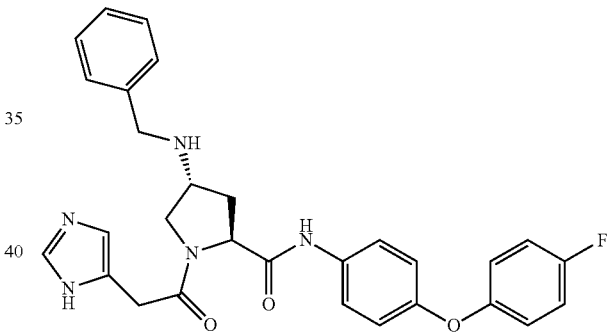

flask was charged with benzyl (3R,5S)-1-(2-(1H-imidazol-5-yl)acetyl)-5-(4-(4-fluorophenoxy)phenylcarbamoyl)pyrrolidin-3-ylcarbamate (800 mg, 1.43 mmol), prepared as in Example 1, palladium on carbon (10%, 80 mg) and methanol (30 mL) and the mixture was placed under a hydrogen atmosphere at 40 psi (parr shaker). The reaction was allowed to proceed for 4 hours and the mixture was filtered and concentrated. Product was purified from the residue by reverse phase HPLC to give (2S,4R)-1-(2-(1H-imidazol-5-yl)acetyl)-4-amino-N-(4-(4-fluorophenoxy)phenyl)pyrrolidine-2-carboxamide (516 mg, 1.22 mmol, 85%) as an off-white solid.

A flask was charged with (2S,4R)-1-(2-(1H-imidazol-5-yl)acetyl)-4-amino-N-(4-(4-fluorophenoxy)phenyl)pyrrolidine-2-carboxamide (150 mg, 0.302 nmol), benzaldehyde (0.031 mL, 0.30 mmol), methylene chloride (5 mL), acetic acid (0.140 mL, 2.45 mmol) and sodium triacetoxyborohydride (22 mg, 0.45 mmol). The reaction mixture was stirred at ambient temperature for 16 hours and then diluted with 2N sodium hydroxide (10 mL). The dilution was extracted with ethyl acetate (20 mL) and the extract was washed with brine (10 mL), dried over anhydrous sodium sulfate, filtered and concentrated. Product was purified from the residue by reverse phase HPLC to give Compound 173, (2S,4R)-1-(2-(1H-imidazol-5-yl)acetyl)-4-(benzylamino)-N-(4-(4-fluorophenoxy)phenyl)pyrrolidine-2-carboxamide (47 mg, 0.091 mmol, 30%), as an off-white solid. $^1$H-NMR (400 MHz, DMSO-D$_6$): 11.94 (s, 1H), 10.09 (s, 1H), 7.60 (d, 2H), 7.34-7.28 (m, 4H), 7.25-7.17 (m, 3H), 7.03-6.96 (m, 6H), 4.48 (t, 1H), 3.60-3.32 (m, 7H), 2.12-1.99 (m, 2H). MS (EI) for C$_{29}$H$_{28}$FN$_5$O$_3$. found 513.9 (MH+).

Example 9

(S)-2-(2-(1H-1,2,4-Triazol-1-yl)acetamido)-5-acetamido-N-(4-(4-fluorophenoxy)phenyl)pentanamide

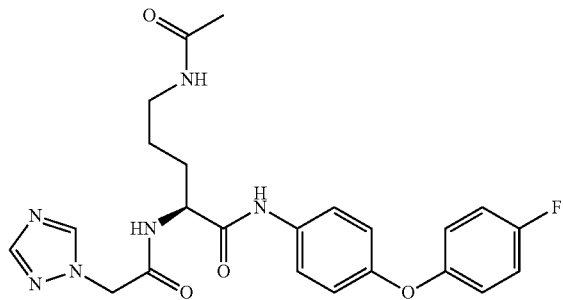 [SMILES: CC(=O)NCCC[C@H](NC(=O)Cn1cncn1)C(=O)Nc1ccc(Oc2ccc(F)cc2)cc1]

Step (a) A flask was charged with (S)-benzyl 4-(2-(1H-1,2,4-triazol-1-yl)acetamido)-5-(4-(4-fluorophenoxy)phenylamino)-5-oxopentylcarbamate (700 mg, 1.25 mmol), prepared as in Example 1, palladium on carbon (10%, 70 mg) and methanol (30 mL) and the mixture was placed under a hydrogen atmosphere (balloon). The mixture was stirred 16 hours at ambient temperature and then concentrated and filtered. Product was purified from the residue by reverse phase HPLC to give (S)-2-(2-(1H-1,2,4-triazol-1-yl)acetamido)-5-amino-N-(4-(4-fluorophenoxy)phenyl)pentanamide (420 mg, 0.985 mmol, 79%) as an off-white solid.

Step (b) DIEA (0.10 mL, 0.57 mmol) and acetic anhydride (0.025 mL, 0.27 mmol) was added to (S)-2-(2-(1H-1,2,4-triazol-1-yl)acetamido)-5-amino-N-(4-(4-fluorophenoxy)phenyl)pentanamide (115 mg, 0.269 mmol) in THF (5 mL). The reaction mixture was stirred for 2 hours and then concentrated. Product was purified from the residue by reverse phase HPLC to give Compound 254, (S)-2-(2-(1H-1,2,4-triazol-1-yl)acetamido)-5-acetamido-N-(4-(4-fluorophenoxy)phenyl)pentanamide (34 mg, 0.073 mmol, 27%) as an off-white solid. $^1$H-NMR (400 MHz, DMSO-d6): 10.21 (s, 1H), 8.75-8.73 (m, 1H), 8.47 (s, 1H), 7.85-7.82 (m, 1H), 7.63-7.58 (m, 2H), 7.24-7.18 (m, 2H), 7.04-6.92 (m, 4H), 4.99 (s, 2H), 4.46-4.38 (m, 1H), 3.12-3.01 (m, 2H), 1.80 (s, 3H), 1.79-1.37 (m, 4H). MS (EI) for C$_{23}$H$_{25}$FN$_6$O$_4$. found 469.1 (MH+).

Example 10

(2S,4S)-1-(2-(1H-1,2,4-triazol-1-yl)acetyl)-4-(4-fluorobenzyl)-N-(4-(4-fluorophenoxy)phenyl)pyrrolidine-2-carboxamide

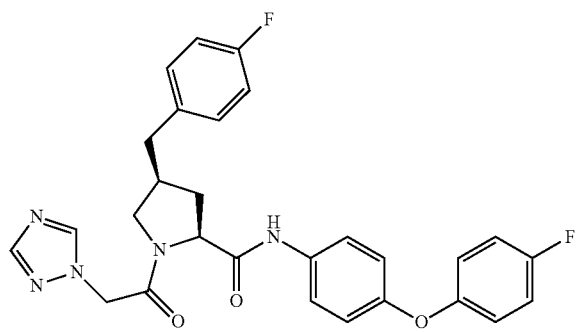 [SMILES: O=C(Nc1ccc(Oc2ccc(F)cc2)cc1)[C@@H]1C[C@H](Cc2ccc(F)cc2)CN1C(=O)Cn1cncn1]

Step (a): DMSO (3.78 mmol, 0.268 mL) was added dropwise to a flask charged with oxalyl chloride (0.165 mL, 1.89 mmol) and methylene chloride (4 mL) at −78° C. The mixture was stirred for 15 minutes and then (2S,4R)-1-(2-(1H-1,2,4-triazol-1-yl)acetyl)-N-(4-(4-fluorophenoxy)phenyl)-4-hydroxypyrrolidine-2-carboxamide (0.20 g, 0.47 mmol), prepared as in Reference 11, in methylene chloride (1 mL) was added via syringe. The reaction mixture then was stirred at 0° C. for 30 minutes and then quenched with triethylamine (2.0 mL, 15 mmol). The mixture was stirred for an additional 5 minutes and then saturated ammonium chloride (aq., 20 mL) was added. Product was purified from the organic layer by chromatography (EtOAc to EtOAc/MeOH (9:1)+1% NEt$_3$) to give (S)-1-(2-(1H-1,2,4-triazol-1-yl)acetyl)-N-(4-(4-fluorophenoxy)phenyl)-4-oxopyrrolidine-2-carboxamide (0.11 g, 0.25 mmol, 53% yield) as an oil.

Step (b) 4-Fluorobenzyl triphenylphosphine chloride (1 g, 2.46 mmol) in DMSO (2 mL) was added to a flask charged with sodium hydride (60% dispersion in oil, 124 mg, 3.10 mmol) and DMSO (2 mL). The reaction mixture was stirred at 70° C. for 3 hours and then (S)-1-(2-(1H-1,2,4-triazol-1-yl)acetyl)-N-(4-(4-fluorophenoxy)phenyl)-4-oxopyrrolidine-2-carboxamide (0.11 g, 0.25 mmol) in DMSO (2 mL) was added. The mixture was stirred for 16 hours at 70° C. and then quenched with saturated ammonium chloride (aq., 10 mL). This mixture was extracted with ethyl acetate (20 mL) and the extract was washed with deionized water (10 mL). Product was purified from the mixture directly by column chromatography (EtOAc to EtOAc/MeOH (9:1)+1% NEt$_3$) to give with (S)-1-(2-(1H-1,2,4-triazol-1-yl)acetyl)-4-(4-fluorobenzylidene)-N-(4-(4-fluorophenoxy)phenyl)pyrrolidine-2-carboxamide (15 mg, 0.027 mmol, 11% yield) as an oil.

Step (c) A flask was charged with (S)-1-(2-(1H-1,2,4-triazol-1-yl)acetyl)-4-(4-fluorobenzylidene)-N-(4-(4-fluorophenoxy)phenyl)pyrrolidine-2-carboxamide (15 mg, 0.027 mmol), palladium on carbon (10%, 50 mg) and methanol (5 mL) and the mixture was placed under a hydrogen atmosphere (balloon). The mixture was stirred for 2 hours at ambient temperature and then concentrated. Product was purified from the residue by chromatography (EtOAc to EtOAc/MeOH (9:1)+1% NEt$_3$) to give Compound 76, (2S,4S)-1-(2-(1H-1,2,4-triazol-1-yl)acetyl)-4-(4-fluorobenzyl)-N-(4-(4-fluorophenoxy)phenyl)pyrrolidine-2-carboxamide (10 mg, 0.019 mmol, 69%), as an off-white solid. $^1$H-NMR (400 MHz, CDCl3): 8.61 (s, 1H), 8.22 (s, 1H), 7.98 (s, 1H), 7.45 (d, J=10.0 Hz, 2H), 7.18-7.14 (m, 2H), 7.03-6.91 (m, 8H), 5.00 (m, 2H), 4.62 (m, 1H), 3.76 (dd, J=11.2, 7.6 Hz, 1H), 3.25 (m, 1H), 2.85 (dd, J=12.8, 7.6 Hz, 1H), 2.73 (dd, J=12.8, 7.6 Hz, 1H), 2.57 (m, 1H), 2.30 (m, 2H). MS (EI) for C$_{28}$H$_{25}$F$_2$N$_5$O$_3$. found 518.2 (MH+).

Example 11

(S)-Benzyl 4-(2-(1H-imidazol-4-yl)acetyl)-3-(4-(4-fluorophenoxy)phenylcarbamoyl)piperazine-1-carboxylate

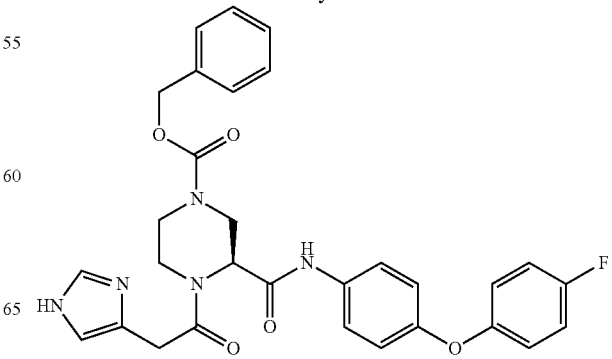

Step (a) A flask was charged with (S)-4-(benzyloxycarbonyl)-1-(tert-butoxycarbonyl)piperazine-2-carboxylic acid (1 g, 2.74 mmol), obtained commercially, 4-(4-fluorophenoxy) aniline (558 mg, 2.75 mmol), DIEA (3 mL, 17.3 mmol), HATU (1.15 g, 3.03 mmol) and DMF (8 mL). The reaction mixture was stirred at ambient temperature for 20 minutes and then quenched with saturated sodium bicarbonate (aq., 10 mL). The mixture was extracted with ethyl acetate (20 mL) and the extract was washed with deionized water (10 mL) and then brine (10 mL), dried over anhydrous sodium sulfate, filtered and concentrated to give (S)-4-benzyl 1-tert-butyl 2-(4-(4-fluorophenoxy)phenylcarbamoyl)piperazine-1,4-dicarboxylate (1.46 g, 2.75 mmol), which was carried forward without further purification.

Step (b) A flask was charged with (S)-4-benzyl 1-tert-butyl 2-(4-(4-fluorophenoxy)phenylcarbamoyl)piperazine-1,4-dicarboxylate (1.46 g, 2.75 mmol) and hydrogen chloride (4N in dioxane, 10 mL). The mixture was stirred at ambient temperature for 1 hour and then quenched with saturated sodium bicarbonate (aq., 40 mL). The mixture was extracted with ethyl acetate (30 mL) and the extract was washed with deionized water (10 mL) and then brine (10 mL), dried over anhydrous sodium sulfate, filtered and concentrated to give crude (S)-benzyl 3-(4-(4-fluorophenoxy)phenylcarbamoyl)piperazine-1-carboxylate (1.08 g, 2.41 mmol), which was carried forward without further purification.

Step (c) A flask was charged with (S)-benzyl 3-(4-(4-fluorophenoxy)phenylcarbamoyl)piperazine-1-carboxylate (1.08 g, 2.41 mmol), 4-imidazoleacetic acid hydrochloride (392 mg, 2.41 mmol), DIEA (1.0 mL, 5.8 mmol), HATU (1.01 g, 2.65 mmol) and DMF (5 mL). The reaction mixture was stirred at ambient temperature for 20 minutes and then quenched with saturated sodium bicarbonate (aq., 10 mL). The mixture was extracted with ethyl acetate (20 mL) and the extract was washed with deionized water (10 mL) and then brine (10 mL), dried over anhydrous sodium sulfate, filtered and concentrated. Product was purified from the residue by reverse phase HPLC to give Compound 257, (S)-benzyl 4-(2-(1H-imidazol-4-yl)acetyl)-3-(4-(4-fluorophenoxy)phenylcarbamoyl)piperazine-1-carboxylate (0.80 g, 1.43 mmol, 67% yield), as an off-white solid. $^1$H-NMR (400 MHz, CDCl$_3$): 10.27 (s, 1H), 9.18 (s, 1H), 7.60-7.49 (m, 3H), 7.47-7.21 (m, 5H), 7.06-6.91 (m, 6H), 5.45 (s, 1H), 5.17 (s, 2H), 5.09-5.00 (m, 2H), 4.04 (m, 2H), 4.09-3.97 (m, 2H), 3.81-3.73 (m, 2H), 3.46-3.77 (m, 1H), 3.17 (dd J=13.6, 4.8 Hz, 1H), 3.13-3.00 (m, 1H). MS (EI) for C$_{30}$H$_{28}$FN$_5$O$_5$. found 558.2 (MH+).

Example 12

(S)-1-(2-(1H-Imidazol-4-yl)acetyl)-4-benzyl-N-(4-(4-fluorophenoxy)phenyl)piperazine-2-carboxamide Step (a) A flask was charged with (S)-benzyl 4-(2-(1H-imidazol-4-yl)acetyl)-3-(4-(4-fluorophenoxy)phenylcarbamoyl)piperazine-1-carboxylate (0.80 g, 1.4 mmol), prepared as in Example 13, methanol (10 mL) and palladium on carbon (10%, 100 mg) and the mixture was stirred at ambient temperature. The reaction mixture was placed under a hydrogen atmosphere (balloon) for 14 hours and then exposed to air, filtered through celite and concentrated. Product was purified from residue by reverse phase HPLC to give (S)-1-(2-(1H-imidazol-4-yl)acetyl)-N-(4-(4-fluorophenoxy)phenyl)piperazine-2-carboxamide (0.5 g, 83% yield) as an off-white solid. $^1$H-NMR (400 MHz, CDCl$_3$): 10.02 (s, 1H), 9.20 (s, 1H), 7.63-7.56 (m, 2H), 7.52 (s, 1H), 7.05-6.93 (m, 7H), 5.34 (s, 1H), 4.05-4.00 (m, 1H), 3.94-3.86 (m, 1H), 3.78-3.71 (m, 2H), 3.28-3.20 (m, 1H), 3.00-2.94 (m, 1H), 2.89-2.74 (m, 2H), 2.61-2.53 (m, 1H). MS (EI) for C$_{22}$H$_{22}$FN$_5$O$_3$. found 424.2 (MH+).

Step (b) A flask was charged with (S)-1-(2-(1H-imidazol-4-yl)acetyl)-N-(4-(4-fluorophenoxy)phenyl)piperazine-2-carboxamide (107 mg, 0.252 mmol), benzaldehyde (0.154 mL, 1.51 mmol), methanol (10 mL) and sodium triacetoxyborohydride (534 mg, 2.52 mmol). The reaction mixture was stirred at ambient temperature for 30 minutes and then diluted with deionized water (15 mL). The mixture was washed with ethylene chloride (20 mL) and the aqueous layer was basified with 2N sodium hydroxide (40 mL) and extracted with ethyl acetate. The extract was washed with brine, dried over anhydrous sodium sulfate, filtered and concentrated to give Compound 175 (S)-1-(2-(1H-imidazol-4-yl)acetyl)-4-benzyl-N-(4-(4-fluorophenoxy)phenyl)piperazine-2-carboxamide (41 mg, 32% yield), as an off-white solid. $^1$H-NMR (400 MHz, CDCl$_3$): 10.23 (s, 1H), 7.63-7.18 (m, 8H), 7.02-6.82 (m, 7H), 5.42 (s, 1H), 4.02-3.90 (m, 1H), 3.88-3.80 (m, 1H), 3.78-3.61 (m, 2H), 3.58-3.34 (m, 2H), 3.08-2.97 (m, 1H), 2.78-2.64 (m, 1H), 2.28-2.18 (m, 1H), 2.11-2.00 (m, 1H). MS (EI) for C$_{29}$H$_{28}$FN$_5$O$_3$. found 514.3 (MH+).

Proceeding as in Examples 11 and 12, but substituting 2-(1H-1,2,4-triazol-1-yl)acetic acid hydrochloride and (S)-benzyl 4-(2-(1H-1,2,4-triazol-1-yl)acetyl)-3-(4-(4-fluorophenoxy)phenylcarbamoyl)piperazine-1-carboxylate, respectively, gave Compound 261, (S)-1-(2-(1H-1,2,4-triazol-1-yl)acetyl)-4-benzyl-N-(4-(4-fluorophenoxy)phenyl)piperazine-2-carboxamide (67.9 mg, 19%). Major isomer: $^1$H-NMR (400 MHz, DMSO-D$_6$): σ 9.83 (s, 1H), 8.45 (s, 1H), 7.96 (s, 1H), 7.51 (d, 2H), 7.28-7.13 (m, 7H), 7.06-6.98 (m, 4H), 5.49 (d, 1H), 5.28 (d, 1H), 4.91-4.89 (m, 1H), 3.68-3.38 (m, 5H), 2.92-2.85 (m, 1H), 2.25-2.17 (m, 2H). MS (EI) for C$_{28}$H$_{27}$FN$_6$O$_3$. found 515.3 (MH+).

Example 13

(2S,4R)-1-(2-(1H-1,2,3-triazol-1-yl)acetyl)-4-(4-fluorobenzyl)-N-(4-(4-fluorophenoxy)phenyl)pyrrolidine-2-carboxamide

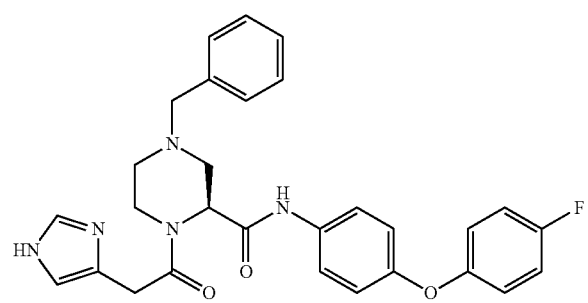 [SMILES: O=C(Nc1ccc(Oc2ccc(F)cc2)cc1)[C@@H]1CN(Cc2ccccc2)CCN1C(=O)Cc1c[nH]cn1]

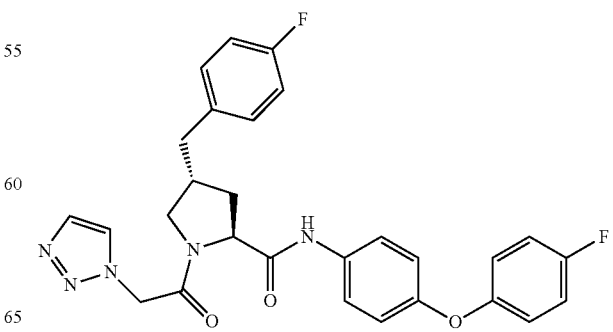

A flask was charged with (2S,4R)-1-(tert-butoxycarbonyl)-4-hydroxypyrrolidine-2-carboxylic acid (0.310 g, 0.963 mmol), HATU (0.439 g, 1.16 mmol), 4-fluorophenoxyaniline (0.196 g, 0.963 mmol), DIEA (1.0 mL, 5.63 mmol) and DMF (5 mL). The reaction mixture was stirred at ambient temperature for 30 minutes and quenched with saturated sodium bicarbonate (aq., 20 mL). The mixture was extracted with ethyl acetate (60 mL) and the extract was washed with deionized water (30 mL) and then brine (30 mL), dried over anhydrous sodium sulfate, filtered and concentrated. The residue was used without further purification.

The residue was combined with hydrogen chloride (4N in dioxane, 10 mL) and the mixture was stirred at ambient temperature for 1 hour and then quenched with saturated sodium bicarbonate (aq., 50 mL). The mixture was extracted with ethyl acetate (30 mL) and the extract was washed with deionized water (30 mL) and then brine (30 mL), dried over anhydrous sodium sulfate, filtered and concentrated to provide crude (2S,4R)—N-(4-(4-fluorophenoxy)phenyl)-4-hydroxypyrrolidine-2-carboxamide.

A flask was charged with crude (2S,4R)—N-(4-(4-fluorophenoxy)phenyl)-4-hydroxypyrrolidine-2-carboxamide (0.452 g), 2-(1H-1,2,3-triazol-1-yl)acetic acid (169 g, 1.33 mmol), DIEA (3.0 mL, 17 mmol), HATU (0.506 g, 1.33 mmol) and DMF (10 mL). The reaction mixture was stirred at ambient temperature for 1 hour and then quenched with saturated sodium bicarbonate (aq., 10 mL). The mixture was extracted with ethyl acetate (20 mL) and the extract was washed with deionized water (10 mL) and then brine (10 mL), dried over anhydrous sodium sulfate, filtered and concentrated. Product was purified from the residue was purified by reverse phase HPLC to provide Compound 75, (2S,4R)-1-(2-(1H-1,2,3-triazol-1-yl)acetyl)-4-(4-fluorobenzyl)-N-(4-(4-fluorophenoxy)phenyl)pyrrolidine-2-carboxamide (0.115 g, 0.222 mmol, 23% yield). $^1$H-NMR (400 MHz, CDCl3): δ 8.95 (s, 1H), 7.77 (d, 2H), 7.43 (d, 2H), 7.16 (dd, 2H), 7.04-6.98 (m, 4H), 6.94-6.89 (m, 3H), 5.28 (d, 1H), 5.14 (d, 1H), 4.80 (d, 1H), 4.12 (dd, 1H), 3.68 (dd, 1H), 3.26 (t, 1H), 3.02-2.92 (m, 1H), 2.89 (dd, 1H), 2.71-2.59 (m, 1H), 2.74-2.65 (m, 1H). MS (EI) for $C_{28}H_{25}F_2N_5O_3$ found 518.2 (MH+).

Example 14

(2S,4R)-1-(2-(2H-1,2,3-triazol-2-yl)acetyl)-4-(4-fluorobenzyl)-N-(4-(4-fluorophenoxy)phenyl)pyrrolidine-2-carboxamide

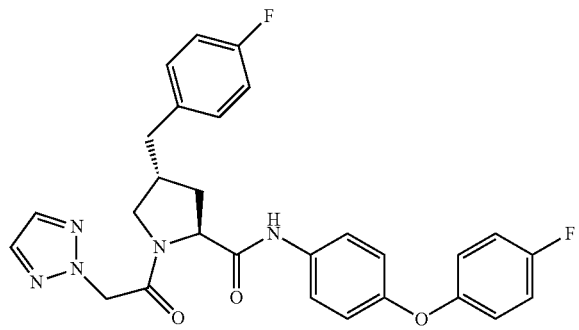 [SMILES: O=C(Nc1ccc(Oc2ccc(F)cc2)cc1)[C@@H]1C[C@@H](Cc2ccc(F)cc2)CN1C(=O)Cn1nccn1]

A round bottom flask was charged with (2S,4R)-4-(4-fluorobenzyl)-N-(4-(4-fluorophenoxy)phenyl)pyrrolidine-2-carboxamide hydrochloride (150 mg, 0.37 mmole, 1 eq), prepared as in Reference 6, 2H-1,2,3-triazole-2-ylacetic acid (51 mg, 0.40 mmole, 1.1 eq), HATU (152 mg, 0.40 mmole, 1.1 eq) and DMF (1 mL). DIEA (195 μL, 1.11 mmole, 3 eq) was added and the mixture stirred at ambient temperature for 18 hours. The reaction mixture was partitioned between ethyl acetate and deionized water. The aqueous layer was separated and extracted twice with ethyl acetate. The combined organics were washed with 5% lithium chloride (3×5 mL), 1N sodium bicarbonate (2×5 mL) and then deionized water (2×5 mL) and concentrated in vacuo. Product was purified from the residue via flash chromatography (silica, 5% MeOH, 95% EtOAc). Clean fractions were combined and concentrated in vacuo to afford Compound 50, (2S,4R)-1-(2-(2H-1,2,3-triazol-2-yl)acetyl)-4-(4-fluorobenzyl)-N-(4-(4-fluorophenoxy)phenyl)pyrrolidine-2-carboxamide (171 mg, 89% yield), as a white solid. Major isomer: $^1$H-NMR (400 MHz, DMSO-$D_6$): σ 9.97 (s, 1H), 7.80 (s, 2H), 7.58-7.51 (m, 2H), 7.34-7.07 (m, 6H), 7.04-6.90 (m, 4H), 5.48 (q, 2H), 4.53-4.46 (m, 1H), 3.85-3.76 (m, 1H), 2.77-2.61 (m, 3H), 2.03-1.86 (m, 2H). MS (EI) for $C_{28}H_{25}F_2N_5O_3$. found 517.9 (MH+).

Example 15

(S)-3-(Benzyloxy)-2-(2-chloroacetamido)-N-(4-(4-fluorophenoxy)phenyl)propanamide

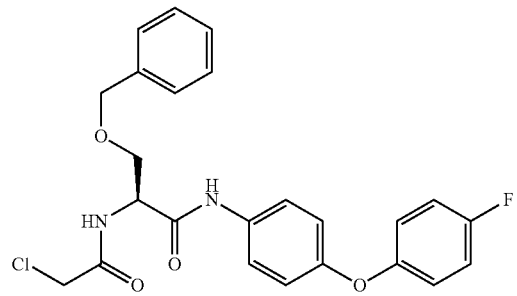 [SMILES: O=C(CCl)N[C@@H](COCc1ccccc1)C(=O)Nc1ccc(Oc2ccc(F)cc2)cc1]

Chloroacetyl chloride (0.92 g, 12.20 mmol) was added slowly to a flask charged with a solution of (S)-2-amino-3-(benzyloxy)-N-(4-(4-fluorophenoxy)phenyl)propanamide bis-trifluoroacetic acid salt (4.95 g, 8.13 mmol), DIEA (7.1 mL, 40.1 mmol) and methylene chloride (100 mL) at 0° C. The mixture was stirred at 0° C. for 1 hour and then diluted with methylene chloride (100 mL) and water (100 mL). The dilution was dried over sodium sulfate, filtered and concentrated. Product was purified from the residue by chromatography (Hex/EtOAc 2:1 to 1:1) to give Compound 136, (S)-3-(benzyloxy)-2-(2-chloroacetamido)-N-(4-(4-fluorophenoxy)phenyl)propanamide (2.58 g, 5.65 mmol), as an off-white solid. 1H-NMR (400 MHz, CDCl$_3$): 8.41 (s, 1H), 7.57 (d, 1H, J=6.4 Hz), 7.39-7.33 (m, 7H), 7.04-6.91 (m, 6H), 4.71-4.67 (m, 2H), 4.58 (d, 1H, J=11.6 Hz), 4.10 (s, 2H), 4.00 (dd, 1H, J=10.0, 4.4 Hz), 3.63 (t, 1H, J=8.8 Hz). MS (EI) for $C_{24}H_{22}ClFN_2O_4$. found 457.0 (MH+).

Example 16

(S)-3-(Benzyloxy)-N-(4-(4-fluorophenoxy)phenyl)-2-(2-(2-methyl-1H-imidazol-1-yl)acetamido)propanamide

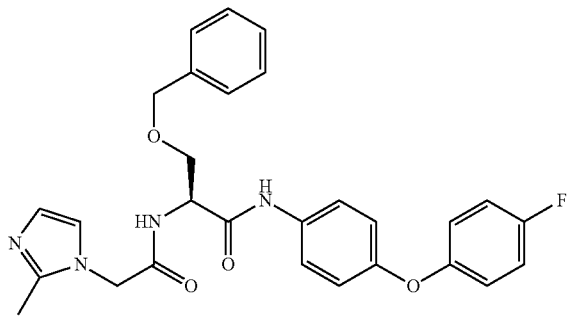 [SMILES: Cc1nccn1CC(=O)N[C@@H](COCc1ccccc1)C(=O)Nc1ccc(Oc2ccc(F)cc2)cc1]

2-Methylimidazole (64 mg, 0.786 mmol) was added to a flask charged with (S)-3-(benzyloxy)-2-(2-chloroacetamido)-N-(4-(4-fluorophenoxy)phenyl)propanamide (150 mg, 0.393 mmol), prepared as in Example 15, and DMF (3 mL). The mixture was stirred at 40° C. for 30 minutes then diluted with ethyl acetate (20 mL). The dilution was washed with brine (20 mL), dried over sodium sulfate, filtered and concentrated. Product was purified from the residue by reverse phase HPLC to provide Compound 160, (S)-3-(benzyloxy)-N-(4-(4-fluorophenoxy)phenyl)-2-(2-(2-methyl-1H-imidazol-1-yl)acetamido)propanamide (100.8 mg, 0.201 mmol, 51% yield) as an off-white solid. $^1$H-NMR (400 MHz, CDCl$_3$): 8.38 (s, 1H), 7.38-7.21 (m, 7H), 7.05-6.89 (m, 7H), 6.45 (d, 1H), 4.66 (d, 1H), 4.61 (s, 2H), 4.55 (d, 1H), 3.91 (dd, 1H), 3.55 (t, 1H), 2.38 (s, 3H). MS (EI) for $C_{28}H_{27}FN_4O_4$. found 502.9 (MH+).

Proceeding as in Example 16, but substituting imidazole, gave Compound 134, (S)-2-(2-(1H-imidazol-1-yl)acetamido)-3-benzyloxy-N-(4-(4-fluorophenoxy)phenyl)propanamide (57 mg, 45%); Major isomer: $^1$H-NMR (400 MHz, DMSO-D$_6$): σ 10.25 (br s, 1H), 8.71-8.67 (d, 1H), 7.63-7.57 (m, 3H), 7.33-7.27 (m, 5H), 7.23-7.19 (t, 2H), 7.09-7.08 (s, 1H), 6.97-6.86 (m, 4H), 6.86 (s, 1H), 4.76 (s, 2H), 4.74-4.69 (m, 1H), 4.53 (s, 2H), 3.68-3.67 (d, 2H). MS (EI) for $C_{27}H_{25}FN_4O_4$. found 489.0 (MH+).

Proceeding by methods analogous to the those described above, the following compounds were prepared: Compound 269, N-(2-oxo-1-{[(phenylmethyl)oxy]methyl}-2-{[4-(phenyloxy)phenyl]amino}ethyl)acetamide; Compound 270, 4-(methyloxy)-N-(2-oxo-1-{[(phenylmethyl)oxy]methyl}-2-{[4-(phenyloxy)phenyl]amino}ethyl)benzamide; 4-benzyloxy-N-(2-oxo-1-{[(phenylmethyl)oxy]methyl}-2-{[4-(phenyloxy)phenyl]amino}ethyl)phenylacetamide; Compound 272, 2-bromo-5-(methyloxy)-N-(2-oxo-1-{[(phenylmethyl)oxy]methyl}-2-{[4-(phenyloxy)phenyl]amino}ethyl)benzamide; Compound 273, N-(2-oxo-1-{[(phenylmethyl)oxy]methyl}-2-{[4-(phenyloxy)phenyl]amino}ethyl)butanamide; Compound 274, 2-chloro-N-(2-oxo-1-{[(phenylmethyl)oxy]methyl}-2-{[4-(phenyloxy)phenyl]amino}ethyl)benzamide; Compound 275, 3-chloro-N-(2-oxo-1-{[(phenylmethyl)oxy]methyl}-2-{[4-(phenyloxy)phenyl]amino}ethyl)benzamide; Compound 276, 4-chloro-N-(2-oxo-1-{[(phenylmethyl)oxy]methyl}-2-{[4-(phenyloxy)phenyl]amino}ethyl)benzamide; Compound 277, N-(2-oxo-1-{[(phenylmethyl)oxy]methyl}-2-{[4-(phenyloxy)phenyl]amino}ethyl)cyclopropylamide; Compound 278, N-(2-oxo-1-{[(phenylmethyl)oxy]methyl}-2-{[4-(phenyloxy)phenyl]amino}ethyl)-3-cyclopentylpropanamide; Compound 279, 3,4-dimethyl-N-(2-oxo-1-{[(phenylmethyl)oxy]methyl}-2-{[4-(phenyloxy)phenyl]amino}ethyl)benzamide; Compound 280, N-(2-oxo-1-{[(phenylmethyl)oxy]methyl}-2-{[4-(phenyloxy)phenyl]amino}ethyl)-2,5-dimethoxyphenylacetamide; Compound 281, 4-(ethyloxy)-N-(2-oxo-1-{[(phenylmethyl)oxy]methyl}-2-{[4-(phenyloxy)phenyl]amino}ethyl)benzamide; Compound 282, N-(3-(benzyloxy)-1-oxo-1-(4-phenoxyphenylamino)propan-2-yl)-2-ethylhexanamide; Compound 283, N-(2-oxo-1-{[(phenylmethyl)oxy]methyl}-2-{[4-(phenyloxy)phenyl]amino}ethyl)furan-2-carboxamide; Compound 284, N-(2-oxo-1-{[(phenylmethyl)oxy]methyl}-2-{[4-(phenyloxy)phenyl]amino}ethyl)-2-methoxyacetamide; Compound 285, N-(2-oxo-1-{[(phenylmethyl)oxy]methyl}-2-{[4-(phenyloxy)phenyl]amino}ethyl)-3-methoxyphenylacetamide; Compound 286, 2-methyl-N-(2-oxo-1-{[(phenylmethyl)oxy]methyl}-2-{[4-(phenyloxy)phenyl]amino}ethyl)pentanamide; Compound 287, 4-methyl-N-(2-oxo-1-{[(phenylmethyl)oxy]methyl}-2-{[4-(phenyloxy)phenyl]amino}ethyl)pentanamide; Compound 288, N-(2-oxo-1-{[(phenylmethyl)oxy]methyl}-2-{[4-(phenyloxy)phenyl]amino}ethyl)naphthalene-2-carboxamide; Compound 289, N-(2-oxo-1-{[(phenylmethyl)oxy]methyl}-2-{[4-(phenyloxy)phenyl]amino}ethyl)phenoxyacetamide; Compound 290, N-(2-oxo-1-{[(phenylmethyl)oxy]methyl}-2-{[4-(phenyloxy)phenyl]amino}ethyl)-2-(phenyloxy)pyridine-3-carboxamide; Compound 291, 3,4,5-tris(methyloxy)-N-(2-oxo-1-{[(phenylmethyl)oxy]methyl}-2-{[4-(phenyloxy)phenyl]amino}ethyl)benzamide; Compound 292, N-(2-oxo-1-{[(phenylmethyl)oxy]methyl}-2-{[4-(phenyloxy)phenyl]amino}ethyl)thiophene-2-carboxamide; Compound 293, N-(2-oxo-1-{[(phenylmethyl)oxy]methyl}-2-{[4-(phenyloxy)phenyl]amino}ethyl)thien-2-ylacetamide; Compound 294, 4-(dimethylamino)-N-(2-oxo-1-{[(phenylmethyl)oxy]methyl}-2-{[4-(phenyloxy)phenyl]amino}ethyl)benzamide; Compound 295, N-(2-oxo-1-{[(phenylmethyl)oxy]methyl}-2-{[4-(phenyloxy)phenyl]amino}ethyl)hexanamide; Compound 296, 2-chloro-N-(2-oxo-1-{[(phenylmethyl)oxy]methyl}-2-{[4-(phenyloxy)phenyl]amino}ethyl)pyridine-3-carboxamide; Compound 297, 3-chloro-N-(2-oxo-1-{[(phenylmethyl)oxy]methyl}-2-{[4-(phenyloxy)phenyl]amino}ethyl)-1-benzothiophene-2-carboxamide; Compound 298, N-(2-oxo-1-{[(phenylmethyl)oxy]methyl}-2-{[4-(phenyloxy)phenyl]amino}ethyl)pent-4-enamide; Compound 299, 3-chloro-2-fluoro-N-(2-oxo-1-{[(phenylmethyl)oxy]methyl}-2-{[4-(phenyloxy)phenyl]amino}ethyl)benzamide; Compound 300, N-(2-oxo-1-{[(phenylmethyl)oxy]methyl}-2-{[4-(phenyloxy)phenyl]amino}ethyl)-4-phenylbutanamide; Compound 301, N-(2-oxo-1-{[(phenylmethyl)oxy]methyl}-2-{[4-(phenyloxy)phenyl]amino}ethyl)-2-bromophenylacetamide; Compound 302, N-(2-oxo-1-{[(phenylmethyl)oxy]methyl}-2-{[4-(phenyloxy)phenyl]amino}ethyl)-1-[4-(trifluoromethyl)pyrimidin-2-yl]piperidine-4-carboxamide; Compound 303, N-(2-oxo-1-{[(phenylmethyl)oxy]methyl}-2-{[4-(phenyloxy)phenyl]amino}ethyl)-2-methoxyethoxyacetamide; Compound 304, N-(2-oxo-1-{[(phenylmethyl)oxy]methyl}-2-{[4-(phenyloxy)phenyl]amino}ethyl)-3-(4-methoxyphenyl)propanamide; Compound 305, N-(2-oxo-1-{[(phenylmethyl)oxy]methyl}-2-{[4-(phenyloxy)phenyl]amino}ethyl)-2-acetylamino-4-methylthiazol-5-ylsulfonamide; Compound 306, 4-(methylthio)-N-(2-oxo-1-{[(phenylmethyl)oxy]methyl}-2-{[4-(phenyloxy)phenyl]amino}ethyl)

benzamide; Compound 307, N-(2-oxo-1-{[(phenylmethyl)oxy]methyl}-2-{[4-(phenyloxy)phenyl]amino}ethyl)-2-(methylthio)acetamide; Compound 308, 5-fluoro-2-(methyloxy)-N-(2-oxo-1-{[(phenylmethyl)oxy]methyl}-2-{[4-(phenyloxy)phenyl]amino}ethyl)benzamide; Compound 309, 2-methyl-4-(methyloxy)-N-(2-oxo-1-{[(phenylmethyl)oxy]methyl}-2-{[4-(phenyloxy)phenyl]amino}ethyl)benzamide; Compound 310, 5-oxo-N-(2-oxo-1-{[(phenylmethyl)oxy]methyl}-2-{[4-(phenyloxy)phenyl]amino}ethyl)hexanamide; Compound 311, 4-bromo-2-methyl-N-(2-oxo-1-{[(phenylmethyl)oxy]methyl}-2-{[4-(phenyloxy)phenyl]amino}ethyl)benzamide; Compound 312, 4-oxo-N-(2-oxo-1-{[(phenylmethyl)oxy]methyl}-2-{[4-(phenyloxy)phenyl]amino}ethyl)-4-(2-thienyl)butanamide; Compound 313, N-(2-oxo-1-{[(phenylmethyl)oxy]methyl}-2-{[4-(phenyloxy)phenyl]amino}ethyl)-2-(phenylthio)acetamide; Compound 314, N-(2-oxo-1-{[(phenylmethyl)oxy]methyl}-2-{[4-(phenyloxy)phenyl]amino}ethyl)-2-(1H-pyrrol-1-yl)benzamide; Compound 315, N-(2-oxo-1-{[(phenylmethyl)oxy]methyl}-2-{[4-(phenyloxy)phenyl]amino}ethyl)-2-[2-(methoxy)ethoxy]ethoxyacetamide; Compound 316, 3,5-bis(methyloxy)-N-(2-oxo-1-{[(phenylmethyl)oxy]methyl}-2-{[4-(phenyloxy)phenyl]amino}ethyl)benzamide; Compound 317, N-(2-oxo-1-{[(phenylmethyl)oxy]methyl}-2-{[4-(phenyloxy)phenyl]amino}ethyl)-3-cyclohexylpropanamide; Compound 318, 5-oxo-N-(2-oxo-1-{[(phenylmethyl)oxy]methyl}-2-{[4-(phenyloxy)phenyl]amino}ethyl)-5-phenylpentanamide; Compound 319, N-(2-oxo-1-{[(phenylmethyl)oxy]methyl}-2-{[4-(phenyloxy)phenyl]amino}ethyl)-4-acetylphenoxyacetamide; Compound 320, 4-[3,4-bis(methyloxy)phenyl]-N-(2-oxo-1-{[(phenylmethyl)oxy]methyl}-2-{[4-(phenyloxy)phenyl]amino}ethyl)butanamide; Compound 321, N-(2-oxo-1-{[(phenylmethyl)oxy]methyl}-2-{[4-(phenyloxy)phenyl]amino}ethyl)-5-[3-(trifluoromethyl)phenyl]furan-2-carboxamide; Compound 322, N-(2-oxo-1-{[(phenylmethyl)oxy]methyl}-2-{[4-(phenyloxy)phenyl]amino}ethyl)-3-(1,3-dioxoisoindolin-2-yl)propanamide; Compound 323, 5-oxo-N-(2-oxo-1-{[(phenylmethyl)oxy]methyl}-2-{[4-(phenyloxy)phenyl]amino}ethyl)-5-(2-thienyl)pentanamide; Compound 324, N-(2-oxo-1-{[(phenylmethyl)oxy]methyl}-2-{[4-(phenyloxy)phenyl]amino}ethyl)-2-oxo-2-phenylacetamide; Compound 325, N-(2-oxo-1-{[(phenylmethyl)oxy]methyl}-2-{[4-(phenyloxy)phenyl]amino}ethyl)-4-(2-thienyl)butanamide; Compound 326, 5-nitro-N-(2-oxo-1-{[(phenylmethyl)oxy]methyl}-2-{[4-(phenyloxy)phenyl]amino}ethyl)furan-2-carboxamide; Compound 328, N-(2-oxo-1-{[(phenylmethyl)oxy]methyl}-2-{[4-(phenyloxy)phenyl]amino}ethyl)-1,3-benzodioxol-5-ylacetamide; Compound 329, 1-(2-chloro-6-fluorophenyl)-N-(2-oxo-1-{[(phenylmethyl)oxy]methyl}-2-{[4-(phenyloxy)phenyl]amino}ethyl)cyclopentanecarboxamide; Compound 330, 4-fluoro-N-(2-oxo-1-{[(phenylmethyl)oxy]methyl}-2-{[4-(phenyloxy)phenyl]amino}ethyl)-2-(trifluoromethyl)benzamide; Compound 331, N-(2-oxo-1-{[(phenylmethyl)oxy]methyl}-2-{[4-(phenyloxy)phenyl]amino}ethyl)-2-(pyrimidin-2-ylthio)acetamide; Compound 332, 2,5-bis(methyloxy)-N-(2-oxo-1-{[(phenylmethyl)oxy]methyl}-2-{[4-(phenyloxy)phenyl]amino}ethyl)benzamide; Compound 333, 4-(methylsulfonyl)-N-(2-oxo-1-{[(phenylmethyl)oxy]methyl}-2-{[4-(phenyloxy)phenyl]amino}ethyl)benzamide; Compound 334, 2-chloro-4-(methylsulfonyl)-N-(2-oxo-1-{[(phenylmethyl)oxy]methyl}-2-{[4-(phenyloxy)phenyl]amino}ethyl)benzamide; Compound 335, N-(2-oxo-1-{[(phenylmethyl)oxy]methyl}-2-{[4-(phenyloxy)phenyl]amino}ethyl)-2-(4-oxo-2-thioxothiazolidin-3-yl)acetamide; Compound 336, N-(2-oxo-1-{[(phenylmethyl)oxy]methyl}-2-{[4-(phenyloxy)phenyl]amino}ethyl)tetrahydrofuran-3-carboxamide; Compound 337, N-(2-oxo-1-{[(phenylmethyl)oxy]methyl}-2-{[4-(phenyloxy)phenyl]amino}ethyl)-3-methoxypropanamide; Compound 338, N-(2-oxo-1-{[(phenylmethyl)oxy]methyl}-2-{[4-(phenyloxy)phenyl]amino}ethyl)-2-ethoxyacetamide; Compound 339, N,N-dimethyl-N'-(2-oxo-1-{[(phenylmethyl)oxy]methyl}-2-{[4-(phenyloxy)phenyl]amino}ethyl)butanediamide; Compound 340, N-(2-oxo-1-{[(phenylmethyl)oxy]methyl}-2-{[4-(phenyloxy)phenyl]amino}ethyl)-N-benzoyl-N-methylaminoacetamide; Compound 341, N-(2-oxo-1-{[(phenylmethyl)oxy]methyl}-2-{[4-(phenyloxy)phenyl]amino}ethyl)-1H-indole-3-carboxamide; Compound 342, N-(2-oxo-1-{[(phenylmethyl)oxy]methyl}-2-{[4-(phenyloxy)phenyl]amino}ethyl)-1H-benzimidazole-5-carboxamide; Compound 343, N-(2-oxo-1-{[(phenylmethyl)oxy]methyl}-2-{[4-(phenyloxy)phenyl]amino}ethyl)-2-(4-ethoxyphenyl)acetamide; Compound 344, N-(2-oxo-1-{[(phenylmethyl)oxy]methyl}-2-{[4-(phenyloxy)phenyl]amino}ethyl)pent-4-ynamide; Compound 345, N-(2-oxo-1-{[(phenylmethyl)oxy]methyl}-2-{[4-(phenyloxy)phenyl]amino}ethyl)-4-(propyloxy)benzamide; Compound 346, 2-methyl-N-(2-oxo-1-{[(phenylmethyl)oxy]methyl}-2-{[4-(phenyloxy)phenyl]amino}ethyl)hexanamide; Compound 347, 4-oxo-N-(2-oxo-1-{[(phenylmethyl)oxy]methyl}-2-{[4-(phenyloxy)phenyl]amino}ethyl)pentanamide; Compound 348, N-(2-oxo-1-{[(phenylmethyl)oxy]methyl}-2-{[4-(phenyloxy)phenyl]amino}ethyl)-3-(3,4-dimethoxyphenyl)propanamide; Compound 349, 4-oxo-N-(2-oxo-1-{[(phenylmethyl)oxy]methyl}-2-{[4-(phenyloxy)phenyl]amino}ethyl)-4-phenylbutanamide; Compound 350, N-(2-oxo-1-{[(phenylmethyl)oxy]methyl}-2-{[4-(phenyloxy)phenyl]amino}ethyl)quinoline-3-carboxamide; Compound 351, N-(2-oxo-1-{[(phenylmethyl)oxy]methyl}-2-{[4-(phenyloxy)phenyl]amino}ethyl)pyrazine-2-carboxamide; Compound 352, N-(2-oxo-1-{[(phenylmethyl)oxy]methyl}-2-{[4-(phenyloxy)phenyl]amino}ethyl)-2-(5-methoxy-2-methyl-1H-indol-3-yl)acetamide; Compound 353, N-(2-oxo-1-{[(phenylmethyl)oxy]methyl}-2-{[4-(phenyloxy)phenyl]amino}ethyl)-2-methoxy-2-phenylacetamide; Compound 354, N-(2-oxo-1-{[(phenylmethyl)oxy]methyl}-2-{[4-(phenyloxy)phenyl]amino}ethyl)-2R-phenylpropanamide; Compound 355, N-(2-oxo-1-{[(phenylmethyl)oxy]methyl}-2-{[4-(phenyloxy)phenyl]amino}ethyl)-1H-pyrazole-4-carboxamide; Compound 356, N-(2-oxo-1-{[(phenylmethyl)oxy]methyl}-2-{[4-(phenyloxy)phenyl]amino}ethyl)cinnoline-4-carboxamide; Compound 357, N-(2-oxo-1-{[(phenylmethyl)oxy]methyl}-2-{[4-(phenyloxy)phenyl]amino}ethyl)quinoline-8-carboxamide; Compound 358, 6-hydroxy-N-(2-oxo-1-{[(phenylmethyl)oxy]methyl}-2-{[4-(phenyloxy)phenyl]amino}ethyl)pyridine-2-carboxamide; Compound 359, N-(2-oxo-1-{[(phenylmethyl)oxy]methyl}-2-{[4-(phenyloxy)phenyl]amino}ethyl)-2-phenylpropanamide; Compound 360, N-(2-oxo-1-{[(phenylmethyl)oxy]methyl}-2-{[4-(phenyloxy)phenyl]amino}ethyl)-1-(4-methoxyphenyl)cyclopropanecarboxamide; Compound 361, N-(2-oxo-1-{[(phenylmethyl)oxy]methyl}-2-{[4-(phenyloxy)phenyl]amino}ethyl)-2-(2,3,6-trifluorophenyl)acetamide; Compound 362, N-(2-oxo-1-{[(phenylmethyl)oxy]methyl}-2-{[4-(phenyloxy)phenyl]amino}ethyl)-2,4-bis(trifluoromethyl)benzamide; Compound 363, N-(2-oxo-1-{[(phenylmethyl)oxy]methyl}-2-{[4-(phenyloxy)phenyl]amino}ethyl)-2-(2,4-difluorophenyl)acetamide; Compound 364, N-(2-oxo-1-{[(phenylmethyl)oxy]methyl}-2-{[4-(phenyloxy)phenyl]amino}ethyl)-2-(1-methyl-1H-indol-3-yl)acetamide; Compound 365, N-(2-oxo-1-{[(phenylmethyl)oxy]methyl}-2-{[4-(phenyloxy)phenyl]amino}ethyl)quinoline-4-carboxamide; Compound 366, N-(2-oxo-1-{[(phenylmethyl)oxy]methyl}-2-{[4-(phenyloxy)phenyl]amino}ethyl)-1-benzofuran-2-carboxamide; Compound 367, 7-(methyloxy)-N-(2-oxo-1-{[(phenylmethyl)oxy]methyl}-2-{[4-(phenyloxy)phenyl]amino}ethyl)-1-benzofuran-2-carboxamide; Compound 368, N-(2-oxo-1-{[(phenylmethyl)oxy]methyl}-2-{[4-(phenyloxy)phenyl]amino}ethyl)-2-(4-fluorophenoxy)acetamide; Compound 369, N-(2-oxo-1-{[(phenylmethyl)oxy]methyl}-2-{[4-(phenyloxy)phenyl]amino}ethyl)-3-(pyridin-3-yl)propanamide; Compound 370, N-(2-oxo-1-{[(phenylmethyl)oxy]methyl}-2-{[4-(phenyloxy)phenyl]amino}ethyl)-2-(3,4-dichlorophenoxy)acetamide; Compound 371, N-(2-oxo-1-{[(phenylmethyl)oxy]methyl}-2-{[4-(phenyloxy)phenyl]amino}ethyl)-2-(naphthalen-1-yloxy)acetamide; Compound 372, N-(2-oxo-1-{[(phenylmethyl)oxy]methyl}-2-{[4-(phenyloxy)phenyl]amino}ethyl)-2-p-tolylacetamide; Compound 373, N-(2-oxo-1-{[(phenylmethyl)oxy]methyl}-2-{[4-(phenyloxy)phenyl]amino}ethyl)-2-(2,5-dimethylphenyl)acetamide; Compound 374, N-(2-oxo-1-{[(phenylmethyl)oxy]methyl}-2-{[4-(phenyloxy)phenyl]amino}ethyl)-2-(benzylthio)acetamide; Compound 375, N-(2-oxo-1-{[(phenylmethyl)oxy]methyl}-2-{[4-(phenyloxy)phenyl]amino}ethyl)-2-(naphthalen-1-yl)acetamide; Compound 376, N-(2-oxo-1-{[(phenylmethyl)oxy]methyl}-2-{[4-(phenyloxy)phenyl]amino}ethyl)-3-ethoxypropanamide; Compound 377, N-(2-oxo-1-{[(phenylmethyl)oxy]methyl}-2-{[4-(phenyloxy)phenyl]amino}ethyl)-2-(3-chlorophenyl)acetamide; Compound 378, 5-butyl-N-(2-oxo-1-{[(phenylmethyl)oxy]methyl}-2-{[4-(phenyloxy)phenyl]amino}ethyl)pyridine-2-carboxamide; Compound 379, 4-chloro-3-methyl-N-(2-oxo-1-{[(phenylmethyl)oxy]methyl}-2-{[4-(phenyloxy)phenyl]amino}ethyl)benzamide; Compound 380, 4-cyano-N-(2-oxo-1-{[(phenylmethyl)oxy]methyl}-2-{[4-(phenyloxy)phenyl]amino}ethyl)benzamide; Compound 381, N-(2-oxo-1-{[(phenylmethyl)oxy]methyl}-2-{[4-(phenyloxy)phenyl]amino}ethyl)-2S-methoxy-2-phenylacetamide; Compound 382, N-(2-oxo-1-{[(phenylmethyl)oxy]methyl}-2-{[4-(phenyloxy)phenyl]amino}ethyl)-3-(2,5-dimethoxyphenyl)propanamide; Compound 383, N-(2-oxo-1-{[(phenylmethyl)oxy]methyl}-2-{[4-(phenyloxy)phenyl]amino}ethyl)-3-(1H-indol-3-yl)propanamide; Compound 384, N-(2-oxo-1-{[(phenylmethyl)oxy]methyl}-2-{[4-(phenyloxy)phenyl]amino}ethyl)-2-(3-bromophenyl)acetamide; Compound 385, 3-methyl-N-(2-oxo-1-{[(phenylmethyl)oxy]methyl}-2-{[4-(phenyloxy)phenyl]amino}ethyl)pentanamide; Compound 386, N-(2-oxo-1-{[(phenylmethyl)oxy]methyl}-2-{[4-(phenyloxy)phenyl]amino}ethyl)-1H-indole-2-carboxamide; Compound 387, 4-chloro-2-fluoro-N-(2-oxo-1-{[(phenylmethyl)oxy]methyl}-2-{[4-(phenyloxy)phenyl]amino}ethyl)benzamide; Compound 388, 2-oxo-2-[(2-oxo-1-{[(phenylmethyl)oxy]methyl}-2-{[4-(phenyloxy)phenyl]amino}ethyl)amino]ethyl acetate; Compound 389, N-(2-oxo-1-{[(phenylmethyl)oxy]methyl}-2-{[4-(phenyloxy)phenyl]amino}ethyl)thiophene-3-carboxamide; Compound 390, N-(2-oxo-1-{[(phenylmethyl)oxy]methyl}-2-{[4-(phenyloxy)phenyl]amino}ethyl)-2-(4-bromophenyl)acetamide; Compound 391, N-(2-oxo-1-{[(phenylmethyl)oxy]methyl}-2-{[4-(phenyloxy)phenyl]amino}ethyl)-2-(2-chlorophenyl)acetamide; Compound 392, N-(2-oxo-1-{[(phenylmethyl)oxy]methyl}-2-{[4-(phenyloxy)phenyl]amino}ethyl)-2-(3,4,5-trimethoxyphenyl)acetamide; Compound 393, N-(2-oxo-1-{[(phenylmethyl)oxy]methyl}-2-{[4-(phenyloxy)phenyl]amino}ethyl)-2-(p-tolyloxy)acetamide; Compound 394, N-(2-oxo-1-{[(phenylmethyl)oxy]methyl}-2-{[4-(phenyloxy)phenyl]amino}ethyl)-3-(2-methoxyphenyl)propanamide; Compound 395, 3-hydroxy-N-(2-oxo-1-{[(phenylmethyl)oxy]methyl}-2-{[4-(phenyloxy)phenyl]amino}ethyl)quinoxaline-2-carboxamide; Compound 396, 4-acetyl-N-(2-oxo-1-{[(phenylmethyl)oxy]methyl}-2-{[4-(phenyloxy)phenyl]amino}ethyl)benzamide; Compound 397, methyl 4-{[(2-oxo-1-{[(phenylmethyl)oxy]methyl}-2-{[4-(phenyloxy)phenyl]amino}ethyl)amino]carbonyl}benzoate; Compound 398, 3-fluoro-N-(2-oxo-1-{[(phenylmethyl)oxy]methyl}-2-{[4-(phenyloxy)phenyl]amino}ethyl)-5-(trifluoromethyl)benzamide; Compound 399, 4-[(difluoromethyl)oxy]-N-(2-oxo-1-{[(phenylmethyl)oxy]methyl}-2-{[4-(phenyloxy)phenyl]amino}ethyl)benzamide; Compound 400, 3-fluoro-4-methyl-N-(2-oxo-1-{[(phenylmethyl)oxy]methyl}-2-{[4-(phenyloxy)phenyl]amino}ethyl)benzamide; Compound 401, 3-methyl-N-(2-oxo-1{[(phenylmethyl)oxy]methyl}-2-{[4-(phenyloxy)phenyl]amino}ethyl)furan-2-carboxamide. Compound 402, N-(2-oxo-1-{[(phenylmethyl)oxy]methyl}-2-{[4-(phenyloxy)phenyl]amino}ethyl)cyclobutanecarboxamide; and Compound 403, N-(2-oxo-1-{[(phenylmethyl)oxy]methyl}-2-{[4-(phenyloxy)phenyl]amino}ethyl)-3-(thiophen-2-yl)propanamide.

Example 17

S1P1R Antagonist Assay

The S1P1R antagonist assay is a fluorescent membrane potential dye measurement assay, indicative of intracellular cAMP changes due to G protein-coupled receptor activation. HEK293 cells engineered to express human S1P1 receptors and a cyclic nucleotide-gated (CNG) channel are obtained from BD Biosciences, 80300-250. The CNG channels are activated by elevated levels of cAMP, resulting in ion flux and cell membrane depolarization. Membrane depolarization is detected with a membrane potential dye. Stimulation of the cells with 5'-(N-ethylcarboxamido)adenosine (NECA), an A2b receptor agonist (Sigma, E2387), elicits an A2bR-dependent increase in cAMP.

Subsequent exposure of the cells to a S1P1R agonist suppresses the NECA induced increase in cAMP through S1P1R-specific signaling by inhibiting adenylyl cyclase and the formation of cAMP from ATP. The degree to which a test compound overcomes the S1P1R agonist suppression of the NECA induced increase in cAMP is a measure of S1P1R antagonist activity. Antagonist activity is quantified as the $IC_{50}$ (i.e., the concentration needed to elicited one-half of the maximum response of the test compound) and/or as the $EC_{50}$ (i.e., the concentration needed to elicited one-half of the NECA induced stimulation).

Day 1: Freshly thawed cells were plated into 384-well plates (Corning, 3683) at a density of 14,000 cells/well in 20 µL, complete media and incubated for 16 hours at 37° C., 5% $CO_2$ and 99% relative humidity. Complete media included Dulbecco's modified Eagle's medium (Invitrogen, 11965-092), 10% Fetal bovine serum (Hyclone, SH30071.03), 250 µg/mL geneticin (Invitrogen, 10131-027), and 1 µg/mL Puromycin (Fluka, 82595).

Day 2: Membrane potential dye (20 µL, BD Biosciences, 341833) was added to each well and the plates were incubated for 2.5 hours at ambient temperature. Test compounds (20 µL) were added to the wells at various concentrations (≤10 µM, 1 to 3 dilutions) in a NECA base solution and incubated for 90 minutes in the presence of the S1P1R agonist {4-((4-phenyl-5-trifluoromethyl-2-thienyl)methoxy)benzyl}-3-azetidinecarboxylic acid (10 nM). The NECA-base solution contained Dulbecco's phosphate-buffered saline (Invitrogen, 14190-136), 2.5% DMSO (Fluka, 41648), 25 µM Ro 20-1724 (Sigma, B8279), and 500 nM NECA).

A HEK293 cell line that expresses the human CB1 receptor and a CNG channel (BD Biosciences, 80500-211) were used as the counterscreen. CB1R cells were stimulated with 500 nM NECA and with CB1R agonist CP-55940 (10 nM) causing a CB1R-specific decrease of NECA-induced elevated levels of cAMP. Specific S1P1R antagonists will have no effect on CB1R activation.

Assay plates were read with a PerkinElmer EnVision reader (Excitation 350 nm, Emission 590 nm) at time T=0 minutes, before compound addition and at time T=90 minutes. The signal was calculated as the ratio T90/T0. Data was analyzed in ActivityBase XE and graphs showing log of compound concentration (X-axis) vs. % activity (Y-axis) were generated for $IC_{50}$ determinations. Percent activity was calculated with the following formula: (Signal−Agonist Control Signal)/(NECA Control Signal−Agonist Control Signal)× 100.

Suitable S1P1R and CB agonists for use in the S1P1R antagonist assay are known in the art. For example, fingolimod or 2-amino-2-(4-nonylphenethyl)propane-1,3-diol, is a known S1P1R agonist. Methods for making and using fingolimod are found in European Patent Application EP0627406. 1-{4-((4-Phenyl-5-trifluoromethyl-2-thienyl)methoxy)benzyl}-3-azetidinecarboxylic acid is a known S1P1R agonist and methods for making and using it are found in WO 03/062252. Suitable CB1R agonists are known in the art, for example, WIN55, 212-2 and CP-55940 are commerically available (Sigma, W102 and C1112, respectively).

The S1P1R antagonists of this invention were assayed by the methods described in Example 17 and were found to inhibit the S1P1R agonist elicited effects at $IC_{50}$ and/or $EC_{50}$ values ranging from about 1 nM to about 2 µM concentrations. In contrast, the S1P1R antagonists of this invention were found not to inhibit CB1R elicited effects. The activities the S1P1R antagonists of this invention are indicated in Table 2, wherein the letters A, B and C denote, respectively, that a compound has an $EC_{50}$ or $IC_{50}$ value of (i) less than or equal to 0.3 µM, (ii) greater than 0.3 µM, but less than or equal to 1 µM, and (iii) greater than 1 µM.

TABLE 2

| 1 | A | 2 | A | 3 | A | 4 | A | 5 | A | 6 | A | 7 | A | 8 | A |
|---|---|---|---|---|---|---|---|---|---|---|---|---|---|---|---|
| 9 | A | 10 | A | 11 | A | 12 | B | 13 | C | 14 | C | 15 | C | 16 | C |
| 17 | C | 18 | C | 19 | C | 20 | C | 21 | C | 22 | B | 23 | C | 24 | C |
| 25 | C | 26 | C | 27 | C | 28 | C | 29 | C | 30 | A | 31 | A | 32 | A |
| 33 | A | 34 | A | 35 | A | 36 | A | 37 | A | 38 | A | 39 | A | 40 | A |
| 41 | C | 42 | C | 43 | C | 44 | C | 45 | C | 46 | C | 47 | C | 48 | A |
| 49 | A | 50 | A | 51 | A | 52 | A | 53 | A | 54 | A | 55 | A | 56 | A |
| 57 | A | 58 | A | 59 | B | 60 | C | 61 | A | 62 | A | 63 | C | 64 | A |
| 65 | A | 66 | A | 67 | A | 68 | A | 69 | A | 70 | A | 71 | A | 72 | A |
| 73 | A | 74 | A | 75 | A | 76 | A | 77 | B | 78 | B | 79 | A | 80 | B |
| 81 | C | 82 | A | 83 | A | 84 | A | 85 | A | 86 | A | 87 | A | 88 | A |
| 89 | A | 90 | A | 91 | A | 92 | A | 93 | A | 94 | A | 95 | A | 96 | A |
| 97 | A | 98 | A | 99 | A | 100 | A | 101 | C | 102 | C | 103 | C | 104 | C |
| 105 | C | 106 | A | 107 | A | 108 | A | 109 | C | 110 | C | 111 | C | 112 | C |
| 113 | C | 114 | C | 115 | A | 116 | A | 117 | A | 118 | A | 119 | A | 120 | A |
| 121 | A | 122 | A | 123 | A | 124 | A | 125 | A | 126 | C | 127 | C | 128 | C |
| 129 | A | 130 | C | 131 | A | 132 | A | 133 | A | 134 | A | 135 | A | 136 | C |
| 137 | A | 138 | A | 139 | A | 140 | A | 141 | A | 142 | A | 143 | A | 144 | A |
| 145 | A | 146 | A | 147 | A | 148 | A | 149 | A | 150 | A | 151 | A | 152 | A |
| 153 | A | 154 | A | 155 | A | 156 | A | 157 | A | 158 | A | 159 | A | 160 | A |
| 161 | A | 162 | A | 163 | A | 164 | A | 165 | A | 166 | A | 167 | A | 168 | A |
| 169 | A | 170 | A | 171 | A | 172 | A | 173 | A | 174 | A | 175 | A | 176 | A |
| 177 | A | 178 | A | 179 | A | 180 | A | 181 | A | 182 | A | 183 | B | 184 | B |
| 185 | A | 186 | B | 187 | B | 188 | B | 189 | B | 190 | B | 191 | B | 192 | B |
| 193 | B | 194 | B | 195 | A | 196 | B | 197 | B | 198 | B | 199 | B | 200 | A |

TABLE 2-continued

| 201 | A | 202 | A | 203 | A | 204 | B | 205 | A | 206 | B | 207 | A | 208 | B |
|---|---|---|---|---|---|---|---|---|---|---|---|---|---|---|---|
| 209 | B | 210 | A | 211 | A | 212 | A | 213 | A | 214 | A | 215 | B | 216 | B |
| 217 | B | 218 | B | 219 | B | 220 | B | 221 | B | 222 | B | 223 | B | 224 | B |
| 225 | B | 226 | A | 227 | A | 228 | A | 229 | B | 230 | B | 231 | B | 232 | C |
| 233 | B | 234 | B | 235 | B | 236 | B | 237 | B | 238 | B | 239 | A | 240 | B |
| 241 | B | 242 | B | 243 | A | 244 | B | 245 | A | 246 | A | 247 | A | 248 | B |
| 249 | B | 250 | A | 251 | A | 252 | A | 253 | C | 254 | A | 255 | B | 256 | A |
| 257 | B | 258 | A | 259 | B | 260 | B | 261 | B | 262 | B | 263 | A | 264 | A |
| 265 | A | 266 | B | 267 | A | 268 | A | 269 | B | 270 | C | 271 | C | 272 | C |
| 273 | C | 274 | C | 275 | C | 276 | C | 277 | A | 278 | C | 279 | C | 280 | C |
| 281 | C | 282 | C | 283 | C | 284 | C | 285 | C | 286 | C | 287 | C | 288 | C |
| 289 | C | 290 | C | 291 | C | 292 | C | 293 | C | 294 | C | 295 | C | 296 | C |
| 297 | C | 298 | C | 299 | C | 300 | C | 301 | B | 302 | C | 303 | B | 304 | C |
| 305 | A | 306 | C | 307 | A | 308 | C | 309 | C | 310 | C | 311 | C | 312 | C |
| 313 | B | 314 | C | 315 | C | 316 | C | 317 | C | 318 | C | 319 | C | 320 | C |
| 321 | C | 322 | C | 323 | B | 324 | C | 325 | B | 326 | A | 327 | B | 328 | C |
| 329 | C | 330 | C | 331 | C | 332 | B | 333 | C | 334 | C | 335 | C | 336 | A |
| 337 | C | 338 | C | 339 | C | 340 | B | 341 | C | 342 | C | 343 | C | 344 | C |
| 345 | C | 346 | B | 347 | C | 348 | B | 349 | B | 350 | C | 351 | C | 352 | C |
| 353 | C | 354 | B | 355 | B | 356 | B | 357 | B | 358 | C | 359 | C | 360 | C |
| 361 | C | 362 | B | 363 | C | 364 | C | 365 | C | 366 | C | 367 | C | 368 | C |
| 369 | C | 370 | B | 371 | C | 372 | C | 373 | C | 374 | C | 375 | C | 376 | C |
| 377 | B | 378 | B | 379 | C | 380 | C | 381 | C | 382 | C | 383 | C | 384 | C |
| 385 | C | 386 | C | 387 | C | 388 | C | 389 | B | 390 | C | 391 | C | 392 | B |
| 393 | C | 394 | C | 395 | C | 396 | C | 397 | B | 398 | C | 399 | C | 400 | C |
| 401 | C | 402 | C | 403 | B | | | | | | | | | | | |

Example 18

Representative Pharmaceutical Formulations Containing a Compound of the Invention

TABLE 3

| Oral Formulation | |
|---|---|
| API | 10-100 mg |
| Citric Acid Monohydrate | 105 mg |
| Sodium Hydroxide | 18 mg |
| Flavoring | |
| Water | q.s. to 100 mL |
| Intravenous Formulation | |
| API | 0.1-10 mg |
| Dextrose Monohydrate | q.s. to make isotonic |
| Tablet Formulation | |
| API | 1% |
| Microcrystalline Cellulsoe | 73% |
| Stearic Acid | 25% |
| Colloidal Silica | 1% |

The active pharmaceutical ingredient (API) in the above representative pharmaceutical formulations means a compound of Formula I, I(a), II, II(a), III, III(a), IV or IV(a).

What is claimed is:
1. A compound of Formula IV:

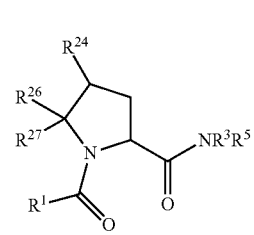

IV or a pharmaceutically acceptable salt thereof, wherein:

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, —$X^1OR^7$, —$X^1$—C(O)$OR^7$, —$X^1$C(O)$NR^7R^7$, —$X^1NR^7$C(O)$OR^7$, —$X^1$OC(O)—$NR^7R^7$, —$X^1NR^7$C(O)—$NR^7R^7$, —$X^1$—S(O)$_{n1}OR^7$, —$X^1$S(O)$_{n1}NR^7R^7$, —$X^1NR^7$S(O)$_{n1}$—$NR^7R^7$, —$X^1NR^7R^7$, —$X^1$—C(O)$R^7$, —$X^1$OC(O)—$R^8$, —$X^1NR^7$C(O)$R^8$, —$X^1$S(O)$_{n1}R^8$, —$X^1$—OS(O)$_{n1}R^8$ or —$X^1NR^7$S(O)$_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$)alkyl or halo-substituted $(C_{1-4})$alkyl and $R^8$ is $(C_{1-4})$alkyl, alkoxy-substituted $(C_{1-4})$)alkyl or halo-substituted $(C_{1-4})$alkyl, or $R^1$ is —$X^2CR^9R^9R^{11}$, —$X^2OR^{11}$, —$X^2$C(O)$OR^{11}$, —$X^2$C(O)$NR^{10}R^{11}$, —$X^2NR^{10}$C(O)O—$R^{11}$, —$X^2$O—C(O)$NR^{10}R^{11}$, —$X^2NR^{10}$C(O)$NR^{10}R^{11}$, S(O)$_{n2}OR^{11}$, —$X^2$S(O)$_{n2}NR^{10}R^{11}$, —$X^2NR^{10}$S(O)$_{n2}$—$NR^{10}R^{11}$, —$X^2NR^{10}R^{11}$, —$X^2$C(O)$R^{11}$, —$X^2$OC(O)$R^{11}$, —$X^2NR^{10}$C(O)$R^{11}$, —$X^2$S(O)$_{n2}R^{11}$, —$X^2$O—S(O)$_{n2}R^{11}$ or —$R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is —$X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with —$X^4CR^{13}R^{13}R^{15}$, —$X^4OR^{15}$, —$X^4$C(O)$OR^{15}$, —$X^4$C(O)—$NR^{14}R^{15}$, —$X^4$—$NR^{14}$C(O)$OR^{15}$, —$X^4$OC(O)$NR^{14}R^{15}$, —$X^4NR^{14}$C(O)$NR^{14}R^{15}$, —$X^4$S(O)$_{n3}$—$OR^{15}$, —$X^4$S(O)$_{n3}$—$NR^{14}R^{15}$, —$X^4NR^{14}$S(O)$_{n3}NR^{14}R^{15}$, —$X^4NR^{14}R^{15}$, —$X^4$C(O)$R^{15}$, —$X^4$—OC(O)$R^{15}$, —$X^4NR^{14}$C(O)$R^{15}$, —$X^4$S(O)$_{n3}R^{15}$, —$X^4$OS(O)$_{n3}R^{15}$ or —$R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is —$X^5R^{16}$ wherein $X^5$ is a bond or $(C_{1-3})$alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, —$X^6OR^{17}$, —$X^6$C(O)$OR^{17}$, —$X^6$C(O)—$NR^{17}R^{17}$, —$X^6NR^{17}$C(O)$OR^{17}$, —$X^6$—OC(O)$NR^{17}R^{17}$, —$X^6NR^{17}$C(O)$NR^{17}R^{17}$, —$X^6$S(O)$_{n4}$—$OR^{17}$, —$X^6$S(O)$_{n4}NR^{17}R^{17}$, —$X^6NR^{17}$S(O)$_{n4}$—$NR^{17}R^{17}$, —$X^6NR^{17}R^{17}$, —$X^6$C(O)$R^{17}$, —$X^6$—OC(O)$R^{18}$, —$X^6NR^{17}$C(O)$R^{18}$, —$X^6$S(O)$_{n4}R^{18}$, —$X^6$O—S(O)$_{n4}R^{18}$ and —$X^6NR^{17}$S(O)$_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$)alkyl or halo-substituted $(C_{1-4})$alkyl;

$R^{24}$ is —$X^9OR^{29}$, —$X^9NR^{28}$C(O)$OR^{29}$, —$X^9NR^{28}R^{29}$, —$X^9$C(O)$OR^{29}$ or —$R^{29}$, wherein $X^9$ is a bond or $(C_{1-3})$alkylene and $R^{28}$ is hydrogen, $(C_{1-4})$alkyl or halo-substituted $(C_{1-4})$)alkyl and $R^{29}$ is —$X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl;

$R^{26}$ and $R^{27}$ are both hydrogen or together form oxo or thioxo;

$R^3$ is phenyl substituted with —$R^{31}$, wherein $R^{31}$ is –$OR^{33}$, —$SR^{33}$ or —$CH_2R^{33}$, wherein $R^{33}$ is —$X^{12}R^{34}$, wherein $X^{12}$ is a bond or methylene and $R^{34}$ is five or six membered cycloalkyl or heterocycloalkyl, phenyl or five or six membered heteroaryl, wherein any cyclic moiety within $R^3$ independently may be substituted with one or two $(C_{1-4})$alkyl, halo or —$OR^{35}$, wherein $R^{35}$ is $(C_{1-4})$alkyl; and $R^5$ is hydrogen or alkyl, wherein the compound of Formula IV can be in the form of any individual stereoisomer or mixture of stereoisomers.

2. The compound of claim 1, a pharmaceutically acceptable salt thereof, wherein:

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, —$X^1OR^7$, —$X^1$—C(O)$OR^7$, —$X^1$C(O)$NR^7R^7$, —$X^1NR^7$C(O)$OR^7$, —$X^1$OC(O)—$NR^7R^7$, —$X^1NR^7$C(O)$NR^7R^7$, —$X^1$—S(O)$_{n1}R^7$, —$X^1$S(O)$_{n1}NR^7R^7$, —$X^1NR^7$S(O)$_{n1}NR^7R^7$, —$X^1NR^7R^7$, —$X^1$C(O)$R^7$, —$X^1$OC(O)—$R^8$, —$X^1NR^7$C(O)$R^8$, —$X^1$S(O)$_{n1}R^8$, —$X^1$OS(O)$_{n1}R^8$ or —$X^1NR^7$S(O)$_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is —$X^2CR^9R^9R^{11}$, —$X^2OR^{11}$, —$X^2$C(O)$OR^{11}$, —$X^2$C(O)$NR^{10}R^{11}$, —$X^2NR^{10}$C(O)—$OR^{11}$, —$X^2$OC(O)$NR^{10}R^{11}$, —$X^2NR^{10}$C(O)$NR^{10}R^{11}$, —$X^2$S(O)$_{n2}OR^{11}$, —$X^2$S(O)$_{n2}$—$NR^{10}R^{11}$, —$X^2NR^{10}$S(O)$_{n2}$—$NR^{10}R^{11}$, —$X^2NR^{10}R^{11}$, —$X^2$C(O)$R^{11}$, —$X^2$OC(O)$R^{11}$, —$X^2NR^{10}$C(O)$R^{11}$, —$X^2$S(O)$_{n2}R^{11}$, —$X^2$O—S(O)$_{n2}R^{11}$ or —$R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is —$X^3R^{12}$, wherein $X^3$ is a bond, alkylene or hydroxy-substituted alkylene and $R^{12}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, —$X^6OR^{17}$, —$X^6$C(O)$OR^{17}$, —$X^6$C(O)—$NR^{17}R^{17}$, —$X^6NR^{17}$C(O)$OR^{17}$, —$X^6$—OC(O)$NR^{17}R^{17}$, —$X^6NR^{17}$C(O)$NR^{17}R^{17}$, —$X^6$S(O)$_{n4}$—$OR^{17}$, —$X^6$S(O)$_{n4}NR^{17}R^{17}$, —$X^6NR^{17}$S(O)$_{n4}$—$NR^{17}R^{17}$, —$X^6NR^{17}R^{17}$, —$X^6$C(O)$R^{17}$, —$X^6$—OC(O)$R^{18}$, —$X^6NR^{17}$C(O)$R^{18}$, —$X^6$S(O)$_{n4}R^{18}$, —$X^6$O—S(O)$_{n4}R^{18}$ and —$X^6NR^{17}$S(O)$_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$)alkyl or halo-substituted $(C_{1-4})$alkyl;

$R^{24}$ is —$X^{11}R^{30}$, wherein $X^{11}$ is methylene, and $R^{30}$ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl;

$R^{26}$ and $R^{27}$ are both hydrogen;

R³ is 4-(4-fluorophenoxy)phenyl, wherein any cyclic moiety within R³ independently may be substituted with one or two (C$_{1-4}$)alkyl, halo or —OR³⁵, wherein R³⁵ is (C$_{1-4}$))alkyl; and R⁵ is hydrogen; wherein the compound of Formula IV can be in the form of any individual stereoisomer or mixture of stereoisomers.

3. The compound of claim 2, or a pharmaceutically acceptable salt thereof, wherein:

R¹ is alkyl, alkenyl, halo-substituted alkyl, nitro-substituted alkyl, cyano-substituted alkyl, —X¹OR⁷, —X¹C(O)OR⁷, —X¹C(O)NR⁷R⁷, —X¹NR⁷R⁷, —X¹C(O)R⁷, —X¹S(O)$_{n1}$R⁸ or —X¹OC(O)R⁸, wherein n1 is 0, 1, or 2, X¹ is a bond or alkylene, R⁷ at each occurrence independently is hydrogen, (C$_{1-4}$)alkyl, alkoxy-substituted (C$_{1-4}$)alkyl or halo-substituted (C$_{1-4}$)alkyl and R⁸ is (C$_{1-4}$)alkyl, alkoxy-substituted (C$_{1-4}$)alkyl or halo-substituted (C$_{1-4}$)alkyl, or R¹ is —X²NR¹⁰R¹¹, —X²OR¹¹, —X²C(O)R¹¹, —X²NR¹⁰C(O)R¹¹, or —R¹¹, wherein X² is a bond or alkylene, R¹⁰ is hydrogen, alkyl or halo-substituted alkyl and R¹¹ is —X³R¹² wherein X³ is a bond, alkylene or hydroxy-substituted alkylene and R¹² is cycloalkyl, aryl, heterocycloalkyl or heteroaryl, wherein any cycloalkyl, aryl, heterocycloalkyl or heteroaryl within R¹ independently may be substituted with one to three groups independently selected from (C$_{1-3}$)alkyl, halo, nitro, halo-substituted (C$_{1-3}$))alkyl, —X⁶—OR¹⁷, —X⁶C(O)OR¹⁷, —X⁶NR¹⁷R¹⁷, —X⁶—C(O)R¹⁷, —X⁶C(O)NR¹⁷R¹⁷, —X⁶—OC(O)R¹⁸ and —X⁶S(O)$_{n4}$R¹⁸, wherein X⁶ is a bond or (C$_{1-3}$)alkylene, R¹⁷ at each occurrence independently is hydrogen, (C$_{1-4}$)alkyl or halo-substituted (C$_{1-4}$)alkyl and R¹⁸ is (C$_{1-4}$)alkyl or halo-substituted (C$_{1-4}$)alkyl;

R²⁴ is —X¹¹R³⁰, wherein X¹¹ is methylene, and R³⁰ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl;

R²⁶ and R²⁷ are both hydrogen;

R³ is 4-(4-fluorophenoxy)phenyl, wherein any cyclic moiety within R³ independently may be substituted with one or two (C$_{1-4}$)alkyl, halo or —OR³⁵, wherein R³⁵ is (C$_{1-4}$))alkyl; and R⁵ is hydrogen; wherein the compound of Formula IV can be in the form of any individual stereoisomer or mixture of stereoisomers.

4. The compound of claim 1 which is a compound of Formula IV(a):

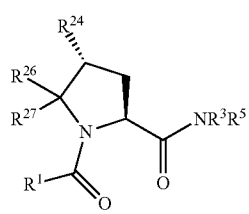

IV(a)

or a pharmaceutically acceptable salt thereof.

5. The compound of claim 4, or a pharmaceutically acceptable salt thereof, wherein R¹ is five-membered heteroaryl, R³ is 4-(4-fluorophenoxy)phenyl, R⁵ is hydrogen, R²⁴ is —X¹¹R³⁰, wherein X¹¹ is methylene, and R³⁰ is phenyl or thienyl, wherein the phenyl may be substituted with one or two substituents independently selected from chloro, fluoro, methoxy, methyl and trifluoromethyl and the thienyl may be substituted with one substituent selected from chloro, fluoro, methoxy, methyl and trifluoromethyl; and R²⁶ and R²⁷ are both hydrogen.

6. The compound of claim 4, or a pharmaceutically acceptable salt thereof, wherein R¹ is 2H-1,2,3-triazol-2-ylmethyl, 1H-1,2,4-triazol-1-ylmethyl or 1H-1,2,3-triazol-1-yl; R³ is 4-(4-fluorophenoxy)phenyl, R⁵ is hydrogen, R²⁴ is —X¹¹R³⁰, wherein X¹¹ is methylene, and R³⁰ is phenyl or thienyl, wherein the phenyl may be substituted with one or two substituents independently selected from chloro, fluoro, methoxy, methyl and trifluoromethyl and the thienyl may be substituted with one substituent selected from bromo, chloro and fluoro; and R²⁶ and R²⁷ are both hydrogen.

7. The compound of claim 6 selected from the group consisting of:

(2S,4R)-1-(2-(1H-1,2,4-triazol-1-yl)acetyl)-4-benzyl-N-(4-(4-fluorophenoxy)phenyl)pyrrolidine-2-carboxamide;

(2S,4R)-1-(2-(1H-1,2,4-triazol-1-yl)acetyl)-4-(4-fluorobenzyl)-N-(4-(4-fluorophenoxy)phenyl)pyrrolidine-2-carboxamide;

(2S,4R)-1-(2-(1H-1,2,4-triazol-1-yl)acetyl)-4-(2-chlorobenzyl)-N-(4-(4-fluorophenoxy)phenyl)pyrrolidine-2-carboxamide;

(2S,4R)-1-(2-(2H-1,2,3-triazol-2-yl)acetyl)-4-(4-fluorobenzyl)-N-(4-(4-fluorophenoxy)phenyl)pyrrolidine-2-carboxamide;

(2S,4R)-1-(2-(1H-1,2,3-triazol-1-yl)acetyl)-4-benzyl-N-(4-(4-fluorophenoxy)phenyl)pyrrolidine-2-carboxamide;

(2S,4R)-1-(2-(2H-1,2,3-triazol-2-yl)acetyl)-4-(2-chlorobenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(2-methylbenzyl)pyrrolidine-2-carboxamide;

(2S,4R)-1-(2-(1H-1,2,3-triazol-1-yl)acetyl)-4-(4-fluorobenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(2-(trifluoromethyl)benzyl)pyrrolidine-2-carboxamide;

(2S,4R)-1-(2-(1H-1,2,4-triazol-1-yl)acetyl)-4-(2-chloro-4-fluorobenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(thiophen-3-ylmethyl)pyrrolidine-2-carboxamide;

(2S,4R)-1-(2-(1H-1,2,4-triazol-1-yl)acetyl)-4-(2,4-difluorobenzyl)-N-(4-(4-fluorophenoxy)phenyl)pyrrolidine-2-carboxamide;

(2S,4R)-1-(2-(1H-1,2,4-triazol-1-yl)acetyl)-4-(3-chlorobenzyl)-N-(4-(4-fluorophenoxy)phenyl)pyrrolidine-2-carboxamide;

(2S,4R)-1-(2-(2H-1,2,3-triazol-2-yl)acetyl)-4-(2,4-difluorobenzyl)-N-(4-(4-fluorophenoxy)phenyl)pyrrolidine-2-carboxamide;

(2S,4R)-1-(2-(1H-1,2,4-triazol-1-yl)acetyl)-4-(3-fluorobenzyl)-N-(4-(4-fluorophenoxy)phenyl)pyrrolidine-2-carboxamide;

(2S,4R)-1-(2-(1H-1,2,3-triazol-1-yl)acetyl)-4-(2,4-difluorobenzyl)-N-(4-(4-fluorophenoxy)phenyl)pyrrolidine-2-carboxamide;

(2S,4R)-1-(2-(2H-1,2,3-triazol-2-yl)acetyl)-4-(3-chlorobenzyl)-N-(4-(4-fluorophenoxy)phenyl)pyrrolidine-2-carboxamide;

(2S,4R)-5-(2-(1H-1,2,4-triazol-1-yl)acetyl)-N-(4-(4-fluorophenoxy)phenyl)-4-(4-methylbenzyl)pyrrolidine-2-carboxamide;

(2S,4R)-1-(2-(2H-1,2,3-triazol-2-yl)acetyl)-4-(3-fluorobenzyl)-N-(4-(4-fluorophenoxy)phenyl)pyrrolidine-2-carboxamide;

(2S,4R)-1-(2-(1H-1,2,4-triazol-1-yl)acetyl)-4-(4-fluoro-2-methylbenzyl)-N-(4-(4-fluorophenoxy)phenyl)pyrrolidine-2-carboxamide;

(2S,4R)-1-(2-(2H-1,2,3-triazol-2-yl)acetyl)-4-(4-fluoro-2-methylbenzyl)-N-(4-(4-fluorophenoxy)phenyl)pyrrolidine-2-carboxamide;

(2S,4R)-1-(2-(1H-1,2,3-triazol-1-yl)acetyl)-4-(4-fluoro-2-methylbenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(3-methoxybenzyl)pyrrolidine-2-carboxamide;

(2S,4R)-1-(2-(2H-1,2,3-triazol-2-yl)acetyl)-N-(4-(4-fluorophenoxy)phenyl)-4-(3-methoxybenzyl)pyrrolidine-2-carboxamide;

(2S,4S)-1-(2-(1H-1,2,4-triazol-1-yl)acetyl)-4-((5-chlorothien-2-yl)methyl)-N-(4-(4-fluorophenoxy)phenyl)pyrrolidine-2-carboxamide;

(2S,4S)-1-(2-(2H-1,2,3-triazol-2-yl)acetyl)-4-((5-chlorothien-2-yl)methyl)-N-(4-(4-fluorophenoxy)phenyl)pyrrolidine-2-carboxamide;

(2S,4S)-1-(2-(2H-1,2,3-triazol-2-yl)acetyl)-N-(4-(4-fluorophenoxy)phenyl)-4-thien-2-ylmethylpyrrolidine-2-carboxamide;

(2S,4R)-1-(2-(2H-1,2,3-triazol-2-yl)acetyl)-4-(2-chloro-4-fluorobenzyl)-N-(4-(4-fluorophenoxy)phenyl)pyrrolidine-2-carboxamide;

(2S,4R)-1-(2-(1H-1,2,3-triazol-1-yl)acetyl)-4-(2-chloro-4-fluorobenzyl)-N-(4-(4-fluorophenoxy)phenyl)pyrrolidine-2-carboxamide;

(2S,4R)-1-(2-(2H-1,2,3-triazol-2-yl)acetyl)-N-(4-(4-fluorophenoxy)phenyl)-4-(2-methylbenzyl)pyrrolidine-2-carboxamide;

(2S,4R)-1-(2-(1H-1,2,3-triazol-1-yl)acetyl)-4-(3-chlorobenzyl)-N-(4-(4-fluorophenoxy)phenyl)pyrrolidine-2-carboxamide;

(2S,4R)-1-(2-(1H-1,2,3-triazol-1-yl)acetyl)-4-(2-fluorobenzyl)-N-(4-(4-fluorophenoxy)phenyl)pyrrolidine-2-carboxamide;

(2S,4R)-1-(2-(2H-1,2,3-triazol-2-yl)acetyl)-4-(2-fluorobenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(3-methylbenzyl)pyrrolidine-2-carboxamide;

(2S,4R)-1-(2-(2H-1,2,3-triazol-2-yl)acetyl)-4-(4-chlorobenzyl)-N-(4-(4-fluorophenoxy)phenyl)pyrrolidine-2-carboxamide;

(2S,4R)-1-(2-(1H-1,2,3-triazol-1-yl)acetyl)-4-(4-chlorobenzyl)-N-(4-(4-fluorophenoxy)phenyl)pyrrolidine-2-carboxamide;

(2S,4R)-1-(2-(1H-1,2,4-triazol-1-yl)acetyl)-N-(4-(4-fluorophenoxy)phenyl)-4-(2,4,6-trifluorobenzyl)pyrrolidine-2-carboxamide;

(2S,4R)-1-(2-(2H-1,2,3-triazol-2-yl)acetyl)-N-(4-(4-fluorophenoxy)phenyl)-4-(2,4,6-trifluorobenzyl)pyrrolidine-2-carboxamide;

(2S,4R)-1-(2-(1H-1,2,3-triazol-1-yl)acetyl)-N-(4-(4-fluorophenoxy)phenyl)-4-(2,4,6-trifluorobenzyl)pyrrolidine-2-carboxamide;

and (2S,4R)-1-(2-(1H-1,2,3-triazol-1-yl)acetyl)-4-(3,4-difluorobenzyl)-N-(4-(4-fluorophenoxy)phenyl)pyrrolidine-2-carboxamide;

or a pharmaceutically acceptable salt of any of the above compounds.

8. A compound of Formula I:

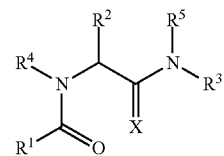

or a pharmaceutically acceptable salt thereof, wherein:

X is O or $NR^6$;

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, $-X^1OR^7$, $-X^1-C(O)OR^7$, $-X^1C(O)NR^7R^7$, $-X^1NR^7C(O)OR^7$, $-X^1OC(O)-NR^7R^7$, $-X^1NR^7C(O)NR^7R^7$, $-X^1-S(O)_{n1}R^7$, $-X^1S(O)_{n1}NR^7R^7$, $-X^1NR^7S(O)_{n1}NR^7R^7$, $-X^1-NR^7R^7$, $-X^1C(O)R^7$, $-X^1OC(O)-R^8$, $-X^1NR^7C(O)R^8$, $-X^1S(O)_{n1}R^8$, $-X^1OS(O)_{n1}R^8$ or $-X^1NR^7S(O)_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $-X^2CR^9R^9R^{11}$, $-X^2OR^{11}$, $-X^2C(O)OR^{11}$, $-X^2C(O)NR^{10}R^{11}$, $-X^2NR^{10}C(O)-OR^{11}$, $-X^2OC(O)NR^{10}R^{11}$, $-X^2NR^{10}C(O)NR^{10}R^{11}$, $-X^2S(O)_{n2}OR^{11}$, $-X^2S(O)_{n2}-NR^{10}R^{11}$, $-X^2NR^{10}S(O)_{n2}-NR^{10}R^{11}$, $-X^2NR^{10}R^{11}$, $-X^2C(O)R^{11}$, $-X^2OC(O)R^{11}$, $-X^2NR^{10}C(O)R^{11}$, $-X^2NR^{10}C(O)R^{11}$, $-X^2S(O)_{n2}R^{11}$, $-X^2O-S(O)_{n2}R^{11}$ or $-R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is $-X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with $-X^4CR^{13}R^{13}R^{15}$, $-X^4OR^{15}$, $-X^4C(O)OR^{15}$, $-X^4C(O)-NR^{14}R^{15}$, $-X^4-NR^{14}C(O)OR^{15}$, $-X^4OC(O)NR^{14}R^{15}$, $-X^4NR^{14}C(O)NR^{14}R^{15}$, $-X^4S(O)_{n3}-OR^{15}$, $-X^4S(O)_{n3}-NR^{14}R^{15}$, $-X^4NR^{14}S(O)_{n3}NR^{14}R^{15}$, $-X^4NR^{14}R^{15}$, $-X^4C(O)R^{15}$, $-X^4-OC(O)R^{15}$, $-X^4NR^{14}C(O)R^{15}$, $-X^4S(O)_{n3}R^{15}$, $-X^4OS(O)_{n3}R^{15}$ or $-R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is $-X^5R^{16}$ wherein $X^5$ is a bond or $(C_{1-3})$alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, $-X^6OR^{17}$, $-X^6C(O)OR^{17}$, $-X^6C(O)NR^{17}R^{17}$, $-X^6-NR^{17}C(O)OR^{17}$, $-X^6-OC(O)NR^{17}R^{17}$, $-X^6NR^{17}C(O)NR^{17}R^{17}$, $-X^6S(O)_{n4}OR^{17}$, $-X^6-S(O)_{n4}NR^{17}R^{17}$, $-X^6NR^{17}S(O)_{n4}-NR^{17}R^{17}$, $-X^6NR^{17}R^{17}$, $-X^6C(O)R^{17}$, $-X^6OC(O)-R^{18}$, $-X^6NR^{17}C(O)R^{18}$, $-X^6S(O)_{n4}R^{18}$, $-X^6-OS(O)_{n4}R^{18}$ and $-X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl;

$R^2$ is $-X^7NHC(O)R^{19}$, $-X^7NR^{20}C(O)OR^{22}$, $-X^7CR^{21}R^{21}R^{22}$, $-X^7OR^{22}$, or $-X^7S(O)_{n5}OR^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$)alkyl, $R^{21}$ is halo and $R^{22}$ is $-X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

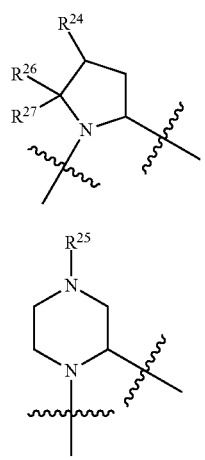

(a)

(b)

wherein $R^{24}$ is $-X^9OR^{29}$, $-X^9NR^{28}C(O)OR^{29}$, $-X^9NR^{28}R^{29}$, $-X^9C(O)OR^{29}$ or $-R^{29}$ and $R^{25}$ is $-X^{10}OR^{29}$, $-X^{10}NR^{28}C(O)OR^{29}$, $-X^{10}NR^{28}R^{29}$, $-X^9C(O)OR^{29}$ or $-R^{29}$ wherein $X^9$ is a bond or $(C_{1-3})$ alkylene, $X^{10}$ is $(C_{1-3})$alkylene and $R^{28}$ is hydrogen, $(C_{1-4})$alkyl or halo-substituted $(C_{1-4})$alkyl and $R^{29}$ is $-X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo or thioxo;

$R^3$ is phenyl substituted with $-R^{31}$ or $R^3$ is a group of Formula (c):

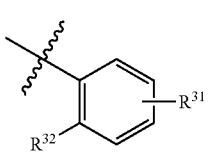

(c)

wherein $R^{31}$ is $-OR^{33}$, $-SR^{33}$ or $-CH_2R^{33}$, wherein $R^{33}$ is $-X^{12}R^{34}$, wherein $X^{12}$ is a bond or methylene and $R^{34}$ is five or six membered cycloalkyl or heterocycloalkyl, phenyl or five or six membered heteroaryl, and when X is $NR^6$, $R^{32}$ together with $R^6$ forms a bond, wherein any cyclic moiety within $R^3$ independently may be substituted with one or two $(C_{1-4})$alkyl, halo or $-OR^{35}$, wherein $R^{35}$ is $(C_{1-4})$alkyl;

$R^4$ is hydrogen, alkyl or as defined above; and $R^5$ is hydrogen or alkyl, wherein the compound of Formula I can be in the form of any individual stereoisomer or mixture of stereoisomers.

9. The compound of claim 8, or a pharmaceutically acceptable salt thereof, wherein:

X is O;

$R^1$ is alkyl, alkenyl, halo-substituted alkyl, halo-substituted alkenyl, nitro-substituted alkyl, nitro-substituted alkenyl, cyano-substituted alkyl, cyano-substituted alkenyl, $-X^1OR^7$, $-X^1-C(O)OR^7$, $-X^1C(O)NR^7R^7$, $-X^1NR^7C(O)OR^7$, $-X^1OC(O)-NR^7R^7$, $-X^1NR^7C(O)NR^7R^7$, $-X^1-S(O)_{n1}OR^7$, $-X^1S(O)_{n1}NR^7R^7$, $-X^1NR^7S(O)_{n1}NR^7R^7$, $-X^1NR^7R^7$, $-X^1C(O)R^7$, $-X^1OC(O)-R^8$, $-X^1NR^7C(O)R^8$, $-X^1S(O)_{n1}R^8$, $-X^1OS(O)_{n1}R^8$ or $-X^1NR^7S(O)_{n1}R^8$, wherein n1 is 0, 1, or 2, $X^1$ is a bond or alkylene, $R^7$ at each occurrence independently is hydrogen, $(C_{1-4})$alkyl, alkoxy-substituted $(C_{1-4})$alkyl or halo-substituted $(C_{1-4})$alkyl and $R^8$ is $(C_{1-4})$alkyl, alkoxy-substituted $(C_{1-4})$alkyl or halo-substituted $(C_{1-4})$alkyl, or $R^1$ is $-X^2CR^9R^9R^{11}$, $-X^2OR^{11}$, $-X^2C(O)OR^{11}$, $-X^2C(O)NR^{10}R^{11}$, $-X^2NR^{10}C(O)O-R^{11}$, $-X^2O-C(O)NR^{10}R^{11}$, $-X^2NR^{10}C(O)NR^{10}R^{11}$, $-X^2S(O)_{n2}OR^{11}$, $-X^2S(O)_{n2}-NR^{10}R^{11}$, $-X^2NR^{10}S(O)_{n2}-NR^{10}R^{11}$, $-X^2NR^{10}R^{11}$, $-X^2C(O)R^{11}$, $-X^2OC(O)-R^{11}$, $-X^2NR^{10}C(O)R^{11}$, $-X^2S(O)_{n2}R^{11}$, $-X^2-OS(O)_{n2}R^{11}$ or $-R^{11}$, wherein n2 is 0, 1, or 2, $X^2$ is a bond or alkylene, $R^9$ at each occurrence independently is halo, $R^{10}$ at each occurrence independently is hydrogen, $(C_{1-4})$alkyl or halo-substituted $(C_{1-4})$alkyl and $R^{11}$ is $-X^3R^{12}$, wherein $X^3$ is a bond, alkylene or hydroxy-substituted alkylene and $R^{12}$ is cycloalkyl, aryl, heterocycloalkyl or heteroaryl, wherein:

$R^{12}$ may be substituted with $-X^4CR^{13}R^{13}R^{15}$, $-X^4OR^{15}$, $-X^4C(O)OR^{15}$, $-X^4C(O)-NR^{14}R^{15}$, $-X^4-NR^{14}C(O)OR^{15}$, $-X^4OC(O)NR^{14}R^{15}$, $-X^4NR^{14}C(O)NR^{14}R^{15}$, $-X^4S(O)_{n3}-OR^{15}$, $-X^4S(O)_{n3}-NR^{14}R^{15}$, $-X^4NR^{14}S(O)_{n3}NR^{14}R^{15}$, $-X^4NR^{14}R^{15}$, $-X^4C(O)R^{15}$, $-X^4O-C(O)R^{15}$, $X^4NR^{14}C(O)R^{15}$, $-X^4S(O)_{n3}R^{15}$, $-X^4OS(O)_{n3}R^{15}$ or $-R^{15}$, wherein n3 is 0, 1, or 2, $X^4$ is a bond or $(C_{1-3})$alkylene, $R^{13}$ at each occurrence independently is halo, $R^{14}$ at each occurrence independently is hydrogen, $(C_{1-4})$alkyl or halo-substituted $(C_{1-4})$alkyl and $R^{15}$ is $-X^5R^{16}$ wherein $X^5$ is a bond or $(C_{1-3})$)alkylene and $R^{16}$ is cycloalkyl, aryl, heterocycloalkyl or heteroaryl, wherein:

any cycloalkyl, aryl, heterocycloalkyl or heteroaryl group within $R^1$ independently may be substituted with one to three groups independently selected from $(C_{1-4})$alkyl, alkylidene, azido, cyano, halo, nitro, oxo, thioxo, halo-substituted $(C_{1-4})$alkyl, nitro-substituted $(C_{1-4})$alkyl, $(C_{2-4})$ alkenyl, $-X^6OR^{17}$, $-X^6C(O)OR^{17}$, $-X^6C(O)-NR^{17}R^{17}$, $-X^6NR^{17}C(O)OR^{17}$, $-X^6-OC(O)NR^{17}R^{17}$, $-X^6NR^{17}C(O)NR^{17}R^{17}$, $-X^6S(O)_{n4}-OR^{17}$, $-X^6S(O)_{n4}NR^{17}R^{17}$, $-X^6NR^{17}S(O)_{n4}-NR^{17}R^{17}$, $-X^6NR^{17}R^{17}$, $-X^6C(O)R^{17}$, $-X^6-OC(O)R^{18}$, $-X^6NR^{17}C(O)R^{18}$, $-X^6S(O)_{n4}R^{18}$, $-X^6-OS(O)_{n4}R^{18}$ and $-X^6NR^{17}S(O)_{n4}R^{18}$, wherein n4 is 0, 1, or 2, $X^6$ is a bond or $(C_{1-3})$alkylene, $R^{17}$ at each occurrence independently is hydrogen, $(C_{1-4})$alkyl or halo-substituted $(C_{1-4})$alkyl and $R^{18}$ is $(C_{1-4})$alkyl or halo-substituted $(C_{1-4})$alkyl;

$R^2$ is —$X^7$NHC(O)$R^{19}$, —$X^7$NR$^{20}$C(O)OR$^{22}$, —$X^7$CR$^{21}$R$^{21}$R$^{22}$, —$X^7$OR$^{22}$, or —$X^7$S(O)$_{n5}$—OR$^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl, $R^{21}$ is halo and $R^{22}$ is —$X^8R^{23}$, wherein $X^8$ is a bond or methylene, and $R^{23}$ is phenyl, or $R^2$ together with $R^4$ and the atoms to which $R^2$ and $R^4$ are attached form a five or six membered ring of Formula (a) or (b):

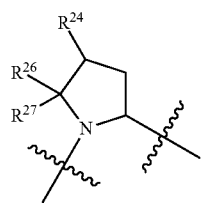

(a)

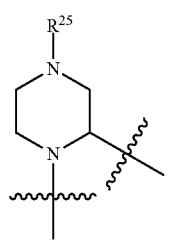

(b)

wherein $R^{24}$ is —$X^9$OR$^{29}$, —$X^9$NR$^{28}$C(O)OR$^{29}$, —$X^9$NR$^{28}$R$^{29}$, —$X^9$C(O)OR$^{29}$ or —$R^{29}$ and $R^{25}$ is —$X^{10}$OR$^{29}$, —$X^{10}$NR$^{28}$C(O)OR$^{29}$, —$X^9$NR$^{28}$R$^{29}$, —$X^9$C(O)OR$^{29}$ or —$R^{29}$ wherein $X^9$ is a bond or $(C_{1-3})$ alkylene, $X^{10}$ is $(C_{1-3})$alkylene and $R^{28}$ is hydrogen, $(C_{1-4})$alkyl or halo-substituted $(C_{1-4})$alkyl and $R^{29}$ is —$X^{11}$R$^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo or thioxo;

$R^3$ is phenyl substituted with —$R^{31}$, wherein $R^{31}$ is —$OR^{33}$, —$SR^{33}$ or —$CH_2R^{33}$, wherein $R^{33}$ is —$X^{12}R^{34}$, wherein $X^{12}$ is a bond or methylene and $R^{34}$ is five or six membered cycloalkyl or heterocycloalkyl, phenyl or five or six membered heteroaryl, wherein any cyclic moiety within $R^3$ independently may be substituted with one or two $(C_{1-4})$)alkyl, halo or —$OR^{35}$, wherein $R^{35}$ is $(C_{1-4})$alkyl;

$R^4$ is hydrogen, alkyl or as defined above; and $R^5$ is hydrogen or alkyl, wherein the compound of Formula I can be in the form of any individual stereoisomer or mixture of stereoisomers.

10. The compound of claim 8 which is a compound of Formula I(a):

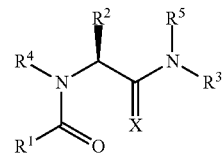

I(a)

or a pharmaceutically acceptable salt thereof.

11. The compound of claim 10, or a pharmaceutically acceptable salt thereof, wherein X is O; $R^1$ is five-membered heteroarylmethyl; $R^2$ is —$X^7$OR$^{22}$, $X^7$ is methylene and $R^{23}$ is phenyl, wherein $R^{23}$ may be substituted with one or two halo; $R^3$ is 4-(4-fluorophenoxy)phenyl, wherein any cyclic moiety within $R^3$ independently may be substituted with one or two $(C_{1-4})$)alkyl, halo or —$OR^{35}$, wherein $R^{35}$ is $(C_{1-4})$ alkyl; and $R^4$ and $R^5$ are hydrogen.

12. The compound of claim 10, or a pharmaceutically acceptable salt thereof, wherein $R^1$ is 2H-1,2,3-triazol-2-ylmethyl, 1H-1,2,4-triazol-1-ylmethyl or 1H-1,2,3-triazol-1-yl; $R^2$ is —$X^7R^{22}$, wherein $X^7$ is $(C_1-C_3)$alkylene and $R^{23}$ is phenyl, wherein $R^{23}$ can be substituted with one halo; and $R^3$ is 4-(4-fluorophenoxy)phenyl.

13. A compound of Formula III:

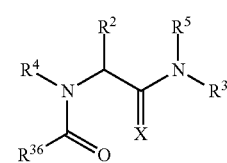

III or a pharmaceutically acceptable salt thereof, wherein:

X is O or NR$^6$;

$R^{36}$ is 1-(4-chlorobenzyl)-5-oxopyrrolidin-3-yl, 1H-imidazol-4-ylmethyl, 1H-indol-4-yl, 2-methylthiopyrid-3-yl, 1R-hydroxy-2-phenylethyl, 2-hydroxyphenoxymethyl, 1S-acetyloxyethyl, (R)-2-chlorophenyl(hydroxy)methyl, tetrahydrofuran-2R-yl, 3-methyloxazol-5-yl, 2,2,2-trifluoroethyl, 2-cyclopropyl-carbonylethyl, 2-bromo-5-fluorophenyl, indol-4-yl, indol-5-yl, indol-6-yl, indan-2-yl, 3-methyl-2-nitrophenyl, methylsulphonylmethyl, 5-methylpyrid-3-yl, 4-acetyloxy-phenyl, 3-hydroxyphenyl(hydroxyl)methyl, 5-(2,5-dioxo-2,5-dihydro-1H-pyrrol-1-yl)pentyl, fur-2-ylcarbonyl, 2R-methyl-2-phenylethyl, 3-chloro-2-fluorobenzyl, 5-chloro-2-fluorobenzyl, 1-acetylpyrrolidin-2-yl, N-benzoyl-N-methylaminomethyl, 1H-imdazol-4-ylmethyl, 1H-tetrazol-1-ylmethyl, 1-methyl-imidazol-4-yl, 2-fluorobenzyl, 1H-1,2,4-triazol-1-ylmethyl, thien-2-ylmethyl, 2,5-dichlorobenzyl, ((1-methyl-1H-benzo[d]imidazol-2-yl)methylamino)methyl or 2,5-dioxoimidazolidin-4-ylmethyl;

$R^2$ is —$X^7$NHC(O)$R^{19}$, —$X^7$NR$^{20}$C(O)OR$^{22}$, —$X^7$CR$^{21}$R$^{21}$R$^{22}$, —$X^7$OR$^{22}$, —$X^7$S(O)$_{n5}$OR$^{22}$, wherein n5 is 0, 1, or 2, $X^7$ is $(C_{1-3})$alkylene, $R^{19}$ is $(C_{1-4})$alkyl or halo-substituted $(C_{1-4})$alkyl, $R^{20}$ is hydrogen, $(C_{1-4})$alkyl or halo-substituted $(C_{1-4})$alkyl, $R^{21}$ is halo and $R^{22}$ is —$X^8R^{23}$, wherein $X^8$ is a bond or $(C_{1-3})$alkylene, and $R^{23}$ is phenyl, wherein $R^{23}$ may be substituted with one or two substituents independently selected from halo, trifluoromethoxy or trifluoromethyl, or $R^2$ together with $R^4$ and the atoms to which $R^2$ and $R^4$ are attached form a five or six membered ring of Formula (a) or (b):

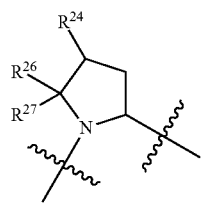

(a)

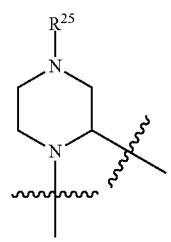

(b)

wherein $R^{24}$ is —$X^9OR^{29}$, —$X^9NR^{28}C(O)OR^{29}$, —$X^9NR^{28}R^{29}$, —$X^9C(O)OR^{29}$ or —$R^{29}$ and $R^{25}$ is —$X^{10}OR^{29}$, —$X^{10}NR^{28}C(O)OR^{29}$, —$X^{10}NR^{28}R^{29}$, —$X^9C(O)OR^{29}$ or —$R^{29}$ wherein $X^9$ is a bond or $(C_{1-3})$ alkylene, $X^{10}$ is $(C_{1-3})$alkylene and $R^{28}$ is hydrogen, $(C_{1-4})$alkyl or halo-substituted $(C_{1-4})$alkyl and $R^{29}$ is —$X^{11}R^{30}$ wherein $X^{11}$ is a bond or $(C_{1-3})$alkylene and $R^{30}$ is phenyl or heteroaryl, wherein $R^{30}$ may be substituted with one to three substituents independently selected from $(C_{1-4})$alkyl, $(C_{1-4})$alkoxy, halo and trifluoromethyl, and $R^{26}$ and $R^{27}$ are both hydrogen or together form oxo or thioxo;

$R^3$ is phenyl substituted with —$R^{31}$ or $R^3$ is a group of Formula (c):

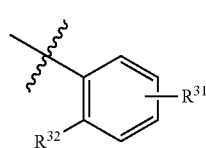

(c)

wherein $R^{31}$ is —$OR^{33}$, —$SR^{33}$ or —$CH_2R^{33}$, wherein $R^{33}$ is —$X^{12}R^{34}$, wherein $X^{12}$ is a bond or methylene and $R^{34}$ is five or six membered cycloalkyl or heterocycloalkyl, phenyl or five or six membered heteroaryl, and, when X is $NR^6$, $R^{32}$ together with $R^6$ forms a bond, wherein any cyclic moiety within $R^3$ independently may be substituted with one or two $(C_{1-4})$alkyl, halo or —$OR^{35}$, wherein $R^{35}$ is $(C_{1-4})$alkyl;

$R^4$ is hydrogen, alkyl or as defined above; and $R^5$ is hydrogen or alkyl, wherein the compound of Formula III can be in the form of any individual stereoisomer or mixture of stereoisomers.

14. A pharmaceutical composition which contains a compound of claim 1 or an individual stereoisomer or mixture of stereoisomers or a pharmaceutically acceptable salt thereof in admixture with one or more suitable excipients.

15. A pharmaceutical composition which contains a compound of claim 8 or an individual stereoisomer or mixture of stereoisomers or a pharmaceutically acceptable salt thereof in admixture with one or more suitable excipients.

\* \* \* \* \*